US012251440B2

(12) United States Patent
Babb et al.

(10) Patent No.: US 12,251,440 B2
(45) **Date of Patent: *Mar. 18, 2025**

(54) ANTI-SARS-CoV-2-SPIKE GLYCOPROTEIN ANTIBODIES AND ANTIGEN-BINDING FRAGMENTS

(71) Applicant: Regeneron Pharmaceuticals, Inc., Tarrytown, NY (US)

(72) Inventors: Robert Babb, River Edge, NJ (US); Alina Baum, Pleasantville, NY (US); Gang Chen, Yorktown Heights, NY (US); Cindy Gerson, Irvington, NY (US); Johanna Hansen, Greenwich, CT (US); Tammy Huang, Cross River, NY (US); Christos Kyratsous, Irvington, NY (US); Wen-Yi Lee, New Hyde Park, NY (US); Marine Malbec, Port Chester, NY (US); Andrew Murphy, Croton-on-Hudson, NY (US); William Olson, Yorktown Heights, NY (US); Neil Stahl, Carmel, NY (US); George D. Yancopoulos, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/216,118

(22) Filed: Jun. 29, 2023

(65) Prior Publication Data

US 2023/0348569 A1 Nov. 2, 2023

Related U.S. Application Data

(63) Continuation of application No. 17/207,524, filed on Mar. 19, 2021, now Pat. No. 11,732,030, which is a continuation of application No. 17/021,286, filed on Sep. 15, 2020, now Pat. No. 10,954,289, which is a continuation of application No. 16/996,297, filed on Aug. 18, 2020, now Pat. No. 10,975,139, which is a continuation of application No. 16/912,678, filed on Jun. 25, 2020, now Pat. No. 10,787,501.

(60) Provisional application No. 63/034,865, filed on Jun. 4, 2020, provisional application No. 63/025,949, filed on May 15, 2020, provisional application No. 63/014,687, filed on Apr. 23, 2020, provisional application No. 63/004,312, filed on Apr. 2, 2020.

(51) Int. Cl.

| | |
|---|---|
| ***A61K 45/06*** | (2006.01) |
| ***A61K 39/15*** | (2006.01) |
| ***A61K 39/395*** | (2006.01) |
| ***C07K 16/10*** | (2006.01) |
| *A61K 39/00* | (2006.01) |

(52) U.S. Cl.

CPC .............. *A61K 45/06* (2013.01); *A61K 39/15* (2013.01); *A61K 39/395* (2013.01); *C07K 16/1003* (2023.08); *A61K 39/00* (2013.01); *C07K 2317/31* (2013.01); *C07K 2317/52* (2013.01); *C07K 2317/565* (2013.01)

(58) Field of Classification Search

None

See application file for complete search history.

(56) References Cited

U.S. PATENT DOCUMENTS

| | | | |
|---|---|---|---|
| 5,908,635 | A | 6/1999 | Thierry |
| 10,787,501 | B1 | 9/2020 | Babb et al. |
| 10,822,379 | B1 | 11/2020 | Dimitrov et al. |
| 10,954,289 | B1 | 3/2021 | Babb et al. |
| 10,975,139 | B1 | 4/2021 | Babb et al. |
| 11,020,474 | B1 | 6/2021 | Xiang et al. |
| 11,021,531 | B1 | 6/2021 | Glanville et al. |
| 11,021,532 | B1 | 6/2021 | Glanville et al. |
| 11,028,150 | B1 | 6/2021 | Glanville et al. |
| 11,028,167 | B1 | 6/2021 | Glanville et al. |
| 11,732,030 | B2 | 8/2023 | Babb et al. |
| 11,999,777 | B2 | 6/2024 | Ganguly et al. |
| 2006/0240551 | A1 | 10/2006 | Jiang et al. |
| 2011/0159001 | A1 | 6/2011 | Lanzavecchia |
| 2017/0096455 | A1 | 4/2017 | Baric et al. |
| 2017/0355756 | A1 | 12/2017 | Julien et al. |
| 2021/0031123 | A1 | 2/2021 | Liu et al. |
| 2021/0093709 | A1 | 4/2021 | Wu et al. |
| 2021/0260201 | A1 | 8/2021 | Chukly et al. |
| 2021/0275665 | A1 | 9/2021 | Cho |
| 2021/0277093 | A1 | 9/2021 | Mond et al. |
| 2021/0388065 | A1 | 12/2021 | Lu et al. |

FOREIGN PATENT DOCUMENTS

| | | | |
|---|---|---|---|
| CN | 111088283 | A | 5/2020 |
| CN | 111285933 | A | 6/2020 |
| CN | 111303254 | A | 6/2020 |
| CN | 111303279 | A | 6/2020 |

(Continued)

OTHER PUBLICATIONS

Almagro et al., "Humanization of Antibodies," Frontiers in Bioscience, vol. 13: 1619-1633, (2008).

(Continued)

*Primary Examiner* — Benjamin P Blumel

(74) *Attorney, Agent, or Firm* — Schwabe, Williamson & Wyatt PC; Gabe Amodeo

(57) ABSTRACT

The present disclosure provides antibodies and antigen-binding fragments thereof that bind specifically to a coronavirus spike protein and methods of using such antibodies and fragments for treating or preventing viral infections (e.g., coronavirus infections).

16 Claims, 16 Drawing Sheets

Specification includes a Sequence Listing.

(56) References Cited

FOREIGN PATENT DOCUMENTS

| | | | |
|---|---|---|---|
| CN | 111303280 | A | 6/2020 |
| CN | 111333704 | B | 6/2020 |
| CN | 111333722 | A | 6/2020 |
| CN | 111420048 | A | 7/2020 |
| CN | 111423508 | A | 7/2020 |
| CN | 111440229 | A | 7/2020 |
| CN | 111471105 | A | 7/2020 |
| CN | 111499692 | A | 8/2020 |
| CN | 111499765 | A | 8/2020 |
| CN | 111518773 | A | 8/2020 |
| CN | 111560399 | A | 8/2020 |
| CN | 111574614 | A | 8/2020 |
| CN | 111592594 | A | 8/2020 |
| CN | 111592595 | B | 8/2020 |
| CN | 111607003 | A | 9/2020 |
| CN | 111620945 | B | 9/2020 |
| CN | 111620946 | B | 9/2020 |
| CN | 111647053 | A | 9/2020 |
| CN | 111647076 | B | 9/2020 |
| CN | 111647077 | B | 9/2020 |
| CN | 111662379 | B | 9/2020 |
| CN | 111690058 | B | 9/2020 |
| CN | 111690059 | A | 9/2020 |
| CN | 111690060 | A | 9/2020 |
| CN | 111714621 | B | 9/2020 |
| CN | 111718411 | A | 9/2020 |
| CN | 111732654 | B | 10/2020 |
| CN | 111732655 | A | 10/2020 |
| CN | 111732664 | B | 10/2020 |
| CN | 111748032 | B | 10/2020 |
| CN | 111778218 | A | 10/2020 |
| CN | 111793129 | A | 10/2020 |
| CN | 111825762 | A | 10/2020 |
| CN | 111825771 | A | 10/2020 |
| CN | 111848750 | A | 10/2020 |
| CN | 111848751 | A | 10/2020 |
| CN | 111848789 | A | 10/2020 |
| CN | 111875701 | A | 11/2020 |
| CN | 111909260 | A | 11/2020 |
| CN | 111909261 | A | 11/2020 |
| CN | 111909262 | A | 11/2020 |
| CN | 111909263 | A | 11/2020 |
| CN | 111925439 | A | 11/2020 |
| CN | 111925440 | A | 11/2020 |
| CN | 111925441 | A | 11/2020 |
| CN | 111925442 | A | 11/2020 |
| CN | 111925443 | A | 11/2020 |
| CN | 111925444 | A | 11/2020 |
| CN | 111944026 | A | 11/2020 |
| CN | 111978377 | A | 11/2020 |
| CN | 111978395 | A | 11/2020 |
| CN | 111978396 | A | 11/2020 |
| CN | 111978397 | A | 11/2020 |
| CN | 111978398 | A | 11/2020 |
| CN | 111978399 | A | 11/2020 |
| CN | 111995672 | A | 11/2020 |
| CN | 111995674 | A | 11/2020 |
| CN | 111995678 | B | 11/2020 |
| CN | 112010962 | A | 12/2020 |
| CN | 112010963 | A | 12/2020 |
| CN | 112010964 | A | 12/2020 |
| CN | 112010967 | B | 12/2020 |
| CN | 112062838 | B | 12/2020 |
| CN | 112062839 | A | 12/2020 |
| CN | 112062840 | A | 12/2020 |
| CN | 112062859 | A | 12/2020 |
| CN | 112076316 | A | 12/2020 |
| CN | 112094326 | A | 12/2020 |
| CN | 112094327 | A | 12/2020 |
| CN | 112094340 | A | 12/2020 |
| CN | 112094342 | A | 12/2020 |
| CN | 112094343 | A | 12/2020 |
| CN | 112125973 | A | 12/2020 |
| CN | 112159469 | A | 1/2021 |
| CN | 112175071 | A | 1/2021 |
| CN | 112175073 | A | 1/2021 |
| CN | 112194711 | A | 1/2021 |
| CN | 112210004 | A | 1/2021 |
| CN | 112250763 | A | 1/2021 |
| CN | 112251414 | A | 1/2021 |
| CN | 112300274 | A | 2/2021 |
| CN | 112341541 | A | 2/2021 |
| CN | 112341542 | B | 2/2021 |
| CN | 112390879 | B | 2/2021 |
| CN | 112409479 | A | 2/2021 |
| CN | 112409488 | A | 2/2021 |
| CN | 112430265 | A | 3/2021 |
| CN | 112442120 | A | 3/2021 |
| CN | 112485455 | A | 3/2021 |
| CN | 112500480 | A | 3/2021 |
| CN | 112500481 | A | 3/2021 |
| CN | 112513076 | A | 3/2021 |
| CN | 112521494 | A | 3/2021 |
| CN | 112521496 | A | 3/2021 |
| CN | 112522203 | A | 3/2021 |
| CN | 112538111 | A | 3/2021 |
| CN | 112552399 | A | 3/2021 |
| CN | 112574299 | A | 3/2021 |
| CN | 112574300 | A | 3/2021 |
| CN | 112625125 | A | 4/2021 |
| CN | 112625136 | A | 4/2021 |
| CN | 112626030 | A | 4/2021 |
| CN | 112626089 | A | 4/2021 |
| CN | 112646005 | A | 4/2021 |
| CN | 112661841 | A | 4/2021 |
| CN | 112724247 | A | 4/2021 |
| CN | 112724248 | A | 4/2021 |
| CN | 112794898 | A | 5/2021 |
| CN | 112794899 | A | 5/2021 |
| CN | 112851804 | A | 5/2021 |
| CN | 112980885 | A | 6/2021 |
| CN | 113045647 | A | 6/2021 |
| CN | 113072640 | A | 7/2021 |
| CN | 113150129 | A | 7/2021 |
| CN | 113150130 | A | 7/2021 |
| CN | 113150132 | A | 7/2021 |
| CN | 113150135 | A | 7/2021 |
| CN | 113151184 | A | 7/2021 |
| CN | 113173995 | A | 7/2021 |
| CN | 113185609 | A | 7/2021 |
| CN | 113214389 | A | 8/2021 |
| CN | 113215106 | A | 8/2021 |
| CN | 113234148 | A | 8/2021 |
| CN | 113234149 | A | 8/2021 |
| CN | 113234150 | A | 8/2021 |
| CN | 113234151 | A | 8/2021 |
| CN | 113248579 | A | 8/2021 |
| CN | 113248581 | A | 8/2021 |
| CN | 113264998 | A | 8/2021 |
| CN | 113292649 | A | 8/2021 |
| CN | 113292650 | A | 8/2021 |
| CN | 113307865 | A | 8/2021 |
| CN | 113336846 | A | 9/2021 |
| CN | 113354731 | A | 9/2021 |
| CN | 113354733 | A | 9/2021 |
| DE | 202020105116 | | 11/2020 |
| EP | 3872091 | A1 | 9/2021 |
| EP | 3885361 | A1 | 9/2021 |
| KR | 102205028 | B1 | 1/2021 |
| KR | 102229225 | B1 | 3/2021 |
| KR | 102233689 | B1 | 3/2021 |
| RU | 2744274 | C1 | 3/2021 |
| WO | 05/018535 | A2 | 3/2005 |
| WO | 05/060520 | A2 | 7/2005 |
| WO | 08/068048 | A2 | 6/2008 |
| WO | 2015/179535 | A1 | 11/2015 |
| WO | 2019/147831 | A1 | 8/2019 |
| WO | 21/001388 | A | 1/2021 |
| WO | 21/001388 | A1 | 1/2021 |
| WO | 21/026074 | A | 2/2021 |
| WO | 21/026074 | A1 | 2/2021 |
| WO | 21/035177 | A2 | 2/2021 |
| WO | 21/045836 | A1 | 3/2021 |

(56) References Cited

FOREIGN PATENT DOCUMENTS

| | | | |
|---|---|---|---|
| WO | 21/058521 | A1 | 4/2021 |
| WO | 21/072399 | A1 | 4/2021 |
| WO | 21/096980 | A1 | 5/2021 |
| WO | 21/148884 | A1 | 7/2021 |
| WO | 21/151100 | A1 | 7/2021 |
| WO | 21/155639 | A1 | 8/2021 |
| WO | 21/163265 | A1 | 8/2021 |
| WO | 21/168483 | A2 | 8/2021 |
| WO | 21/173879 | A1 | 9/2021 |
| WO | 21/180602 | A1 | 9/2021 |
| WO | 21/183790 | A1 | 9/2021 |
| WO | 2021/183195 | A1 | 9/2021 |
| WO | 2021/183359 | A1 | 9/2021 |
| WO | 2021/190980 | A1 | 9/2021 |
| WO | 2021/203053 | A1 | 10/2021 |
| WO | 2021/222935 | A2 | 11/2021 |
| WO | 2021/226560 | A1 | 11/2021 |
| WO | 2021/233834 | A1 | 11/2021 |
| WO | 21/242815 | A1 | 12/2021 |
| WO | 21/247779 | A1 | 12/2021 |
| WO | 2021/239935 | A1 | 12/2021 |
| WO | 2021/245184 | A1 | 12/2021 |
| WO | 2021/249547 | A1 | 12/2021 |
| WO | 2022/090353 | A1 | 5/2022 |
| WO | 2022/162587 | A1 | 8/2022 |

OTHER PUBLICATIONS

Andreano et al., "Identification of neutralizing human monoclonal antibodies from Italian Covid-19 convalescent patients," bioRxiv 2020.05.05.078154; (2020) doi: https://doi.org/10.1101/2020.05.05.078154.

Barnes et al., "Structures of human antibodies bound to SARS-CoV-2 spike reveal common epitopes and recurrent features of antibodies," Structures of human antibodies bound to SARS-CoV-2 spike reveal common epitopes and recurrent features of antibodies, Cell (2020), doi: https://doi.org/10.1016/j.cell.2020.06.025.

Barnes et al., "Structures of Human Antibodies Bound to SARS-CoV-2 Spike Reveal Common Epitopes and Recurrent Features of Antibodies," Cell, vol. 182, Issue 4): 828-842, Jun. 23, 2020 (2020).

Barnes et al., "SARS-CoV-2 neutralizing antibody structures inform therapeutic strategies," Nature, vol. 588, No. 7839, pp. 682-687, (2020). [Retrieved from the Internet: <URL: http://www.nature.com/articles/s41586-020-2852-1>].

Baum A, Copin R, Ajithdoss D, et al. REGN-COV2 antibody cocktail prevents and treats SARS-CoV-2 infection in rhesus macaques and hamsters. bioRxiv 2020:2020.08.02.233320.

Baum A, Fulton BO, Wloga E, et al. Antibody cocktail to SARS-CoV-2 spike protein prevents rapid mutational escape seen with individual antibodies. Science 2020.

Baum et al., "Antibody cocktail to SARS-CoV-2 spike protein prevents rapid mutational escape seen with individual antibodies," Science, vol. 1:1-17, (2020). [Retrieved from the Internet Jun. 30, 2020: <URL: http://science.sciencemag.org].

Baum et al., "Antibody cocktail to SARS-CoV-2 spike protein prevens rapid mutational escape seen with individual antibodies," Science, pp. 1-8, (Jun. 15, 2020). [Retrieved from the Internet Jun. 23, 2020 from http://science.sciencemag.org/].

Baum et al., "REGN-CoV2 antibodies prevent and treat SARS-CoV-2 infection in rhesus macaques and hamsters," Science, vol. 370, No. 6520:1110-1115, (2020).

Bertoglio et al., "SARS-CoV-2 neutralizing human recombinant antibodies selected from pre-pandemic healthy donors binding at RBD-ACE2 interface," bioRxiv 2020.06.05.135921; (2020) doi: https://doi.org/10.1101/2020.06.05.135921.

Blanco-Melo D, Nilsson-Payant BE, Liu WC, et al. Imbalanced Host Response to SARS-CoV-2 Drives Development of COVID-19. Cell 2020;181:1036-45 e9.

Brouwer et al., "Potent neutralizing antibodies from Covid-19 patients define multiple targets of vulnerability" Science 10.1126/Science.abc5902 (2020).

Brouwer et al., "Potent neutralizing antibodies from Covid-19 patients define multiple targets of vulnerability" bioRxiv 2020.05.12.088716; doi: https://doi.org/10.1101/2020.05.12.088716.

Brouwer et al., "Potent neutralizing antibodies from Covid-19 patients define multiple targets of vulnerability," bioRxiv 2020.05.12.088716; (2020) doi: https://doi.org/10.1101/2020.05.12.088716.

Bruel et al., "Serum neutralization of SARS-COV-2 Omicron sublineages BA.1 and BA.2 in patients receiving monoclonal antibodies," Nature Medicine, Nature Publishing Group US, vol. 28 No. 6: 1297-1302, (2022). [Retrieved from the Internet Mar. 23, 2022; ISSN: 1078-8956, DOI:10.1038/S41591-022-01792-5].

Cao et al., "Potent Neutralizing Antibodies against SARS-CoV-2 identified by high-throughput single-cell sequencing of convalescent patients' B cells," Cell (2020), doi: https://doi.org/10.1016/j.cell.2020.05.025.

Cao et al., "Potent Neurtalizing Antibodies against SARS-CoV-2 Identified by High-Throughput Single-Cell Sequencing of Convalescent Pateitns'B Cells," Cell, vol. 182: 73-84, (2020). [https://doi.org/10.1016/j.cell.2020.05.025].

Case et al., "Neutralizing antibody and soluble ACE2 inhibition of a replication-competent VSV-SARS-CoV-2 and a clinical isolate of SARS-CoV-2," bioRxiv 2020.05.18.102038; (2020) doi: https://doi.org/10.1101/2020.05.18.102038.

Chen et al., "Human monoclonal antibodies block the binding of SARS-CoV-2 spike protein to angiotensin converting enzyme 2 receptor," Cellular & Molecular Immunology (2020) https://doi.org/10.1038/s41423-020-0426-7.

Chen et al., "Resistance of SARS-CoV-2 variants to neutralization by monoclonal and serum-derived polyclonal antibodies," Nature Medicine, vol. 27: 717-726, (2021). [https://doi.org/10.1038/s41591-021-01294-w].

Cheng et al., "Impact of South African 501.V2 Variant on SARS-CoV-2 Spike Infectivity and Neutrlization: A Structure-based Computational Assessment," Bioinformatics, pp. 1-7, (2021). [https://doi.org/10.1101/2021.01.10.426143].

Cheng et al., "An insertion unique to SARS-CoV-2 exhibits superantigenic character strengthened by recent mutations," bioRxiv 2020.05.21.109272; (2020) doi: https://doi.org/10.1101/2020.05.21.109272.

Chi et al., "A neutralizing human antibody binds to the N-terminal domain of the Spike protein of SARS-CoV-2," Science 11.1126/science.abc6952 (2020).

Chi et al., "A potent neutralizing human antibody reveals the N-terminal domain in the Spike protein of SARS-CoV-2 as a site of vulnerability," bioRxiv 2020.05.08.083964; (2020) doi: https://doi.org/10.1101/2020.05.08.083964.

Chi et al., "Humanized Single Domain Antibodies Neutralize SARS-CoV-2 by Targeting Spike Receptor Binding Domain," bioRxiv 2020.04.14.042010; (2020) doi: https://doi.org/10.1101/2020.04.14.042010.

Choi et al., "Characterization of a human monoclonal antibody generated from a B-cell specific for a prefusion-stabilized spike protein of Middle East respiratory syndrome coronavirus," PLoS One 15(5): e0232757. https://doi.org/10.1371/journal.pone.0232757.

Choudhury et al., "In silico studies on the comparative characterization of the interactions of SARS-CoV-2 spike glycoprotein with ACE-2 receptor homologs and humans TLRs," (2020) doi: 10.1002/jmv.25987.

Copin et al., "The monoclonal antibody combination REGEN-COV protects against SARS-CoV-2 mutational escape in preclinical and human studies" Cell, vol. 184: 3949-3961, (Jul. 22, 2021). [https://doi.org/10.1016/j.cell.2021.06.002].

Crooke et al., "Immunoinformatic identification of B cell and T cell epitopes in the SARS-CoV-2 proteome," bioRxiv 2020.05.14.093757; (2020) doi: https://doi.org/10.1101/2020.05.14.093757.

Custodio et al., "Selection, biophysical and structural analysis of synthetic nanobodies that effectively neutralize SARS-CoV-2," bioRxiv 2020.06.23.165415; (2020) doi: https://doi.org/10.1101/2020.06.23.165415.

(56) References Cited

OTHER PUBLICATIONS

Coronavirus Disease 2019 (COVID-19) Situation Report—101. 2020. (Accessed Oct. 6, 2020, at https://www.who.int/docs/default-source/coronaviruse/situation-reports/20200430-sitrep-101-covid-19.pdf?sfvrsn=2ba4e093_2.).
Davidson et al., "Mechanism of Binding to Ebola Virus Glycoprotein by the ZMapp, ZMAb, and MB-003 Cocktail Antibodies," Journal of Virology, vol. 89.21: 10982-10992, (2015).
Deeks et al., "Casirivimab/Imdevimab: First Approval," Drugs, vol. 81 No. 17: 2047-2055, (2021). [URL: https://link.springer.com/article/10.1007/s40265-021-01620-z/fulltext.html].
Deshpande et al., "Epitope Classification and RBD Binding Properties of Neutralizing Antibodies Against SARS-CoV-2 Variants of Concern," Frontiers in Immunology, vol. 12, Jun. 4, 2021; 30 pages.
Dinnon, III et al., "A mouse-adapter SARS-CoV-2 model for the evaluation of Covid-19 medical countermeasures," bioRxiv 2020.05.06.081497; (2020) doi: https://doi.org/10.1101/2020.05.06.081497.
Dong et al., "Development of multi-specific humanized llama antibodies blocking SARS-CoV-2/ACE2 interaction with high affinity and avidity," Emerging Microbes & Infections, 9:1, 1034-1036, DOI: 10.1080/22221751.2020.1768806.
Edwards et al., "The Remarkable Flexibility of the Human Antibody Repertoire; Isolation of Over One Thousand Different Anibodies to a Single Protein, BLyS,"JMB, vol. 334: 103-118, (2003). [doi:10.1016/jmb.2003.09.054>].
Ejemel et al., "IgA Mab blocks SARS-CoV-2 Spike-ACE2 interaction providing mucosal immunity," bioRxiv 2020.05.15.096719; doi: https://doi.org/10.1101/2020.05.15.096719.
European Medicines Agency (EMA), "Assesment report Regeneron Ireland DAC use of casirivimab and imdevimab for the treatment of Covid-19," Chapter 2.2, (2021). [Retrieved from the Internet URL:https://www.ema.europa.eu/en/documents/referral/regn-cov2-antibody-combination-casirivimab/imdevimab-covid19-article-53-procedure-assessment-report_en.pdf].
Galson et al., "Deep sequencing of B cell receptor repertoires from COVID-19 patients reveal strong convergent immune signature," bioRxiv 2020.05.20.106294; doi: https://doi.org/10.1101/2020.05.20.106294.
Garde et al., "In the race to develop a coronavirus treatment, Regeneron thinks it has the inside track," STAT, pp. 1-7, Feb. 5, 2020 (2020). [https://www.statnews.com/2020/02/05/in-the-race-to-develop-a-coronavirus-treatment-regeneron-thinks-it-has-the-inside-track/].
Giron et al., "On the Interactions of the receptor-binging domain of SARS-CoV-1 and SARS-CoV-2 spike proteins with monoclonal antibodies and the receptor ACE2," Virus Research 285 (2020) 198021.
Goncalves et al., "SARS-CoV-2 mutations and where to find them: An in silico perspective of structural changes and antigenicity of the Spike protein," bioRxiv 2020.05.21.108563; (2020) doi: https://doi.org/10.1101/2020.05.21.108563.
Goyal P, Choi JJ, Pinheiro LC, et al. Clinical Characteristics of Covid-19 in New York City. N Engl J Med 2020.
Grifoni et al., "Targets of T cell responses to SARS-CoV-2 coronavirus in humans with Covid-19 disease and unexposed individuals," Cell (2020), doi: https://doi.org/10.1016/j.cell.2020.05.015.
Group RC, Horby P, Lim WS, et al. Dexamethasone in Hospitalized Patients with Covid-19—Preliminary Report. N Engl J Med 2020.
Guan WJ, Ni ZY, Hu Y, et al. Clinical Characteristics of Coronavirus Disease 2019 in China. N Engl J Med 2020;382:1708-20.
Gudbjartsson DF, Helgason A, Jonsson H, et al. Spread of SARS-CoV-2 in the Icelandic Population. N Engl J Med 2020;382:2302-15.
Hanke et al., "An alpaca nanobody neutralizes SARS-CoV-2 by blocking receptor interaction," bioRxiv 2020.06.02.130161; (2020) doi: https://doi.org/10.1101/2020.06.02.130161.
Hansen et al., "Studies in humanized mice and convalescent humans yield a SARS-CoV-2 antibody cocktail," Science, vol. 1:1-47, (2020). [Retrieved from the Internet Jun. 30, 2020: <URL: http://science.sciencemag.org].
Hansen et al., "Studies in humanized mice and convalescent humans yield a SARS-CoV-2 antibody cocktail," Science, 1-10, (2020). [Retrieved from the Internet Jul. 29, 2020: <http://science.sciencemag.org>].
Hansen J, Baum A, Pascal KE, et al. Studies in humanized mice and convalescent humans yield a SARS-CoV-2 antibody cocktail. Science 2020.
Hansen et al., "Studies in humanized mice and convalescent humans yield a SARS-CoV-2 antibody cocktail," Science, pp. 1-10, (Jun. 15, 2020). [Retrieved from the Internet Jun. 23, 2020 from http://science.sciencemag.org/].
Hansen et al.,supplementary materials for "Studies in humanized mice and convalescent humans yield a SARS-CoV-2 antibody cocktail," Science, pp. 1-30, (Jun. 15, 2020). [science.scieocemag.org/cgi/conrent/fu1Vscience.abd0827/DCJ].
Heurich et al., "TMPRSS2 and ADAM17 Cleave ACE2 Differentially and Only Proteolysis by TMPRSS2 Augments Entry Driven by the Severe Acute Respiratory Syndrome Coronavirus Spike Protein," Journal of Virology, vol. 88, No. 2; Jan. 2014; p. 1293-1307.
Hsieh et al., "Structure-based design of prefusion-stabilized SARS-CoV-2 Spikes," bioRxiv 2020.05.30.125484; (2020) doi: https://doi.org/10.1101/2020.05.30.125484.
Huibin et al., "Cross-reactive Antibody Response between SARS-CoV-2 and SARS-CoV Infections," Cell Reports 31, 107725; Jun. 2, 2020. https://doi.org/10.1016/j.celrep.2020.107725.
Hulburt et al., "Structural basis for potent neurtralization of SARS-CoV-2 and role of antibody affinity maturation," bioRxiv 2020.06.12.148692; doi: https://doi.org/10.1101/2020.06.12.148692.
Huo et al., "Neutralization of SARS-CoV-2 by destruction of the prefusion Spike," bioRxiv 2020.05.05.079202; (2020) doi: https://doi.org/10.1101/2020.05.05.079202.
Jacobs et al., "Neutralizing antibodies mediate virus-immune pathology of Covid-19," Science Direct, Medical Hypotheses 143; 109884, pp. 1-4. (2020).
Ju et al., "Human neutralizing antibodies elicited by SARS-CoV-2 infection," Nature https://doi.org/10.1038/s41586-020-2380-z (2020).
Ju et al., "Potent human neutralizing antibodies elicited by SARS-CoV-2 infection," bioRxiv 2020.03.21.990770; (2020) doi: https://doi.org/10.1101/2020.03.21.990770.
Jones et al., "LY-CoV555, a rapidly isolated potent neutralizing antibody, provides protection in a non-human primate model of SARS-COV-2 infection," bioRxiv, Oct. 9, 2020; 29 pages. [Retrieved from the Internet May 23, 2021: <URL: http://www.biorxiv.org/content/10.1101/2020.09.30.318972x3>].
Keeffe et al., "A Combination of Two Human Monoclonal Antibodies Prevents Zika Virus Escape Mutations in Non-human Primates," Cell Reports, vol. 25: 1385-1394, (2018). [https://doi.org/10.1016/j.celrep.2018.10.031].
Kreer et al., "Longitudinal isolation of potent near-germline SARS-CoV-2-neutralizing antibodies from Covid-19 patients," bioRxiv 2020.06.12.146290; doi: https://doi.org/10.1101/2020.06.12.146290.
Kugelman et al., "Emergence of Ebola Virus Escape Variants in Infected Nonhuman Primates Treated with the MB-003 Antibody Cocktail," Cell Reports, vol. 12: 2111-2120, (2015). [http://dx.doi.org/10.1016/j.celrep.2015.08.038].
Kussie et al., "A Single engineered amino acid substitution changes antibody fine specificity," The Journal of Immunology, vol. 152 1: 146-152, (1994). [https://doi:org/10.4049/jimmunol.152.1.146].
Interim Clinical Guidance for Management of Patients with Confirmed Coronavirus Disease (Covid-19)—Clinical Care Guidance—Updated Sep. 10, 2020. 2020. (Accessed Oct. 6, 2020).
Joyner MJ, Senefeld JW, Klassen SA, et al. Effect of Convalescent Plasma on Mortality among Hospitalized Patients with Covid-19: Initial Three-Month Experience. medRxiv 2020:2020.08.12.20169359.
Lagadinou et al., "Prognosis of Covid-19: Changes in laboratory parameters," Le Infezioni in Medicina, Suppl. 1, p. 89-95 (2020).

(56) References Cited

OTHER PUBLICATIONS

Lan et al., "Structure of the SARS-CoV-2 spike receptor-binding domain bound to the ACE2 receptor," Nature, vol. 581, May 14, 2020.
Larsen et al., "Afucosylated immunoglobulin G resposnes are a hallmark of enveloped virus infections and show an exacerbated phenotype in Covid-19," bioRxiv 2020.05.18.099507; doi: https://doi.org/10.1101/2020.05.18.099507.
Lavezzo E, Franchin E, Ciavarella C, et al. Suppression of a SARS-CoV-2 outbreak in the Italian municipality of Vo'. Nature 2020;584:425-9.
Lee et al., "CD-8+ T cell cross-reactivity against SARS-CoV-2 conferred by toerh coronavirus strains and influenza virus," bioRxiv 2020.05.20.107292; doi: https://doi.org/10.1101/2020.05.20.107292.
Lee S, Kim T, Lee E, et al. Clinical Course and Molecular Viral Shedding Among Asymptomatic and Symptomatic Patients With SARS-CoV-2 Infection in a Community Treatment Center in the Republic of Korea. JAMA Intern Med 2020.
Li et al., "Potent neutralization of SARS-CoV-2 in vitro and in an animal model by a human monoclonal antibody," bioRxiv 2020.05.13.093088; doi: https://doi.org/10.1101/2020.05.13.093088.
Li et al., "Potent synthetic nanobodies against SARS-CoV-2 and molecular basis for neutralization," bioRxiv 2020.06.09.143438; doi: https://doi.org/10.1101/2020.06.09.143438.
Li L, Zhang W, Hu Y, et al. Effect of Convalescent Plasma Therapy on Time to Clinical Improvement in Patients With Severe and Life-threatening Covid-19: A Randomized Clinical Trial. JAMA 2020;324:460-70.
Li et al., "Repurposing host-based therapeutics to control coronavirus and influenza virus," Drug Discovery Today, vol. 24 (No. 3): 726-736, (Mar. 2019). [https://doi.org/10.1016/j.drudis.2019.01.018].
Lotfi et al., "covid-19: Transmission, prevention, and potential therapeutic opportunities," Science Direct, Clinica Chimica Acta (508): 254-266, (2020).
Lou et al., "Cross-neutralization antibodies against SARS-cOv-2 and RBD mutations from convalescent patient antibody libraries," bioRxiv 2020.06.06.137513; doi: https://doi.org/10.1101/2020.06.06.137513.
Lui et al., "Trimeric SARS-CoV-2 Spike interacts with dimeric ACE2 with limited intra-Spike avidity," bioRxiv 2020.05.21.109157; doi: https://doi.org/10.1101/2020.05.21.109157.
Lv et al., "Structural basis for neutralization of SARS-CoV-2 and SARS-CoV by a potent therapeutic antibody," bioRxiv 2020.06.02.129098; doi: https://doi.org/10.1101/2020.06.02.129098.
Magleby R, Westblade LF, Trzebucki A, et al. Impact of SARS-CoV-2 Viral Load on Risk of Intubation and Mortality Among Hospitalized Patients with Coronavirus Disease 2019. Clin Infect Dis 2020.
Matsuyama et al., "Enhanced isolation of SARS-CoV-2 by TMPRSS2-expressing cells," PNAS, vol. 117 (No. 13), pp. 7001-7003, (Mar. 31, 2020). [<www.pnas.org/cgi/doi/10.1073/pnas.2002589117>].
Martinez-Navio et al., "Long-Term Delivery of an Anti-SIV Monoclonal Antibody With AAV," Frontiers in Immunology, vol. 11(Article 449): 1-9, (Mar. 2020). [doi: 10.3389/fimmu.2020.00449].
Mazzaferri et al., "Exploratory data on the clinical efficacy of monoclonal antibodies against SARS-DOV-2 Omicron Variant of Concern," medRxiv, pp. 1-21, (2022). [Retrieved from the Internet Jun. 27, 2022: < URL: http://www.medrxiv.org/content/10.1101/2022.05.06.22274613v1>].
Meirson et al., "Structural basis of SARS-CoV-2 spike protein induced by ACE2," bioRxiv 2020.05.24.113175; doi: https://doi.org/10.1101/2020.05.24.113175.
Meulen et al., "Human Monoclonal Antibody Combination against SARS Coronavirus: Synergy and Coverage of Escape Mutants," PLoS Medicine, vol. 3.7: 1071-1079, (2006). [www.plosmedicine.org].
Miersch et al., "Synthetic Antibodies neutralized SARS-CoV-2 infection of mammalian cells," bioRxiv 2020.06.05.137349; doi: https://doi.org/10.1101/2020.06.05.137349.
Mossel et al., "Exogenous ACE2 Expression Allows Refractory Cell Lines to Support Severe Acute Respiratory Syndrome Coronavirus Replication," Journal of Virology, vol. 79, No. 6; Mar. 2005; pp. 3846-3850.
Nascimento Jr. et al., "SARS, MERS and SARS-CoV-2 (COVI19) treatment: a patent review," Expert Opinion on Therapeutic Patents, DOI: 10.1080/13543776.2020.1772231.
Ng et al., "Pre-existing and de novo humoral immunity to SARS-CoV-2 in humans," bioRxiv 2020.05.14.095414; doi: https://doi.org/10.1101/2020.05.14.095414.
Ni et al., "Detection of SARS-COV-2-Specific Humoral and Cellular Immunity in COVID-19 Convalescent Individuals," Immunity 52, 1-7; Jun. 16, 2020.
Nieto et al., "Fast isolation of sub-nanomolar affinity alpaca nanobody against the Spike RBD of SARSCoV-2 by combining bacterial display and a simple single-step density gradient selection," bioRxiv, vol. 1:1-27, (2020). [https://doi.org/10.1101/2020.06.09.137935].
Noy-Porat et al., "Tiger team: a panel of human neutralizing mAbs targeting SARS-CoV-2 spike at multiple epitopes," bioRxiv 2020.05.20.106609.
Okba et al., "Severe Acute Respiratory Syndrome Coronavirus 2-Specific Antibody Responses in Coronavirus Disease 2019 Patients," Research vol. 26, No. 7; Apr. 8, 2020.
Oran DP, Topol EJ. Prevalence of Asymptomatic SARS-CoV-2 Infection : A Narrative Review. Ann Intern Med 2020;173:362-7.
Park et al., "Spike protein binding prediction with neutralizing antibodies of SARS-CoV-2", bioRxiv 2020.02.22.951178; (2020) doi: https://doi.org/10.1101/2020.02.22.951178.
Pascal et al., "Pre- and postexposure efficacy of fully human antibodies against Spike protein in a novel humanized mouse model of MERS-CoV infection," PNAS, vol. 112 No. 28): 8738-8743, (2015). [www.pnas.org/cgi/doi/10.1073/pnas.1510830112].
Pascal et al., "Development of Clinical-Stage Human Monoclonal Antibodies That Treat Advanced Ebola Virus Disease in Nonhuman Primates," The Journal of Infectious Diseases, vol. 218: S612-S626, (2018).
Pinto et al., "Cross-neutralization of SARS-CoV-2 by a human monoclonal SARS-CoV antibody," Nature https://doi.org/10.1038/s41586-020-2349-y (2020).
Pinto et al., "Cross-neutralization of SARS-CoV-2 by a human monoclonal SARS-CoV antibody," Nature, vol. 583: 290-308, (2020). [https://doi.org/10.1038/s41586-020-2 349-y].
Poh et al., "Two linear epitopes on the SARS-CoV-2 spike protein that elicit neutralising antibodies in Covid-19 patients," Nature Communications (2020)11:2806. https://doi.org/10.1038s41467-020-16638-2.
Qiang et al., "Monoclonal Antibodies Capable of Binding SARS-CoV-2 Spike Protein Receptor Binding Motif Specifically Prevent GM-CSF Induction," bioRxiv, pp. 1-27, Sep. 4, 2020 (2020).
Ravichandran et al., "Antibody repertoire induced by SARS-CoV-2 spike protein immunogens," bioRxiv 2020.05.12.091918; doi: https://doi.org/10.1101/2020.05.12.091918.
Raybould et al., "CoV-AbDab: the Coronavirus Antibody Database," bioRxiv 2020.05.15.077313; doi: https://doi.org/10.1101/2020.05.15.077313.
Regeneron. Regeneron and Sanofi Provide Update On Kevzara (Sarilumab) Phase 3 U.S. Trial in Covid-19 Patients. 2020.
Reichert, "Coronavirus in the crosshairs, Part 1—The Antibody Society," pp. 1-7, (2020). [https://www.antibodysociety.org/coronavirus/coronavirus-in-the-crosshairs/].
Reichert, "Coronavirus in the crosshairs, Part 4: Antibody therapeutics—The Antibody Society," pp. 1-10, (2020). [https://www.antibodysociety.org/covid-19/coronavirus-in-the-crosshairs-part-4-antibody-therapeutics/].
Richardson S, Hirsch JS, Narasimhan M, et al. Presenting Characteristics, Comorbidities, and Outcomes Among 5700 Patients Hospitalized With Covid-19 in the New York City Area. JAMA 2020.
Robbiani et al., "Convergent antibody responses to SARS-CoV-2 in convalescent individuals," Nature https://doi.org/10.1038/s41586-020-2456-9 (2020).

(56) References Cited

OTHER PUBLICATIONS

Robbiani et al., "Convergent Antibody Responses to SARS-CoV-2 Infection in Convalescent Individuals," bioRxiv 2020.05.13. 092619; (2020) doi: https://doi.org/10.1101/2020.05.13.092619.
Rockx et al., "Escape from Human Monoclonal Antibody Neutralization Affects in Vitro and In Vivo Fitness of Severe Acute Respiratory Syndrome Coronavirus," The Journal of Infectious Diseases, vol. 201: 946-955, (2010). [DOI: 10.1086/651022].
Roche. Roche Provides an Update on the Phase III Covacta Trial of ACTEMRA/ROACTEMRA in Hospitalized Patients with Severe Covid-19 Associated Pneumonia. 2020.
Rogers et al., "Isolation of potent SARS-CoV-2 neutralizing antibodies and protection from disease in a small animal model," Science 10.1126/scienec.abc7520 (2020).
Rogers et al., "Rapid isolation of potent SARS-CoV-2 neutralizing antibodies and protection in a small animal model," bioRxiv 2020. 05.11.088674; doi: https://doi.org/10.1101/2020.05.11.088674.
Rouet et al., "Potent SARS-CoV-2 binding and neutralization through maturation of iconic SARS-COV-1 antibodies," bioRxiv, pp. 1-52, (2020). [https://doi.org/10.1101/2020.12.14.422791].
Rosas I, Bräu N, Waters M, et al. Tocilizumab in Hospitalized Patients With Covid-19 Pneumonia. medRxiv 2020:2020.08.27. 20183442.
Rudikoff et al., "Single amino acid substitution altering antigen-binding specificity," Proc. Natl. Acad. Sci. USA, vol. 79:1979-1983, (Mar. 1982).
Seydoux et al., "Analysis of a SARS-CoV-2 infected individual reveals development of potent neutralizing antibodies to distinct epitopes with limited somatic mutation ," Immunity 4384; https://doi.org/10.1016/j.immuni.2020.06.001.
Seydoux et al., "Characterization of neutralizing antibodies from a SARS-CoV-2 infected individual," bioRxiv 2020.05.12.091298; doi: https://doi.org/10.1101/2020.05.12.091298.
Shen et al., "TMPRSS2: A potential target for treatment of influenza virus and coronavirus infections," Biochimie at ScienceDirect, vol. 142: 1-10, (2017). [http://dx.doi.org/10.1016/j.biochi.2017.07.016].
Shi et al., "A Human neutralizing antibody targets the receptor binding cite of SARS-CoV-2," Nature https://doi.org/10.1038/s41586-020-2381-y (2020).
Simoes EAF, Forleo-Neto E, Geba GP, et al. Suptavumab for the Prevention of Medically Attended Respiratory Syncytial Virus Infection in Preterm Infants. Clin Infect Dis 2020.
Suthar et al., "Rapid generation of neutralizing antibody responses in Covid-19 patients," Cell Reports Medicine, 1-36 pages (2020). [https://doi.org/10.1016/j.xcrm.2020.100040].
Stave et al., "Antibody and Antigen Contact Residues Define Epitope and Paratope Size and Structure," The Journal of Immunology, vol. 191: 1428-1435, (2013). [www.jimmunol.org/cgi/doi/10.4049/jimmunol.1203198].
Supasa et al., "Reduced neutralization of SARS-CoV-2 B.1.1.7 variant by convalescent and vaccine sera," Cell, vol. 184: 2201-2211, (2021). Https://doi.org/10.1016/j.cell.2021.02.033].
Tai et al., "Identification of SARS-CoV RBD-targeting monoclonal antibodies with crossreactive or neutralizing activity against SARS-CoV-2," Antiviral Research, Science Direct, vol. 179:1-6, (2020). [www.elsevier.com/locate/antiviral].
Tatham et al., "Lack of Ronapreve (REGN-COV;casirivimab and imdevimab) virological efficacy against the SARS-COV-2 Omicron variant (B.1.1.529) in K18-hACE2 mice," bioRxiv, (2022). [Retrieved from the Internet Feb. 14, 2023 URL:https://www.biorxiv.org/content/10.1101.2022.01.23.477397v1].
Teng et al., "Systemic Effects of Missense Mutations on SARS-CoV-2 Spike Glycoprotein Stability and Receptor Binding Affinity," bioRxiv, vol. 1:1-36, (2020). [https://doi.org/10.1101/2020.05.21.109835].
Tenforde MW, Kim SS, Christopher J. Lindsell, et al. Symptom Duration and Risk Factors for Delayed Return to Usual Health Among Outpatients with Covid-19 in a Multistate Health Care Systems Network—United States, Mar.-Jun. 2020. MMWR Morb Mortal Wkly Rep 2020;60:993-8.
Tian et al., "Potent binding of 2019 novel coronavirus spike protein by a SARS coronavirus-specific human monoclonal antibody," Emerging Microbes & Infections, vol. 17: 647-649, Feb. 17, 2020 (2020).
Tortorici et al., "Ultrapotent human antobodies protect against SARS-CoV-2 challenge via multiple mechanisms," Science, vol. 370:950-957, (2020). [Retrieved from the Internet Apr. 14, 2021: <URL: http://www.science.sciencemag.org/content/sci/370/6519/950.full.pdf>].
Uraki et al., "Characterization and antiviral susceptibility of SARS-COV-2 Omicron BA.2," Nature, Nature Publishing Group UK, London, vol. 607 No. 7917: 119-127, (2022). [Retrieved from the Internet May 16, 2022, ISSN: 0028-0836, DOI: 10.1038/S41586-022-04856-1].
U.S. Appl. No. 16/912,678, Notice of Allowance mailed Jul. 29, 2020.
U.S. Appl. No. 16/996,297, Non-Final Office Action mailed Dec. 8, 2020.
U.S. Appl. No. 17/021,286, Non-Final Office Action mailed Dec. 23, 2020.
U.S. Appl. No. 17/021,286, Notice of Allowance mailed Jan. 22, 2021.
U.S. Appl. No. 16/996,297, Notice of Allowance mailed Jan. 25, 2021.
U.S. Appl. No. 17/337,396, Non-Final Office Action mailed Nov. 14, 2022.
U.S. Appl. No. 17/207,524, Requirement for Restriction/Election mailed Sep. 7, 2022.
U.S. Appl. No. 17/207,524, Non-Final Office Action mailed Nov. 22, 2022.
U.S. Appl. No. 17/207,524, Notice of Allowance mailed Mar. 30, 2023.
U.S. Appl. No. 17/337,396, Non-Final Office Action mailed Apr. 11, 2023.
U.S. Appl. No. 17/337,396, Final Office Action mailed Oct. 4, 2023.
Vandergaast et al., "Development and validation of Immuno-COVTM: a high-throughput clinical assay for detecting antibodies that neutralize SARS-CoV-2," bioRxiv, pp. 1-32, (2020). [https://doi.org/10.1101/2020.05.26.117549].
Van Blargan et al., "A potently neutralizing SARS-CoV-2 antibody inhibits variants of concern by utilizing unique binding residues in a highly conserved epitope," Immunity, vol. 54, No. 10, pp. 2399-2416, (2021).
Walker et al., "Passive immunotherapy of viral infections: 'super-antibodies' enter the fray," Nature Reviews at Immunology, vol. 18: 297-308, (2018). [doi:10.1038/nri.2017.148].
Wan et al., "Human IgG cell neutralizing monoclonal antibodies block SARS-CoV-2 infect," bioRxiv, vol. 1:1-25, (2020). [https://doi.org/10.1101/2020.05.19.104117].
Wan et al., "Human IgG cell neutralizing monoclonal antibodies block SARS-CoV-2 infection," bioRxiv, pp. 1-28, (May 21, 2020). [doi:https://doi.org/10.1101/2020.05.19.104117].
Wang et al., "A human monoclonal antibody blocking SARS-CoV-2 infection," bioRxiv, pp. 1-24, (Mar. 12, 2020). [doi:https://doi.org/10.1101/2020.03.11.987958].
Wang et al., "Importance of Neutralizing Monoclonal Antibodies Targeting Multiple Antigenic Sites on the Middle East Respiratory Syndrome Coronavirus Spike Glycoproein to Avoid Neutralization Escape," Vaccines and Antiviral Agents, Journal of Virology, vol. 92 No. 10: 1-21, ( May 2018). [Retrieved from the Internet May 5, 2020: <URL: http://jvi.asm.org>].
Wang et al., "A human monoclonal antibody blocking SARS-CoV-2 infection," Supplemental information, 1-13 pages (2020).
Wang et al., "A human monoclonal antibody blocking SARS-CoV-2 infection," Nature Communications, 1-7, (2020). [https://doi.org/10.1038/s41467-020-16256-y | www.nature.com/naturecommunications].
Wang et al., "SARS-CoV-2 Neutralizing Antibody Responses Are More Robust in Patients with Severe Disease," bioRxiv, vol. 1:1-9, (2020). [https://doi.org/10.1101/2020.06.13.150250].
Wang et al., "Structural and Functional Basis of SARS-CoV-2 Entry by Using Human ACE2," Cell, vol. 181:894-904, (2020). [https://doi.org/10.1016/j.cell.2020.03.045].

(56) References Cited

OTHER PUBLICATIONS

Wang et al., "E484K mutation in SARS-CoV-2 RBD enahnces binding affinity with hACE2 but reduces interactions with neutralizing antibodies and nanobodies: Binding free energy calculation studies," bioRxiv, pp. 1-18, (2021).

Wang et al., "Evaluation of the efficacy and safety of intravenous remdesivir in adult patients with severe Covid-19: study protocol for a phase 3 randomized, double-blind, placebo-controlled, multicentre trial," Trials, vol. 21:422, 11 pages, (2020). DOI: https://doi.org/10.1186/s13063-020-04352-9.

Watanabe et al., "Site-specific glycan analysis of the SARS-CoV-2 spike," Science, vol.. 1:1-9, (2020). [Retrieved from the Internet May 13, 2020: <URL: http://science.sciencemag.org>; Y. Watanabe et al., Science 10.1126/science.abb9983 (2020)].

Watanabe et al., "Vulnerabilities in coronavirus glycan shields despite extensive glycosylation," Nature Communications, vol. 11:1-10, (2020). [https://doi.org/10.1038/s41467-020-16567-0].

Wec et al., "Broad neutralization of SARS-related viruses by human monoclonal antibodies," Science, vol. 1:1-12, (2020). [Retrieved from the Internet Jun. 17, 2020: <URL: http://science.sciencemag.org>; A. Z. Wec et al., Science 10.1126/science.abc7424 (2020)].

Wec et al., "Broad neutralization of SARS-related viruses by human monoclonal antibodies," Science, vol. 1:1-30, (2020). [science.sciencemag.org/cgi/content/full/science.abc7424/DC1>].

Wec et al., "Broad sarbecovirus neutralizing antibodies define a key site of vulnerability on the SARS-CoV-2 spike protein," bioRxiv, 1-18, (2020). [https://doi.org/10.1101/2020.05.15.096511].

Weinreich et al., "REGN-CoV, a Neutralizing Antibody Cocktail, in Outpatients with Covid-19," The New England Journal of Medicine, vol. 384(3):238-251, (2020). [Retrieved from the Internet: <URL: http://www.nehm.org/doi/pds/10.1056/NEJMao2035002?articleTools=true>].

WHO Director-General's Opening Remarks at the Media Briefing on Covid-19—Mar. 11, 2020. 2020. (Accessed Jun. 9, 2020, at https://www.who.int/dg/speeches/detail/who-director-general-s-opening-remarks-at-the-media-briefing-on-covid-19---11-march-2020.).

Wiegang et al., "The Rise and Fall of SARS-CoV-2 Variants and Ongoing Diversification of Omicron," Viruses, vol. 14 No. 9 : p. 2009, (2022). [URL: http://www.mdpi.com/1999-4915/14/9/20/09>].

WIPO Application No. PCT/US2020/039707, PCT International Search Report and Written Opinion of the International Searching Authority mailed Nov. 9, 2020.

WIPO Application No. PCT/US2021/034187, PCT International Search Report and Written Opinion of the International Searching Authority mailed Nov. 2, 2021.

WIPO Application No. PCT/US2021/035556, PCT International Search Report and Written Opinion of the International Searching Authority mailed Sep. 10, 2021.

WIPO Application No. PCT/US2020/039707, PCT Third Party Observation Communication mailed May 2, 2022.

WIPO Application No. PCT/US2022/018918, PCT International Search Report and Written Opinion of the International Searching Authority mailed Jun. 17, 2022.

WIPO Application No. PCT/US2022/036950, PCT International Search Report and Written Opinion of the International Searching Authority mailed Nov. 29, 2022; 30 pages.

WIPO Application No. PCT/US2022/036950, PCT Invitation to Pay Additional Fees, and Where Applicable, Protest Fee, mailed Oct. 7, 2022.

WIPO Application No. PCT/US2022/049069, PCT Invitation to Pay Additional Fees and, where Applicable, Protest Fee of the International Searching Authority mailed Mar. 2, 2023.

WIPO Application No. PCT/US2022/049069, PCT International Search Report and Written Opinion of the International Searching Authority mailed Apr. 26, 2023.

Wolfel R, Corman VM, Guggemos W, et al. Virological assessment of hospitalized patients with Covid-2019. Nature 2020;581:465-9.

Wrapp et al., "Structural Basis for Potent Neutralization of Betacoronaviruses by Single-Domain Camelid Antibodies," Cell, vol. 181:1-12, (2020). [https://doi.org/10.1016/j.cell.2020.04.031].

Wrapp et al., "Cryo-EM structure of the 2019-nCoV spike in the prefusion conformation," Science, vol. 367:1260-1263, (2020). [Retrieved from the Internet Jul. 29, 2020: <http://science.sciencemag.org>].

Wu et al., "A noncompeting pair of human neutralizing antibodies block Covid-19 virus binding to its receptor ACE2," Science, 1-8, (2020). [Retrieved from the Internet May 14, 2020: <URL: http://science.sciencemag.org>; Y. Wu et al., Science 10.1126/science.abc2241 (2020)].

Wu et al., "Fully human single-domain antibodies against SARS-CoV-2," bioRxiv 2020.03.30.015990; (2020) doi: https://doi.org/10.1101/2020.03.30.015990.

Wu et al., "Identification of Human Single-Domain Antibodies against SARS-CoV-2," Cell Host & Microbe, vol. 27:1-8, (2020). [https://doi.org/10.1016/j.chom.2020.04.023].

Wu et al., "Identification of Human Single-Domain Antibodies against SARS-CoV-2," Cell Host & Microbe, vol. 27:S 891-898, (2020).

Yi et al., "Key residues of the receptor binding motif in the spike protein of SARS-CoV-2 that interact with ACE2 and neutralizing antibodies," Cellular & Molecular Immunology, vol. 17: 621-630, (2020). [www.nature.com/cmi].

Yi et al., "Key residues of the receptor binding motif in the spike protein of SARS-CoV-2 that interact with ACE2 and neutralizing antibodies," Cellular & Molecular Immunology, 1-10, (2020).

Yu et al., "DNA vaccine protection against SARS-CoV-2 in rhesus macaques," Science, 1-11, (2020). [Retrieved from the Internet May 22, 2020: <URL: http://science.sciencemag.org>; J. Yu et al., Science 10.1126/science.abc6284 (2020)].

Yuan et al., "A highly conserved cryptic epitope in the receptor binding domains of SARS-CoV-2 and SARS-CoV," Science, vol. 368:630-633, (2020). [Retrieved from the Internet May 20, 2020: <URL: http://science.sciencemag.org>].

Yuan et al., "Isolation of and Characterization of Neutralizing Antibodies to Covid-19 from a Large Human Naïve scFv Phage Display Library," bioRxiv, 1-15, (2020). [https://doi.org/10.1101/2020.05.19.104281].

Yuan et al., "Structural and functional ramifications of antigenic drift in recent SARS-CoV-2 variants," bioRxiv, pp. 1-50, (2021). [https://doi.org/10.1101.2021.02.16.430500].

Zhang et al., "The use of anti-inflammatory drugs in the treatment of people with severe coronavirus disease 2019 (Covid-19): The Perspectives of clinical immunologists from China," Clinical Immunology at ScienceDirect, vol. 214, (2020). [https://doi.org/10.1016/j.clim.2020.108393].

Zhang et al., "Immunization with the receptor-binding domain of SARS-CoV-2 elicits antibodies cross-neutralizing SARS-CoV-2 and SARS-CoV without antibody-dependent enhancement," bioRxiv, 1-33, (2020). [https://doi.org/10.1101/2020.05.21.107565].

Zhao et al., "Isolation and identification of an scFv antibody against nucleocapsid protein of SARS-CoV," Microbes and Infection 9 (2007) 1026-1033. [doi:10.1016/j.micinf.2007.04.008].

Zheng et al., "Isolation of a human monoclonal antibody specific for the receptor binding domain of SARS-CoV-2 using a competitive phage biopanning strategy," Antibody Therapeutics, vol. 3.2:95-100, (2020). [Retrieved from the Internet May 27, 2020: <URL: https://academic.oup.com/abt/article-abstract/3/2/95/5827124>].

Zheng et al., "Novel antibody epitopes dominate the antigenicity of spike glycoprotein in SARS-CoV-2 compared to SARS-CoV," Cellular & Molecular Immunology, vol. 17:536-538, (2020). [https://doi.org/10.1038/s41423-020-0385-z].

Zhiqiang Ku et al., "Molecular determinants and mechanism for antibody cocktail preventing SARS-CoV-2 escape," Nature Communications, vol. 12(469), 13 pages (2021). [Retrieved from the Internet Apr. 14, 2022 <URL: http://www.nature.com.articles/s41467-020-20789-7.pdf>].

Zhu et al., "Safety, tolerability, and immunogenicity of a recombinant adenovirus type-5 vectored Covid-19 vaccine: a dose-

(56) References Cited

OTHER PUBLICATIONS escalation, open-label, non-randomised, first-in-human trial ," the lancet, vol. 395: 1845-1854, (May 22, 2020). [https://doi.org/10.1016/ 50140-6736(20)31208-3].
Zhou et al., "A pneumonia outbreak associated with a new coronavirus of probable bat origin," Nature, vol. 579: 270-289, (2020). [https://doi.org/10.1038/s41586-020-2012-7].
Zhou et al., "Evidence of escape of SARS-CoV-2 variant B.1.351 from natural and vaccine-induced sera," Cell, vol. 189: 2348-2361, (2021). [https://doi.org/10.1016/j.cell.2021.02.037].
Zost et al., "Potently neutralizing human antibodies that block SARS-CoV-2 receptor binding and protect animals," bioRxiv, 1-35, (2020). [https://doi.org/10.1101/2020.05.22.111005].
Zost et al., "Rapid isolation and profiling of a diverse panel of human monoclonal antibodies targeting the SARS-CoV-2 spike protein," bioRxiv, 1-48, (2020). [https://doi.org/10.1101/2020.05.12.091462].
U.S. Appl. No. 16/912,678, filed Jun. 25, 2020, Issued.
U.S. Appl. No. 17/927,649, filed May 26, 2021, Pending.
PCT/US2021/035556, Jun. 2, 2021, WO 2021/247779, Published.
U.S. Appl. No. 17/337,396, filed Jun. 2, 2021, US2021-095345, Published.
PCT/US2022/018918, Mar. 4m, 2022, WO 2022/187626, Published.
PCT/US2022/049069, Nov. 6, 2022, Pending.
U.S. Appl. No. 17/337,396, Notice of Allowance mailed Jan. 29, 2024.
U.S. Appl. No. 17/863,864, Requirement for Restriction/Election mailed Jun. 28, 2024.
U.S. Appl. No. 63/004,312, filed Apr. 2, 2020, Expired.
U.S. Appl. No. 63/014,687, filed Apr. 23, 2020, Expired.
U.S. Appl. No. 63/025,949, filed May 15, 2020, Expired.
U.S. Appl. No. 63/030,260, filed May 26, 2020, Expired.
U.S. Appl. No. 63/033,198, filed Jun. 1, 2020, Expired.
U.S. Appl. No. 63/034,348, filed Jun. 3, 2020, Expired.
U.S. Appl. No. 63/034,865, filed Jun. 4, 2020, Expired.
U.S. Appl. No. 63/036,956, filed Jun. 9, 2020, Expired.
U.S. Appl. No. 63/038,274, filed Jun. 12, 2020, Expired.
U.S. Appl. No. 63/043,336, filed Jun. 24, 2020, Expired.
U.S. Appl. No. 16/912,678, filed Jun. 25, 2020, U.S. Pat. No. 10,787,501, Issued.
PCT/US2020/039707, Jun. 25, 2020, WO 2021/045836, Expired.
U.S. Appl. No. 63/060,592, filed Aug. 3, 2020, Expired.
U.S. Appl. No. 63/062,961, filed Aug. 7, 2020, Expired.
U.S. Appl. No. 63/065,799, filed Aug. 14, 2020, Expired.
U.S. Appl. No. 16/996,297, filed Aug. 18, 2020, U.S. Pat. No. 10,975,139, Issued.
U.S. Appl. No. 17/021,286, filed Sep. 15, 2020, U.S. Pat. No. 10,954,289, Issued.
U.S. Appl. No. 17/207,524, filed Mar. 19, 2021, U.S. Pat. No. 11,732,030, Issued.
U.S. Appl. No. 63/084,881, filed Sep. 29, 2020, Expired.
U.S. Appl. No. 63/085,066, filed Sep. 29, 2020, Expired.
U.S. Appl. No. 63/089,399, filed Oct. 8, 2020, Expired.
U.S. Appl. No. 63/090,690, filed Oct. 12, 2020, Expired.
U.S. Appl. No. 63/094,133, filed Oct. 20, 2020, Expired.
U.S. Appl. No. 63/093,888, filed Oct. 20, 2020, Expired.
U.S. Appl. No. 63/105,779, filed Oct. 26, 2020, Expired.
U.S. Appl. No. 63/106,696, filed Oct. 28, 2020, Expired.
U.S. Appl. No. 63/112,140, filed Nov. 10, 2020, Expired.
U.S. Appl. No. 63/112,143, filed Nov. 10, 2020, Expired.
U.S. Appl. No. 63/116,773, filed Nov. 20, 2020, Expired.
U.S. Appl. No. 63/119,593, filed Nov. 30, 2020, Expired .
U.S. Appl. No. 63/120,065, filed Dec. 1, 2020, Expired.
U.S. Appl. No. 63/124,980, filed Dec. 14, 2020, Expired.
U.S. Appl. No. 63/131,627, filed Dec. 29, 2020, Expired.
U.S. Appl. No. 63/141,423, filed Jan. 25, 2021, Expired.
U.S. Appl. No. 63/141,952, filed Jan. 26, 2021, Expired.
U.S. Appl. No. 63/141,956, filed Jan. 26, 2021, Expired.
U.S. Appl. No. 63/142,471, filed Jan. 27, 2021, Expired.
U.S. Appl. No. 63/142,472, filed Jan. 27, 2021, Expired.
U.S. Appl. No. 63/144,789, filed Feb. 2, 2021, Expired.
U.S. Appl. No. 63/145,389, filed Feb. 3, 2021, Expired.
U.S. Appl. No. 63/150,978, filed Feb. 18, 2021, Expired.
U.S. Appl. No. 63/157,556, filed Mar. 5, 2021, Expired.
U.S. Appl. No. 63/159,437, filed Mar. 10, 2021, Expired.
U.S. Appl. No. 63/162,504, filed Mar. 17, 2021, Expired.
U.S. Appl. No. 63/162,996, filed Mar. 18, 2021, Expired.
U.S. Appl. No. 63/164,488, filed Mar. 22, 2021, Expired.
U.S. Appl. No. 63/165,654, filed Mar. 24, 2021, Expired.
U.S. Appl. No. 63/166,187, filed Mar. 25, 2021, Expired.
U.S. Appl. No. 63/173,468, filed Apr. 11, 2021, Expired.
U.S. Appl. No. 63/185,301, filed May 6, 2021, Expired.
U.S. Appl. No. 63/186,029, filed May 7, 2021, Expired.
PCT/US2021/034187, May 26, 2021, WO 2021/242815, Published.
U.S. Appl. No. 17/927,649, filed May 26, 2021, US-2024-0043504, Published.
PCT/US2021/035556, Jun. 2, 2021, WO 2021/247779, Expired.
U.S. Appl. No. 17/337,396, filed Jun. 2, 2021, U.S. Pat. No. 11,999,777, Issued.
U.S. Appl. No. 63/221,846, filed Jul. 14, 2021, Expired.
U.S. Appl. No. 63/245,020, filed Sep. 16, 2021, Expired.
U.S. Appl. No. 63/286,514, filed Dec. 6, 2021, Expired.
U.S. Appl. No. 63/289,126, filed Dec. 13, 2021, Expired.
U.S. Appl. No. 63/289,419, filed Dec. 14, 2021, Expired.
U.S. Appl. No. 63/291,328, filed Dec. 17, 2021, Expired.
U.S. Appl. No. 63/301,002, filed Jan. 19, 2022, Expired.
U.S. Appl. No. 63/306,909, filed Feb. 4, 2022, Expired.
PCT/US2022/018918, Mar. 4, 2022, WO 2022/187626, Expired.
U.S. Appl. No. 63/354,632, filed Jun. 22, 2022, Expired.
PCT/US2022/036950, Jul. 13, 2022, WO 2023/287875, Published.
U.S. Appl. No. 17/863,864, filed Jul. 13, 2022, US-2023-0125469, Published.
U.S. Appl. No. 63/276,658, filed Nov. 7, 2021, Expired.
U.S. Appl. No. 63/278,459, filed Nov. 11, 2021, Expired.
U.S. Appl. No. 63/291,226, filed Dec. 17, 2021, Expired.
U.S. Appl. No. 63/312,182, filed Feb. 21, 2022, Expired.
U.S. Appl. No. 63/327,292, filed Apr. 4, 2022, Expired.
U.S. Appl. No. 63/416,457, filed Oct. 14, 2022, Expired.
U.S. Appl. No. 63/416,879, filed Oct. 17, 2022, Expired.
PCT/US2022/049069, Nov. 6, 2022, WO 2023/081434, Expired.
Chen et al., "Enhancement and destruction of antibody function by somatic mutation unequal occurrence is controlled by V gene combinatorial associations," The EMBO Journal, vol. 14 (No. 12): 2784-2794, (1995).
Koenig et al., "Mutational landscape of antibody variable domains reveals a switch modulating the interdomain conformational dynamics and antigen binding," PNAS, E486-E495, (2017). [www.pnas.org/cgi/doi/10.1073/pnas.1613231114].
U.S. Appl. No. 17/863,864, Non-Final Office Action mailed Oct. 9, 2024.

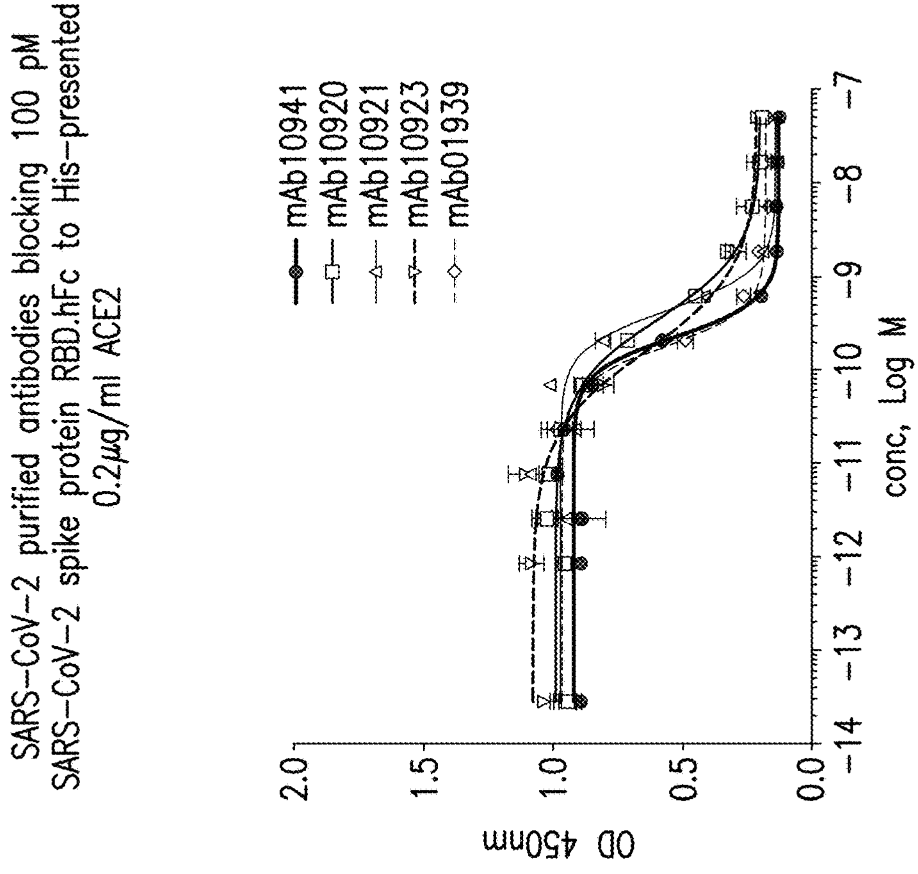
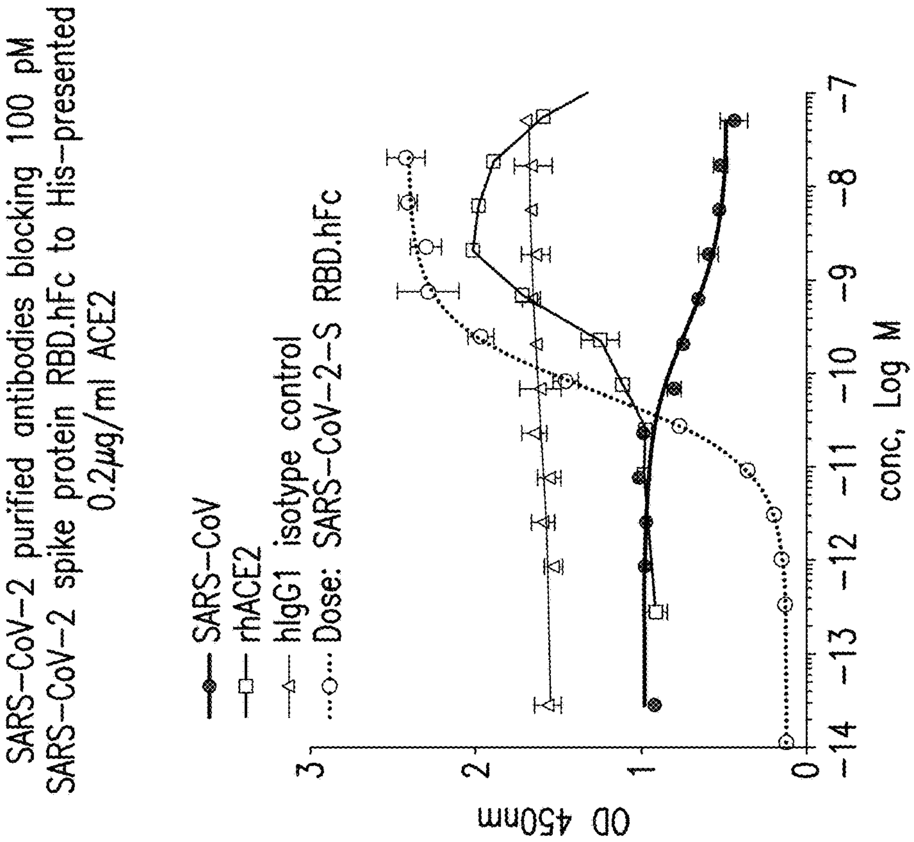
FIG. 2

Pre-mix Competition between anti-SARS-CoV-2 mAbs

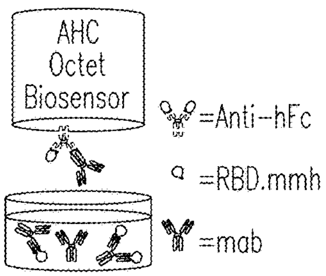

Bi-directional competition

Partial competition

No competition

Self-self competition

| Phase I | Measure mAb1 captured | Phase II measure IgG blocking mAb (nm) | Phase III, Response of 100 nM SARS CoV-2 RBD-MMH complexed 600 nM of mAb2 binding site (nm) Pre-mix Competition | | | | | | | | |
|---|---|---|---|---|---|---|---|---|---|---|---|
| mAb | nm captured mAb | nm mAb bound | mAb10977 | mAb10989 | mAb10933 | mAb10964 | mAb10984 | mAb10986 | mAb10954 | mAb10934 | mAb10987 |
| mAb10977 | 1.69±0.05 | 0.27+.08 | 0.00 | −0.03 | −0.01 | −0.04 | −0.02 | 0.46 | 0.33 | 0.00 | 0.96 |
| mAb10989 | 1.95±0.03 | | 0.07 | 0.00 | −0.04 | −0.03 | −0.04 | 0.03 | −0.01 | −0.07 | 0.30 |
| mAb10933 | 1.73±0.06 | | 0.10 | 0.04 | 0.00 | −0.01 | −0.01 | 0.04 | 0.00 | 0.25 | 1.52 |
| mAb10964 | 1.90±0.03 | | 0.04 | 0.02 | 0.04 | 0.00 | −0.01 | 0.05 | 0.04 | 0.38 | 1.37 |
| mAb10984 | 1.88±0.04 | | 0.11 | 0.03 | 0.15 | 0.02 | 0.00 | 0.08 | 0.06 | 0.55 | 1.13 |
| mAb10986 | 1.73±0.04 | | 1.09 | 0.14 | 0.32 | −0.03 | −0.06 | 0.00 | −0.04 | 0.86 | 1.21 |
| mAb10954 | 1.83±0.04 | | 0.85 | 0.03 | 0.53 | −0.01 | −0.04 | 0.02 | 0.00 | 1.12 | 1.16 |
| mAb10934 | 1.78±0.06 | | 0.07 | 0.05 | 0.03 | −0.03 | 0.65 | 1.23 | 1.60 | 0.00 | 0.31 |
| mAb10987 | 1.83±0.04 | | 1.29 | 0.06 | 0.76 | 0.85 | 1.03 | 1.05 | 1.07 | −0.08 | 0.00 |

FIG. 11

| | SARS-CoV-2 RBD: mAb10933 : mAb10987 complex |
|---|---|
| **Data collection and processing** | |
| Magnification | 105,000 |
| Voltage (kV) | 300 |
| Electron exposure ($e^-/Å^2$) | 40 |
| Defocus range (μm) | 1.6–3.0 |
| Pixel size (Å) | 0.85 |
| Symmetry imposed | C1 |
| Initial number of particles | 989,553 |
| Final selected particles | 61,707 |
| Map resolution (Å) | 3.9 |
| FSC threshold | 0.143 |
| **Refinement** | |
| Map sharpening B factor ($Å^2$) | −122 |
| Model composition (# of atoms) | 7979 |
| Model vs. map correlation coefficient | 0.64 |
| **R.m.s. deviations** | |
| Bond lengths (Å) | 0.02 |
| Bond angles (°) | 1.12 |
| **Validation** | |
| MolProbity score | 2.7 |
| Rotameric outliers (%) | 1.0 |
| **Ramachandran plot** | |
| Favored (%) | 83.0 |
| Allowed (%) | 16.3 |
| Disallowed (%) | 0.7 |

FIG. 14

ANTI-SARS-CoV-2-SPIKE GLYCOPROTEIN ANTIBODIES AND ANTIGEN-BINDING FRAGMENTS

CROSS-REFERENCE TO RELATED APPLICATIONS

This application is a continuation of U.S. application Ser. No. 17/207,524, filed Mar. 19, 2021, which is a continuation of U.S. application Ser. No. 17/021,286, filed Sep. 15, 2020, which is a continuation of U.S. application Ser. No. 16/996,297, filed Aug. 18, 2020, which is a continuation of U.S. application Ser. No. 16/912,678, filed Jun. 25, 2020, which claims the benefit under 35 USC § 119(e) of U.S. Provisional Application Nos.: 63/004,312, filed Apr. 2, 2020; 63/014,687, filed Apr. 23, 2020; 63/025,949, filed May 15, 2020; and 63/034,865, filed Jun. 4, 2020, each of which is incorporated herein by reference in its entirety for all purposes.

SEQUENCE LISTING

This application incorporates by reference a computer readable Sequence Listing in ST.26 XML format, titled 10753US05_Sequence, created on Jun. 29, 2023, and containing 1,279,099 bytes.

FIELD OF THE INVENTION

The present invention relates to antibodies and antigen-binding fragments that bind specifically to coronavirus spike proteins and methods for treating or preventing coronavirus infections with said antibodies and fragments.

BACKGROUND OF THE INVENTION

Newly identified viruses, such as coronaviruses, can be difficult to treat because they are not sufficiently characterized. The emergence of these newly identified viruses highlights the need for the development of novel antiviral strategies. Severe acute respiratory syndrome coronavirus 2 (SARS-CoV-2) is a newly-emergent coronavirus which causes a severe acute respiratory disease, COVID-19. SARS-CoV-2 was first identified from an outbreak in Wuhan, China and as of Mar. 20, 2020, the World Health Organization has reported 209,839 confirmed cases in 168 countries, areas, or territories, resulting in 8,778 deaths. Clinical features of COVID-19 include fever, dry cough, and fatigue, and the disease can cause respiratory failure resulting in death.

Thus far, there has been no vaccine or therapeutic agent to prevent or treat SARS-CoV-2 infection. In view of the continuing threat to human health, there is an urgent need for preventive and therapeutic antiviral therapies for SARS-CoV-2 control. Because this virus uses its spike glycoprotein for interaction with the cellular receptor ACE2 and the serine protease TMPRSS2 for entry into a target cell, this spike protein represents an attractive target for antibody therapeutics. In particular, fully human antibodies that specifically bind to the SARS-CoV-2-Spike protein (SARS-CoV-2-S) with high affinity and that inhibit virus infectivity could be important in the prevention and treatment of COVID-19.

SUMMARY OF THE INVENTION

There is a need for neutralizing therapeutic anti-SARS-CoV-2-Spike protein (SARS-CoV-2-S) antibodies and their use for treating or preventing viral infection. The present disclosure addresses this need, in part, by providing human anti-SARS-CoV-2-S antibodies, such as those of Table 4, and combinations thereof including, for example, combinations with other therapeutics (e.g., anti-inflammatory agents, antimalarial agents, antiviral agents, or other antibodies or antigen-binding fragments), and methods of use thereof for treating viral infections.

The present disclosure provides neutralizing human antigen-binding proteins that specifically bind to SARS-CoV-2-S, for example, antibodies or antigen-binding fragments thereof.

In one aspect, the present disclosure provides an isolated recombinant antibody or antigen-binding fragment thereof that specifically binds to a coronavirus spike protein (CoV-S), wherein the antibody has one or more of the following characteristics: (a) binds to CoV-S with an $EC_{50}$ of less than about $10^{-9}$ M; (b) demonstrates an increase in survival in a coronavirus-infected animal after administration to said coronavirus-infected animal, as compared to a comparable coronavirus-infected animal without said administration; and/or (c) comprises three heavy chain complementarity determining regions (CDRs) (CDR-H1, CDR-H2, and CDR-H3) contained within a heavy chain variable region (HCVR) comprising an amino acid sequence having at least about 90% sequence identity to an HCVR of Table 4; and three light chain CDRs (CDR-L1, CDR-L2, and CDR-L3) contained within a light chain variable region (LCVR) comprising an amino acid sequence having at least about 90% sequence identity to an LCVR Table 4.

In some embodiments, the antibody or antigen-binding fragment comprises: (a) an immunoglobulin heavy chain variable region comprising the CDR-H1, CDR-H2, and CDR-H3 of an antibody of Table 4; and/or (b) an immunoglobulin light chain variable region comprising the CDR-L1, CDR-L2, and CDR-L3 of an antibody of Table 4.

In some embodiments, the antibody or antigen-binding fragment comprises: (a) a heavy chain immunoglobulin variable region comprising an amino acid sequence having at least 90% amino acid sequence identity to an HCVR sequence of Table 4; and/or (b) a light chain immunoglobulin variable region comprising an amino acid sequence having at least 90% amino acid sequence identity to an LCVR sequence of Table 4.

In some embodiments, the antibody or antigen-binding fragment comprises the CDR-H1, CDR-H2, CDR-H3, CDR-L1, CDR-L2, and CDR-L3 of a single antibody of Table 4. In some embodiments, the antibody or antigen-binding fragment comprises an immunoglobulin that comprises the HCVR and the LCVR of a single antibody of Table 4.

In one aspect, the present disclosure provides an antigen-binding protein that competes with any one of the antibodies or antigen-binding fragments discussed above or herein for binding to CoV-S.

In one aspect, the present disclosure provides an antigen-binding protein that binds to the same epitope as, or to an overlapping epitope on, CoV-S as any one of the antibodies or antigen-binding fragments discussed above or herein.

In any of the various embodiments, the antibody or antigen-binding fragment may be multispecific.

In any of the various embodiments, the antibody or antigen-binding fragment may comprise one or more of the following properties: a) inhibits growth of coronavirus; b) binds to the surface of a coronavirus; c) limits spread of coronavirus infection of cells in vitro; and d) protects mice engineered to express the human ACE2 or TMPRSS2 protein from death and/or weight loss caused by coronavirus infection.

In any of the various embodiments, CoV-S is SARS-CoV-2-S.

In one aspect, the present disclosure provides a complex comprising an antibody or antigen-binding fragment as discussed above or herein bound to a CoV-S polypeptide. In some embodiments, the CoV-S is SARS-CoV-2-S.

In one aspect, the present disclosure provides a method for making an antibody or antigen-binding fragment as discussed above or herein, comprising: (a) introducing into a host cell one or more polynucleotides encoding said antibody or antigen-binding fragment; (b) culturing the host cell under conditions favorable to expression of the one or more polynucleotides; and (c) optionally, isolating the antibody or antigen-binding fragment from the host cell and/or a medium in which the host cell is grown. In some embodiments, the host cell is a Chinese hamster ovary cell.

In one aspect, the present disclosure provides an antibody or antigen-binding fragment that is a product of the method discussed above.

In one aspect, the present disclosure provides a polypeptide comprising: (a) CDR-H1, CDR-H2, and CDR-H3 of an HCVR domain of an antibody or antigen-binding fragment that comprises an HCVR amino acid sequence set forth in Table 4; or (b) CDR-L1, CDR-L2, and CDR-L3 of an LCVR domain of an immunoglobulin chain that comprises an LCVR amino acid sequence set forth in Table 4.

In one aspect, the present disclosure provides a polynucleotide encoding the polypeptide discussed above.

In one aspect, the present disclosure provides a vector comprising the polynucleotide discussed above.

In one aspect, the present disclosure provides a host cell comprising the antibody or antigen-binding fragment or polypeptide or polynucleotide or vector as discussed above or herein.

In one aspect, the present disclosure provides a composition or kit comprising the antibody or antigen-binding fragment discussed above or herein in association with a further therapeutic agent.

In one aspect, the present disclosure provides a pharmaceutical composition comprising the antigen-binding protein, antibody or antigen-binding fragment discussed above or herein and a pharmaceutically acceptable carrier and, optionally, a further therapeutic agent. In some embodiments, the further therapeutic agent is an anti-viral drug or a vaccine. In some embodiments, the further therapeutic agent is selected from the group consisting of: an anti-inflammatory agent, an antimalarial agent, an antibody or antigen-binding fragment thereof that specifically binds TMPRSS2, and an antibody or antigen-binding fragment thereof that specifically binds to CoV-S. In some cases, the antimalarial agent is chloroquine or hydroxychloroquine. In some cases, the anti-inflammatory agent is an antibody, such as sarilumab, tocilizumab, or gimsilumab. In some embodiments, the further therapeutic agent is a second antibody or antigen-binding fragment comprising HCDR1, HCDR2, HCDR3, LCDR1, LCDR2, and LCDR3 sequences of Table 4.

In one aspect, the present disclosure provides a vessel or injection device comprising the antigen-binding protein, antibody or antigen-binding fragment, or composition as discussed above or herein.

In one aspect, the present disclosure provides a method for treating or preventing infection with a coronavirus, in a subject in need thereof, comprising administering a therapeutically effective amount of an antigen-binding protein, antibody or antigen-binding fragment as discussed above or herein. In some embodiments, the coronavirus is selected from the group consisting of SARS-CoV-2, SARS-CoV, and MERS-CoV.

In some embodiments of the method for treating or preventing infection with a coronavirus, the subject is administered one or more further therapeutic agents. In some cases, the one or more further therapeutic agents is an anti-viral drug or a vaccine. In some cases, the one or more further therapeutic agents is selected from the group consisting of: an anti-inflammatory agent, an antimalarial agent, an antibody or antigen-binding fragment thereof that specifically binds TMPRSS2, and an antibody or antigen-binding fragment thereof that specifically binds to CoV-S. In some cases, the antimalarial agent is chloroquine or hydroxychloroquine. In some cases, the anti-inflammatory agent is an antibody, such as for example, sarilumab, tocililumab, or gimsilumab. In some embodiments, the further therapeutic agent is a second antibody or antigen-binding fragment comprising HCDR1, HCDR2, HCDR3, LCDR1, LCDR2, and LCDR3 sequences of Table 4. Other antibodies that can be used alone or in combination with one another or with one or more of the antibodies disclosed herein for use in the context of the methods of the present disclosure include, e.g., LY-CoV555 (Eli Lilly); 47D11 (Wang et al Nature Communications Article No. 2251); B38, H4, B5 and/or H2 (Wu et al., 10.1126/science.abc2241 (2020); STI-1499 (Sorrento Therapeutics); VIR-7831 and VIR-7832 (Vir Biotherapeutics).

In one aspect, the present disclosure provides a method for administering an antibody or antigen-binding fragment discussed above or herein into the body of a subject comprising injecting the antibody or antigen-binding fragment into the body of the subject. In some embodiments, the antibody or antigen-binding fragment is injected into the body of the subject subcutaneously, intravenously or intramuscularly.

In any of the various embodiments discussed above or herein, the antibody or antigen-binding fragment comprises a VH3-66 or Vk1-33 variable domain sequence.

In one aspect, the present disclosure provides an isolated antibody or antigen-binding fragment thereof that binds a SARS-CoV-2 spike protein comprising the amino acid sequence set forth in SEQ ID NO: 832, wherein said isolated antibody or antigen-binding fragment comprises three heavy chain complementarity determining regions (CDRs) (HCDR1, HCDR2 and HCDR3) contained within a heavy chain variable region (HCVR) comprising the amino acid sequence set forth in SEQ ID NO: 202, and three light chain complementarity determining regions (CDRs) (LCDR1, LCDR2 and LCDR3) contained within a light chain variable region (LCVR) comprising the amino acid sequence set forth in SEQ ID NO: 210.

In some embodiments, the HCDR1 comprises the amino acid sequence set forth in SEQ ID NO: 204, the HCDR2 comprises the amino acid sequence set forth in SEQ ID NO: 206, the HCDR3 comprises the amino acid sequence set forth in SEQ ID NO: 208, the LCDR1 comprises the amino acid sequence set forth in SEQ ID NO: 212, the LCDR2 comprises the amino acid sequence AAS, and the LCDR3 comprises the amino acid sequence set forth in SEQ ID NO: 214. In some embodiments, the isolated antibody or antigen-binding fragment thereof comprises an HCVR that comprises the amino acid sequence set forth in SEQ ID NO: 202. In some embodiments, the isolated antibody or antigen-binding fragment thereof comprises an LCVR that comprises the amino acid sequence set forth in SEQ ID NO: 210. In some embodiments, the isolated antibody or antigen-binding fragment thereof comprises an HCVR that comprises the amino acid sequence set forth in SEQ ID NO: 202 and an LCVR that comprises the amino acid sequence set forth in SEQ ID NO: 210.

In one aspect, the present disclosure provides an isolated antibody that binds a SARS-CoV-2 spike protein comprising the amino acid sequence set forth in SEQ ID NO: 832, wherein said isolated antibody comprises an immunoglobulin constant region, three heavy chain complementarity determining regions (CDRs) (HCDR1, HCDR2 and HCDR3) contained within a heavy chain variable region (HCVR) comprising the amino acid sequence set forth in SEQ ID NO: 202, and three light chain complementarity determining regions (CDRs) (LCDR1, LCDR2 and LCDR3) contained within a light chain variable region (LCVR) comprising the amino acid sequence set forth in SEQ ID NO: 210.

In some embodiments, the HCDR1 comprises the amino acid sequence set forth in SEQ ID NO: 204, the HCDR2 comprises the amino acid sequence set forth in SEQ ID NO: 206, the HCDR3 comprises the amino acid sequence set forth in SEQ ID NO: 208, the LCDR1 comprises the amino acid sequence set forth in SEQ ID NO: 212, the LCDR2 comprises the amino acid sequence AAS, and the LCDR3 comprises the amino acid sequence set forth in SEQ ID NO: 214. In some embodiments, the isolated antibody comprises an HCVR that comprises the amino acid sequence set forth in SEQ ID NO: 202 and an LCVR that comprises the amino acid sequence set forth in SEQ ID NO: 210. In some embodiments, the isolated antibody comprises a heavy chain comprising the amino acid sequence set forth in SEQ ID NO: 216 and a light chain comprising the amino acid sequence set forth in SEQ ID NO: 218. In some cases, the immunoglobulin constant region is an IgG1 constant region. In some cases, the isolated antibody is a recombinant antibody. In some cases, the isolated antibody is multispecific.

In one aspect, the present disclosure provides a pharmaceutical composition comprising an isolated antibody as discussed above or herein, and a pharmaceutically acceptable carrier or diluent.

In some embodiments, the pharmaceutical composition further comprises a second therapeutic agent. In some cases, the second therapeutic agent is selected from the group consisting of: a second antibody, or an antigen-binding fragment thereof, that binds a SARS-CoV-2 spike protein comprising the amino acid sequence set forth in SEQ ID NO: 832, an anti-inflammatory agent, an antimalarial agent, and an antibody or antigen-binding fragment thereof that binds TMPRSS2.

In some embodiments, the second therapeutic agent is a second antibody, or an antigen-binding fragment thereof, that binds a SARS-COV-2 spike protein comprising the amino acid sequence set forth in SEQ ID NO: 832. In some cases, the second antibody or antigen-binding fragment thereof comprises three heavy chain CDRs (HCDR1, HCDR2 and HCDR3) contained within an HCVR comprising the amino acid sequence set forth in SEQ ID NO: 640, and three light chain CDRs (LCDR1, LCDR2 and LCDR3) contained within an LCVR comprising the amino acid sequence set forth in SEQ ID NO: 646. In some cases, the second antibody or antigen-binding fragment thereof comprises: HCDR1, comprising the amino acid sequence set forth in SEQ ID NO: 642; HCDR2, comprising the amino acid sequence set forth in SEQ ID NO: 499; HCDR3, comprising the amino acid sequence set forth in SEQ ID NO: 644; LCDR1, comprising the amino acid sequence set forth in SEQ ID NO: 648; LCDR2, comprising the amino acid sequence DVS; and LCDR3, comprising the amino acid sequence set forth in SEQ ID NO: 652. In some cases, the second antibody or antigen-binding fragment thereof comprises an HCVR comprising the amino acid sequence set forth in SEQ ID NO: 640 and an LCVR comprising the amino acid sequence set forth in SEQ ID NO: 646. In some cases, the second antibody or antigen-binding fragment thereof comprises a heavy chain comprising the amino acid sequence set forth in SEQ ID NO: 654 and a light chain comprising the amino acid sequence set forth in SEQ ID NO: 656.

In one aspect, the present disclosure provides an isolated antibody or antigen-binding fragment thereof that binds a SARS-CoV-2 spike protein comprising the amino acid sequence set forth in SEQ ID NO: 832, wherein said isolated antibody or antigen-binding fragment comprises three heavy chain complementarity determining regions (CDRs) (HCDR1, HCDR2 and HCDR3) contained within a heavy chain variable region (HCVR) comprising the amino acid sequence set forth in SEQ ID NO: 640, and three light chain complementarity determining regions (CDRs) (LCDR1, LCDR2 and LCDR3) contained within a light chain variable region (LCVR) comprising the amino acid sequence set forth in SEQ ID NO: 646.

In some embodiments, the HCDR1 comprises the amino acid sequence set forth in SEQ ID NO: 642, the HCDR2 comprises the amino acid sequence set forth in SEQ ID NO: 499, the HCDR3 comprises the amino acid sequence set forth in SEQ ID NO: 644, the LCDR1 comprises the amino acid sequence set forth in SEQ ID NO: 648, the LCDR2 comprises the amino acid sequence DVS, and the LCDR3 comprises the amino acid sequence set forth in SEQ ID NO: 652. In some embodiments, the isolated antibody or antigen-binding fragment thereof comprises an HCVR that comprises an amino acid sequence set forth in SEQ ID NO: 640. In some embodiments, the isolated antibody or antigen-binding fragment thereof comprises an LCVR that comprises an amino acid sequence set forth in SEQ ID NO: 646. In some embodiments, the isolated antibody or antigen-binding fragment thereof comprises an HCVR that comprises an amino acid sequence set forth in SEQ ID NO: 640 and an LCVR that comprises an amino acid sequence set forth in SEQ ID NO: 646.

In one aspect, the present disclosure provides an isolated antibody that binds a SARS-CoV-2 spike protein comprising the amino acid sequence set forth in SEQ ID NO: 832, wherein said isolated antibody comprises an immunoglobulin constant region, three heavy chain complementarity determining regions (CDRs) (HCDR1, HCDR2 and HCDR3) contained within a heavy chain variable region (HCVR) comprising the amino acid sequence set forth in SEQ ID NO: 640, and three light chain complementarity determining regions (CDRs) (LCDR1, LCDR2 and LCDR3) contained within a light chain variable region (LCVR) comprising the amino acid sequence set forth in SEQ ID NO: 646.

In some embodiments, the HCDR1 comprises the amino acid sequence set forth in SEQ ID NO: 642, the HCDR2 comprises the amino acid sequence set forth in SEQ ID NO: 499, the HCDR3 comprises the amino acid sequence set forth in SEQ ID NO: 644, the LCDR1 comprises the amino acid sequence set forth in SEQ ID NO: 648, the LCDR2 comprises the amino acid sequence DVS, and the LCDR3 comprises the amino acid sequence set forth in SEQ ID NO:

652. In some embodiments, the isolated antibody comprises an HCVR that comprises the amino acid sequence set forth in SEQ ID NO: 640 and an LCVR that comprises the amino acid sequence set forth in SEQ ID NO: 646. In some embodiments, the isolated antibody comprises a heavy chain comprising the amino acid sequence set forth in SEQ ID NO: 654 and a light chain comprising the amino acid sequence set forth in SEQ ID NO: 656. In some cases, the immunoglobulin constant region is an IgG1 constant region. In some cases, the isolated antibody is a recombinant antibody. In some cases, the isolated antibody is multispecific.

In one aspect, the present disclosure provides a pharmaceutical composition comprising an isolated antibody, as discussed above or herein, and a pharmaceutically acceptable carrier or diluent.

In some embodiments, the pharmaceutical composition further comprising a second therapeutic agent. In some cases, the second therapeutic agent is selected from the group consisting of: a second antibody, or an antigen-binding fragment thereof, that binds a SARS-CoV-2 spike protein comprising the amino acid sequence set forth in SEQ ID NO: 832, an anti-inflammatory agent, an antimalarial agent, and an antibody or antigen-binding fragment thereof that binds TMPRSS2.

In some embodiments, the second therapeutic agent is a second antibody, or an antigen-binding fragment thereof, that binds a SARS-COV-2 spike protein comprising the amino acid sequence set forth in SEQ ID NO: 832. In some cases, the second antibody or antigen-binding fragment thereof comprises three heavy chain CDRs (HCDR1, HCDR2 and HCDR3) contained within an HCVR comprising the amino acid sequence set forth in SEQ ID NO: 202, and three light chain CDRs (LCDR1, LCDR2 and LCDR3) contained within an LCVR comprising the amino acid sequence set forth in SEQ ID NO: 210. In some cases, the second antibody or antigen-binding fragment thereof comprises: HCDR1, comprising the amino acid sequence set forth in SEQ ID NO: 204; HCDR2, comprising the amino acid sequence set forth in SEQ ID NO: 206; HCDR3, comprising the amino acid sequence set forth in SEQ ID NO: 208 LCDR1, comprising the amino acid sequence set forth in SEQ ID NO: 212; LCDR2, comprising the amino acid sequence AAS; and LCDR3, comprising the amino acid sequence set forth in SEQ ID NO: 214. In some cases, the second antibody or antigen-binding fragment thereof comprises an HCVR comprising the amino acid sequence set forth in SEQ ID NO: 202 and an LCVR comprising the amino acid sequence set forth in SEQ ID NO: 210. In some cases, the second antibody or antigen-binding fragment thereof comprises a heavy chain comprising the amino acid sequence set forth in SEQ ID NO: 216 and a light chain comprising the amino acid sequence set forth in SEQ ID NO: 218.

In various embodiments, any of the features or components of embodiments discussed above or herein may be combined, and such combinations are encompassed within the scope of the present disclosure. Any specific value discussed above or herein may be combined with another related value discussed above or herein to recite a range with the values representing the upper and lower ends of the range, and such ranges are encompassed within the scope of the present disclosure.

BRIEF DESCRIPTION OF THE FIGURES

FIG. 2 shows ELISA blocking data for selected anti-SARS-CoV-2-S antibodies against SARS-CoV-2 spike protein, preventing the spike protein from binding to its receptor ACE2.

FIG. 10A displays the neutralization potency of anti-SARS-CoV-2 Spike mAbs. Serial dilutions of anti-Spike mAbs, IgG1 isotype control, and recombinant dimeric ACE2 (hACE2.hFc) were added with pVSV-SARS-CoV-2-S-mNeon to Vero cells and mNeon expression was measured 24 hours post-infection as a read-out for virus infectivity. Data is graphed as percent neutralization relative to virus only infection control. FIG. 10B displays neutralization potency of individual anti-Spike mAbs and combinations of mAbs against SARS-CoV-2-S virus in VeroE6 cells.

FIG. 11 displays epitope bin analysis from a matrix of pre-mix binding assays for different anti-SARS-CoV-2 mAbs. Epitope binning was performed against nine anti-SARS-CoV-2 mAb as described. There were three phases (I, II, and III) for each graph. In phase I anti-SARS-CoV-2 mAb (20 ug/ml) was loaded to the anti-human Fc probe. In phase II human IgG1 blocking mAb solution (100 ug/ml). In phase III a solution of 100 nM SARS CoV-2 RBD-MMH pre-mix complex of each 600 nM anti-SARS-CoV-2 mAb binding site flowed over the mAb capture probe.

FIG. 13A displays a 3.9 Å cryoEM map of mAb10933+RBD+mAb10987 complex, shaded according to the chains in the refined model of FIG. 13B.RBD, mAb10933 heavy and light chains, and mAb10987 heavy and light chain are identified.

FIG. 14 displays cryoEM data statistics. Data collection and refinement statistics are reported for the mAb10987+mAb10933+SARS-CoV-2 RBD complex structure shown in FIG. 13A and FIG. 13B.

DETAILED DESCRIPTION OF THE INVENTION

Figure 1:
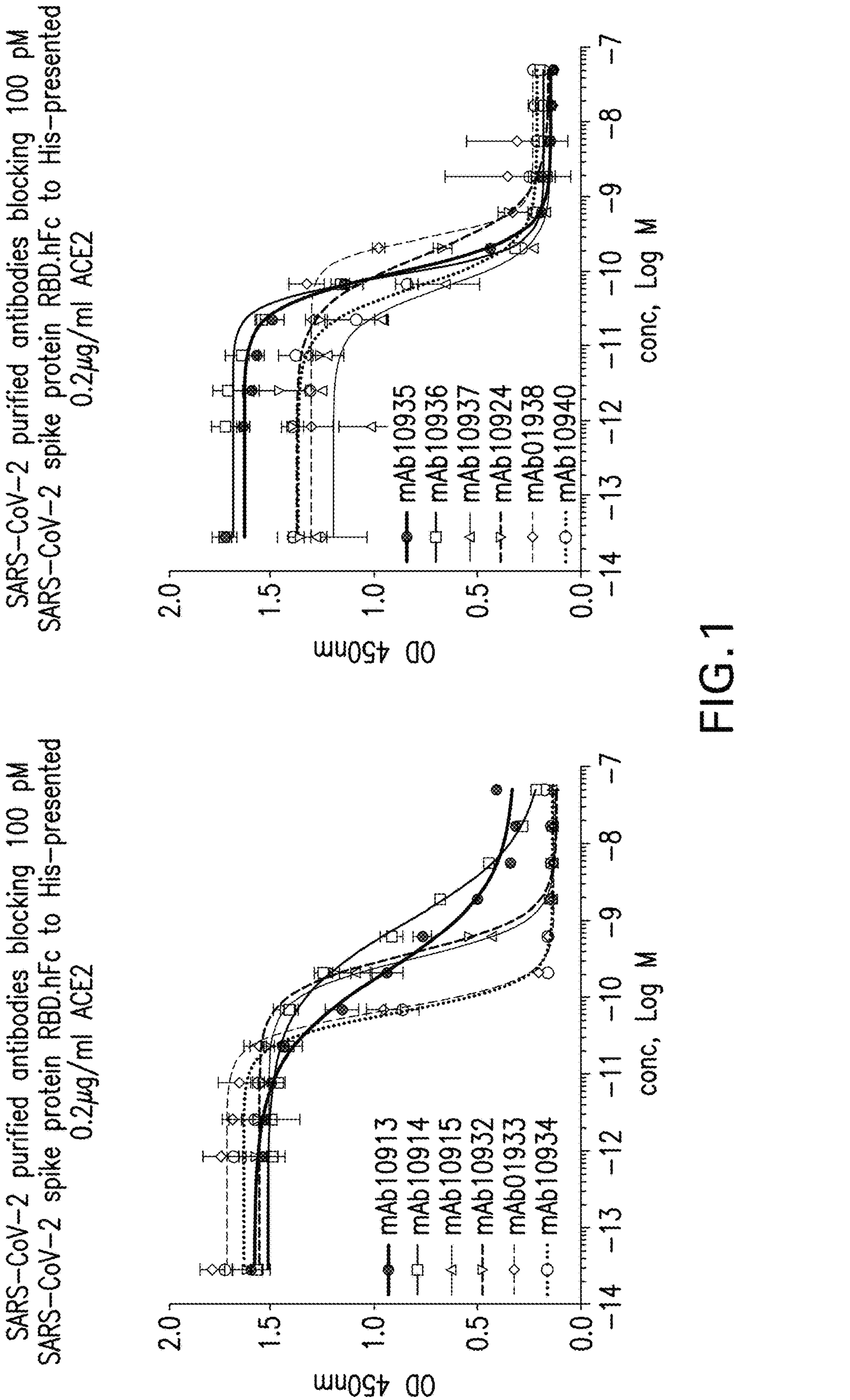
FIG. 1 shows ELISA blocking data for selected anti-SARS-CoV-2-S antibodies against SARS-CoV-2 spike protein, preventing the spike protein from binding to its receptor ACE2.
Figure 3:
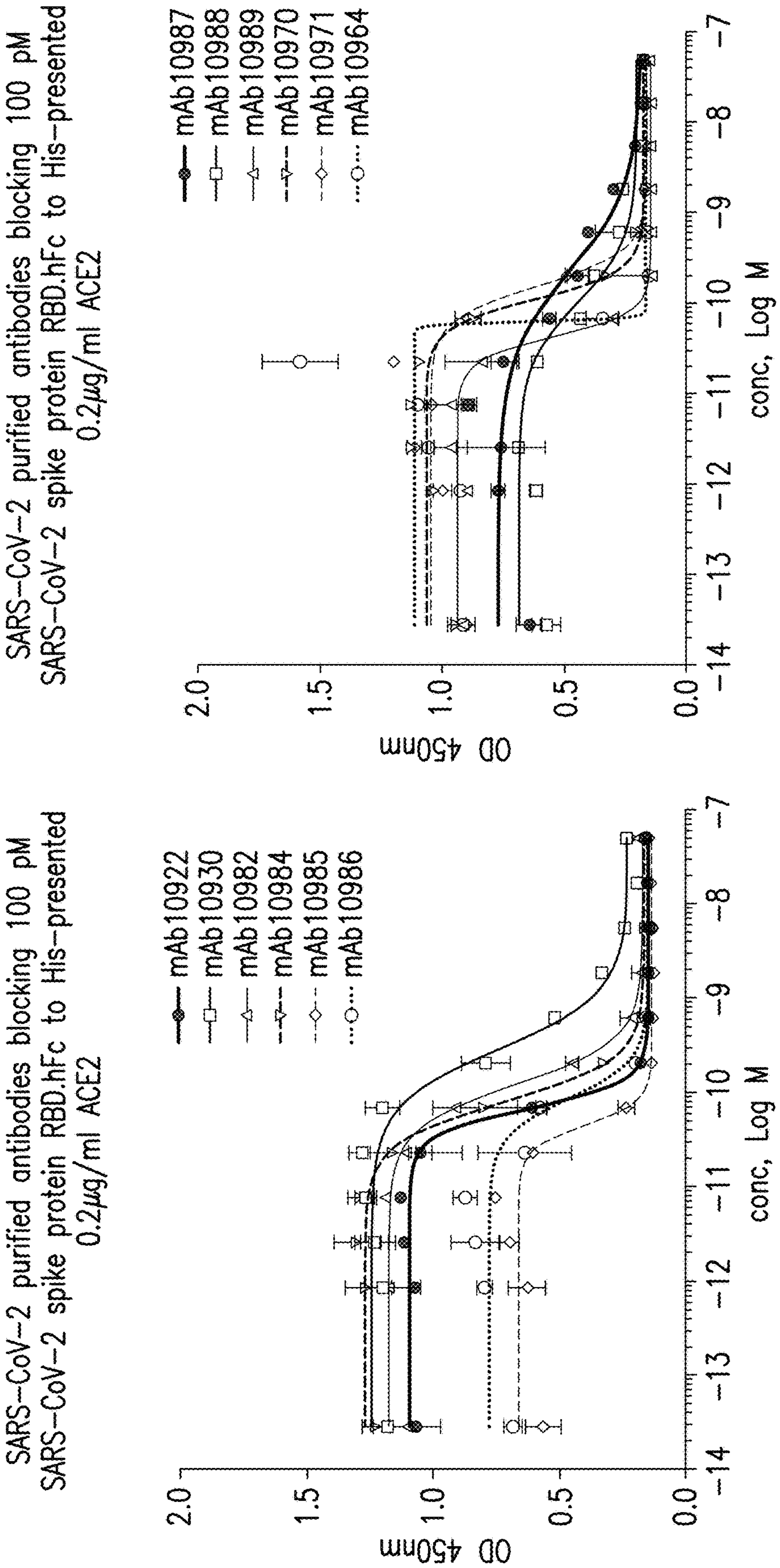
FIG. 3 shows ELISA blocking data for selected anti-SARS-CoV-2-S antibodies against SARS-CoV-2 spike protein, preventing the spike protein from binding to its receptor ACE2.
Figure 4:
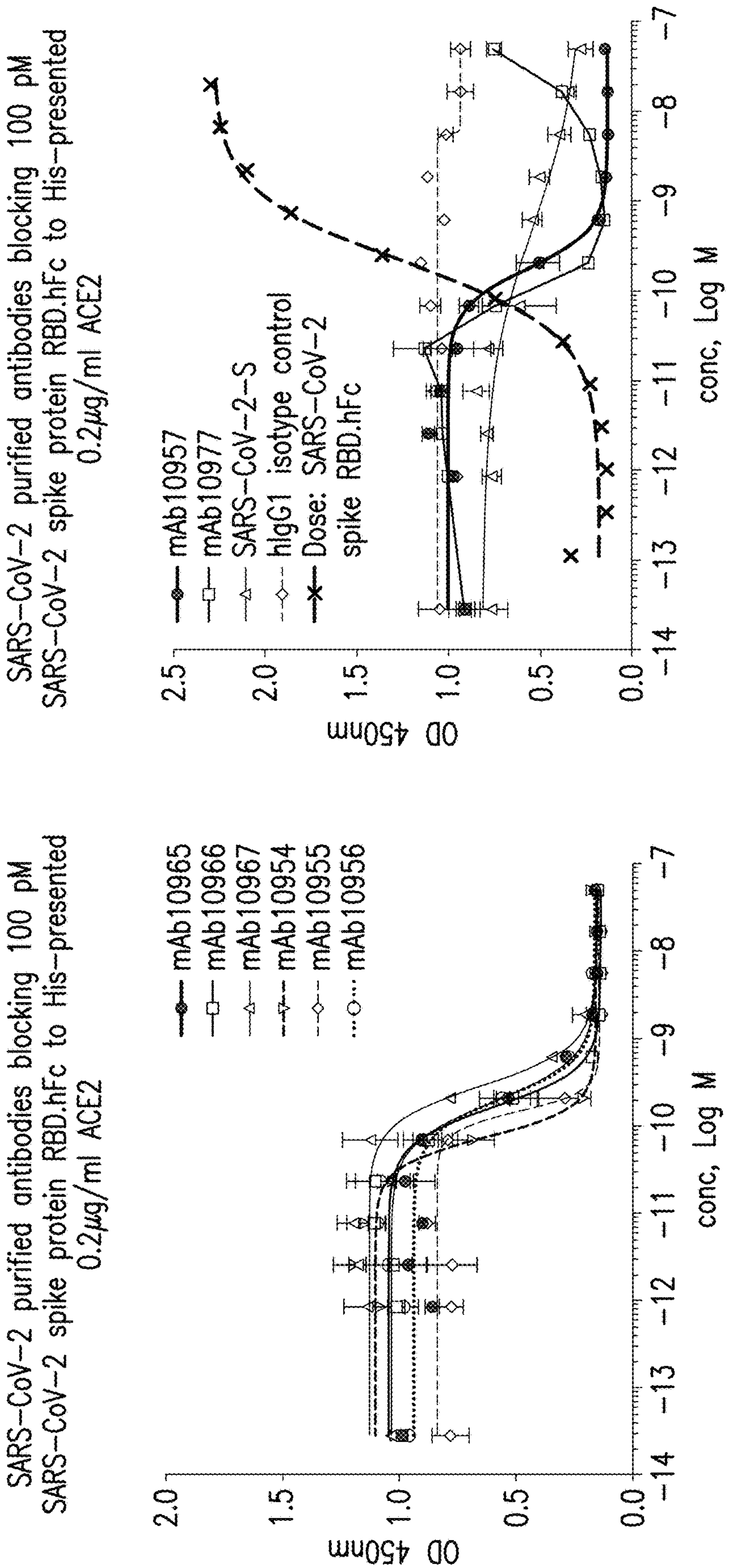
FIG. 4 shows ELISA blocking data for selected anti-SARS-CoV-2-S antibodies against SARS-CoV-2 spike protein, preventing the spike protein from binding to its receptor ACE2.
Figure 5:
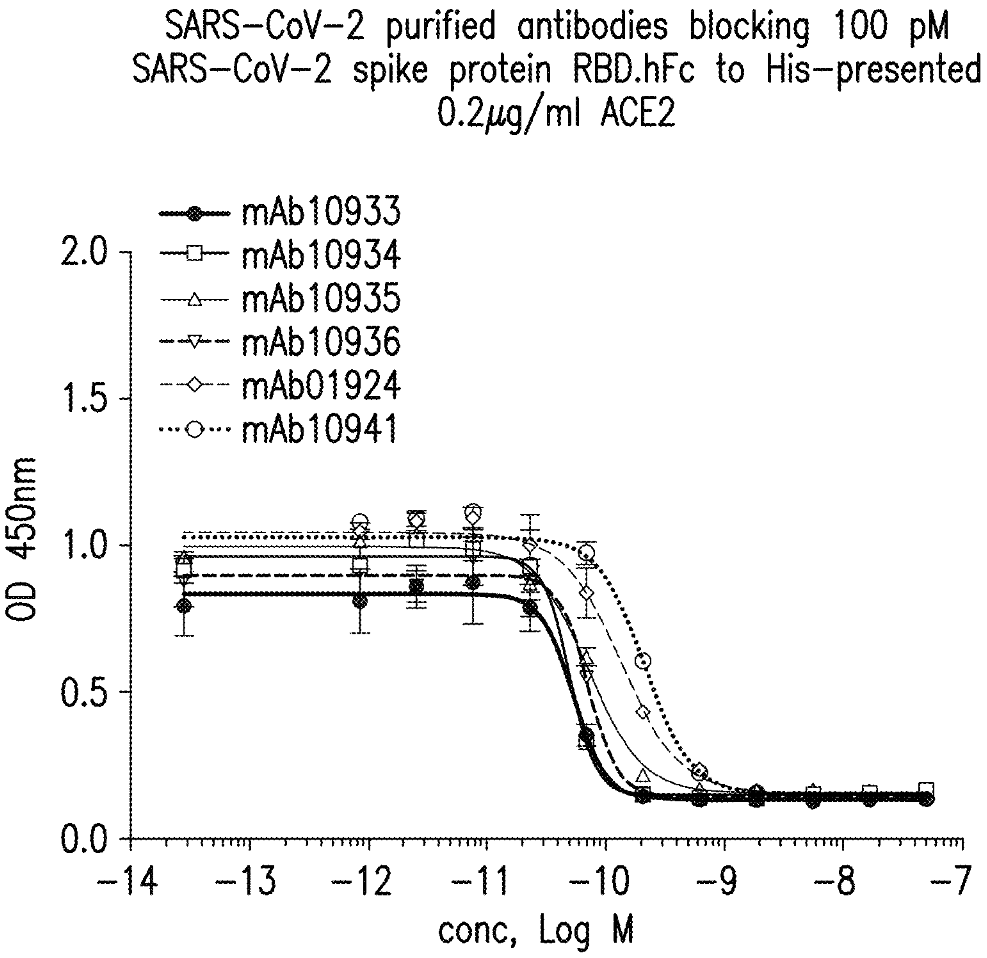
FIG. 5 shows ELISA blocking data for selected anti-SARS-CoV-2-S antibodies against SARS-CoV-2 spike protein, preventing the spike protein from binding to its receptor ACE2.
Figure 6:
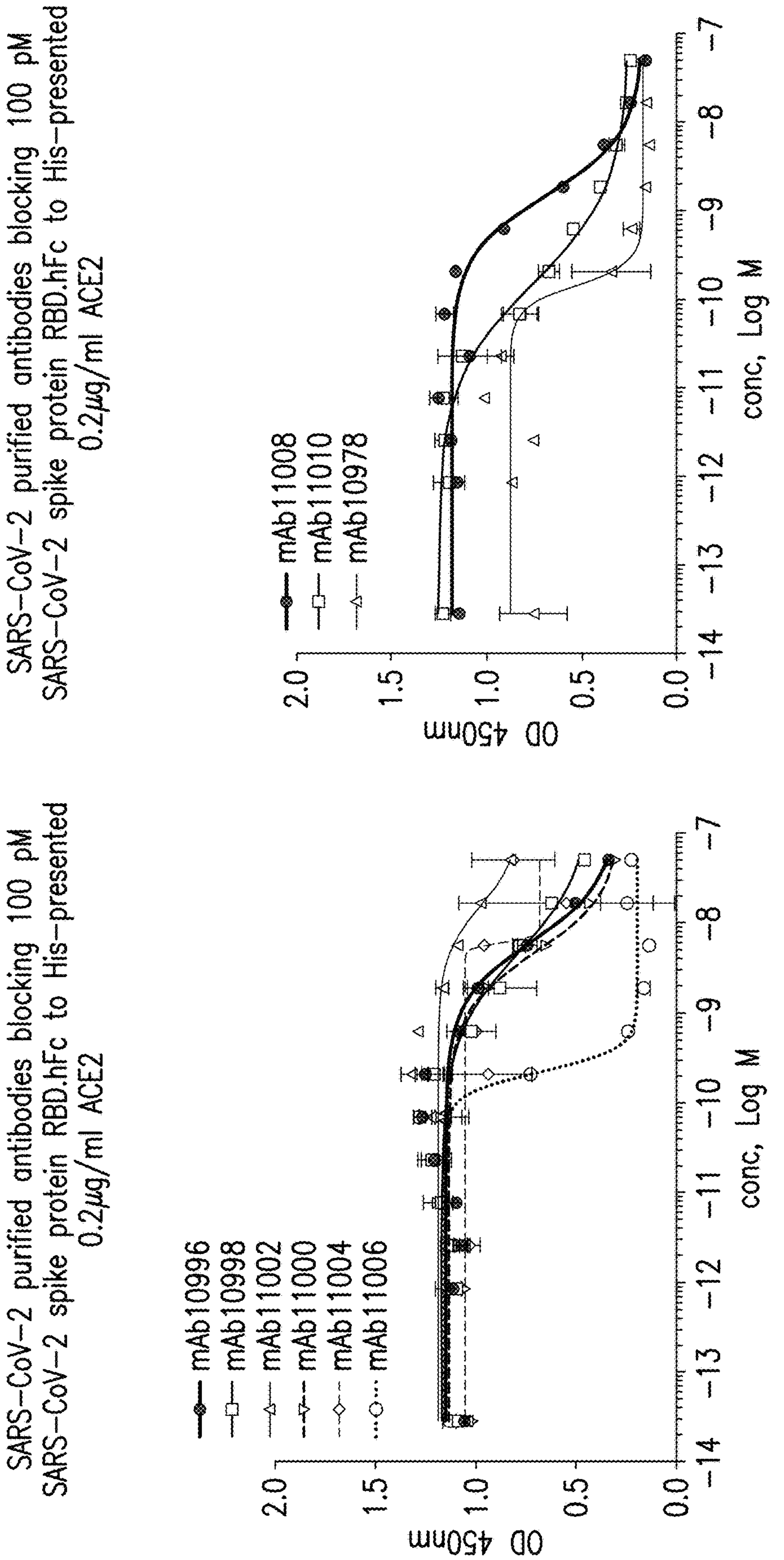
FIG. 6 shows ELISA blocking data for selected anti-SARS-CoV-2-S antibodies against SARS-CoV-2 spike protein, preventing the spike protein from binding to its receptor ACE2.
Figure 7:
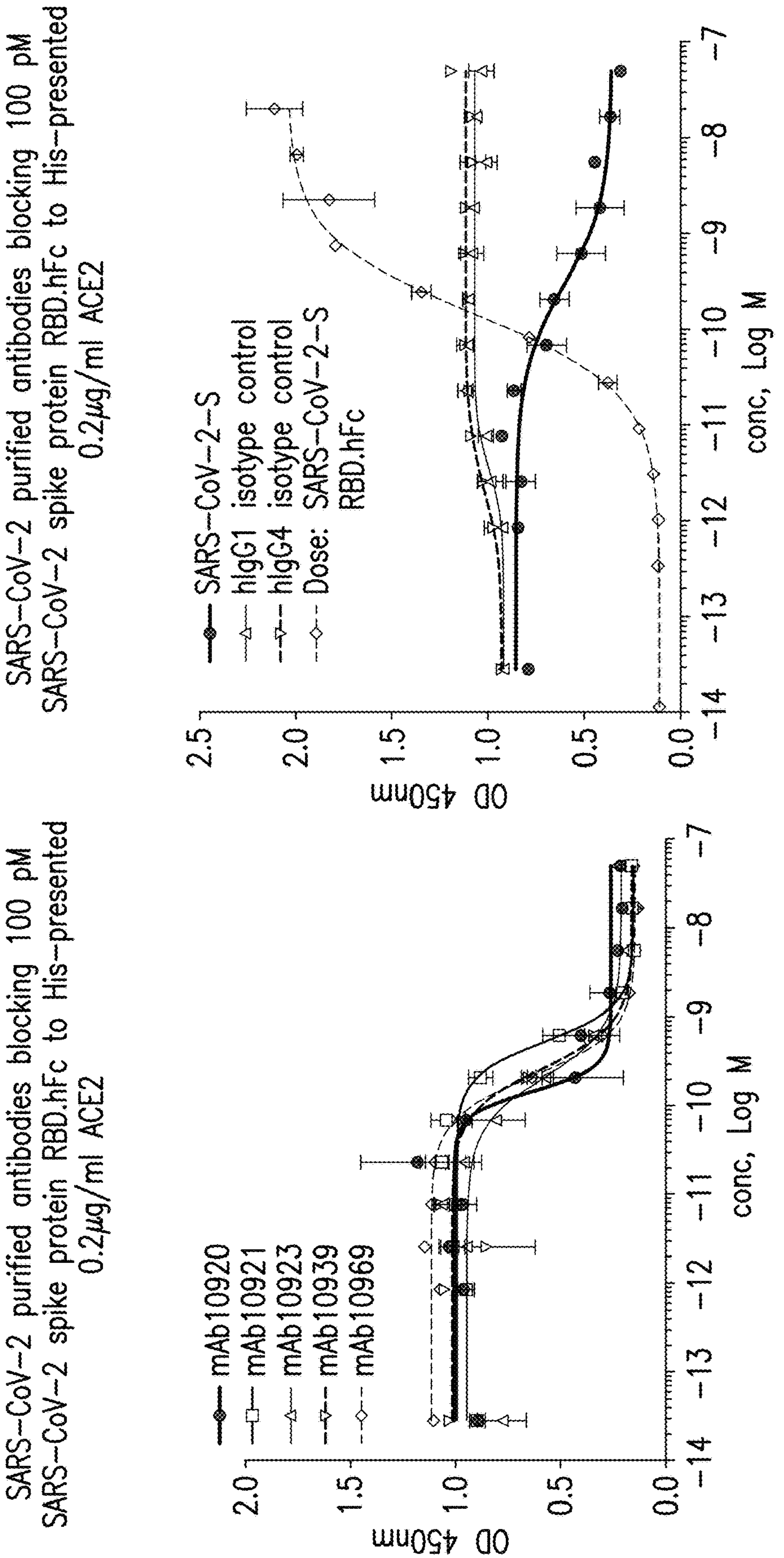
FIG. 7 shows ELISA blocking data for selected anti-SARS-CoV-2-S antibodies against SARS-CoV-2 spike protein, preventing the spike protein from binding to its receptor ACE2.
Figure 8:
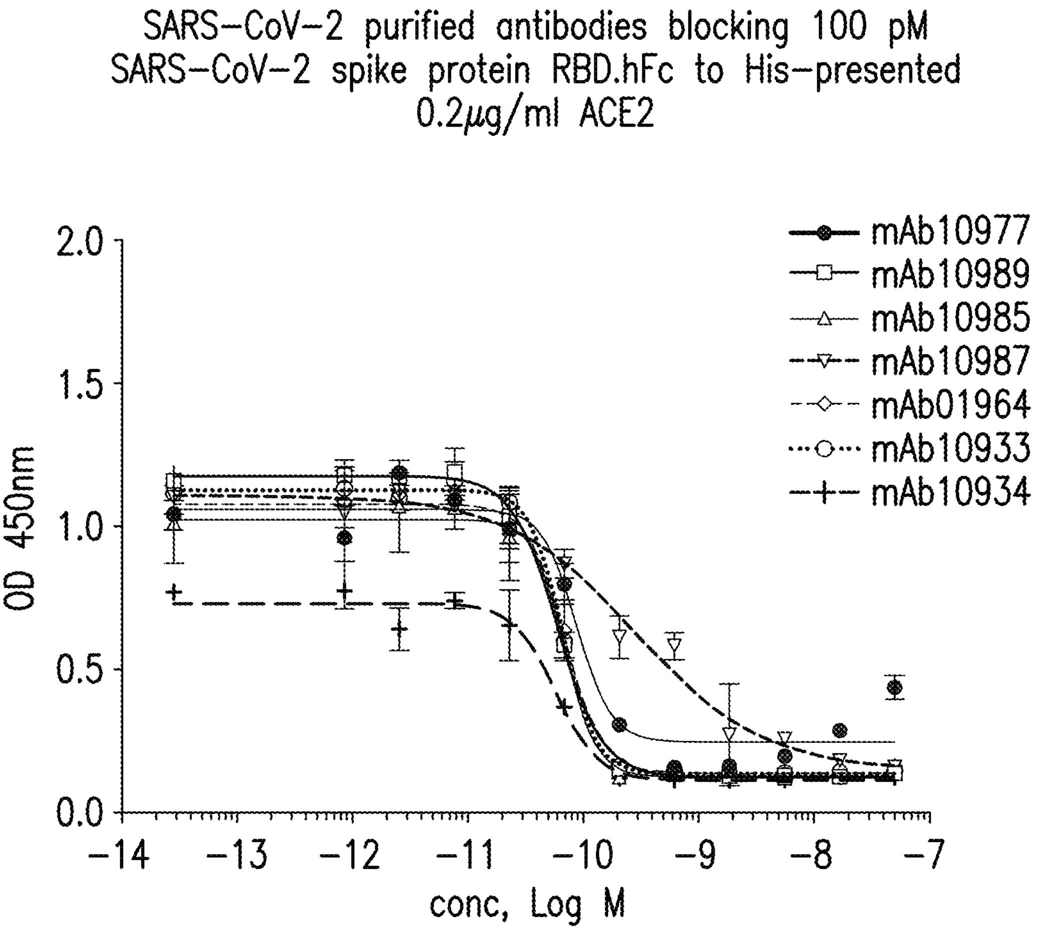
FIG. 8 shows ELISA blocking data for selected anti-SARS-CoV-2-S antibodies against SARS-CoV-2 spike protein, preventing the spike protein from binding to its receptor ACE2.
Figure 9A:
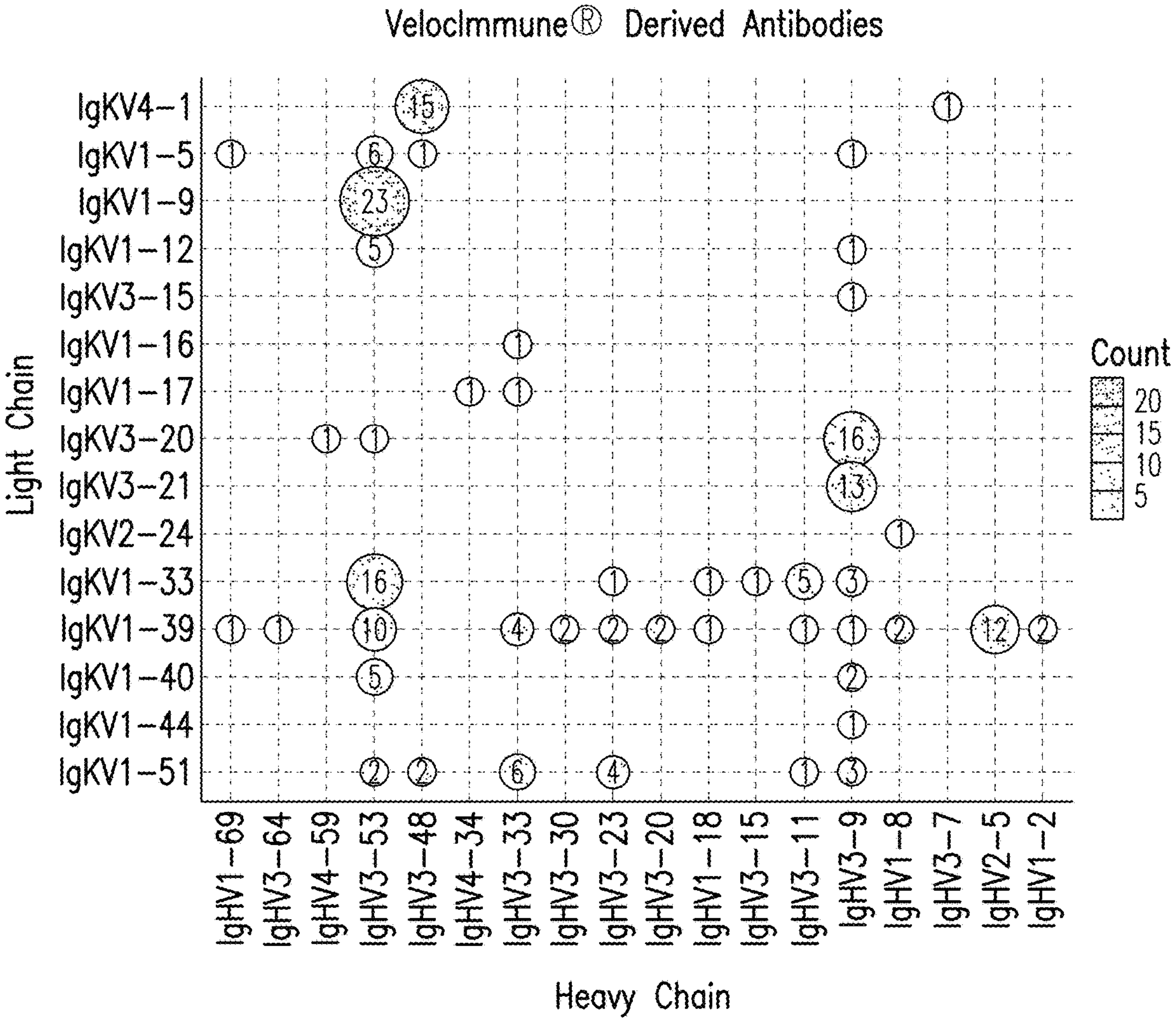
FIG. 9A and FIG. 9B display V gene frequencies for paired Heavy (X-axis) and Light (Y-axis) chains of isolated neutralizing antibodies to SARS-CoV-2 for Veloclmmune® mice (FIG. 9A; N=185) and convalescent human donors (FIG. 9B; N=68). The shade and size of the circle corresponds to the number of Heavy and Light chain pairs present in the repertoires of isolated neutralizing antibodies. Neutralization is defined as >70% with 1:4 dilution of antibody (~2 μg/ml) in VSV pseudoparticle neutralization assay.
Figure 9B:
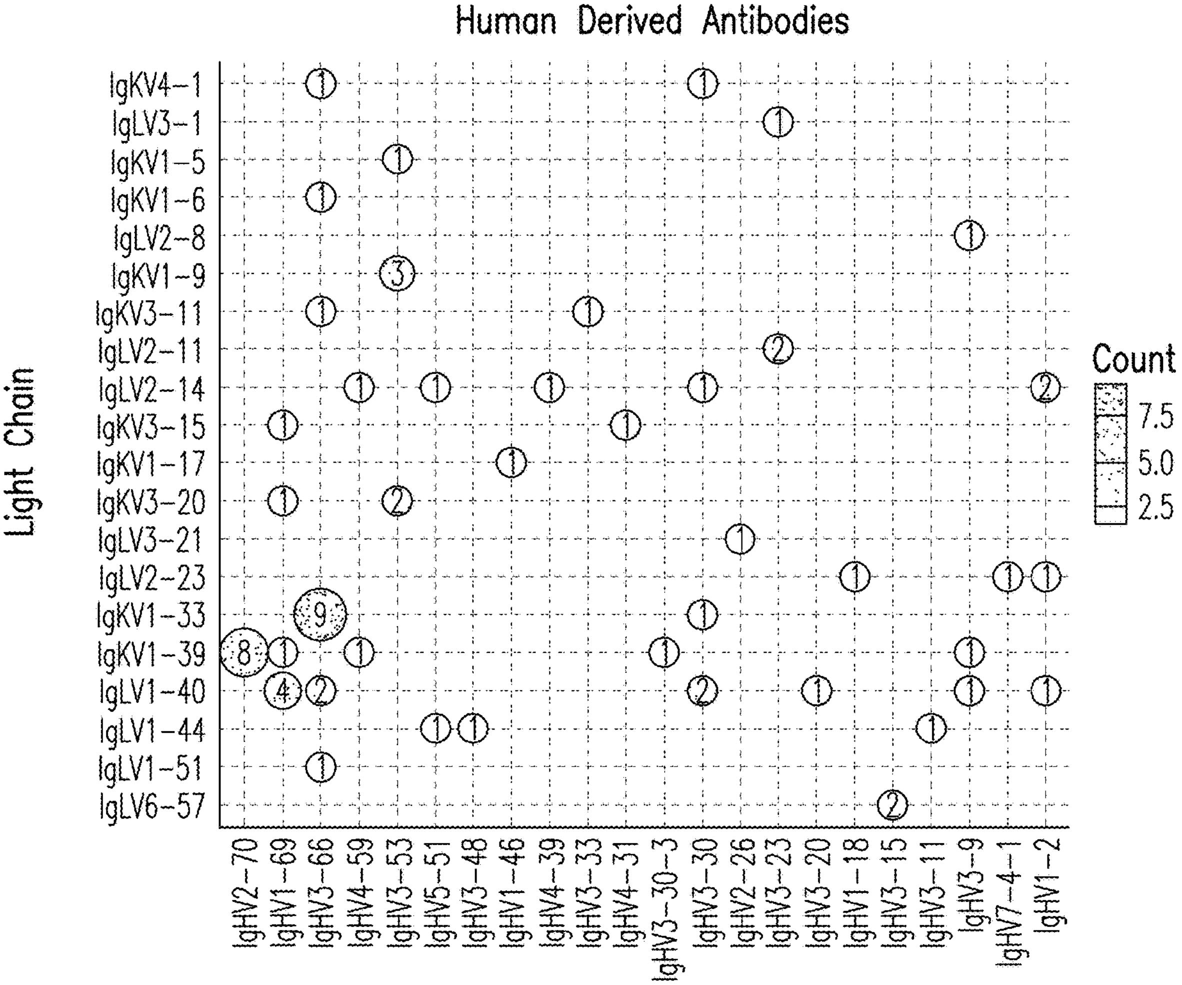

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, preferred methods and materials are now described. All publications mentioned herein are incorporated herein by reference in their entirety.

The term "coronavirus" or "CoV" refers to any virus of the coronavirus family, including but not limited to SARS-CoV-2, MERS-CoV, and SARS-CoV. SARS-CoV-2 refers to the newly-emerged coronavirus which was identified as the cause of a serious outbreak starting in Wuhan, China, and which is rapidly spreading to other areas of the globe. SARS-CoV-2 has also been known as 2019-nCoV and Wuhan coronavirus. It binds via the viral spike protein to human host cell receptor angiotensin-converting enzyme 2 (ACE2). The spike protein also binds to and is cleaved by TMPRSS2, which activates the spike protein for membrane fusion of the virus.

The term "CoV-S", also called "S" or "S protein" refers to the spike protein of a coronavirus, and can refer to specific S proteins such as SARS-CoV-2-S, MERS-CoV S, and SARS-CoV S. The SARS-CoV-2-Spike protein is a 1273 amino acid type I membrane glycoprotein which assembles into trimers that constitute the spikes or peplomers on the surface of the enveloped coronavirus particle. The protein has two essential functions, host receptor binding and membrane fusion, which are attributed to the N-terminal (S1) and C-terminal (S2) halves of the S protein. CoV-S binds to its cognate receptor via a receptor binding domain (RBD) present in the S1 subunit. The amino acid sequence of full-length SARS-CoV-2 spike protein is exemplified by the amino acid sequence provided in SEQ ID NO: 832. The term "CoV-S" includes protein variants of CoV spike protein isolated from different CoV isolates as well as recombinant CoV spike protein or a fragment thereof. The term also encompasses CoV spike protein or a fragment thereof coupled to, for example, a histidine tag, mouse or human Fc, or a signal sequence such as ROR1.

The term "coronavirus infection" or "CoV infection," as used herein, refers to infection with a coronavirus such as SARS-CoV-2, MERS-CoV, or SARS-CoV. The term includes coronavirus respiratory tract infections, often in the lower respiratory tract. Symptoms can include high fever, dry cough, shortness of breath, pneumonia, gastro-intestinal symptoms such as diarrhea, organ failure (kidney failure and renal dysfunction), septic shock, and death in severe cases.

Viruses

The present invention includes methods for treating or preventing a viral infection in a subject. The term "virus" includes any virus whose infection in the body of a subject is treatable or preventable by administration of an anti-CoV-S antibody or antigen-binding fragment thereof (e.g., wherein infectivity of the virus is at least partially dependent on CoV-S). In an embodiment of the invention, a "virus" is any virus that expresses spike protein (e.g., CoV-S). The term "virus" also includes a CoV-S-dependent respiratory virus which is a virus that infects the respiratory tissue of a subject (e.g., upper and/or lower respiratory tract, trachea, bronchi, lungs) and is treatable or preventable by administration of an anti-CoV-S antibody or antigen-binding fragment thereof. For example, in an embodiment of the invention, virus includes coronavirus, SARS-CoV-2 (severe acute respiratory syndrome coronavirus 2), SARS-CoV (severe acute respiratory syndrome coronavirus), and MERS-CoV (Middle East respiratory syndrome (MERS) coronavirus). Coronaviruses can include the genera of alphacoronaviruses, betacoronaviruses, gammacoronaviruses, and deltacoronaviruses. In some embodiments, the antibodies or antigen-binding fragments provided herein can bind to and/or neutralize an alphacoronavirus, a betacoronavirus, a gammacoronavirus, and/or a deltacoronavirus. In certain embodiments, this binding and/or neutralization can be specific for a particular genus of coronavirus or for a particular subgroup of a genus. "Viral infection" refers to the invasion and multiplication of a virus in the body of a subject.

Coronavirus virions are spherical with diameters of approximately 125 nm. The most prominent feature of coronaviruses is the club-shape spike projections emanating from the surface of the virion. These spikes are a defining feature of the virion and give them the appearance of a solar corona, prompting the name, coronaviruses. Within the envelope of the virion is the nucleocapsid. Coronaviruses have helically symmetrical nucleocapsids, which is uncommon among positive-sense RNA viruses, but far more common for negative-sense RNA viruses. SARS-CoV-2, MERS-CoV, and SARS-CoV belong to the coronavirus family. The initial attachment of the virion to the host cell is initiated by interactions between the S protein and its receptor. The sites of receptor binding domains (RBD) within the S1 region of a coronavirus S protein vary depending on the virus, with some having the RBD at the C-terminus of S1. The S-protein/receptor interaction is the primary determinant for a coronavirus to infect a host species and also governs the tissue tropism of the virus. Many coronaviruses utilize peptidases as their cellular receptor. Following receptor binding, the virus must next gain access to the host cell cytosol. This is generally accomplished by acid-dependent proteolytic cleavage of S protein by a cathepsin, TMPRRS2 or another protease, followed by fusion of the viral and cellular membranes.

Anti-CoV-S Antibodies and Antigen-Binding Fragments

The present invention provides antigen-binding proteins, such as antibodies and antigen-binding fragments thereof, that specifically bind to CoV spike protein or an antigenic fragment thereof.

The term "antibody", as used herein, refers to immunoglobulin molecules comprising four polypeptide chains, two heavy chains (HCs) and two light chains (LCs) inter-connected by disulfide bonds (i.e., "full antibody molecules"), as well as multimers thereof (e.g. IgM). Exemplary antibodies include, for example, those listed in Table 4. Each heavy chain comprises a heavy chain variable region ("HCVR" or "$V_H$") and a heavy chain constant region (comprised of domains $C_H1$, $C_H2$ and $C_H3$). Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ comprises three CDRs and four FRs, arranged from amino-terminus to carboxy-terminus in the following order: FR1, CDR1, FR2, CDR2, FR3, CDR3, FR4. Heavy chain CDRs can also be referred to as HCDRs or CDR-Hs, and numbered as described above (e.g., HCDR1, HCDR2, and HCDR3 or CDR-H1, CDR-H2, and CDR-H3) Likewise, light chain CDRs can be referred to as LCDRs or CDR-Ls, and numbered LCDR1, LCDR2, and LCDR3, or CDR-L1, CDR-L2, and CDR-L3. In certain embodiments of the invention, the FRs of the antibody (or antigen binding fragment thereof) are identical to the human germline sequences, or are naturally or artificially modified. Exemplary human germline sequences include, but are not limited to, VH3-66 and Vk1-33. Thus, the present disclosure provides anti-CoV-S antibodies or antigen-binding fragments thereof (e.g., anti-SARS-CoV-2-S antibodies or antigen-binding fragments thereof) comprising HCDR and LCDR sequences of Table 4 within a VH3-66 or Vk1-33 variable heavy chain or light chain region. The present disclosure further provides anti-CoV-S antibodies or antigen-binding fragments thereof (e.g., anti-SARS-CoV-2-S antibodies or antigen-binding fragments thereof) comprising HCDR and LCDR sequences of Table 4 within a combination of a light chain selected from IgKV4-1, IgKV 1-5, IgKV1-9, IgKV1-12, IgKV3-15, IgKV1-16, IgKV1-17, IgKV3-20, IgLV3-21, IgKV2-24, IgKV1-33, IgKV1-39, IgLV1-40, IgLV1-44, IgLV1-51, IgLV3-1, IgKV1-6, IgLV2-8, IgKV3-11, IgLV2-11, IgLV2-14, IgLV2-23, or IgLV6-57, and a heavy chain selected from IgHV1-69, IgHV3-64, IgHV4-59, IgHV3-53, IgHV3-48, IgHV4-34, IgHV3-33, IgHV3-30, IgHV3-23, IgHV3-20, IgHV1-18, IgHV3-15, IgHV3-11, IgHV3-9, IgHV1-8, IgHV3-7, IgHV2-5, IgHV1-2, IgHV2-70, IgHV3-66, IgHV5-51, IgHV1-46, IgHV4-39, IgHV4-31, IgHV3-30-3, IgHV2-26, or IgHV7-4-1. The present disclosure further provides anti-CoV-S antibodies or antigen-binding fragments thereof (e.g., anti-SARS-CoV-2-S antibodies or antigen-binding fragments thereof) comprising HCVR and LCVR sequences of Table 4 within a combination of a light chain selected from IgKV4-1, IgKV 1-5, IgKV1-9, IgKV1-12, IgKV3-15, IgKV1-16, IgKV1-17, IgKV3-20, IgLV3-21, IgKV2-24, IgKV1-33, IgKV1-39, IgLV1-40, IgLV1-44, IgLV1-51, IgLV3-1, IgKV1-6, IgLV2-8, IgKV3-11, IgLV2-11, IgLV2-14, IgLV2-23, or IgLV6-57, and a heavy chain selected from IgHV1-69, IgHV3-64, IgHV4-59, IgHV3-53, IgHV3-48, IgHV4-34, IgHV3-33, IgHV3-30, IgHV3-23, IgHV3-20, IgHV1-18, IgHV3-15, IgHV3-11, IgHV3-9, IgHV1-8, IgHV3-7, IgHV2-5, IgHV1-2, IgHV2-70, IgHV3-66, IgHV5-51, IgHV1-46, IgHV4-39, IgHV4-31, IgHV3-30-3, IgHV2-26, or IgHV7-4-1.

Typically, the variable domains of both the heavy and light immunoglobulin chains comprise three hypervariable regions, also called complementarity determining regions (CDRs), located within relatively conserved framework regions (FR). In general, from N-terminal to C-terminal, both light and heavy chains variable domains comprise FR1, CDR1, FR2, CDR2, FR3, CDR3 and FR4. In an embodiment of the invention, the assignment of amino acids to each domain is in accordance with the definitions of Sequences of Proteins of Immunological Interest, Kabat, et al.; National Institutes of Health, Bethesda, Md.; 5th ed.; NIH Publ. No. 91-3242 (1991); Kabat (1978) Adv. Prot. Chem. 32:1-75; Kabat, et al., (1977) J. Biol. Chem. 252:6609-6616; Chothia, et al., (1987) J Mol. Biol. 196:901-917 or Chothia, et al., (1989) Nature 342:878-883.

The present invention includes monoclonal anti-CoV-S antigen-binding proteins, e.g., antibodies and antigen-binding fragments thereof, as well as monoclonal compositions comprising a plurality of isolated monoclonal antigen-binding proteins. The term "monoclonal antibody", as used herein, refers to a population of substantially homogeneous antibodies, i.e., the antibody molecules comprising the population are identical in amino acid sequence except for possible naturally occurring mutations that may be present in minor amounts. A "plurality" of such monoclonal antibodies and fragments in a composition refers to a concentration of identical (i.e., as discussed above, in amino acid sequence except for possible naturally occurring mutations that may be present in minor amounts) antibodies and fragments which is above that which would normally occur in nature, e.g., in the blood of a host organism such as a mouse or a human.

In an embodiment of the invention, an anti-CoV-S antigen-binding protein, e.g., antibody or antigen-binding fragment comprises a heavy chain constant domain, e.g., of the type IgA (e.g., IgA1 or IgA2), IgD, IgE, IgG (e.g., IgG1, IgG2, IgG3 and IgG4) or IgM. In an embodiment of the invention, an antigen-binding protein, e.g., antibody or antigen-binding fragment comprises a light chain constant domain, e.g., of the type kappa or lambda.

The term "human" antigen-binding protein, such as an antibody, as used herein, includes antibodies having variable and constant regions derived from human germline immunoglobulin sequences whether in a human cell or grafted into a non-human cell, e.g., a mouse cell. See e.g., U.S. Pat. Nos. 8,502,018, 6,596,541 or 5,789,215. The human mAbs of the invention may include amino acid residues not encoded by human germline immunoglobulin sequences (e.g., mutations introduced by random or site-specific mutagenesis in vitro or by somatic mutation in vivo), for example in the CDRs and, in particular, CDR3. However, the term "human antibody", as used herein, is not intended to include mAbs in which CDR sequences derived from the germline of another mammalian species (e.g., mouse) have been grafted onto human FR sequences. The term includes antibodies recombinantly produced in a non-human mammal or in cells of a non-human mammal. The term is not intended to include antibodies isolated from or generated in a human subject. See below.

The present invention includes anti-CoV-S chimeric antigen-binding proteins, e.g., antibodies and antigen-binding fragments thereof, and methods of use thereof. As used herein, a "chimeric antibody" is an antibody having the variable domain from a first antibody and the constant domain from a second antibody, where the first and second antibodies are from different species. (U.S. Pat. No. 4,816,567; and Morrison et al., (1984) Proc. Natl. Acad. Sci. USA 81: 6851-6855).

The present invention includes anti-CoV-S hybrid antigen-binding proteins, e.g., antibodies and antigen-binding fragments thereof, and methods of use thereof. As used herein, a "hybrid antibody" is an antibody having the variable domain from a first antibody and the constant domain from a second antibody, wherein the first and second antibodies are from different animals, or wherein the variable domain, but not the constant region, is from a first animal. For example, a variable domain can be taken from an antibody isolated from a human and expressed with a fixed constant region not isolated from that antibody. Exemplary hybrid antibodies are described in Example 1, which refers to antibody heavy chain variable region and light chain variable region derived PCR products that were cloned into expression vectors containing a heavy constant region and a light constant region, respectively. Hybrid antibodies are synthetic and non-naturally occurring because the variable and constant regions they contain are not isolated from a single natural source.

The term "recombinant" antigen-binding proteins, such as antibodies or antigen-binding fragments thereof, refers to such molecules created, expressed, isolated or obtained by technologies or methods known in the art as recombinant DNA technology which include, e.g., DNA splicing and transgenic expression. The term includes antibodies expressed in a non-human mammal (including transgenic non-human mammals, e.g., transgenic mice), or a cell (e.g., CHO cells) expression system, or a non-human cell expression system, or isolated from a recombinant combinatorial human antibody library. In some embodiments, a recombinant antibody shares a sequence with an antibody isolated from an organism (e.g., a mouse or a human), but has been expressed via recombinant DNA technology. Such antibodies may have post-translational modifications (e.g., glycosylation) that differ from the antibody as isolated from the organism.

Recombinant anti-CoV-S antigen-binding proteins, e.g., antibodies and antigen-binding fragments, disclosed herein may also be produced in an *E. coli*/T7 expression system. In this embodiment, nucleic acids encoding the anti-CoV-S antibody immunoglobulin molecules of the invention (e.g., as found in Table 4) may be inserted into a pET-based plasmid and expressed in the *E. coli*/T7 system. For example, the present invention includes methods for expressing an antibody or antigen-binding fragment thereof or immunoglobulin chain thereof in a host cell (e.g., bacterial host cell such as *E. coli* such as BL21 or BL21DE3) comprising expressing T7 RNA polymerase in the cell which also includes a polynucleotide encoding an immunoglobulin chain that is operably linked to a T7 promoter. For example, in an embodiment of the invention, a bacterial host cell, such as an *E. coli*, includes a polynucleotide encoding the T7 RNA polymerase gene operably linked to a lac promoter and expression of the polymerase and the chain is induced by incubation of the host cell with IPTG (isopropyl-beta-D-thiogalactopyranoside). See U.S. Pat. Nos. 4,952,496 and 5,693,489 or Studier & Moffatt, Use of bacteriophage T7 RNA polymerase to direct selective high-level expression of cloned genes, J. Mol. Biol. 1986 May 5; 189(1): 113-30.

There are several methods by which to produce recombinant antibodies which are known in the art. One example of a method for recombinant production of antibodies is disclosed in U.S. Pat. No. 4,816,567.

Transformation can be by any known method for introducing polynucleotides (e.g., DNA or RNA, including mRNA) into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, lipid nanoparticle technology, biolistic injection and direct microinjection of the DNA into nuclei. In addition, nucleic acid molecules may be introduced into mammalian cells by viral vectors such as lentivirus or adeno-associated virus. Methods of transforming cells are well known in the art. See, for example, U.S. Pat. Nos. 4,399,216; 4,912,040; 4,740,461 and 4,959,455. In some embodiments, an antibody or antigen-binding fragment thereof of the present disclosure can be introduced to a subject in nucleic acid form (e.g, DNA or RNA, including mRNA), such that the subject's own cells produce the antibody. The present disclosure further provides modifications to nucleotide sequences encoding the anti-CoV-S antibodies described herein that result in increased antibody expression, increased antibody stability, increased nucleic acid (e.g., mRNA) stability, or improved affinity or specificity of the antibodies for the CoV spike protein.

Thus, the present invention includes recombinant methods for making an anti-CoV-S antigen-binding protein, such as an antibody or antigen-binding fragment thereof of the present invention, or an immunoglobulin chain thereof, comprising (i) introducing one or more polynucleotides (e.g., including the nucleotide sequence of any one or more of the sequences of Table 5) encoding light and/or heavy immunoglobulin chains, or CDRs, of the antigen-binding protein, e.g., of Table 4, for example, wherein the polynucleotide is in a vector; and/or integrated into a host cell chromosome and/or is operably linked to a promoter; (ii) culturing the host cell (e.g., CHO or *Pichia* or *Pichia pastoris*) under condition favorable to expression of the polynucleotide and, (iii) optionally, isolating the antigen-binding protein, (e.g., antibody or fragment) or chain from the host cell and/or medium in which the host cell is grown. For example, a polynucleotide can be integrated into a host cell chromosome through targeted insertion with a vector such as adeno-associated virus (AAV), e.g., after cleavage of the chromosome using a gene editing system (e.g., CRISPR (for example, CRISPR-Cas9), TALEN, megaTAL, zinc finger, or Argonaute). Targeted insertions can take place, for example, at host cell loci such as an albumin or immunoglopbulin genomic locus. Alternatively, insertion can be at a random locus, e.g., using a vector such as lentivirus. When making an antigen-binding protein (e.g., antibody or antigen-binding fragment) comprising more than one immunoglobulin chain, e.g., an antibody that comprises two heavy immunoglobulin chains and two light immunoglobulin chains, co-expression of the chains in a single host cell leads to association of the chains, e.g., in the cell or on the cell surface or outside the cell if such chains are secreted, so as to form the antigen-binding protein (e.g., antibody or antigen-binding fragment). The methods include those wherein only a heavy immunoglobulin chain or only a light immunoglobulin chain (e.g., any of those discussed herein including mature fragments and/or variable domains thereof) is expressed. Such chains are useful, for example, as intermediates in the expression of an antibody or antigen-binding fragment that includes such a chain. For example, the present invention also includes anti-CoV-S antigen-binding proteins, such as antibodies and antigen-binding fragments thereof, comprising a heavy chain immunoglobulin (or variable domain thereof or comprising the CDRs thereof) encoded by a polynucleotide comprising a nucleotide sequence set forth in Table 5 and a light chain immunoglobulin (or variable domain thereof or comprising the CDRs thereof) encoded by a nucleotide sequence set forth in Table 5 which are the product of such production methods, and, optionally, the purification methods set forth herein. For example, in some embodiments, the product of the method is an anti-CoV-S antigen-binding protein which is an antibody or fragment comprising an HCVR comprising an amino acid sequence set forth in Table 4 and an LCVR comprising an amino acid sequence set forth in Table 4, wherein the HCVR and LCVR sequences are selected from a single antibody listed in Table 4. In some embodiments, the product of the method is an anti-CoV-S antigen-binding protein which is an antibody or fragment comprising HCDR1, HCDR2, and HCDR3 comprising amino acid sequences set forth in Table 4 and LCDR1, LCDR2, and LCDR3 comprising amino acid sequences set forth in Table 4, wherein the six CDR sequences are selected from a single antibody listed in Table 4. In some embodiments, the product of the method is an anti-CoV-S antigen-binding protein which is an antibody or fragment comprising a heavy chain comprising an HC amino acid sequence set forth in Table 4 and a light chain comprising an LC amino acid sequence set forth in Table 4.

Eukaryotic and prokaryotic host cells, including mammalian cells, may be used as hosts for expression of an anti-CoV-S antigen-binding protein. Such host cells are well known in the art and many are available from the American Type Culture Collection (ATCC). These host cells include, inter alia, Chinese hamster ovary (CHO) cells, NS0, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines. Mammalian host cells include human, mouse, rat, dog, monkey, pig, goat, bovine, horse and hamster cells. Other cell lines that may be used are insect cell lines (e.g., *Spodoptera frugiperda* or *Trichoplusia ni*), amphibian cells, bacterial cells, plant cells and fungal cells. Fungal cells include yeast and filamentous fungus cells including, for example, *Pichia pastoris, Pichia finlandica, Pichia trehalophila, Pichia koclamae, Pichia membranaefaciens, Pichia minuta* (*Ogataea minuta, Pichia lindneri*), *Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Physcomitrella patens* and *Neurospora crassa*. The present invention includes an isolated host cell (e.g., a CHO cell) comprising an antigen-binding protein, such as those of Table 4; or a polynucleotide encoding such a polypeptide thereof.

The term “specifically binds” refers to those antigen-binding proteins (e.g., mAbs) having a binding affinity to an antigen, such as a CoV-S protein (e.g., SARS-CoV-2-S), expressed as $K_D$, of at least about $10^{-8}$ M, as measured by real-time, label free bio-layer interferometry assay, for example, at 25° C. or 37° C., e.g., an Octet® HTX biosensor, or by surface plasmon resonance, e.g., BIACORE™, or by solution-affinity ELISA. The present invention includes antigen-binding proteins that specifically bind to a CoV-S protein.

The terms “antigen-binding portion” or “antigen-binding fragment” of an antibody or antigen-binding protein, and the like, as used herein, include any naturally occurring, enzymatically obtainable, synthetic, or genetically engineered polypeptide or glycoprotein that specifically binds an antigen to form a complex. Non-limiting examples of antigen-binding fragments include: (i) Fab fragments; (ii) $F(ab')_2$ fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, mini-bodies, nanobodies (e.g., as defined in WO08/020079 or WO09/138519) (e.g., monovalent nanobodies, bivalent nanobodies, etc.), small modular immunopharmaceuticals (SMIPs), and shark variable IgNAR domains, are also encompassed within the expression “antigen-binding fragment,” as used herein. In an embodiment of the invention, the antigen-binding fragment comprises three or more CDRs of an antibody of Table 4 (e.g., CDR-H1, CDR-H2 and CDR-H3; or CDR-L1, CDR-L2 and CDR-L3).

An antigen-binding fragment of an antibody will, in an embodiment of the invention, comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

Antigen-binding proteins (e.g., antibodies and antigen-binding fragments) may be mono-specific or multi-specific (e.g., bi-specific). Multispecific antigen-binding proteins are discussed further herein.

In specific embodiments, antibody or antibody fragments of the invention may be conjugated to a moiety such a ligand or a therapeutic moiety (“immunoconjugate”), such as an anti-viral drug, a second anti-influenza antibody, or any other therapeutic moiety useful for treating a viral infection, e.g., influenza viral infection. See below.

The present invention also provides a complex comprising an anti-CoV-S antigen-binding protein, e.g., antibody or antigen-binding fragment, discussed herein complexed with CoV-S polypeptide or an antigenic fragment thereof and/or with a secondary antibody or antigen-binding fragment thereof (e.g., detectably labeled secondary antibody) that binds specifically to the anti-CoV-S antibody or fragment. In an embodiment of the invention, the antibody or fragment is in vitro (e.g., is immobilized to a solid substrate) or is in the body of a subject. In an embodiment of the invention, the CoV-S is in vitro (e.g., is immobilized to a solid substrate) or is on the surface of a virus or is in the body of a subject. Immobilized anti-CoV-S antibodies and antigen-binding fragments thereof which are covalently linked to an insoluble matrix material (e.g., glass or polysaccharide such as agarose or sepharose, e.g., a bead or other particle thereof) are also part of the present invention; optionally, wherein the immobilized antibody is complexed with CoV-S or antigenic fragment thereof or a secondary antibody or fragment thereof.

"Isolated" antigen-binding proteins, antibodies or antigen-binding fragments thereof, polypeptides, polynucleotides and vectors, are at least partially free of other biological molecules from the cells or cell culture from which they are produced. Such biological molecules include nucleic acids, proteins, other antibodies or antigen-binding fragments, lipids, carbohydrates, or other material such as cellular debris and growth medium. An isolated antibody or antigen-binding fragment may further be at least partially free of expression system components such as biological molecules from a host cell or of the growth medium thereof. Generally, the term "isolated" is not intended to refer to a complete absence of such biological molecules or to an absence of water, buffers, or salts or to components of a pharmaceutical formulation that includes the antibodies or fragments.

The term "epitope" refers to an antigenic determinant (e.g., a CoV-S polypeptide) that interacts with a specific antigen-binding site of an antigen-binding protein, e.g., a variable region of an antibody molecule, known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may be linear or conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

Methods for determining the epitope of an antigen-binding protein, e.g., antibody or fragment or polypeptide, include alanine scanning mutational analysis, peptide blot analysis (Reineke (2004) Methods Mol. Biol. 248: 443-63), peptide cleavage analysis, crystallographic studies and NMR analysis. In addition, methods such as epitope excision, epitope extraction and chemical modification of antigens can be employed (Tomer (2000) Prot. Sci. 9: 487-496). Another method that can be used to identify the amino acids within a polypeptide with which an antigen-binding protein (e.g., antibody or fragment or polypeptide) (e.g., coversin) interacts is hydrogen/deuterium exchange detected by mass spectrometry. In general terms, the hydrogen/deuterium exchange method involves deuterium-labeling the protein of interest, followed by binding the antigen-binding protein, e.g., antibody or fragment or polypeptide, to the deuterium-labeled protein. Next, the CoV-S protein/antigen-binding protein complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antigen-binding protein interface may retain deuterium and therefore exhibit relatively higher mass compared to amino acids not included in the interface. After dissociation of the antigen-binding protein (e.g., antibody or fragment or polypeptide), the target protein is subjected to protease cleavage and mass spectrometry analysis, thereby revealing the deuterium-labeled residues which correspond to the specific amino acids with which the antigen-binding protein interacts. See, e.g., Ehring (1999) Analytical Biochemistry 267: 252-259; Engen and Smith (2001) Anal. Chem. 73: 256A-265A.

The term "competes" as used herein, refers to an antigen-binding protein (e.g., antibody or antigen-binding fragment thereof) that binds to an antigen (e.g., CoV-S) and inhibits or blocks the binding of another antigen-binding protein (e.g., antibody or antigen-binding fragment thereof) to the antigen. The term also includes competition between two antigen-binding proteins e.g., antibodies, in both orientations, i.e., a first antibody that binds and blocks binding of second antibody and vice versa. In certain embodiments, the first antigen-binding protein (e.g., antibody) and second antigen-binding protein (e.g., antibody) may bind to the same epitope. Alternatively, the first and second antigen-binding proteins (e.g., antibodies) may bind to different, but, for example, overlapping epitopes, wherein binding of one inhibits or blocks the binding of the second antibody, e.g., via steric hindrance. Competition between antigen-binding proteins (e.g., antibodies) may be measured by methods known in the art, for example, by a real-time, label-free bio-layer interferometry assay. Epitope mapping (e.g., via alanine scanning or hydrogen-deuterium exchange (HDX)) can be used to determine whether two or more antibodies are non-competing (e.g., on a spike protein receptor binding domain (RBD) monomer), competing for the same epitope, or competing but with diverse micro-epitopes (e.g., identified through HDX). In an embodiment of the invention, competition between a first and second anti-CoV-S antigen-binding protein (e.g., antibody) is determined by measuring the ability of an immobilized first anti-CoV-S antigen-binding protein (e.g., antibody) (not initially complexed with CoV-S protein) to bind to soluble CoV-S protein complexed with a second anti-CoV-S antigen-binding protein (e.g., antibody). A reduction in the ability of the first anti-CoV-S antigen-binding protein (e.g., antibody) to bind to the complexed CoV-S protein, relative to uncomplexed CoV-S protein, indicates that the first and second anti-CoV-S antigen-binding proteins (e.g., antibodies) compete. The degree of competition can be expressed as a percentage of the reduction in binding. Such competition can be measured using a real time, label-free bio-layer interferometry assay, e.g., on an Octet RED384 biosensor (Pall ForteBio Corp.), ELISA (enzyme-linked immunosorbent assays) or SPR (surface plasmon resonance).

Binding competition between anti-CoV-S antigen-binding proteins (e.g., monoclonal antibodies (mAbs)) can be determined using a real time, label-free bio-layer interferometry assay on an Octet RED384 biosensor (Pall ForteBio Corp.). For example, to determine competition between two anti-CoV-S monoclonal antibodies, the anti-CoV-S mAb can be first captured onto anti-hFc antibody coated Octet biosensor tips (Pall ForteBio Corp., #18-5060) by submerging the tips into a solution of anti-CoV-S mAb (subsequently referred to as "mAb1"). As a positive-control for blocking, the antibody captured biosensor tips can then be saturated with a known blocking isotype control mAb (subsequently referred to as "blocking mAb") by dipping into a solution of blocking mAb. To determine if mAb2 competes with mAb1, the biosensor tips can then be subsequently dipped into a co-complexed solution of CoV-S polypeptide and a second anti-CoV-S mAb (subsequently referred to as "mAb2"), that had been pre-incubated for a period of time and binding of mAb1 to the CoV-S polypeptide can be determined. The biosensor tips can be washed in buffer in between every step of the experiment. The real-time binding response can be monitored during the course of the experiment and the binding response at the end of every step can be recorded.

For example, in an embodiment of the invention, the competition assay is conducted at 25° C. and pH about 7, e.g., 7.4, e.g., in the presence of buffer, salt, surfactant and a non-specific protein (e.g., bovine serum albumin).

Typically, an antibody or antigen-binding fragment of the invention which is modified in some way retains the ability to specifically bind to CoV-S, e.g., retains at least 10% of its CoV-S binding activity (when compared to the parental antibody) when that activity is expressed on a molar basis. Preferably, an antibody or antigen-binding fragment of the invention retains at least 20%, 50%, 70%, 80%, 90%, 95% or 100% or more of the CoV-S binding affinity as the parental antibody. It is also intended that an antibody or antigen-binding fragment of the invention can include conservative or non-conservative amino acid substitutions (referred to as "conservative variants" or "function conserved variants" of the antibody) that do not substantially alter its biologic activity.

A "variant" of a polypeptide, such as an immunoglobulin chain (e.g., mAb8021 $V_H$, $V_L$, HC, or LC, mAb8028 $V_H$, $V_L$, HC, or LC, or mAb8029 $V_H$, $V_L$, HC, or LC), refers to a polypeptide comprising an amino acid sequence that is at least about 70-99.9% (e.g., 70, 72, 74, 75, 76, 79, 80, 81, 82, 83, 84, 85, 86, 87, 88, 89, 90, 91, 92, 93, 94, 95, 96, 97, 98, 99, 99.5, 99.9%) identical or similar to a referenced amino acid sequence that is set forth herein (e.g., SEQ ID NO: 2, 10, 18, 20, 22, 30, 38, 40, 42, 50, 58, or 60); when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment).

A "variant" of a polynucleotide refers to a polynucleotide comprising a nucleotide sequence that is at least about 70-99.9% (e.g., at least about 70, 72, 74, 75, 76, 79, 80, 81, 82, 83, 84, 85, 86, 87, 88, 89, 90, 91, 92, 93, 94, 95, 96, 97, 98, 99, 99.5, or 99.9%) identical to a referenced nucleotide sequence that is set forth herein (e.g., SEQ ID NO: 1, 9, 17, 19, 21, 29, 37, 39, 41, 49, 57, or 59); when the comparison is performed by a BLAST algorithm wherein the parameters of the algorithm are selected to give the largest match between the respective sequences over the entire length of the respective reference sequences (e.g., expect threshold: 10; word size: 28; max matches in a query range: 0; match/mismatch scores: 1, −2; gap costs: linear).

Anti-CoV-S antigen-binding proteins, e.g., antibodies and antigen-binding fragments thereof of the present invention, in an embodiment of the invention, include a heavy chain immunoglobulin variable region having at least 70% (e.g., 80%, 85%, 90%, 91%, 92%, 93%, 94%, 95%, 96%, 97%, 98%, 99%, or greater) amino acid sequence identity to the HCVR amino acid sequences set forth in Table 4; and/or a light chain immunoglobulin variable region having at least 70% (e.g., 80%, 85%, 90%, 91%, 92%, 93%, 94%, 95%, 96%, 97%, 98%, 99%, or greater) amino acid sequence identity to the LCVR amino acid sequences set forth in Table 4.

In addition, a variant anti-CoV-S antigen-binding protein may include a polypeptide comprising an amino acid sequence that is set forth herein except for one or more (e.g., 1, 2, 3, 4, 5, 6, 7, 8, 9 or 10) mutations such as, for example, missense mutations (e.g., conservative substitutions), non-sense mutations, deletions, or insertions. For example, the present invention includes antigen-binding proteins which include an immunoglobulin light chain variant comprising an LCVR amino acid sequence set forth in Table 4 but having one or more of such mutations and/or an immunoglobulin heavy chain variant comprising an HCVR amino acid sequence set forth in Table 4 but having one or more of such mutations. In an embodiment of the invention, a variant anti-CoV-S antigen-binding protein includes an immunoglobulin light chain variant comprising CDR-L1, CDR-L2 and CDR-L3 wherein one or more (e.g., 1 or 2 or 3) of such CDRs has one or more of such mutations (e.g., conservative substitutions) and/or an immunoglobulin heavy chain variant comprising CDR-H1, CDR-H2 and CDR-H3 wherein one or more (e.g., 1 or 2 or 3) of such CDRs has one or more of such mutations (e.g., conservative substitutions). Substitutions can be in a CDR, framework, or constant region.

The invention further provides variant anti-CoV-S antigen-binding proteins, e.g., antibodies or antigen-binding fragments thereof, comprising one or more variant CDRs (e.g., any one or more of CDR-L1, CDR-L2, CDR-L3, CDR-H1, CDR-H2 and/or CDR-H3) that are set forth herein with at least 70%, 75%, 80%, 85%, 90%, 91%, 92%, 93%, 94%, 95%, 96%, 97%, 98%, 99%, or 99.9% sequence identity or similarity to, e.g., the heavy chain and light chain CDRs of Table 4.

Embodiments of the present invention also include variant antigen-binding proteins, e.g., anti-CoV-S antibodies and antigen-binding fragments thereof, that comprise immunoglobulin $V_H$s and $V_L$s; or HCs and LCs, which comprise an amino acid sequence having 70% or more (e.g., 80%, 85%, 90%, 91%, 92%, 93%, 94%, 95%, 96%, 97%, 98%, 99%, or greater) overall amino acid sequence identity or similarity to the amino acid sequences of the corresponding $V_H$s, $V_L$s, HCs or LCs specifically set forth herein, but wherein the CDR-L1, CDR-L2, CDR-L3, CDR-H1, CDR-H2 and CDR-H3 of such immunoglobulins are not variants and comprise CDR amino acid sequence set forth in Table 4. Thus, in such embodiments, the CDRs within variant antigen-binding proteins are not, themselves, variants.

Conservatively modified variant anti-CoV-S antibodies and antigen-binding fragments thereof are also part of the present invention. A "conservatively modified variant" or a "conservative substitution" refers to a variant wherein there is one or more substitutions of amino acids in a polypeptide with other amino acids having similar characteristics (e.g. charge, side-chain size, hydrophobicity/hydrophilicity, backbone conformation and rigidity, etc.). Such changes can frequently be made without significantly disrupting the biological activity of the antibody or fragment. Those of skill in this art recognize that, in general, single amino acid substitutions in non-essential regions of a polypeptide do not substantially alter biological activity (see, e.g., Watson et al. (1987) Molecular Biology of the Gene, The Benjamin/

Cummings Pub. Co., p. 224 (4th Ed.)). In addition, substitutions of structurally or functionally similar amino acids are less likely to significantly disrupt biological activity.

Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45.

Function-conservative variants of the anti-CoV-S antibodies and antigen-binding fragments thereof are also part of the present invention. Any of the variants of the anti-CoV-S antibodies and antigen-binding fragments thereof (as discussed herein) may be "function-conservative variants". Such function-conservative variants may, in some cases, also be characterized as conservatively modified variants. "Function-conservative variants," as used herein, refers to variants of the anti-CoV-S antibodies or antigen-binding fragments thereof in which one or more amino acid residues have been changed without significantly altering one or more functional properties of the antibody or fragment. In an embodiment of the invention, a function-conservative variant anti-CoV-S antibody or antigen-binding fragment thereof of the present invention comprises a variant amino acid sequence and exhibits one or more of the following functional properties:

- Inhibits growth of coronavirus (e.g., SARS-CoV-2, SARS-CoV, and/or MERS-CoV) in ACE2- and/or TMPRSS2-expressing cells (e.g., Calu-3 cells); Does not significantly bind to MDCK/Tet-on cells which do not express ACE2 and/or TMPRSS2;
- Limits spread of coronavirus infection (e.g., by SARS-CoV-2, SARS-CoV, and/or MERS-CoV) of cells, e.g., Calu-3, in vitro; and/or
- Protects a mouse engineered to express the human TMPRSS2 and/or ACE2 protein from death caused by coronavirus infection (e.g., SARS-CoV-2, SARS-CoV, or MERS-CoV), for example, wherein the mice are infected with an otherwise lethal dose of the virus, optionally when combined with a second therapeutic agent.
- Protects a mouse engineered to express the human TMPRSS2 and/or ACE2 protein from weight loss caused by coronavirus infection (e.g., SARS-CoV-2, SARS-CoV, or MERS-CoV), for example, wherein the mice are infected with a dose of the virus that would otherwise cause weight loss, optionally when combined with a second therapeutic agent.

A "neutralizing" or "antagonist" anti-CoV-S antigen-binding protein, e.g., antibody or antigen-binding fragment, refers to a molecule that inhibits an activity of CoV-S to any detectable degree, e.g., inhibits the ability of CoV-S to bind to a receptor such as ACE2, to be cleaved by a protease such as TMPRSS2, or to mediate viral entry into a host cell or viral reproduction in a host cell.

Table 4 refers to antigen-binding proteins, such as antibodies and antigen-binding fragments thereof, that comprise the heavy chain or $V_H$ (or a variant thereof) and light chain or $V_L$ (or a variant thereof) as set forth below; or that comprise a $V_H$ that comprises the CDRs thereof (CDR-H1 (or a variant thereof), CDR-H2 (or a variant thereof) and CDR-H3 (or a variant thereof)) and a $V_L$ that comprises the CDRs thereof (CDR-L1 (or a variant thereof), CDR-L2 (or a variant thereof) and CDR-L3 (or a variant thereof)), e.g., wherein the immunoglobulin chains, variable regions and/or CDRs comprise the specific amino acid sequences described below.

The antibodies described herein also include embodiments wherein the $V_H$ is fused to a wild-type IgG4 (e.g., wherein residue 108 is S) or to IgG4 variants (e.g., wherein residue 108 is P).

Antibodies and antigen-binding fragments of the present invention comprise immunoglobulin chains including the amino acid sequences set forth herein as well as cellular and in vitro post-translational modifications to the antibody. For example, the present invention includes antibodies and antigen-binding fragments thereof that specifically bind to CoV-S comprising heavy and/or light chain amino acid sequences set forth herein (e.g., CDR-H1, CDR-H2, CDR-H3, CDR-L1, CDR-L2 and/or CDR-L3) as well as antibodies and fragments wherein one or more amino acid residues is glycosylated, one or more Asn residues is deamidated, one or more residues (e.g., Met, Trp and/or His) is oxidized, the N-terminal Gln is pyroglutamate (pyroE) and/or the C-terminal Lysine is missing.

The amino acid and nucleotide sequences of exemplary anti-SARS-CoV-2-Spike protein (SARS-CoV-2-S) antibodies are shown in Table 1 (Table of Exemplary Sequences), below.

TABLE 1

Table of Exemplary Sequences

| Antibody Designation | Component Part | Sequence | SEQ ID NO |
|---|---|---|---|
| | | Amino Acids | |
| mAb10933 | HCVR | QVQLVESGGGLVKPGGSLRLSCAASGFTFSDYYMSWIRQAPGKGLEWVSYITYSGSTIYYADSVKGRFTISRDNAKSSLYLQMNSLRAEDTAVYYCARDRGTTMVPFDYWGQGTLVTVSS | 202 |
| | HCDR1 | GFTFSDYY | 204 |
| | HCDR2 | ITYSGSTI | 206 |
| | HCDR3 | ARDRGTTMVPFDY | 208 |
| | LCVR | DIQMTQSPSSLSASVGDRVTITCQASQDITNYLNWYQQKPGKAPKLLIYAASNLETGVPSRFSGSGSG | 210 |

TABLE 1-continued

Table of Exemplary Sequences

| Antibody Designation | Component Part | Sequence | SEQ ID NO |
|---|---|---|---|
| | | TDFTFTISGLQPEDIATYYCQQYDNLPLTFGGGT KVEIK | |
| | LCDR1 | QDITNY | 212 |
| | LCDR2 | AAS | |
| | LCDR3 | QQYDNLPLT | 214 |
| | HC | QVQLVESGGGLVKPGGSLRLSCAASGFTFSDYYM SWIRQAPGKGLEWVSYITYSGSTIYYADSVKGRF TISRDNAKSSLYLQMNSLRAEDTAVYYCARDRGT TMVPFDYWGQGTLVTVSSASTKGPSVFPLAPSSK STSGGTAALGCLVKDYFPEPVTVSWNSGALTSGV HTFPAVLQSSGLYSLSSVVTVPSSSLGTQTYICN VNHKPSNTKVDKKVEPKSCDKTHTCPPCPAPELL GGPSVFLFPPKPKDTLMISRTPEVTCVVVDVSHE DPEVKFNWYVDGVEVHNAKTKPREEQYNSTYRVV SVLTVLHQDWLNGKEYKCKVSNKALPAPIEKTIS KAKGQPREPQVYTLPPSRDELTKNQVSLTCLVKG FYPSDIAVEWESNGQPENNYKTTPPVLDSDGSFF LYSKLTVDKSRWQQGNVFSCSVMHEALHNHYTQK SLSLSPGK | 216 |
| | LC | DIQMTQSPSSLSASVGDRVTITCQASQDITNYLN WYQQKPGKAPKLLIYAASNLETGVPSRFSGSGSG TDFTFTISGLQPEDIATYYCQQYDNLPLTFGGGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC | 218 |
| | | Nucleic Acids | |
| | HCVR | CAGGTGCAGCTGGTGGAGTCTGGGGGAGGCTTGG TCAAGCCTGGAGGGTCCCTGAGACTCTCCTGTGC AGCCTCTGGATTCACCTTCAGTGACTACTACATG AGCTGGATCCGCCAGGCTCCAGGGAAGGGGCTGG AGTGGGTTTCATACATTACTTATAGTGGTAGTAC CATATACTACGCAGACTCTGTGAAGGGCCGATTC ACCATCTCCAGGGACAACGCCAAGAGCTCACTGT ATCTGCAAATGAACAGCCTGAGAGCCGAGGACAC GGCCGTGTATTACTGTGCGAGAGATCGCGGTACA ACTATGGTCCCCTTTGACTACTGGGGCCAGGGAA CCCTGGTCACCGTCTCCTCA | 201 |
| | HCDR1 | GGATTCACCTTCAGTGACTACTAC | 203 |
| | HCDR2 | ATTACTTATAGTGGTAGTACCATA | 205 |
| | HCDR3 | GCGAGAGATCGCGGTACAACTATGGTCCCCTTTG ACTAC | 207 |
| | LCVR | GACATCCAGATGACCCAGTCTCCATCCTCCCTGT CTGCATCTGTAGGAGACAGAGTCACCATCACTTG CCAGGCGAGTCAGGACATTACCAACTATTTAAAT TGGTATCAGCAGAAACCAGGGAAAGCCCCTAAGC TCCTGATCTACGCTGCATCCAATTTGGAAACAGG GGTCCCATCAAGGTTCAGTGGAAGTGGATCTGGG ACAGATTTTACTTTCACCATCAGCGGCCTGCAGC CTGAAGATATTGCAACATATTACTGTCAACAGTA TGATAATCTCCCTCTCACTTTCGGCGGAGGGACC AAGGTGGAGATCAAA | 209 |
| | LCDR1 | CAGGACATTACCAACTAT | 211 |
| | LCDR2 | GCTGCATCC | |
| | LCDR3 | CAACAGTATGATAATCTCCCTCTCACT | 213 |
| | HC | CAGGTGCAGCTGGTGGAGTCTGGGGGAGGCTTGG TCAAGCCTGGAGGGTCCCTGAGACTCTCCTGTGC AGCCTCTGGATTCACCTTCAGTGACTACTACATG AGCTGGATCCGCCAGGCTCCAGGGAAGGGGCTGG AGTGGGTTTCATACATTACTTATAGTGGTAGTAC CATATACTACGCAGACTCTGTGAAGGGCCGATTC ACCATCTCCAGGGACAACGCCAAGAGCTCACTGT ATCTGCAAATGAACAGCCTGAGAGCCGAGGACAC GGCCGTGTATTACTGTGCGAGAGATCGCGGTACA ACTATGGTCCCCTTTGACTACTGGGGCCAGGGAA CCCTGGTCACCGTCTCCTCAGCCTCCACCAAGGG CCCATCGGTCTTCCCCCTGGCACCCTCCTCCAAG AGCACCTCTGGGGGCACAGCGGCCCTGGGCTGCC TGGTCAAGGACTACTTCCCCGAACCGGTGACGGT GTCGTGGAACTCAGGCGCCCTGACCAGCGGCGTG CACACCTTCCCGGCTGTCCTACAGTCCTCAGGAC TCTACTCCCTCAGCAGCGTGGTGACCGTGCCCTC CAGCAGCTTGGGCACCCAGACCTACATCTGCAAC | 215 |

TABLE 1-continued

| Antibody Designation | Component Part | Sequence | SEQ ID NO |
|---|---|---|---|
| | | Table of Exemplary Sequences | |
| | | GTGAATCACAAGCCCAGCAACACCAAGGTGGACA AGAAAGTTGAGCCCAAATCTTGTGACAAAACTCA CACATGCCCACCGTGCCCAGCACCTGAACTCCTG GGGGGACCGTCAGTCTTCCTCTTCCCCCCAAAAC CCAAGGACACCCTCATGATCTCCCGGACCCCTGA GGTCACATGCGTGGTGGTGGACGTGAGCCACGAA GACCCTGAGGTCAAGTTCAACTGGTACGTGGACG GCGTGGAGGTGCATAATGCCAAGACAAAGCCGCG GGAGGAGCAGTACAACAGCACGTACCGTGTGGTC AGCGTCCTCACCGTCCTGCACCAGGACTGGCTGA ATGGCAAGGAGTACAAGTGCAAGGTCTCCAACAA AGCCCTCCCAGCCCCCATCGAGAAAACCATCTCC AAAGCCAAAGGGCAGCCCCGAGAACCACAGGTGT ACACCCTGCCCCCATCCCGGGATGAGCTGACCAA GAACCAGGTCAGCCTGACCTGCCTGGTCAAAGGC TTCTATCCCAGCGACATCGCCGTGGAGTGGGAGA GCAATGGGCAGCCGGAGAACAACTACAAGACCAC GCCTCCCGTGCTGGACTCCGACGGCTCCTTCTTC CTCTACAGCAAGCTCACCGTGGACAAGAGCAGGT GGCAGCAGGGGAACGTCTTCTCATGCTCCGTGAT GCATGAGGCTCTGCACAACCACTACACGCAGAAG TCCCTCTCCCTGTCTCCGGGTAAATGA | |
| | LC | GACATCCAGATGACCCAGTCTCCATCCTCCCTGT CTGCATCTGTAGGAGACAGAGTCACCATCACTTG CCAGGCGAGTCAGGACATTACCAACTATTTAAAT TGGTATCAGCAGAAACCAGGGAAAGCCCCTAAGC TCCTGATCTACGCTGCATCCAATTTGGAAACAGG GGTCCCATCAAGGTTCAGTGGAAGTGGATCTGGG ACAGATTTTACTTTCACCATCAGCGGCCTGCAGC CTGAAGATATTGCAACATATTACTGTCAACAGTA TGATAATCTCCCTCTCACTTTCGGCGGAGGGACC AAGGTGGAGATCAAACGAACTGTGGCTGCACCAT CTGTCTTCATCTTCCCGCCATCTGATGAGCAGTT GAAATCTGGAACTGCCTCTGTTGTGTGCCTGCTG AATAACTTCTATCCCAGAGAGGCCAAAGTACAGT GGAAGGTGGATAACGCCCTCCAATCGGGTAACTC CCAGGAGAGTGTCACAGAGCAGGACAGCAAGGAC AGCACCTACAGCCTCAGCAGCACCCTGACGCTGA GCAAAGCAGACTACGAGAAACACAAAGTCTACGC CTGCGAAGTCACCCATCAGGGCCTGAGCTCGCCC GTCACAAAGAGCTTCAACAGGGGAGAGTGTTAG | 217 |
| | | Amino Acids | |
| mAb10934 | HCVR | EVQLVESGGGLVKPGGSLRLSCAASGITFSNAWM SWVRQAPGKGLEWVGRIKSKTDGGTTDYAAPVKG RFTISRDDSKNTLYLQMNSLKTEDTAVYYCTTAR WDWYFDLWGRGTLVTVSS | 220 |
| | HCDR1 | GITFSNAW | 222 |
| | HCDR2 | IKSKTDGGTT | 224 |
| | HCDR3 | TTARWDWYFDL | 226 |
| | LCVR | DIQMTQSPSSLSASVGDRVTITCQASQDIWNYIN WYQQKPGKAPKLLIYDASNLKTGVPSRFSGSGSG TDFTFTISSLQPEDIATYYCQQHDDLPPTFGQGT KVEIK | 228 |
| | LCDR1 | QDIWNY | 230 |
| | LCDR2 | DAS | |
| | LCDR3 | QQHDDLPPT | 232 |
| | HC | EVQLVESGGGLVKPGGSLRLSCAASGITFSNAWM SWVRQAPGKGLEWVGRIKSKTDGGTTDYAAPVKG RFTISRDDSKNTLYLQMNSLKTEDTAVYYCTTAR WDWYFDLWGRGTLVTVSSASTKGPSVFPLAPSSK STSGGTAALGCLVKDYFPEPVTVSWNSGALTSGV HTFPAVLQSSGLYSLSSVVTVPSSSLGTQTYICN VNHKPSNTKVDKKVEPKSCDKTHTCPPCPAPELL GGPSVFLFPPKPKDTLMISRTPEVTCVVVDVSHE DPEVKFNWYVDGVEVHNAKTKPREEQYNSTYRVV SVLTVLHQDWLNGKEYKCKVSNKALPAPIEKTIS KAKGQPREPQVYTLPPSRDELTKNQVSLTCLVKG FYPSDIAVEWESNGQPENNYKTTPPVLDSDGSFF LYSKLTVDKSRWQQGNVFSCSVMHEALHNHYTQK SLSLSPGK | 234 |
| | LC | DIQMTQSPSSLSASVGDRVTITCQASQDIWNYIN WYQQKPGKAPKLLIYDASNLKTGVPSRFSGSGSG TDFTFTISSLQPEDIATYYCQQHDDLPPTFGQGT | 236 |

TABLE 1-continued

Table of Exemplary Sequences

| Antibody Designation | Component Part | Sequence | SEQ ID NO |
|---|---|---|---|
| | | KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC | |
| | Nucleic Acids | | |
| | HCVR | GAGGTGCAGCTGGTGGAGTCTGGGGGAGGCTTGG TAAAGCCTGGGGGGTCCCTTAGACTCTCCTGTGC AGCCTCTGGAATCACTTTCAGTAACGCCTGGATG AGTTGGGTCCGCCAGGCTCCAGGGAAGGGGCTGG AGTGGGTTGGCCGTATTAAAAGCAAAACTGATGG TGGGACAACAGACTACGCCGCACCCGTGAAAGGC AGATTCACCATCTCAAGAGATGATTCAAAAAACA CGCTGTATCTACAAATGAACAGCCTGAAAACCGA GGACACAGCCGTGTATTACTGTACCACAGCGAGG TGGGACTGGTACTTCGATCTCTGGGGCCGTGGCA CCCTGGTCACTGTCTCCTCA | 219 |
| | HCDR1 | GGAATCACTTTCAGTAACGCCTGG | 221 |
| | HCDR2 | ATTAAAAGCAAAACTGATGGTGGGACAACA | 223 |
| | HCDR3 | ACCACAGCGAGGTGGGACTGGTACTTCGATCTC | 225 |
| | LCVR | GACATCCAGATGACCCAGTCTCCATCCTCCCTGT CTGCATCTGTAGGAGACAGAGTCACCATCACTTG CCAGGCGAGTCAGGACATTTGGAATTATATAAAT TGGTATCAGCAGAAACCAGGGAAGGCCCCTAAGC TCCTGATCTACGATGCATCCAATTTGAAAACAGG GGTCCCATCAAGGTTCAGTGGAAGTGGATCTGGG ACAGATTTTACTTTCACCATCAGCAGCCTGCAGC CTGAAGATATTGCAACATATTACTGTCAACAGCA TGATGATCTCCCTCCGACCTTCGGCCAAGGGACC AAGGTGGAAATCAAA | 227 |
| | LCDR1 | CAGGACATTTGGAATTAT | 229 |
| | LCDR2 | GATGCATCC | |
| | LCDR3 | CAACAGCATGATGATCTCCCTCCGACC | 231 |
| | HC | GAGGTGCAGCTGGTGGAGTCTGGGGGAGGCTTGG TAAAGCCTGGGGGGTCCCTTAGACTCTCCTGTGC AGCCTCTGGAATCACTTTCAGTAACGCCTGGATG AGTTGGGTCCGCCAGGCTCCAGGGAAGGGGCTGG AGTGGGTTGGCCGTATTAAAAGCAAAACTGATGG TGGGACAACAGACTACGCCGCACCCGTGAAAGGC AGATTCACCATCTCAAGAGATGATTCAAAAAACA CGCTGTATCTACAAATGAACAGCCTGAAAACCGA GGACACAGCCGTGTATTACTGTACCACAGCGAGG TGGGACTGGTACTTCGATCTCTGGGGCCGTGGCA CCCTGGTCACTGTCTCCTCAGCCTCCACCAAGGG CCCATCGGTCTTCCCCCTGGCACCCTCCTCCAAG AGCACCTCTGGGGGCACAGCGGCCCTGGGCTGCC TGGTCAAGGACTACTTCCCCGAACCGGTGACGGT GTCGTGGAACTCAGGCGCCCTGACCAGCGGCGTG CACACCTTCCCGGCTGTCCTACAGTCCTCAGGAC TCTACTCCCTCAGCAGCGTGGTGACCGTGCCCTC CAGCAGCTTGGGCACCCAGACCTACATCTGCAAC GTGAATCACAAGCCCAGCAACACCAAGGTGGACA AGAAAGTTGAGCCCAAATCTTGTGACAAAACTCA CACATGCCCACCGTGCCCAGCACCTGAACTCCTG GGGGGACCGTCAGTCTTCCTCTTCCCCCCAAAAC CCAAGGACACCCTCATGATCTCCCGGACCCCTGA GGTCACATGCGTGGTGGTGGACGTGAGCCACGAA GACCCTGAGGTCAAGTTCAACTGGTACGTGGACG GCGTGGAGGTGCATAATGCCAAGACAAAGCCGCG GGAGGAGCAGTACAACAGCACGTACCGTGTGGTC AGCGTCCTCACCGTCCTGCACCAGGACTGGCTGA ATGGCAAGGAGTACAAGTGCAAGGTCTCCAACAA AGCCCTCCCAGCCCCCATCGAGAAAACCATCTCC AAAGCCAAAGGGCAGCCCCGAGAACCACAGGTGT ACACCCTGCCCCCATCCCGGGATGAGCTGACCAA GAACCAGGTCAGCCTGACCTGCCTGGTCAAAGGC TTCTATCCCAGCGACATCGCCGTGGAGTGGGAGA GCAATGGGCAGCCGGAGAACAACTACAAGACCAC GCCTCCCGTGCTGGACTCCGACGGCTCCTTCTTC CTCTACAGCAAGCTCACCGTGGACAAGAGCAGGT GGCAGCAGGGGAACGTCTTCTCATGCTCCGTGAT GCATGAGGCTCTGCACAACCACTACACGCAGAAG TCCCTCTCCCTGTCTCCGGGTAAATGA | 233 |

TABLE 1-continued

Table of Exemplary Sequences

| Antibody Designation | Component Part | Sequence | SEQ ID NO |
|---|---|---|---|
| | LC | GACATCCAGATGACCCAGTCTCCATCCTCCCTGT CTGCATCTGTAGGAGACAGAGTCACCATCACTTG CCAGGCGAGTCAGGACATTTGGAATTATATAAAT TGGTATCAGCAGAAACCAGGGAAGGCCCCTAAGC TCCTGATCTACGATGCATCCAATTTGAAAACAGG GGTCCCATCAAGGTTCAGTGGAAGTGGATCTGGG ACAGATTTTACTTTCACCATCAGCAGCCTGCAGC CTGAAGATATTGCAACATATTACTGTCAACAGCA TGATGATCTCCCTCCGACCTTCGGCCAAGGGACC AAGGTGGAAATCAAACGAACTGTGGCTGCACCAT CTGTCTTCATCTTCCCGCCATCTGATGAGCAGTT GAAATCTGGAACTGCCTCTGTTGTGTGCCTGCTG AATAACTTCTATCCCAGAGAGGCCAAAGTACAGT GGAAGGTGGATAACGCCCTCCAATCGGGTAACTC CCAGGAGAGTGTCACAGAGCAGGACAGCAAGGAC AGCACCTACAGCCTCAGCAGCACCCTGACGCTGA GCAAAGCAGACTACGAGAAACACAAAGTCTACGC CTGCGAAGTCACCCATCAGGGCCTGAGCTCGCCC GTCACAAAGAGCTTCAACAGGGGAGAGTGTTAG | 235 |
| | | Amino Acids | |
| mAb10987 | HCVR | QVQLVESGGGVVQPGRSLRLSCAASGFTFSNYAM YWVRQAPGKGLEWVAVISYDGSNKYYADSVKGRF TISRDNSKNTLYLQMNSLRTEDTAVYYCASGSDY GDYLLVYWGQGTLVTVSS | 640 |
| | HCDR1 | GFTFSNYA | 642 |
| | HCDR2 | ISYDGSNK | 499 |
| | HCDR3 | ASGSDYGDYLLVY | 644 |
| | LCVR | QSALTQPASVSGSPGQSITISCTGTSSDVGGYNY VSWYQQHPGKAPKLMIYDVSKRPSGVSNRFSGSK SGNTASLTISGLQSEDEADYYCNSLTSISTWVFG GGTKLTVL | 646 |
| | LCDR1 | SSDVGGYNY | 648 |
| | LCDR2 | DVS | |
| | LCDR3 | NSLTSISTWV | 652 |
| | HC | QVQLVESGGGVVQPGRSLRLSCAASGFTFSNYAM YWVRQAPGKGLEWVAVISYDGSNKYYADSVKGRF TISRDNSKNTLYLQMNSLRTEDTAVYYCASGSDY GDYLLVYWGQGTLVTVSSASTKGPSVFPLAPSSK STSGGTAALGCLVKDYFPEPVTVSWNSGALTSGV HTFPAVLQSSGLYSLSSVVTVPSSSLGTQTYICN VNHKPSNTKVDKKVEPKSCDKTHTCPPCPAPELL GGPSVFLFPPKPKDTLMISRTPEVTCVVVDVSHE DPEVKFNWYVDGVEVHNAKTKPREEQYNSTYRVV SVLTVLHQDWLNGKEYKCKVSNKALPAPIEKTIS KAKGQPREPQVYTLPPSRDELTKNQVSLTCLVKG FYPSDIAVEWESNGQPENNYKTTPPVLDSDGSFF LYSKLTVDKSRWQQGNVFSCSVMHEALHNHYTQK SLSLSPGK | 654 |
| | LC | QSALTQPASVSGSPGQSITISCTGTSSDVGGYNY VSWYQQHPGKAPKLMIYDVSKRPSGVSNRFSGSK SGNTASLTISGLQSEDEADYYCNSLTSISTWVFG GGTKLTVLGQPKAAPSVTLFPPSSEELQANKATL VCLISDFYPGAVTVAWKADSSPVKAGVETTTPSK QSNNKYAASSYLSLTPEQWKSHRSYSCQVTHEGS TVEKTVAPTECS | 656 |
| | | Nucleic Acids | |
| | HCVR | CAGGTGCAGCTGGTGGAGTCTGGGGGAGGCGTGG TCCAGCCTGGGAGGTCCCTGAGACTCTCCTGTGC AGCCTCTGGATTCACCTTCAGTAACTATGCTATG TACTGGGTCCGCCAGGCTCCAGGCAAGGGGCTGG AGTGGGTGGCAGTTATATCATATGATGGAAGTAA TAAATACTATGCAGACTCCGTGAAGGGCCGATTC ACCATCTCCAGAGACAATTCCAAGAACACGCTGT ATCTGCAAATGAACAGCCTGAGAACTGAGGACAC GGCTGTGTATTACTGTGCGAGTGGCTCCGACTAC GGTGACTACTTATTGGTTTACTGGGGCCAGGGAA CCCTGGTCACCGTCTCCTCA | 639 |
| | HCDR1 | GGATTCACCTTCAGTAACTATGCT | 641 |
| | HCDR2 | ATATCATATGATGGAAGTAATAAA | 498 |
| | HCDR3 | GCGAGTGGCTCCGACTACGGTGACTACTTATTGG TTTAC | 643 |

TABLE 1-continued

Table of Exemplary Sequences

| Antibody Designation | Component Part | Sequence | SEQ ID NO |
|---|---|---|---|
| | LCVR | CAGTCTGCCCTGACTCAGCCTGCCTCCGTGTCTG GGTCTCCTGGACAGTCGATCACCATCTCCTGCAC TGGAACCAGCAGTGACGTTGGTGGTTATAACTAT GTCTCCTGGTACCAACAACACCCAGGCAAAGCCC CCAAACTCATGATTTATGATGTCAGTAAGCGGCC CTCAGGGGTTTCTAATCGCTTCTCTGGCTCCAAG TCTGGCAACACGGCCTCCCTGACCATCTCTGGGC TCCAGTCTGAGGACGAGGCTGATTATTACTGCAA CTCTTTGACAAGCATCAGCACTTGGGTGTTCGGC GGAGGGACCAAGCTGACCGTCCTA | 645 |
| | LCDR1 | AGCAGTGACGTTGGTGGTTATAACTAT | 647 |
| | LCDR2 | GATGTCAGT | |
| | LCDR3 | AACTCTTTGACAAGCATCAGCACTTGGGTG | 651 |
| | HC | CAGGTGCAGCTGGTGGAGTCTGGGGGAGGCGTGG TCCAGCCTGGGAGGTCCCTGAGACTCTCCTGTGC AGCCTCTGGATTCACCTTCAGTAACTATGCTATG TACTGGGTCCGCCAGGCTCCAGGCAAGGGGCTGG AGTGGGTGGCAGTTATATCATATGATGGAAGTAA TAAATACTATGCAGACTCCGTGAAGGGCCGATTC ACCATCTCCAGAGACAATTCCAAGAACACGCTGT ATCTGCAAATGAACAGCCTGAGAACTGAGGACAC GGCTGTGTATTACTGTGCGAGTGGCTCCGACTAC GGTGACTACTTATTGGTTTACTGGGGCCAGGGAA CCCTGGTCACCGTCTCCTCAGCCTCCACCAAGGG CCCATCGGTCTTCCCCCTGGCACCCTCCTCCAAG AGCACCTCTGGGGGCACAGCGGCCCTGGGCTGCC TGGTCAAGGACTACTTCCCCGAACCGGTGACGGT GTCGTGGAACTCAGGCGCCCTGACCAGCGGCGTG CACACCTTCCCGGCTGTCCTACAGTCCTCAGGAC TCTACTCCCTCAGCAGCGTGGTGACCGTGCCCTC | 653 |
| | LC | CAGCAGCTTGGGCACCCAGACCTACATCTGCAAC GTGAATCACAAGCCCAGCAACACCAAGGTGGACA AGAAAGTTGAGCCCAAATCTTGTGACAAAACTCA CACATGCCCACCGTGCCCAGCACCTGAACTCCTG GGGGGACCGTCAGTCTTCCTCTTCCCCCCAAAAC CCAAGGACACCCTCATGATCTCCCGGACCCCTGA GGTCACATGCGTGGTGGTGGACGTGAGCCACGAA GACCCTGAGGTCAAGTTCAACTGGTACGTGGACG GCGTGGAGGTGCATAATGCCAAGACAAAGCCGCG GGAGGAGCAGTACAACAGCACGTACCGTGTGGTC AGCGTCCTCACCGTCCTGCACCAGGACTGGCTGA ATGGCAAGGAGTACAAGTGCAAGGTCTCCAACAA AGCCCTCCCAGCCCCCATCGAGAAAACCATCTCC AAAGCCAAAGGGCAGCCCCGAGAACCACAGGTGT ACACCCTGCCCCCATCCCGGGATGAGCTGACCAA GAACCAGGTCAGCCTGACCTGCCTGGTCAAAGGC TTCTATCCCAGCGACATCGCCGTGGAGTGGGAGA GCAATGGGCAGCCGGAGAACAACTACAAGACCAC GCCTCCCGTGCTGGACTCCGACGGCTCCTTCTTC CTCTACAGCAAGCTCACCGTGGACAAGAGCAGGT GGCAGCAGGGGAACGTCTTCTCATGCTCCGTGAT GCATGAGGCTCTGCACAACCACTACACGCAGAAG TCCCTCTCCCTGTCTCCGGGTAAATGA CAGTCTGCCCTGACTCAGCCTGCCTCCGTGTCTG GGTCTCCTGGACAGTCGATCACCATCTCCTGCAC TGGAACCAGCAGTGACGTTGGTGGTTATAACTAT GTCTCCTGGTACCAACAACACCCAGGCAAAGCCC CCAAACTCATGATTTATGATGTCAGTAAGCGGCC CTCAGGGGTTTCTAATCGCTTCTCTGGCTCCAAG TCTGGCAACACGGCCTCCCTGACCATCTCTGGGC TCCAGTCTGAGGACGAGGCTGATTATTACTGCAA CTCTTTGACAAGCATCAGCACTTGGGTGTTCGGC GGAGGGACCAAGCTGACCGTCCTAGGCCAGCCCA AGGCCGCCCCCTCCGTGACCCTGTTCCCCCCCTC CTCCGAGGAGCTGCAGGCCAACAAGGCCACCCTG GTGTGCCTGATCTCCGACTTCTACCCCGGCGCCG TGACCGTGGCCTGGAAGGCCGACTCCTCCCCCGT GAAGGCCGGCGTGGAGACCACCACCCCCTCCAAG CAGTCCAACAACAAGTACGCCGCCTCCTCCTACC TGTCCCTGACCCCCGAGCAGTGGAAGTCCCACCG GTCCTACTCCTGCCAGGTGACCCACGAGGGCTCC ACCGTGGAGAAGACCGTGGCCCCCACCGAGTGCT CCTGA | 655 |

TABLE 1-continued

Table of Exemplary Sequences

| Antibody Designation | Component Part | Sequence | SEQ ID NO |
|---|---|---|---|
| | | **Amino Acids** | |
| mAb10989 | HCVR | QVQLVQSGAEVKKPGASVKVSCKASGYIFTGYYMHWVRQAPGQGLEWMGWINPNSGGANYAQKFQGRVTLTRDTSITTVYMELSRLRFDDTAVYYCARGSRYDWNQNNWFDPWGQGTLVTVSS | 678 |
| | HCDR1 | GYIFTGYY | 680 |
| | HCDR2 | INPNSGGA | 682 |
| | HCDR3 | ARGSRYDWNQNNWFDP | 684 |
| | LCVR | QSALTQPASVSGSPGQSITISCTGTSSDVGTYNYVSWYQQHPGKAPKLMIFDVSNRPSGVSDRFSGSKSGNTASLTISGLQAEDEADYYCSSFTTSSTVVFGGGTKLTVL | 686 |
| | LCDR1 | SSDVGTYNY | 688 |
| | LCDR2 | DVS | |
| | LCDR3 | SSFTTSSTVV | 690 |
| | HC | QVQLVQSGAEVKKPGASVKVSCKASGYIFTGYYMHWVRQAPGQGLEWMGWINPNSGGANYAQKFQGRVTLTRDTSITTVYMELSRLRFDDTAVYYCARGSRYDWNQNNWFDPWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 692 |
| | LC | QSALTQPASVSGSPGQSITISCTGTSSDVGTYNYVSWYQQHPGKAPKLMIFDVSNRPSGVSDRFSGSKSGNTASLTISGLQAEDEADYYCSSFTTSSTVVFGGGTKLTVLGQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS | 694 |
| | | **Nucleic Acids** | |
| | HCVR | CAGGTGCAGCTGGTGCAGTCTGGGGCTGAGGTGAAGAAGCCTGGGGCCTCAGTGAAGGTCTCCTGCAAGGCTTCTGGATACATCTTCACCGGCTACTATATGCACTGGGTGCGACAGGCCCCTGGACAGGGGCTTGAGTGGATGGGATGGATCAACCCTAACAGTGGTGGCGCAAACTATGCACAGAAGTTTCAGGGCAGGGTCACCCTGACCAGGGACACGTCCATCACCACAGTCTACATGGAACTGAGCAGGCTGAGATTTGACGACACGGCCGTGTATTACTGTGCGAGAGGATCCCGGTATGACTGGAACCAGAACAACTGGTTCGACCCCTGGGGCCAGGGAACCCTGGTCACCGTCTCCTCA | 677 |
| | HCDR1 | GGATACATCTTCACCGGCTACTAT | 679 |
| | HCDR2 | ATCAACCCTAACAGTGGTGGCGCA | 681 |
| | HCDR3 | GCGAGAGGATCCCGGTATGACTGGAACCAGAACAACTGGTTCGACCCC | 683 |
| | LCVR | CAGTCTGCCCTGACTCAGCCTGCCTCCGTGTCTGGGTCTCCTGGACAGTCGATCACCATCTCCTGCACTGGAACCAGCAGTGACGTTGGTACTTATAACTATGTCTCCTGGTACCAACAACACCCAGGCAAAGCCCCCAAACTCATGATTTTTGATGTCAGTAATCGGCCCTCAGGGGTTTCTGATCGCTTCTCTGGCTCCAAGTCTGGCAACACGGCCTCCCTGACCATCTCTGGGCTCCAGGCTGAGGACGAGGCTGATTATTACTGCAGCTCATTTACAACCAGCAGCACTGTGGTTTTCGGCGGAGGGACCAAGCTGACCGTCCTA | 685 |
| | LCDR1 | AGCAGTGACGTTGGTACTTATAACTAT | 687 |
| | LCDR2 | GATGTCAGT | |
| | LCDR3 | AGCTCATTTACAACCAGCAGCACTGTGGTT | 689 |
| | HC | CAGGTGCAGCTGGTGCAGTCTGGGGCTGAGGTGAAGAAGCCTGGGGCCTCAGTGAAGGTCTCCTGCAAGGCTTCTGGATACATCTTCACCGGCTACTATATGCACTGGGTGCGACAGGCCCCTGGACAGGGGCTTGAGTGGATGGGATGGATCAACCCTAACAGTGGTGGCGCAAACTATGCACAGAAGTTTCAGGGCAGGGTC | 691 |

TABLE 1-continued

Table of Exemplary Sequences

| Antibody Designation | Component Part | Sequence | SEQ ID NO |
|---|---|---|---|
| | | ACCCTGACCAGGGACACGTCCATCACCACAGTCT<br>ACATGGAACTGAGCAGGCTGAGATTTGACGACAC<br>GGCCGTGTATTACTGTGCGAGAGGATCCCGGTAT<br>GACTGGAACCAGAACAACTGGTTCGACCCCTGGG<br>GCCAGGGAACCCTGGTCACCGTCTCCTCAGCCTC<br>CACCAAGGGCCCATCGGTCTTCCCCCTGGCACCC<br>TCCTCCAAGAGCACCTCTGGGGGCACAGCGGCCC<br>TGGGCTGCCTGGTCAAGGACTACTTCCCCGAACC<br>GGTGACGGTGTCGTGGAACTCAGGCGCCCTGACC<br>AGCGGCGTGCACACCTTCCCGGCTGTCCTACAGT<br>CCTCAGGACTCTACTCCCTCAGCAGCGTGGTGAC<br>CGTGCCCTCCAGCAGCTTGGGCACCCAGACCTAC<br>ATCTGCAACGTGAATCACAAGCCCAGCAACACCA<br>AGGTGGACAAGAAAGTTGAGCCCAAATCTTGTGA<br>CAAAACTCACACATGCCCACCGTGCCCAGCACCT<br>GAACTCCTGGGGGGACCGTCAGTCTTCCTCTTCC<br>CCCCAAAACCCAAGGACACCCTCATGATCTCCCG<br>GACCCCTGAGGTCACATGCGTGGTGGTGGACGTG<br>AGCCACGAAGACCCTGAGGTCAAGTTCAACTGGT<br>ACGTGGACGGCGTGGAGGTGCATAATGCCAAGAC<br>AAAGCCGCGGGAGGAGCAGTACAACAGCACGTAC<br>CGTGTGGTCAGCGTCCTCACCGTCCTGCACCAGG<br>ACTGGCTGAATGGCAAGGAGTACAAGTGCAAGGT<br>CTCCAACAAAGCCCTCCCAGCCCCCATCGAGAAA<br>ACCATCTCCAAAGCCAAAGGGCAGCCCCGAGAAC<br>CACAGGTGTACACCCTGCCCCCATCCCGGGATGA<br>GCTGACCAAGAACCAGGTCAGCCTGACCTGCCTG<br>GTCAAAGGCTTCTATCCCAGCGACATCGCCGTGG<br>AGTGGGAGAGCAATGGGCAGCCGGAGAACAACTA<br>CAAGACCACGCCTCCCGTGCTGGACTCCGACGGC<br>TCCTTCTTCCTCTACAGCAAGCTCACCGTGGACA<br>AGAGCAGGTGGCAGCAGGGGAACGTCTTCTCATG<br>CTCCGTGATGCATGAGGCTCTGCACAACCACTAC<br>ACGCAGAAGTCCCTCTCCCTGTCTCCGGGTAAAT<br>GA | |
| | | LCCAGTCTGCCCTGACTCAGCCTGCCTCCGTGTCTG<br>GGTCTCCTGGACAGTCGATCACCATCTCCTGCAC<br>TGGAACCAGCAGTGACGTTGGTACTTATAACTAT<br>GTCTCCTGGTACCAACAACACCCAGGCAAAGCCC<br>CCAAACTCATGATTTTTGATGTCAGTAATCGGCC<br>CTCAGGGGTTTCTGATCGCTTCTCTGGCTCCAAG<br>TCTGGCAACACGGCCTCCCTGACCATCTCTGGGC<br>TCCAGGCTGAGGACGAGGCTGATTATTACTGCAG<br>CTCATTTACAACCAGCAGCACTGTGGTTTTCGGC<br>GGAGGGACCAAGCTGACCGTCCTAGGCCAGCCCA<br>AGGCCGCCCCCTCCGTGACCCTGTTCCCCCCCTC<br>CTCCGAGGAGCTGCAGGCCAACAAGGCCACCCTG<br>GTGTGCCTGATCTCCGACTTCTACCCCGGCGCCG<br>TGACCGTGGCCTGGAAGGCCGACTCCTCCCCCGT<br>GAAGGCCGGCGTGGAGACCACCACCCCCTCCAAG<br>CAGTCCAACAACAAGTACGCCGCCTCCTCCTACC<br>TGTCCCTGACCCCCGAGCAGTGGAAGTCCCACCG<br>GTCCTACTCCTGCCAGGTGACCCACGAGGGCTCC<br>ACCGTGGAGAAGACCGTGGCCCCCACCGAGTGCT<br>CCTGA | 693 |

Administration of Antibodies

The present invention provides methods for administering an anti-CoV-S antigen-binding protein of the present invention, e.g., those of Table 4, comprising introducing the antigen-binding protein into the body of a subject (e.g., a human). For example, the method comprises piercing the body of the subject with a needle of a syringe and injecting the antigen-binding protein into the body of the subject, e.g., into the vein, artery, tumor, muscular tissue or subcutis of the subject.

The present invention provides a vessel (e.g., a plastic or glass vial, e.g., with a cap or a chromatography column, hollow bore needle or a syringe cylinder) comprising an anti-CoV-S antigen-binding protein of the present invention, e.g., those of Table 4.

The present invention also provides an injection device comprising one or more antigen-binding proteins (e.g., antibody or antigen-binding fragment) that bind specifically to CoV-S, e.g., those of Table 4, or a pharmaceutical composition thereof. The injection device may be packaged into a kit. An injection device is a device that introduces a substance into the body of a subject via a parenteral route, e.g., intramuscular, subcutaneous or intravenous. For example, an injection device may be a syringe (e.g., pre-filled with the pharmaceutical composition, such as an auto-injector) which, for example, includes a cylinder or barrel for holding fluid to be injected (e.g., comprising the antibody or fragment or a pharmaceutical composition thereof), a needle for piecing skin and/or blood vessels for injection of the fluid; and a plunger for pushing the fluid out of the cylinder and through the needle bore. In an embodiment of the invention, an injection device that comprises an antigen-binding protein, e.g., an antibody or antigen-binding fragment thereof, from a combination of the present invention, or a pharmaceutical composition thereof is an intravenous (IV) injection device. Such a device can include the antigen-binding protein or a pharmaceutical composition thereof in a cannula or trocar/needle which may be attached to a tube which may be attached to a bag or reservoir for holding fluid (e.g., saline) introduced into the body of the subject through the cannula or trocar/needle. The antibody or fragment or a pharmaceutical composition thereof may, in an embodiment of the invention, be introduced into the device once the trocar and cannula are inserted into the vein of a subject and the trocar is removed from the inserted cannula. The IV device may, for example, be inserted into a peripheral vein (e.g., in the hand or arm); the superior vena cava or inferior vena cava, or within the right atrium of the heart (e.g., a central IV); or into a subclavian, internal jugular, or a femoral vein and, for example, advanced toward the heart until it reaches the superior vena cava or right atrium (e.g., a central venous line). In an embodiment of the invention, an injection device is an autoinjector; a jet injector or an external infusion pump. A jet injector uses a high-pressure narrow jet of liquid which penetrate the epidermis to introduce the antibody or fragment or a pharmaceutical composition thereof to a subject's body. External infusion pumps are medical devices that deliver the antibody or fragment or a pharmaceutical composition thereof into a subject's body in controlled amounts. External infusion pumps may be powered electrically or mechanically. Different pumps operate in different ways, for example, a syringe pump holds fluid in the reservoir of a syringe, and a moveable piston controls fluid delivery, an elastomeric pump holds fluid in a stretchable balloon reservoir, and pressure from the elastic walls of the balloon drives fluid delivery. In a peristaltic pump, a set of rollers pinches down on a length of flexible tubing, pushing fluid forward. In a multi-channel pump, fluids can be delivered from multiple reservoirs at multiple rates.

Preparation of Human Antibodies

Methods for generating human antibodies in transgenic mice are known in the art. Any such known methods can be used in the context of the present invention to make human antibodies that specifically bind to CoV-S. An immunogen comprising any one of the following can be used to generate antibodies to CoV-S. In certain embodiments of the invention, the antibodies of the invention are obtained from mice immunized with a full length, native CoV-S, or with a live attenuated or inactivated virus, or with DNA encoding the protein or fragment thereof. Alternatively, the CoV-S protein or a fragment thereof may be produced using standard biochemical techniques and modified and used as immunogen. In one embodiment of the invention, the immunogen is a recombinantly produced CoV-S protein or fragment thereof. In certain embodiments of the invention, the immunogen may be a CoV-S polypeptide vaccine. In certain embodiments, one or more booster injections may be administered. In certain embodiments, the immunogen may be a recombinant CoV-S polypeptide expressed in *E. coli* or in any other eukaryotic or mammalian cells such as Chinese hamster ovary (CHO) cells.

Using VELOCIMMUNE® technology (see, for example, U.S. Pat. No. 6,596,541, Regeneron Pharmaceuticals, VELOCIMMUNE®) or any other known method for generating monoclonal antibodies, high affinity chimeric antibodies to CoV-S can be initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

Anti-Coronavirus Spike Protein Antibodies Comprising Fc Variants

According to certain embodiments of the present invention, anti-CoV-S antigen-binding proteins, e.g., antibodies or antigen-binding fragments, are provided comprising an Fc domain comprising one or more mutations, which, for example, enhance or diminish antibody binding to the FcRn receptor, e.g., at acidic pH as compared to neutral pH. For example, the present invention includes anti-CoV-S antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., A, W, H, F or Y [N434A, N434W, N434H, N434F or N434Y]); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P). In yet another embodiment, the modification comprises a 265A (e.g., D265A) and/or a 297A (e.g., N297A) modification.

For example, the present invention includes anti-CoV-S antigen-binding proteins, e.g., antibodies or antigen-binding fragments, comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); 257I and 311I (e.g., P257I and Q311I); 257I and 434H (e.g., P257I and N434H); 376V and 434H (e.g., D376V and N434H); 307A, 380A and 434A (e.g., T307A, E380A and N434A); and 433K and 434F (e.g., H433K and N434F).

Anti-CoV-S antigen-binding proteins, e.g., antibodies and antigen-binding fragments thereof, that comprise a $V_H$ and/or $V_L$ as set forth herein comprising any possible combinations of the foregoing Fc domain mutations, are contemplated within the scope of the present invention.

The present invention also includes anti-CoV-S antigen-binding proteins, antibodies or antigen-binding fragments, comprising a $V_H$ set forth herein and a chimeric heavy chain constant ($C_H$) region, wherein the chimeric $C_H$ region comprises segments derived from the $C_H$ regions of more than one immunoglobulin isotype. For example, the antibodies of the invention may comprise a chimeric $C_H$ region comprising part or all of a $C_H2$ domain derived from a human IgG1, human IgG2 or human IgG4 molecule, combined with part or all of a $C_H3$ domain derived from a human IgG1, human IgG2 or human IgG4 molecule. According to certain embodiments, the antibodies of the invention comprise a chimeric $C_H$ region having a chimeric hinge region. For example, a chimeric hinge may comprise an "upper hinge" amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 or a human IgG4 hinge region. According to certain embodiments, the chimeric hinge region comprises amino acid residues derived from a human IgG1 or a human IgG4 upper hinge and amino acid residues derived from a human IgG2 lower hinge. An antibody comprising a chimeric $C_H$ region as described herein may, in certain embodiments, exhibit modified Fc effector functions without adversely affecting the therapeutic or pharmacokinetic properties of the antibody. (See, e.g., WO2014/022540).

Immunoconjugates

The invention encompasses an anti-CoV-S antigen-binding proteins, e.g., antibodies or antigen-binding fragments, conjugated to another moiety, e.g., a therapeutic moiety (an "immunoconjugate"), such as a toxoid or an anti-viral drug to treat influenza virus infection. In an embodiment of the invention, an anti-CoV-S antibody or fragment is conjugated to any of the further therapeutic agents set forth herein. As used herein, the term "immunoconjugate" refers to an antigen-binding protein, e.g., an antibody or antigen-binding fragment, which is chemically or biologically linked to a radioactive agent, a cytokine, an interferon, a target or reporter moiety, an enzyme, a peptide or protein or a therapeutic agent. The antigen-binding protein may be linked to the radioactive agent, cytokine, interferon, target or reporter moiety, enzyme, peptide or therapeutic agent at any location along the molecule so long as it is able to bind its target (CoV-S). Examples of immunoconjugates include antibody-drug conjugates and antibody-toxin fusion proteins. In one embodiment of the invention, the agent may be a second, different antibody that binds specifically to CoV-S. The type of therapeutic moiety that may be conjugated to the anti-CoV-S antigen-binding protein (e.g., antibody or fragment) will take into account the condition to be treated and the desired therapeutic effect to be achieved. See, e.g., Arnon et al., "Monoclonal Antibodies For Immunotargeting Of Drugs In Cancer Therapy", Monoclonal Antibodies And Cancer Therapy, Reisfeld et al. (eds.), pp. 243-56 (Alan R. Liss, Inc. 1985); Hellstrom et al., "Antibodies For Drug Delivery", Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", Monoclonal Antibodies 1984: Biological And Clinical Applications, Pinchera et al. (eds.), pp. 475-506 (1985); "Analysis, Results, And Future Prospective Of The Therapeutic Use Of Radiolabeled Antibody In Cancer Therapy", Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62: 119-58 (1982).

Multi-Specific Antibodies

The present invention includes anti-CoV-S antigen-binding proteins, e.g., antibodies and antigen-binding fragments thereof, as well as methods of use thereof and methods of making such antigen-binding proteins. The term "anti-CoV-S" antigen-binding proteins, e.g., antibodies or antigen-binding fragments, includes multispecific (e.g., bispecific or biparatopic) molecules that include at least one first antigen-binding domain that specifically binds to CoV-S (e.g., an antigen-binding domain from an antibody of Table 4) and at least one second antigen-binding domain that binds to a different antigen or to an epitope in CoV-S which is different from that of the first antigen-binding domain. In some embodiments, the first antigen-binding domain and the second antigen-binding domain are both selected from the antigen-binding domains of Table 4. In an embodiment of the invention, the first and second epitopes overlap. In another embodiment of the invention, the first and second epitopes do not overlap. For example, in an embodiment of the invention, a multispecific antibody is a bispecific IgG antibody (e.g., IgG1 or IgG4) that includes a first antigen-binding domain that binds specifically to CoV-S including the heavy and light immunoglobulin chain of an antibody of Table 4, and a second antigen-binding domain that binds specifically to a different epitope of CoV-S. In some embodiments, a bispecific IgG antibody (e.g., IgG1 or IgG4) includes a first antigen-binding domain that binds specifically to CoV-S and a second binding domain that binds to a host cell protein, e.g., ACE2 or TMPRSS2.

The antibodies of Table 4 include multispecific molecules, e.g., antibodies or antigen-binding fragments, that include the CDR-Hs and CDR-Ls, $V_H$ and $V_L$, or HC and LC of those antibodies, respectively (including variants thereof as set forth herein).

In an embodiment of the invention, an antigen-binding domain that binds specifically to CoV-S, which may be included in a multispecific molecule, comprises:

(1)

(i) a heavy chain variable domain sequence that comprises CDR-H1, CDR-H2, and CDR-H3 amino acid sequences set forth in Table 4, and (ii) a light chain variable domain sequence that comprises CDR-L1, CDR-L2, and CDR-L3 amino acid sequences set forth in Table 4;

or, (2)

(i) a heavy chain variable domain sequence comprising an amino acid sequence set forth in Table 4, and (ii) a light chain variable domain sequence comprising an amino acid sequence set forth in Table 4;

or, (3)

(i) a heavy chain immunoglobulin sequence comprising an amino acid sequence set forth in Table 4, and (ii) a light chain immunoglobulin sequence comprising an amino acid sequence set forth in Table 4.

In an embodiment of the invention, the multispecific antibody or fragment includes more than two different binding specificities (e.g., a trispecific molecule), for example, one or more additional antigen-binding domains which are the same or different from the first and/or second antigen-binding domain.

In one embodiment of the invention, a bispecific antigen-binding fragment comprises a first scFv (e.g., comprising $V_H$ and $V_L$ sequences of Table 4) having binding specificity for a first epitope (e.g., CoV-S) and a second scFv having binding specificity for a second, different epitope. For example, in an embodiment of the invention, the first and second scFv are tethered with a linker, e.g., a peptide linker (e.g., a GS linker such as (GGGGS), (SEQ ID NO: 834) wherein n is, for example, 1, 2, 3, 4, 5, 6, 7, 8, 9 or 10). Other bispecific antigen-binding fragments include an $F(ab)_2$ of a bispecific IgG antibody which comprises the heavy and light chain CDRs of Table 4 and of another antibody that binds to a different epitope.

Therapeutic Methods

The present invention provides methods for treating or preventing viral infection (e.g., coronavirus infection) by administering a therapeutically effective amount of anti-CoV-S antigen-binding protein, e.g., antibody or antigen-binding fragment, (e.g., of Table 4) to a subject (e.g., a human) in need of such treatment or prevention.

Coronavirus infection may be treated or prevented, in a subject, by administering an anti-CoV-S antigen-binding protein of the present invention to a subject.

An effective or therapeutically effective dose of anti-CoV-S antigen-binding protein, e.g., antibody or antigen-binding fragment (e.g., of Table 4), for treating or preventing a viral infection refers to the amount of the antibody or fragment sufficient to alleviate one or more signs and/or symptoms of the infection in the treated subject, whether by inducing the regression or elimination of such signs and/or symptoms or by inhibiting the progression of such signs and/or symptoms. The dose amount may vary depending upon the age and the size of a subject to be administered, target disease, conditions, route of administration, and the like. In an embodiment of the invention, an effective or therapeutically effective dose of antibody or antigen-binding fragment thereof of the present invention, for treating or preventing viral infection, e.g., in an adult human subject, is about 0.01 to about 200 mg/kg, e.g., up to about 150 mg/kg. In an embodiment of the invention, the dosage is up to about 10.8 or 11 grams (e.g., about 1, 2, 3, 4, 5, 6, 7, 8, 9, 10 or 11 grams). Depending on the severity of the infection, the frequency and the duration of the treatment can be adjusted. In certain embodiments, the antigen-binding protein of the present invention can be administered at an initial dose, followed by one or more secondary doses. In certain embodiments, the initial dose may be followed by administration of a second or a plurality of subsequent doses of antibody or antigen-binding fragment thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

As used herein, the term "subject" refers to a mammal (e.g., rat, mouse, cat, dog, cow, pig, sheep, horse, goat, rabbit), preferably a human, for example, in need of prevention and/or treatment of a disease or disorder such as viral infection or cancer. The subject may have a viral infection, e.g., an influenza infection, or be predisposed to developing an infection. Subjects predisposed to developing an infection, or subjects who may be at elevated risk for contracting an infection (e.g., of coronavirus or influenza virus), include subjects with compromised immune systems because of autoimmune disease, subjects receiving immunosuppressive therapy (for example, following organ transplant), subjects afflicted with human immunodeficiency syndrome (HIV) or acquired immune deficiency syndrome (AIDS), subjects with forms of anemia that deplete or destroy white blood cells, subjects receiving radiation or chemotherapy, or subjects afflicted with an inflammatory disorder. Additionally, subjects of very young (e.g., 5 years of age or younger) or old age (e.g., 65 years of age or older) are at increased risk. Moreover, a subject may be at risk of contracting a viral infection due to proximity to an outbreak of the disease, e.g. subject resides in a densely-populated city or in close proximity to subjects having confirmed or suspected infections of a virus, or choice of employment, e.g. hospital worker, pharmaceutical researcher, traveler to infected area, or frequent flier.

"Treat" or "treating" means to administer an anti-CoV-S antigen-binding protein, e.g., antibody or antigen-binding fragment of the present invention (e.g., of Table 4), to a subject having one or more signs or symptoms of a disease or infection, e.g., viral infection, for which the antigen-binding protein is effective when administered to the subject at an effective or therapeutically effective amount or dose (as discussed herein).

The present invention also encompasses prophylactically administering an anti-CoV-S antigen-binding protein, e.g., antibody or antigen-binding fragment thereof of the present invention (e.g., of Table 4), to a subject who is at risk of viral infection so as to prevent such infection. Passive antibody-based immunoprophylaxis has proven an effective strategy for preventing subject from viral infection. See e.g., Berry et al., Passive broad-spectrum influenza immunoprophylaxis. Influenza Res Treat. 2014; 2014:267594. Epub 2014 Sep. 22; and Jianqiang et al., Passive immune neutralization strategies for prevention and control of influenza A infections, Immunotherapy. 2012 February; 4(2): 175-186; Prabhu et al., Antivir Ther. 2009; 14(7):911-21, Prophylactic and therapeutic efficacy of a chimeric monoclonal antibody specific for H5 hemagglutinin against lethal H5N1 influenza. "Prevent" or "preventing" means to administer an anti-CoV-S antigen-binding protein, e.g., antibody or antigen-binding fragment of the present invention (e.g., of Table 4), to a subject to inhibit the manifestation of a disease or infection (e.g., viral infection) in the body of a subject, for which the antigen-binding protein is effective when administered to the subject at an effective or therapeutically effective amount or dose (as discussed herein).

In an embodiment of the invention, a sign or symptom of a viral infection in a subject is survival or proliferation of virus in the body of the subject, e.g., as determined by viral titer assay (e.g., coronavirus propagation in embryonated chicken eggs or coronavirus spike protein assay). Other signs and symptoms of viral infection are discussed herein.

As noted above, in some embodiments the subject may be a non-human animal, and the antigen-binding proteins (e.g., antibodies and antigen-binding fragments) discussed herein may be used in a veterinary context to treat and/or prevent disease in the non-human animals (e.g., cats, dogs, pigs, cows, horses, goats, rabbits, sheep, and the like).

The present invention provides a method for treating or preventing viral infection (e.g., coronavirus infection) or for inducing the regression or elimination or inhibiting the progression of at least one sign or symptom of viral infection such as:

- fever or feeling feverish/chills;
- cough;
- sore throat;
- runny or stuffy nose;
- sneezing;
- muscle or body aches;
- headaches;
- fatigue (tiredness);
- vomiting;
- diarrhea;
- respiratory tract infection;
- chest discomfort;
- shortness of breath;
- bronchitis; and/or
- pneumonia, which sign or symptom is secondary to viral infection, in a subject in need thereof (e.g., a human), by administering a therapeutically effective amount of anti-CoV-S antigen-binding protein (e.g., of Table 4) to the subject, for example, by injection of the protein into the body of the subject.

Combinations and Pharmaceutical Compositions

To prepare pharmaceutical compositions of the anti-CoV-S antigen-binding proteins, e.g., antibodies and antigen-binding fragments thereof (e.g., of Table 4), antigen-binding protein is admixed with a pharmaceutically acceptable carrier or excipient. See, e.g., Remington's Pharmaceutical Sciences and U.S. Pharmacopeia: National Formulary, Mack Publishing Company, Easton, Pa. (1984); Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y. In an embodiment of the invention, the pharmaceutical composition is sterile. Such compositions are part of the present invention.

The scope of the present invention includes desiccated, e.g., freeze-dried, compositions comprising an anti-CoV-S antigen-binding proteins, e.g., antibody or antigen-binding fragment thereof (e.g., of Table 4), or a pharmaceutical composition thereof that includes a pharmaceutically acceptable carrier but substantially lacks water.

In a further embodiment of the invention, a further therapeutic agent that is administered to a subject in association with an anti-CoV-S antigen-binding protein, e.g., antibody or antigen-binding fragment thereof (e.g., of Table 4), disclosed herein is administered to the subject in accordance with the Physicians' Desk Reference 2003 (Thomson Healthcare; 57th edition (Nov. 1, 2002)).

The mode of administration can vary. Routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal or intra-arterial.

The present invention provides methods for administering an anti-CoV-S antigen-binding protein, e.g., antibody or antigen-binding fragment thereof (e.g., of Table 4), comprising introducing the protein into the body of a subject. For example, the method comprises piercing the body of the subject with a needle of a syringe and injecting the antigen-binding protein into the body of the subject, e.g., into the vein, artery, tumor, muscular tissue or subcutis of the subject.

The present invention provides a vessel (e.g., a plastic or glass vial, e.g., with a cap or a chromatography column, hollow bore needle or a syringe cylinder) comprising any of the anti-CoV-S antigen-binding proteins, e.g., antibodies or antigen-binding fragments thereof (e.g., of Table 4), polypeptides (e.g., an HC, LC, $V_H$ or $V_L$ of Table 4) or polynucleotides (e.g., of Table 5) or vectors set forth herein or a pharmaceutical composition thereof comprising a pharmaceutically acceptable carrier.

In an embodiment of the present disclosure, an anti-CoV-S antigen-binding protein, e.g., antibody or antigen-binding fragment thereof of the present invention (e.g., of Table 4), is administered in association with one or more further therapeutic agents. A further therapeutic agent includes, but is not limited to: an anti-inflammatory agent, an antimalarial agent, a second antibody or antigen-binding fragment thereof that specifically binds TMPRSS2, and a second antibody or antigen-binding fragment thereof that specifically binds to CoV-S. In some embodiments, an antimalarial agent is chloroquine or hydroxychloroquine. In some embodiments, an anti-inflammatory agent is an antibody such as sarilumab, tocilizumab, or gimsilumab. In some embodiments, the further therapeutic agent is a second antibody or antigen-binding fragment disclosed herein, e.g., of Table 4. In certain embodiments, one, two, three, four, or more antibodies, or antigen-binding fragments thereof, of Table 4 can be administered in combination (e.g., concurrently or sequentially). Particular combinations of antibodies of Table 4 are listed in Table 2 (Table of Exemplary Antibody Combinations), below (each number representing a specific combination, e.g., mAb10989 and mAb10987 is Combination 1, mAb10989 and mAb10934 is Combination 2, and so on). In some embodiments, a combination of antibodies can be selected from among those binding to different epitope clusters. For example, certain antibodies described herein belong to epitope clusters as follows: Cluster 1, mAb10987, mAb10922, mAb10936, and mAb10934; Cluster 2, mAb10989, mAb10977, and mAb10933; Cluster 3, mAb10920; Cluster 4, mAb10954, mAb10986, and mAb10964; and Cluster 5, mAb10984. Thus, a combination of two antibodies can be selected from, for example, Cluster 1 and Cluster 2, Cluster 1 and Cluster 3, Cluster 1 and Cluster 4, Cluster 1 and Cluster 5, Cluster 2 and Cluster 3, Cluster 2 and Cluster 4, Cluster 2 and Cluster 5, Cluster 3 and Cluster 4, Cluster 3 and Cluster 5, and Cluster 4 and Cluster 5. In some embodiments, an antibody that specifically binds TMPRSS2 is H1H7017N, as described in International Patent Pub. No. WO/2019/147831.

TABLE 2

Table of Exemplary Antibody Combinations

| | mAb10989 | mAb10987 | mAb10934 | mAb10933 | mAb10920 | mAb10922 |
|---|---|---|---|---|---|---|
| mAb10989 | X | 1 | 2 | 3 | 4 | 5 |
| mAb10987 | 12 | X | 13 | 14 | 15 | 16 |
| mAb10934 | 23 | 24 | X | 25 | 26 | 27 |
| mAb10933 | 34 | 35 | 36 | X | 37 | 38 |
| mAb10920 | 45 | 46 | 47 | 48 | X | 49 |
| mAb10922 | 56 | 57 | 58 | 59 | 60 | X |
| mAb10936 | 67 | 68 | 69 | 70 | 71 | 72 |
| mAb10954 | 78 | 79 | 80 | 81 | 82 | 83 |
| mAb10964 | 89 | 90 | 91 | 92 | 93 | 94 |
| mAb10977 | 100 | 101 | 102 | 103 | 104 | 105 |
| mAb10984 | 111 | 112 | 113 | 114 | 115 | 116 |
| mAb10986 | 122 | 123 | 124 | 125 | 126 | 127 |

| | mAb10936 | mAb10954 | mAb10964 | mAb10977 | mAb10984 | mAb10986 |
|---|---|---|---|---|---|---|
| mAb10989 | 6 | 7 | 8 | 9 | 10 | 11 |
| mAb10987 | 17 | 18 | 19 | 20 | 21 | 22 |
| mAb10934 | 28 | 29 | 30 | 31 | 32 | 33 |
| mAb10933 | 39 | 40 | 41 | 42 | 43 | 44 |
| mAb10920 | 50 | 51 | 52 | 53 | 54 | 55 |
| mAb10922 | 61 | 62 | 63 | 64 | 65 | 66 |
| mAb10936 | X | 73 | 74 | 75 | 76 | 77 |
| mAb10954 | 84 | X | 85 | 86 | 87 | 88 |
| mAb10964 | 95 | 96 | X | 97 | 98 | 99 |
| mAb10977 | 106 | 107 | 108 | X | 109 | 110 |
| mAb10984 | 117 | 118 | 119 | 120 | X | 121 |
| mAb10986 | 128 | 129 | 130 | 131 | 132 | X |

In some embodiments, anti-CoV-S antigen-binding proteins (e.g., anti-SARS-CoV-2-S antibodies or antigen-binding fragments thereof) from different human donors may be combined. The present invention includes a composition comprising two (or more) anti-SARS-CoV-2-S antibodies or antigen-binding fragments comprising variable domains from human subjects, wherein the two (or more) antibodies or antigen-binding fragments are derived from different subjects (e.g., two different human subjects). Antibody variable regions derived from human B cells are discussed, e.g., in Examples 1 and 2 (Table 6), which describes that variable domains cloned from such B cells are combined with a constant region not from those B cells to produce hybrid antibodies. The source (Donor) of such antibody variable regions is shown in Table 3 (Table of Exemplary Human-Derived Antibody Variable Regions), below. In some embodiments, a composition may comprise a combination of an antibody or antigen-binding fragment thereof with variable domains derived from donor 1 and an antibody or antigen-binding fragment thereof with variable domains derived from donor 2. In some embodiments, a composition may comprise a combination of an antibody or antigen-binding fragment thereof with variable domains derived from donor 1 and an antibody or antigen-binding fragment thereof with variable domains derived from donor 3. In some embodiments, a composition may comprise a combination of an antibody or antigen-binding fragment thereof with variable domains derived from donor 2 and an antibody or antigen-binding fragment thereof with variable domains derived from donor 3. In some embodiments, a composition may comprise a combination of mAb10987 (e.g., an antibody comprising the CDRs, the variable regions, or the heavy and light chain sequences shown in Table 4) from Donor 1, and mAb10989 (e.g., an antibody comprising the CDRs, the variable regions, or the heavy and light chain sequences shown in Table 4) from Donor 3.

TABLE 3

Table of Exemplary Human-Derived Antibody Variable Regions

| mAb | Donor |
|---|---|
| mAb10954 | Donor 3 |
| mAb10955 | Donor 3 |
| mAb10956 | Donor 3 |
| mAb10957 | Donor 3 |
| mAb10964 | Donor 1 |
| mAb10965 | Donor 2 |
| mAb10966 | Donor 3 |
| mAb10967 | Donor 3 |
| mAb10970 | Donor 1 |
| mAb10971 | Donor 1 |
| mAb10977 | Donor 1 |
| mAb10984 | Donor 1 |
| mAb10985 | Donor 1 |
| mAb10986 | Donor 1 |
| mAb10987 | Donor 1 |
| mAb10988 | Donor 3 |
| mAb10989 | Donor 3 |
| mAb10969 | Donor 1 |

In some embodiments, the further therapeutic agent is an anti-viral drug and/or a vaccine. As used herein, the term “anti-viral drug” refers to any anti-infective drug or therapy used to treat, prevent, or ameliorate a viral infection in a subject. The term “anti-viral drug” includes, but is not limited to a cationic steroid antimicrobial, leupeptin, aprotinin, ribavirin, or interferon-alpha2b. Methods for treating or preventing virus (e.g., coronavirus) infection in a subject in need of said treatment or prevention by administering an antibody or antigen-binding fragment of Table 4 in association with a further therapeutic agent are part of the present invention.

For example, in an embodiment of the invention, the further therapeutic agent is a vaccine, e.g., a coronavirus vaccine. In an embodiment of the invention, a vaccine is an inactivated/killed virus vaccine, a live attenuated virus vaccine or a virus subunit vaccine.

For example, in an embodiment of the invention, the further therapeutic agent is:
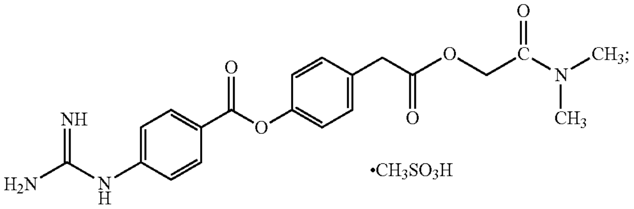
(camostat mesylate)
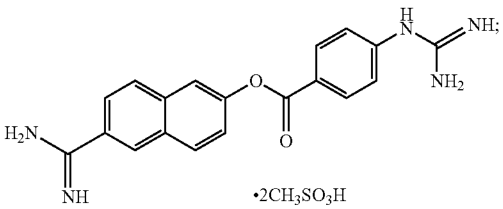
(nafamostat mesylate)
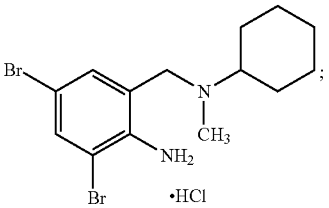
(bromhexine hydrochloride (BHH))
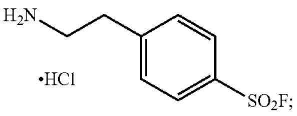
(4-(2-aminomethyl)benzene-sulfonyl fluoride hydrochloride (AEBSF))
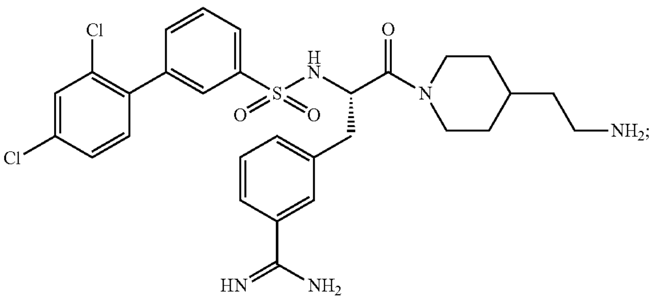
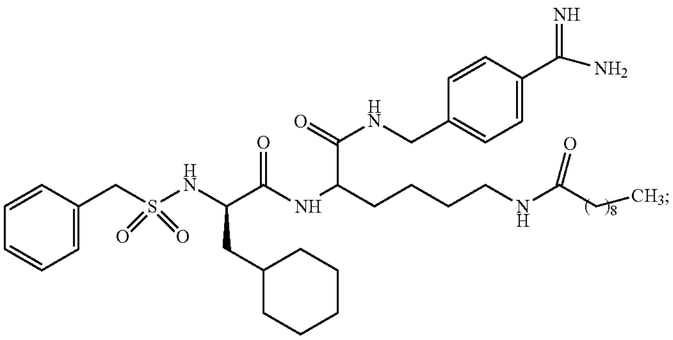
or -continued

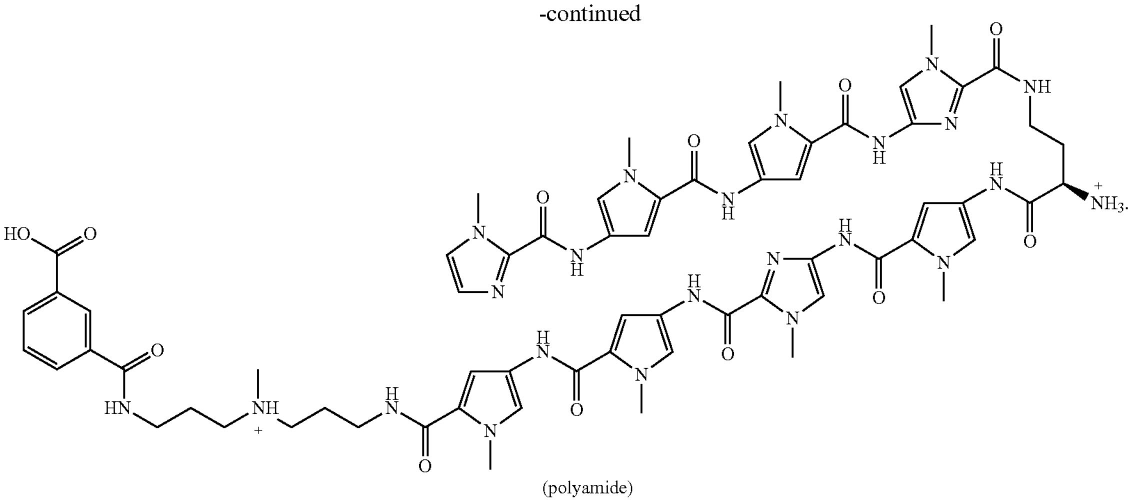

(polyamide)

See Shen et al. Biochimie 142: 1-10 (2017).

In an embodiment of the invention, the anti-viral drug is an antibody or antigen-binding fragment that binds specifically to coronavirus, e.g., SARS-CoV-2, SARS-CoV, or MERS-CoV. Exemplary anti-CoV-S antibodies include, but are not limited to: H4sH15188P; H1H15188P; H1H15211P; H1H15177P; H4sH15211P; H1H15260P2; H1H15259P2; H1H15203P; H4sH15260P2; H4sH15231P2; H1H15237P2; H1H15208P; H1H15228P2; H1H15233P2; H1H15264P2; H1H15231P2; H1H15253P2; H1H15215P; and H1H15249P2, as set forth in International patent application publication no. WO/2015/179535, or an antigen-binding fragment thereof, e.g., wherein the antibody or fragment comprises a light chain immunoglobulin that includes CDR-L1, CDR-L2 and CDR-L3 (e.g., the $V_L$ or light chain thereof); and a heavy chain that includes CDR-H1, CDR-H2 and CDR-H3 (e.g., the $V_H$ or heavy chain thereof) of any of the foregoing anti-CoV-S antibodies.

In a certain embodiment of the invention, the further therapeutic agent is not aprotinin, leupeptin, a cationic steroid antimicrobial, an influenza vaccine (e.g., killed, live, attenuated whole virus or subunit vaccine), or an antibody against influenza virus (e.g., an anti-hemagglutinin antibody).

The term "in association with" indicates that the components, an anti-CoV-S antigen-binding protein, e.g., antibody or antigen-binding fragment thereof of the present invention, along with another agent, can be formulated into a single composition, e.g., for simultaneous delivery, or formulated separately into two or more compositions (e.g., a kit). Each component can be administered to a subject at a different time than when the other component is administered; for example, each administration may be given non-simultaneously (e.g., separately or sequentially) at intervals over a given period of time. Moreover, the separate components may be administered to a subject by the same or by a different route (e.g., wherein an anti-CoV-S antibody or antigen-binding fragment thereof.

Kits

Further provided are kits comprising one or more components that include, but are not limited to, an anti-CoV-S antigen-binding protein, e.g., an antibody or antigen-binding fragment as discussed herein (e.g., of Table 4), in association with one or more additional components including, but not limited to, a further therapeutic agent, as discussed herein. The antigen-binding protein and/or the further therapeutic agent can be formulated as a single composition or separately in two or more compositions, e.g., with a pharmaceutically acceptable carrier, in a pharmaceutical composition.

In one embodiment of the invention, the kit includes an anti-CoV-S antigen-binding protein, e.g., an antibody or antigen-binding fragment thereof of the invention (e.g., of Table 4), or a pharmaceutical composition thereof in one container (e.g., in a sterile glass or plastic vial) and a further therapeutic agent in another container (e.g., in a sterile glass or plastic vial).

In another embodiment, the kit comprises a combination of the invention, including an anti-CoV-S antigen-binding protein, e.g., antibody or antigen-binding fragment thereof of the invention (e.g., of Table 4), or pharmaceutical composition thereof in combination with one or more further therapeutic agents formulated together, optionally, in a pharmaceutical composition, in a single, common container.

If the kit includes a pharmaceutical composition for parenteral administration to a subject, the kit can include a device (e.g., an injection device) for performing such administration. For example, the kit can include one or more hypodermic needles or other injection devices as discussed above containing the anti-CoV-S antigen-binding protein, e.g., antibody or antigen-binding fragment thereof of the present invention (e.g., of Table 4).

The kit can include a package insert including information concerning the pharmaceutical compositions and dosage forms in the kit. Generally, such information aids patients and physicians in using the enclosed pharmaceutical compositions and dosage forms effectively and safely. For example, the following information regarding a combination of the invention may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references, manufacturer/distributor information and patent information.

Diagnostic Uses of the Antibodies

The anti-CoV-S antigen-binding proteins, e.g., antibodies or antigen-binding fragments thereof of the present invention (e.g., of Table 4), may be used to detect and/or measure CoV-S in a sample. Exemplary assays for CoV-S may include, e.g., contacting a sample with an anti-CoV-S antigen-binding protein of the invention, wherein the anti-CoV-S antigen-binding protein is labeled with a detectable label or reporter molecule or used as a capture ligand to selectively isolate CoV-S from samples. The presence of an anti-CoV-S antigen-binding protein complexed with CoV-S indicates the presence of CoV-S in the sample. Alternatively, an unlabeled anti-CoV-S antibody can be used in combination with a secondary antibody which is itself detectably labeled. The detectable label or reporter molecule can be a radioisotope, such as $^{3}H$, $^{14}C$, $^{32}P$, $^{35}S$, or $^{125}I$; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure CoV-S in a sample include neutralization assays, enzyme-linked immunosorbent assay (ELISA), radioimmunoassay (RIA), and fluorescence-activated cell sorting (FACS). Thus, the present invention includes a method for detecting the presence of spike protein polypeptide in a sample comprising contacting the sample with an anti-CoV-S antigen-binding protein and detecting the presence of a CoV-S/anti-CoV-S antigen-binding protein wherein the presence of the complex indicates the presence of CoV-S.

An anti-CoV-S antigen-binding protein of the invention (e.g., of Table 4) may be used in a Western blot or immune-protein blot procedure for detecting the presence of CoV-S or a fragment thereof in a sample. Such a procedure forms part of the present invention and includes the steps of e.g.:

(1) providing a membrane or other solid substrate comprising a sample to be tested for the presence of CoV-S, e.g., optionally including the step of transferring proteins from a sample to be tested for the presence of CoV-S (e.g., from a PAGE or SDS-PAGE electrophoretic separation of the proteins in the sample) onto a membrane or other solid substrate using a method known in the art (e.g., semi-dry blotting or tank blotting); and contacting the membrane or other solid substrate to be tested for the presence of CoV-S or a fragment thereof with an anti-CoV-S antigen-binding protein of the invention.

Such a membrane may take the form, for example, of a nitrocellulose or vinyl-based (e.g., polyvinylidene fluoride (PVDF)) membrane to which the proteins to be tested for the presence of CoV-S in a non-denaturing PAGE (polyacrylamide gel electrophoresis) gel or SDS-PAGE (sodium dodecyl sulfate polyacrylamide gel electrophoresis) gel have been transferred (e.g., following electrophoretic separation in the gel). Before contacting the membrane with the anti-CoV-S antigen-binding protein, the membrane is optionally blocked, e.g., with non-fat dry milk or the like so as to bind non-specific protein binding sites on the membrane.

(2) washing the membrane one or more times to remove unbound anti-CoV-S antigen-binding protein and other unbound substances; and (3) detecting the bound anti-CoV-S antigen-binding protein.

Detection of the bound antigen-binding protein indicates that the CoV-S protein is present on the membrane or substrate and in the sample. Detection of the bound antigen-binding protein may be by binding the antigen-binding protein with a secondary antibody (an anti-immunoglobulin antibody) which is detectably labeled and, then, detecting the presence of the secondary antibody label.

The anti-CoV-S antigen-binding proteins (e.g., antibodies and antigen-binding fragments (e.g., of Table 4)) disclosed herein may also be used for immunohistochemistry. Such a method forms part of the present invention and comprises, e.g., (1) contacting tissue to be tested for the presence of CoV-S protein with an anti-CoV-S antigen-binding protein of the invention; and (2) detecting the antigen-binding protein on or in the tissue.

If the antigen-binding protein itself is detectably labeled, it can be detected directly. Alternatively, the antigen-binding protein may be bound by a detectably labeled secondary antibody wherein the label is then detected.

EXAMPLES

The following examples are put forth so as to provide those of ordinary skill in the art with a complete disclosure and description of how to make and use the methods and compositions of the invention and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, room temperature is about 25° C., and pressure is at or near atmospheric.

Example 1: Generation of Human Antibodies to SARS-CoV-2 Spike Protein (SARS-CoV-2-S)

Human antibodies to SARS-CoV-2-Spike protein (SARS-CoV-2-S) were generated in a VELOCIMMUNE® mouse comprising DNA encoding human immunoglobulin heavy and kappa light chain variable regions or human immunoglobulin heavy and lambda light chain variable regions. Each mouse was immunized with a vector expressing the SARS-CoV-2-S receptor binding domain (RBD) (amino acids 1-1273 of NCBI accession number (MN908947.3), SEQ ID NO: 832), followed by a booster with a SARS-CoV-2-S vector or a SARS-CoV-2-S protein. The antibody immune response was monitored by a SARS-CoV-2-S-specific immunoassay. When a desired immune response was achieved, lymphocytes were harvested and fused with mouse myeloma cells to preserve their viability and form hybridoma cell lines. The hybridoma cell lines were screened and selected to identify cell lines that produce SARS-CoV-2-S-specific antibodies. Anti-SARS-CoV-2-S antibodies were also isolated directly from antigen-positive mouse B cells without fusion to myeloma cells, as described in U.S. Pat. No. 7,582,298, herein specifically incorporated by reference in its entirety. Using this method, fully human anti-SARS-CoV-2-S antibodies (i.e., antibodies possessing human variable domains and human constant domains) were obtained.

Antibody variable regions were also isolated from human blood samples. Whole blood was received from patients 3-4 weeks after a laboratory-confirmed PCR positive test for SARS-CoV-2 and symptomatic COVID-19 disease. Red blood cells were lysed using an ammonium chloride based lysis buffer (Life Technologies) and B cells were enriched by negative selection. Single B cells that bound the SARS-CoV-2 spike protein were isolated by fluorescent-activated cell sorting (FACS). Isolated B cells were single-well plated and mixed with antibody light and heavy variable region-specific PCR primers. cDNAs for each single B cell were synthesized via a reverse transcriptase (RT) reaction. Each resulting RT product was then split and transferred into two corresponding wells for subsequent antibody heavy and light chain PCRs. One set of the resulting RT products was first amplified by PCR using a 5' degenerate primer specific for antibody heavy variable region leader sequence or a 5' degenerate primer specific for antibody light chain variable region leader sequence and a 3' primer specific for antibody constant region, to form an amplicon. The amplicons were then amplified again by PCR using a 5' degenerate primer specific for antibody heavy variable region framework 1 or a 5' degenerate primer specific for antibody light chain variable region framework 1 and a 3' primer specific for antibody constant region, to generate amplicons for cloning. The antibody heavy chain and light chain derived PCR products were cloned into expression vectors containing heavy constant region and light constant region, respectively, thereby producing expression vectors for hybrid antibodies. The expression vectors expressing full-length heavy and light chain pairs were transfected into CHO cells to produce antibody proteins for testing.

The biological properties of exemplary antibodies generated in accordance with the methods of this Example are described in detail in the Examples set forth below.

Example 2: Heavy and Light Chain Variable Region Amino Acid and Nucleotide Sequences Table 4 sets forth the amino acid sequence identifiers of the heavy and light chain variable regions and CDRs, as well as the heavy chain and light chain sequences, of exemplary anti-SARS-CoV-2-S antibodies. The corresponding nucleic acid sequence identifiers are set forth in Table 5.

TABLE 4

| Amino Acid Sequence Identifiers | | | | | | | | | | |
|---|---|---|---|---|---|---|---|---|---|---|
| | SEQ ID NOs* (*refers to a Sequence No. in Table 42) | | | | | | | | | |
| Antibody Designation | HCVR | HCDR 1 | HCDR 2 | HCDR 3 | LCVR | LCDR 1 | LCDR 2 | LCDR 3 | HC | LC |
| mAb10913 | 2 | 4 | 6 | 8 | 10 | 12 | 14* | 16 | 18 | 20 |
| mAb10915 | 22 | 24 | 26 | 28 | 30 | 32 | 34* | 36 | 38 | 40 |
| mAb10916 | 2 | 4 | 6 | 8 | 10 | 12 | 14* | 16 | 42 | 20 |
| mAb10917 | 44 | 46 | 26 | 49 | 51 | 53 | 55* | 57 | 59 | 61 |
| mAb10918 | 22 | 24 | 26 | 28 | 30 | 32 | 34* | 36 | 63 | 40 |
| mAb10920 | 65 | 67 | 69 | 71 | 73 | 75 | 55* | 77 | 79 | 81 |
| mAb10921 | 83 | 85 | 26 | 87 | 89 | 91 | 55* | 93 | 95 | 97 |
| mAb10922 | 99 | 101 | 103 | 105 | 107 | 109 | 111* | 113 | 115 | 117 |
| mAb10923 | 119 | 121 | 123 | 125 | 127 | 129 | 55* | 131 | 133 | 135 |
| mAb10924 | 137 | 139 | 141 | 143 | 145 | 147 | 149* | 151 | 153 | 155 |
| mAb10925 | 65 | 67 | 69 | 71 | 73 | 75 | 55* | 77 | 157 | 81 |
| mAb10926 | 83 | 85 | 26 | 87 | 89 | 91 | 55* | 93 | 159 | 97 |
| mAb10927 | 99 | 101 | 103 | 105 | 107 | 109 | 111* | 113 | 161 | 117 |
| mAb10928 | 119 | 121 | 123 | 125 | 127 | 129 | 55* | 131 | 163 | 135 |
| mAb10929 | 137 | 139 | 141 | 143 | 145 | 147 | 149* | 151 | 165 | 155 |
| mAb10930 | 167 | 169 | 171 | 173 | 175 | 129 | 55* | 177 | 179 | 181 |
| mAb10931 | 167 | 169 | 171 | 173 | 175 | 129 | 55* | 177 | 183 | 181 |
| mAb10932 | 185 | 187 | 26 | 189 | 191 | 75 | 194* | 196 | 198 | 200 |
| mAb10933 | 202 | 204 | 206 | 208 | 210 | 212 | 55* | 214 | 216 | 218 |
| mAb10934 | 220 | 222 | 224 | 226 | 228 | 230 | 194* | 232 | 234 | 236 |
| mAb10935 | 238 | 24 | 26 | 240 | 242 | 244 | 194* | 246 | 248 | 250 |
| mAb10936 | 252 | 254 | 256 | 258 | 260 | 129 | 55* | 262 | 264 | 266 |
| mAb10937 | 268 | 270 | 272 | 274 | 276 | 129 | 55* | 278 | 280 | 282 |
| mAb10940 | 284 | 169 | 286 | 288 | 290 | 292 | 294* | 296 | 298 | 300 |
| mAb10938 | 302 | 24 | 26 | 304 | 306 | 308 | 194* | 310 | 312 | 314 |
| mAb10939 | 316 | 187 | 319 | 321 | 323 | 325 | 55* | 327 | 329 | 331 |
| mAb10941 | 333 | 85 | 26 | 336 | 338 | 340 | 294* | 296 | 342 | 344 |
| mAb10942 | 185 | 187 | 26 | 189 | 191 | 75 | 194* | 196 | 346 | 200 |
| mAb10943 | 202 | 204 | 206 | 208 | 210 | 212 | 55* | 214 | 348 | 218 |
| mAb10944 | 220 | 222 | 224 | 226 | 228 | 230 | 194* | 232 | 350 | 236 |
| mAb10945 | 238 | 24 | 26 | 240 | 242 | 244 | 194* | 246 | 352 | 250 |
| mAb10946 | 252 | 254 | 256 | 258 | 260 | 129 | 55* | 262 | 354 | 266 |
| mAb10947 | 268 | 270 | 272 | 274 | 276 | 129 | 55* | 278 | 356 | 282 |
| mAb10948 | 302 | 24 | 26 | 304 | 306 | 308 | 194* | 310 | 358 | 314 |
| mAb10949 | 316 | 187 | 319 | 321 | 323 | 325 | 55* | 327 | 360 | 331 |
| mAb10951 | 333 | 85 | 26 | 336 | 338 | 340 | 294* | 296 | 362 | 344 |
| mAb10950 | 284 | 169 | 286 | 288 | 290 | 292 | 294* | 296 | 364 | 300 |
| mAb10954 | 366 | 85 | 26 | 370 | 372 | 244 | 194* | 375 | 377 | 379 |
| mAb10955 | 381 | 383 | 26 | 385 | 387 | 389 | 194* | 310 | 392 | 394 |
| mAb10956 | 396 | 187 | 26 | 399 | 401 | 389 | 194* | 403 | 405 | 407 |
| mAb10957 | 409 | 411 | 26 | 414 | 416 | 53 | 55* | 418 | 420 | 422 |
| mAb10958 | 366 | 85 | 26 | 370 | 372 | 244 | 194* | 375 | 424 | 379 |
| mAb10959 | 381 | 383 | 26 | 385 | 387 | 389 | 194* | 310 | 426 | 394 |
| mAb10960 | 396 | 187 | 26 | 399 | 401 | 389 | 194* | 403 | 428 | 407 |
| mAb10961 | 409 | 411 | 26 | 414 | 416 | 53 | 55* | 418 | 430 | 422 |
| mAb10964 | 432 | 434 | 436 | 438 | 440 | 442 | 55* | 445 | 447 | 449 |
| mAb10965 | 451 | 453 | 26 | 455 | 457 | 459 | 34* | 462 | 464 | 466 |
| mAb10966 | 468 | 187 | 26 | 470 | 472 | 389 | 194* | 474 | 476 | 478 |
| mAb10967 | 480 | 24 | 483 | 485 | 487 | 389 | 194* | 489 | 491 | 493 |
| mAb10969 | 495 | 497 | 499 | 501 | 503 | 389 | 194* | 214 | 506 | 508 |
| mAb10970 | 510 | 24 | 26 | 512 | 514 | 516 | 194* | 518 | 520 | 522 |
| mAb10971 | 524 | 411 | 26 | 528 | 530 | 532 | 55* | 534 | 536 | 538 |
| mAb10973 | 432 | 434 | 436 | 438 | 440 | 442 | 55* | 445 | 540 | 449 |
| mAb10974 | 451 | 453 | 26 | 455 | 457 | 459 | 34* | 462 | 542 | 466 |

TABLE 4-continued

| Amino Acid Sequence Identifiers | | | | | | | | | | |
|---|---|---|---|---|---|---|---|---|---|---|
| | SEQ ID NOs* (*refers to a Sequence No. in Table 42) | | | | | | | | | |
| Antibody Designation | HCVR | HCDR 1 | HCDR 2 | HCDR 3 | LCVR | LCDR 1 | LCDR 2 | LCDR 3 | HC | LC |
| mAb10975 | 468 | 187 | 26 | 470 | 472 | 389 | 194* | 474 | 544 | 478 |
| mAb10976 | 480 | 24 | 483 | 485 | 487 | 389 | 194* | 489 | 546 | 493 |
| mAb10977 | 548 | 550 | 552 | 554 | 556 | 558 | 294* | 560 | 562 | 564 |
| mAb10978 | 495 | 497 | 499 | 501 | 503 | 389 | 194* | 214 | 566 | 508 |
| mAb10979 | 510 | 24 | 26 | 512 | 514 | 516 | 194* | 518 | 568 | 522 |
| mAb10980 | 524 | 411 | 26 | 528 | 530 | 532 | 55* | 534 | 570 | 538 |
| mAb10981 | 548 | 550 | 552 | 554 | 556 | 558 | 294* | 560 | 572 | 564 |
| mAb10982 | 574 | 187 | 576 | 578 | 580 | 582 | 584* | 586 | 588 | 590 |
| mAb10983 | 574 | 187 | 576 | 578 | 580 | 582 | 584* | 586 | 592 | 590 |
| mAb10984 | 594 | 596 | 26 | 598 | 600 | 12 | 14* | 602 | 604 | 606 |
| mAb10985 | 608 | 169 | 610 | 612 | 614 | 616 | 584* | 618 | 620 | 622 |
| mAb10986 | 624 | 626 | 26 | 628 | 630 | 582 | 632* | 634 | 636 | 638 |
| mAb10987 | 640 | 642 | 499 | 644 | 646 | 648 | 650* | 652 | 654 | 656 |
| mAb10988 | 658 | 660 | 662 | 664 | 666 | 668 | 670* | 672 | 674 | 676 |
| mAb10989 | 678 | 680 | 682 | 684 | 686 | 688 | 650* | 690 | 692 | 694 |
| mAb10990 | 594 | 596 | 26 | 598 | 600 | 12 | 14* | 602 | 696 | 606 |
| mAb10991 | 608 | 169 | 610 | 612 | 614 | 616 | 584* | 618 | 698 | 622 |
| mAb10992 | 624 | 626 | 26 | 628 | 630 | 582 | 632* | 634 | 700 | 638 |
| mAb10993 | 640 | 642 | 499 | 644 | 646 | 648 | 650* | 652 | 702 | 656 |
| mAb10994 | 658 | 660 | 662 | 664 | 666 | 668 | 670* | 672 | 704 | 676 |
| mAb10995 | 678 | 680 | 682 | 684 | 686 | 688 | 650* | 690 | 706 | 694 |
| mAb10996 | 708 | 24 | 26 | 711 | 713 | 129 | 55* | 715 | 717 | 719 |
| mAb10997 | 708 | 24 | 26 | 711 | 713 | 129 | 55* | 715 | 721 | 719 |
| mAb10998 | 723 | 187 | 26 | 725 | 727 | 129 | 55* | 729 | 731 | 733 |
| mAb10999 | 723 | 187 | 26 | 725 | 727 | 129 | 55* | 729 | 735 | 733 |
| mAb11000 | 737 | 24 | 26 | 739 | 741 | 743 | 55* | 745 | 747 | 749 |
| mAb11001 | 737 | 24 | 26 | 739 | 741 | 743 | 55* | 745 | 751 | 749 |
| mAb11002 | 753 | 24 | 26 | 755 | 713 | 129 | 55* | 715 | 757 | 719 |
| mAb11003 | 753 | 24 | 26 | 755 | 713 | 129 | 55* | 715 | 759 | 719 |
| mAb10914 | 44 | 46 | 26 | 49 | 51 | 53 | 55* | 57 | 762 | 61 |
| mAb11004 | 764 | 766 | 499 | 768 | 770 | 91 | 55* | 772 | 774 | 776 |
| mAb11005 | 764 | 766 | 499 | 768 | 770 | 91 | 55* | 772 | 778 | 776 |
| mAb11006 | 780 | 782 | 26 | 784 | 786 | 53 | 55* | 788 | 790 | 792 |
| mAb11007 | 780 | 782 | 26 | 784 | 786 | 53 | 55* | 788 | 794 | 792 |
| mAb11008 | 796 | 24 | 26 | 798 | 800 | 53 | 55* | 802 | 804 | 806 |
| mAb11009 | 796 | 24 | 26 | 798 | 800 | 53 | 55* | 802 | 808 | 806 |
| mAb11010 | 810 | 812 | 814 | 816 | 818 | 129 | 820* | 822 | 824 | 826 |
| mAb11011 | 810 | 812 | 814 | 816 | 818 | 129 | 820* | 822 | 828 | 826 |

TABLE 5

| Nucleic Acid Sequence Identifiers | | | | | | | | | | |
|---|---|---|---|---|---|---|---|---|---|---|
| | SEQ ID NOs* (*referes to a Sequence No. in Table 42) | | | | | | | | | |
| Antibody Designation | HCVR | HCDR 1 | HCDR 2 | HCDR 3 | LCVR | LCDR 1 | LCDR 2 | LCDR 3 | HC | LC |
| mAb10913 | 1 | 3 | 5 | 7 | 9 | 11 | 13* | 15 | 17 | 19 |
| mAb10915 | 21 | 23 | 25 | 27 | 29 | 31 | 33* | 35 | 37 | 39 |
| mAb10916 | 1 | 3 | 5 | 7 | 9 | 11 | 13* | 15 | 41 | 19 |
| mAb10917 | 43 | 45 | 47 | 48 | 50 | 52 | 54* | 56 | 58 | 60 |
| mAb10918 | 21 | 23 | 25 | 27 | 29 | 31 | 33* | 35 | 62 | 39 |
| mAb10920 | 64 | 66 | 68 | 70 | 72 | 74 | 54* | 76 | 78 | 80 |
| mAb10921 | 82 | 84 | 47 | 86 | 88 | 90 | 54* | 92 | 94 | 96 |
| mAb10922 | 98 | 100 | 102 | 104 | 106 | 108 | 110* | 112 | 114 | 116 |
| mAb10923 | 118 | 120 | 122 | 124 | 126 | 128 | 54* | 130 | 132 | 134 |
| mAb10924 | 136 | 138 | 140 | 142 | 144 | 146 | 148* | 150 | 152 | 154 |
| mAb10925 | 64 | 66 | 68 | 70 | 72 | 74 | 54* | 76 | 156 | 80 |
| mAb10926 | 82 | 84 | 47 | 86 | 88 | 90 | 54* | 92 | 158 | 96 |
| mAb10927 | 98 | 100 | 102 | 104 | 106 | 108 | 110* | 112 | 160 | 116 |
| mAb10928 | 118 | 120 | 122 | 124 | 126 | 128 | 54* | 130 | 162 | 134 |
| mAb10929 | 136 | 138 | 140 | 142 | 144 | 146 | 148* | 150 | 164 | 154 |
| mAb10930 | 166 | 168 | 170 | 172 | 174 | 128 | 54* | 176 | 178 | 180 |
| mAb10931 | 166 | 168 | 170 | 172 | 174 | 128 | 54* | 176 | 182 | 180 |
| mAb10932 | 184 | 186 | 47 | 188 | 190 | 192 | 193* | 195 | 197 | 199 |
| mAb10933 | 201 | 203 | 205 | 207 | 209 | 211 | 54* | 213 | 215 | 217 |
| mAb10934 | 219 | 221 | 223 | 225 | 227 | 229 | 193* | 231 | 233 | 235 |
| mAb10935 | 237 | 23 | 47 | 239 | 241 | 243 | 193* | 245 | 247 | 249 |
| mAb10936 | 251 | 253 | 255 | 257 | 259 | 128 | 54* | 261 | 263 | 265 |

TABLE 5-continued

Nucleic Acid Sequence Identifiers

| Antibody Designation | SEQ ID NOs* (*referes to a Sequence No. in Table 42) HCVR | HCDR 1 | HCDR 2 | HCDR 3 | LCVR | LCDR 1 | LCDR 2 | LCDR 3 | HC | LC |
|---|---|---|---|---|---|---|---|---|---|---|
| mAb10937 | 267 | 269 | 271 | 273 | 275 | 128 | 54* | 277 | 279 | 281 |
| mAb10940 | 283 | 168 | 285 | 287 | 289 | 291 | 293* | 295 | 297 | 299 |
| mAb10938 | 301 | 23 | 47 | 303 | 305 | 307 | 193* | 309 | 311 | 313 |
| mAb10939 | 315 | 317 | 318 | 320 | 322 | 324 | 54* | 326 | 328 | 330 |
| mAb10941 | 332 | 334 | 47 | 335 | 337 | 339 | 293* | 295 | 341 | 343 |
| mAb10942 | 184 | 186 | 47 | 188 | 190 | 192 | 193* | 195 | 345 | 199 |
| mAb10943 | 201 | 203 | 205 | 207 | 209 | 211 | 54* | 213 | 347 | 217 |
| mAb10944 | 219 | 221 | 223 | 225 | 227 | 229 | 193* | 231 | 349 | 235 |
| mAb10945 | 237 | 23 | 47 | 239 | 241 | 243 | 193* | 245 | 351 | 249 |
| mAb10946 | 251 | 253 | 255 | 257 | 259 | 128 | 54* | 261 | 353 | 265 |
| mAb10947 | 267 | 269 | 271 | 273 | 275 | 128 | 54* | 277 | 355 | 281 |
| mAb10948 | 301 | 23 | 47 | 303 | 305 | 307 | 193* | 309 | 357 | 313 |
| mAb10949 | 315 | 317 | 318 | 320 | 322 | 324 | 54* | 326 | 359 | 330 |
| mAb10951 | 332 | 334 | 47 | 335 | 337 | 339 | 293* | 295 | 361 | 343 |
| mAb10950 | 283 | 168 | 285 | 287 | 289 | 291 | 293* | 295 | 363 | 299 |
| mAb10954 | 365 | 367 | 368 | 369 | 371 | 373 | 193* | 374 | 376 | 378 |
| mAb10955 | 380 | 382 | 47 | 384 | 386 | 388 | 193* | 390 | 391 | 393 |
| mAb10956 | 395 | 397 | 47 | 398 | 400 | 388 | 193* | 402 | 404 | 406 |
| mAb10957 | 408 | 410 | 412 | 413 | 415 | 52 | 54* | 417 | 419 | 421 |
| mAb10958 | 365 | 367 | 368 | 369 | 371 | 373 | 193* | 374 | 423 | 378 |
| mAb10959 | 380 | 382 | 47 | 384 | 386 | 388 | 193* | 390 | 425 | 393 |
| mAb10960 | 395 | 397 | 47 | 398 | 400 | 388 | 193* | 402 | 427 | 406 |
| mAb10961 | 408 | 410 | 412 | 413 | 415 | 52 | 54* | 417 | 429 | 421 |
| mAb10964 | 431 | 433 | 435 | 437 | 439 | 441 | 443* | 444 | 446 | 448 |
| mAb10965 | 450 | 452 | 47 | 454 | 456 | 458 | 460* | 461 | 463 | 465 |
| mAb10966 | 467 | 397 | 412 | 469 | 471 | 388 | 193* | 473 | 475 | 477 |
| mAb10967 | 479 | 481 | 482 | 484 | 486 | 388 | 193* | 488 | 490 | 492 |
| mAb10969 | 494 | 496 | 498 | 500 | 502 | 388 | 193* | 504 | 505 | 507 |
| mAb10970 | 509 | 481 | 412 | 511 | 513 | 515 | 193* | 517 | 519 | 521 |
| mAb10971 | 523 | 525 | 526 | 527 | 529 | 531 | 54* | 533 | 535 | 537 |
| mAb10973 | 431 | 433 | 435 | 437 | 439 | 441 | 443* | 444 | 539 | 448 |
| mAb10974 | 450 | 452 | 47 | 454 | 456 | 458 | 460* | 461 | 541 | 465 |
| mAb10975 | 467 | 397 | 412 | 469 | 471 | 388 | 193* | 473 | 543 | 477 |
| mAb10976 | 479 | 481 | 482 | 484 | 486 | 388 | 193* | 488 | 545 | 492 |
| mAb10977 | 547 | 549 | 551 | 553 | 555 | 557 | 293* | 559 | 561 | 563 |
| mAb10978 | 494 | 496 | 498 | 500 | 502 | 388 | 193* | 504 | 565 | 507 |
| mAb10979 | 509 | 481 | 412 | 511 | 513 | 515 | 193* | 517 | 567 | 521 |
| mAb10980 | 523 | 525 | 526 | 527 | 529 | 531 | 54* | 533 | 569 | 537 |
| mAb10981 | 547 | 549 | 551 | 553 | 555 | 557 | 293* | 559 | 571 | 563 |
| mAb10982 | 573 | 186 | 575 | 577 | 579 | 581 | 583* | 585 | 587 | 589 |
| mAb10983 | 573 | 186 | 575 | 577 | 579 | 581 | 583* | 585 | 591 | 589 |
| mAb10984 | 593 | 595 | 47 | 597 | 599 | 11 | 13* | 601 | 603 | 605 |
| mAb10985 | 607 | 168 | 609 | 611 | 613 | 615 | 583* | 617 | 619 | 621 |
| mAb10986 | 623 | 625 | 47 | 627 | 629 | 581 | 631* | 633 | 635 | 637 |
| mAb10987 | 639 | 641 | 498 | 643 | 645 | 647 | 649* | 651 | 653 | 655 |
| mAb10988 | 657 | 659 | 661 | 663 | 665 | 667 | 669* | 671 | 673 | 675 |
| mAb10989 | 677 | 679 | 681 | 683 | 685 | 687 | 649* | 689 | 691 | 693 |
| mAb10990 | 593 | 595 | 47 | 597 | 599 | 11 | 13* | 601 | 695 | 605 |
| mAb10991 | 607 | 168 | 609 | 611 | 613 | 615 | 583* | 617 | 697 | 621 |
| mAb10992 | 623 | 625 | 47 | 627 | 629 | 581 | 631* | 633 | 699 | 637 |
| mAb10993 | 639 | 641 | 498 | 643 | 645 | 647 | 649* | 651 | 701 | 655 |
| mAb10994 | 657 | 659 | 661 | 663 | 665 | 667 | 669* | 671 | 703 | 675 |
| mAb10995 | 677 | 679 | 681 | 683 | 685 | 687 | 649* | 689 | 705 | 693 |
| mAb10996 | 707 | 709 | 47 | 710 | 712 | 128 | 54* | 714 | 716 | 718 |
| mAb10997 | 707 | 709 | 47 | 710 | 712 | 128 | 54* | 714 | 720 | 718 |
| mAb10998 | 722 | 186 | 47 | 724 | 726 | 128 | 54* | 728 | 730 | 732 |
| mAb10999 | 722 | 186 | 47 | 724 | 726 | 128 | 54* | 728 | 734 | 732 |
| mAb11000 | 736 | 23 | 47 | 738 | 740 | 742 | 54* | 744 | 746 | 748 |
| mAb11001 | 736 | 23 | 47 | 738 | 740 | 742 | 54* | 744 | 750 | 748 |
| mAb11002 | 752 | 23 | 47 | 754 | 712 | 128 | 54* | 714 | 756 | 718 |
| mAb11003 | 752 | 23 | 47 | 754 | 712 | 128 | 54* | 714 | 758 | 718 |
| mAb10914 | 760 | 45 | 47 | 48 | 50 | 52 | 54* | 56 | 761 | 60 |
| mAb11004 | 763 | 765 | 498 | 767 | 769 | 90 | 54* | 771 | 773 | 775 |
| mAb11005 | 763 | 765 | 498 | 767 | 769 | 90 | 54* | 771 | 777 | 775 |
| mAb11006 | 779 | 781 | 47 | 783 | 785 | 52 | 54* | 787 | 789 | 791 |
| mAb11007 | 779 | 781 | 47 | 783 | 785 | 52 | 54* | 787 | 793 | 791 |
| mAb11008 | 795 | 709 | 47 | 797 | 799 | 52 | 54* | 801 | 803 | 805 |
| mAb11009 | 795 | 709 | 47 | 797 | 799 | 52 | 54* | 801 | 807 | 805 |
| mAb11010 | 809 | 811 | 813 | 815 | 817 | 128 | 819* | 821 | 823 | 825 |
| mAb11011 | 809 | 811 | 813 | 815 | 817 | 128 | 819* | 821 | 827 | 825 |

Antibodies disclosed herein have fully human variable regions but can have mouse constant regions (e.g., a mouse IgG1 Fc or a mouse IgG2 Fc (a or b isotype)) or human constant regions (e.g., a human IgG1 Fc or a human IgG4 Fc). As will be appreciated by a person of ordinary skill in the art, an antibody having a particular Fc isotype can be converted to an antibody with a different Fc isotype (e.g., an antibody with a mouse IgG1 Fc can be converted to an antibody with a human IgG4, etc.), but in any event, the variable domains (including the CDRs)— which are indicated by the numerical identifiers shown in Tables 4 and 5 will remain the same, and the binding properties to antigen are expected to be identical or substantially similar regardless of the nature of the constant domain.

Figure 10A:
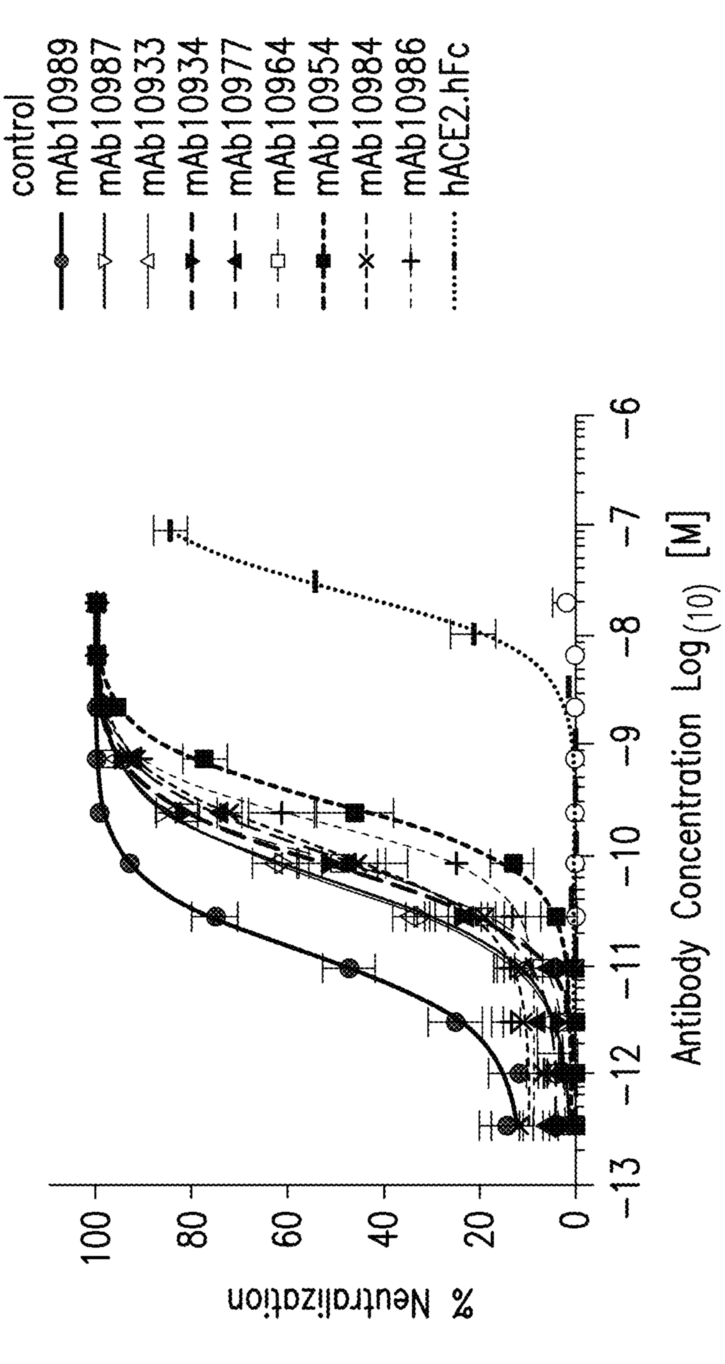
FIG. 10A and FIG. 10B display neutralization potency.
Figure 10B:
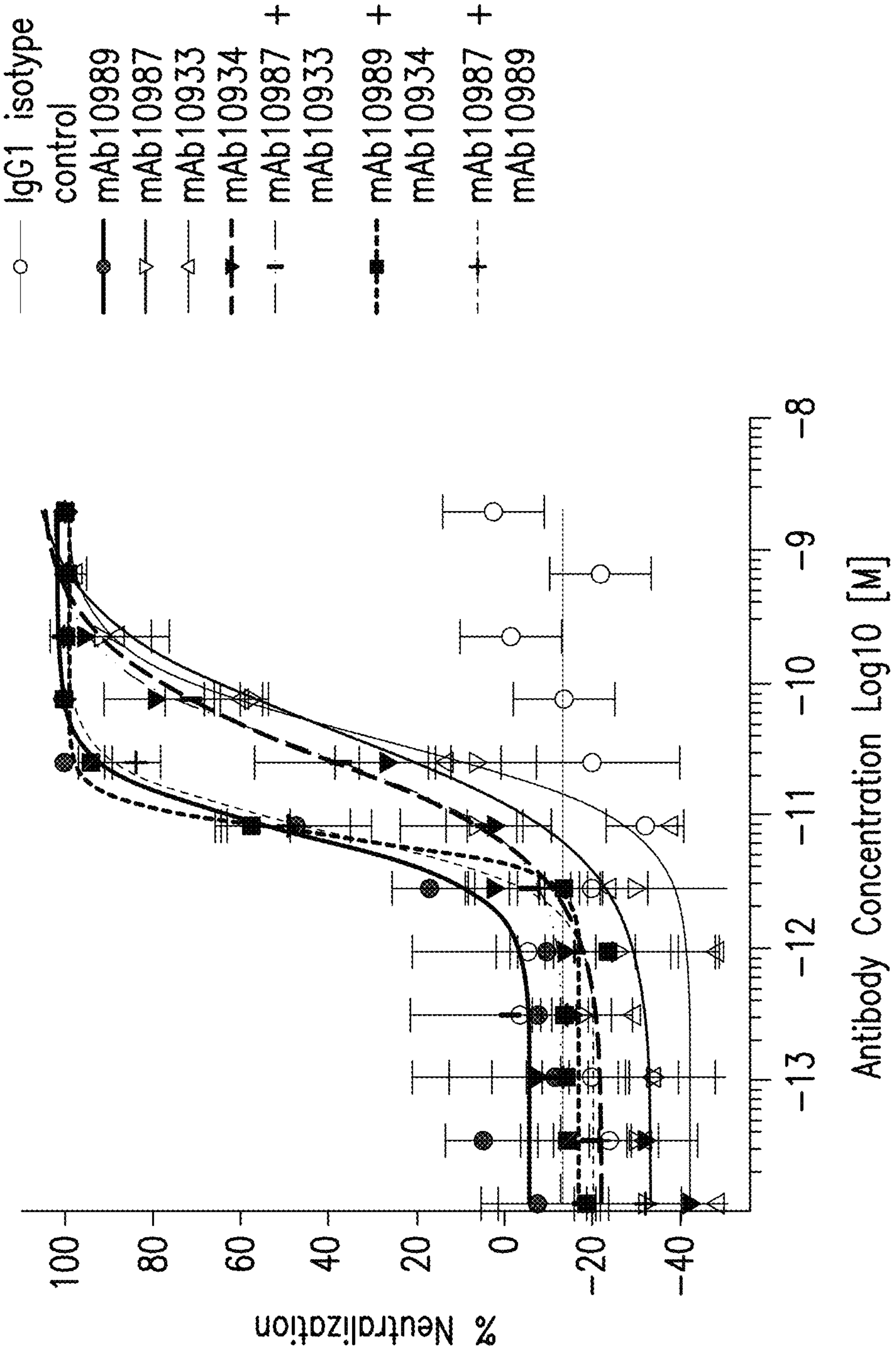

The variable regions of antibodies derived from VELOCIMMUNE® mice and from human samples were sequenced by Next Generation Sequencing and the repertoire for heavy and light chain pairs was identified (FIG. 10A and FIG. 10B). The predominant lineage of VI antibodies utilized VH3-53 paired with VK1-9, VK1-33, or VK1-39 while human-derived antibodies utilized VH3-66 paired with VK1-33 or VH2-70 paired with VK1-39. Further analysis of overlaid sequences showed strong overlap in the repertoire of isolated kappa chains between VI and human-derived antibodies. Although the repertoire of Lambda chains did not overlap well, that may be due to only two lambda mice being included in this trial. The average CDR length for heavy chain was similar between VI and human derived antibodies with an average length of 13 and 14.5 amino acids, respectively. Average kappa CDR length was the same for VI and human derived antibodies at 9 amino acids and was close for lambda chains with an average length of 11.1 and 10.6 amino acids, respectively. Availability of humanized mouse and human-derived antibodies allowed for more diversity of V genes and enabled the later identification of noncompeting antibodies.

As described above, the antibodies were obtained from hybridomas generated from VELOCIMMUNE® mice, by direct isolation from antigen-positive VELOCIMMUNE® mouse B cells, or derived from variable regions cloned from antigen-positive human B cells. A summary of these sources is shown in Table 6.

TABLE 6

Antibody/Variable Region sources

| Antibody | Source |
|---|---|
| mAb10913 | mouse B cells |
| mAb10915 | mouse B cells |
| mAb10916 | mouse B cells |
| mAb10917 | mouse B cells |
| mAb10918 | mouse B cells |
| mAb10920 | mouse B cells |
| mAb10921 | mouse B cells |
| mAb10922 | mouse B cells |
| mAb10923 | mouse B cells |
| mAb10924 | mouse B cells |
| mAb10925 | mouse B cells |
| mAb10926 | mouse B cells |
| mAb10927 | mouse B cells |
| mAb10928 | mouse B cells |
| mAb10929 | mouse B cells |
| mAb10930 | mouse B cells |
| mAb10931 | mouse B cells |
| mAb10932 | mouse B cells |
| mAb10933 | mouse B cells |
| mAb10934 | mouse B cells |
| mAb10935 | mouse B cells |
| mAb10936 | mouse B cells |

TABLE 6-continued

Antibody/Variable Region sources

| Antibody | Source |
|---|---|
| mAb10937 | mouse B cells |
| mAb10940 | mouse B cells |
| mAb10938 | mouse B cells |
| mAb10939 | mouse B cells |
| mAb10941 | mouse B cells |
| mAb10942 | mouse B cells |
| mAb10943 | mouse B cells |
| mAb10944 | mouse B cells |
| mAb10945 | mouse B cells |
| mAb10946 | mouse B cells |
| mAb10947 | mouse B cells |
| mAb10948 | mouse B cells |
| mAb10949 | mouse B cells |
| mAb10951 | mouse B cells |
| mAb10950 | mouse B cells |
| mAb10954 | human B cells |
| mAb10955 | human B cells |
| mAb10956 | human B cells |
| mAb10957 | human B cells |
| mAb10958 | human B cells |
| mAb10959 | human B cells |
| mAb10960 | human B cells |
| mAb10961 | human B cells |
| mAb10964 | human B cells |
| mAb10965 | human B cells |
| mAb10966 | human B cells |
| mAb10967 | human B cells |
| mAb10969 | human B cells |
| mAb10970 | human B cells |
| mAb10971 | human B cells |
| mAb10973 | human B cells |
| mAb10974 | human B cells |
| mAb10975 | human B cells |
| mAb10976 | human B cells |
| mAb10977 | human B cells |
| mAb10978 | human B cells |
| mAb10979 | human B cells |
| mAb10980 | human B cells |
| mAb10981 | human B cells |
| mAb10982 | mouse B cells |
| mAb10983 | mouse B cells |
| mAb10984 | human B cells |
| mAb10985 | human B cells |
| mAb10986 | human B cells |
| mAb10987 | human B cells |
| mAb10988 | human B cells |
| mAb10989 | human B cells |
| mAb10990 | human B cells |
| mAb10991 | human B cells |
| mAb10992 | human B cells |
| mAb10993 | human B cells |
| mAb10994 | human B cells |
| mAb10995 | human B cells |
| mAb10996 | hybridoma |
| mAb10997 | hybridoma |
| mAb10998 | hybridoma |
| mAb10999 | hybridoma |
| mAb11000 | hybridoma |
| mAb11001 | hybridoma |
| mAb11002 | hybridoma |
| mAb11003 | hybridoma |
| mAb10914 | mouse B cells |
| mAb11004 | hybridoma |
| mAb11005 | hybridoma |
| mAb11006 | hybridoma |
| mAb11007 | hybridoma |
| mAb11008 | hybridoma |
| mAb11009 | hybridoma |
| mAb11010 | hybridoma |
| mAb11011 | hybridoma |

Example 3: Characterization of Hybridoma Supernatants by Binding ELISA

An ELISA binding assay was performed to identify antibody supernatants that bound to the SARS-CoV-2-Spike protein receptor binding domain (RBD). A protein composed of the RBD of SARS-CoV-2 (amino acids 319-541) expressed with a 6× histidine tag and two myc epitope tags at the C-terminus (SARS-CoV-2-S-RBD-mmH; see also NCBI Accession Number MN908947.3) was coated at 1 μg/ml on a 96-well plate in PBS buffer overnight at 4° C. Nonspecific binding sites were subsequently blocked using a 0.5% (w/v) solution of BSA in PBS. Antibody supernatants or media alone were diluted 1:40 or 1:50 in the PSA+0.5% BSA blocking buffer and transferred to the washed microtiter plates. After one hour of incubation at room temperature, the wells were washed, and plate-bound supernatant was detected with either goat-anti-human IgG antibody conjugated with horseradish peroxidase (HRP) (Jackson Immunoresearch), or anti-mouse IgG antibody conjugated with horseradish peroxidase (HRP) (Jackson Immunoresearch). The plates were then developed using TMB substrate solution (BD Biosciences) according to manufacturer's recommendation and absorbance at 450 nm was measured on a Victor X5 plate reader.

The ability of anti-SARS-CoV-2-S antibodies to bind the receptor binding domain of SARS-CoV-2-S(SARS-CoV-2-S-RBD) was assessed, as described above, using a binding ELISA with the SARS-CoV-2-S-RBD-mmH protein coated on a microplate. Single point antibody supernatant binding to SARS-COV-2-S-RBD-mmH coated on 96-well microtiter plates was detected with an HRP conjugated anti-hFc or anti-mFc antibody.

The binding results of three trials are summarized in Table 7. The SARS-CoV-2 binding signals (absorbance 450 nm) are indicated, with the media only background provided as a negative reference per experiment. A sample marked IC (Inconclusive) had an experimental anomaly to the plate and is therefore reported without a value. As shown in comparison to the media only control, the supernatants tested showed substantial binding to the SARS-CoV-2-S-RBD.

TABLE 7

Supernatant binding to SARS-CoV-2 spike protein receptor binding domain

| Supernatant | Supernatant Dilution | Detection Antibody | Binding Signal (absorbance at 450 nm) |
|---|---|---|---|
| mAb10913 | 1:50 | a-hFc | 2.752 |
| mAb10914 | 1:50 | a-hFc | 2.857 |
| mAb10915 | 1:50 | a-hFc | 2.76 |
| mAb10932 | 1:50 | a-hFc | 2.718 |
| mAb10933 | 1:50 | a-hFc | 2.762 |
| mAb10934 | 1:50 | a-hFc | 2.688 |
| mAb10935 | 1:50 | a-hFc | 2.676 |
| mAb10936 | 1:50 | a-hFc | 2.644 |
| mAb10937 | 1:50 | a-hFc | 2.664 |
| mAb10920 | 1:50 | a-hFc | 2.683 |
| mAb10921 | 1:50 | a-hFc | 2.633 |
| mAb10922 | 1:50 | a-hFc | 2.595 |
| mAb10923 | 1:50 | a-hFc | 2.353 |
| mAb10924 | 1:50 | a-hFc | 2.269 |
| mAb10930 | 1:50 | a-hFc | 2.451 |
| mAb10938 | 1:50 | a-hFc | 2.536 |
| mAb10939 | 1:50 | a-hFc | 2.516 |
| mAb10940 | 1:50 | a-hFc | 2.77 |
| mAb10941 | 1:50 | a-hFc | IC |
| mAb10982 | 1:50 | a-hFc | 2.537 |

TABLE 7-continued

Supernatant binding to SARS-CoV-2 spike protein receptor binding domain

| Supernatant | Supernatant Dilution | Detection Antibody | Binding Signal (absorbance at 450 nm) |
|---|---|---|---|
| mAb10984 | 1:50 | a-hFc | 0.716 |
| mAb10985 | 1:50 | a-hFc | 2.35 |
| mAb10986 | 1:50 | a-hFc | 2.331 |
| mAb10987 | 1:50 | a-hFc | 2.438 |
| mAb10988 | 1:50 | a-hFc | 3.062 |
| mAb10989 | 1:50 | a-hFc | 3.116 |
| mAb10969 | 1:50 | a-hFc | 2.629 |
| mAb10970 | 1:50 | a-hFc | 2.807 |
| mAb10971 | 1:50 | a-hFc | 3.052 |
| mAb10964 | 1:50 | a-hFc | 3.086 |
| mAb10965 | 1:50 | a-hFc | 2.918 |
| mAb10966 | 1:50 | a-hFc | 0.421 |
| mAb10967 | 1:50 | a-hFc | 1.732 |
| mAb10954 | 1:50 | a-hFc | 1.963 |
| mAb10955 | 1:50 | a-hFc | 2.469 |
| mAb10956 | 1:50 | a-hFc | 2.6 |
| mAb10957 | 1:50 | a-hFc | 2.49 |
| mAb10977 | 1:50 | a-hFc | 2.925 |
| mAb11010 | 1:40 | a-mFc | 2.896 |
| mAb11004 | 1:40 | a-mFc | 2.908 |
| mAb11000 | 1:40 | a-mFc | 2.725 |
| mAb11006 | 1:40 | a-mFc | 2.619 |
| mAb11008 | 1:40 | a-mFc | 2.907 |
| mAb10998 | 1:40 | a-mFc | 2.835 |
| mAb10996 | 1:40 | a-mFc | 2.826 |
| mAb11002 | 1:40 | a-mFc | 2.581 |
| Media only | 1:50 | a-hFc | 0.069 |
| Media only | 1:40 | a-mFc | 0.058 |
| Media only | 1:50 | a-hFc | 0.055 |

Example 4: Antibody Binding to SARS-CoV-2-S-Expressing Virus-Like Particle

To investigate the ability of a panel of anti-SARS-CoV-2-S monoclonal antibodies to bind the SARS-CoV-2 spike glycoprotein, an in vitro binding assay utilizing SARS-CoV-2 spike protein-expressing viral-like particles (VLPs) in an electrochemiluminescence based detection platform (MSD) was developed.

To transiently express the SARS-CoV-2 spike protein (NCBI Accession number MN908947.3, amino acids 16-1211; SEQ ID NO: 833), Vesicular stomatitis virus (VSV) lacking glycoprotein G (VSV delta G) was pseudotyped with SARS-CoV-2 spike protein (VSV-SARS-CoV-2-S) and generated in HEK293T cells. As a negative binding control, VSV delta G was pseudotyped with VSV G protein (VSV-G).

Experiments were carried out according to following procedure. The two types of VLPs described above were diluted in PBS, seeded into 96-well carbon electrode plates (MULTI-ARRAY high bind plate, MSD), and incubated overnight at 4° C. to allow the VLPs to adhere. Nonspecific binding sites were blocked by 2% BSA (w/v) in PBS for 1 hour at room temperature. Supernatants containing antibodies produced from SARS CoV-2-immunized mice or infected human sera, along with media-only controls which were diluted 1:10 or 1:20 in 1×PBS+0.5% BSA buffer, were added to the plate-bound particles. The plates were then incubated for 1 hour at room temperature with shaking, after which the plates were washed with 1×PBS to remove the unbound antibodies using an AquaMax2000 plate washer (MDS Analytical Technologies). The plate-bound antibodies were detected with a SULFO-TAG™-conjugated anti-human IgG antibody (Jackson Immunoresearch) or a SULFO- TAG™-conjugated anti-mouse IgG antibody (Jackson Immunoresearch) for 1 hour at room temperature. After washes, the plates were developed with the Read Buffer (MSD) according to manufacturer's recommended procedure and the luminescent signals were recorded with a SECTOR Imager 600 (Meso Scale Development) instrument. Direct binding signals (in RLU) were captured, and a ratio of SARS-CoV-2-S-expressing VLPs to the irrelevant VLP was calculated.

The ability of the anti-SARS-CoV-2-S monoclonal antibodies to bind to SARS-CoV-2-S-expressing VLPs compared with binding to irrelevant VSV-expressing VLPs was assessed using an immunobinding assay, as described above. Single-point binding to the immobilized VLPs on 96-well High Bind plates (MSD) was performed with an antibody supernatant dilution of 1:10 or 1:20, bound for 1 hour, and detected using SULFO-TAG™-conjugated anti-human IgG or anti-mouse IgG antibody. The binding signals from electrochemiluminescence were recorded on a Sector Imager 600 (MSD). RLU values were determined for the antibody binding to VLPs. Ratios were calculated comparing the SARS-CoV-2-S-expressing VLP binding signals to control VLPs.

The binding results from three experiments are summarized in Table 8. A signal observed from SARS-COV-2-S-expressing VLPs indicates binding, while comparison with negative VLPs provides a relative background. Media alone samples provide baseline signals of secondary antibody binding to samples with no supernatant. The 46 antibodies bound specifically at >4-fold higher than the media-only samples (20-35 RLU) on the SARS-CoV-2-S-expressing VLPs, with a range of binding signals from 85-13,600 RLU. The ratios of SARS-CoV-2-S-expressing VSV: VSV-VLPs (negative control) ranged from 1.1-22.7, with many having high background on VSV-VLPs. The ratio of mAb11002 of 0.9 is likely due to a low concentration of monoclonal antibody in the supernatant sample.

TABLE 8

SARS-CoV-2-S VLP binding

| Supernatant | Supernatant Dilution | Secondary Detection Antibody | VSV-VLP Binding Signal (RLU) | VSV-SARS-CoV-2-S VLP Binding Signal (RLU) | Ratio of Binding Signals: VSV-SARS-CoV-2-S/VSV-VLP |
|---|---|---|---|---|---|
| mAb10913 | 1:10 | a-hFc | 2155 | 3244 | 1.5 |
| mAb10914 | 1:10 | a-hFc | 3885 | 5181 | 1.3 |
| mAb10915 | 1:10 | a-hFc | 980 | 9022 | 9.2 |
| mAb10932 | 1:10 | a-hFc | 989 | 10451 | 10.6 |
| mAb10933 | 1:10 | a-hFc | 507 | 966 | 1.9 |
| mAb10934 | 1:10 | a-hFc | 3876 | 5041 | 1.3 |
| mAb10935 | 1:10 | a-hFc | 2087 | 3867 | 1.9 |
| mAb10936 | 1:10 | a-hFc | 2325 | 8076 | 3.5 |
| mAb10937 | 1:10 | a-hFc | 1404 | 1920 | 1.4 |
| mAb10920 | 1:10 | a-hFc | 8366 | 10041 | 1.2 |
| mAb10921 | 1:10 | a-hFc | 1194 | 5436 | 4.6 |
| mAb10922 | 1:10 | a-hFc | 1473 | 2229 | 1.5 |
| mAb10923 | 1:10 | a-hFc | 1224 | 1859 | 1.5 |
| mAb10924 | 1:10 | a-hFc | 487 | 969 | 2 |
| mAb10930 | 1:10 | a-hFc | 1769 | 3207 | 1.8 |
| mAb10938 | 1:10 | a-hFc | 1232 | 6623 | 5.4 |
| mAb10939 | 1:10 | a-hFc | 1777 | 5074 | 2.9 |
| mAb10940 | 1:10 | a-hFc | 606 | 2072 | 3.4 |
| mAb10941 | 1:10 | a-hFc | 673 | 4588 | 6.8 |
| mAb10982 | 1:10 | a-hFc | 1178 | 2016 | 1.7 |
| mAb10984 | 1:10 | a-hFc | 2486 | 8989 | 3.6 |

TABLE 8-continued

SARS-CoV-2-S VLP binding

| Supernatant | Supernatant Dilution | Secondary Detection Antibody | VSV-VLP Binding Signal (RLU) | VSV-SARS-CoV-2-S VLP Binding Signal (RLU) | Ratio of Binding Signals: VSV-SARS-CoV-2-S/VSV-VLP |
|---|---|---|---|---|---|
| mAb10985 | 1:10 | a-hFc | 2049 | 3279 | 1.6 |
| mAb10986 | 1:10 | a-hFc | 2044 | 10831 | 5.3 |
| mAb10987 | 1:10 | a-hFc | 1839 | 2450 | 1.3 |
| mAb10988 | 1:10 | a-hFc | 1832 | 2305 | 1.3 |
| mAb10989 | 1:10 | a-hFc | 672 | 1999 | 3 |
| mAb10969 | 1:10 | a-hFc | 3096 | 3313 | 1.1 |
| mAb10970 | 1:10 | a-hFc | 1364 | 5712 | 4.2 |
| mAb10971 | 1:10 | a-hFc | 1135 | 7266 | 6.4 |
| mAb10964 | 1:10 | a-hFc | 1439 | 8601 | 6 |
| mAb10965 | 1:10 | a-hFc | 743 | 1370 | 1.8 |
| mAb10966 | 1:10 | a-hFc | 1428 | 6574 | 4.6 |
| mAb10967 | 1:10 | a-hFc | 1446 | 9510 | 6.6 |
| mAb10954 | 1:10 | a-hFc | 641 | 6308 | 9.8 |
| mAb10955 | 1:10 | a-hFc | 932 | 1788 | 1.9 |
| mAb10956 | 1:10 | a-hFc | 1030 | 1581 | 1.5 |
| mAb10957 | 1:10 | a-hFc | 604 | 5544 | 9.2 |
| mAb10977 | 1:10 | a-hFc | 4141 | 13600 | 3.3 |
| mAb11010 | 1:20 | a-mFc | 96 | 363 | 3.8 |
| mAb11004 | 1:20 | a-mFc | 110 | 406 | 3.7 |
| mAb11000 | 1:20 | a-mFc | 333 | 592 | 1.8 |
| mAb11006 | 1:20 | a-mFc | 165 | 3747 | 22.7 |
| mAb11008 | 1:20 | a-mFc | 103 | 324 | 3.1 |
| mAb10998 | 1:20 | a-mFc | 74 | 218 | 2.9 |
| mAb10996 | 1:20 | a-mFc | 51 | 85 | 1.7 |
| mAb11002 | 1:20 | a-mFc | 156 | 146 | 0.9 |
| Media only | 1:10 | a-hFc | 30 | 35 | 1.2 |
| Media only | 1:20 | a-mFc | 35 | 20 | 0.6 |
| Media only | 1:10 | a-hFc | 39 | 29 | 0.7 |

Example 5: Antibody Neutralization of VSV-SARS-CoV-2-S Pseudovirus Infectivity To investigate the ability of a panel of anti-SARS-CoV-2-S monoclonal antibodies to neutralize SARS-CoV-2, an in vitro neutralization assay utilizing VSV-SARS-CoV-2-S pseudovirus was developed.

As described above, VSV pseudotype viruses were generated by transiently transfecting 293T cells with a plasmid encoding for SARS-CoV-2 spike protein. Cells were seeded in 15 cm plates at $1.2\times10^7$ cells per plate in DMEM complete media one day prior to transfection with 15 μg/plate spike protein DNA using 125 μL Lipofectamine LTX, 30 μL PLUS reagent, and up to 3 mL Opti-Mem. 24 hours post transfection, the cells were washed with 10 mL PBS, then infected with an MOI of 0.1 $VSV^{\Delta G:mNeon}$ virus in 10 mL Opti-Mem. Virus was incubated on cells for 1 hour, with gentle rocking every 10 minutes. Cells were washed 3 times with 10 mL PBS, then overlaid with 20 mL Infection media before incubation at 37 C, 5% $CO_2$ for 24 hours. Supernatant was collected into 250 mL centrifuge tubes on ice, then centrifuged at 3000 rpm for 5 minutes to pellet any cellular debris, aliquoted on ice, then frozen to −80° C. Infectivity was tested on Vero cells prior to use in neutralization assays. This material will be referred to as VSV-SARS-CoV-2-S.

Neutralization Assay with VSV-SARS-CoV-2-S

On day 1, Vero cells were seeded at 80% confluency in T225 flasks. To seed cells, media was removed from the cells, the cells were washed with 20 mL PBS (Gibco: 20012-043), and 5 mL TrypLE was added and incubated for ~5 minutes at 37° C. until the cells dislodged. 5 mL of complete DMEM was added to inactivate the trypsin, and pipetted up and down to distribute the cells. To count the resuspended cells, 20,000 Vero cells were plated in 100 μL prewarmed Complete DMEM per well in a 96 Well Black Polystyrene Microplate (Corning: 3904).

On day 2, VSV-SARS-CoV-2-S was thawed on ice and diluted 1:1 with infection media.

In a V-bottom 96 well plate, a dilution of each supernatant was generated in 60 ul infection media. For media (negative) controls, 60 μl of diluted conditioned media was added to the wells. 60 μL of diluted VSV-SARS-CoV-2-S were added to every well except the media control wells. To those wells, 60 μL of infection media was added. Pseudoviruses were then incubated with supernatant dilutions for 30 minutes at room temperature. Media was removed from the Vero cell plates, 100 μL of supernatant/pseudovirus mixtures were transferred to the cells, and the plate was incubated at 37° C., 5% $CO_2$ for 24 hours. The final supernatant dilutions of 1:4 and 1:20, and for some samples 1:100, were used to assess neutralization of VSV-SARS-CoV-2-S pseudoviruses.

On day 3, after the 24 hr incubation, supernatant was removed from the cell wells and replaced with 100 μL of PBS. The plates were then read on a SpectraMax i3 with MiniMax imaging cytometer.

The ability of the anti-SARS-CoV-2-S antibodies to neutralize VSV-based SARS-CoV-2-S-expressing pseudotyped virus was assessed using a neutralization fluorescence focus assay. The binding results of three assays are summarized below. The neutralization potency of antibody at each dilution is represented as a percentage compared to mock supernatant control. All antibodies demonstrated neutralization capacity, and particularly for the set of antibodies that were evaluated 1:100, those showing higher neutralization may represent more potent neutralization capacity.

TABLE 9

| Neutralization of VLPs | | | |
|---|---|---|---|
| Supernatant | Neutralization (1:4 dilution) | Neutralization (1:20 dilution) | Neutralization (1:100 dilution) |
| mAb10913 | 99.5 | 95.5 | 69.1 |
| mAb10914 | 94.2 | 74.8 | 43.6 |
| mAb10915 | 96.7 | 74.2 | 29.6 |
| mAb10932 | 99.8 | 94.6 | 68 |
| mAb10933 | 99.8 | 98.9 | 88.4 |
| mAb10934 | 99.9 | 99.8 | 98.4 |
| mAb10935 | 99.6 | 98.5 | 88.8 |
| mAb10936 | 99.7 | 99.1 | 92.9 |
| mAb10937 | 97.5 | 87.7 | 56.3 |
| mAb10920 | 99.5 | 95.5 | 69.1 |
| mAb10921 | 98.2 | 91.4 | 46.1 |
| mAb10922 | 99.8 | 99.1 | 88.4 |
| mAb10923 | 99.5 | 92.9 | 67.7 |
| mAb10924 | 98.1 | 85.4 | 55.2 |
| mAb10930 | 99.1 | 91.1 | 59 |
| mAb10938 | 98.1 | 83 | 54.2 |
| mAb10939 | 98.6 | 90.5 | 64 |
| mAb10940 | 97 | 89.9 | 66.4 |
| mAb10941 | 98.9 | 92.9 | 73.8 |
| mAb10982 | 97.4 | 83.8 | 44.5 |
| mAb10984 | 99.8 | 95.1 | 83.4 |
| mAb10985 | 99.7 | 88.4 | 63.5 |
| mAb10986 | 99.7 | 98 | 86 |
| mAb10987 | 99.3 | 97.7 | 94.6 |
| mAb10988 | 97.6 | 87.6 | 62.2 |
| mAb10989 | 100 | 99.8 | 98.2 |
| mAb10969 | 97.2 | 91 | 63.7 |
| mAb10970 | 99.6 | 96.7 | 82.4 |
| mAb10971 | 99.5 | 97 | 73.9 |
| mAb10964 | 99.7 | 99.7 | 94.1 |
| mAb10965 | 98.5 | 87.6 | 68.6 |

TABLE 9-continued

| Neutralization of VLPs | | | |
|---|---|---|---|
| Supernatant | Neutralization (1:4 dilution) | Neutralization (1:20 dilution) | Neutralization (1:100 dilution) |
| mAb10966 | 99.5 | 95.5 | 76.2 |
| mAb10967 | 98.9 | 91.4 | 69.2 |
| mAb10954 | 99.8 | 96 | 70.7 |
| mAb10955 | 98.8 | 88.6 | 62.7 |
| mAb10956 | 97.1 | 84.1 | 61.6 |
| mAb10957 | 97.6 | 76.4 | 48 |
| mAb10977 | 95.5 | 79 | 47.7 |
| mAb11010 | 85 | 54 | NT |
| mAb11004 | 77 | 40 | NT |
| mAb11000 | 98 | 82 | NT |
| mAb11006 | 91 | 54 | NT |
| mAb11008 | 96 | 77 | NT |
| mAb10998 | 88 | 59 | NT |
| mAb10996 | 85 | 58 | NT |
| mAb11002 | 35 | −1 | NT |

*NT: not tested

Example 6: Characterization of Antibodies in an Antibody-Dependent Cell-Mediated Toxicity Surrogate Assay The ability of antibodies targeting the spike protein of SARS-CoV-2 to interact with FcγR3a, an Fc-receptor prominently expressed on natural killer (NK) cells that induces antibody dependent cell-mediated cytotoxicity (ADCC), was measured in a surrogate bioassay using reporter cells and target cells bound to antibodies. This assay used Jurkat T cells that were engineered to express the reporter gene luciferase under the control of the transcription factor NFAT (NFAT-Luc) along with the high affinity human FcγR3a 176Val allotype receptor (Jurkat/NFAT-Luc/hFcγR3a 176Val). Target cells were engineered Jurkat T cells expressing human CD20 (used as a positive control with a CD20-targeting human IgG1 antibody) and the full-length SARS-CoV-2 spike protein controlled by a doxycycline-inducible promoter. Reporter cells were incubated with target cells and engagement of FcγR3a via the Fc domain of human IgG1 antibodies bound to target cells led to the activation of the transcription factor NFAT in the reporter cells and drove the expression of luciferase which was then measured via a luminescence readout.

Jurkat T cells were engineered to constitutively express full length human CD20 (amino acids M1-P297 of NCBI accession number NP_690605.1), Tet3G transactivator protein (cloned using a Takara pEF1α-Tet3G Vector, Catalog #631167), as well as a doxycycline-inducible full-length SARS-CoV-2 spike protein (amino acids M1-T1273 of NCBI accession number YP_009724390.1). Engineered Jurkat/Tet3G/hCD20/SARS-CoV2 spike protein-expressing cells were sorted for high expression of the spike protein and subsequently maintained in RPMI+10% Tet-free FBS+P/S/G+500 μg/ml G418+μg/ml puromycin+250 μg/ml hygromycin growth medium.

Jurkat T cells were engineered to stably express a Nuclear Factor of Activated T-cells (NFAT) luciferase reporter construct along with the high affinity human FcγR3a 176Val allotype receptor (amino acids M1-K254 of NCBI accession number P08637 VAR 003960). Engineered reporter cells were maintained in RPMI1640+10% FBS+P/S/G+0.5 μg/ml puromycin+500 μm/ml G418 growth media.

36 hours prior to the start of the surrogate ADCC assay, $5\times10^5$ target cells/ml were induced in RPMI+10% Tet-free FBS+P/S/G cell culture media containing 1 μg/ml doxycycline (Sigma). A day before the experiment, reporter cells were split to a density of $7.5\times10^5$ cells/ml in RPMI 1640+10% FBS+P/S/G+0.5 μg/ml puromycin+500 μm/ml G418 growth media.

Briefly, on the day of the experiment, the target and reporter cells were transferred into assay media (RPMI+10% Tet-free FBS+P/S/G) and added at a 3:2 ratio ($3\times10^4$/well target cells and $2\times10^4$/well reporter cells) to 384-well white microtiter plates, followed by the addition of anti-SARS-CoV-2-S antibody supernatant of varying concentrations. A positive control (CD20 antibody with human IgG1) sample and a negative control sample containing no antibody was included on each plate to normalize detected ADCC activities of anti-SARS-CoV-2-S antibody supernatants. Plates were incubated at 37° C./5% $CO_2$ for 5 h followed by the addition of an equal volume of ONE-Glo™ (Promega) reagent to lyse cells and detect luciferase activity. The emitted light was captured in Relative Light Units (RLU) on a multi-label plate reader Envision (PerkinElmer), and data was analyzed and normalized using the following equation:

$$ADCC\ \text{activity}\ (\%) = 100\times\frac{(\text{Mean } RLU\ (\text{test samples}) - \text{Mean } RLU\ (\text{background signal}))}{(\text{Mean } RLU\ (\text{positive control}) - \text{Mean } RLU\ (\text{background signal}))}$$

The ability of anti-SARS-COV-2-S antibodies to activate FcγR3a receptors was evaluated in a surrogate ADCC assay using Jurkat/NFAT-Luc/FcγR3a 176Val) as reporter cells and Jurkat/hCD20/SARS-CoV2 Spike as target cells. Each antibody tested contained an IgG1 domain.

Table 10 summarizes the results, showing the raw luciferase activity and the calculated % of positive control are indicated. A range of % ADCC activity was observed indicating FcγR3a activation by the antibody supernatants. All samples demonstrated some measure of surrogate ADCC activity, and 10 of the antibody supernatants demonstrated surrogate ADCC activity better than observed in positive controls.

TABLE 10

ADCC surrogate activity of anti-SARS-CoV-2-S antibody supernatants.

| mAb | ADCC Mean RLU | ADCC (Activity (%) |
|---|---|---|
| mAb10913 | 11,480 | 111.9 |
| mAb10914 | 21,960 | 265.8 |
| mAb10915 | 14,280 | 153 |
| mAb10932 | 13,020 | 108.8 |
| mAb10933 | 9,740 | 68.5 |
| mAb10934 | 11,680 | 92 |
| mAb10935 | 11,540 | 90.4 |
| mAb10936 | 15,160 | 133.8 |
| mAb10937 | 12,340 | 100.1 |
| mAb10920 | 15,480 | 137.8 |
| mAb10921 | 10,080 | 67.7 |
| mAb10922 | 9,140 | 56.3 |
| mAb10923 | 13,340 | 107.1 |
| mAb10924 | 7,220 | 33 |
| mAb10930 | 8,900 | 53.4 |
| mAb10938 | 12,960 | 102.5 |
| mAb10939 | 9,440 | 59.7 |
| mAb10940 | 12,520 | 106.2 |
| mAb10941 | 10,340 | 77.2 |
| mAb10982 | 7,900 | 59.4 |
| mAb10984 | 6780 | 6.8 |
| mAb10985 | 5840 | 2.8 |

TABLE 10-continued

ADCC surrogate activity of anti-SARS-CoV-2-S antibody supernatants.

| mAb | ADCC Mean RLU | ADCC (Activity (%) |
|---|---|---|
| mAb10986 | 6200 | 4.4 |
| mAb10987 | 12020 | 29.4 |
| mAb10988 | 7200 | 8.7 |
| mAb10989 | 10200 | 21.5 |
| mAb10969 | 10500 | 23.1 |
| mAb10970 | 7640 | 10.6 |
| mAb10971 | 7480 | 10 |
| mAb10964 | 6380 | 5.1 |
| mAb10965 | 6780 | 6.9 |
| mAb10966 | 7080 | 10.4 |
| mAb10967 | 6740 | 8.6 |
| mAb10954 | 6940 | 9.8 |
| mAb10955 | 6740 | 8.7 |
| mAb10956 | 6760 | 8.8 |
| mAb10957 | 7120 | 10.8 |
| mAb10977 | 12980 | 33.8 |

Example 7: Anti-SARS-CoV-2-S Antibody Binding Specificity Assay

A Luminex binding assay was performed to determine the binding of anti-SARS-COV-2-S antibodies to a panel of antigens. For this assay, antigens were amine-coupled or captured by streptavidin to Luminex microspheres as follows: approximately 10 million MagPlex microspheres (Luminex Corp., MagPlex Microspheres, Cat. No. MC10000 and MC12000), were resuspended by vortexing in 500 μL 0.1M $NaPO_4$, pH 6.2 (activation buffer) and then centrifuged to remove the supernatant. Microspheres were protected from light, as they are light sensitive. The microspheres were resuspended in 160 μL of activation buffer and the carboxylate groups (—COOH) were activated by addition of 20 μL of 50 mg/mL of N-hydroxysuccinimide (NHS, Thermo Scientific, Cat. No. 24525) followed by addition of 20 μL of 50 mg/mL 1-ethyl-3-[3-dimethylaminopropyl]carbodiimide (EDC, ThermoScientific, Cat. No. 22980) at 25° C. After 10 minutes, the pH of the reaction was reduced to 5.0 with the addition of 600 μL 50 mM MES, pH 5 (coupling buffer), and the microspheres were vortexed and centrifuged to remove supernatant. The activated microspheres were immediately mixed with 500 μL of 25 μg/mL of the protein antigen or Streptavidin in coupling buffer and incubated for two hours at 25° C. The coupling reaction was quenched by addition of 50 μL of 1M Tris-HCl, pH 8.0 and the microspheres were vortexed, centrifuged, and washed three times with 800 μL of PBS 0.005% (Tween20 0.05%), to remove uncoupled proteins and other reaction components. Microspheres were resuspended in 1 mL of PBS 2% BSA 0.05% Na Azide at 10 million microspheres/mL. For Streptavidin capture of antigens, 500 μL of 12.5 μg/mL of biotinylated protein in PBS was added to Streptavidin-coupled microspheres and incubated for one hour at 25° C. Microspheres were vortexed, centrifuged, and washed three times with 800 μL of PBS, and then blocked using 500 μL 30 mM Biotin (Millipore-Sigma, Cat. No. B4501) in 0.15M Tris pH 8.0. Microspheres were incubated for 30 minutes then vortexed, centrifuged, and washed three times with 800 μL of PBS. Microspheres were resuspended in 1 mL of PBS 2% BSA 0.05% Na Azide at 10 million microspheres/mL.

Microspheres for the different proteins and biotinylated proteins were mixed at 2700 beads/ml, and 75 μL of microspheres were plated per well on a 96 well ProcartaPlex flat bottom plate (ThermoFisher, Cat. No: EPX-44444-000) and mixed with 25 µL of individual anti-SARS-CoV-2 supernatant containing antibody. Samples and microspheres were incubated for two hours at 25° C. and then washed twice with 200 µL of DPBS with 0.05% Tween 20. To detect bound antibody levels to individual microspheres, 100 µL of 2.5 µg/mL R-Phycoerythrin conjugated goat F(ab')2 anti-human kappa (Southern Biotech, Cat #2063-09) in blocking buffer (for antibodies with murine Fc regions) or 100 µL of 1.25 µg/mL R-Phycoerythrin AffiniPure F(ab')2 Fragment Goat Anti-Mouse IgG, F(ab')2 Fragment Specific (Jackson Immunoresearch, Cat. No: 115-116-072) in blocking buffer (for antibodies with human Fc regions), was added and incubated for 30 minutes at 25° C. After 30 minutes, the samples were washed twice with 200 µl of washing buffer and resuspended in 150 µL of wash buffer. The plates were read in a Luminex FlexMap 3D® (Luminex Corp.) and Luminex xPonent® software version 4.3 (Luminex Corp.). The SARS-CoV-2 proteins used in the assay are as follows:

RBD_(R319-F541).mmh: SEQ ID NO: 829

RBD_(R319-F541).mFc: SEQ ID NO: 830

RBD_(R319-F541).hFc): SEQ ID NO: 831

The results of the Luminex binding are shown in Table 11 and Table 12 as median fluorescence intensity (MFI) signal intensities. The results show that the 46 anti-SARS-CoV-2-S antibody supernatants bound specifically to SARS-CoV-2-S RBD proteins. These results also show that five of these antibodies cross-react with SARS Coronavirus spike RBD proteins with binding signal greater than 1000 MFI.

TABLE 11

Binding signal (MFI) of SARS-CoV-2 Spike RBD, SARS-CoV-2 Spike S1, SARS RBD, SARS Spike S1, MERS Spike and MERS RBD proteins to anti-SARS-CoV-2 monoclonal antibodies (with hFc)

| | SARS-CoV-2 | | | | | | | | |
|---|---|---|---|---|---|---|---|---|---|
| Supernatant | SARS-CoV-2 Spike Protein (RBD) (R319-F541). mmH | SARS-CoV-2 Spike Protein (RBD) (R319-F541). mmH | Bt-SARS-CoV-2 Spike Protein (RBD) (R319-F541). mFc | SARS-CoV-2 Spike Protein (RBD) (R319-F541). mFc | Bt-SARS-CoV-2 Spike Protein (RBD) (R319-F541). hFc | SARS-CoV-2 Spike Protein (RBD) (R319-F541). hFc | SARS-CoV-2 Spike (RBD, Fc Tag) (Sino 40592-V05H) | SARS-CoV-2 Spike Protein (S1 Subunit, Fc Tag) (Sino 40591-V02H) | SARS-CoV-2 Spike Protein (S1 Subunit, His Tag) (Sino 40591-V08H) |
| mAb10913 | 30709 | 29247 | 16645 | 33023 | 27452 | 31929 | 31561 | 18899 | 24931 |
| mAb10914 | 31967 | 29650 | 15986 | 30740 | 25957 | 30464 | 30591 | 14914 | 21609 |
| mAb10915 | 31795 | 30293 | 20062 | 31772 | 30625 | 32437 | 31267 | 17595 | 22917 |
| mAb10932 | 29984 | 30133 | 17697 | 30640 | 26220 | 30559 | 29880 | 17627 | 22099 |
| mAb10933 | 33356 | 32090 | 19383 | 34944 | 30110 | 35106 | 34484 | 21178 | 27509 |
| mAb10934 | 33797 | 32649 | 21238 | 34325 | 33016 | 35841 | 33636 | 20643 | 27483 |
| mAb10935 | 34853 | 32603 | 19328 | 35886 | 31444 | 35611 | 35037 | 19991 | 25554 |
| mAb10936 | 33947 | 32305 | 21636 | 33740 | 32810 | 33912 | 33613 | 19487 | 25187 |
| mAb10937 | 33866 | 32225 | 19689 | 34233 | 31501 | 34624 | 33878 | 19553 | 26404 |
| mAb10920 | 34842 | 34440 | 20254 | 36415 | 31708 | 36828 | 36277 | 21085 | 28516 |
| mAb10921 | 24977 | 23596 | 11307 | 19429 | 18186 | 22306 | 21766 | 8959 | 12212 |
| mAb10922 | 31768 | 30755 | 18629 | 32355 | 27854 | 33609 | 31376 | 18287 | 24678 |
| mAb10923 | 35208 | 34289 | 19593 | 37372 | 33555 | 37756 | 36324 | 22502 | 28855 |
| mAb10924 | 29730 | 27987 | 17044 | 28308 | 26898 | 28744 | 28423 | 15672 | 20577 |
| mAb10930 | 25119 | 25131 | 16563 | 28560 | 25922 | 28870 | 28744 | 16530 | 21151 |
| mAb10938 | 29409 | 27069 | 17205 | 30533 | 24638 | 29593 | 29134 | 15431 | 21163 |
| mAb10939 | 32196 | 30883 | 18746 | 33900 | 28857 | 32864 | 32472 | 18171 | 23928 |
| mAb10940 | 35221 | 35290 | 21000 | 35978 | 30675 | 36507 | 34945 | 21350 | 25807 |
| mAb10941 | 32392 | 31171 | 20428 | 34061 | 28431 | 33347 | 33232 | 19668 | 26738 |
| mAb10982 | 24263 | 22180 | 12278 | 23296 | 19935 | 23020 | 23066 | 10847 | 14017 |
| mAb10984 | 27854 | 26197 | 17054 | 28350 | 22479 | 28442 | 27808 | 15590 | 19245 |
| mAb10985 | 30214 | 27854 | 15488 | 29443 | 24827 | 31054 | 28936 | 16219 | 20787 |
| mAb10986 | 27187 | 25196 | 15921 | 28407 | 23388 | 27693 | 27693 | 16034 | 19061 |
| mAb10987 | 32171 | 29074 | 16736 | 33115 | 26059 | 32757 | 31238 | 17465 | 23089 |
| mAb10988 | 23858 | 22160 | 12659 | 26095 | 21793 | 24822 | 23949 | 12910 | 16208 |
| mAb10989 | 17687 | 17286 | 11189 | 19568 | 16117 | 22435 | 19316 | 12263 | 14234 |
| mAb10969 | 29550 | 27587 | 15391 | 31386 | 26565 | 31042 | 30950 | 18466 | 23959 |
| mAb10970 | 33154 | 31662 | 20184 | 34739 | 29182 | 34991 | 34704 | 21047 | 24625 |
| mAb10971 | 29355 | 28850 | 16660 | 28746 | 24602 | 30032 | 29848 | 16986 | 21579 |
| mAb10964 | 31754 | 28907 | 19225 | 32420 | 27736 | 33074 | 32317 | 18650 | 24154 |
| mAb10965 | 30812 | 26863 | 13707 | 27139 | 23351 | 29618 | 28034 | 14133 | 18864 |
| mAb10966 | 30939 | 27440 | 17905 | 30363 | 25115 | 30778 | 29869 | 16403 | 23308 |
| mAb10967 | 28453 | 26496 | 16771 | 29650 | 24263 | 28660 | 28061 | 15776 | 21869 |
| mAb10954 | 30410 | 28281 | 18394 | 31284 | 24677 | 31768 | 29604 | 16626 | 21270 |
| mAb10955 | 29627 | 28476 | 16785 | 30790 | 24689 | 31227 | 31054 | 17858 | 22675 |
| mAb10956 | 27900 | 25690 | 12891 | 28349 | 24505 | 30225 | 28810 | 15013 | 19981 |
| mAb10957 | 23411 | 20615 | 10566 | 18692 | 16725 | 22560 | 20258 | 8451 | 11989 |
| mAb10977 | 16770 | 14605 | 8845 | 13827 | 12774 | 15216 | 16783 | 6476 | 9406 |

TABLE 11-continued

Binding signal (MFI) of SARS-CoV-2 Spike RBD, SARS-CoV-2 Spike S1, SARS RBD, SARS Spike S1, MERS Spike and MERS RBD proteins to anti-SARS-CoV-2 monoclonal antibodies (with hFc)

| | SARS | | | MERS | | |
|---|---|---|---|---|---|---|
| Supernatant | Human SARS Coronavirus Spike Protein (Receptor Binding Domain) rabbit Fc (Sino 40150-V31B2) | Human SARS Coronavirus Spike Protein (Receptor Binding Domain, His Tag) (Sino 40150-V08B2) | Human SARS Coronavirus Spike S1 Subunit Protein (His Tag) (Sino 40150-V08B1) | MERS-CoV (SARS-CoV-2) Spike Protein (ECD, aa 1-1297, His Tag) (Sino 40069-V08B) | MERS-CoV (SARS-CoV-2) Spike Protein S2 (aa 726-1296, His Tag) (Sino 40070-V08B) | MERS-CoV (SARS-CoV-2) Spike Protein S1 (aa 1-725, His Tag) (Sino 40069-V08H) |
| mAb10913 | 35 | 39 | 21 | 20 | 26 | 14 |
| mAb10914 | 47 | 39 | 22 | 19 | 28 | 15 |
| mAb10915 | 42 | 40 | 21 | 18 | 23 | 15 |
| mAb10932 | 34 | 26 | 19 | 14 | 19 | 12 |
| mAb10933 | 39 | 31 | 18 | 14 | 19 | 14 |
| mAb10934 | 38 | 27 | 18 | 15 | 18 | 10 |
| mAb10935 | 37 | 25 | 21 | 15 | 18 | 14 |
| mAb10936 | 46 | 36 | 20 | 19 | 21 | 13 |
| mAb10937 | 44 | 50 | 21 | 19 | 26 | 14 |
| mAb10920 | 59 | 68 | 26 | 24 | 30 | 13 |
| mAb10921 | 35 | 31 | 19 | 19 | 19 | 12 |
| mAb10922 | 36 | 41 | 18 | 19 | 18 | 9 |
| mAb10923 | 53 | 66 | 29 | 23 | 36 | 14 |
| mAb10924 | 41 | 30 | 18 | 17 | 19 | 12 |
| mAb10930 | 42 | 49 | 19 | 16 | 20 | 14 |
| mAb10938 | 38 | 36 | 19 | 16 | 19 | 13 |
| mAb10939 | 38 | 50 | 19 | 16 | 18 | 14 |
| mAb10940 | 32 | 28 | 20 | 15 | 18 | 11 |
| mAb10941 | 45 | 37 | 22 | 19 | 22 | 15 |
| mAb10982 | 30 | 54 | 24 | 17 | 21 | 13 |
| mAb10984 | 33 | 31 | 22 | 21 | 25 | 13 |
| mAb10985 | 31537 | 32343 | 22721 | 18 | 28 | 14 |
| mAb10986 | 39 | 38 | 21 | 15 | 19 | 14 |
| mAb10987 | 33 | 27 | 22 | 15 | 23 | 15 |
| mAb10988 | 41 | 67 | 25 | 17 | 29 | 14 |
| mAb10989 | 47 | 73 | 21 | 16 | 22 | 11 |
| mAb10969 | 37 | 34 | 20 | 16 | 20 | 11 |
| mAb10970 | 38 | 25 | 19 | 14 | 16 | 15 |
| mAb10971 | 32 | 31 | 20 | 15 | 13 | 13 |
| mAb10964 | 19999 | 23855 | 5186 | 15 | 17 | 13 |
| mAb10965 | 30 | 23 | 16 | 19 | 20 | 12 |
| mAb10966 | 35 | 21 | 20 | 16 | 16 | 12 |
| mAb10967 | 35 | 30 | 21 | 17 | 19 | 13 |
| mAb10954 | 30 | 26 | 15 | 17 | 16 | 10 |
| mAb10955 | 36 | 21 | 14 | 15 | 18 | 16 |
| mAb10956 | 32 | 24 | 16 | 15 | 16 | 13 |
| mAb10957 | 32 | 22 | 16 | 15 | 18 | 11 |
| mAb10977 | 36 | 28 | 23 | 17 | 19 | 13 |

| | MERS | | | | |
|---|---|---|---|---|---|
| Supernatant | MERS-CoV (NCoV/Novel coronavirus) Spike Protein fragment (RBD, aa 367-606, His Tag) (Sino 40071-V08B1) | MERS-CoV (NCoV/Novel coronavirus) Spike Protein S1 Protein (aa 1-725, His Tag) (Sino 40069-V08B1) | MERS. mFc (mAb2663-L1) | MERS. hFc (mAb2664-L1) | Bt-MERS. hFc (mAb2664-L2) |
| mAb10913 | 34 | 26 | 29 | 28 | 29 |
| mAb10914 | 31 | 23 | 86 | 71 | 49 |
| mAb10915 | 31 | 24 | 86 | 91 | 56 |
| mAb10932 | 26 | 19 | 60 | 49 | 40 |
| mAb10933 | 24 | 17 | 22 | 21 | 26 |
| mAb10934 | 24 | 20 | 77 | 68 | 47 |
| mAb10935 | 25 | 17 | 74 | 67 | 42 |
| mAb10936 | 29 | 20 | 32 | 26 | 32 |
| mAb10937 | 27 | 22 | 21 | 23 | 29 |
| mAb10920 | 39 | 27 | 38 | 35 | 44 |
| mAb10921 | 23 | 18 | 55 | 44 | 39 |

TABLE 11-continued

Binding signal (MFI) of SARS-CoV-2 Spike RBD, SARS-CoV-2 Spike S1, SARS RBD, SARS Spike S1, MERS Spike and MERS RBD proteins to anti-SARS-CoV-2 monoclonal antibodies (with hFc)

| | | | | | |
|---|---|---|---|---|---|
| mAb10922 | 29 | 22 | 20 | 21 | 24 |
| mAb10923 | 37 | 25 | 24 | 29 | 39 |
| mAb10924 | 29 | 22 | 19 | 22 | 28 |
| mAb10930 | 27 | 22 | 29 | 24 | 29 |
| mAb10938 | 25 | 20 | 86 | 65 | 46 |
| mAb10939 | 27 | 19 | 41 | 27 | 30 |
| mAb10940 | 22 | 19 | 18 | 21 | 25 |
| mAb10941 | 30 | 24 | 82 | 69 | 47 |
| mAb10982 | 29 | 20 | 64 | 60 | 42 |
| mAb10984 | 29 | 20 | 237 | 341 | 172 |
| mAb10985 | 31 | 22 | 168 | 195 | 159 |
| mAb10986 | 27 | 20 | 233 | 286 | 184 |
| mAb10987 | 28 | 23 | 196 | 235 | 172 |
| mAb10988 | 32 | 25 | 169 | 181 | 130 |
| mAb10989 | 24 | 19 | 161 | 206 | 186 |
| mAb10969 | 26 | 19 | 21 | 22 | 29 |
| mAb10970 | 23 | 17 | 35 | 23 | 28 |
| mAb10971 | 20 | 19 | 44 | 29 | 24 |
| mAb10964 | 20 | 19 | 19 | 22 | 26 |
| mAb10965 | 26 | 23 | 58 | 53 | 43 |
| mAb10966 | 24 | 16 | 56 | 53 | 42 |
| mAb10967 | 23 | 21 | 61 | 71 | 45 |
| mAb10954 | 18 | 21 | 57 | 61 | 41 |
| mAb10955 | 20 | 19 | 57 | 48 | 42 |
| mAb10956 | 22 | 24 | 58 | 49 | 41 |
| mAb10957 | 22 | 19 | 40 | 29 | 28 |
| mAb10977 | 24 | 21 | 17 | 20 | 25 |

TABLE 12

Binding signal (MFI) of SARS-CoV-2 RBD, SARS-CoV-2 Spike S1, SARS RBD, SARS Spike S1, MERS SPIKE and MERS RBD proteins to anti-SARS-CoV-2-S monoclonal antibodies (with mFc)

| | SARS-CoV-2 | | | | |
|---|---|---|---|---|---|
| Supernatant | SARS-CoV-2 Spike Protein (RBD)(R319-F541).mmH (mAb10620-L1) | SARS-CoV-2 Spike Protein (RBD)(R319-F541).mmH (mAb10620-L2) | Bt-SARS-CoV-2 Spike Protein (RBD)(R319-F541).mFc (mAb10621-L2) | SARS-CoV-2 Spike Protein (RBD)(R319-F541).mFc (mAb10621-L1) | Bt-SARS-CoV-2 Spike Protein (RBD)(R319-F541).hFc (mAb10622-L2) |
| mAb11010 | 11024 | 12885 | 9349 | 14432 | 15688 |
| mAb11004 | 3350 | 11337 | 4299 | 4583 | 7625 |
| mAb11000 | 17802 | 10971 | 11335 | 23007 | 11593 |
| mAb11006 | 5134 | 4744 | 1396 | 2866 | 3812 |
| mAb11008 | 4047 | 3178 | 3047 | 4260 | 4106 |
| mAb10998 | 1847 | 3837 | 2228 | 2230 | 467 |
| mAb10996 | 9142 | 2906 | 4319 | 8738 | 5398 |
| mAb11002 | 11558 | 10181 | 2197 | 9530 | 5471 |

| | SARS-CoV-2 | | | |
|---|---|---|---|---|
| Supernatant | SARS-CoV-2 Spike Protein (RBD)(R319-F541).hFc (mAb10622-L1) | SARS-CoV-2 Spike (RBD, Fc Tag) (Sino 40592-V05H) | SARS-CoV-2 (2019-nCoV) Spike Protein (S1 Subunit, Fc Tag) (Sino 40591-V02H) | SARS-CoV-2 (2019-nCoV) Spike Protein (S1 Subunit, His Tag) (Sino 40591-V08H) t |
| mAb11010 | 8880 | 9628 | 5136 | 10794 |
| mAb11004 | 4877 | 6905 | 4482 | 9526 |
| mAb11000 | 22316 | 5671 | 9356 | 5415 |
| mAb11006 | 3985 | 3749 | 2052 | 1037 |
| mAb11008 | 2570 | 2311 | 6880 | 1419 |
| mAb10998 | 1740 | 2005 | 724 | 717 |
| mAb10996 | 2084 | 16101 | 1425 | 6232 |
| mAb11002 | 9382 | 8461 | 1107 | 2867 |

TABLE 12-continued

Binding signal (MFI) of SARS-CoV-2 RBD, SARS-CoV-2 Spike S1, SARS RBD, SARS Spike S1, MERS SPIKE and MERS RBD proteins to anti-SARS-CoV-2-S monoclonal antibodies (with mFc)

| | SARS | | | MERS | | |
|---|---|---|---|---|---|---|
| Supernatant | Human SARS Coronavirus Spike Protein (Receptor Binding Domain) rabbit Fc (Sino 40150-V31B2) | Human SARS Coronavirus Spike Protein (Receptor Binding Domain, His Tag) (Sino 40150-V08B2) | Human SARS Coronavirus Spike S1 Subunit Protein (His Tag) (Sino 40150-V08B1) | MERS-CoV (NCoV/Novel coronavirus) Spike Protein (ECD, aa 1-1297, His Tag) (Sino 40069-V08B) | MERS-CoV (NCoV/Novel coronavirus) Spike Protein S2 (aa 726-1296, His Tag) (Sino 40070- V08B) | MERS-CoV (NCoV/Novel coronavirus) Spike Protein S1 (aa 1-725, His Tag) (Sino 40069-V08H) |
| mAb11010 | 18276 | 16793 | 7421 | 7 | 14 | 14 |
| mAb11004 | 5524 | 740 | 33 | 15 | 20 | 12 |
| mAb11000 | 39 | 31 | 18 | 13 | 19 | 9 |
| mAb11006 | 615 | 667 | 339 | 18 | 17 | 13 |
| mAb11008 | 120 | 174 | 31 | 18 | 16 | 15 |
| mAb10998 | 29 | 37 | 16 | 19 | 18 | 14 |
| mAb10996 | 1355 | 1279 | 28 | 13 | 21 | 14 |
| mAb11002 | 80 | 56 | 31 | 10 | 22 | 13 |

| | MERS | | | | |
|---|---|---|---|---|---|
| Supernatant | MERS-CoV (NCoV/Novel coronavirus) Spike Protein fragment (RBD, aa 367-606, His Tag) (Sino 40071-V08B1) | MERS-CoV (NCoV/Novel coronavirus) Spike Protein S1 Protein (aa 1-725, His Tag) (Sino 40069-V08B1) | MERS mFc (mAb2663-L1) | MER.hFc (mAb2664-L1) | Bt-MERS.hFc (mAb2664-L2) |
| mAb11010 | 19 | 18 | 134 | 28 | 28 |
| mAb11004 | 26 | 17 | 228 | 24 | 25 |
| mAb11000 | 27 | 17 | 384 | 82 | 49 |
| mAb11006 | 15 | 18 | 156 | 16 | 24 |
| mAb11008 | 20 | 18 | 45 | 19 | 32 |
| mAb10998 | 24 | 19 | 48 | 29 | 32 |
| mAb10996 | 26 | 18 | 185 | 132 | 95 |
| mAb11002 | 25 | 18 | 288 | 52 | 32 |

Example 8: Anti-SARS-CoV-2-S Antibody Diversity Assay

A binding assay was performed to determine the binding profile of anti-SARS-COV-2-S antibodies. For this assay, antigens were amine coupled as described for the Luminex binding assay above. Briefly, approximately 9 million Mag-Plex microspheres for 16 different bead regions (Luminex Corp., MagPLex Microspheres, Cat. No. MagPLex MC10000 and MC12000), were resuspended by vortexing in 500 µL 0.1M $NaPO_4$, pH 6.2 and then centrifuged to remove the supernatant. The microspheres were resuspended in 160 µL of activation buffer and the carboxylate groups (—COOH) were activated by addition of 20 µL of 50 mg/mL of N-hydroxysuccinimide (NHS, Thermo Scientific, Cat #24525) followed by addition of 20 µL of 50 mg/mL of 1-ethyl-3-[3-dimethylaminopropyl]carbodiimide (EDC, ThermoScientific, Cat #22980) at 25° C. After 10 minutes, the pH of the reaction was reduced to 5.0 with the addition of 600 µL of 50 mM MES, pH 5 (coupling buffer), and the microspheres were vortexed and centrifuged to remove supernatant. The activated microspheres were immediately mixed with 500 µL of 20 µg/mL of SARS-CoV-2 Spike Protein (RBD)(R319-F541)-mmH in coupling buffer and incubated for two hours at 25° C. The coupling reaction was quenched by addition of 50 µL of 1M Tris-HCl, pH 8.0 and the microspheres were vortexed, centrifuged, and washed three times with 1000 µL of PBS. Microspheres were resuspended in 250 µL of PBS at 9 million microspheres/mL.

15 out of the 16 microsphere regions with amine-coupled protein were modified for the binning assay as follows: microspheres were washed twice with PBS 5% DMSO, and 500 ill of a chemical or enzyme were dissolved per manufacturing recommendations and added at 10 nM to the amine-coupled microspheres described above. This was subsequently vortexed and incubated for 2 hours at room temperature with rotation. Wash microspheres 3 times with PBS 2% BSA. Microspheres were resuspended in 1 mL of PBS at 9 million microspheres/mL.

Protein-modified and protein-unmodified (intact) microspheres were mixed at 2700 beads/ml, and 75 µL of microspheres were plated per well on a 96 well ProcartaPlex 96 well flat bottom plate (ThermoFisher, Cat. No: EPX-44444-000) and mixed with 25 µL of individual anti-SARS-CoV-2-S supernatant-containing antibody. Samples and microspheres were incubated for two hours at 25° C. and then washed twice with 200 µL of DPBS with 0.05% Tween 20. To detect bound antibody levels to individual microspheres, 100 µL of 2.5 µg/mL R-Phycoerythrin conjugated goat F(ab')2 anti-human kappa (Southern Biotech, Cat #2063-09) in blocking buffer (for antibodies with hFc), or 100 µL of 1.25 µg/mL R-Phycoerythrin AffiniPure F(ab')2 Fragment Goat Anti-Mouse IgG, F(ab')2 Fragment Specific (Jackson Immunoresearch, Cat. No: 115-116-072) in blocking buffer (for antibodies with mFc), or 100 µL of 1.25 µg/mL R-Phycoerythrin Anti-His (Biolegend, Cat. No: 362603) in blocking buffer (for ACE-2 control, R&D, Cat. No. 933-ZN), was added and incubated for 30 minutes at 25° C. After 30 minutes, the samples were washed twice with 200 µl of washing buffer and resuspended in 150 µL of wash buffer. The plates were read in FlexMap 3D® (Luminex Corp.) and Luminex xPonent® software version 4.3 (Luminex Corp.).

The results of the Luminex binning results are shown in Table 13 as median fluorescence intensity (MFI) signal intensities. To determine clusters, data was normalized to the intact protein (unmodified microspheres) and clustered. The 46 anti-SARS-CoV-2 antibodies were classified in 9 clusters with 2 or more antibodies, and 11 antibodies were classified as single nodes. Clusters were assigned by based on these results of the hierarchical clustering and dendrogram. These results show that the 46 anti-SARS-CoV-2-S antibody supernatants had diverse binding characteristics and profiles, suggesting that the collection of antibodies bound to different epitopes on the SARS-CoV-2 spike protein.

TABLE 13

Binding signal (MFI) and cluster assignment of anti-SARS-CoV-2-S monoclonal antibodies to SARS-COV-2-S RBD · mmH (unmodified and chemically or enzymatically modified)

| Sample | CLUSTER | UNMODIFIED-SARS-CoV-2 Spike Protein (RBD) (R319-F541) · mmH | MOD1-SARS-CoV-2 Spike Protein (RBD) (R319-F541) · mmH | MOD2-SARS-CoV-2 Spike Protein (RBD) (R319-F541) · mmH | MOD3-SARS-CoV-2 Spike Protein (RBD) (R319-F541) · mmH | MOD4-SARS-CoV-2 Spike Protein (RBD) (R319-F541) · mmH | MOD5-SARS-CoV-2 Spike Protein (RBD) (R319-F541) · mmH | MOD6-SARS-CoV-2 Spike Protein (RBD) (R319-F541) · mmH | MOD7-SARS-CoV-2 Spike Protein (RBD) (R319-F541) · mmH |
|---|---|---|---|---|---|---|---|---|---|
| Human_ACE2 (10 nM) | 1 | 5727 | 873 | 5119 | 1852 | 5106 | 202 | 5408 | 5013 |
| Human_ACE2 (100 nM) | 1 | 10681 | 1447 | 10320 | 2260 | 9661 | 559 | 9593 | 8624 |
| Human_ACE2 (50 nM) | 1 | 9269 | 991 | 8238 | 2185 | 7707 | 391 | 7859 | 7577 |
| mAb10969 | 3 | 28551 | 54 | 24177 | 425 | 26049 | 3546 | 20577 | 23878 |
| mAb10965 | 3 | 28080 | 38 | 21996 | 135 | 25727 | 3250 | 22419 | 24062 |
| mAb10913 | 4 | 31694 | 102 | 28389 | 23270 | 29344 | 5018 | 28738 | 27854 |
| mAb10920 | 4 | 35534 | 162 | 26783 | 28090 | 32185 | 7105 | 32942 | 30958 |
| mAb10923 | 4 | 38711 | 153 | 32305 | 33866 | 36082 | 7540 | 35335 | 33924 |
| mAb10930 | 4 | 29502 | 110 | 21579 | 21533 | 27843 | 6195 | 26600 | 25103 |
| mAb10940 | 4 | 38871 | 94 | 34337 | 33453 | 36690 | 7817 | 36128 | 34544 |
| mAb10989 | 4 | 19671 | 49 | 16697 | 18260 | 15785 | 3369 | 19568 | 15206 |
| mAb11006 | 4 | 2044 | 30 | 705 | 3773 | 2553 | 517 | 2024 | 2503 |
| mAb10934 | 5 | 33057 | 81 | 27716 | 25092 | 31664 | 6648 | 30801 | 29926 |
| mAb10924 | 5 | 39205 | 118 | 32707 | 29366 | 36507 | 6378 | 35565 | 34210 |
| mAb10939 | 5 | 33647 | 62 | 24895 | 26392 | 31390 | 6276 | 31275 | 29594 |
| mAb10988 | 5 | 23009 | 68 | 15983 | 14842 | 20830 | 3536 | 20176 | 19499 |
| mAb10957 | 5 | 20879 | 52 | 15728 | 19383 | 19993 | 3582 | 17727 | 17989 |
| mAb10914 | 6 | 36047 | 143 | 32282 | 26967 | 34199 | 7162 | 32787 | 31823 |
| mAb10915 | 6 | 36690 | 159 | 32489 | 26427 | 33545 | 9731 | 33568 | 31823 |
| mAb10932 | 6 | 34024 | 191 | 28833 | 28557 | 31560 | 9946 | 31123 | 29765 |
| mAb10938 | 6 | 34522 | 174 | 28465 | 19403 | 31252 | 8932 | 29225 | 30918 |
| mAb10941 | 6 | 36369 | 140 | 31868 | 26129 | 33637 | 9455 | 33154 | 31478 |
| mAb10984 | 6 | 25759 | 109 | 22445 | 20925 | 24747 | 6880 | 23630 | 23895 |
| mAb10985 | 6 | 27394 | 99 | 24286 | 22986 | 26151 | 5519 | 25874 | 25023 |
| mAb10986 | 6 | 25414 | 118 | 20868 | 20557 | 23619 | 6591 | 23066 | 22813 |
| mAb10977 | 6 | 16980 | 54 | 14108 | 16590 | 15851 | 3505 | 14528 | 12779 |
| mAb10933 | 7 | 35267 | 69 | 30617 | 5243 | 32665 | 6161 | 32930 | 31043 |
| mAb10982 | 7 | 27505 | 80 | 20338 | 6650 | 25051 | 4585 | 24178 | 23770 |
| mAb10987 | 7 | 29327 | 54 | 25311 | 2235 | 27981 | 4110 | 27095 | 25690 |
| mAb10935 | 8 | 31883 | 81 | 28683 | 12724 | 30329 | 6457 | 27417 | 27785 |
| mAb10970 | 8 | 32271 | 94 | 26863 | 22547 | 30537 | 7029 | 27679 | 28333 |
| mAb10971 | 8 | 27415 | 106 | 23890 | 22184 | 27850 | 6869 | 25337 | 25164 |
| mAb10964 | 8 | 29963 | 122 | 23580 | 23419 | 27896 | 7085 | 27483 | 25968 |
| mAb10921 | 9 | 31657 | 91 | 28216 | 18123 | 30441 | 6821 | 28629 | 28756 |
| mAb10966 | 9 | 29489 | 85 | 22836 | 19866 | 25736 | 5869 | 24217 | 26013 |
| mAb10967 | 9 | 26784 | 107 | 20787 | 13760 | 25104 | 6192 | 21329 | 23434 |
| mAb10954 | 9 | 28476 | 74 | 21915 | 19038 | 26186 | 5948 | 25299 | 24332 |
| mAb10955 | 9 | 28637 | 39 | 24585 | 21155 | 27912 | 4141 | 23849 | 24862 |
| mAb10996 | S1 | 3403 | 20 | 5275 | 164 | 5562 | 488 | 3042 | 9125 |
| mAb10937 | S2 | 33561 | 94 | 24890 | 104 | 31164 | 5904 | 30327 | 28675 |
| mAb10936 | S3 | 32919 | 136 | 26818 | 312 | 31261 | 7856 | 31008 | 29293 |
| mAb10922 | S4 | 33183 | 102 | 25384 | 1107 | 31348 | 5822 | 31313 | 29386 |
| mAb11002 | S5 | 9881 | 16 | 3348 | 155 | 8615 | 153 | 9542 | 7562 |
| mAb10956 | S6 | 24562 | 29 | 21685 | 19337 | 23769 | 2275 | 19422 | 21961 |
| mAb11010 | S7 | 6388 | 18 | 4155 | 5441 | 8832 | 384 | 7444 | 5766 |
| mAb11008 | S8 | 7096 | 26 | 926 | 1525 | 2776 | 198 | 2750 | 1007 |
| mAb10998 | S9 | 2557 | 18 | 247 | 1336 | 1524 | 104 | 2937 | 723 |
| mAb11004 | S10 | 6514 | 18 | 2205 | 604 | 3566 | 1155 | 4522 | 2229 |
| mAb11000 | S11 | 16670 | 19 | 3416 | 12787 | 13493 | 2009 | 17756 | 12409 |

TABLE 13-continued

Binding signal (MFI) and cluster assignment of anti-SARS-CoV-2-S monoclonal antibodies to SARS-COV-2-S RBD · mmH (unmodified and chemically or enzymatically modified)

| Sample | CLUSTER | MOD8-SARS-CoV-2 Spike Protein (RBD) (R319-F541) · mmH | MOD9-SARS-CoV-2 Spike Protein (RBD) (R319-F541) · mmH | MOD10-SARS-CoV-2 Spike Protein (RBD) (R319-F541) · mmH | MOD11-SARS-CoV-2 Spike Protein (RBD) (R319-F541) · mmH | MOD12-SARS-CoV-2 Spike Protein (RBD) (R319-F541) · mmH | MOD13-SARS-CoV-2 Spike Protein (RBD) (R319-F541) · mmH | MOD14-SARS-CoV-2 Spike Protein (RBD) (R319-F541) · mmH | MOD15-SARS-CoV-2 Spike Protein (RBD) (R319-F541) · mmH |
|---|---|---|---|---|---|---|---|---|---|
| Human_ACE2 (10 nM) | 1 | 36 | 4500 | 4091 | 4618 | 4505 | 5094 | 4743 | 3173 |
| Human_ACE2 (100 nM) | 1 | 36 | 6212 | 7922 | 8440 | 8957 | 8948 | 7927 | 5370 |
| Human_ACE2 (50 nM) | 1 | 35 | 5518 | 6447 | 7064 | 7233 | 7600 | 7112 | 4407 |
| mAb10969 | 3 | 154 | 18918 | 24407 | 22409 | 27036 | 24269 | 23672 | 14196 |
| mAb10965 | 3 | 110 | 19061 | 22355 | 21414 | 25635 | 23144 | 23156 | 14072 |
| mAb10913 | 4 | 15939 | 28645 | 27110 | 28878 | 31159 | 28971 | 27784 | 26272 |
| mAb10920 | 4 | 17228 | 32758 | 31463 | 31910 | 35144 | 32185 | 32323 | 29949 |
| mAb10923 | 4 | 20961 | 34187 | 33809 | 36323 | 38596 | 35381 | 33338 | 33131 |
| mAb10930 | 4 | 10235 | 23744 | 24516 | 26738 | 27958 | 26968 | 25126 | 23951 |
| mAb10940 | 4 | 14572 | 35967 | 34704 | 36070 | 39285 | 35462 | 34922 | 33614 |
| mAb10989 | 4 | 6136 | 17756 | 15530 | 16838 | 15137 | 17411 | 18100 | 15946 |
| mAb11006 | 4 | 299 | 2442 | 3749 | 1076 | 4622 | 2818 | 3344 | 3568 |
| mAb10934 | 5 | 6410 | 31261 | 30364 | 30709 | 32873 | 30502 | 28591 | 27785 |
| mAb10924 | 5 | 6594 | 32856 | 33797 | 35875 | 38424 | 34647 | 33476 | 31524 |
| mAb10939 | 5 | 4808 | 28465 | 29444 | 30699 | 33475 | 30596 | 29721 | 27129 |
| mAb10988 | 5 | 2980 | 18329 | 19660 | 20692 | 21770 | 20130 | 18948 | 16558 |
| mAb10957 | 5 | 2171 | 17357 | 19487 | 18596 | 21247 | 18757 | 17810 | 16081 |
| mAb10914 | 6 | 5475 | 31226 | 31467 | 33235 | 35175 | 32626 | 31100 | 29217 |
| mAb10915 | 6 | 9277 | 33442 | 31984 | 32902 | 35462 | 31937 | 32397 | 30009 |
| mAb10932 | 6 | 9711 | 30122 | 29074 | 30433 | 33379 | 30283 | 29880 | 26795 |
| mAb10938 | 6 | 7536 | 28109 | 30308 | 31264 | 33394 | 30814 | 30538 | 27751 |
| mAb10941 | 6 | 7518 | 29802 | 31421 | 33958 | 35290 | 32925 | 31777 | 29159 |
| mAb10984 | 6 | 3527 | 20212 | 22065 | 22318 | 26163 | 23227 | 22283 | 19349 |
| mAb10985 | 6 | 6821 | 23642 | 23572 | 24654 | 27394 | 24677 | 24493 | 20787 |
| mAb10986 | 6 | 2838 | 20672 | 21766 | 21720 | 25207 | 23400 | 22214 | 19694 |
| mAb10977 | 6 | 4005 | 14193 | 12616 | 13320 | 16332 | 13632 | 14312 | 13136 |
| mAb10933 | 7 | 1556 | 27705 | 29926 | 30801 | 34427 | 30409 | 30525 | 24367 |
| mAb10982 | 7 | 1065 | 20361 | 23131 | 23247 | 26412 | 24027 | 23549 | 16765 |
| mAb10987 | 7 | 1444 | 25621 | 25345 | 26335 | 29995 | 27049 | 26082 | 22871 |
| mAb10935 | 8 | 2534 | 26151 | 27958 | 28752 | 30847 | 28522 | 27452 | 24816 |
| mAb10970 | 8 | 1968 | 25233 | 27793 | 27610 | 31869 | 29871 | 26909 | 23775 |
| mAb10971 | 8 | 1598 | 22587 | 25646 | 24384 | 27391 | 25761 | 24774 | 19590 |
| mAb10964 | 8 | 2414 | 24740 | 25658 | 26439 | 29113 | 27243 | 26783 | 22405 |
| mAb10921 | 9 | 941 | 23674 | 27586 | 27367 | 30969 | 28480 | 28331 | 21220 |
| mAb10966 | 9 | 833 | 21800 | 24332 | 24977 | 27440 | 26554 | 24585 | 18580 |
| mAb10967 | 9 | 574 | 19521 | 22352 | 22997 | 25506 | 22641 | 22836 | 17387 |
| mAb10954 | 9 | 929 | 22237 | 24516 | 23457 | 28200 | 24897 | 24539 | 19717 |
| mAb10955 | 9 | 1141 | 22191 | 24805 | 23688 | 27210 | 25575 | 24677 | 18944 |
| mAb10996 | S1 | 28 | 8940 | 6336 | 6789 | 6229 | 5821 | 3484 | 1312 |
| mAb10937 | S2 | 1231 | 27597 | 27092 | 29937 | 32116 | 29661 | 29386 | 20543 |
| mAb10936 | S3 | 2916 | 29074 | 28775 | 30813 | 31711 | 29189 | 28522 | 21674 |
| mAb10922 | S4 | 2248 | 29845 | 28629 | 30373 | 32931 | 30625 | 28962 | 23399 |
| mAb11002 | S5 | 17 | 4144 | 6415 | 6790 | 8465 | 7688 | 6804 | 2016 |
| mAb10956 | S6 | 331 | 16954 | 21282 | 21524 | 26646 | 21547 | 22767 | 15077 |
| mAb11010 | S7 | 162 | 5567 | 6718 | 9557 | 12522 | 5287 | 5898 | 4915 |
| mAb11008 | S8 | 60 | 2350 | 2759 | 2824 | 3301 | 2745 | 2130 | 2831 |
| mAb10998 | S9 | 85 | 1611 | 2260 | 1206 | 2513 | 2186 | 727 | 1029 |
| mAb11004 | S10 | 71 | 1465 | 12665 | 10667 | 5925 | 5531 | 11578 | 1144 |
| mAb11000 | S11 | 56 | 14151 | 19230 | 17204 | 21718 | 17952 | 17117 | 5151 |

Example 9: Biacore Binding Kinetics of Anti-SARS-CoV-2-S Monoclonal Antibodies Equilibrium dissociation constants ($K_D$) for different SARS-CoV-2-S antibodies from primary supernatants from CHOt cells or from hybridomas were determined using a real-time surface plasmon resonance-based Biacore T200/Biacore 8K biosensor. All binding studies were performed in 10 mM HEPES, 150 mM NaCl, 3 mM EDTA, and 0.05% v/v Surfactant Tween-20, pH 7.4 (HBS-ET) running buffer at 25° C. The Biacore CM5 sensor chip surface was first derivatized by amine coupling with either mouse anti-human Fc specific mAb or rabbit anti-mouse Fcγ monoclonal antibody (GE, Catalog #BR-1008-38) to capture anti-SARS-CoV-2 antibodies. Binding studies were performed on a human SARS-CoV-2 RBD extracellular domain expressed with a C-terminal myc-myc-hexahistidine tag (SARS-COV-2 RBD-MMH), SARS-CoV-2 RBD extracellular domain expressed with a C-terminal mouse IgG2a (SARS-COV-2 RBD-mFc), or SARS-CoV-2 RBD extracellular domain expressed with a C-terminal human IgG1 (SARS-COV-2 RBD-hFc). Single concentrations of SARS-COV-2

RBD-MMH, (100 nM); SARS-COV-2 RBD-mFc (50 nM), or SARS-COV-2 RBD-hFc (50 nM), prepared in HBS-ET running buffer, were injected for 1.5 minutes at a flow rate of 30 μL/min while the dissociation of antibody-bound different SARS-CoV-2 RBD reagents was monitored for 2 minutes in HBS-ET running buffer. At the end of each cycle, the SARS-CoV-2 RBD antibody capture surface was regenerated using either a 10 sec injection of 20 mM phosphoric acid for the mouse anti-human Fc specific monoclonal antibody surface or a 40 sec injection of 10 mM Glycine, HCl, pH1.5 for the rabbit anti-mouse Fey specific polyclonal antibody. The association rate ($k_a$) and dissociation rate ($k_d$) were determined by fitting the real-time binding sensorgrams to a 1:1 binding model with mass transport limitation using BiaEvaluation software v3.1 or Biacore Insight Evaluation software v2.0. or curve-fitting software. Binding dissociation equilibrium constant ($K_D$) and dissociative half-life (t½) were calculated from the kinetic rates as:

$$K_D(M) = \frac{kd}{ka},\ \text{and}\ t1/2\,(\text{min}) = \frac{\ln(2)}{60 * kd}$$

Binding kinetics parameters for different SARS-CoV-2 monoclonal antibodies binding to different anti-SARS-COV-2 RBD reagents of the invention at 25° C. are shown in Tables 14 and 15.

TABLE 14

Binding kinetics of SARS-COV-2 RBD-MMH binding to anti-SARS-CoV-2 monoclonal antibodies at 25° C.

| Super-natant | mAb Capture Level (RU) | 50 nM Ag Bound (RU) | $k_a$ (1/Ms) | $k_d$ (1/s) | KD (M) | t½ (min) |
|---|---|---|---|---|---|---|
| mAb10913 | 2010 | 381 | 4.91E+05 | 2.28E−02 | 4.64E−08 | 0.5 |
| mAb10914 | 3169 | 174 | 3.49E+05 | 1.36E−02 | 3.89E−08 | 0.8 |
| mAb10915 | 824 | 109 | 8.85E+04 | 3.18E−04 | 3.59E−09 | 36.3 |
| mAb10932 | 2261 | 326 | 8.50E+04 | 1.26E−04 | 1.48E−09 | 92 |
| mAb10933 | 1414 | 428 | 1.05E+06 | 4.08E−03 | 3.88E−09 | 2.8 |
| mAb10934 | 2918 | 981 | 1.01E+06 | 4.35E−03 | 4.32E−09 | 2.7 |
| mAb10935 | 3293 | 694 | 2.11E+05 | 3.99E−03 | 1.89E−08 | 2.9 |
| mAb10936 | 2491 | 717 | 3.03E+05 | 8.81E−04 | 2.91E−09 | 13.1 |
| mAb10937 | 1846 | 504 | 3.81E+05 | 5.73E−03 | 1.50E−08 | 2 |
| mAb10920 | 1295 | 234 | 6.22E+05 | 2.20E−02 | 3.54E−08 | 0.5 |
| mAb10921 | 1024 | 141 | 9.52E+04 | 4.99E−04 | 5.24E−09 | 23.1 |
| mAb10922 | 2395 | 786 | 3.91E+05 | 2.00E−03 | 5.11E−09 | 5.8 |
| mAb10923 | 1278 | 322 | 2.94E+05 | 6.04E−03 | 2.06E−08 | 1.9 |
| mAb10924 | 766 | 166 | 1.97E+05 | 3.65E−03 | 1.85E−08 | 3.2 |
| mAb10930 | 3137 | 328 | 8.90E+04 | 1.85E−03 | 2.08E−08 | 6.2 |
| mAb10938 | 2167 | 180 | 6.60E+04 | 3.48E−04 | 5.28E−09 | 33.2 |
| mAb10939 | 1505 | 241 | 1.69E+05 | 3.38E−03 | 2.00E−08 | 3.4 |
| mAb10940 | 2149 | 698 | 3.34E+05 | 2.38E−03 | 7.15E−09 | 4.9 |
| mAb10941 | 1811 | 288 | 9.85E+04 | 5.17E−04 | 5.25E−09 | 22.3 |
| mAb10982 | 1096 | 188 | 1.32E+05 | 2.71E−03 | 2.06E−08 | 4.3 |
| mAb10984 | 1654 | 387 | 1.55E+05 | 3.70E−04 | 2.39E−09 | 31.2 |
| mAb10985 | 1974 | 749 | 9.41E+05 | 1.45E−03 | 1.54E−09 | 8 |
| mAb10986 | 1560 | 524 | 3.21E+05 | 2.56E−04 | 7.97E−10 | 45.2 |
| mAb10987 | 1242 | 356 | 4.50E+05 | 1.04E−02 | 2.32E−08 | 1.1 |
| mAb10988 | 1227 | 291 | 1.27E+06 | 3.52E−02 | 2.77E−08 | 0.3 |
| mAb10989 | 692 | 257 | 1.60E+06 | 3.14E−03 | 1.96E−09 | 3.7 |
| mAb10969 | 2200 | 427 | 1.80E+05 | 4.71E−03 | 2.61E−08 | 2.5 |
| mAb10970 | 1865 | 438 | 1.37E+05 | 7.99E−04 | 5.82E−09 | 14.4 |
| mAb10971 | 1482 | 358 | 1.68E+05 | 4.49E−04 | 2.67E−09 | 25.8 |
| mAb10964 | 1208 | 460 | 1.06E+06 | 7.56E−04 | 7.14E−10 | 15.3 |
| mAb10965 | 1046 | 168 | 1.19E+05 | 2.73E−03 | 2.28E−08 | 4.2 |
| mAb10966 | 1422 | 343 | 1.57E+05 | 4.40E−04 | 2.81E−09 | 26.3 |
| mAb10967 | 1421 | 175 | 1.12E+05 | 1.08E−04 | 9.66E−10 | 106.9 |
| mAb10954 | 1150 | 338 | 2.34E+05 | 4.05E−04 | 1.73E−09 | 28.5 |
| mAb10955 | 1032 | 199 | 1.38E+05 | 2.69E−03 | 1.95E−08 | 4.3 |
| mAb10956 | 1303 | 184 | 2.02E+05 | 5.31E−03 | 2.62E−08 | 2.2 |
| mAb10957 | 736 | 163 | 1.34E+05 | 3.15E−04 | 2.35E−09 | 36.7 |
| mAb10977 | 221 | 57 | 2.33E+05 | 7.17E−04 | 3.08E−09 | 16.1 |
| mAb11010 | 1027 | 108 | 3.35E+05 | 1.48E−03 | 4.42E−09 | 7.8 |
| mAb11004 | 1111 | 161 | 1.88E+05 | 3.12E−03 | 1.66E−08 | 3.7 |
| mAb11000 | 381 | 16 | 1.40E+05 | 2.41E−02 | 1.72E−07 | 0.5 |
| mAb11006 | 1118 | 49 | 8.97E+04 | 3.67E−04 | 4.10E−09 | 31.5 |
| mAb11008 | 887 | 56 | 6.73E+04 | 4.00E−03 | 5.94E−08 | 2.9 |
| mAb10998 | 1155 | 69 | 1.95E+05 | 2.28E−02 | 1.17E−07 | 0.5 |
| mAb10996 | 616 | 28 | 1.53E+05 | 1.10E−02 | 7.18E−08 | 1.1 |
| mAb11002 | 1070 | 8 | 3.21E+05 | 2.54E−02 | 7.93E−08 | 0.5 |

TABLE 15

Binding kinetics of SARS-COV-2 RBD-mFc or SARS-COV-2 RBD-hFc binding to anti-SARS-CoV-2-S monoclonal antibodies at 25° C.

| Supernatant | mAb Capture Level (RU) | 50 nM Ag Bound (RU) | $k_a$ (1/Ms) | $k_d$ (1/s) | KD (M) | t½ (min) |
|---|---|---|---|---|---|---|
| mAb10913 | 961 | 575 | 6.23E+05 | 1.52E−04 | 2.44E−10 | 76.1 |
| mAb10914 | 1467 | 313 | 1.83E+05 | 1.00E−05* | 5.47E−11 | 1155* |
| mAb10915 | 392 | 141 | 2.81E+05 | 1.00E−05* | 3.56E−11 | 1155* |
| mAb10932 | 1060 | 372 | 2.42E+05 | 1.00E−05* | 4.13E−11 | 1155* |
| mAb10933 | 681 | 465 | 1.23E+06 | 2.12E−04 | 1.73E−10 | 54.4 |
| mAb10934 | 1401 | 949 | 1.41E+06 | 1.17E−04 | 8.32E−11 | 98.3 |
| mAb10935 | 1667 | 830 | 3.83E+05 | 1.00E−05* | 2.61E−11 | 1155* |
| mAb10936 | 1171 | 699 | 6.52E+05 | 1.00E−05* | 1.53E−11 | 1155* |
| mAb10937 | 904 | 575 | 6.39E+05 | 7.28E−05 | 1.14E−10 | 158.7 |
| mAb10920 | 617 | 357 | 7.02E+05 | 2.92E−04 | 4.16E−10 | 39.5 |
| mAb10921 | 489 | 170 | 2.66E+05 | 1.00E−05* | 3.75E−11 | 1155* |
| mAb10922 | 1286 | 828 | 7.19E+05 | 2.42E−05 | 3.36E−11 | 478.2 |
| mAb10923 | 613 | 362 | 6.51E+05 | 2.83E−05 | 4.35E−11 | 407.7 |
| mAb10924 | 465 | 223 | 3.67E+05 | 8.13E−05 | 2.22E−10 | 142.1 |
| mAb10930 | 2156 | 449 | 2.32E+05 | 1.00E−05* | 4.31E−11 | 1155* |
| mAb10938 | 1363 | 333 | 3.11E+05 | 1.00E−05* | 3.22E−11 | 1155* |
| mAb10939 | 904 | 324 | 2.99E+05 | 1.15E−05 | 3.87E−11 | 1004.3 |
| mAb10940 | 1508 | 893 | 5.61E+05 | 2.86E−05 | 5.09E−11 | 403.8 |
| mAb10941 | 1132 | 371 | 2.60E+05 | 1.00E−05* | 2.15E−11 | 1155* |
| mAb10982 | 529 | 236 | 3.10E+05 | 1.69E−05 | 5.44E−11 | 683.6 |
| mAb10984 | 1213 | 573 | 4.02E+05 | 1.00E−05* | 2.49E−11 | 1155* |
| mAb10985 | 1463 | 1040 | 1.09E+06 | 1.27E−05 | 1.17E−11 | 910.9 |
| mAb10986 | 1168 | 752 | 6.33E+05 | 1.00E−05* | 1.58E−11 | 1155* |
| mAb10987 | 902 | 632 | 8.20E+05 | 1.70E−04 | 2.08E−10 | 67.8 |
| mAb10988 | 892 | 628 | 1.24E+06 | 3.46E−04 | 2.79E−10 | 33.4 |
| mAb10989 | 505 | 378 | 2.07E+06 | 9.30E−05 | 4.50E−11 | 124.2 |
| mAb10969 | 1658 | 738 | 3.05E+05 | 1.51E−05 | 4.96E−11 | 764 |
| mAb10970 | 1370 | 661 | 3.48E+05 | 1.00E−05* | 2.88E−11 | 1155* |
| mAb10971 | 1081 | 556 | 3.95E+05 | 1.00E−05* | 2.53E−11 | 1155* |
| mAb10964 | 875 | 651 | 1.43E+06 | 1.00E−05* | 7.00E−12 | 1155* |
| mAb10965 | 762 | 322 | 2.97E+05 | 1.00E−05* | 3.36E−11 | 1155* |
| mAb10966 | 921 | 430 | 4.02E+05 | 1.00E−05* | 2.49E−11 | 1155* |
| mAb10967 | 945 | 355 | 3.99E+05 | 1.00E−05* | 2.51E−11 | 1155* |
| mAb10954 | 734 | 414 | 5.77E+05 | 1.00E−05* | 1.73E−11 | 1155* |
| mAb10955 | 634 | 292 | 3.96E+05 | 2.34E−05 | 5.92E−11 | 493.6 |
| mAb10956 | 842 | 339 | 3.74E+05 | 1.48E−04 | 3.95E−10 | 78 |
| mAb10957 | 449 | 209 | 3.58E+05 | 1.00E−05* | 2.79E−11 | 1155* |
| mAb10977 | 161 | 102 | 5.56E+05 | 1.04E−04 | 1.87E−10 | 110.9 |
| mAb11010 | 1014 | 163 | 4.24E+05 | 1.00E−05* | 2.36E−11 | 1155* |
| mAb11004 | 1101 | 241 | 3.46E+05 | 6.63E−05 | 1.91E−10 | 174.2 |
| mAb11000 | 380 | 61 | 4.38E+05 | 1.83E−03 | 4.17E−09 | 6.3 |
| mAb11006 | 1112 | 75 | 1.88E+05 | 1.00E−05* | 5.32E−11 | 1155* |
| mAb11008 | 872 | 110 | 1.61E+05 | 1.15E−04 | 7.15E−10 | 100.4 |
| mAb10998 | 1140 | 227 | 3.30E+05 | 5.21E−04 | 1.58E−09 | 22.2 |
| mAb10996 | 629 | 83 | 2.88E+05 | 9.32E−04 | 3.24E−09 | 12.4 |
| mAb11002 | 1068 | 60 | 2.69E+05 | 4.49E−03 | 1.67E−08 | 2.6 |

*Estimated value based on the limit of measurement of the dissociative rate constant and dissociative half-life under the experimental conditions.

Example 10: Characterization of Anti-SARS-CoV-2-S Monoclonal Antibodies by Blocking ELISA An ELISA-based blocking assay was developed to determine the ability of anti-SARS-CoV2-S antibodies to block the binding of the SARS-CoV-2 spike protein receptor binding domain (RBD) to human angiotensin converting enzyme 2 (hACE2).

The SARS-CoV-2 protein used in the experiments was comprised of the receptor binding domain (RBD) portion of the SARS-CoV-2 spike protein (amino acids Arg319 to Phe541) expressed with the Fc portion of the human IgG1 at the c-terminus (SARS-CoV-2 RBD-hFc; see NCBI accession number MN908947.3) The human ACE2 protein used in the experiments was purchased from R&D systems and is comprised of amino acids glutamine 18 to serine 740 with a c-terminal 10×-Histidine tag (hACE2-His; NCBI accession number Q9BYF1).

Experiments were carried out using the following procedure. A monoclonal anti-Penta-His antibody (Qiagen) was coated at 1 μg/ml in PBS on a 96-well microtiter plate overnight at 4° C. The hACE2-His receptor was added at 0.2 μg/ml in PBS and bound for 2 hours at room temperature. Nonspecific binding sites were subsequently blocked using a 0.5% (w/v) solution of BSA in PBS. In other microtiter plates, a constant amount of 10 pM or 15 pM (as indicated in Table 16) of SARS-CoV-2 RBD-hFc protein was bound with antibodies diluted 1:10 or 1:20 in PBS+0.5% BSA. These antibody-protein complexes, after a one-hour incubation, were transferred to the microtiter plate coated with hACE2-His. After 1.5 hours of incubation at RT, the wells were washed, and plate-bound SARS-CoV-2 RBD-hFc protein was detected with goat-anti-human IgG antibody conjugated with horseradish peroxidase (HRP) (Jackson). The plates were then developed using TMB substrate solution (BD Biosciences, catalog #555214) according to manufacturer's recommendation and absorbance at 450 nm was measured on a Victor X5 plate reader.

Data analysis was performed by calculating the % reduction of signal of the fixed SARS-CoV-2-S RBD-hFc concentration in the presence of the antibody vs in the absence of the antibody. In the calculation, binding signal of the sample of the constant SARS-CoV-2-S RBD-hFc without the presence of the antibody for each plate was referenced as 100% binding or 0% blocking; and the baseline signal of the sample of media only without the presence of SARS-CoV-2 RBD-hFc was referenced as 0% binding or 100% blocking.

The ability of anti-SARS-CoV-2-S antibodies to block SARS-CoV-2-S RBD from binding to human ACE2 was assessed using a blocking ELISA format. Single point test antibody supernatant blocking of either 10 pM or 15 pM SARS-CoV-2-S RBD-hFc binding to hACE2-His, which was presented on anti-His antibody coated on 96-well microtiter plates, was detected with an HRP conjugated anti-hFc antibody.

The blocking results of three assays are summarized in Table 16. The SARS-CoV-2-S binding signal (450 nm) and the G calculated % blocking are indicated. A range of blocking is observed for the test samples. For samples where an NA is indicated in columns 6 and 7, a plate-corrected value is included in columns 4 and 5, as data was consistent with a single plate switch occurring for those samples. 43 of 46 antibody supernatants blocked greater than 50% of the SARS-CoV-2-S RBD-hFc binding to plate-coated human ACE2, with 16 of them blocking >90% of the signal.

TABLE 16

Blocking ELISA Results

| Supernatant | SARS-CoV-2 RBD Fixed Concentration | Supernatant dilution | Plate corrected SARS-CoV-2 RBD-hFc Binding to His presented ACE2 (Abs 450 nm) | Plate corrected SARS-CoV-2 RBD-hFc Binding to His presented ACE2 % Blocking | SARS-CoV-2 RBD-hFc Binding to His presented ACE2 (Abs 450 nm) | SARS-CoV-2 RBD-hFc Binding to His presented ACE2 % Blocking |
|---|---|---|---|---|---|---|
| mAb10913 | 15 pM | 1:10 | 0.206 | 80.5 | 0.206 | 80.5 |
| mAb10914 | 15 pM | 1:10 | 0.326 | 59.1 | 0.326 | 59.1 |
| mAb10915 | 15 pM | 1:10 | 0.171 | 89.7 | 0.171 | 89.7 |
| mAb10932 | 15 pM | 1:10 | 0.254 | 57.3 | 0.254 | 57.3 |
| mAb10933 | 15 pM | 1:10 | 0.158 | 96.3 | 0.158 | 96.3 |
| mAb10934 | 15 pM | 1:10 | 0.209 | 78 | 0.209 | 78 |
| mAb10935 | 15 pM | 1:10 | 0.238 | 69.4 | 0.238 | 69.4 |
| mAb10936 | 15 pM | 1:10 | 0.234 | 70.6 | 0.234 | 70.6 |
| mAb10937 | 15 pM | 1:10 | 0.176 | 88.1 | 0.176 | 88.1 |
| mAb10920 | 15 pM | 1:10 | 0.601 | −56.5 | 0.601 | −56.5 |
| mAb10921 | 15 pM | 1:10 | 0.192 | 82.7 | 0.192 | 82.7 |
| mAb10922 | 15 pM | 1:10 | 0.181 | 86.4 | 0.181 | 86.4 |
| mAb10923 | 15 pM | 1:10 | 0.237 | 43.6 | 0.237 | 43.6 |
| mAb10924 | 15 pM | 1:10 | 0.175 | 78.2 | 0.175 | 78.2 |
| mAb10930 | 15 pM | 1:10 | 0.241 | 42.5 | 0.241 | 42.5 |
| mAb10938 | 15 pM | 1:10 | 0.169 | 87.5 | 0.169 | 87.5 |
| mAb10939 | 15 pM | 1:10 | 0.204 | 65.6 | 0.204 | 65.6 |
| mAb10940 | 15 pM | 1:10 | 0.152 | 95.2 | 0.152 | 95.2 |
| mAb10941 | 15 pM | 1:10 | 0.174 | 97.2 | 0.174 | 97.2 |
| mAb10982 | 15 pM | 1:10 | 0.195 | 83.5 | 0.195 | 83.5 |
| mAb10984 | 15 pM | 1:10 | 0.166 | 96.3 | NA | NA |
| mAb10985 | 15 pM | 1:10 | 0.162 | 97 | NA | NA |
| mAb10986 | 15 pM | 1:10 | 0.158 | 97.8 | NA | NA |
| mAb10987 | 15 pM | 1:10 | 0.243 | 81.8 | NA | NA |
| mAb10988 | 15 pM | 1:10 | 0.244 | 84 | 0.244 | 84 |
| mAb10989 | 15 pM | 1:10 | 0.155 | 101.8 | 0.155 | 101.8 |
| mAb10969 | 15 pM | 1:10 | 0.221 | 87.8 | 0.221 | 87.8 |
| mAb10970 | 15 pM | 1:10 | 0.164 | 97.7 | 0.164 | 97.7 |
| mAb10971 | 15 pM | 1:10 | 0.17 | 96.7 | 0.17 | 96.7 |
| mAb10964 | 15 pM | 1:10 | 0.169 | 96.9 | 0.169 | 96.9 |
| mAb10965 | 15 pM | 1:10 | 0.158 | 98.8 | 0.158 | 98.8 |
| mAb10966 | 15 pM | 1:10 | 0.157 | 94.2 | 0.157 | 94.2 |
| mAb10967 | 15 pM | 1:10 | 0.145 | 97.9 | 0.145 | 97.9 |
| mAb10954 | 15 pM | 1:10 | 0.147 | 97.3 | 0.147 | 97.3 |
| mAb10955 | 15 pM | 1:10 | 0.162 | 92.7 | 0.162 | 92.7 |
| mAb10956 | 15 pM | 1:10 | 0.189 | 84.5 | 0.189 | 84.5 |
| mAb10957 | 15 pM | 1:10 | 0.154 | 95.1 | 0.154 | 95.1 |
| mAb10977 | 15 pM | 1:10 | 0.315 | 71.5 | 0.315 | 71.5 |
| mAb11010 | 10 pM | 1:20 | 0.186 | 82.1 | 0.186 | 82.1 |
| mAb11004 | 10 pM | 1:20 | 0.211 | 70 | 0.211 | 70 |
| mAb11000 | 10 pM | 1:20 | 0.173 | 72.7 | 0.173 | 72.7 |
| mAb11006 | 10 pM | 1:20 | 0.236 | 58 | 0.236 | 58 |
| mAb11008 | 10 pM | 1:20 | 0.213 | 69.1 | 0.213 | 69.1 |
| mAb10998 | 10 pM | 1:20 | 0.185 | 61.6 | 0.185 | 61.6 |
| mAb10996 | 10 pM | 1:20 | 0.295 | −18.1 | 0.295 | −18.1 |
| mAb11002 | 10 pM | 1:20 | 0.177 | 79.2 | 0.177 | 79.2 |

Example 11: Epitope Mapping of Anti-SARS-CoV-2-S Monoclonal Antibodies to Spike Glycoprotein by Hydrogen-Deuterium Exchange Mass Spectrometry Hydrogen-Deuterium Exchange Mass Spectrometry (HDX-MS) was performed to determine the amino acid residues of the SARS-CoV-2 Spike Protein Receptor Binding Domain (RBD (amino acids R319-F541)) that interact with mAb10989, mAb10987, mAb10934, mAb10933, mAb10920, mAb10922, mAb10936, mAb10954, mAb10964, mAb10977, mAb10984, and mAb10986. A general description of the HDX-MS method is set forth in e.g., Ehring (1999) Analytical Biochemistry 267(2):252-259; and Engen and Smith (2001) Anal. Chem. 73:256A-265A.

The HDX-MS experiments were performed on an integrated HDX-MS platform, consisting of a Leaptec HDX PAL system for the deuterium labeling and quenching, a Waters Acquity I-Class (Binary Solvent Manager) for the sample digestion and loading, a Waters Acquity I-Class (Binary Solvent Manager) for the analytical gradient, and a Thermo Q Exactive HF mass spectrometer for peptide mass measurement.

The labeling solution was prepared as PBS buffer in $D_2O$ at pD 7.0 (10 mM phosphate buffer, 140 mM NaCl, and 3 mM KCl, equivalent to pH 7.4 at 25° C.). For deuterium labeling, 10 μL of the RBD protein or RBD protein premixed with each one of the 12 antibodies listed above were incubated at 20° C. with 90 μL of $D_2O$ labeling solution for various timepoints, in duplicate. For mAb10989, mAb10987, mAb10934, and mAb10933, the time points were 0 min (non-deuterated control), 5 min, and 10 min. For mAb10920, mAb10922, mAb10936, mAb10954, mAb10964, mAb10977, mAb10984, and mAb10986, the time points were 0 min (non-deuterated control) and 10 min. The deuteration reaction was quenched by adding 90 μL of pre-chilled quench buffer (0.5 M TCEP-HCl, 4 M urea and 0.5% formic acid) to each sample for a 90 second incubation at 20° C. The quenched samples were then injected into the Leaptec HDX PAL system for online pepsin/protease XIII digestion. The digested peptides were trapped by a C18 column (2.1 mm×5 mm, Waters) and separated by another C18 column (2.1 mm×50 mm, Waters) at −5° C. with a 20 minute gradient (for mAb10989, mAb10987, mAb10934, and mAb10933) or a 10 minute gradient (for mAb10920, mAb10922, mAb10936, mAb10954, mAb10956, mAb10964, mAb10977, and mAb10984) from 0% to 90% of mobile phase B solution (mobile phase A solution: 0.5% formic acid and 4.5% acetonitrile in water, mobile phase B solution: 0.5% formic acid in acetonitrile). The eluted peptides were analyzed by a Thermo Q Exactive HF mass spectrometry in LC-MS/MS or LC-MS mode.

The LC-MS/MS data from the undeuterated RBD protein sample were searched against a database including amino acid sequences of the RBD protein, pepsin, protease XIII, and their reversed sequences using Byonic search engine (Protein Metrics). The search parameters were set as default using non-specific enzymatic digestion and human glycosylation as common variable modification. The list of identified peptides was then imported into HDExaminer software (version 3.1) to calculate the deuterium uptake (D-uptake) and differences in deuterium uptake percentage (Δ% D) for all deuterated samples. Difference in deuterium uptake percentage (Δ% D) was calculated as follows.

$$\text{Difference in deuterium uptake } (\Delta D) = D\text{–uptake } (RBD\text{–}mAb) - D\text{–uptake } (RBD \text{ alone})$$

$$\text{Difference in deuterium uptake percentage } (\Delta\,\%\,D) = \frac{\Delta D}{\text{Theoretical maximum } D \text{ uptake of the peptide}} \times 100$$

A total of 190 peptides from the RBD were identified from both RBD alone and RBD in complex with mAb10989 samples, representing 86.06% sequence coverage of the RBD. Any peptide that exhibited a reduction in deuterium uptake of 5% or greater (i.e., a Δ% D value of less than −5%, such as −6%, −10%, and so on) upon mAb binding was defined as significantly protected. Peptides corresponding to amino acids 467-513 (DISTEIYQAGSTPCNGVEGFNCYFPLQSYGFQPTNGVGYQPYRVVVL) (SEQ ID NO: 835) of the RBD were significantly protected by mAb10989.

A total of 187 peptides from the RBD were identified from both RBD alone and RBD in complex with mAb10987 samples, representing 86.06% sequence coverage of RBD. Any peptide that exhibited a reduction in deuterium uptake of 5% or greater (i.e., a Δ% D value of less than −5%, such as −6%, −10%, and so on) upon mAb binding was defined as significantly protected. Peptides corresponding to amino acids 432-452 (CVIAWNSNNLDSKVGGNYNYL) (SEQ ID NO: 836) of the RBD were significantly protected by mAb10987.

A total of 188 peptides from the RBD were identified from both RBD alone and RBD in complex with mAb10934 samples, representing 86.06% sequence coverage of the RBD. Any peptide that exhibited a reduction in deuterium uptake of 5% or greater (i.e., a Δ% D value of less than −5%, such as −6%, −10%, and so on) upon mAb binding was defined as significantly protected. Peptides corresponding to amino acids 432-452 (CVIAWNSNNLDSKVGGNYNYL) (SEQ ID NO: 836), 467-474 (DISTEIYQ) (SEQ ID NO: 837), and 480-513 (CNGVEGFNCYFPLQSYGFQPTNGVGYQPYRVVVL) (SEQ ID NO: 838) of the RBD were significantly protected by mAb10934.

A total of 188 peptides from the RBD were identified from both RBD alone and RBD in complex with mAb10933 samples, representing 86.06% sequence coverage of the RBD. Any peptide that exhibited a reduction in deuterium uptake of 5% or greater (i.e., a Δ% D value of less than −5%, such as −6%, −10%, and so on) upon mAb binding was defined as significantly protected. Peptides corresponding to amino acids 467-510 (DISTEIYQAGSTPCNGVEGFNCYFPLQSYGFQPTNGVGYQPYRV) (SEQ ID NO: 839) of the RBD were significantly protected by mAb10933.

A total of 75 peptides from the RBD were identified from both RBD alone and RBD in complex with mAb10920 samples, representing 83.27% sequence coverage of the RBD. Any peptide that exhibited a reduction in deuterium uptake of 5% or greater (i.e., a Δ% D value of less than −5%, such as −6%, −10%, and so on) upon mAb binding was defined as significantly protected. Peptides corresponding to amino acids 471-486 (EIYQAGSTPCNGVEGF) (SEQ ID NO: 840), and 491-515 (PLQSYGFQPTNGVGYQPYRVVVLSF) (SEQ ID NO: 841) of the RBD were significantly protected by mAb10920.

A total of 86 peptides from the RBD were identified from both RBD alone and RBD in complex with mAb10922 samples, representing 87.25% sequence coverage of the RBD. Any peptide that exhibited a reduction in deuterium uptake of 5% or greater (i.e., a Δ% D value of less than −5%, such as −6%, −10%, and so on) upon mAb binding was defined as significantly protected. Peptides corresponding to amino acids 432-452 (CVIAWNSNNLDSKVGGNYNYL) (SEQ ID NO: 836) of the RBD were significantly protected by mAb10922.

A total of 81 peptides from the RBD were identified from both RBD alone and RBD in complex with mAb10936 samples, representing 82.07% sequence coverage of the RBD. Any peptide that exhibited a reduction in deuterium uptake of 5% or greater (i.e., a Δ% D value of less than −5%, such as −6%, −10%, and so on) upon mAb binding was defined as significantly protected. Peptides corresponding to amino acids 351-360 (YAWNRKRISN) (SEQ ID NO: 842), 432-452 (CVIAWNSNNLDSKVGGNYNYL) (SEQ ID NO: 836), 467-486 (DISTEIYQAGSTPCNGVEGF) (SEQ ID NO: 843), and 491-513 (PLQSYGFQPTNGVGYQPYRVVVL) (SEQ ID NO: 844) of the RBD were significantly protected by mAb10936.

A total of 84 peptides from the RBD were identified from both RBD alone and RBD in complex with mAb10954 samples, representing 87.25% sequence coverage of the RBD. Any peptide that exhibited a reduction in deuterium uptake of 5% or greater (i.e., a Δ% D value of less than −5%, such as −6%, −10%, and so on) upon mAb binding was defined as significantly protected. Peptides corresponding to amino acids 400-422 (FVIRGDEVRQIAPGQTGKIADYN) (SEQ ID NO: 845), 453-486 (YRLFRKSNLKPFERDISTEIYQAGSTPCNGVEGF) (SEQ ID NO: 846), and 490-515 (FPLQSYGFQPTNGVGYQPYRVVVLSF) (SEQ ID NO: 847) of the RBD were significantly protected by mAb10954.

A total of 109 peptides from the RBD were identified from both RBD alone and RBD in complex with mAb10964 samples, representing 83.67% sequence coverage of RBD. Any peptide that exhibited a reduction in deuterium uptake of 5% or greater (i.e., a Δ% D value of less than −5%, such as −6%, −10%, and so on) upon mAb binding was defined as significantly protected. Peptides corresponding to amino acids 401-424 (VIRGDEVRQIAPGQTGKIADYNYK) (SEQ ID NO: 848), and 471-513 (EIYQAGSTPCNGVEGFNCYFPLQSYGFQPTNGVGYQPYRVVVL) (SEQ ID NO: 849) of the RBD were significantly protected by mAb10964.

A total of 78 peptides from the RBD were identified from both RBD alone and RBD in complex with mAb10977 samples, representing 87.25% sequence coverage of the RBD. Any peptide that exhibited a reduction in deuterium uptake of 5% or greater (i.e., a Δ% D value of less than −5%, such as −6%, −10%, and so on) upon mAb binding was defined as significantly protected. Peptides corresponding to amino acids 351-364 (YAWNRKRISNCVAD) (SEQ ID NO: 850), and 471-486 (EIYQAGSTPCNGVEGF) (SEQ ID NO: 840) of the RBD were significantly protected by mAb10977.

A total of 88 peptides from the RBD were identified from both RBD alone and RBD in complex with mAb10984 samples, representing 87.25% sequence coverage of RBD. Any peptide that exhibited a reduction in deuterium uptake of 5% or greater (i.e., a Δ% D value of less than −5%, such as −6%, −10%, and so on) upon mAb binding was defined as significantly protected. Peptides corresponding to amino acids 400-422 (FVIRGDEVRQIAPGQTGKIADYN) (SEQ ID NO: 845), and 453-486 (YRLFRKSNLKPFERDISTEIYQAGSTPCNGVEGF) (SEQ ID NO: 846) of the RBD were significantly protected by mAb10984.

A total of 84 peptides from the RBD were identified from both RBD alone and RBD in complex with mAb10986 samples, representing 87.25% sequence coverage of the RBD. Any peptide that exhibited a reduction in deuterium uptake of 5% or greater (i.e., a Δ% D value of less than −5%, such as −6%, −10%, and so on) upon mAb binding was defined as significantly protected. Peptides corresponding to amino acids 400-422 (FVIRGDEVRQIAPGQTGKIADYN) (SEQ ID NO: 845), 453-486 (YRLFRKSNLKPFERDISTEIYQAGSTPCNGVEGF) (SEQ ID NO: 846), and 490-515 (FPLQSYGFQPTNGVGYQPYRVVVLSF) (SEQ ID NO: 847) of the RBD were significantly protected by mAb10986.

In sum, the majority of the neutralizing antibodies tested contact the RBD in a manner that overlaps the RBD residues that comprise the ACE2 interface; furthermore, the antibodies can be grouped based on their pattern of contacting the RBD surface, as shown in FIG. 15. The above data are also summarized in Tables 17-28.

TABLE 17

Spike protein receptor binding domain (RBD) peptides with significant protection upon formation of RBD-mAbcompared to RBD alone

| | 5 min incubation | | | 10 min incubation | | | |
|---|---|---|---|---|---|---|---|
| RBD Residues | RBD-mAb10989 D-uptake | RBD D-uptake | ΔD | RBD-mAb10989 D-uptake | RBD D-uptake | ΔD | Δ % D |
| 467-474 | 2.67 | 3.16 | −0.49 | 2.53 | 3.17 | −0.64 | −10.5 |
| 470-473 | 0.48 | 0.98 | −0.50 | 0.47 | 0.98 | −0.51 | −28.0 |
| 470-474 | 0.99 | 1.46 | −0.47 | 0.99 | 1.44 | −0.45 | −16.9 |
| 471-474 | 0.51 | 0.89 | −0.38 | 0.51 | 0.89 | −0.38 | −20.9 |
| 475-486 | 2.20 | 2.93 | −0.73 | 2.11 | 2.94 | −0.83 | −9.7 |
| 475-487 | 3.31 | 4.50 | −1.19 | 3.61 | 4.48 | −0.87 | −11.4 |
| 475-489 | 2.77 | 4.48 | −1.71 | 2.78 | 4.53 | −1.75 | −16.0 |
| 475-490 | 2.63 | 4.96 | −2.33 | 2.67 | 4.97 | −2.30 | −19.8 |
| 480-489 | 1.82 | 3.67 | −1.85 | 1.77 | 3.69 | −1.92 | −26.2 |
| 483-486 | 0.31 | 0.78 | −0.47 | 0.30 | 0.78 | −0.48 | −26.5 |
| 487-489 | 0.05 | 0.40 | −0.35 | 0.02 | 0.39 | −0.37 | −40.4 |
| 487-490 | 0.11 | 0.90 | −0.79 | 0.11 | 0.84 | −0.73 | −42.3 |
| 487-491 | 0.10 | 1.05 | −0.95 | 0.10 | 1.03 | −0.93 | −52.0 |
| 487-495 | 0.62 | 1.59 | −0.97 | 0.67 | 1.57 | −0.90 | −17.4 |
| 487-509 | 5.63 | 6.99 | −1.36 | 5.68 | 7.02 | −1.34 | −8.3 |
| 487-510 | 6.08 | 7.37 | −1.29 | 6.08 | 7.44 | −1.36 | −7.7 |
| 487-512 | 5.72 | 6.48 | −0.76 | 5.60 | 6.77 | −1.17 | −5.1 |
| 487-513 | 5.15 | 6.16 | −1.01 | 5.07 | 6.14 | −1.07 | −5.3 |

TABLE 17-continued

Spike protein receptor binding domain (RBD) peptides with significant protection upon formation of RBD-mAbcompared to RBD alone

| | 5 min incubation | | | 10 min incubation | | | |
|---|---|---|---|---|---|---|---|
| RBD Residues | RBD-mAb10989 D-uptake | RBD D-uptake | ΔD | RBD-mAb10989 D-uptake | RBD D-uptake | ΔD | Δ % D |
| 488-490 | 0.03 | 0.22 | −0.19 | 0.00 | 0.23 | −0.23 | −23.2 |
| 488-491 | 0.04 | 0.37 | −0.33 | 0.04 | 0.36 | −0.32 | −36.3 |

TABLE 18

Spike protein RBD peptides with significant protection upon formation of RBD-mAb10987 complex comparing to RBD alone

| | 5 min incubation | | | 10 min incubation | | | |
|---|---|---|---|---|---|---|---|
| RBD Residues | RBD-mAb10987 D-uptake | RBD D-uptake | ΔD | RBD-mAb10987 D-uptake | RBD D-uptake | ΔD | Δ % D |
| 432-441 | 1.62 | 2.17 | −0.55 | 1.64 | 2.18 | −0.54 | −7.6 |
| 432-449 | 5.60 | 6.59 | −0.99 | 5.54 | 6.59 | −1.05 | −7.1 |
| 432-452 | 6.20 | 7.49 | −1.29 | 6.20 | 7.46 | −1.26 | −7.5 |
| 433-441 | 1.50 | 2.00 | −0.50 | 1.49 | 2.01 | −0.52 | −8.1 |
| 440-452 | 3.95 | 4.81 | −0.86 | 4.03 | 4.80 | −0.77 | −8.3 |
| 442-449 | 2.49 | 2.98 | −0.49 | 2.60 | 2.99 | −0.39 | −8.2 |

TABLE 19

RBD peptides with significant protection upon formation of RBD-mAb10934 complex comparing to RBD alone

| | 5 min incubation | | | 10 min incubation | | | |
|---|---|---|---|---|---|---|---|
| RBD Residues | RBD-mAb10934 D-uptake | RBD D-uptake | ΔD | RBD-mAb10934 D-uptake | RBD D-uptake | ΔD | Δ % D |
| 432-452 | 5.70 | 7.49 | −1.79 | 5.62 | 7.46 | −1.84 | −10.6 |
| 433-441 | 1.60 | 2.00 | −0.40 | 1.63 | 2.01 | −0.38 | −6.2 |
| 434-441 | 2.24 | 2.42 | −0.18 | 2.13 | 2.52 | −0.39 | −5.3 |
| 440-452 | 3.12 | 4.81 | −1.69 | 3.10 | 4.80 | −1.70 | −17.1 |
| 442-449 | 2.37 | 2.98 | −0.61 | 2.37 | 2.99 | −0.62 | −11.4 |
| 442-452 | 2.67 | 4.21 | −1.54 | 2.66 | 4.23 | −1.57 | −19.1 |
| 443-452 | 2.53 | 3.78 | −1.25 | 2.52 | 3.78 | −1.26 | −17.5 |
| 444-451 | 1.79 | 2.73 | −0.94 | 1.80 | 2.73 | −0.93 | −17.2 |
| 444-452 | 1.82 | 3.09 | −1.27 | 1.75 | 3.09 | −1.34 | −20.7 |
| 445-452 | 1.24 | 2.42 | −1.18 | 1.24 | 2.43 | −1.19 | −22.0 |
| 467-474 | 2.64 | 3.16 | −0.52 | 2.58 | 3.17 | −0.59 | −10.2 |
| 470-473 | 0.51 | 0.98 | −0.47 | 0.55 | 0.98 | −0.43 | −25.0 |
| 470-474 | 1.03 | 1.46 | −0.43 | 1.01 | 1.44 | −0.43 | −16.0 |
| 471-474 | 0.56 | 0.89 | −0.33 | 0.55 | 0.89 | −0.34 | −18.6 |
| 480-489 | 3.19 | 3.67 | −0.48 | 3.19 | 3.69 | −0.50 | −6.8 |
| 487-489 | 0.04 | 0.40 | −0.36 | 0.06 | 0.39 | −0.33 | −38.6 |
| 487-490 | 0.54 | 0.90 | −0.36 | 0.53 | 0.84 | −0.31 | −18.8 |
| 487-491 | 0.63 | 1.05 | −0.42 | 0.70 | 1.03 | −0.33 | −20.5 |
| 487-495 | 0.73 | 1.59 | −0.86 | 0.71 | 1.57 | −0.86 | −16.0 |
| 487-509 | 5.55 | 6.99 | −1.44 | 5.57 | 7.02 | −1.45 | −8.9 |
| 487-510 | 5.89 | 7.37 | −1.48 | 6.00 | 7.44 | −1.44 | −8.5 |
| 487-513 | 4.37 | 6.16 | −1.79 | 4.79 | 6.14 | −1.35 | −7.9 |
| 488-509 | 4.50 | 5.49 | −0.99 | 4.60 | 5.52 | −0.92 | −6.2 |
| 488-510 | 5.84 | 6.58 | −0.74 | 5.65 | 6.67 | −1.02 | −5.4 |
| 490-509 | 5.16 | 6.01 | −0.85 | 5.30 | 6.12 | −0.82 | −5.8 |
| 490-512 | 5.15 | 6.37 | −1.22 | 5.30 | 6.28 | −0.98 | −6.4 |
| 490-513 | 4.90 | 6.10 | −1.20 | 5.05 | 6.05 | −1.00 | −6.1 |
| 503-509 | 1.19 | 1.39 | −0.20 | 1.21 | 1.41 | −0.20 | −5.5 |

TABLE 20

RBD peptides with significant protection upon formation of RBD-mAb10933 complex comparing to RBD alone

| RBD Residues | 5 min incubation RBD-mAb10933 D-uptake | RBD D-uptake | ΔD | 10 min incubation RBD-mAb10933 D-uptake | RBD D-uptake | ΔD | Δ % D |
|---|---|---|---|---|---|---|---|
| 467-474 | 2.52 | 3.16 | −0.64 | 2.55 | 3.17 | −0.62 | −11.7 |
| 470-474 | 1.03 | 1.46 | −0.43 | 1.03 | 1.44 | −0.41 | −15.6 |
| 471-474 | 0.54 | 0.89 | −0.35 | 0.54 | 0.89 | −0.35 | −19.5 |
| 475-487 | 3.62 | 4.50 | −0.88 | 3.63 | 4.48 | −0.85 | −9.6 |
| 475-489 | 3.21 | 4.48 | −1.27 | 3.26 | 4.53 | −1.27 | −11.8 |
| 480-486 | 1.79 | 2.06 | −0.27 | 1.87 | 2.07 | −0.20 | −5.1 |
| 480-489 | 2.13 | 3.67 | −1.54 | 2.18 | 3.69 | −1.51 | −21.2 |
| 483-486 | 0.61 | 0.78 | −0.17 | 0.62 | 0.78 | −0.16 | −9.3 |
| 487-489 | 0.02 | 0.40 | −0.38 | 0.02 | 0.39 | −0.37 | −41.6 |
| 487-490 | 0.42 | 0.90 | −0.48 | 0.40 | 0.84 | −0.44 | −25.6 |
| 487-491 | 0.46 | 1.05 | −0.59 | 0.46 | 1.03 | −0.57 | −32.0 |
| 487-495 | 0.74 | 1.59 | −0.85 | 0.82 | 1.57 | −0.75 | −14.8 |
| 487-509 | 6.01 | 6.99 | −0.98 | 6.14 | 7.02 | −0.88 | −5.7 |
| 487-510 | 6.29 | 7.37 | −1.08 | 6.14 | 7.44 | −1.30 | −7.0 |
| 488-490 | 0.19 | 0.22 | −0.03 | 0.13 | 0.23 | −0.10 | −7.4 |
| 488-491 | 0.26 | 0.37 | −0.11 | 0.25 | 0.36 | −0.11 | −12.3 |

TABLE 21

RBD peptides with significant protection upon formation of RBD-mAb10920 complex comparing to RBD alone

| RBD Residues | 10 min incubation RBD-mAb10920 D-uptake | RBD D-uptake | ΔD | Δ% D |
|---|---|---|---|---|
| 471-486 | 4.63 | 5.40 | −0.77 | −6.6 |
| 475-486 | 2.74 | 3.27 | −0.53 | −6.5 |
| 491-513 | 5.45 | 6.57 | −1.12 | −6.6 |
| 495-510 | 4.51 | 5.43 | −0.92 | −8.5 |
| 495-513 | 4.41 | 5.13 | −0.72 | −5.4 |
| 496-515 | 3.58 | 4.35 | −0.77 | −5.4 |

TABLE 22

RBD peptides with significant protection upon formation of RBD-mAb10922 complex comparing to RBD alone

| RBD Residues | 10 min incubation RBD-mAb10922 D-uptake | RBD D-uptake | ΔD | Δ% D |
|---|---|---|---|---|
| 432-441 | 1.86 | 2.23 | −0.37 | −5.3 |
| 442-452 | 3.52 | 4.57 | −1.05 | −13.0 |

TABLE 23

RBD peptides with significant protection upon formation of RBD-mAb10936 complex comparing to RBD alone

| RBD Residues | 10 min incubation RBD-mAb10936 D-uptake | RBD D-uptake | ΔD | Δ% D |
|---|---|---|---|---|
| 351-360 | 2.68 | 3.10 | −0.42 | −5.9 |
| 432-441 | 1.85 | 2.23 | −0.38 | −5.3 |
| 442-452 | 2.55 | 4.57 | −2.02 | −25.0 |
| 443-452 | 2.98 | 4.01 | −1.03 | −14.2 |
| 467-470 | 0.69 | 0.84 | −0.15 | −8.1 |

TABLE 23-continued

RBD peptides with significant protection upon formation of RBD-mAb10936 complex comparing to RBD alone

| RBD Residues | 10 min incubation RBD-mAb10936 D-uptake | RBD D-uptake | ΔD | Δ% D |
|---|---|---|---|---|
| 471-486 | 4.73 | 5.40 | −0.67 | −5.8 |
| 491-513 | 5.48 | 6.57 | −1.09 | −6.4 |
| 495-510 | 4.38 | 5.43 | −1.05 | −9.8 |

TABLE 24

RBD peptides with significant protection upon formation of RBD-mAb10954 complex comparing to RBD alone

| RBD Residues | 10 min incubation RBD-mAb10954 D-uptake | RBD D-uptake | ΔD | Δ% D |
|---|---|---|---|---|
| 400-420 | 3.67 | 4.56 | −0.89 | −5.5 |
| 401-420 | 3.39 | 4.22 | −0.83 | −5.5 |
| 401-421 | 3.44 | 4.28 | −0.84 | −5.2 |
| 406-420 | 3.32 | 4.10 | −0.78 | −7.2 |
| 406-421 | 3.23 | 4.11 | −0.88 | −7.6 |
| 406-422 | 3.41 | 4.16 | −0.75 | −5.9 |
| 407-420 | 2.86 | 3.62 | −0.76 | −7.7 |
| 407-422 | 2.97 | 3.74 | −0.77 | −6.6 |
| 453-466 | 1.53 | 2.23 | −0.70 | −7.1 |
| 453-470 | 3.63 | 4.53 | −0.90 | −6.7 |
| 453-471 | 4.42 | 5.22 | −0.80 | −5.6 |
| 471-486 | 4.34 | 5.40 | −1.06 | −9.1 |
| 472-486 | 4.47 | 5.29 | −0.82 | −7.6 |
| 490-512 | 5.64 | 6.65 | −1.01 | −5.9 |
| 490-513 | 5.61 | 6.57 | −0.96 | −5.3 |
| 491-513 | 5.26 | 6.57 | −1.31 | −7.7 |
| 493-512 | 4.86 | 5.69 | −0.83 | −5.7 |
| 493-513 | 4.74 | 5.72 | −0.98 | −6.4 |
| 495-510 | 4.77 | 5.43 | −0.66 | −6.2 |
| 495-513 | 4.10 | 5.13 | −1.03 | −7.6 |
| 496-512 | 3.60 | 4.60 | −1.00 | −8.6 |
| 496-515 | 3.43 | 4.35 | −0.92 | −6.4 |

TABLE 25

| RBD peptides with significant protection upon formation of RBD-mAb10964 complex comparing to RBD alone | | | | |
|---|---|---|---|---|
| | 10 min incubation | | | |
| RBD Residues | RBD-mAb10964 D-uptake | RBD D-uptake | ΔD | Δ% D |
| 401-421 | 3.87 | 4.84 | −0.97 | −6.0 |
| 406-419 | 3.34 | 3.91 | −0.57 | −5.8 |
| 406-420 | 3.47 | 4.15 | −0.68 | −6.3 |
| 406-421 | 3.53 | 4.22 | −0.69 | −5.9 |
| 406-422 | 3.66 | 4.37 | −0.71 | −5.6 |
| 406-424 | 3.31 | 4.24 | −0.93 | −6.5 |
| 410-422 | 3.04 | 3.56 | −0.52 | −5.8 |
| 471-486 | 4.65 | 5.41 | −0.76 | −6.4 |
| 475-489 | 3.34 | 4.56 | −1.22 | −11.3 |
| 480-489 | 2.32 | 3.19 | −0.87 | −12.1 |
| 487-509 | 6.38 | 7.58 | −1.20 | −7.4 |
| 495-513 | 4.50 | 5.20 | −0.70 | −5.2 |
| 496-512 | 4.17 | 4.80 | −0.63 | −5.4 |
| 496-513 | 3.90 | 4.85 | −0.95 | −7.5 |

TABLE 26

| RBD peptides with significant protection upon formation of RBD-mAb10977 complex comparing to RBD alone | | | | |
|---|---|---|---|---|
| | 10 min incubation | | | |
| RBD Residues | RBD-mAb10977 D-uptake | RBD D-uptake | ΔD | Δ% D |
| 351-364 | 4.82 | 5.38 | −0.56 | −5.2 |
| 471-486 | 3.81 | 5.40 | −1.59 | −13.6 |
| 472-486 | 4.20 | 5.29 | −1.09 | −10.1 |

TABLE 27

| RBD peptides with significant protection upon formation of RBD-mAb10984 complex comparing to RBD alone | | | | |
|---|---|---|---|---|
| | 10 min incubation | | | |
| RBD Residues | RBD-mAb10984 D-uptake | RBD D-uptake | ΔD | Δ% D |
| 400-420 | 3.73 | 4.56 | −0.83 | −5.2 |
| 401-421 | 3.47 | 4.28 | −0.81 | −5.1 |
| 406-420 | 3.35 | 4.10 | −0.75 | −7.0 |
| 406-421 | 3.31 | 4.11 | −0.80 | −6.9 |
| 406-422 | 3.47 | 4.16 | −0.69 | −5.5 |
| 407-420 | 2.88 | 3.62 | −0.74 | −7.5 |
| 407-422 | 2.94 | 3.74 | −0.80 | −6.8 |
| 453-466 | 1.51 | 2.23 | −0.72 | −7.3 |
| 453-470 | 3.70 | 4.53 | −0.83 | −6.2 |
| 453-471 | 4.49 | 5.22 | −0.73 | −5.1 |
| 471-486 | 4.45 | 5.40 | −0.95 | −8.1 |
| 472-486 | 4.63 | 5.29 | −0.66 | −6.1 |

TABLE 28

| RBD peptides with significant protection upon formation of RBD-mAb10986 complex comparing to RBD alone | | | | |
|---|---|---|---|---|
| | 10 min incubation | | | |
| RBD Residues | RBD-mAb10986 D-uptake | RBD D-uptake | ΔD | Δ% D |
| 400-420 | 3.58 | 4.56 | −0.98 | −6.1 |
| 400-421 | 3.60 | 4.61 | −1.01 | −5.9 |
| 401-420 | 3.30 | 4.22 | −0.92 | −6.1 |
| 401-421 | 3.29 | 4.28 | −0.99 | −6.1 |
| 401-422 | 3.44 | 4.43 | −0.99 | −5.8 |
| 406-420 | 3.28 | 4.10 | −0.82 | −7.6 |
| 406-421 | 3.24 | 4.11 | −0.87 | −7.5 |
| 406-422 | 3.35 | 4.16 | −0.81 | −6.4 |
| 407-420 | 2.81 | 3.62 | −0.81 | −8.2 |
| 407-422 | 2.91 | 3.74 | −0.83 | −7.1 |
| 453-466 | 1.53 | 2.23 | −0.70 | −7.1 |
| 453-470 | 3.55 | 4.53 | −0.98 | −7.3 |
| 453-471 | 4.41 | 5.22 | −0.81 | −5.6 |
| 471-486 | 4.13 | 5.40 | −1.27 | −10.9 |
| 490-510 | 5.13 | 6.44 | −1.31 | −8.6 |
| 490-512 | 5.33 | 6.65 | −1.32 | −7.7 |
| 490-513 | 5.25 | 6.57 | −1.32 | −7.3 |
| 491-513 | 4.29 | 6.57 | −2.28 | −13.3 |
| 493-512 | 4.46 | 5.69 | −1.23 | −8.5 |
| 493-513 | 4.62 | 5.72 | −1.10 | −7.2 |
| 495-513 | 3.89 | 5.13 | −1.24 | −9.3 |
| 496-513 | 3.36 | 4.53 | −1.17 | −9.3 |
| 496-515 | 3.05 | 4.35 | −1.30 | −9.1 |

Example 12: Neutralization of SARS-CoV-2 Wild-Type and Variant Spike Proteins To test whether anti-SARS-CoV-2 spike protein antibodies can neutralize SARS-CoV-2 variants, these antibodies were screened against a panel of VSV pseudotype viruses expressing wild-type and variant spike proteins. VSV pseudotype viruses were generated by transiently transfecting 293T cells with a plasmid encoding the SARS-CoV-2 spike protein or the same plasmid containing nucleotide variations that encode for known variants of the SARS-CoV-2 spike protein amino acid sequence. All plasmids were confirmed by Sanger sequencing. Cells were seeded in 15 cm plates at $1.2\times10^7$ cells per plate in DMEM Complete Media (1000 mL DMEM, Gibco; 100 mL FBS, Gibco; 10 mL PSG, Gibco) one day prior to transfection with 15 μg/plate Spike DNA using 125 μL Lipofectamine LTX, 30 μL PLUS reagent, and up to 3 mL Opti-Mem. 24 hours post transfection, the cells were washed with 10 mL PBS, then infected with an MOI of 0.1 $VSV^{\Delta G:mNeon}$ virus in 10 mL of Opti-Mem. Virus was incubated on cells for 1 hour, with gentle rocking every 10 minutes. Cells were washed 3 times with 10 mL PBS, then overlaid with 20 mL Infection media (1000 mL DMEM, Gibco; 10 mL Sodium Pyruvate, Gibco; 7 mL BSA, Sigma; 5 mL Gentamicin, Gibco) before incubation at 37° C., 5% $CO_2$ for 24 hours. Pseudovirus supernatant was collected into 250 mL centrifuge tubes on ice, then centrifuged at 3000 rpm for 5 minutes to pellet any cellular debris, aliquoted on ice, then frozen to −80° C. Infectivity was tested on Vero cells prior to use in neutralization assays. This material will be referred to as $VSV^{\Delta G:mNeon}$/Spike pseudovirus, or $VSV^{\Delta G:mNeon}$/Spike (variant amino acid mutation) (for example, $VSV^{\Delta G:mNeon}$/Spike_H49Y).

On Day 1, Vero cells were seeded to 80% confluency in T225 flasks, the cells were washed with PBS (Gibco: 20012-043), TrypLE was added to detach cells from the flask, and Complete DMEM was added to inactivate trypsin. 20,000 Vero cells were plated in in 100 μL of prewarmed Complete DMEM per well in 96 Well Black Polystyrene Microplate (Corning: 3904). On Day 2, $VSV^{\Delta G:mNeon}$/Spike pseudovirus was thawed on ice and diluted with Infection media. Antibodies were diluted in a U-bottom 96 well plate, generating a dilution of each antibody in 210 μl Infection media at 2× assay concentration. 120 μL of diluted antibodies were transferred to a fresh U-bottom plate, and media and an IgG1 control antibody were added to each plate. 120 μl of diluted pseudovirus was added to every well except the media control wells. To those wells, 120 μL of Infection media was added. Pseudovirus with antibodies were incubated for 30 minutes at room temperature, then media was removed from Vero cells. 100 μL of antibody/pseudovirus mixture were added to the cells, and then incubated at 37° C., 5% $CO_2$ for 24 hours. On day 3, supernatant was removed from cell wells and replaced with 100 μL of PBS. Plates were read on a SpectraMax i3 with MiniMax imaging cytometer.

In addition to testing neutralization capacity with non-replicating VSV-SARS-CoV-2-S virus, antibodies also were tested with SARS-CoV-2 virus. Monoclonal antibodies and antibody combinations were serially diluted in DMEM (Quality Biological), supplemented with 10% (v/v) heat inactivated fetal bovine serum (Sigma), 1% (v/v) penicillin/streptomycin (Gemini Bio-products) and 1% (v/v) L-glutamine (2 mM final concentration, Gibco) (VeroE6 media) to a final volume of 250 pt. Next, 250 μL of VeroE6 media containing SARS-CoV-2 (WA-1) (1000 PFU/mL) was added to each serum dilution and to 250 μL media as an untreated control. The virus-antibody mixtures were incubated for 60 min at 37° C. Following incubation, virus titers of the mixtures were determined by plaque assay. Finally, 50% plaque reduction neutralization titer (PRNT50) values (the serum dilutions at which plaque formation was reduced by 50% relative to that of the untreated control) were calculated using a 4-parameter logistic curve fit to the percent neutralization data (GraphPad Software, La Jolla, CA).

Individual monoclonal antibody half maximal inhibitory concentration (IC50) against VSV-SARS-CoV-2 spike protein (S)-expressing pseudovirus encoding the Wuhan-Hu-1 (NCBI Accession Number MN908947.3) sequence of spike protein (S-wt) were determined in Vero cells (Table 29). The majority of antibodies displayed neutralization potency in the picomolar range (pM), with some exhibiting neutralization potency in nanomolar (nM) range.

While recombinant ACE2 was able to mediate neutralization of the VSV-spike pseudoparticles, as previously reported, its potency was far inferior to that of the monoclonal antibodies, with more than 1000-fold decrease in potency seen relative to the best neutralizing mAbs (FIG. 10A). In addition, the potent neutralizing activity of mAb10987, mAb10989, mAb10933, and mAb10934 was confirmed in neutralization assays, including neutralization of SARS-CoV-2 in VeroE6 cells (FIG. 10B). All neutralization assays generated similar potency across the four mAbs (mAb10987, mAb10989, mAb10933, and mAb10934) and no combinations demonstrated synergistic neutralization activity (FIG. 10B).

TABLE 29 mAb neutralization potency (IC50 (M)) against wild-type strain of VSV-SARS-CoV-2-S pseudoparticles in Vero cells

| Antibody | IC50 (M) |
|---|---|
| mAb10934 | 5.44E−11 |
| mAb10936 | 1.11E−10 |
| mAb10987 | 4.06E−11 |
| mAb10924 | 1.36E−10 |
| mAb10935 | 2.21E−10 |
| mAb10913 | 2.31E−10 |
| mAb10939 | 2.36E−10 |
| mAb10937 | 2.62E−10 |
| mAb10920 | 2.64E−10 |
| mAb10941 | 2.78E−10 |
| mAb10923 | 3.29E−10 |
| mAb10915 | 3.40E−10 |
| mAb10932 | 3.58E−10 |
| mAb10921 | 3.74E−10 |
| mAb10914 | 3.94E−10 |
| mAb10940 | 5.43E−10 |
| mAb10989 | 7.23E−12 |
| mAb10938 | 6.65E−10 |
| mAb10922 | 1.21E−10 |
| mAb10930 | 1.07E−09 |
| mAb10954 | 9.22E−11 |
| mAb10955 | 1.19E−10 |
| mAb10933 | 4.28E−11 |
| mAb10956 | 1.28E−10 |
| mAb10957 | 1.76E−10 |
| mAb10964 | 5.70E−11 |
| mAb10965 | 1.42E−10 |
| mAb10966 | 1.00E−10 |
| mAb10967 | 2.43E−10 |
| mAb10970 | 1.26E−10 |
| mAb10971 | 1.55E−10 |
| mAb10977 | 5.15E−11 |
| mAb10982 | 3.69E−10 |
| mAb10984 | 9.73E−11 |
| mAb10985 | 2.57E−10 |
| mAb10986 | 9.91E−11 |
| mAb10988 | 2.98E−10 |
| mAb10969 | 2.27E−09 |
| mAb10996 | 1.13E−08 |
| mAb10998 | 9.51E−09 |
| mAb11002 | non-neutralizing |
| mAb11000 | 2.79E−08 |
| mAb11004 | 6.00E−09 |
| mAb11006 | 1.40E−09 |
| mAb11008 | 2.05E−08 |
| mAb11010 | non-neutralizing |

Amino acid variants in spike (S) protein were identified from over 7000 publicly available SARS-CoV-2 sequences, representing globally circulating isolates, and cloned into VSV pseudoparticles. Neutralization assays with variant-encoding pseudoparticles were performed to assess the impact of each variant on neutralization potency of the monoclonal antibodies. Table 30 illustrates the relative neutralization potency of monoclonal antibodies against variant encoding pseudoparticles relative to SARS-CoV-2 spike (S-wt) at a single concentration of 5 μg/ml. Percent of neutralization relative to S-wt was captured for each individual antibody and variant. None of the antibodies demonstrated loss of neutralization potency at the 5 μg/ml concentration with the exception of mAb10985 and the R4081 variant. These data demonstrate broad functional neutralization coverage of monoclonal antibodies against globally circulating SARS-CoV-2 spike variants.

To further interrogate the impact of the S protein variants on neutralization potency of the monoclonal antibodies, full neutralization curves were run to determine the IC50 value of the most potent neutralizing antibodies against a subset of variants localized within the receptor binding domain (RBD) of the S protein. Table 31 shows the IC50 neutralization values for each variant pseudoparticle. Intrinsic variability of up to 3-fold can be observed between pseudoparticle neutralization assays and does not indicate a change in neutralization potency. These data demonstrate that the antibodies retained their neutralization potency against a diverse panel of S protein RBD variants.

TABLE 30

Relative neutralization of VSV-SARS-CoV-2 variants encoding S protein at 5 μg/ml antibody concentration in Vero cells

| mAb | wt | H49Y | S50L | V341I | N354D | S359N | V367F | K378R |
|---|---|---|---|---|---|---|---|---|
| mAb10989 | 100% | 100% | 88% | 100% | 100% | 99% | 100% | 100% |
| mAb10987 | 100% | 100% | 96% | 99% | 100% | 99% | 100% | 100% |
| mAb10933 | 100% | 100% | 96% | 99% | 100% | 99% | 100% | 99% |
| mAb10977 | 100% | 100% | 98% | 100% | 99% | 100% | 100% | 100% |
| mAb10934 | 100% | 100% | 95% | 100% | 100% | 99% | 100% | 99% |
| mAb10964 | 100% | 100% | 90% | 100% | 99% | 99% | 100% | 100% |
| mAb10954 | 100% | 100% | 92% | 100% | 100% | 99% | 100% | 100% |
| mAb10984 | 100% | 100% | 95% | 100% | 99% | 99% | 100% | 99% |
| mAb10986 | 100% | 100% | 98% | 100% | 99% | 99% | 100% | 100% |
| mAb10966 | 100% | 100% | 90% | 100% | 99% | 99% | 100% | 100% |
| mAb10936 | 100% | 100% | 96% | 100% | 99% | 99% | 100% | 100% |
| mAb10955 | 100% | 100% | 95% | 99% | 99% | 99% | 100% | 100% |
| mAb10922 | 100% | 100% | 98% | 99% | 99% | 99% | 100% | 99% |
| mAb10970 | 100% | 100% | 99% | 100% | 100% | 100% | 100% | 99% |
| mAb10956 | 100% | 100% | 96% | 99% | 99% | 99% | 100% | 100% |
| mAb10924 | 100% | 100% | 96% | 100% | 99% | 99% | 100% | 99% |
| mAb10965 | 100% | 100% | 96% | 100% | 99% | 100% | 100% | 100% |
| mAb10971 | 100% | 100% | 90% | 99% | 99% | 99% | 100% | 99% |
| mAb10957 | 100% | 100% | 91% | 99% | 99% | 98% | 100% | 99% |
| mAb10935 | 100% | NR | NR | NR | NR | 99% | NR | 99% |
| mAb10913 | 100% | 100% | 93% | 100% | 99% | 98% | 100% | 99% |
| mAb10939 | 100% | 100% | 93% | 98% | 99% | 100% | 100% | 99% |
| mAb10967 | 100% | 100% | 90% | 99% | 99% | 98% | 100% | 100% |
| mAb10985 | 100% | 100% | 96% | 99% | 99% | 98% | 100% | 99% |
| mAb10937 | 100% | 100% | 92% | 99% | 100% | 98% | 100% | 99% |
| mAb10920 | 100% | 100% | 92% | 99% | 99% | 99% | 100% | 99% |
| mAb10941 | 100% | 99% | 97% | 99% | 100% | 99% | 100% | 100% |
| mAb10988 | 100% | 100% | 99% | 100% | 99% | 98% | 100% | 100% |
| mAb10923 | 100% | 101% | 102% | 97% | 103% | 105% | 104% | 103% |
| mAb10915 | 100% | 100% | 95% | 100% | 99% | 99% | 100% | 99% |
| mAb10932 | 100% | 100% | 93% | 100% | 99% | 99% | 100% | 99% |
| mAb10982 | 100% | 100% | 94% | 99% | 99% | 99% | 100% | 100% |

| mAb | R408I | Q409E | A435S | K458R | G476S | Y483A | Y508H | H519P | D614G |
|---|---|---|---|---|---|---|---|---|---|
| mAb10989 | 100% | 101% | 100% | 99% | 99% | 100% | 100% | 97% | 100% |
| mAb10987 | 99% | 100% | 100% | 99% | 99% | 99% | 100% | 97% | 100% |
| mAb10933 | 100% | 99% | 100% | 99% | 99% | 100% | 100% | 98% | 100% |
| mAb10977 | 100% | 100% | 99% | 99% | 99% | 99% | 100% | 97% | 100% |
| mAb10934 | 100% | 100% | 100% | 98% | 98% | 99% | 100% | 97% | 100% |
| mAb10964 | 99% | 100% | 99% | 98% | 100% | 99% | 100% | 96% | 100% |
| mAb10954 | 100% | 100% | 100% | 100% | 100% | 100% | 100% | 97% | 100% |
| mAb10984 | 99% | 100% | 100% | 99% | 99% | 100% | 100% | 96% | 100% |
| mAb10986 | 100% | 100% | 100% | 98% | 99% | 100% | 100% | 99% | 100% |
| mAb10966 | 99% | 100% | 100% | 99% | 100% | 99% | 100% | 96% | 100% |
| mAb10936 | 99% | 100% | 100% | 99% | 99% | 99% | 100% | 97% | 100% |
| mAb10955 | 100% | 100% | 99% | 99% | 99% | 99% | 100% | 97% | 100% |
| mAb10922 | 99% | 100% | 100% | 98% | 99% | 99% | 100% | 97% | 99% |
| mAb10970 | 100% | 101% | 100% | 100% | 99% | 99% | 100% | 99% | 100% |
| mAb10956 | 100% | 100% | 99% | 99% | 100% | 99% | 100% | 97% | 100% |
| mAb10924 | 99% | 100% | 100% | 99% | 99% | 99% | 99% | 98% | 100% |
| mAb10965 | 99% | 100% | 100% | 99% | 100% | 99% | 100% | 98% | 100% |
| mAb10971 | 99% | 100% | 100% | 99% | 99% | 99% | 100% | 98% | 100% |
| mAb10957 | 99% | 100% | 99% | 98% | 99% | 99% | 100% | 98% | 100% |
| mAb10935 | NR | NR | NR | NR | 98% | NR | 99% | NR | NR |
| mAb10913 | 99% | 100% | 100% | 99% | 98% | 99% | 99% | 97% | 100% |
| mAb10939 | 99% | 100% | 99% | 98% | 97% | 98% | 100% | 96% | 100% |
| mAb10967 | 99% | 99% | 99% | 98% | 99% | 98% | 100% | 97% | 100% |
| mAb10985 | 26% | 100% | 100% | 99% | 99% | 100% | 99% | 97% | 99% |
| mAb10937 | 100% | 99% | 99% | 99% | 99% | 100% | 99% | 98% | 100% |
| mAb10920 | 99% | 100% | 100% | 99% | 98% | 100% | 99% | 98% | 100% |
| mAb10941 | 99% | 100% | 100% | 98% | 98% | 98% | 100% | 96% | 100% |
| mAb10988 | 100% | 101% | 99% | 99% | 99% | 100% | 99% | 98% | 100% |
| mAb10923 | 103% | 104% | 100% | 100% | 96% | 98% | 101% | 97% | 101% |
| mAb10915 | 98% | 100% | 100% | 98% | 97% | 100% | 99% | 97% | 100% |
| mAb10932 | 99% | 100% | 99% | 99% | 98% | 100% | 99% | 98% | 100% |
| mAb10982 | 99% | 100% | 99% | 98% | 99% | 99% | 100% | 98% | 100% |

TABLE 31

Neutralization IC50 (M) of VSV-SARS-CoV-2-S RBD variants in Vero cells

| | Q321S | V341I | A348T | N354D | S359N | V376F | K378S | R408I |
|---|---|---|---|---|---|---|---|---|
| mAb10933 | 6.85E−11 | 3.37E−11 | 4.13E−11 | 5.89E−11 | 2.12E−11 | 2.40E−11 | 3.52E−11 | 1.98E−11 |
| mAb10934 | 6.84E−11 | 7.42E−11 | 1.42E−10 | 9.76E−11 | 3.04E−11 | 3.20E−11 | 4.65E−11 | 2.75E−11 |
| mAb10984 | 2.75E−10 | 2.49E−10 | 2.01E−10 | 2.64E−10 | 1.23E−10 | 1.53E−10 | 1.88E−10 | 1.35E−10 |
| mAb10986 | 2.06E−10 | 1.92E−10 | 1.03E−10 | 2.49E−10 | 8.91E−11 | 1.49E−10 | 1.54E−10 | 6.14E−11 |
| mAb10987 | 5.02E−11 | 3.38E−11 | 2.98E−11 | 2.68E−11 | 2.41E−11 | 1.78E−11 | 2.40E−11 | 1.71E−11 |
| mAb10989 | 1.46E−11 | 1.61E−11 | 7.33E−12 | 1.14E−11 | 4.30E−12 | 1.33E−11 | 1.21E−11 | 1.09E−11 |
| mAb10964 | 5.65E−11 | 1.13E−10 | 3.52E−11 | 1.93E−10 | 6.83E−11 | 8.92E−11 | 6.19E−11 | 4.96E−11 |
| mAb10954 | 2.32E−10 | 2.52E−10 | 1.84E−10 | 2.84E−10 | 1.09E−10 | 1.29E−10 | 1.65E−10 | 9.88E−11 |
| IgG1 Isotype Control | N/A | N/A | N/A | N/A | N/A | N/A | N/A | N/A |

| | Q409E | A435S | K458R | I472V | G476S | V483A | Y508H | H519P |
|---|---|---|---|---|---|---|---|---|
| mAb10933 | 5.65E−11 | 4.71E−11 | 3.43E−11 | 9.17E−11 | 1.41E−10 | 1.54E−11 | 4.77E−11 | 3.03E−11 |
| mAb10934 | 5.94E−11 | 8.07E−11 | 3.46E−11 | 9.40E−11 | 3.51E−11 | 4.43E−11 | 6.73E−11 | 3.56E−11 |
| mAb10984 | 1.52E−10 | 2.18E−10 | 1.59E−10 | 2.61E−10 | 2.10E−10 | 1.71E−10 | 2.83E−10 | 1.08E−10 |
| mAb10986 | 1.95E−10 | 1.51E−10 | 1.00E−10 | 2.24E−10 | 1.13E−10 | 9.70E−11 | 2.01E−10 | 6.14E−11 |
| mAb10987 | 4.06E−11 | 3.88E−11 | 1.68E−11 | 4.18E−11 | 1.86E−11 | 2.60E−11 | 2.75E−11 | 2.20E−11 |
| mAb10989 | 2.12E−11 | 1.10E−11 | 7.51E−12 | 2.27E−11 | 6.80E−12 | 8.78E−12 | 1.71E−11 | 4.51E−12 |
| mAb10964 | 6.61E−11 | 7.90E−11 | 5.46E−11 | 1.01E−10 | 3.42E−11 | 4.50E−11 | 1.02E−10 | 4.45E−11 |
| mAb10954 | 2.64E−10 | 2.11E−10 | 1.45E−10 | 3.44E−10 | 1.83E−10 | 1.12E−10 | 2.05E−10 | 1.40E−10 |
| IgG1 Isotype Control | N/A | N/A | N/A | N/A | N/A | N/A | N/A | N/A |

Example 13: Biacore Binding Kinetics of Purified Anti-SARS-CoV-2-S Monoclonal Antibodies Equilibrium dissociation constant ($K_D$) for different SARS-COV-2 RBD reagents binding to purified CHOt anti-SARS-COV-2 monoclonal antibodies (mAbs) were determined using a real-time surface plasmon resonance based Biacore T200/Biacore 8K biosensor. All binding studies were performed in 10 mM HEPES, 150 mM NaCl, 3 mM EDTA, and 0.05% v/v Surfactant Tween-20, pH 7.4 (HBS-ET) running buffer at 25° C. and 37° C. The Biacore CM5 sensor chip surface was first derivatized by amine coupling with either mouse anti-human Fc specific mAb (Regeneron, mAb2567) to capture anti-SARS-COV-2bmAbs. Binding studies were performed on human SARS-COV-2 RBD extracellular domain expressed with a C-terminal myc-myc-hexahistidine (SARS-COV-2 RBD-MMH) and SARS-COV-2 RBD extracellular domain expressed with a C-terminal mouse IgG2a (SARS-COV-2 RBD-mFc). Use of these reagents allowed for the testing of the antibodies' ability to bind monomeric and dimeric RBD peptides, respectively.

Different concentrations of hSARS-COV-2 RBD-MMH, (90 nM-3.33 nM, 3-fold dilution) and SARS-COV-2 RBD-mFc (30 nM-1.11 nM 3-fold dilution) prepared in HBS-ET running buffer, were injected for 3 minutes at a flow rate of 50 μL/min while the dissociation of mAb bound different SARS-COV-2 RBD reagents was monitored for 6-10 minutes in HBS-ET running buffer. At the end of each cycle, the SARS-COV-2 RBD mAb capture surface was regenerated using either 12 sec injection of 20 mM phosphoric acid for mouse anti-human Fc specific mAb surface. The association rate ($k_a$) and dissociation rate ($k_d$) were determined by fitting the real-time binding sensorgrams to a 1:1 binding model with mass transport limitation using BiaEvaluation software v3.1 or Biacore Insight Evaluation software v2.0. or curve-fitting software. Binding dissociation equilibrium constant ($K_D$) and dissociative half-life (t½) were calculated from the kinetic rates as:

$$K_D(M) = \frac{kd}{ka}, \text{ and } t1/2\,(\text{min}) = \frac{\ln(2)}{60 * kd}$$

Binding kinetics parameters for different SARS-COV-2 mAbs binding to different anti-SARS-COV-2 RBD reagents of the invention at 25° C. and 37° C. are shown in Tables 32 through 35, respectively.

TABLE 32

Binding kinetics parameters of SARS-COV-2 RBD-MMH binding to anti-SARS-COV-2-S monoclonal antibodies at 25° C.

| mAb Captured (mAb#) | mAb Capture Level (RU) | 90 nM Ag Bound (RU) | $k_a$ (1/Ms) | $k_d$ (1/s) | KD (M) | t½ (min) |
|---|---|---|---|---|---|---|
| mAb10913 | 287 ± 3 | 55.9 | 4.04E+05 | 2.12E−02 | 5.26E−08 | 0.5 |
| mAb10914 | 310 ± 2 | 51.1 | 8.81E+04 | 3.76E−03 | 4.26E−08 | 3.1 |
| mAb10915 | 310 ± 2 | 63.2 | 9.61E+04 | 1.08E−04 | 1.13E−09 | 106.9 |
| mAb10920 | 307 ± 3 | 73.9 | 4.52E+05 | 1.30E−02 | 2.87E−08 | 0.9 |
| mAb10921 | 307 ± 3 | 61.4 | 1.01E+05 | 4.75E−04 | 4.71E−09 | 24.3 |
| mAb10922 | 312.2 ± 1.7 | 120.2 | 6.14E+05 | 1.48E−03 | 2.41E−09 | 7.8 |
| mAb10923 | 283 ± 2 | 80.4 | 4.66E+05 | 6.17E−03 | 1.32E−08 | 1.9 |
| mAb10924 | 319 ± 2 | 94.6 | 2.07E+05 | 1.74E−03 | 8.40E−09 | 6.6 |
| mAb10930 | 284.7 ± 0.7 | 59.6 | 1.24E+05 | 3.34E−03 | 2.70E−08 | 3.5 |
| mAb10932 | 315 ± 3 | 79.4 | 8.99E+04 | 1.21E−04 | 1.35E−09 | 95.5 |

TABLE 32-continued

Binding kinetics parameters of SARS-COV-2 RBD-MMH binding to anti-SARS-COV-2-S monoclonal antibodies at 25° C.

| mAb Captured (mAb#) | mAb Capture Level (RU) | 90 nM Ag Bound (RU) | $k_a$ (1/Ms) | $k_d$ (1/s) | KD (M) | t½ (min) |
|---|---|---|---|---|---|---|
| mAb10933 | 280 ± 1 | 99.8 | 1.52E+06 | 2.78E−03 | 1.83E−09 | 4.2 |
| mAb10934 | 280 ± 1 | 103.4 | 4.82E+06 | 5.77E−03 | 1.20E−09 | 2.0 |
| mAb10935 | 337 ± 2 | 107.8 | 3.93E+05 | 4.19E−03 | 1.07E−08 | 2.8 |
| mAb10936 | 311 ± 2 | 107.3 | 5.45E+05 | 1.07E−03 | 1.97E−09 | 10.8 |
| mAb10937 | 311 ± 2 | 102.2 | 5.72E+05 | 4.76E−03 | 8.34E−09 | 2.4 |
| mAb10938 | 338 ± 3 | 61.5 | 7.27E+04 | 1.75E−04 | 2.41E−09 | 66.0 |
| mAb10939 | 343 ± 2 | 82.3 | 1.63E+05 | 2.84E−03 | 1.74E−08 | 4.1 |
| mAb10940 | 338 ± 3 | 103.5 | 8.01E+05 | 2.51E−03 | 3.13E−09 | 4.6 |
| mAb10941 | 327 ± 1 | 92.1 | 1.20E+05 | 4.12E−04 | 3.43E−09 | 28.0 |
| mAb10954 | 286.9 ± 3 | 110.5 | 4.04E+05 | 3.64E−04 | 8.99E−10 | 31.7 |
| mAb10955 | 298.3 ± 2.5 | 88.8 | 1.61E+05 | 2.12E−03 | 1.32E−08 | 5.4 |
| mAb10956 | 293.7 ± 0.6 | 86.6 | 2.22E+05 | 4.06E−03 | 1.82E−08 | 2.8 |
| mAb10957 | 286.7 ± 2 | 93.0 | 1.38E+05 | 2.53E−04 | 1.84E−09 | 45.7 |
| mAb10964 | 259.6 ± 1.2 | 99.9 | 1.65E+06 | 3.90E−04 | 2.36E−10 | 29.6 |
| mAb10965 | 253.1 ± 1.9 | 63.6 | 1.24E+05 | 2.92E−03 | 2.35E−08 | 4.0 |
| mAb10966 | 266.6 ± 3 | 97.4 | 2.37E+05 | 3.65E−04 | 1.54E−09 | 31.6 |
| mAb10967 | 260.2 ± 0.9 | 70.7 | 1.24E+05 | 6.28E−05 | 5.08E−10 | 183.9 |
| mAb10969 | 272.2 ± 1.3 | 87.1 | 2.45E+05 | 3.80E−03 | 1.55E−08 | 3.0 |
| mAb10970 | 307.3 ± 1.3 | 102.8 | 2.27E+05 | 1.10E−03 | 4.85E−09 | 10.5 |
| mAb10971 | 263.1 ± 1.1 | 89.3 | 2.15E+05 | 3.75E−04 | 1.74E−09 | 30.8 |
| mAb10977 | 305 ± 3 | 98.5 | 2.43E+05 | 2.57E−04 | 1.06E−09 | 44.9 |
| mAb10982 | 267.8 ± 0.5 | 69.3 | 1.23E+05 | 2.06E−03 | 1.68E−08 | 5.6 |
| mAb10984 | 334 ± 2.1 | 117.9 | 2.04E+05 | 4.26E−04 | 2.09E−09 | 27.1 |
| mAb10985 | 306.9 ± 2.1 | 113.4 | 1.44E+06 | 1.55E−03 | 1.08E−09 | 7.5 |
| mAb10986 | 268.8 ± 0.9 | 104.3 | 4.64E+05 | 1.49E−04 | 3.21E−10 | 77.5 |
| mAb10987 | 270.8 ± 1.3 | 78.0 | 5.60E+05 | 1.20E−02 | 2.14E−08 | 1.0 |
| mAb10988 | 279.2 ± 2.3 | 63.6 | 8.29E+05 | 2.71E−02 | 3.27E−08 | 0.4 |
| mAb10989 | 316.7 ± 1.6 | 114.3 | 1.86E+06 | 2.78E−03 | 1.50E−09 | 4.2 |
| mAb10996 | 414.2 ± 2.8 | 37.5 | 1.41E+05 | 2.28E−02 | 1.61E−07 | 0.5 |
| mAb10998 | 212.3 ± 1 | 17.7 | 3.54E+05 | 1.84E−02 | 5.21E−08 | 0.6 |
| mAb11000 | 322.6 ± 3.5 | 73.6 | 1.09E+06 | 1.14E−03 | 1.04E−09 | 10.1 |
| mAb11002 | 291.7 ± 2.7 | 13.8 | 1.65E+05 | 6.73E−03 | 4.07E−08 | 1.7 |
| mAb11004 | 232.9 ± 0.6 | 76.4 | 3.79E+05 | 3.24E−03 | 8.54E−09 | 3.6 |
| mAb11006 | 277.2 ± 1.1 | 66.9 | 9.67E+04 | 4.40E−04 | 4.55E−09 | 26.3 |
| mAb11008 | 214.9 ± 1.5 | 40.8 | 9.30E+04 | 3.27E−03 | 3.52E−08 | 3.5 |
| mAb11010 | 221.8 ± 1.3 | 76.8 | 1.11E+06 | 2.74E−03 | 2.47E−09 | 4.2 |
| mAb1932 | 205 ± 0.8 | 5.3 | NB | NB | NB | NB |

TABLE 33

Binding kinetics parameters of SARS-COV-2 RBD-MMH binding to anti-SARS-COV-2-S monoclonal antibodies at 37° C.

| mAb Captured (mAb#) | mAb Capture Level (RU) | 90 nM Ag Bound (RU) | $k_a$ (1/Ms) | $k_d$ (1/s) | KD (M) | t½ (min) |
|---|---|---|---|---|---|---|
| mAb10913 | 366 ± 6 | 49 | 5.29E+05 | 5.56E−02 | 1.05E−07 | 0.2 |
| mAb10914 | 401 ± 3 | 63 | 2.51E+05 | 1.58E−02 | 6.27E−08 | 0.7 |
| mAb10915 | 401 ± 3 | 93 | 1.57E+05 | 7.57E−04 | 4.84E−09 | 15.3 |
| mAb10920 | 394 ± 3 | 73 | 6.10E+05 | 3.41E−02 | 5.60E−08 | 0.3 |
| mAb10921 | 394 ± 3 | 87 | 1.60E+05 | 2.07E−03 | 1.29E−08 | 5.6 |
| mAb10922 | 405.6 ± 1.7 | 130 | 1.04E+06 | 9.27E−03 | 8.89E−09 | 1.2 |
| mAb10923 | 355 ± 3 | 84 | 6.15E+05 | 2.76E−02 | 4.48E−08 | 0.4 |
| mAb10924 | 406 ± 5 | 110 | 2.99E+05 | 6.18E−03 | 2.07E−08 | 1.9 |
| mAb10930 | 373.9 ± 3.5 | 42 | 2.30E+05 | 1.87E−02 | 8.14E−08 | 0.6 |
| mAb10932 | 406 ± 4 | 119 | 1.43E+05 | 6.55E−04 | 4.57E−09 | 17.6 |
| mAb10933 | 368 ± 3 | 124 | 2.37E+06 | 8.28E−03 | 3.49E−09 | 1.4 |
| mAb10934 | 368 ± 3 | 117 | 4.62E+06 | 2.32E−02 | 5.02E−09 | 0.5 |
| mAb10935 | 430 ± 5 | 75 | 4.37E+05 | 3.74E−02 | 8.56E−08 | 0.3 |
| mAb10936 | 402 ± 3 | 126 | 9.75E+05 | 5.51E−03 | 5.65E−09 | 2.1 |
| mAb10937 | 402 ± 3 | 107 | 9.68E+05 | 2.43E−02 | 2.51E−08 | 0.5 |
| mAb10938 | 434 ± 3 | 100 | 1.06E+05 | 1.12E−03 | 1.05E−08 | 10.3 |
| mAb10939 | 439 ± 5 | 90 | 2.40E+05 | 9.46E−03 | 3.95E−08 | 1.2 |
| mAb10940 | 434 ± 3 | 124 | 1.42E+06 | 1.23E−02 | 8.70E−09 | 0.9 |
| mAb10941 | 418 ± 3 | 134 | 1.97E+05 | 1.75E−03 | 8.87E−09 | 6.6 |
| mAb10954 | 371.8 ± 2 | 131 | 5.68E+05 | 1.35E−03 | 2.38E−09 | 8.6 |
| mAb10955 | 384.1 ± 6.3 | 81 | 2.85E+05 | 1.26E−02 | 4.43E−08 | 0.9 |
| mAb10956 | 383 ± 2.3 | 89 | 3.56E+05 | 1.30E−02 | 3.65E−08 | 0.9 |
| mAb10957 | 322 ± 2.1 | 124 | 2.44E+05 | 6.19E−04 | 2.54E−09 | 18.7 |

TABLE 33-continued

Binding kinetics parameters of SARS-COV-2 RBD-MMH binding to anti-SARS-COV-2-S monoclonal antibodies at 37° C.

| mAb Captured (mAb#) | mAb Capture Level (RU) | 90 nM Ag Bound (RU) | $k_a$ (1/Ms) | $k_d$ (1/s) | KD (M) | t½ (min) |
|---|---|---|---|---|---|---|
| mAb10964 | 333.3 ± 4.6 | 121 | 3.68E+06 | 2.08E−03 | 5.64E−10 | 5.6 |
| mAb10965 | 326.8 ± 1.2 | 67 | 2.23E+05 | 9.19E−03 | 4.12E−08 | 1.3 |
| mAb10966 | 350.2 ± 2.9 | 118 | 4.40E+05 | 1.67E−03 | 3.79E−09 | 6.9 |
| mAb10967 | 336 ± 2.2 | 108 | 1.91E+05 | 2.62E−04 | 1.38E−09 | 44.1 |
| mAb10969 | 349.5 ± 3 | 86 | 4.07E+05 | 1.59E−02 | 3.92E−08 | 0.7 |
| mAb10970 | 393.8 ± 3.4 | 104 | 3.33E+05 | 7.58E−03 | 2.28E−08 | 1.5 |
| mAb10971 | 347 ± 1.9 | 116 | 3.92E+05 | 9.79E−04 | 2.50E−09 | 11.8 |
| mAb10977 | 341 ± 1.4 | 122 | 4.35E+05 | 1.31E−03 | 3.01E−09 | 8.8 |
| mAb10982 | 347.5 ± 1.3 | 67 | 1.94E+05 | 9.42E−03 | 4.85E−08 | 1.2 |
| mAb10984 | 422.5 ± 0.7 | 144 | 3.28E+05 | 1.82E−03 | 5.55E−09 | 6.3 |
| mAb10985 | 395.5 ± 2.5 | 134 | 2.57E+06 | 4.23E−03 | 1.65E−09 | 2.7 |
| mAb10986 | 349.3 ± 1.5 | 129 | 8.24E+05 | 5.83E−04 | 7.07E−10 | 19.8 |
| mAb10987 | 354 ± 5.3 | 82 | 8.38E+05 | 2.51E−02 | 3.00E−08 | 0.5 |
| mAb10988 | 364.4 ± 2.6 | 52 | 9.19E+05 | 5.78E−02 | 6.29E−08 | 0.2 |
| mAb10989 | 405.6 ± 1.9 | 128 | 2.97E+06 | 1.16E−02 | 3.90E−09 | 1.0 |
| mAb10996 | 524.3 ± 2.8 | 43 | 1.06E+05 | 1.25E−02 | 1.19E−07 | 0.9 |
| mAb10998 | 271.1 ± 0.6 | 15 | 2.81E+05 | 7.54E−03 | 2.68E−08 | 1.5 |
| mAb11000 | 418.2 ± 1 | 87 | 2.89E+05 | 9.10E−03 | 3.14E−08 | 1.3 |
| mAb11002 | 370.1 ± 2.5 | 12 | 2.81E+05 | 7.54E−03 | 2.68E−08 | 1.5 |
| mAb11004 | 297.8 ± 0.4 | 79 | 1.75E+06 | 1.48E−03 | 8.48E−10 | 7.8 |
| mAb11006 | 350.2 ± 1.2 | 92 | 6.28E+05 | 1.48E−02 | 2.35E−08 | 0.8 |
| mAb11008 | 289.4 ± 2.7 | 38 | 1.42E+05 | 1.51E−03 | 1.06E−08 | 7.6 |
| mAb11010 | 286.3 ± 0.5 | 96 | 1.67E+05 | 1.45E−02 | 8.71E−08 | 0.8 |
| mAb1932 | 265.3 ± 1.4 | 5 | NB | NB | NB | NB |

TABLE 34

Binding kinetics parameters of SARS-COV-2 RBD-mFc binding to anti-SARS-COV-2-S monoclonal antibodies at 25° C.

| mAb Captured (mAb#) | mAb Capture Level (RU) | 30 nM Ag Bound (RU) | $k_a$ (1/Ms) | $k_d$ (1/s) | KD (M) | t½ (min) |
|---|---|---|---|---|---|---|
| mAb10913 | 107 ± 0.4 | 65 | 5.00E+06 | 2.77E−04 | 5.53E−11 | 41.7 |
| mAb10914 | 116 ± 0.8 | 44 | 2.59E+05 | 1.40E−04 | 5.40E−10 | 82.5 |
| mAb10915 | 103 ± 0.2 | 41 | 2.83E+05 | 9.13E−06 | 3.23E−11 | 1265.1 |
| mAb10920 | 116 ± 0.9 | 69 | 5.08E+06 | 2.55E−04 | 5.02E−11 | 45.3 |
| mAb10921 | 104 ± 0.2 | 39 | 2.66E+05 | 3.34E−05 | 1.25E−10 | 345.8 |
| mAb10922 | 111.4 ± 0.8 | 80 | 3.20E+06 | 5.64E−05 | 1.76E−11 | 204.8 |
| mAb10923 | 110 ± 1.0 | 71 | 3.69E+06 | 1.35E−04 | 3.67E−11 | 85.6 |
| mAb10924 | 121 ± 0.5 | 74 | 8.09E+05 | 7.63E−05 | 9.43E−11 | 151.4 |
| mAb10930 | 104.2 ± 0.9 | 61 | 9.43E+05 | 1.71E−04 | 1.81E−10 | 67.5 |
| mAb10932 | 121 ± 0.8 | 60 | 2.95E+05 | 2.85E−05 | 9.67E−11 | 405.3 |
| mAb10933 | 108 ± 0.5 | 72 | 6.16E+06 | 6.10E−05 | 9.89E−12 | 189.3 |
| mAb10934 | 113 ± 0.5 | 70 | 1.12E+07 | 1.56E−04 | 1.39E−11 | 74.0 |
| mAb10935 | 128 ± 0.8 | 88 | 1.35E+06 | 1.07E−04 | 7.94E−11 | 107.9 |
| mAb10936 | 117 ± 0.4 | 74 | 1.78E+06 | 5.04E−05 | 2.83E−11 | 229.2 |
| mAb10937 | 106 ± 0.3 | 67 | 1.78E+06 | 5.40E−05 | 3.04E−11 | 213.9 |
| mAb10938 | 128 ± 1.5 | 47 | 2.42E+05 | 1.69E−05 | 7.02E−11 | 683.4 |
| mAb10939 | 127 ± 0.8 | 67 | 7.22E+05 | 8.74E−05 | 1.21E−10 | 132.2 |
| mAb10940 | 102 ± 0.4 | 67 | 3.72E+06 | 4.66E−05 | 1.25E−11 | 247.9 |
| mAb10941 | 125 ± 0.2 | 68 | 3.70E+05 | 3.48E−05 | 9.43E−11 | 331.9 |
| mAb10954 | 108.8 ± 1 | 86 | 2.35E+06 | 4.78E−05 | 2.03E−11 | 241.6 |
| mAb10955 | 109.8 ± 0.8 | 76 | 1.20E+06 | 9.22E−05 | 7.71E−11 | 125.3 |
| mAb10956 | 104.1 ± 0.5 | 74 | 1.46E+06 | 1.30E−04 | 8.87E−11 | 88.8 |
| mAb10957 | 104.7 ± 0.5 | 77 | 1.02E+06 | 3.35E−05 | 3.27E−11 | 344.8 |
| mAb10964 | 93.3 ± 0.3 | 70 | 9.30E+06 | 3.69E−05 | 3.97E−12 | 313.0 |
| mAb10965 | 94.2 ± 0.8 | 63 | 6.94E+05 | 1.56E−04 | 2.25E−10 | 74.0 |
| mAb10966 | 100.2 ± 0.4 | 73 | 1.50E+06 | 3.37E−05 | 2.24E−11 | 342.7 |
| mAb10967 | 93.3 ± 0.2 | 60 | 6.64E+05 | 1.35E−05 | 2.03E−11 | 855.6 |
| mAb10969 | 111.4 ± 0.8 | 80 | 4.64E+05 | 1.00E−04 | 2.16E−10 | 115.5 |
| mAb10970 | 113.4 ± 0.7 | 85 | 2.19E+06 | 4.05E−04 | 1.85E−10 | 28.5 |
| mAb10971 | 99 ± 0.5 | 72 | 1.40E+06 | 4.09E−05 | 2.92E−11 | 282.4 |
| mAb10977 | 109.1 ± 0.4 | 73 | 1.82E+06 | 2.29E−05 | 1.26E−11 | 504.4 |
| mAb10982 | 94.8 ± 0.1 | 59 | 9.10E+05 | 8.06E−05 | 8.86E−11 | 143.3 |
| mAb10984 | 121 ± 0.6 | 89 | 1.39E+06 | 3.97E−05 | 2.86E−11 | 290.9 |
| mAb10985 | 112.7 ± 0.3 | 77 | 8.09E+06 | 8.51E−05 | 1.05E−11 | 135.7 |
| mAb10986 | 94.2 ± 0.5 | 66 | 2.70E+06 | 2.40E−05 | 8.88E−12 | 481.3 |
| mAb10987 | 98 ± 0.7 | 73 | 3.19E+06 | 4.24E−04 | 1.33E−10 | 27.2 |

TABLE 34-continued

Binding kinetics parameters of SARS-COV-2 RBD-mFc binding to anti-SARS-COV-2-S monoclonal antibodies at 25° C.

| mAb Captured (mAb#) | mAb Capture Level (RU) | 30 nM Ag Bound (RU) | $k_a$ (1/Ms) | $k_d$ (1/s) | KD (M) | t½ (min) |
|---|---|---|---|---|---|---|
| mAb10988 | 101.6 ± 0.6 | 69 | 4.96E+06 | 5.08E−04 | 1.02E−10 | 22.7 |
| mAb10989 | 112.1 ± 0.4 | 77 | 1.08E+07 | 9.63E−05 | 8.95E−12 | 119.9 |
| mAb10996 | 104.2 ± 0.9 | 61 | 5.62E+05 | 8.02E−04 | 1.43E−09 | 14.4 |
| mAb10998 | 94.8 ± 0.1 | 59 | 1.47E+06 | 3.58E−03 | 2.44E−09 | 3.2 |
| mAb11000 | 112.7 ± 0.3 | 77 | 1.11E+06 | 1.27E−04 | 1.15E−10 | 90.9 |
| mAb11002 | 121 ± 0.6 | 89 | 5.54E+05 | 2.47E−03 | 4.46E−09 | 4.7 |
| mAb11004 | 94.2 ± 0.5 | 66 | 6.95E+05 | 6.40E−05 | 9.21E−11 | 180.5 |
| mAb11006 | 98 ± 0.7 | 73 | 3.30E+05 | 5.21E−05 | 1.58E−10 | 221.7 |
| mAb11008 | 101.6 ± 0.6 | 69 | 3.90E+05 | 1.92E−04 | 4.92E−10 | 60.2 |
| mAb11010 | 112.1 ± 0.4 | 77 | 1.14E+06 | 8.99E−05 | 7.89E−11 | 128.5 |
| mAb1932 | 97.8 ± 0.2 | 3 | NB | NB | NB | NB |

TABLE 35

Binding kinetics parameters of SARS-COV-2 RBD-mFc binding to anti-SARS-COV-2-S monoclonal antibodies at 37° C.

| mAb Captured (mAb#) | mAb Capture Level (RU) | 30 nM Ag Bound (RU) | $k_a$ (1/Ms) | $k_d$ (1/s) | KD (M) | t½ (min) |
|---|---|---|---|---|---|---|
| mAb10913 | 147 ± 0.8 | 75 | 6.32E+06 | 1.73E−03 | 2.74E−10 | 6.7 |
| mAb10914 | 163 ± 1.2 | 70 | 6.91E+05 | 2.20E−04 | 3.18E−10 | 52.5 |
| mAb10915 | 141 ± 0.6 | 63 | 4.41E+05 | 6.89E−05 | 1.56E−10 | 167.6 |
| mAb10920 | 155 ± 1.1 | 83 | 6.31E+06 | 7.53E−04 | 1.19E−10 | 15.3 |
| mAb10921 | 135 ± 0.3 | 62 | 4.58E+05 | 1.25E−04 | 2.73E−10 | 92.4 |
| mAb10922 | 149.1 ± 1 | 97 | 4.60E+06 | 1.60E−04 | 3.49E−11 | 72.2 |
| mAb10923 | 144 ± 0.8 | 88 | 5.53E+06 | 1.85E−04 | 3.36E−11 | 62.4 |
| mAb10924 | 160 ± 1.1 | 98 | 1.17E+06 | 1.31E−04 | 1.12E−10 | 88.2 |
| mAb10930 | 142.9 ± 0.4 | 72 | 1.49E+06 | 5.97E−04 | 3.99E−10 | 19.3 |
| mAb10932 | 164 ± 1.5 | 89 | 4.48E+05 | 6.86E−05 | 1.53E−10 | 168.4 |
| mAb10933 | 152 ± 0.9 | 89 | 7.30E+06 | 7.94E−05 | 1.09E−11 | 145.5 |
| mAb10934 | 151 ± 0.7 | 87 | 1.36E+07 | 2.93E−04 | 2.16E−11 | 39.4 |
| mAb10935 | 171 ± 0.8 | 101 | 5.68E+06 | 4.94E−04 | 8.69E−11 | 23.4 |
| mAb10936 | 161 ± 1.0 | 94 | 3.81E+06 | 6.75E−05 | 1.77E−11 | 171.1 |
| mAb10937 | 141 ± 0.6 | 85 | 4.47E+06 | 5.74E−05 | 1.29E−11 | 201.2 |
| mAb10938 | 172 ± 1.2 | 76 | 3.78E+05 | 6.56E−05 | 1.73E−10 | 176.1 |
| mAb10939 | 169 ± 0.6 | 92 | 1.06E+06 | 1.65E−04 | 1.55E−10 | 70.0 |
| mAb10940 | 136 ± 0.6 | 85 | 5.54E+06 | 5.04E−05 | 9.10E−12 | 229.2 |
| mAb10941 | 164 ± 0.8 | 100 | 8.02E+05 | 8.01E−05 | 1.00E−10 | 144.2 |
| mAb10954 | 142.4 ± 0.8 | 105 | 3.02E+06 | 1.12E−04 | 3.69E−11 | 103.1 |
| mAb10955 | 146.8 ± 0.7 | 91 | 1.92E+06 | 3.88E−04 | 2.02E−10 | 29.8 |
| mAb10956 | 136.6 ± 0.4 | 91 | 2.17E+06 | 3.42E−04 | 1.58E−10 | 33.8 |
| mAb10957 | 137.7 ± 1.2 | 100 | 1.55E+06 | 7.19E−05 | 4.63E−11 | 160.6 |
| mAb10964 | 122.5 ± 0.3 | 84 | 1.05E+07 | 1.26E−04 | 1.20E−11 | 91.7 |
| mAb10965 | 125.7 ± 1 | 81 | 1.42E+06 | 3.38E−04 | 2.37E−10 | 34.2 |
| mAb10966 | 137.3 ± 1.1 | 92 | 2.45E+06 | 9.93E−05 | 4.05E−11 | 116.3 |
| mAb10967 | 123.3 ± 0.9 | 81 | 1.45E+06 | 3.33E−05 | 2.29E−11 | 346.8 |
| mAb10969 | 149.1 ± 1 | 97 | 8.11E+05 | 1.41E−04 | 1.74E−10 | 81.9 |
| mAb10970 | 149.9 ± 0.6 | 102 | 2.18E+06 | 4.20E−04 | 1.92E−10 | 27.5 |
| mAb10971 | 136.1 ± 0.8 | 90 | 2.37E+06 | 9.41E−05 | 3.97E−11 | 122.7 |
| mAb10977 | 145.8 ± 0.7 | 93 | 2.50E+06 | 1.07E−04 | 4.28E−11 | 107.9 |
| mAb10982 | 125.5 ± 0.8 | 74 | 1.23E+06 | 2.58E−04 | 2.10E−10 | 44.8 |
| mAb10984 | 158.4 ± 0.7 | 110 | 2.07E+06 | 8.36E−05 | 4.04E−11 | 138.2 |
| mAb10985 | 151.8 ± 0.7 | 87 | 9.36E+06 | 3.75E−04 | 4.01E−11 | 30.8 |
| mAb10986 | 125 ± 0.7 | 83 | 4.59E+06 | 5.79E−05 | 1.26E−11 | 199.5 |
| mAb10987 | 131.5 ± 0.7 | 87 | 5.04E+06 | 3.90E−04 | 7.75E−11 | 29.6 |
| mAb10988 | 138.6 ± 0.5 | 82 | 8.34E+06 | 7.90E−04 | 9.47E−11 | 14.6 |
| mAb10989 | 146.1 ± 0.6 | 92 | 1.38E+07 | 3.65E−04 | 2.65E−11 | 31.6 |
| mAb10996 | 142.9 ± 0.4 | 72 | 9.35E+05 | 2.47E−03 | 2.64E−09 | 4.7 |
| mAb10998 | 125.5 ± 0.8 | 74 | 8.79E+05 | 1.97E−02 | 2.24E−08 | 0.6 |
| mAb11000 | 151.8 ± 0.7 | 87 | 1.63E+06 | 2.71E−04 | 1.66E−10 | 42.6 |
| mAb11002 | 158.4 ± 0.7 | 110 | 5.06E+05 | 1.65E−02 | 3.26E−08 | 0.7 |
| mAb11004 | 125 ± 0.7 | 83 | 1.01E+06 | 1.18E−04 | 1.17E−10 | 97.9 |
| mAb11006 | 131.5 ± 0.7 | 87 | 3.88E+05 | 7.65E−05 | 1.97E−10 | 151.0 |
| mAb11008 | 138.6 ± 0.5 | 82 | 4.64E+05 | 4.05E−04 | 8.72E−10 | 28.5 |
| mAb11010 | 146.1 ± 0.6 | 92 | 1.59E+06 | 8.02E−05 | 5.05E−11 | 144.0 |
| mAb1932 | 128 ± 0.3 | 5 | NB | NB | NB | NB |

Example 14: Anti-SARS-CoV-2 Antibodies Block RBD Binding to hACE2 as Determined by ELISA An ELISA-based blocking assay was used to determine the ability of anti-SARS-CoV-2 antibodies to block the binding of the SARS-COV-2 Spike protein receptor binding domain (RBD) to its receptor, human angiotensin converting enzyme 2 (hACE2).

The SARS-CoV-2 protein used in this assay was comprised of the receptor binding domain (RBD) portion of the SARS-CoV-2 Spike protein (amino acids Arg319-Phe541) expressed with the Fc portion of the human IgG1 at the c-terminus (SARS-CoV-2 RBD-hFc) The human ACE2 protein used in the experiments was purchased from R&D Systems and was comprised of amino acids Gln18-Ser740 with a C-terminal 10×-Histidine tag (hACE2-His; NCBI Accession No. Q9BYF1).

Experiments were carried out using the following procedure. A monoclonal anti-Penta-His antibody (Qiagen) was coated at 1 μg/ml in PBS on a 96-well microtiter plate overnight at 4° C. The hACE2-His receptor was added at 0.2 ug/ml in PBS and bound for two hours at room temperature (RT). Nonspecific binding sites were subsequently blocked using a 0.5% (w/v) solution of BSA in PBS. In other microtiter plates, a constant amount of 100 pM of SARS-CoV-2 RBD-hFc protein was bound with anti-SARS-COV-2 antibodies and an isotype IgG1 antibody control at dilutions from 0.0008 nM to 50 nM in PBS+0.5% BSA. After a one-hour incubation, the mixture solutions were transferred to the microtiter plate coated hACE2-His. After 1.5 hours of incubation at RT, the wells were washed, and plate-bound SARS-COV2 was detected with goat-anti-human IgG antibody conjugated with horseradish peroxidase (HRP) (Jackson). The plates were then developed using TMB substrate solution (BD Biosciences, #555214) according to manufacturer's recommendation and absorbance at 450 nm was measured on a Victor X5 plate reader.

Binding data were analyzed using a sigmoidal dose-response model within Prism™ software (GraphPad). The calculated IC50 value, defined as the concentration of antibody required to block 50% of SARS-CoV-2 RBD-hFc binding to plate-coated hACE2-His, was used as an indicator of blocking potency. Percent blocking was defined based on the background-corrected binding signal observed at the highest antibody concentration tested using this formula and reported for all tested antibodies:

$$\%\ \text{Blocking} = 100 - \left(\frac{[\text{Experimental Signal}_{(highest\ Ab\ conc)} - \text{Background Signal}_{(buffer)}]}{[\text{Maximum Signal}_{(hEGF.mFc\ alone)} - \text{Background Signal}_{(buffer)}]} \times 100\right)$$

Antibodies that blocked binding less than or equal to 50% at the highest concentration tested were classified as non-blockers and IC50 values were not reported for those antibodies.

The ability of anti-SARS-CoV-2 antibodies to block SARS-CoV-2 RBD binding to human ACE2 was assessed using a blocking ELISA. In this assay 100 pM SARS-COV-2 RBD-hFc was titrated with a wide range of the concentrations of the anti-SARS-CoV-2-S antibody and the inhibition of the presence of the antibody on RBD binding to hACE2-His was evaluated. The plate-bound RBD-hFc was detected with an HRP conjugated anti-hFc antibody.

The blocking IC50s and maximum blocking at the highest tested concentrations of the anti-SARS-CoV-2-S antibodies are summarized in Table 36, and the blocking curves shown in FIGS. 1-8. Of the 46 antibodies tested, 44 displayed antibody concentration-dependent blocking of RBD.hFc binding to hACE-2. IC50 values ranged from 41 pM to 4.5 nM and maximum blocking ranging from 55% to about 100% at the highest antibody concentration tested. Two antibodies out of 46 tested showed no blocking activities under the assay conditions. The irrelevant isotype control antibody showed no blocking activity, as expected.

TABLE 36

Blocking potency of Anti-SAR-COV-2 Antibodies on Spike RBD-hFc Binding to Immobilized Human ACE-2

| mAb | Assay Run # | Blocking 100 pM (RBD).hFc to ACE2 $IC_{50}$, M | Blocking 100 pM (RBD).hFc to ACE2 % Blocking |
|---|---|---|---|
| mAb10913 | 1 | 2.17E−10 | 80 |
| mAb10914 | 1 | 9.80E−10 | 93 |
| mAb10915 | 1 | 3.21E−10 | 99 |
| mAb10920 | 1 | 3.38E−10 | 95 |
| mAb10920 | 3 | 1.39E−10 | 87 |
| mAb10921 | 1 | 4.33E−10 | 99 |
| mAb10921 | 3 | 5.07E−10 | 94 |
| mAb10922 | 2 | 6.65E−11 | 97 |
| mAb10923 | 1 | 1.49E−10 | 94 |
| mAb10923 | 3 | 1.84E−10 | 85 |
| mAb10924 | 1 | 1.63E−10 | 98 |
| mAb10924 | 2 | 1.27E−10 | 98 |
| mAb10930 | 2 | 2.82E−10 | 86 |
| mAb10932 | 1 | 3.73E−10 | 99 |
| mAb10933 | 1 | 7.07E−11 | 99 |
| mAb10933 | 3 | 6.53E−11 | 95 |
| mAb10933 | 2 | 5.22E−11 | 101 |
| mAb10934 | 1 | 6.60E−11 | 96 |
| mAb10934 | 3 | 5.97E−11 | 98 |
| mAb10934 | 2 | 4.80E−11 | 96 |
| mAb10935 | 1 | 1.02E−10 | 99 |
| mAb10935 | 2 | 6.94E−11 | 98 |
| mAb10936 | 1 | 8.75E−11 | 95 |
| mAb10936 | 2 | 7.10E−11 | 97 |
| mAb10937 | 1 | 6.49E−11 | 99 |
| mAb10938 | 1 | 2.75E−10 | 99 |
| mAb10939 | 1 | 1.75E−10 | 97 |
| mAb10939 | 3 | 2.63E−10 | 93 |
| mAb10940 | 1 | 6.52E−11 | 92 |
| mAb10941 | 1 | 2.27E−10 | 100 |
| mAb10941 | 2 | 2.06E−10 | 100 |
| mAb10954 | 2 | 7.11E−11 | 95 |
| mAb10955 | 2 | 1.41E−10 | 97 |
| mAb10956 | 2 | 1.85E−10 | 99 |
| mAb10957 | 2 | 1.69E−10 | 99 |
| mAb10964 | 3 | 6.83E−11 | 93 |
| mAb10964 | 2 | 6.25E−11 | 95 |
| mAb10965 | 2 | 2.13E−10 | 97 |
| mAb10966 | 2 | 1.60E−10 | 99 |
| mAb10967 | 2 | 2.80E−10 | 98 |
| mAb10969 | 3 | 2.15E−10 | 95 |
| mAb10970 | 2 | 1.07E−10 | 97 |
| mAb10971 | 2 | 1.49E−10 | 98 |
| mAb10977 | 3 | 8.71E−11 | 77 |
| mAb10977 | 2 | 7.11E−11 | 65 |
| mAb10982 | 2 | 1.16E−10 | 93 |
| mAb10984 | 2 | 7.75E−11 | 90 |
| mAb10985 | 3 | 6.96E−11 | 97 |
| mAb10985 | 2 | 4.11E−11 | 99 |
| mAb10986 | 2 | 7.54E−11 | 98 |
| mAb10987 | 3 | 2.85E−10 | 93 |
| mAb10987 | 2 | 1.81E−10 | 95 |
| mAb10988 | 2 | 8.64E−11 | 95 |
| mAb10989 | 3 | 5.91E−11 | 96 |
| mAb10989 | 2 | 4.28E−11 | 98 |
| mAb10996 | 3 | 6.10E−09 | 71 |

TABLE 36-continued

Blocking potency of Anti-SAR-COV-2 Antibodies on Spike RBD-hFc Binding to Immobilized Human ACE-2

| mAb | Assay Run # | Blocking 100 pM (RBD).hFc to ACE2 $IC_{50}$, M | Blocking 100 pM (RBD).hFc to ACE2 % Blocking |
|---|---|---|---|
| mAb10998 | 3 | 4.30E−09 | 55 |
| mAb11000 | 3 | 4.50E−09 | 75 |
| mAb11002 | 3 | NBD | 7 |
| mAb11004 | 3 | NBD | 9 |
| mAb11006 | 3 | 2.20E−10 | 85 |
| mAb11008 | 3 | 1.49E−09 | 93 |
| mAb11010 | 3 | 1.47E−10 | 83 |
| mAb193250 IgG1 Control | 1 | — | −8 |
| mAb193250 IgG1 Control | 3 | — | −19 |
| mAb193250 IgG1 Control | 2 | — | −15 |

Note:
RBD-hFc at 100 pM was titrated with anti-SARS-COV-2-S antibodies in serial dilutions from 50 nM and bound RBD-hFc on immobilized hACE2 with a 10× histidine tag, and detected with HRP-conjugated anti-hFc antibody.
NBD; no blocking detected.

Example 15: Cross-Competition Between mAb10987, mAb10989, mAb10933, and mAb10934 mAb10987, mAb10989, mAb10933, and mAb10934 were examined in cross-competition binding assays (FIG. 11), identifying several pairs of non-competing mAbs with picomolar neutralization potency that could potentially be combined to form antibody cocktails, e.g., mAb10987 and mAb0933.

Epitope binning of the anti-SARS-CoV-2-S mAbs was conducted in a pre-mix sandwich format involving competing mAbs against one another in a pairwise combinatorial manner for binding to SARS-CoV-2 RBD-MMH protein using a ForteBio Octet HTX biolayer interferometry instrument (Molecular Devices ForteBio LLC, Fremont, CA) with running buffer of 10 mM HEPES, 150 mM NaCl, 0.05% (v/v) Tween-20, pH 7.4, 1 mg/mL BSA. Assays were performed at 30° C. with continuous agitation at 1000 rpm. After obtaining an initial baseline in running buffer 20 μg/mL of anti-COVID19 mAbs was captured onto anti-human Fc (AHC) biosensor tips for 300 s. To block remaining free unsaturated binding sites on AHC biosensor tips, all sensors were exposed for 240 s to blocking solution well containing 100 μg/mL irrelevant IgG1. Following this process, biosensors were immersed into wells containing pre-mix solution of 100 nM SARS CoV-2 RBD-MMH protein and 600 nM of anti-COVID19 mAb binding site of a second mAbs for 300 s. Binding response at each step was recorded and specific signal was normalized by subtracting self-blocking mAb competing control from dataset. Data analysis was performed with Octet Data Analysis HT 10.0 software using the Epitope Binning.

Figure 12:
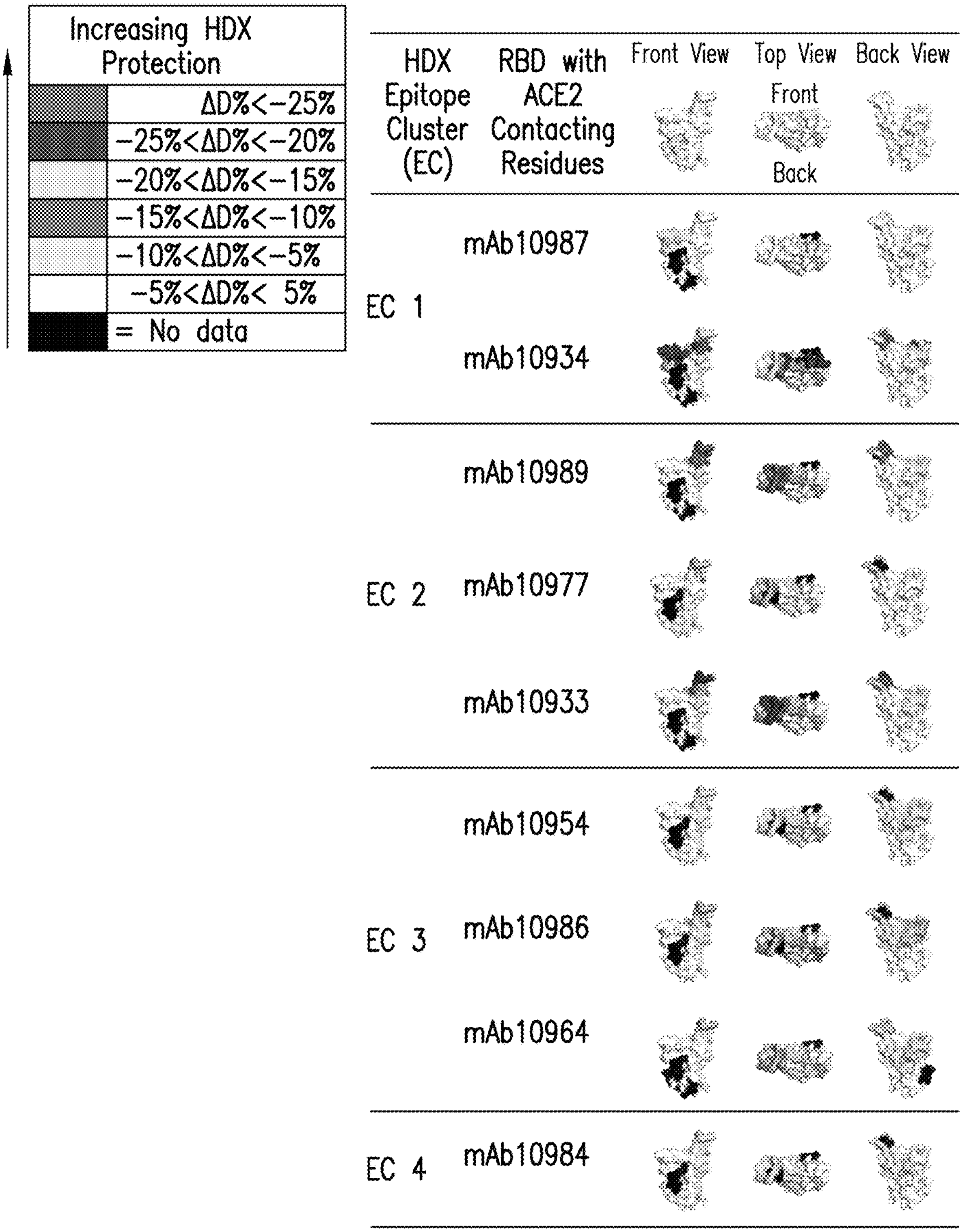
FIG. 12 displays a 3D surface model for the structure of the Spike protein RBD domain showing the ACE2 interface and HDX-MS epitope mapping results. RBD residues protected by anti-SARS-CoV2-Spike antibodies are indicated with shading that represent the extent of protection as determined by HDX-MS experiments. The RBD structure is reproduced from PDB 6M17.

Comparing the cross-competition binding assays with the HDX-MS results described above provides structural insights into the mechanism by which non-competing pairs of antibodies can simultaneously bind the RBD, and can thus be ideal partners for a therapeutic antibody cocktail. mAb10987 and mAb10933 represent such a pair of antibodies. mAb10933 targets the spike-like loop region on one edge of the ACE2 interface. Within that region, the residues that show the most significant HDX protection by mAb10933 face upward, suggesting that the Fab region of mAb10933 binds the RBD from the top direction, where mAb10933 will have significant collisions with ACE2. In order to avoid competition with mAb10933, mAb10987 only binds to the HDX-defined protected regions from the front or the lower left side (in the front view of mAb10987 in FIG. 12). This is consistent with the neutralization data described above, as mAb10987 would orient it in a position that has high probability to interfere with ACE2.

Example 16: Structure Determination of Antibody-Bound Spike Protein

To better understand the binding of mAb10933 and mAb10987 to the spike protein RBD, structural analysis was performed via cryo-electron microscopy (cryoEM). Fab fragments of mAb10933 and mAb10987 were isolated using FabALACTICA kit (Genovis). 600 μg of the mAb10933 Fab and 600 μg of mAb10987 Fab were mixed with 300 μg of SARS-CoV-2-S RBD and incubated on ice for −1 hour then injected into a Superdex 200 increase gel filtration column equilibrated to 50 mM Tris pH 7.5, 150 mM NaCl. Peak fractions containing the mAb10933 Fab-mAb10987 Fab-RBD complex were collected and concentrated using a 10 kDa MWCO centrifugal filter. For cryoEM grid preparation, the protein sample was diluted to 1.5 mg/mL and 0.15% PMAL-C8 amphipol was added. 3.5 μL of protein was deposited onto a freshly plasma cleaned UltrAufoil grid (1.2/1.3, 300 mesh). Excess solution was blotted away using filter paper and plunge frozen into liquid ethane using a Vitrobot Mark IV. The cryoEM grid was transferred to a Titan Krios (Thermo Fisher) equipped with a K3 detector (Gatan). Movies were collected using EPU (Thermo Fisher) at 105,000× magnification, corresponding to a pixel size of 0.85 Å. A dose rate of 15 electrons per pixel per second was used and each movie was 2 seconds, corresponding to a total dose of −40 electrons per Å2.

All cryoEM data processing was carried out using cryoSPARC v2.14.2. 2,821 movies were aligned using patch motion correction and patch CTF estimation. 2,197 aligned micrographs were selected for further processing on the basis of estimated defocus values and CTF fit resolutions. An initial set of particles picked using blob picker were subjected to 2D classification to generate templates for template picking. 989,553 particles picked by template picking were subjected to multiple rounds of 2D classification to remove unbound fabs and particles containing an incomplete complex. Ab initio reconstruction with three classes generated a single class containing 61,707 particles that corresponded to the mAb10933 Fab-mAb10987 Fab-RBD complex. Heterogenous refinement of the particles in this class followed by non-uniform refinement resulted in a 3.9 Å resolution (FSC=0.143) map containing 48,140 particles that was used for model building. Into this map, models of the RBD (taken from PDB code 6M17) and the two Fabs (taken from prior antibody structures, except for the lambda light chain of mAb10987 which came from PDB code 5U15), were manually placed. These models were then manually rebuilt using Coot and real-space refined against the map using Phenix.

Figure 13A:
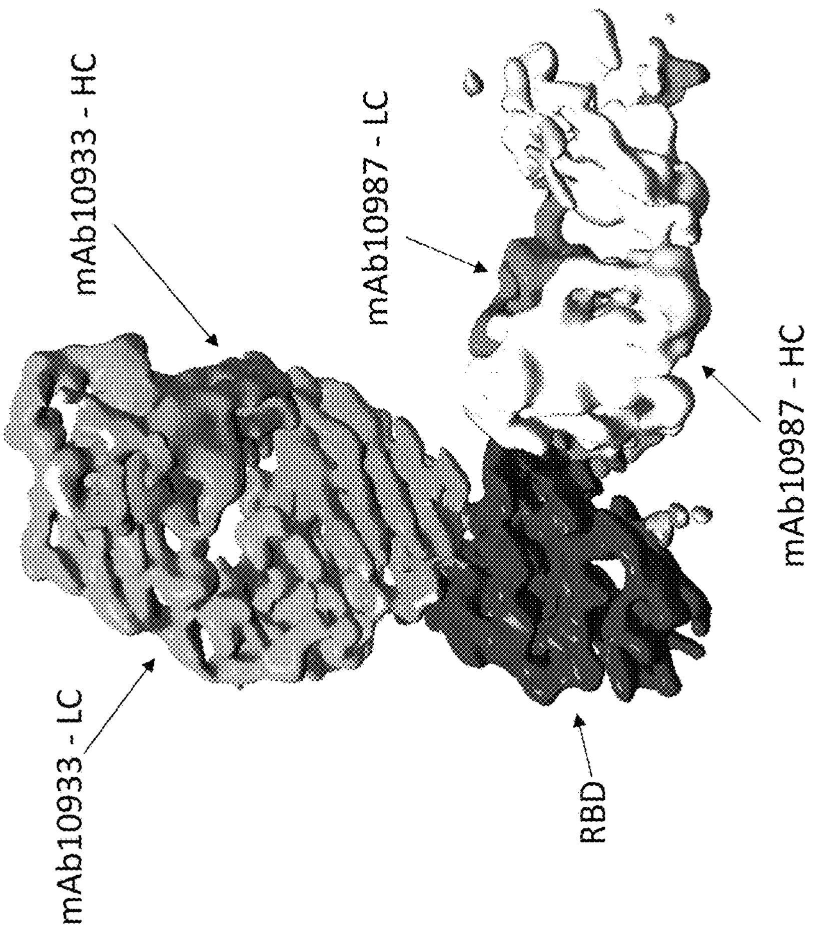
FIG. 13A and FIG. 13B display a complex of mAb10933 and mAb10987 with the SARS-CoV-2 RBD.
Figure 13B:
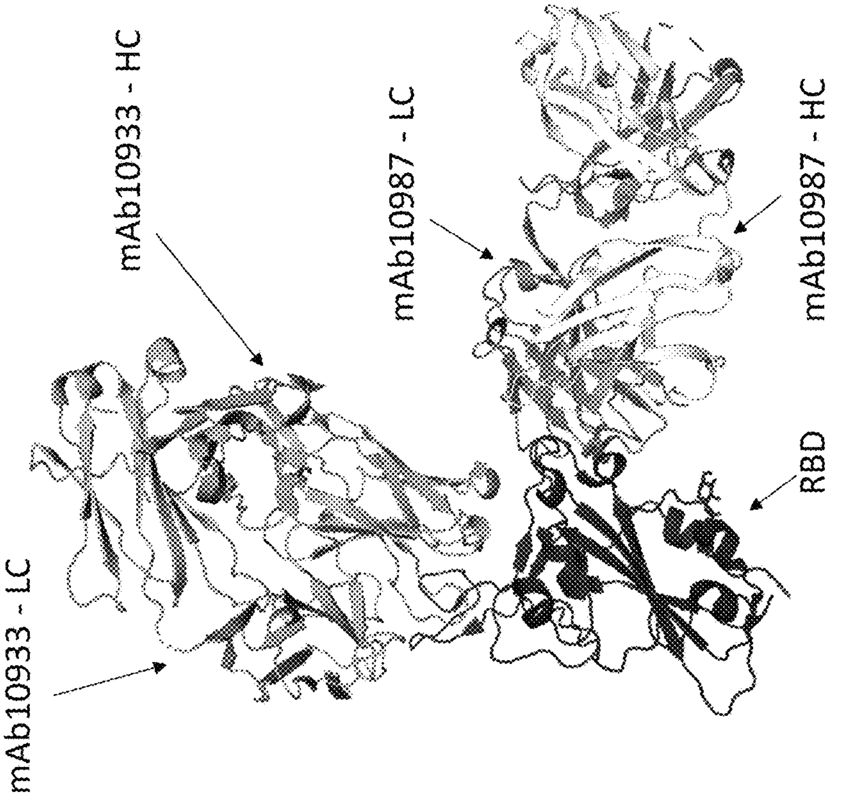

Confirming the above-described data, single-particle cryoEM of the complex of SARS-CoV-2 spike RBD bound to Fab fragments of mAb10933 and mAb10987 shows that the two antibodies in this cocktail can simultaneously bind to distinct regions of the RBD (FIG. 13A, FIG. 13B, and FIG. 14). A 3D reconstructed map of the complex with nominal resolution of 3.9 Å shows that the both Fab fragments bind at different epitopes on the RBD, confirming that they are non-competing antibodies. mAb10933 binds at the top of the RBD, extensively overlapping the binding site for ACE2. On the other hand, the epitope for mAb10987 is located on the side of the RBD, well away from the mAb10933 epitope, and has little to no overlap with the ACE2 binding site.

Example 17: Cross-Competition Between Anti-SARS-CoV-2-S mAbs

Binding competition between anti-SARS-CoV-2-S monoclonal antibodies (mAbs) was determined using a real time, label-free bio-layer interferometry (BLI) assay on the Octet HTX biosensor platform (Pall ForteBio Corp.). The entire experiment was performed at 25° C. in 10 mM HEPES, 150 mM NaCl, 3 mM EDTA, and 0.05% v/v Surfactant Tween-20, 1 mg/mL BSA, pH 7.4 (HBS-EBT) buffer with the plate shaking at a speed of 1000 rpm. To assess whether two mAbs were able to compete with one another for binding to their respective epitopes on the SARS-COV-2-S RBD extracellular domain expressed with a C-terminal myc-myc-hexahistidine (SARS-COV-2 RBD-MMH), ~0.51 nm of SARS-COV-2-S RBD-MMH was first captured onto anti-Penta-His antibody coated Octet biosensor tips (Fortebio Inc, #18-5122) by submerging the biosensor tips for 1 minute in wells containing a 10 μg/mL solution of SARS-COV-2-S RBD-MMH. The SARS-COV-2-S RBD-MMH captured biosensor tips were then saturated with a first anti-SARS-CoV-2-S monoclonal antibody (subsequently referred to as mAb-1) by dipping into wells containing 50 μg/mL solution of mAb-1 for 5 minutes. The biosensor tips were then subsequently dipped into wells containing 50 μg/mL solution of a second anti-SARS-CoV-2 monoclonal antibody (subsequently referred to as mAb-2) for 5 minutes. The biosensor tips were washed in HBS-ETB buffer in between every step of the experiment. The real-time binding response was monitored during the entire course of the experiment and the binding response at the end of every step was recorded. The response of mAb-2 binding to SARS-COV-2 RBD-MMH pre-complexed with mAb-1 was compared and competitive/non-competitive behavior of different anti-SARS-CoV-2 monoclonal antibodies was determined as shown in Table 37.

TABLE 37

Cross-competition between anti-SARS-CoV-2-S antibodies

| mAb-1 | mAb-2 Competing with mAb-1 |
|---|---|
| mAb10977 | mAb10924 |
| | mAb10989 |
| | mAb10920 |
| | mAb10913 |
| | mAb10923 |
| | mAb10930 |
| | mAb10969 |
| | mAb10988 |
| | mAb10964 |
| | mAb10996 |
| | mAb10966 |
| | mAb10998 |
| | mAb10984 |
| | mAb11006 |
| | mAb10921 |

TABLE 37-continued

Cross-competition between anti-SARS-CoV-2-S antibodies

| mAb-1 | mAb-2 Competing with mAb-1 |
|---|---|
| | mAb10971 |
| | mAb10938 |
| | mAb10932 |
| | mAb10970 |
| | mAb10957 |
| | mAb10956 |
| | mAb10941 |
| | mAb10939 |
| | mAb10935 |
| | mAb10914 |
| | mAb10982 |
| | mAb11008 |
| | mAb11002 |
| | mAb10933 |
| | mAb10940 |
| | mAb10922 |
| | mAb11004 |
| | mAb10937 |
| | mAb10936 |
| | mAb10934 |
| mAb10924 | mAb10977 |
| | mAb10989 |
| | mAb10920 |
| | mAb10913 |
| | mAb10923 |
| | mAb10930 |
| | mAb10969 |
| | mAb10988 |
| | mAb10964 |
| | mAb10996 |
| | mAb10966 |
| | mAb10998 |
| | mAb10984 |
| | mAb11006 |
| | mAb10921 |
| | mAb10971 |
| | mAb10938 |
| | mAb10932 |
| | mAb10970 |
| | mAb10957 |
| | mAb10956 |
| | mAb10941 |
| | mAb10939 |
| | mAb10935 |
| | mAb10914 |
| | mAb10982 |
| | mAb11008 |
| | mAb10915 |
| | mAb10965 |
| | mAb10967 |
| | mAb10986 |
| | mAb10955 |
| | mAb10954 |
| | mAb10933 |
| | mAb11000 |
| | mAb10985 |
| | mAb10937 |
| | mAb10936 |
| | mAb10934 |
| mAb10989 | mAb10977 |
| | mAb10924 |
| | mAb10920 |
| | mAb10913 |
| | mAb10923 |
| | mAb10930 |
| | mAb10969 |
| | mAb10988 |
| | mAb10964 |
| | mAb10996 |
| | mAb10966 |
| | mAb10998 |
| | mAb10984 |
| | mAb11006 |
| | mAb10921 |
| | mAb10971 |

TABLE 37-continued

Cross-competition between anti-SARS-CoV-2-S antibodies

| mAb-1 | mAb-2 Competing with mAb-1 |
|---|---|
| | mAb10938 |
| | mAb10932 |
| | mAb10970 |
| | mAb10957 |
| | mAb10956 |
| | mAb10941 |
| | mAb10939 |
| | mAb10935 |
| | mAb10914 |
| | mAb10982 |
| | mAb11008 |
| | mAb10915 |
| | mAb10965 |
| | mAb10967 |
| | mAb10986 |
| | mAb10955 |
| | mAb10954 |
| | mAb10933 |
| | mAb10987 |
| | mAb10940 |
| | mAb10922 |
| | mAb11004 |
| | mAb10937 |
| | mAb10936 |
| | mAb10934 |
| mAb10920 | mAb10977 |
| | mAb10924 |
| | mAb10989 |
| | mAb10913 |
| | mAb10923 |
| | mAb10930 |
| | mAb10969 |
| | mAb10988 |
| | mAb10964 |
| | mAb10996 |
| | mAb10966 |
| | mAb10998 |
| | mAb10984 |
| | mAb11006 |
| | mAb10921 |
| | mAb10971 |
| | mAb10938 |
| | mAb10932 |
| | mAb10970 |
| | mAb10957 |
| | mAb10956 |
| | mAb10941 |
| | mAb10939 |
| | mAb10935 |
| | mAb10914 |
| | mAb10982 |
| | mAb11008 |
| | mAb10915 |
| | mAb10965 |
| | mAb10967 |
| | mAb10986 |
| | mAb10955 |
| | mAb10954 |
| | mAb11002 |
| | mAb10933 |
| | mAb10987 |
| | mAb10940 |
| | mAb10922 |
| | mAb11004 |
| | mAb10937 |
| | mAb10936 |
| | mAb10934 |
| mAb10913 | mAb10977 |
| | mAb10924 |
| | mAb10989 |
| | mAb10920 |
| | mAb10923 |
| | mAb10930 |
| | mAb10969 |
| | mAb10988 |

TABLE 37-continued

Cross-competition between anti-SARS-CoV-2-S antibodies

| mAb-1 | mAb-2 Competing with mAb-1 |
|---|---|
| | mAb10964 |
| | mAb10996 |
| | mAb10966 |
| | mAb10998 |
| | mAb10984 |
| | mAb11006 |
| | mAb10921 |
| | mAb10971 |
| | mAb10938 |
| | mAb10932 |
| | mAb10970 |
| | mAb10957 |
| | mAb10956 |
| | mAb10941 |
| | mAb10939 |
| | mAb10935 |
| | mAb10914 |
| | mAb10982 |
| | mAb11008 |
| | mAb10915 |
| | mAb10965 |
| | mAb10967 |
| | mAb10986 |
| | mAb10955 |
| | mAb10954 |
| | mAb11002 |
| | mAb10933 |
| | mAb11004 |
| | mAb10937 |
| | mAb10936 |
| | mAb10934 |
| mAb10923 | mAb10977 |
| | mAb10924 |
| | mAb10989 |
| | mAb10920 |
| | mAb10913 |
| | mAb10930 |
| | mAb10969 |
| | mAb10988 |
| | mAb10964 |
| | mAb10996 |
| | mAb10966 |
| | mAb10998 |
| | mAb10984 |
| | mAb11006 |
| | mAb10921 |
| | mAb10971 |
| | mAb10938 |
| | mAb10932 |
| | mAb10970 |
| | mAb10957 |
| | mAb10956 |
| | mAb10941 |
| | mAb10939 |
| | mAb10935 |
| | mAb10914 |
| | mAb10982 |
| | mAb11008 |
| | mAb10915 |
| | mAb10965 |
| | mAb10967 |
| | mAb10986 |
| | mAb10955 |
| | mAb10954 |
| | mAb11002 |
| | mAb10933 |
| | mAb11004 |
| | mAb10937 |
| | mAb10936 |
| | mAb10934 |
| mAb10930 | mAb10977 |
| | mAb10924 |
| | mAb10989 |
| | mAb10920 |
| | mAb10913 |

TABLE 37-continued

| Cross-competition between anti-SARS-CoV-2-S antibodies | |
|---|---|
| mAb-1 | mAb-2 Competing with mAb-1 |
| | mAb10923 |
| | mAb10969 |
| | mAb10988 |
| | mAb10964 |
| | mAb10996 |
| | mAb10966 |
| | mAb10998 |
| | mAb10984 |
| | mAb11006 |
| | mAb10921 |
| | mAb10971 |
| | mAb10938 |
| | mAb10932 |
| | mAb10970 |
| | mAb10957 |
| | mAb10956 |
| | mAb10941 |
| | mAb10939 |
| | mAb10935 |
| | mAb10914 |
| | mAb10982 |
| | mAb11008 |
| | mAb10915 |
| | mAb10965 |
| | mAb10967 |
| | mAb10986 |
| | mAb10955 |
| | mAb10954 |
| | mAb11002 |
| | mAb10933 |
| | mAb10937 |
| | mAb10936 |
| | mAb10934 |
| mAb10969 | mAb10977 |
| | mAb10924 |
| | mAb10989 |
| | mAb10920 |
| | mAb10913 |
| | mAb10923 |
| | mAb10930 |
| | mAb10988 |
| | mAb10964 |
| | mAb10966 |
| | mAb10998 |
| | mAb10984 |
| | mAb11006 |
| | mAb10921 |
| | mAb10971 |
| | mAb10938 |
| | mAb10932 |
| | mAb10970 |
| | mAb10957 |
| | mAb10956 |
| | mAb10941 |
| | mAb10939 |
| | mAb10935 |
| | mAb10914 |
| | mAb10982 |
| | mAb11008 |
| | mAb10915 |
| | mAb10965 |
| | mAb10967 |
| | mAb10986 |
| | mAb10955 |
| | mAb10954 |
| | mAb11002 |
| | mAb10933 |
| | mAb10985 |
| | mAb10937 |
| | mAb10936 |
| | mAb10934 |
| mAb10988 | mAb10977 |
| | mAb10924 |
| | mAb10989 |
| | mAb10920 |

TABLE 37-continued

| Cross-competition between anti-SARS-CoV-2-S antibodies | |
|---|---|
| mAb-1 | mAb-2 Competing with mAb-1 |
| | mAb10913 |
| | mAb10923 |
| | mAb10930 |
| | mAb10969 |
| | mAb10964 |
| | mAb10996 |
| | mAb10966 |
| | mAb10998 |
| | mAb10984 |
| | mAb11006 |
| | mAb10921 |
| | mAb10971 |
| | mAb10938 |
| | mAb10932 |
| | mAb10970 |
| | mAb10957 |
| | mAb10956 |
| | mAb10941 |
| | mAb10939 |
| | mAb10935 |
| | mAb10914 |
| | mAb10982 |
| | mAb11008 |
| | mAb10915 |
| | mAb10965 |
| | mAb10967 |
| | mAb10986 |
| | mAb10955 |
| | mAb10954 |
| | mAb10933 |
| | mAb10936 |
| | mAb10934 |
| mAb10964 | mAb10977 |
| | mAb10924 |
| | mAb10989 |
| | mAb10920 |
| | mAb10913 |
| | mAb10923 |
| | mAb10930 |
| | mAb10969 |
| | mAb10988 |
| | mAb10996 |
| | mAb10966 |
| | mAb10998 |
| | mAb10984 |
| | mAb11006 |
| | mAb10921 |
| | mAb10971 |
| | mAb10938 |
| | mAb10932 |
| | mAb10970 |
| | mAb10957 |
| | mAb10956 |
| | mAb10941 |
| | mAb10939 |
| | mAb10935 |
| | mAb10914 |
| | mAb10982 |
| | mAb11008 |
| | mAb10915 |
| | mAb10965 |
| | mAb10967 |
| | mAb10986 |
| | mAb10955 |
| | mAb10954 |
| | mAb11002 |
| | mAb10933 |
| | mAb10936 |
| | mAb10934 |
| mAb10996 | mAb10977 |
| | mAb10924 |
| | mAb10989 |
| | mAb10920 |
| | mAb10913 |
| | mAb10923 |

TABLE 37-continued

Cross-competition between anti-SARS-CoV-2-S antibodies

| mAb-1 | mAb-2 Competing with mAb-1 |
|---|---|
| | mAb10930 |
| | mAb10969 |
| | mAb10988 |
| | mAb10964 |
| | mAb10966 |
| | mAb10998 |
| | mAb10984 |
| | mAb11006 |
| | mAb10921 |
| | mAb10971 |
| | mAb10938 |
| | mAb10932 |
| | mAb10970 |
| | mAb10957 |
| | mAb10956 |
| | mAb10941 |
| | mAb10939 |
| | mAb10935 |
| | mAb10914 |
| | mAb10982 |
| | mAb11008 |
| | mAb10915 |
| | mAb10965 |
| | mAb10967 |
| | mAb10986 |
| | mAb10955 |
| | mAb10954 |
| | mAb11002 |
| | mAb10933 |
| | mAb10985 |
| | mAb10934 |
| mAb10966 | mAb10977 |
| | mAb10924 |
| | mAb10989 |
| | mAb10920 |
| | mAb10913 |
| | mAb10923 |
| | mAb10930 |
| | mAb10969 |
| | mAb10988 |
| | mAb10964 |
| | mAb10996 |
| | mAb10998 |
| | mAb10984 |
| | mAb11006 |
| | mAb10921 |
| | mAb10971 |
| | mAb10938 |
| | mAb10932 |
| | mAb10970 |
| | mAb10957 |
| | mAb10956 |
| | mAb10941 |
| | mAb10939 |
| | mAb10935 |
| | mAb10914 |
| | mAb10982 |
| | mAb11008 |
| | mAb10915 |
| | mAb10965 |
| | mAb10967 |
| | mAb10986 |
| | mAb10955 |
| | mAb10954 |
| | mAb11002 |
| | mAb10933 |
| | mAb10985 |
| | mAb10934 |
| mAb10998 | mAb10977 |
| | mAb10924 |
| | mAb10989 |
| | mAb10920 |
| | mAb10913 |
| | mAb10923 |
| | mAb10930 |

TABLE 37-continued

Cross-competition between anti-SARS-CoV-2-S antibodies

| mAb-1 | mAb-2 Competing with mAb-1 |
|---|---|
| | mAb10969 |
| | mAb10988 |
| | mAb10964 |
| | mAb10996 |
| | mAb10966 |
| | mAb10984 |
| | mAb11006 |
| | mAb10921 |
| | mAb10971 |
| | mAb10938 |
| | mAb10932 |
| | mAb10970 |
| | mAb10957 |
| | mAb10956 |
| | mAb10941 |
| | mAb10939 |
| | mAb10935 |
| | mAb10914 |
| | mAb10982 |
| | mAb11008 |
| | mAb10915 |
| | mAb10965 |
| | mAb10967 |
| | mAb10986 |
| | mAb10955 |
| | mAb10954 |
| | mAb11002 |
| | mAb10985 |
| | mAb10936 |
| mAb10984 | mAb10977 |
| | mAb10924 |
| | mAb10989 |
| | mAb10920 |
| | mAb10913 |
| | mAb10923 |
| | mAb10930 |
| | mAb10969 |
| | mAb10988 |
| | mAb10964 |
| | mAb10996 |
| | mAb10966 |
| | mAb10998 |
| | mAb11006 |
| | mAb10921 |
| | mAb10971 |
| | mAb10938 |
| | mAb10932 |
| | mAb10970 |
| | mAb10957 |
| | mAb10956 |
| | mAb10941 |
| | mAb10939 |
| | mAb10935 |
| | mAb10914 |
| | mAb10982 |
| | mAb11008 |
| | mAb10915 |
| | mAb10965 |
| | mAb10967 |
| | mAb10986 |
| | mAb10955 |
| | mAb10954 |
| | mAb11002 |
| | mAb10985 |
| mAb11006 | mAb10977 |
| | mAb10924 |
| | mAb10989 |
| | mAb10920 |
| | mAb10913 |
| | mAb10923 |
| | mAb10930 |
| | mAb10969 |
| | mAb10988 |
| | mAb10964 |
| | mAb10996 |

TABLE 37-continued

Cross-competition between anti-SARS-CoV-2-S antibodies

| mAb-1 | mAb-2 Competing with mAb-1 |
|---|---|
| | mAb10966 |
| | mAb10998 |
| | mAb10984 |
| | mAb10921 |
| | mAb10971 |
| | mAb10938 |
| | mAb10932 |
| | mAb10970 |
| | mAb10957 |
| | mAb10956 |
| | mAb10941 |
| | mAb10939 |
| | mAb10935 |
| | mAb10914 |
| | mAb10982 |
| | mAb11008 |
| | mAb10915 |
| | mAb10965 |
| | mAb10967 |
| | mAb10986 |
| | mAb10955 |
| | mAb10954 |
| | mAb11002 |
| | mAb10933 |
| | mAb10985 |
| mAb10921 | mAb10977 |
| | mAb10924 |
| | mAb10989 |
| | mAb10920 |
| | mAb10913 |
| | mAb10923 |
| | mAb10930 |
| | mAb10969 |
| | mAb10988 |
| | mAb10964 |
| | mAb10996 |
| | mAb10966 |
| | mAb10998 |
| | mAb10984 |
| | mAb11006 |
| | mAb10971 |
| | mAb10938 |
| | mAb10932 |
| | mAb10970 |
| | mAb10957 |
| | mAb10956 |
| | mAb10941 |
| | mAb10939 |
| | mAb10935 |
| | mAb10914 |
| | mAb10982 |
| | mAb11008 |
| | mAb10915 |
| | mAb10965 |
| | mAb10967 |
| | mAb10986 |
| | mAb10955 |
| | mAb10954 |
| | mAb11002 |
| | mAb10985 |
| mAb10971 | mAb10977 |
| | mAb10924 |
| | mAb10989 |
| | mAb10920 |
| | mAb10913 |
| | mAb10923 |
| | mAb10930 |
| | mAb10969 |
| | mAb10988 |
| | mAb10964 |
| | mAb10996 |
| | mAb10966 |
| | mAb10998 |
| | mAb10984 |
| | mAb11006 |

TABLE 37-continued

Cross-competition between anti-SARS-CoV-2-S antibodies

| mAb-1 | mAb-2 Competing with mAb-1 |
|---|---|
| | mAb10921 |
| | mAb10938 |
| | mAb10932 |
| | mAb10970 |
| | mAb10957 |
| | mAb10956 |
| | mAb10941 |
| | mAb10939 |
| | mAb10935 |
| | mAb10914 |
| | mAb10982 |
| | mAb11008 |
| | mAb10915 |
| | mAb10965 |
| | mAb10967 |
| | mAb10986 |
| | mAb10955 |
| | mAb10954 |
| | mAb11002 |
| | mAb10985 |
| mAb10938 | mAb10977 |
| | mAb10924 |
| | mAb10989 |
| | mAb10920 |
| | mAb10913 |
| | mAb10923 |
| | mAb10930 |
| | mAb10969 |
| | mAb10988 |
| | mAb10964 |
| | mAb10996 |
| | mAb10966 |
| | mAb10998 |
| | mAb10984 |
| | mAb11006 |
| | mAb10921 |
| | mAb10971 |
| | mAb10932 |
| | mAb10970 |
| | mAb10957 |
| | mAb10956 |
| | mAb10941 |
| | mAb10939 |
| | mAb10935 |
| | mAb10914 |
| | mAb10982 |
| | mAb11008 |
| | mAb10915 |
| | mAb10965 |
| | mAb10967 |
| | mAb10986 |
| | mAb10955 |
| | mAb10954 |
| | mAb11002 |
| | mAb10985 |
| mAb10932 | mAb10977 |
| | mAb10924 |
| | mAb10989 |
| | mAb10920 |
| | mAb10913 |
| | mAb10923 |
| | mAb10930 |
| | mAb10969 |
| | mAb10988 |
| | mAb10964 |
| | mAb10996 |
| | mAb10966 |
| | mAb10998 |
| | mAb10984 |
| | mAb11006 |
| | mAb10921 |
| | mAb10971 |
| | mAb10938 |
| | mAb10970 |
| | mAb10957 |

TABLE 37-continued

Cross-competition between anti-SARS-CoV-2-S antibodies

| mAb-1 | mAb-2 Competing with mAb-1 |
|---|---|
| | mAb10956 |
| | mAb10941 |
| | mAb10939 |
| | mAb10935 |
| | mAb10914 |
| | mAb10982 |
| | mAb11008 |
| | mAb10915 |
| | mAb10965 |
| | mAb10967 |
| | mAb10986 |
| | mAb10955 |
| | mAb10954 |
| | mAb11002 |
| | mAb10985 |
| mAb10970 | mAb10977 |
| | mAb10924 |
| | mAb10989 |
| | mAb10920 |
| | mAb10913 |
| | mAb10923 |
| | mAb10930 |
| | mAb10969 |
| | mAb10988 |
| | mAb10964 |
| | mAb10996 |
| | mAb10966 |
| | mAb10998 |
| | mAb10984 |
| | mAb11006 |
| | mAb10921 |
| | mAb10971 |
| | mAb10938 |
| | mAb10932 |
| | mAb10957 |
| | mAb10956 |
| | mAb10941 |
| | mAb10939 |
| | mAb10935 |
| | mAb10914 |
| | mAb10982 |
| | mAb11008 |
| | mAb10915 |
| | mAb10965 |
| | mAb10967 |
| | mAb10986 |
| | mAb10955 |
| | mAb10954 |
| | mAb11002 |
| | mAb10985 |
| | mAb10936 |
| mAb10957 | mAb10977 |
| | mAb10924 |
| | mAb10989 |
| | mAb10920 |
| | mAb10913 |
| | mAb10923 |
| | mAb10930 |
| | mAb10969 |
| | mAb10988 |
| | mAb10964 |
| | mAb10996 |
| | mAb10966 |
| | mAb10998 |
| | mAb10984 |
| | mAb11006 |
| | mAb10921 |
| | mAb10971 |
| | mAb10938 |
| | mAb10932 |
| | mAb10970 |
| | mAb10956 |
| | mAb10941 |
| | mAb10939 |
| | mAb10935 |

TABLE 37-continued

Cross-competition between anti-SARS-CoV-2-S antibodies

| mAb-1 | mAb-2 Competing with mAb-1 |
|---|---|
| | mAb10914 |
| | mAb10982 |
| | mAb11008 |
| | mAb10915 |
| | mAb10965 |
| | mAb10967 |
| | mAb10986 |
| | mAb10955 |
| | mAb10954 |
| | mAb11002 |
| | mAb10985 |
| mAb10956 | mAb10977 |
| | mAb10924 |
| | mAb10989 |
| | mAb10920 |
| | mAb10913 |
| | mAb10923 |
| | mAb10930 |
| | mAb10969 |
| | mAb10988 |
| | mAb10964 |
| | mAb10996 |
| | mAb10966 |
| | mAb10998 |
| | mAb10984 |
| | mAb11006 |
| | mAb10921 |
| | mAb10971 |
| | mAb10938 |
| | mAb10932 |
| | mAb10970 |
| | mAb10957 |
| | mAb10941 |
| | mAb10939 |
| | mAb10935 |
| | mAb10914 |
| | mAb10982 |
| | mAb11008 |
| | mAb10915 |
| | mAb10965 |
| | mAb10967 |
| | mAb10986 |
| | mAb10955 |
| | mAb10954 |
| | mAb11002 |
| | mAb10985 |
| mAb10941 | mAb10977 |
| | mAb10924 |
| | mAb10989 |
| | mAb10920 |
| | mAb10913 |
| | mAb10923 |
| | mAb10930 |
| | mAb10969 |
| | mAb10988 |
| | mAb10964 |
| | mAb10996 |
| | mAb10966 |
| | mAb10998 |
| | mAb10984 |
| | mAb11006 |
| | mAb10921 |
| | mAb10971 |
| | mAb10938 |
| | mAb10932 |
| | mAb10970 |
| | mAb10957 |
| | mAb10956 |
| | mAb10939 |
| | mAb10935 |
| | mAb10914 |
| | mAb10982 |
| | mAb11008 |
| | mAb10915 |
| | mAb10965 |

TABLE 37-continued

Cross-competition between anti-SARS-CoV-2-S antibodies

| mAb-1 | mAb-2 Competing with mAb-1 |
|---|---|
| | mAb10967 |
| | mAb10986 |
| | mAb10955 |
| | mAb10954 |
| | mAb11002 |
| | mAb10985 |
| mAb10939 | mAb10977 |
| | mAb10924 |
| | mAb10989 |
| | mAb10920 |
| | mAb10913 |
| | mAb10923 |
| | mAb10930 |
| | mAb10969 |
| | mAb10988 |
| | mAb10964 |
| | mAb10996 |
| | mAb10966 |
| | mAb10998 |
| | mAb10984 |
| | mAb11006 |
| | mAb10921 |
| | mAb10971 |
| | mAb10938 |
| | mAb10932 |
| | mAb10970 |
| | mAb10957 |
| | mAb10956 |
| | mAb10941 |
| | mAb10935 |
| | mAb10914 |
| | mAb10982 |
| | mAb11008 |
| | mAb10915 |
| | mAb10965 |
| | mAb10967 |
| | mAb10986 |
| | mAb10955 |
| | mAb10954 |
| | mAb11002 |
| mAb10935 | mAb10977 |
| | mAb10924 |
| | mAb10989 |
| | mAb10920 |
| | mAb10913 |
| | mAb10923 |
| | mAb10930 |
| | mAb10969 |
| | mAb10988 |
| | mAb10964 |
| | mAb10996 |
| | mAb10966 |
| | mAb10998 |
| | mAb10984 |
| | mAb11006 |
| | mAb10921 |
| | mAb10971 |
| | mAb10938 |
| | mAb10932 |
| | mAb10970 |
| | mAb10957 |
| | mAb10956 |
| | mAb10941 |
| | mAb10939 |
| | mAb10914 |
| | mAb10982 |
| | mAb11008 |
| | mAb10915 |
| | mAb10965 |
| | mAb10967 |
| | mAb10986 |
| | mAb10955 |
| | mAb10954 |
| | mAb11002 |
| | mAb10985 |

TABLE 37-continued

Cross-competition between anti-SARS-CoV-2-S antibodies

| mAb-1 | mAb-2 Competing with mAb-1 |
|---|---|
| mAb10914 | mAb10977 |
| | mAb10924 |
| | mAb10989 |
| | mAb10920 |
| | mAb10913 |
| | mAb10923 |
| | mAb10930 |
| | mAb10969 |
| | mAb10988 |
| | mAb10964 |
| | mAb10996 |
| | mAb10966 |
| | mAb10998 |
| | mAb10984 |
| | mAb11006 |
| | mAb10921 |
| | mAb10971 |
| | mAb10938 |
| | mAb10932 |
| | mAb10970 |
| | mAb10957 |
| | mAb10956 |
| | mAb10941 |
| | mAb10939 |
| | mAb10935 |
| | mAb10982 |
| | mAb11008 |
| | mAb10915 |
| | mAb10965 |
| | mAb10967 |
| | mAb10986 |
| | mAb10955 |
| | mAb10954 |
| | mAb11002 |
| | mAb10933 |
| | mAb10985 |
| mAb10982 | mAb10977 |
| | mAb10924 |
| | mAb10989 |
| | mAb10920 |
| | mAb10913 |
| | mAb10923 |
| | mAb10930 |
| | mAb10969 |
| | mAb10988 |
| | mAb10964 |
| | mAb10996 |
| | mAb10966 |
| | mAb10998 |
| | mAb10984 |
| | mAb11006 |
| | mAb10921 |
| | mAb10971 |
| | mAb10938 |
| | mAb10932 |
| | mAb10970 |
| | mAb10957 |
| | mAb10956 |
| | mAb10941 |
| | mAb10939 |
| | mAb10935 |
| | mAb10914 |
| | mAb11008 |
| | mAb10915 |
| | mAb10965 |
| | mAb10967 |
| | mAb10986 |
| | mAb10955 |
| | mAb10954 |
| | mAb11002 |
| | mAb10985 |
| mAb11008 | mAb10977 |
| | mAb10924 |
| | mAb10989 |
| | mAb10920 |

TABLE 37-continued

Cross-competition between anti-SARS-CoV-2-S antibodies

| mAb-1 | mAb-2 Competing with mAb-1 |
|---|---|
| | mAb10913 |
| | mAb10923 |
| | mAb10930 |
| | mAb10969 |
| | mAb10988 |
| | mAb10964 |
| | mAb10996 |
| | mAb10966 |
| | mAb10998 |
| | mAb10984 |
| | mAb11006 |
| | mAb10921 |
| | mAb10971 |
| | mAb10938 |
| | mAb10932 |
| | mAb10970 |
| | mAb10957 |
| | mAb10956 |
| | mAb10941 |
| | mAb10939 |
| | mAb10935 |
| | mAb10914 |
| | mAb10982 |
| | mAb10915 |
| | mAb10965 |
| | mAb10967 |
| | mAb10986 |
| | mAb10955 |
| | mAb10954 |
| | mAb11002 |
| | mAb10933 |
| | mAb10985 |
| mAb10915 | mAb10924 |
| | mAb10989 |
| | mAb10920 |
| | mAb10913 |
| | mAb10923 |
| | mAb10930 |
| | mAb10969 |
| | mAb10988 |
| | mAb10964 |
| | mAb10996 |
| | mAb10966 |
| | mAb10998 |
| | mAb10984 |
| | mAb11006 |
| | mAb10921 |
| | mAb10971 |
| | mAb10938 |
| | mAb10932 |
| | mAb10970 |
| | mAb10957 |
| | mAb10956 |
| | mAb10941 |
| | mAb10939 |
| | mAb10935 |
| | mAb10914 |
| | mAb10982 |
| | mAb11008 |
| | mAb10965 |
| | mAb10967 |
| | mAb10986 |
| | mAb10955 |
| | mAb10954 |
| | mAb11002 |
| | mAb10985 |
| mAb10965 | mAb10924 |
| | mAb10989 |
| | mAb10920 |
| | mAb10913 |
| | mAb10923 |
| | mAb10930 |
| | mAb10969 |
| | mAb10988 |
| | mAb10964 |

TABLE 37-continued

Cross-competition between anti-SARS-CoV-2-S antibodies

| mAb-1 | mAb-2 Competing with mAb-1 |
|---|---|
| | mAb10996 |
| | mAb10966 |
| | mAb10998 |
| | mAb10984 |
| | mAb11006 |
| | mAb10921 |
| | mAb10971 |
| | mAb10938 |
| | mAb10932 |
| | mAb10970 |
| | mAb10957 |
| | mAb10956 |
| | mAb10941 |
| | mAb10939 |
| | mAb10935 |
| | mAb10914 |
| | mAb10982 |
| | mAb11008 |
| | mAb10915 |
| | mAb10967 |
| | mAb10986 |
| | mAb10955 |
| | mAb10954 |
| | mAb11002 |
| | mAb10985 |
| mAb10967 | mAb10924 |
| | mAb10989 |
| | mAb10920 |
| | mAb10913 |
| | mAb10923 |
| | mAb10930 |
| | mAb10969 |
| | mAb10988 |
| | mAb10964 |
| | mAb10996 |
| | mAb10966 |
| | mAb10998 |
| | mAb10984 |
| | mAb11006 |
| | mAb10921 |
| | mAb10971 |
| | mAb10938 |
| | mAb10932 |
| | mAb10970 |
| | mAb10957 |
| | mAb10956 |
| | mAb10941 |
| | mAb10939 |
| | mAb10935 |
| | mAb10914 |
| | mAb10982 |
| | mAb11008 |
| | mAb10915 |
| | mAb10965 |
| | mAb10986 |
| | mAb10955 |
| | mAb10954 |
| | mAb11002 |
| | mAb10985 |
| mAb10986 | mAb10924 |
| | mAb10989 |
| | mAb10920 |
| | mAb10913 |
| | mAb10923 |
| | mAb10930 |
| | mAb10969 |
| | mAb10988 |
| | mAb10964 |
| | mAb10996 |
| | mAb10966 |
| | mAb10998 |
| | mAb10984 |
| | mAb11006 |
| | mAb10921 |
| | mAb10971 |

TABLE 37-continued

Cross-competition between anti-SARS-CoV-2-S antibodies

| mAb-1 | mAb-2 Competing with mAb-1 |
|---|---|
| | mAb10938 |
| | mAb10932 |
| | mAb10970 |
| | mAb10957 |
| | mAb10956 |
| | mAb10941 |
| | mAb10939 |
| | mAb10935 |
| | mAb10914 |
| | mAb10982 |
| | mAb11008 |
| | mAb10915 |
| | mAb10965 |
| | mAb10967 |
| | mAb10955 |
| mAb10955 | mAb10954 |
| | mAb11002 |
| | mAb10985 |
| | mAb10924 |
| | mAb10989 |
| | mAb10920 |
| | mAb10913 |
| | mAb10923 |
| | mAb10930 |
| | mAb10969 |
| | mAb10988 |
| | mAb10964 |
| | mAb10996 |
| | mAb10966 |
| | mAb10998 |
| | mAb10984 |
| | mAb11006 |
| | mAb10921 |
| | mAb10971 |
| | mAb10938 |
| | mAb10932 |
| | mAb10970 |
| | mAb10957 |
| | mAb10956 |
| | mAb10941 |
| | mAb10939 |
| | mAb10935 |
| | mAb10914 |
| | mAb10982 |
| | mAb11008 |
| | mAb10915 |
| | mAb10965 |
| | mAb10967 |
| | mAb10986 |
| mAb10954 | mAb10954 |
| | mAb11002 |
| | mAb10985 |
| | mAb10924 |
| | mAb10989 |
| | mAb10920 |
| | mAb10913 |
| | mAb10923 |
| | mAb10930 |
| | mAb10969 |
| | mAb10988 |
| | mAb10964 |
| | mAb10996 |
| | mAb10966 |
| | mAb10998 |
| | mAb10984 |
| | mAb11006 |
| | mAb10921 |
| | mAb10971 |
| | mAb10938 |
| | mAb10932 |
| | mAb10970 |
| | mAb10957 |
| | mAb10956 |
| | mAb10941 |
| | mAb10939 |
| | mAb10935 |
| | mAb10914 |
| | mAb10982 |
| | mAb11008 |
| | mAb10915 |
| | mAb10965 |
| | mAb10967 |
| | mAb10986 |
| | mAb10955 |
| | mAb11002 |
| | mAb10985 |
| mAb11002 | mAb10977 |
| | mAb10920 |
| | mAb10913 |
| | mAb10923 |
| | mAb10930 |
| | mAb10969 |
| | mAb10964 |
| | mAb10996 |
| | mAb10966 |
| | mAb10998 |
| | mAb10984 |
| | mAb11006 |
| | mAb10921 |
| | mAb10971 |
| | mAb10938 |
| | mAb10932 |
| | mAb10970 |
| | mAb10957 |
| | mAb10956 |
| | mAb10941 |
| | mAb10939 |
| | mAb10935 |
| | mAb10914 |
| | mAb10982 |
| | mAb11008 |
| | mAb10915 |
| | mAb10965 |
| | mAb10967 |
| | mAb10986 |
| | mAb10955 |
| | mAb10954 |
| | mAb10933 |
| | mAb10985 |
| | mAb10936 |
| mAb10933 | mAb10977 |
| | mAb10924 |
| | mAb10989 |
| | mAb10920 |
| | mAb10913 |
| | mAb10923 |
| | mAb10930 |
| | mAb10969 |
| | mAb10988 |
| | mAb10964 |
| | mAb10996 |
| | mAb10966 |
| | mAb11006 |
| | mAb10914 |
| | mAb11008 |
| | mAb11002 |
| | mAb11000 |
| | mAb10937 |
| | mAb10936 |
| | mAb10934 |
| mAb11000 | mAb10924 |
| | mAb10933 |
| | mAb10985 |
| | mAb11010 |
| mAb10985 | mAb10924 |
| | mAb10969 |
| | mAb10996 |
| | mAb10966 |
| | mAb10998 |
| | mAb10984 |

TABLE 37-continued

| Cross-competition between anti-SARS-CoV-2-S antibodies | |
|---|---|
| mAb-1 | mAb-2 Competing with mAb-1 |
| | mAb11006 |
| | mAb10921 |
| | mAb10971 |
| | mAb10938 |
| | mAb10932 |
| | mAb10970 |
| | mAb10957 |
| | mAb10956 |
| | mAb10941 |
| | mAb10935 |
| | mAb10914 |
| | mAb10982 |
| | mAb11008 |
| | mAb10915 |
| | mAb10965 |
| | mAb10967 |
| | mAb10986 |
| | mAb10955 |
| | mAb10954 |
| | mAb11002 |
| | mAb11000 |
| | mAb11010 |
| mAb11010 | mAb11000 |
| | mAb10985 |
| mAb10987 | mAb10989 |
| | mAb10920 |
| | mAb10940 |
| | mAb10922 |
| | mAb11004 |
| | mAb10937 |
| | mAb10936 |
| | mAb10934 |
| mAb10940 | mAb10977 |
| | mAb10989 |
| | mAb10920 |
| | mAb10987 |
| | mAb10922 |
| | mAb11004 |
| | mAb10937 |
| | mAb10936 |
| | mAb10934 |
| mAb10922 | mAb10977 |
| | mAb10989 |
| | mAb10920 |
| | mAb10987 |
| | mAb10940 |
| | mAb11004 |
| | mAb10937 |
| | mAb10936 |
| | mAb10934 |
| mAb11004 | mAb10977 |
| | mAb10989 |
| | mAb10920 |
| | mAb10913 |
| | mAb10923 |
| | mAb10987 |
| | mAb10940 |
| | mAb10922 |
| | mAb10937 |
| | mAb10936 |
| | mAb10934 |
| mAb10937 | mAb10977 |
| | mAb10924 |
| | mAb10989 |
| | mAb10920 |
| | mAb10913 |
| | mAb10923 |
| | mAb10930 |
| | mAb10969 |
| | mAb10933 |
| | mAb10987 |
| | mAb10940 |
| | mAb10922 |
| | mAb11004 |
| | mAb10936 |
| | mAb10934 |
| mAb10936 | mAb10977 |
| | mAb10924 |
| | mAb10989 |
| | mAb10920 |
| | mAb10913 |
| | mAb10923 |
| | mAb10930 |
| | mAb10969 |
| | mAb10988 |
| | mAb10964 |
| | mAb10998 |
| | mAb10970 |
| | mAb11002 |
| | mAb10933 |
| | mAb10987 |
| | mAb10940 |
| | mAb10922 |
| | mAb11004 |
| | mAb10937 |
| | mAb10934 |
| mAb10934 | mAb10977 |
| | mAb10924 |
| | mAb10989 |
| | mAb10920 |
| | mAb10913 |
| | mAb10923 |
| | mAb10930 |
| | mAb10969 |
| | mAb10988 |
| | mAb10964 |
| | mAb10996 |
| | mAb10966 |
| | mAb10933 |
| | mAb10987 |
| | mAb10940 |
| | mAb10922 |
| | mAb11004 |
| | mAb10937 |
| | mAb10936 |

Example 18: pH Sensitivity of Anti-SARS-CoV-2-S Monoclonal Antibodies Binding to Monomeric SARS-CoV-2-S RBD Reagents Measured at 37° C.

The dissociation rate constants ($k_d$) for different anti-SARS-CoV-2-S monoclonal antibodies in pH 7.4, pH 6.0, and pH5.0 buffers were determined using a real-time surface plasmon resonance (SPR)-based Biacore T200 biosensor. All binding studies were performed at 37° C. using three running buffers, (i) PBS, 0.05% v/v Surfactant Tween-20, pH7.4 (PBS-T-pH7.4) (ii) PBS, 0.05% v/v Surfactant Tween-20, pH6.0 (PBS-T-pH6.0), and (iii) PBS, 0.05% v/v Surfactant Tween-20, pH5.0 (PBS-T-pH5.0). The Biacore CM5 sensor chip surface was first derivatized by amine coupling with a mouse anti-human Fc specific mAb (Regeneron) to capture anti-SARS-CoV-2-S monoclonal antibodies. Binding studies were performed on human SARS-COV-2-S RBD extracellular domain expressed with a C-terminal myc-myc-hexahistidine (SARS-COV-2 RBD-MMH), Single concentrations of SARS-COV-2-S RBD-MMH (90 nM) prepared in PBS-T-pH 7.4 buffer were injected at a flow rate of 250 μL/min for 3 minutes followed by the dissociation of bound SARS-COV-2-S RBD-MMH in PBS-T-pH 7.4, PBS-T-pH 6.0 or PBS-T PBS-T-pH 5.0 running buffers for 5 minutes.

The dissociation rate constants ($k_d$) in four pH running buffers were determined by fitting the real-time binding sensorgrams to a 1:1 binding model using Scrubber 2.0c curve-fitting software. The dissociative half-life (t½) was calculated from the $k_d$ values as:

$$t1/2\ (\text{min}) = \frac{\ln(2)}{60 * kd}$$

The $k_d$ and t½ values for SARS-COV-2-S RBD-MMH binding to different anti-SARS-CoV-2-S monoclonal antibodies in PBS-T-pH 7.4 followed by dissociation in PBS-T-pH 7.4 and PBS-T-pH 6.0 at 37° C. are shown in Table 38. The $k_d$ and t½ values for SARS-COV-2-S RBD-MMH binding to different anti-SARS-CoV-2-S monoclonal antibodies in PBS-T-pH 7.4 followed by dissociation in PBS-T-pH 7.4 and PBS-T-pH 5.0 at 37° C. are shown in Table 39. The comparison of the dissociative half-life (t½) of SARS-COV-2 RBD-MMH in pH 7.4, pH 6.0 and pH 5.0 buffers.

TABLE 38

Binding of SARS-COV-2-S RBD-MMH to anti-SARS-CoV-2-S monoclonal antibodies in PBS-T-pH 7.4 buffer and dissociation in PBS-T-pH 7.4 & pH 6.0 buffer at 37° C.

| | Running Buffer: PBS-T, pH 7.4 @ 37° C. | | | | Running Buffer: PBS-T, Chase in pH 6.0 @ 37° C. | | | | t½ |
|---|---|---|---|---|---|---|---|---|---|
| mAb Captured | mAb Capture Level (RU) | 90 nM RBD.mmh Bound (RU) | kd (1/s) | t½ (min) | mAb Capture Level (RU) | 90 nM RBD.mmh Bound (RU) | kd (1/s) | t½ (min) | Ratio pH 7.4/ pH 6.0 |
| mAb10913 | 427 | 69 | 4.30E-02 | 0.3 | 421 | 67 | 4.38E-02 | 0.3 | 1 |
| mAb10914 | 388 | 69 | 9.41E-03 | 1.2 | 386 | 62 | 1.16E-02 | 1 | 1.2 |
| mAb10915 | 319 | 84 | 7.43E-04 | 15.5 | 312 | 88 | 1.51E-03 | 7.7 | 2 |
| mAb10932 | 432 | 133 | 6.60E-04 | 17.5 | 438 | 131 | 1.28E-03 | 9 | 1.9 |
| mAb10933 | 360 | 124 | 7.85E-03 | 1.5 | 353 | 119 | 8.53E-03 | 1.4 | 1.1 |
| mAb10934 | 341 | 107 | 1.74E-02 | 0.7 | 334 | 108 | 2.11E-02 | 0.5 | 1.2 |
| mAb10935 | 407 | 76 | 2.78E-02 | 0.4 | 404 | 72 | 1.71E-02 | 0.7 | 0.6 |
| mAb10936 | 381 | 124 | 5.29E-03 | 2.2 | 375 | 120 | 8.69E-03 | 1.3 | 1.6 |
| mAb10937 | 330 | 94 | 2.09E-02 | 0.6 | 323 | 98 | 2.09E-02 | 0.6 | 1 |
| mAb10924 | 385 | 111 | 5.69E-03 | 2 | 379 | 110 | 1.20E-02 | 1 | 2.1 |
| mAb10938 | 407 | 95 | 1.05E-03 | 11 | 407 | 90 | 2.99E-03 | 3.9 | 2.8 |
| mAb10940 | 343 | 119 | 1.08E-02 | 1.1 | 339 | 127 | 1.04E-02 | 1.1 | 1 |
| mAb10941 | 398 | 129 | 1.65E-03 | 7 | 396 | 127 | 2.04E-03 | 5.7 | 1.2 |
| mAb10920 | 383 | 79 | 2.47E-02 | 0.5 | 380 | 73 | 5.39E-02 | 0.2 | 2.2 |
| mAb10921 | 345 | 89 | 1.79E-03 | 6.5 | 339 | 92 | 2.01E-02 | 0.6 | 11.3 |
| mAb10923 | 355 | 87 | 2.35E-02 | 0.5 | 349 | 88 | 2.43E-02 | 0.5 | 1 |
| mAb10939 | 410 | 90 | 9.48E-03 | 1.2 | 412 | 83 | 1.18E-02 | 1 | 1.2 |
| mAb10922 | 251 | 85 | 9.07E-03 | 1.3 | 240 | 92 | 9.61E-03 | 1.2 | 1.1 |
| mAb10930 | 377 | 50 | 1.92E-02 | 0.6 | 372 | 46 | 1.67E-02 | 0.7 | 0.9 |
| mAb10982 | 389 | 79 | 9.90E-03 | 1.2 | 387 | 74 | 7.72E-03 | 1.5 | 0.8 |
| mAb10984 | 378 | 133 | 1.71E-03 | 6.8 | 370 | 135 | 1.94E-03 | 5.9 | 1.1 |
| mAb10985 | 457 | 172 | 3.63E-03 | 3.2 | 464 | 172 | 3.19E-03 | 3.6 | 0.9 |
| mAb10986 | 413 | 155 | 6.29E-04 | 18.4 | 411 | 152 | 1.24E-03 | 9.3 | 2 |
| mAb10987 | 379 | 105 | 2.37E-02 | 0.5 | 372 | 109 | 1.83E-02 | 0.6 | 0.8 |
| mAb10988 | 467 | 109 | 4.35E-02 | 0.3 | 469 | 103 | 5.37E-02 | 0.2 | 1.2 |
| mAb10989 | 382 | 126 | 9.32E-03 | 1.2 | 375 | 119 | 7.36E-03 | 1.6 | 0.8 |
| mAb10970 | 340 | 93 | 7.65E-03 | 1.5 | 334 | 96 | 6.37E-03 | 1.8 | 0.8 |
| mAb10971 | 350 | 125 | 9.44E-04 | 12.2 | 342 | 125 | 1.27E-03 | 9.1 | 1.3 |
| mAb10964 | 380 | 140 | 1.94E-03 | 6 | 379 | 137 | 2.51E-03 | 4.6 | 1.3 |
| mAb10965 | 290 | 65 | 8.66E-03 | 1.3 | 281 | 70 | 9.47E-03 | 1.2 | 1.1 |
| mAb10966 | 417 | 152 | 1.60E-03 | 7.2 | 409 | 149 | 1.41E-03 | 8.2 | 0.9 |
| mAb10967 | 372 | 118 | 2.98E-04 | 38.8 | 367 | 115 | 3.45E-04 | 33.5 | 1.2 |
| mAb10954 | 336 | 118 | 1.74E-03 | 6.6 | 331 | 124 | 2.70E-03 | 4.3 | 1.6 |
| mAb10955 | 404 | 100 | 1.22E-02 | 0.9 | 403 | 97 | 1.46E-02 | 0.8 | 1.2 |
| mAb10956 | 452 | 114 | 1.25E-02 | 0.9 | 446 | 106 | 1.50E-02 | 0.8 | 1.2 |
| mAb10957 | 388 | 136 | 5.80E-04 | 19.9 | 382 | 140 | 7.67E-04 | 15.1 | 1.3 |
| mAb10977 | 293 | 44 | 1.59E-02 | 0.7 | 285 | 44 | 3.39E-02 | 0.3 | 2.1 |
| mAb10969 | 340 | 72 | 1.86E-02 | 0.6 | 336 | 71 | 1.01E-02 | 1.1 | 0.5 |
| mAb10996 | 408 | 35 | 4.69E-02 | 0.2 | 405 | 37 | 4.37E-02 | 0.3 | 0.9 |
| mAb10998 | 308 | 20 | 2.86E-02 | 0.4 | 307 | 19 | 2.84E-02 | 0.4 | 1 |
| mAb11002 | 373 | 10 | 2.60E-02 | 0.4 | 368 | 4 | 5.91E-03 | 2 | 0.2 |
| mAb11000 | 404 | 88 | 1.48E-03 | 7.8 | 403 | 90 | 2.85E-03 | 4.1 | 1.9 |
| mAb11004 | 356 | 97 | 1.47E-02 | 0.8 | 353 | 96 | 2.09E-02 | 0.6 | 1.4 |
| mAb11006 | 398 | 105 | 1.46E-03 | 7.9 | 398 | 98 | 1.98E-03 | 5.8 | 1.4 |
| mAb11008 | 341 | 112 | 1.33E-03 | 8.7 | 338 | 118 | 1.28E-03 | 9 | 1 |
| mAb11010 | 432 | 157 | 3.90E-03 | 3 | 431 | 156 | 7.51E-03 | 1.5 | 1.9 |
| Isotype Control | 430 | 4 | NB | NB | 427 | 9 | NB | NB | NB |

TABLE 39

Binding of SARS-COV-2-S RBD-MMH to anti-SARS-CoV-2 monoclonal antibodies in PBS-T-pH 7.4 buffer and the dissociation in PBS-T-pH 7.4 & pH 5.0 buffer at 37° C.

| | Running Buffer: PBS-T, pH 7.4 @ 37° C. | | | | Running Buffer: PBS-T, Chase in pH 5.0 @ 37° C. | | | | t½ |
|---|---|---|---|---|---|---|---|---|---|
| mAb Captured | mAb Capture Level (RU) | 90 nM RBD.mmh Bound (RU) | kd (1/s) | t½ (min) | mAb Capture Level (RU) | 90 nM RBD.mmh Bound (RU) | kd (1/s) | t½ (min) | Ratio pH 7.4/ pH 5.0 |
| mAb10913 | 427 | 69 | 4.30E−02 | 0.3 | 430 | 65 | 3.53E−02 | 0.3 | 0.8 |
| mAb10914 | 388 | 69 | 9.41E−03 | 1.2 | 391 | 57 | 1.00E−02 | 1.2 | 1.1 |
| mAb10915 | 319 | 84 | 7.43E−04 | 15.5 | 316 | 94 | 2.05E−03 | 5.6 | 2.8 |
| mAb10932 | 432 | 133 | 6.60E−04 | 17.5 | 452 | 131 | 2.11E−03 | 5.5 | 3.2 |
| mAb10933 | 360 | 124 | 7.85E−03 | 1.5 | 353 | 114 | 1.14E−02 | 1 | 1.5 |
| mAb10934 | 341 | 107 | 1.74E−02 | 0.7 | 338 | 109 | 1.71E−02 | 0.7 | 1 |
| mAb10935 | 407 | 76 | 2.78E−02 | 0.4 | 413 | 70 | 1.28E−02 | 0.9 | 0.5 |
| mAb10936 | 381 | 124 | 5.29E−03 | 2.2 | 379 | 116 | 1.60E−02 | 0.7 | 3 |
| mAb10937 | 330 | 94 | 2.09E−02 | 0.6 | 326 | 104 | 1.55E−02 | 0.7 | 0.7 |
| mAb10924 | 385 | 111 | 5.69E−03 | 2 | 390 | 113 | 1.48E−02 | 0.8 | 2.6 |
| mAb10938 | 407 | 95 | 1.05E−03 | 11 | 417 | 82 | 7.61E−03 | 1.5 | 7.2 |
| mAb10940 | 343 | 119 | 1.08E−02 | 1.1 | 341 | 135 | 8.23E−03 | 1.4 | 0.8 |
| mAb10941 | 398 | 129 | 1.65E−03 | 7 | 407 | 128 | 2.21E−03 | 5.2 | 1.3 |
| mAb10920 | 383 | 79 | 2.47E−02 | 0.5 | 382 | 68 | 2.93E−02 | 0.4 | 1.2 |
| mAb10921 | 345 | 89 | 1.79E−03 | 6.5 | 345 | 100 | 5.46E−02 | 0.2 | 30.6 |
| mAb10923 | 355 | 87 | 2.35E−02 | 0.5 | 357 | 90 | 2.13E−02 | 0.5 | 0.9 |
| mAb10939 | 410 | 90 | 9.48E−03 | 1.2 | 419 | 78 | 1.14E−02 | 1 | 1.2 |
| mAb10922 | 251 | 85 | 9.07E−03 | 1.3 | 240 | 102 | 8.08E−03 | 1.4 | 0.9 |
| mAb10930 | 377 | 50 | 1.92E−02 | 0.6 | 383 | 44 | 1.20E−02 | 1 | 0.6 |
| mAb10982 | 389 | 79 | 9.90E−03 | 1.2 | 391 | 66 | 6.27E−03 | 1.8 | 0.6 |
| mAb10984 | 378 | 133 | 1.71E−03 | 6.8 | 378 | 140 | 2.33E−03 | 5 | 1.4 |
| mAb10985 | 457 | 172 | 3.63E−03 | 3.2 | 471 | 170 | 3.36E−03 | 3.4 | 0.9 |
| mAb10986 | 413 | 155 | 6.29E−04 | 18.4 | 417 | 148 | 3.18E−03 | 3.6 | 5.1 |
| mAb10987 | 379 | 105 | 2.37E−02 | 0.5 | 377 | 115 | 8.80E−03 | 1.3 | 0.4 |
| mAb10988 | 467 | 109 | 4.35E−02 | 0.3 | 492 | 103 | 6.98E−02 | 0.2 | 1.6 |
| mAb10989 | 382 | 126 | 9.32E−03 | 1.2 | 379 | 105 | 6.13E−03 | 1.9 | 0.7 |
| mAb10970 | 340 | 93 | 7.65E−03 | 1.5 | 341 | 102 | 6.02E−03 | 1.9 | 0.8 |
| mAb10971 | 350 | 125 | 9.44E−04 | 12.2 | 352 | 129 | 1.70E−03 | 6.8 | 1.8 |
| mAb10964 | 380 | 140 | 1.94E−03 | 6 | 379 | 132 | 3.02E−03 | 3.8 | 1.6 |
| mAb10965 | 290 | 65 | 8.66E−03 | 1.3 | 284 | 77 | 7.40E−03 | 1.6 | 0.9 |
| mAb10966 | 417 | 152 | 1.60E−03 | 7.2 | 422 | 151 | 1.25E−03 | 9.2 | 0.8 |
| mAb10967 | 372 | 118 | 2.98E−04 | 38.8 | 377 | 114 | 4.05E−04 | 28.5 | 1.4 |
| mAb10954 | 336 | 118 | 1.74E−03 | 6.6 | 335 | 132 | 5.33E−03 | 2.2 | 3.1 |
| mAb10955 | 404 | 100 | 1.22E−02 | 0.9 | 416 | 96 | 1.85E−02 | 0.6 | 1.5 |
| mAb10956 | 452 | 114 | 1.25E−02 | 0.9 | 462 | 101 | 2.18E−02 | 0.5 | 1.7 |
| mAb10957 | 388 | 136 | 5.80E−04 | 19.9 | 390 | 146 | 7.93E−04 | 14.6 | 1.4 |
| mAb10977 | 293 | 44 | 1.59E−02 | 0.7 | 287 | 46 | 4.81E−02 | 0.2 | 3 |
| mAb10969 | 340 | 72 | 1.86E−02 | 0.6 | 344 | 69 | 1.33E−02 | 0.9 | 0.7 |
| mAb10996 | 408 | 35 | 4.69E−02 | 0.2 | 415 | 42 | 9.02E−02 | 0.1 | 1.9 |
| mAb10998 | 308 | 20 | 2.86E−02 | 0.4 | 311 | 21 | 2.32E−02 | 0.5 | 0.8 |
| mAb11002 | 373 | 10 | 2.60E−02 | 0.4 | 371 | 1 | 7.15E−04 | 16.2 | 0 |
| mAb11000 | 404 | 88 | 1.48E−03 | 7.8 | 411 | 96 | 2.46E−03 | 4.7 | 1.7 |
| mAb11004 | 356 | 97 | 1.47E−02 | 0.8 | 362 | 98 | 2.70E−02 | 0.4 | 1.8 |
| mAb11006 | 398 | 105 | 1.46E−03 | 7.9 | 411 | 93 | 2.10E−03 | 5.5 | 1.4 |
| mAb11008 | 341 | 112 | 1.33E−03 | 8.7 | 340 | 127 | 1.10E−03 | 10.5 | 0.8 |
| mAb11010 | 432 | 157 | 3.90E−03 | 3 | 440 | 156 | 7.15E−03 | 1.6 | 1.8 |
| Isotype Control | 430 | 4 | NB | NB | 435 | 15 | NB | NB | NB |

Example 19: Anti-SARS-CoV-2-S Antibodies Binding to Virus-Like Particles

To investigate the ability of a panel of anti-SARS-CoV-2 monoclonal antibodies to bind SARS-CoV-2 Spike glycoprotein, an in vitro binding assay utilizing vesicular stomatitis virus (VSV) pseudotyped with SARS-CoV-2 Spike protein in an electrochemiluminescence based detection platform (MSD) was developed.

Pseudotyped vesicular stomatitis virus (VSV) viral like particles (VLPs) were generated from HEK293T cells to transiently express the SARS-CoV-2 Spike Protein (Accession number MN908947.3, amino acids 16-1211). VLPs expressing VSV only were also generated as a negative binding control.

Experiments were carried out according to following procedure. VLPs from the two sources described above were diluted in PBS, seeded into the 96-well carbon electrode plates (MULTI-ARRAY high bind plate, MSD) and incubated overnight at 4° C. to allow the VLPs to adhere. Nonspecific binding sites were blocked by 2% BSA (w/v) in PBS for 1 hour at room temperature. To the plate-bound particles, anti-SARS-CoV-2 antibodies and a non-binding human IgG1 control, diluted in PBS+0.5% BSA at a range of concentrations from 0.0008 nM to 50 nM, and buffer with no antibody were added in duplicate and the plates incubated for 1 hour at room temperature with shaking. The plates were then washed with 1×PBS to remove the unbound antibodies using an AquaMax2000 plate washer (MDS Analytical Technologies). The plate-bound antibodies were detected with a SULFO-TAG™-conjugated anti-human IgG antibody (Jackson Immunoresearch) for 1 hour at room temperature. After washes, the plates were developed with the Read Buffer (MSD) according to manufacturer's recommended procedure and the luminescent signals were recorded with a SECTOR Imager 600 (Meso Scale Development) instrument. The direct binding signals (in RLU) were captured for SARS-CoV-2-expressing VLPs and VSV only VLPs.

The ability of the anti-SARS-CoV-2-S monoclonal antibodies to bind to SARS-CoV-2-S expressing VLPs compared with binding to irrelevant VSV expressing VLPs was assessed using an immunobinding assay. Binding to the immobilized VLPs on 96-well High Bind plates (MSD) was performed with a series of antibody dilutions and the bound antibodies were detected using SULFO-TAG™-conjugated anti-human IgG. The binding signals from electrochemiluminescence were recorded on a Sector Imager 600 (MSD). RLU values were determined for the antibody binding to VLPs. All antibodies displayed a concentration-dependent binding and the ratios of binding on the SARS-COV-2-S expressing VLPs to VSV only were analyzed at 5.5 nM and 0.20 nM.

The binding results of anti-SARS-CoV-2-S mAbs at the two concentrations to VSV/spike and VSV-only VLPs are summarized in Table 40. Of 46 antibodies tested, 44 antibodies bound specifically to VSV/spike with a ratio to VSV of 3 or higher at either concentration. At 0.2 nM antibody, the ratio of VSV/spike to VSV ranged from 3 to 56, and at 5 nM the ratio ranged from 3 to 303. Although two antibodies (mAb10998 and mAb11002) displayed weak binding to the VSV/Spike VLPs, with ratios of less than 3 to the VSV VLPs, the signals at 5 nM were higher on the VSV/spike than the VSV. An irrelevant IgG1 isotype antibody showed minimal binding, as expected.

TABLE 40

Specificity of anti-SARS-COV-2-S antibodies binding to spike protein-expressing VSV VLPs vs VSV by Electrochemiluminescence

| | Antibody Concentration | | | | | | |
|---|---|---|---|---|---|---|---|
| | Antibody Binding Signal (RLU) | | | | Ratio | | |
| | 5.5 nM | | 0.20 nM | | 5.5 nM | 0.20 nM | |
| mAb# | VSV/ Spike | VSV | VSV/ Spike | VSV | VSV/ Spike:VSV | VSV/ Spike:VSV | Expt# |
| mAb10913 | 1140 | 302 | 434 | 51 | 4 | 9 | 1 |
| mAb10914 | 6139 | 1823 | 911 | 85 | 3 | 11 | 1 |
| mAb10915 | 16763 | 702 | 2868 | 77 | 24 | 37 | 1 |
| mAb10920 | 7757 | 2536 | 1332 | 102 | 3 | 13 | 3 |
| mAb10921 | 8174 | 705 | 938 | 89 | 12 | 11 | 3 |
| mAb10922 | 1458 | 129 | 562 | 39 | 11 | 6 | 2 |
| mAb10923 | 1444 | 132 | 446 | 33 | 11 | 14 | 3 |
| mAb10924 | 1922 | 353 | 375 | 57 | 5 | 7 | 1 |
| mAb10930 | 1488 | 291 | 429 | 38 | 5 | 4 | 2 |
| mAb10932 | 11774 | 105 | 1282 | 35 | 113 | 37 | 1 |
| mAb10933 | 631 | 82 | 446 | 29 | 8 | 16 | 1 |
| mAb10934 | 1099 | 124 | 648 | 29 | 9 | 22 | 1 |
| mAb10935 | 2526 | 387 | 611 | 47 | 7 | 13 | 1 |
| mAb10936 | 5087 | 228 | 1702 | 41 | 22 | 42 | 1 |
| mAb10937 | 1056 | 204 | 374 | 43 | 5 | 9 | 1 |
| mAb10938 | 11418 | 395 | 1223 | 37 | 29 | 33 | 1 |
| mAb10939 | 4656 | 637 | 948 | 99 | 7 | 10 | 3 |
| mAb10940 | 947 | 58 | 384 | 34 | 16 | 11 | 1 |
| mAb10941 | 7297 | 69 | 958 | 17 | 106 | 56 | 1 |
| mAb10954 | 9727 | 205 | 2114 | 48 | 47 | 8 | 2 |
| mAb10955 | 2189 | 270 | 397 | 55 | 8 | 6 | 2 |
| mAb10956 | 1006 | 373 | 263 | 71 | 3 | 6 | 2 |
| mAb10957 | 10624 | 127 | 1606 | 68 | 84 | 11 | 2 |
| mAb10964 | 14252 | 47 | 9486 | 26 | 303 | 24 | 2 |
| mAb10965 | 1039 | 87 | 279 | 58 | 12 | 14 | 2 |
| mAb10966 | 9176 | 97 | 1406 | 88 | 95 | 15 | 2 |
| mAb10967 | 10744 | 122 | 1090 | 32 | 88 | 8 | 2 |
| mAb10969 | 1163 | 334 | 262 | 42 | 3 | 6 | 3 |
| mAb10970 | 5640 | 76 | 1061 | 50 | 74 | 13 | 2 |
| mAb10971 | 7995 | 60 | 1372 | 27 | 134 | 20 | 2 |
| mAb10977 | 26895 | 4283 | 9330 | 165 | 6 | 2 | 2 |
| mAb10982 | 1875 | 220 | 427 | 36 | 9 | 6 | 2 |
| mAb10984 | 9142 | 195 | 2270 | 33 | 47 | 9 | 2 |
| mAb10985 | 1497 | 90 | 529 | 65 | 17 | 8 | 2 |
| mAb10986 | 11155 | 177 | 2315 | 65 | 63 | 11 | 2 |
| mAb10987 | 1146 | 168 | 699 | 53 | 7 | 8 | 2 |
| mAb10988 | 967 | 163 | 438 | 39 | 6 | 4 | 2 |
| mAb10989 | 2195 | 128 | 1533 | 66 | 17 | 13 | 2 |

TABLE 40-continued

Specificity of anti-SARS-COV-2-S antibodies binding to spike protein-expressing VSV VLPs vs VSV by Electrochemiluminescence

| | Antibody Concentration | | | | | | |
|---|---|---|---|---|---|---|---|
| | Antibody Binding Signal (RLU) | | | | Ratio | | |
| | 5.5 nM | | 0.20 nM | | 5.5 nM | 0.20 nM | |
| mAb# | VSV/ Spike | VSV | VSV/ Spike | VSV | VSV/ Spike:VSV | VSV/ Spike:VSV | Expt# |
| mAb10996 | 812 | 309 | 82 | 65 | 3 | 1 | 3 |
| mAb10998 | 2253 | 1590 | 122 | 104 | 1 | 1 | 3 |
| mAb11000 | 580 | 139 | 94 | 47 | 4 | 2 | 3 |
| mAb11002 | 419 | 283 | 47 | 50 | 1 | 1 | 3 |
| mAb11004 | 1061 | 56 | 386 | 28 | 19 | 14 | 3 |
| mAb11006 | 26528 | 6299 | 7159 | 247 | 4 | 29 | 3 |
| mAb11008 | 508 | 48 | 80 | 28 | 11 | 3 | 3 |
| mAb11010 | 349 | 64 | 96 | 30 | 5 | 3 | 3 |
| IgG1 Isotype Control | 113 | 84 | 32 | 21 | 1 | 2 | 1 |
| IgG1 Isotype Control | 167 | 127 | 75 | 35 | 1 | 2 | 3 |
| IgG1 Isotype Control | 94 | 99 | 99 | 31 | 1 | 1 | 2 |

Example 20: Anti-SARS-CoV-2-S Antibodies Binding to Spike Protein-Expressing Cells To investigate the ability of a panel of anti-SARS-CoV-2-S monoclonal antibodies to bind to SARS-CoV-2-S expressing cells, an in vitro binding assay utilizing SARS-CoV-2-S expressing cells in an electrochemiluminescence based detection platform (MSD) was developed.

Jurkat/Tet3G/hCD20/Tet-3G inducible cells were engineered to transiently express the SARS-CoV-2 Spike Protein (Accession number MN908947.3, amino acids 16-1211, Jurkat/Tet3G/hCD20/Tet-On 3G Inducible COVID-19 Spike Protein High Sorted), and flow cytometry sorted for selection of high expression of the SARS-CoV-2 protein. Parental Jurkat/Tet3G/hCD20/Tet-3G were also included in the experiments as a negative binding control.

Experiments were carried out according to following procedure. Cells from the two lines described above were induced with 1 μg/ml doxycycline at 37° C. for 36 hours prior to harvest, spun down, washed with PBS, then diluted in PBS, seeded into the 96-well carbon electrode plates (MULTI-ARRAY high bind plate, MSD), and incubated overnight at 4° C. to allow the cells to adhere. Nonspecific binding sites were blocked by 2% BSA (w/v) in PBS for one hour at room temperature. To the plate-bound cells, anti-SARS-CoV-2 antibodies and a non-binding human IgG1 control, diluted in PBS+0.5% BSA at a range of concentrations from 0.0008 nM to 50 nM, and buffer with no antibody were added in duplicate and the plates incubated for one hour at room temperature with shaking. The plates were then washed with 1×PBS to remove the unbound antibodies using an AquaMax2000 plate washer (MDS Analytical Technologies). The plate-bound antibodies were detected with a SULFO-TAG™-conjugated anti-human IgG antibody (Jackson Immunoresearch) for one hour at room temperature. After washes, the plates were developed with the Read Buffer (MSD) according to manufacturer's recommended procedure and the luminescent signals were recorded with a SECTOR Imager 600 (Meso Scale Development) instrument. The direct binding signals (in RLU) were captured for SARS-CoV-2-S expressing cells and a negative control cell line.

The ability of the anti-SARS-CoV-2 monoclonal antibodies to bind to SARS-CoV-2 Spike Protein expressing cells compared with binding to parental cells was assessed using an immunobinding assay. Binding to the immobilized cells on 96-well high bind plates (MSD) was performed with a series of antibody dilutions and the bound antibodies were detected using SULFO-TAG™-conjugated anti-human IgG. The binding signals from electrochemiluminescence were recorded on a Sector Imager 600 (MSD). All antibodies displayed a concentration-dependent binding and the ratio of the binding on spike expressing cells to the parental cells were analyzed at the concentration of 5.5 nM and 0.20 nM.

The binding results of the anti-SARS-COV-2-S mAbs at the two concentrations to Spike protein expressing and parental Jurkat cells are summarized in Table 41. Of the 46 antibodies tested, 44 antibodies bound specifically to Jurkat/spike cells (Jurkat/Tet3G/hCD20/Tet-On 3G Inducible SARS-CoV-2 Spike Protein High Sorted cells) with a ratio to the parental cells of 4 or higher at either concentration. At 0.2 nM, the ratios of the binding signals on Jurkat/spike cells to the parental cells ranged from 4 to 36, and at 5 nM the ratio ranged from 4 to 63. Although the two antibodies (mAb10998 and mAb11002) displayed weak binding to Jurkat/spike cells with binding ratio to the parental cells less than 4, at 5 nM the binding signals were higher on Jurket/spike than on the parental cells. An irrelevant IgG1 isotype antibody showed minimal binding, as expected.

TABLE 41

Specificity of anti-SARS-CoV-2-S antibodies binding to spike protein-expressing Jurkat cells vs parental cells by electrochemiluminescence

| | Antibody Concentration | | | | | |
|---|---|---|---|---|---|---|
| | Antibody Binding Signal (RLU) | | | | Ratio | |
| | 5.5 nM | | 0.2 nM | | 5.5 nM | 0.2 nM |
| mAb# | Jurkat/ Spike | Parental | Jurkat/ Spike | Parental | Jurkat/ Spike:Parental | Jurkat/ Spike:Parental |
| mAb10913 | 907 | 174 | 576 | 36 | 5 | 16 |
| mAb10914 | 1624 | 569 | 262 | 64 | 3 | 4 |
| mAb10915 | 1814 | 217 | 269 | 42 | 8 | 6 |
| mAb10920 | 3501 | 597 | 1970 | 80 | 6 | 25 |
| mAb10921 | 3746 | 272 | 436 | 60 | 14 | 7 |
| mAb10922 | 399 | 63 | 225 | 22 | 6 | 10 |
| mAb10923 | 2561 | 103 | 1137 | 46 | 25 | 25 |
| mAb10924 | 1418 | 121 | 336 | 24 | 12 | 14 |
| mAb10930 | 673 | 151 | 175 | 25 | 4 | 7 |
| mAb10932 | 1525 | 65 | 206 | 29 | 23 | 7 |
| mAb10933 | 898 | 171 | 671 | 73 | 5 | 9 |
| mAb10934 | 762 | 146 | 697 | 46 | 5 | 15 |
| mAb10935 | 1572 | 209 | 513 | 28 | 8 | 19 |
| mAb10936 | 995 | 116 | 567 | 28 | 9 | 21 |
| mAb10937 | 867 | 95 | 388 | 30 | 9 | 13 |
| mAb10938 | 1678 | 165 | 195 | 30 | 10 | 7 |
| mAb10939 | 3195 | 292 | 901 | 119 | 11 | 8 |
| mAb10940 | 657 | 51 | 291 | 19 | 13 | 16 |
| mAb10941 | 1196 | 37 | 192 | 33 | 33 | 6 |
| mAb10954 | 929 | 110 | 327 | 46 | 8 | 7 |
| mAb10955 | 750 | 134 | 274 | 28 | 6 | 10 |
| mAb10956 | 801 | 136 | 214 | 42 | 6 | 5 |
| mAb10957 | 846 | 76 | 211 | 48 | 11 | 4 |
| mAb10964 | 896 | 37 | 724 | 20 | 24 | 36 |
| mAb10965 | 681 | 49 | 135 | 69 | 14 | 2 |
| mAb10966 | 969 | 65 | 245 | 53 | 15 | 5 |
| mAb10967 | 928 | 121 | 168 | 26 | 8 | 6 |
| mAb10969 | 2793 | 124 | 774 | 35 | 23 | 22 |
| mAb10970 | 743 | 59 | 246 | 57 | 13 | 4 |
| mAb10971 | 839 | 42 | 263 | 23 | 20 | 12 |
| mAb10977 | 2031 | 975 | 604 | 76 | 2 | 8 |
| mAb10982 | 737 | 117 | 211 | 25 | 6 | 8 |
| mAb10984 | 889 | 95 | 282 | 26 | 9 | 11 |
| mAb10985 | 527 | 63 | 179 | 65 | 8 | 3 |
| mAb10986 | 1050 | 92 | 341 | 33 | 11 | 10 |
| mAb10987 | 632 | 83 | 471 | 31 | 8 | 15 |
| mAb10988 | 367 | 83 | 272 | 41 | 4 | 7 |
| mAb10989 | 778 | 62 | 778 | 38 | 13 | 20 |
| mAb10996 | 1399 | 172 | 185 | 27 | 8 | 7 |
| mAb10998 | 1277 | 393 | 128 | 65 | 3 | 2 |
| mAb11000 | 1745 | 70 | 261 | 22 | 25 | 12 |
| mAb11002 | 241 | 160 | 30 | 36 | 2 | 1 |
| mAb11004 | 2031 | 48 | 748 | 34 | 43 | 22 |
| mAb11006 | 5052 | 1055 | 1044 | 70 | 5 | 15 |
| mAb11008 | 2382 | 38 | 237 | 50 | 63 | 5 |
| mAb11010 | 387 | 52 | 140 | 33 | 8 | 4 |
| IgG1 isotype control | 95 | 34 | 62 | 22 | 3 | 3 |
| IgG1 isotype control | 58 | 65 | 21 | 48 | 1 | 0 |
| IgG1 isotype control | 64 | 73 | 118 | 62 | 1 | 2 |

All references cited herein are incorporated by reference to the same extent as if each individual publication, database entry (e.g., Genbank sequences or GeneID entries), patent application, or patent, was specifically and individually indicated to be incorporated by reference. This statement of incorporation by reference is intended by Applicants to relate to each and every individual publication, database entry (e.g., Genbank sequences or GeneID entries), patent application, or patent identified even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

TABLE 42

| Sequences Excluded from ST.26-Formatted Sequence Listing | |
|---|---|
| Sequence No. | Sequence |
| 13 | gacaataat |
| 14 | DNN |
| 33 | aaggcgtct |
| 34 | KAS |
| 54 | gctgcatcc |
| 55 | AAS |
| 110 | tgggcatct |
| 111 | WAS |
| 148 | ggtgtatcc |
| 149 | GVS |
| 193 | gatgcatcc |
| 194 | DAS |
| 293 | ggtgcatcc |

TABLE 42-continued

| Sequences Excluded from ST.26-Formatted Sequence Listing | |
|---|---|
| Sequence No. | Sequence |
| 294 | GAS |
| 443 | gctgcctcc |
| 460 | aaggcatct |
| 583 | ggtaacagc |
| 584 | GNS |
| 631 | ggtaacacc |
| 632 | GNT |
| 649 | gatgtcagt |
| 650 | DVS |
| 669 | agtaataat |
| 670 | SNN |
| 819 | actgcatcc |
| 820 | TAS |

We claim:

1. An isolated antibody or antigen-binding fragment thereof that binds a SARS-COV-2 spike protein comprising the amino acid sequence set forth in SEQ ID NO: 832, wherein said isolated antibody or antigen-binding fragment comprises three heavy chain complementarity determining regions (CDRs) (HCDR1, HCDR2 and HCDR3) contained within a heavy chain variable region (HCVR) comprising the amino acid sequence set forth in SEQ ID NO: 640, and three light chain complementarity determining regions (CDRs) (LCDR1, LCDR2 and LCDR3) contained within a light chain variable region (LCVR) comprising the amino acid sequence set forth in SEQ ID NO: 646.

2. The isolated antibody or antigen-binding fragment thereof of claim 1, wherein HCDR1 comprises the amino acid sequence set forth in SEQ ID NO: 642, HCDR2 comprises the amino acid sequence set forth in SEQ ID NO: 499, HCDR3 comprises the amino acid sequence set forth in SEQ ID NO: 644, LCDR1 comprises the amino acid sequence set forth in SEQ ID NO: 648, LCDR2 comprises the amino acid sequence DVS, and LCDR3 comprises the amino acid sequence set forth in SEQ ID NO: 652.

3. The isolated antibody or antigen-binding fragment thereof of claim 2, comprising an HCVR that comprises the amino acid sequence set forth in SEQ ID NO: 640.

4. The isolated antibody or antigen-binding fragment thereof of claim 2, comprising an LCVR that comprises the amino acid sequence set forth in SEQ ID NO: 646.

5. The isolated antibody or antigen-binding fragment thereof of claim 2, comprising an HCVR that comprises the amino acid sequence set forth in SEQ ID NO: 640 and an LCVR that comprises the amino acid sequence set forth in SEQ ID NO: 646.

6. An isolated antibody that binds a SARS-COV-2 spike protein comprising the amino acid sequence set forth in SEQ ID NO: 832, wherein said isolated antibody comprises an immunoglobulin constant region, three heavy chain complementarity determining regions (CDRs) (HCDR1, HCDR2 and HCDR3) contained within a heavy chain variable region (HCVR) comprising the amino acid sequence set forth in SEQ ID NO: 640, and three light chain complementarity determining regions (CDRs) (LCDR1, LCDR2 and LCDR3) contained within a light chain variable region (LCVR) comprising the amino acid sequence set forth in SEQ ID NO: 646.

7. The isolated antibody of claim 6, wherein HCDR1 comprises the amino acid sequence set forth in SEQ ID NO: 642, HCDR2 comprises the amino acid sequence set forth in SEQ ID NO: 499, HCDR3 comprises the amino acid sequence set forth in SEQ ID NO: 644, LCDR1 comprises the amino acid sequence set forth in SEQ ID NO: 648, LCDR2 comprises the amino acid sequence DVS, and LCDR3 comprises the amino acid sequence set forth in SEQ ID NO: 652.

8. The isolated antibody of claim 6, comprising an HCVR that comprises the amino acid sequence set forth in SEQ ID NO: 640 and an LCVR that comprises the amino acid sequence set forth in SEQ ID NO: 646.

9. The isolated antibody of claim 6, wherein said isolated antibody comprises a heavy chain comprising the amino acid sequence set forth in SEQ ID NO: 654 and a light chain comprising the amino acid sequence set forth in SEQ ID NO: 656.

10. The isolated antibody of claim 6, wherein said immunoglobulin constant region is an IgG1 constant region.

11. The isolated antibody of claim 6 which is a recombinant antibody.

12. The isolated antibody of claim 6 which is multispecific.

13. A pharmaceutical composition comprising the isolated antibody of claim 6 and a pharmaceutically acceptable carrier or diluent.

14. The pharmaceutical composition of claim 13, further comprising a second therapeutic agent.

15. The pharmaceutical composition of claim 14, wherein the second therapeutic agent is selected from the group consisting of: an anti-inflammatory agent, and an antimalarial agent.

16. The pharmaceutical composition of claim 14, wherein the second therapeutic agent is a second antibody, or an antigen-binding fragment thereof, that binds a SARS-COV-2 spike protein comprising the amino acid sequence set forth in SEQ ID NO: 832, and wherein the second antibody or antigen-binding fragment thereof comprises three heavy chain CDRs (HCDR1, HCDR2 and HCDR3) contained within an HCVR, and three light chain CDRs (LCDR1, LCDR2 and LCDR3) contained within an LCVR, wherein the HCVR and the LCVR comprise, respectively, the amino acid sequences set forth in:

(a) SEQ ID NOs: 2 and 10;
(b) SEQ ID NOs: 22 and 30;
(c) SEQ ID NOs: 44 and 51;
(d) SEQ ID NOs: 65 and 73;
(e) SEQ ID NOs: 83 and 89;
(f) SEQ ID NOs: 99 and 107;
(g) SEQ ID NOs: 119 and 127;
(h) SEQ ID NOs: 137 and 145;
(i) SEQ ID NOs: 167 and 175;
(j) SEQ ID NOs: 185 and 191;
(k) SEQ ID NOs: 202 and 210;
(l) SEQ ID NOs: 220 and 228;
(m) SEQ ID NOs: 238 and 242;
(n) SEQ ID NOs: 252 and 260;
(o) SEQ ID NOs: 268 and 276;
(p) SEQ ID NOs: 284 and 290;
(q) SEQ ID NOs: 302 and 306;
(r) SEQ ID NOs: 316 and 323;
(s) SEQ ID NOs: 333 and 338;
(t) SEQ ID NOs: 366 and 372;
(u) SEQ ID NOs: 381 and 387;
(v) SEQ ID NOs: 396 and 401;
(w) SEQ ID NOs: 409 and 416;
(x) SEQ ID NOs: 432 and 440;
(y) SEQ ID NOs: 451 and 457;
(z) SEQ ID NOs: 468 and 472;
(aa) SEQ ID NOs: 480 and 487;
(bb) SEQ ID NOs: 495 and 503;
(cc) SEQ ID NOs: 510 and 514;
(dd) SEQ ID NOs: 524 and 530;
(ee) SEQ ID NOs: 548 and 556;
(ff) SEQ ID NOs: 574 and 580;
(gg) SEQ ID NOs: 594 and 600;
(hh) SEQ ID NOs: 608 and 614;
(ii) SEQ ID NOs: 624 and 630;
(jj) SEQ ID NOs: 658 and 666;
(kk) SEQ ID NOs: 678 and 686;
(ll) SEQ ID NOs: 708 and 713;
(mm) SEQ ID NOs: 723 and 727;
(nn) SEQ ID NOs: 737 and 741;
(oo) SEQ ID NOs: 753 and 713;
(pp) SEQ ID NOs: 764 and 770;
(qq) SEQ ID NOs: 780 and 786;
(rr) SEQ ID NOs: 796 and 800; or
(ss) SEQ ID NOs: 810 and 818.

* * * * *

SEQUENCE LISTING

```
Sequence total quantity: 850
SEQ ID NO: 1            moltype = DNA  length = 360
FEATURE                 Location/Qualifiers
misc_feature            1..360
                        note = Synthetic
source                  1..360
                        mol_type = other DNA
                        organism = synthetic construct
SEQUENCE: 1
gaggtgcagc tggtggagtc tgggggaggc ttggtacagc ctggagggtc cctgagactc  60
tcctgtgcag cctctggatt caccttcagg aattatgaaa tgaactgggt ccgccaggct  120
ccagggaagg ggctggagtg ggtttcatac attactagta gtggtagtac catgtactac  180
gcagactctg tgaagggccg attcaccatc tccagagaca acgccaagaa ctcactgtat  240
ctgcaaatga acagcctgag agccgaggac acggctgttt attactgtgc gagagacggc  300
ttttactact actacgctat ggacgtctgg ggccaaggga ccacggtcac cgtctcctca  360

SEQ ID NO: 2            moltype = AA  length = 120
FEATURE                 Location/Qualifiers
REGION                  1..120
                        note = Synthetic
source                  1..120
                        mol_type = protein
                        organism = synthetic construct
SEQUENCE: 2
EVQLVESGGG LVQPGGSLRL SCAASGFTFR NYEMNWVRQA PGKGLEWVSY ITSSGSTMYY  60
ADSVKGRFTI SRDNAKNSLY LQMNSLRAED TAVYYCARDG FYYYYAMDVW GQGTTVTVSS  120

SEQ ID NO: 3            moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 3
ggattcacct tcaggaatta tgaa                                          24

SEQ ID NO: 4            moltype = AA  length = 8
FEATURE                 Location/Qualifiers
REGION                  1..8
                        note = Synthetic
source                  1..8
```

-continued

```
                        mol_type = protein
                        organism = synthetic construct
SEQUENCE: 4
GFTFRNYE                                                        8

SEQ ID NO: 5            moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 5
attactagta gtggtagtac catg                                      24

SEQ ID NO: 6            moltype = AA  length = 8
FEATURE                 Location/Qualifiers
REGION                  1..8
                        note = Synthetic
source                  1..8
                        mol_type = protein
                        organism = synthetic construct
SEQUENCE: 6
ITSSGSTM                                                        8

SEQ ID NO: 7            moltype = DNA  length = 39
FEATURE                 Location/Qualifiers
misc_feature            1..39
                        note = Synthetic
source                  1..39
                        mol_type = other DNA
                        organism = synthetic construct
SEQUENCE: 7
gcgagagacg gcttttacta ctactacgct atggacgtc                      39

SEQ ID NO: 8            moltype = AA  length = 13
FEATURE                 Location/Qualifiers
REGION                  1..13
                        note = Synthetic
source                  1..13
                        mol_type = protein
                        organism = synthetic construct
SEQUENCE: 8
ARDGFYYYYA MDV                                                  13

SEQ ID NO: 9            moltype = DNA  length = 333
FEATURE                 Location/Qualifiers
misc_feature            1..333
                        note = Synthetic
source                  1..333
                        mol_type = other DNA
                        organism = synthetic construct
SEQUENCE: 9
cagtctgtgt tgacgcagcc gccctcagtg tctgcggccc caggacagaa ggtcaccatc  60
tcctgctctg gaagcagctc caacattggg aataattatg tatcctggta ccagcagctc  120
ccaggaacag cccccaaact cctcatttat gacaataata agcgaccctc agggattcct  180
gaccgattct ctggctccaa gtctggcacg tcagccaccc tgggcatcac cggactccag  240
actggggacg aggccgatta ttactgcgga acatgggata gcagcctgag tgttggccga  300
gtcttcggaa ctgggaccaa ggtcaccgtc cta                            333

SEQ ID NO: 10           moltype = AA  length = 111
FEATURE                 Location/Qualifiers
REGION                  1..111
                        note = Synthetic
source                  1..111
                        mol_type = protein
                        organism = synthetic construct
SEQUENCE: 10
QSVLTQPPSV SAAPGQKVTI SCSGSSSNIG NNYVSWYQQL PGTAPKLLIY DNNKRPSGIP  60
DRFSGSKSGT SATLGITGLQ TGDEADYYCG TWDSSLSVGR VFGTGTKVTV L           111

SEQ ID NO: 11           moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 11
```

```
agctccaaca ttgggaataa ttat                                  24

SEQ ID NO: 12          moltype = AA  length = 8
FEATURE                Location/Qualifiers
REGION                 1..8
                       note = Synthetic
source                 1..8
                       mol_type = protein
                       organism = synthetic construct
SEQUENCE: 12
SSNIGNNY                                                    8

SEQ ID NO: 13          moltype =   length =
SEQUENCE: 13
000

SEQ ID NO: 14          moltype =   length =
SEQUENCE: 14
000

SEQ ID NO: 15          moltype = DNA  length = 36
FEATURE                Location/Qualifiers
misc_feature           1..36
                       note = Synthetic
source                 1..36
                       mol_type = other DNA
                       organism = synthetic construct
SEQUENCE: 15
ggaacatggg atagcagcct gagtgttggc cgagtc                     36

SEQ ID NO: 16          moltype = AA  length = 12
FEATURE                Location/Qualifiers
REGION                 1..12
                       note = Synthetic
source                 1..12
                       mol_type = protein
                       organism = synthetic construct
SEQUENCE: 16
GTWDSSLSVG RV                                               12

SEQ ID NO: 17          moltype = DNA  length = 1353
FEATURE                Location/Qualifiers
misc_feature           1..1353
                       note = Synthetic
source                 1..1353
                       mol_type = other DNA
                       organism = synthetic construct
SEQUENCE: 17
gaggtgcagc tggtggagtc tgggggaggc ttggtacagc ctggagggtc cctgagactc  60
tcctgtgcag cctctggatt caccttcagg aattatgaaa tgaactgggt ccgccaggct  120
ccagggaagg ggctggagtg ggtttcatac attactagta gtggtagtac catgtactac  180
gcagactctg tgaagggccg attcaccatc tccagagaca acgccaagaa ctcactgtat  240
ctgcaaatga acagcctgag agccgaggac acggctgttt attactgtgc gagagacggc  300
ttttactact actacgctat ggacgtctgg ggccaaggga ccacggtcac cgtctcctca  360
gcctccacca agggcccatc ggtcttcccc ctggcaccct cctccaagag cacctctggg  420
ggcacagcgg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacccagacc  600
tacatctgca acgtgaatca caagcccagc aacaccaagg tggacaagaa agttgagccc  660
aaatcttgtg acaaaactca cacatgccca ccgtgcccag cacctgaact cctgggggga  720
ccgtcagtct tcctcttccc cccaaaaccc aaggacaccc tcatgatctc ccggacccct  780
gaggtcacat gcgtggtggt ggacgtgagc cacgaagacc ctgaggtcaa gttcaactgg  840
tacgtggacg gcgtggaggt gcataatgcc aagacaaagc cgcgggagga gcagtacaac  900
agcacgtacc gtgtggtcag cgtcctcacc gtcctgcacc aggactggct gaatggcaag  960
gagtacaagt gcaaggtctc caacaaagcc ctcccagccc ccatcgagaa aaccatctcc  1020
aaagccaaag ggcagccccg agaaccacag gtgtacaccc tgcccccatc ccgggatgag  1080
ctgaccaaga accaggtcag cctgacctgc ctggtcaaag gcttctatcc cagcgacatc  1140
gccgtggagt gggagagcaa tgggcagccg gagaacaact acaagaccac gcctcccgtg  1200
ctggactccg acggctcctt cttcctctac agcaagctca ccgtggacaa gagcaggtgg  1260
cagcagggga acgtcttctc atgctccgtg atgcatgagg ctctgcacaa ccactacacg  1320
cagaagtccc tctccctgtc tccgggtaaa tga                        1353

SEQ ID NO: 18          moltype = AA  length = 450
FEATURE                Location/Qualifiers
REGION                 1..450
                       note = Synthetic
source                 1..450
                       mol_type = protein
                       organism = synthetic construct
```

-continued

```
SEQUENCE: 18
EVQLVESGGG LVQPGGSLRL SCAASGFTFR NYEMNWVRQA PGKGLEWVSY ITSSGSTMYY  60
ADSVKGRFTI SRDNAKNSLY LQMNSLRAED TAVYYCARDG FYYYYAMDVW GQGTTVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 19          moltype = DNA  length = 654
FEATURE                Location/Qualifiers
misc_feature           1..654
                       note = Synthetic
source                 1..654
                       mol_type = other DNA
                       organism = synthetic construct
SEQUENCE: 19
cagtctgtgt tgacgcagcc gccctcagtg tctgcggccc caggacagaa ggtcaccatc  60
tcctgctctg gaagcagctc caacattggg aataattatg tatcctggta ccagcagctc  120
ccaggaacag cccccaaact cctcatttat gacaataata agcgaccctc agggattcct  180
gaccgattct ctggctccaa gtctggcacg tcagccaccc tgggcatcac cggactccag  240
actggggacg aggccgatta ttactgcgga acatgggata gcagcctgag tgttggccga  300
gtcttcggaa ctgggaccaa ggtcaccgtc ctaggccagc ccaaggccgc cccctccgtg  360
accctgttcc ccccctcctc cgaggagctg caggccaaca aggccaccct ggtgtgcctg  420
atctccgact tctaccccgg cgccgtgacc gtggcctgga aggccgactc ctcccccgtg  480
aaggccggcg tggagaccac cacccctcc aagcagtcca acaacaagta cgccgcctcc  540
tcctacctgt ccctgacccc cgagcagtgg aagtcccacc ggtcctactc ctgccaggtg  600
acccacgagg gctccaccgt ggagaagacc gtggccccca ccgagtgctc ctga        654

SEQ ID NO: 20          moltype = AA  length = 217
FEATURE                Location/Qualifiers
REGION                 1..217
                       note = Synthetic
source                 1..217
                       mol_type = protein
                       organism = synthetic construct
SEQUENCE: 20
QSVLTQPPSV SAAPGQKVTI SCSGSSSNIG NNYVSWYQQL PGTAPKLLIY DNNKRPSGIP  60
DRFSGSKSGT SATLGITGLQ TGDEADYYCG TWDSSLSVGR VFGTGTKVTV LGQPKAAPSV  120
TLFPPSSEEL QANKATLVCL ISDFYPGAVT VAWKADSSPV KAGVETTTPS KQSNNKYAAS  180
SYLSLTPEQW KSHRSYSCQV THEGSTVEKT VAPTECS                          217

SEQ ID NO: 21          moltype = DNA  length = 348
FEATURE                Location/Qualifiers
misc_feature           1..348
                       note = Synthetic
source                 1..348
                       mol_type = other DNA
                       organism = synthetic construct
SEQUENCE: 21
gaggtgcagc tggtggagtc tggaggaggc ttggtccagc ctgggggtc cctgagactc  60
tcctgtgcag cctctgggtt caccgtcagt agcaactaca tgaactgggt ccgccaggct  120
ccagggaagg ggctggagtg ggtctcagtt atttatagcg gtggcagcac attctacgca  180
gactccgtga agggccgatt caccatctcc agacacaatt ccaagaacac gctgtatctt  240
caaatgaaca gcctgagacc tgaggacacg gccgtgtatt actgtgcgag agatctgggg  300
ggatactttg actactgggg ccagggaacc ctggtcaccg tctcctca              348

SEQ ID NO: 22          moltype = AA  length = 116
FEATURE                Location/Qualifiers
REGION                 1..116
                       note = Synthetic
source                 1..116
                       mol_type = protein
                       organism = synthetic construct
SEQUENCE: 22
EVQLVESGGG LVQPGGSLRL SCAASGFTVS SNYMNWVRQA PGKGLEWVSV IYSGGSTFYA  60
DSVKGRFTIS RHNSKNTLYL QMNSLRPEDT AVYYCARDLG GYFDYWGQGT LVTVSS      116

SEQ ID NO: 23          moltype = DNA  length = 24
FEATURE                Location/Qualifiers
misc_feature           1..24
                       note = Synthetic
source                 1..24
                       mol_type = other DNA
                       organism = synthetic construct
SEQUENCE: 23
gggttcaccg tcagtagcaa ctac                                        24
```

-continued

```
SEQ ID NO: 24          moltype = AA  length = 8
FEATURE                Location/Qualifiers
REGION                 1..8
                       note = Synthetic
source                 1..8
                       mol_type = protein
                       organism = synthetic construct
SEQUENCE: 24
GFTVSSNY                                                          8

SEQ ID NO: 25          moltype = DNA  length = 21
FEATURE                Location/Qualifiers
misc_feature           1..21
                       note = Synthetic
source                 1..21
                       mol_type = other DNA
                       organism = synthetic construct
SEQUENCE: 25
atttatagcg gtggcagcac a                                           21

SEQ ID NO: 26          moltype = AA  length = 7
FEATURE                Location/Qualifiers
REGION                 1..7
                       note = Synthetic
source                 1..7
                       mol_type = protein
                       organism = synthetic construct
SEQUENCE: 26
IYSGGST                                                           7

SEQ ID NO: 27          moltype = DNA  length = 30
FEATURE                Location/Qualifiers
misc_feature           1..30
                       note = Synthetic
source                 1..30
                       mol_type = other DNA
                       organism = synthetic construct
SEQUENCE: 27
gcgagagatc tggggggata ctttgactac                                  30

SEQ ID NO: 28          moltype = AA  length = 10
FEATURE                Location/Qualifiers
REGION                 1..10
                       note = Synthetic
source                 1..10
                       mol_type = protein
                       organism = synthetic construct
SEQUENCE: 28
ARDLGGYFDY                                                        10

SEQ ID NO: 29          moltype = DNA  length = 318
FEATURE                Location/Qualifiers
misc_feature           1..318
                       note = Synthetic
source                 1..318
                       mol_type = other DNA
                       organism = synthetic construct
SEQUENCE: 29
gacatccaga tgacccagtc tccttccacc ctgtctgcat ctgtaggaga cagagtcacc  60
atcacttgcc gggccagtca gagttttagt agctggttgg cctggtatca gcagaaacca  120
gggaaagccc ctaagctcct gatctataag gcgtctagtt tagagagtgg ggtcccatca  180
aggttcagcg gcagtggatc tgggacagaa ttcactctca ccatcagcag cctgcagcct  240
gatgattttg caacttatta ctgccaacag tataatagtt attacacttt tggccagggg  300
accaagctgg agatcaaa                                               318

SEQ ID NO: 30          moltype = AA  length = 106
FEATURE                Location/Qualifiers
REGION                 1..106
                       note = Synthetic
source                 1..106
                       mol_type = protein
                       organism = synthetic construct
SEQUENCE: 30
DIQMTQSPST LSASVGDRVT ITCRASQSFS SWLAWYQQKP GKAPKLLIYK ASSLESGVPS  60
RFSGSGSGTE FTLTISSLQP DDFATYYCQQ YNSYYTFGQG TKLEIK                106

SEQ ID NO: 31          moltype = DNA  length = 18
FEATURE                Location/Qualifiers
misc_feature           1..18
```

```
                            note = Synthetic
source                      1..18
                            mol_type = other DNA
                            organism = synthetic construct
SEQUENCE: 31
cagagtttta gtagctgg                                                  18

SEQ ID NO: 32               moltype = AA   length = 6
FEATURE                     Location/Qualifiers
REGION                      1..6
                            note = Synthetic
source                      1..6
                            mol_type = protein
                            organism = synthetic construct
SEQUENCE: 32
QSFSSW                                                                6

SEQ ID NO: 33               moltype =    length =
SEQUENCE: 33
000

SEQ ID NO: 34               moltype =    length =
SEQUENCE: 34
000

SEQ ID NO: 35               moltype = DNA   length = 24
FEATURE                     Location/Qualifiers
misc_feature                1..24
                            note = Synthetic
source                      1..24
                            mol_type = other DNA
                            organism = synthetic construct
SEQUENCE: 35
caacagtata atagttatta cact                                           24

SEQ ID NO: 36               moltype = AA   length = 8
FEATURE                     Location/Qualifiers
REGION                      1..8
                            note = Synthetic
source                      1..8
                            mol_type = protein
                            organism = synthetic construct
SEQUENCE: 36
QQYNSYYT                                                              8

SEQ ID NO: 37               moltype = DNA   length = 1341
FEATURE                     Location/Qualifiers
misc_feature                1..1341
                            note = Synthetic
source                      1..1341
                            mol_type = other DNA
                            organism = synthetic construct
SEQUENCE: 37
gaggtgcagc tggtggagtc tggaggaggc ttggtccagc ctggggggtc cctgagactc    60
tcctgtgcag cctctgggtt caccgtcagt agcaactaca tgaactgggt ccgccaggct   120
ccagggaagg ggctggagtg ggtctcagtt atttatagcg gtggcagcac attctacgca   180
gactccgtga agggccgatt caccatctcc agacacaatt ccaagaacac gctgtatctt   240
caaatgaaca gcctgagacc tgaggacacg gccgtgtatt actgtgcgag agatctgggg   300
ggatactttg actactgggg ccagggaacc ctggtcaccg tctcctcagc ctccaccaag   360
ggcccatcgg tcttccccct ggcaccctcc tccaagagca cctctggggg cacagcggcc   420
ctgggctgcc tggtcaagga ctacttcccc gaaccggtga cggtgtcgtg gaactcaggc   480
gccctgacca gcggcgtgca caccttcccg gctgtcctac agtcctcagg actctactcc   540
ctcagcagcg tggtgaccgt gccctccagc agcttgggca cccagaccta catctgcaac   600
gtgaatcaca agcccagcaa caccaaggtg gacaagaaag ttgagcccaa atcttgtgac   660
aaaactcaca catgcccacc gtgcccagca cctgaactcc tggggggacc gtcagtcttc   720
ctcttccccc caaaacccaa ggacaccctc atgatctccc ggacccctga ggtcacatgc   780
gtggtggtgg acgtgagcca cgaagaccct gaggtcaagt tcaactggta cgtggacggc   840
gtggaggtgc ataatgccaa gacaaagccg cgggaggagc agtacaacag cacgtaccgt   900
gtggtcagcg tcctcaccgt cctgcaccag gactggctga atggcaagga gtacaagtgc   960
aaggtctcca acaaagccct cccagccccc atcgagaaaa ccatctccaa agccaaaggg  1020
cagccccgag aaccacaggt gtacaccctg cccccatccc gggatgagct gaccaagaac  1080
caggtcagcc tgacctgcct ggtcaaaggc ttctatccca gcgacatcgc cgtggagtgg  1140
gagagcaatg ggcagccgga gaacaactac aagaccacgc tcccgtgctg gactccgac   1200
ggctccttct tcctctacag caagctcacc gtggacaaga gcaggtggca gcaggggaac  1260
gtcttctcat gctccgtgat gcatgaggct ctgcacaacc actacacgca gaagtccctc  1320
tccctgtctc cgggtaaatg a                                            1341

SEQ ID NO: 38               moltype = AA   length = 446
FEATURE                     Location/Qualifiers
```

-continued

```
REGION                  1..446
                        note = Synthetic
source                  1..446
                        mol_type = protein
                        organism = synthetic construct
SEQUENCE: 38
EVQLVESGGG LVQPGGSLRL SCAASGFTVS SNYMNWVRQA PGKGLEWVSV IYSGGSTFYA  60
DSVKGRFTIS RHNSKNTLYL QMNSLRPEDT AVYYCARDLG GYFDYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSRDELTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGK                                     446

SEQ ID NO: 39           moltype = DNA  length = 642
FEATURE                 Location/Qualifiers
misc_feature            1..642
                        note = Synthetic
source                  1..642
                        mol_type = other DNA
                        organism = synthetic construct
SEQUENCE: 39
gacatccaga tgacccagtc tccttccacc ctgtctgcat ctgtaggaga cagagtcacc  60
atcacttgcc gggccagtca gagttttagt agctggttgg cctggtatca gcagaaacca  120
gggaaagccc ctaagctcct gatctataag gcgtctagtt tagagagtgg ggtcccatca  180
aggttcagcg gcagtggatc tgggacagaa ttcactctca ccatcagcag cctgcagcct  240
gatgattttg caacttatta ctgccaacag tataatagtt attacacttt tggccagggg  300
accaagctgg agatcaaacg aactgtggct gcaccatctg tcttcatctt cccgccatct  360
gatgagcagt tgaaatctgg aactgcctct gttgtgtgcc tgctgaataa cttctatccc  420
agagaggcca aagtacagtg gaaggtggat aacgccctcc aatcgggtaa ctcccaggag  480
agtgtcacag agcaggacag caaggacagc acctacagcc tcagcagcac cctgacgctg  540
agcaaagcag actacgagaa acacaaagtc tacgcctgcg aagtcaccca tcagggcctg  600
agctcgcccg tcacaaagag cttcaacagg ggagagtgtt ag                   642

SEQ ID NO: 40           moltype = AA  length = 213
FEATURE                 Location/Qualifiers
REGION                  1..213
                        note = Synthetic
source                  1..213
                        mol_type = protein
                        organism = synthetic construct
SEQUENCE: 40
DIQMTQSPST LSASVGDRVT ITCRASQSFS SWLAWYQQKP GKAPKLLIYK ASSLESGVPS  60
RFSGSGSGTE FTLTISSLQP DDFATYYCQQ YNSYYTFGQG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                              213

SEQ ID NO: 41           moltype = DNA  length = 1341
FEATURE                 Location/Qualifiers
misc_feature            1..1341
                        note = Synthetic
source                  1..1341
                        mol_type = other DNA
                        organism = synthetic construct
SEQUENCE: 41
gaggtgcagc tggtggagtc tgggggaggc ttggtacagc ctggagggtc cctgagactc  60
tcctgtgcag cctctggatt caccttcagg aattatgaaa tgaactgggt ccgccaggct  120
ccagggaagg ggctggagtg ggtttcatac attactagta gtggtagtac catgtactac  180
gcagactctg tgaagggccg attcaccatc tccagagaca acgccaagaa ctcactgtat  240
ctgcaaatga acagcctgag agccgaggac acggctgttt attactgtgc gagagacggc  300
ttttactact actacgctat ggacgtctgg ggccaaggga ccacggtcac cgtctcctca  360
gcctccacca agggcccatc ggtcttcccc ctggcgccct gctccaggag cacctccgag  420
agcacagccg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacgaagacc  600
tacacctgca acgtagatca caagcccagc aacaccaagg tggacaagag agttgagtcc  660
aaatatggtc ccccatgccc accgtgccca gcaccaggcg gtggcggacc atcagtcttc  720
ctgttccccc caaaacccaa ggacactctc atgatctccc ggacccctga ggtcacgtgc  780
gtggtggtgg acgtgagcca ggaagacccc gaggtccagt tcaactggta cgtggatggc  840
gtggaggtgc ataatgccaa gacaaagccg cgggaggagc agttcaacag cacgtaccgt  900
gtggtcagcg tcctcaccgt cctgcaccag gactggctga acggcaagga gtacaagtgc  960
aaggtctcca acaaaggcct cccgtcctcc atcgagaaaa ccatctccaa agccaaaggg  1020
cagccccgag agccacaggt gtacaccctg cccccatccc aggaggagat gaccaagaac  1080
caggtcagcc tgacctgcct ggtcaaaggc ttctacccca gcgacatcgc cgtggagtgg  1140
gagagcaatg ggcagccgga gaacaactac aagaccacgc ctcccgtgct ggactccgac  1200
ggctccttct tcctctacag caggctcacc gtggacaaga gcaggtggca ggaggggaat  1260
gtcttctcat gctccgtgat gcatgaggct ctgcacaacc actacacaca gaagtccctc  1320
tccctgtctc tgggtaaatg a                                          1341
```

```
SEQ ID NO: 42          moltype = AA  length = 446
FEATURE                Location/Qualifiers
REGION                 1..446
                       note = Synthetic
source                 1..446
                       mol_type = protein
                       organism = synthetic construct
SEQUENCE: 42
EVQLVESGGG LVQPGGSLRL SCAASGFTFR NYEMNWVRQA PGKGLEWVSY ITSSGSTMYY  60
ADSVKGRFTI SRDNAKNSLY LQMNSLRAED TAVYYCARDG FYYYYAMDVW GQGTTVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APGGGGPSVF  240
LFPPKPKDTL MISRTPEVTC VVVDVSQEDP EVQFNWYVDG VEVHNAKTKP REEQFNSTYR  300
VVSVLTVLHQ DWLNGKEYKC KVSNKGLPSS IEKTISKAKG QPREPQVYTL PPSQEEMTKN  360
QVSLTCLVKG FYPSDIAVEW ESNGQPENNY KTTPPVLDSD GSFFLYSRLT VDKSRWQEGN  420
VFSCSVMHEA LHNHYTQKSL SLSLGK                                      446

SEQ ID NO: 43          moltype = DNA  length = 351
FEATURE                Location/Qualifiers
misc_feature           1..351
                       note = Synthetic
source                 1..351
                       mol_type = other DNA
                       organism = synthetic construct
SEQUENCE: 43
gaggtgcagc tggtggagtc tggaggaggc ttggtccagc ctggggggtc cctgagactc  60
tcctgtgcag cctctgggtt aatagtcagt cgcaactaca tgatctgggt ccgccaggct  120
ccagggaagg ggctggagtg ggtctcagtt atttatagcg gtggtagcac attctacgca  180
gactccgtga agggccgatt caccatctcc agacacaatt ccaagaacac gctgtatctt  240
caaatgaaca gcctgagagc tgaggacacg gccgtatatt actgtgcgag agatctgggt  300
acaggaggta tggacgtctg gggccaaggg accacggtca ccgtctcctc a            351

SEQ ID NO: 44          moltype = AA  length = 117
FEATURE                Location/Qualifiers
REGION                 1..117
                       note = Synthetic
source                 1..117
                       mol_type = protein
                       organism = synthetic construct
SEQUENCE: 44
EVQLVESGGG LVQPGGSLRL SCAASGLIVS RNYMIWVRQA PGKGLEWVSV IYSGGSTFYA  60
DSVKGRFTIS RHNSKNTLYL QMNSLRAEDT AVYYCARDLG TGGMDVWGQG TTVTVSS     117

SEQ ID NO: 45          moltype = DNA  length = 24
FEATURE                Location/Qualifiers
misc_feature           1..24
                       note = Synthetic
source                 1..24
                       mol_type = other DNA
                       organism = synthetic construct
SEQUENCE: 45
gggttaatag tcagtcgcaa ctac                                        24

SEQ ID NO: 46          moltype = AA  length = 8
FEATURE                Location/Qualifiers
REGION                 1..8
                       note = Synthetic
source                 1..8
                       mol_type = protein
                       organism = synthetic construct
SEQUENCE: 46
GLIVSRNY                                                          8

SEQ ID NO: 47          moltype = DNA  length = 21
FEATURE                Location/Qualifiers
misc_feature           1..21
                       note = Synthetic
source                 1..21
                       mol_type = other DNA
                       organism = synthetic construct
SEQUENCE: 47
atttatagcg gtggtagcac a                                           21

SEQ ID NO: 48          moltype = DNA  length = 33
FEATURE                Location/Qualifiers
misc_feature           1..33
                       note = Synthetic
source                 1..33
```

-continued

```
                         mol_type = other DNA
                         organism = synthetic construct
SEQUENCE: 48
gcgagagatc tgggtacagg aggtatggac gtc                              33

SEQ ID NO: 49            moltype = AA  length = 11
FEATURE                  Location/Qualifiers
REGION                   1..11
                         note = Synthetic
source                   1..11
                         mol_type = protein
                         organism = synthetic construct
SEQUENCE: 49
ARDLGTGGMD V                                                      11

SEQ ID NO: 50            moltype = DNA  length = 321
FEATURE                  Location/Qualifiers
misc_feature             1..321
                         note = Synthetic
source                   1..321
                         mol_type = other DNA
                         organism = synthetic construct
SEQUENCE: 50
gacatccagt tgacccagtc tccatccttc ctgtctgcat ctgtaggaga cagagtcacc  60
atcacttgct gggccagtca gggcattagc agttatttag cctggtatca gcaaaaacca  120
gggaaagccc ctaagctcct gatctatgct gcatccactt tgcaaagtgg ggtcccatca  180
aggttcagcg gcagtggatc tgggacagaa ttcactctca caatcagcag cctgcagcct  240
gaagattttg caacttatta ctgtcaacag cttaatagtt accctctcac tttcggcgga  300
gggaccaagg tggagatcaa a                                           321

SEQ ID NO: 51            moltype = AA  length = 107
FEATURE                  Location/Qualifiers
REGION                   1..107
                         note = Synthetic
source                   1..107
                         mol_type = protein
                         organism = synthetic construct
SEQUENCE: 51
DIQLTQSPSF LSASVGDRVT ITCWASQGIS SYLAWYQQKP GKAPKLLIYA ASTLQSGVPS  60
RFSGSGSGTE FTLTISSLQP EDFATYYCQQ LNSYPLTFGG GTKVEIK               107

SEQ ID NO: 52            moltype = DNA  length = 18
FEATURE                  Location/Qualifiers
misc_feature             1..18
                         note = Synthetic
source                   1..18
                         mol_type = other DNA
                         organism = synthetic construct
SEQUENCE: 52
cagggcatta gcagttat                                               18

SEQ ID NO: 53            moltype = AA  length = 6
FEATURE                  Location/Qualifiers
REGION                   1..6
                         note = Synthetic
source                   1..6
                         mol_type = protein
                         organism = synthetic construct
SEQUENCE: 53
QGISSY                                                            6

SEQ ID NO: 54            moltype =   length =
SEQUENCE: 54
000

SEQ ID NO: 55            moltype =   length =
SEQUENCE: 55
000

SEQ ID NO: 56            moltype = DNA  length = 27
FEATURE                  Location/Qualifiers
misc_feature             1..27
                         note = Synthetic
source                   1..27
                         mol_type = other DNA
                         organism = synthetic construct
SEQUENCE: 56
caacagctta atagttaccc tctcact                                     27
```

-continued

```
SEQ ID NO: 57          moltype = AA  length = 9
FEATURE                Location/Qualifiers
REGION                 1..9
                       note = Synthetic
source                 1..9
                       mol_type = protein
                       organism = synthetic construct
SEQUENCE: 57
QQLNSYPLT                                                      9

SEQ ID NO: 58          moltype = DNA  length = 1332
FEATURE                Location/Qualifiers
misc_feature           1..1332
                       note = Synthetic
source                 1..1332
                       mol_type = other DNA
                       organism = synthetic construct
SEQUENCE: 58
gaggtgcagc tggtggagtc tggaggaggc ttggtccagc ctgggggtc cctgagactc  60
tcctgtgcag cctctgggtt aatagtcagt cgcaactaca tgatctgggt ccgccaggct  120
ccagggaagg ggctggagtg ggtctcagtt atttatagcg gtggtagcac attctacgca  180
gactccgtga agggccgatt caccatctcc agacacaatt ccaagaacac gctgtatctt  240
caaatgaaca gcctgagagc tgaggacacg gccgtatatt actgtgcgag agatctgggt  300
acaggaggta tggacgtctg gggccaaggg accacggtca ccgtctcctc agcctccacc  360
aagggcccat cggtcttccc cctggcgccc tgctccagga gcacctccga gagcacagcc  420
gccctgggct gcctggtcaa ggactacttc cccgaaccgg tgacggtgtc gtggaactca  480
ggcgccctga ccagcggcgt gcacaccttc ccggctgtcc tacagtcctc aggactctac  540
tccctcagca gcgtggtgac cgtgccctcc agcagcttgg gcacgaagac ctacacctgc  600
aacgtagatc acaagcccag caacaccaag gtggacaaga gagttgagtc caaatatggt  660
cccccatgcc caccgtgccc agcaccaggc ggtggcggac catcagtctt cctgttcccc  720
ccaaaaccca aggacactct catgatctcc cggacccctg aggtcacgtg cgtggtggtg  780
gacgtgagcc aggaagaccc cgaggtccag ttcaactggt acgtggatgg cgtggaggtg  840
cataatgcca agacaaagcc gcgggaggag cagttcaaca gcacgtaccg tgtggtcagc  900
gtcctcaccg tcctgcacca ggactggctg aacggcaagg agtacaagtg caaggtctcc  960
aacaaaggcc tcccgtcctc catcgagaaa accatctcca aagccaaagg gcagccccga  1020
gagccacagg tgtacaccct gcccccatcc caggaggaga tgaccaagaa ccaggtcagc  1080
ctgacctgcc tggtcaaagg cttctacccc agcgacatcg ccgtggagtg ggagagcaat  1140
gggcagccgg agaacaacta caagaccacg cctcccgtgc tggactccga cggctccttc  1200
ttcctctaca gcaggctcac cgtggacaag agcaggtggc aggaggggaa tgtcttctca  1260
tgctccgtga tgcatgaggc tctgcacaac cactacacac agaagtccct ctccctgtct  1320
ctgggtaaat ga                                                  1332

SEQ ID NO: 59          moltype = AA  length = 443
FEATURE                Location/Qualifiers
REGION                 1..443
                       note = Synthetic
source                 1..443
                       mol_type = protein
                       organism = synthetic construct
SEQUENCE: 59
EVQLVESGGG LVQPGGSLRL SCAASGLIVS RNYMIWVRQA PGKGLEWVSV IYSGGSTFYA  60
DSVKGRFTIS RHNSKNTLYL QMNSLRAEDT AVYYCARDLG TGGMDVWGQG TTVTVSSAST  120
KGPSVFPLAP CSRSTSESTA ALGCLVKDYF PEPVTVSWNS GALTSGVHTF PAVLQSSGLY  180
SLSSVVTVPS SSLGTKTYTC NVDHKPSNTK VDKRVESKYG PPCPPCPAPG GGGPSVFLFP  240
PKPKDTLMIS RTPEVTCVVV DVSQEDPEVQ FNWYVDGVEV HNAKTKPREE QFNSTYRVVS  300
VLTVLHQDWL NGKEYKCKVS NKGLPSSIEK TISKAKGQPR EPQVYTLPPS QEEMTKNQVS  360
LTCLVKGFYP SDIAVEWESN GQPENNYKTT PPVLDSDGSF FLYSRLTVDK SRWQEGNVFS  420
CSVMHEALHN HYTQKSLSLS LGK                                      443

SEQ ID NO: 60          moltype = DNA  length = 645
FEATURE                Location/Qualifiers
misc_feature           1..645
                       note = Synthetic
source                 1..645
                       mol_type = other DNA
                       organism = synthetic construct
SEQUENCE: 60
gacatccagt tgacccagtc tccatccttc ctgtctgcat ctgtaggaga cagagtcacc  60
atcacttgct gggccagtca gggcattagc agttatttag cctggtatca gcaaaaacca  120
gggaaagccc ctaagctcct gatctatgct gcatccactt tgcaaagtgg ggtcccatca  180
aggttcagcg gcagtggatc tgggacagaa ttcactctca caatcagcag cctgcagcct  240
gaagattttg caacttatta ctgtcaacag cttaatagtt accctctcac tttcggcgga  300
gggaccaagg tggagatcaa acgaactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttag               645
```

-continued

```
SEQ ID NO: 61          moltype = AA  length = 214
FEATURE                Location/Qualifiers
REGION                 1..214
                       note = Synthetic
source                 1..214
                       mol_type = protein
                       organism = synthetic construct
SEQUENCE: 61
DIQLTQSPSF LSASVGDRVT ITCWASQGIS SYLAWYQQKP GKAPKLLIYA ASTLQSGVPS  60
RFSGSGSGTE FTLTISSLQP EDFATYYCQQ LNSYPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 62          moltype = DNA  length = 1329
FEATURE                Location/Qualifiers
misc_feature           1..1329
                       note = Synthetic
source                 1..1329
                       mol_type = other DNA
                       organism = synthetic construct
SEQUENCE: 62
gaggtgcagc tggtggagtc tggaggaggc ttggtccagc ctggggggtc cctgagactc  60
tcctgtgcag cctctgggtt caccgtcagt agcaactaca tgaactgggt ccgccaggct  120
ccagggaagg ggctggagtg ggtctcagtt atttatagcg gtggcagcac attctacgca  180
gactccgtga agggccgatt caccatctcc agacacaatt ccaagaacac gctgtatctt  240
caaatgaaca gcctgagacc tgaggacacg gccgtgtatt actgtgcgag agatctgggg  300
ggatactttg actactgggg ccagggaacc ctggtcaccg tctcctcagc ctccaccaag  360
ggcccatcgg tcttccccct ggcgccctgc tccaggagca cctccgagag cacagccgcc  420
ctgggctgcc tggtcaagga ctacttcccc gaaccggtga cggtgtcgtg gaactcaggc  480
gccctgacca gcggcgtgca caccttcccg gctgtcctac agtcctcagg actctactcc  540
ctcagcagcg tggtgaccgt gccctccagc agcttgggca cgaagaccta cacctgcaac  600
gtagatcaca agcccagcaa caccaaggtg gacaagagag ttgagtccaa atatggtccc  660
ccatgcccac cgtgcccagc accaggcggt ggcggaccat cagtcttcct gttcccccca  720
aaacccaagg acactctcat gatctcccgg acccctgagg tcacgtgcgt ggtggtggac  780
gtgagccagg aagaccccga ggtccagttc aactggtacg tggatggcgt ggaggtgcat  840
aatgccaaga caaagccgcg ggaggagcag ttcaacagca cgtaccgtgt ggtcagcgtc  900
ctcaccgtcc tgcaccagga ctggctgaac ggcaaggagt acaagtgcaa ggtctccaac  960
aaaggcctcc cgtcctccat cgagaaaacc atctccaaag ccaaagggca gccccgagag  1020
ccacaggtgt acaccctgcc cccatcccag gaggagatga ccaagaacca ggtcagcctg  1080
acctgcctgg tcaaaggctt ctaccccagc gacatcgccg tggagtggga gagcaatggg  1140
cagccggaga acaactacaa gaccacgcct cccgtgctgg actccgacgg ctccttcttc  1200
ctctacagca ggctcaccgt ggacaagagc aggtggcagg aggggaatgt cttctcatgc  1260
tccgtgatgc atgaggctct gcacaaccac tacacacaga agtccctctc cctgtctctg  1320
ggtaaatga                                                          1329

SEQ ID NO: 63          moltype = AA  length = 442
FEATURE                Location/Qualifiers
REGION                 1..442
                       note = Synthetic
source                 1..442
                       mol_type = protein
                       organism = synthetic construct
SEQUENCE: 63
EVQLVESGGG LVQPGGSLRL SCAASGFTVS SNYMNWVRQA PGKGLEWVSV IYSGGSTFYA  60
DSVKGRFTIS RHNSKNTLYL QMNSLRPEDT AVYYCARDLG GYFDYWGQGT LVTVSSASTK  120
GPSVFPLAPC SRSTSESTAA LGCLVKDYFP EPVTVSWNSG ALTSGVHTFP AVLQSSGLYS  180
LSSVVTVPSS SLGTKTYTCN VDHKPSNTKV DKRVESKYGP PCPPCPAPGG GGPSVFLFPP  240
KPKDTLMISR TPEVTCVVVD VSQEDPEVQF NWYVDGVEVH NAKTKPREEQ FNSTYRVVSV  300
LTVLHQDWLN GKEYKCKVSN KGLPSSIEKT ISKAKGQPRE PQVYTLPPSQ EEMTKNQVSL  360
TCLVKGFYPS DIAVEWESNG QPENNYKTTP PVLDSDGSFF LYSRLTVDKS RWQEGNVFSC  420
SVMHEALHNH YTQKSLSLSL GK                                           442

SEQ ID NO: 64          moltype = DNA  length = 360
FEATURE                Location/Qualifiers
misc_feature           1..360
                       note = Synthetic
source                 1..360
                       mol_type = other DNA
                       organism = synthetic construct
SEQUENCE: 64
caggtgcagc tggtggagtc tgggggaggc gtggtccagc ctgggaggtc cctgagactc  60
tcctgtgcag cgtctggatt caccttcagt tactatggca tgcactgggt ccgccaggct  120
ccaggcaagg ggctggagtg ggtggcagtt atatggtatg atggaagtaa taaattctat  180
gcagactccg tgaagggccg attcaccatc tccagagaca attccaagaa cacgctgtat  240
ctgcaaatga acagcctgag agccgaggac acggctgtgt attactgtgc ggcagctcgg  300
ccgggctact actacggtat ggacgtctgg ggccaaggga ccacggtcac cgtctcctca  360

SEQ ID NO: 65          moltype = AA  length = 120
FEATURE                Location/Qualifiers
```

-continued

```
REGION                  1..120
                        note = Synthetic
source                  1..120
                        mol_type = protein
                        organism = synthetic construct
SEQUENCE: 65
QVQLVESGGG VVQPGRSLRL SCAASGFTFS YYGMHWVRQA PGKGLEWVAV IWYDGSNKFY  60
ADSVKGRFTI SRDNSKNTLY LQMNSLRAED TAVYYCAAAR PGYYYGMDVW GQGTTVTVSS  120

SEQ ID NO: 66           moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 66
ggattcacct tcagttacta tggc                                         24

SEQ ID NO: 67           moltype = AA  length = 8
FEATURE                 Location/Qualifiers
REGION                  1..8
                        note = Synthetic
source                  1..8
                        mol_type = protein
                        organism = synthetic construct
SEQUENCE: 67
GFTFSYYG                                                           8

SEQ ID NO: 68           moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 68
atatggtatg atggaagtaa taaa                                         24

SEQ ID NO: 69           moltype = AA  length = 8
FEATURE                 Location/Qualifiers
REGION                  1..8
                        note = Synthetic
source                  1..8
                        mol_type = protein
                        organism = synthetic construct
SEQUENCE: 69
IWYDGSNK                                                           8

SEQ ID NO: 70           moltype = DNA  length = 39
FEATURE                 Location/Qualifiers
misc_feature            1..39
                        note = Synthetic
source                  1..39
                        mol_type = other DNA
                        organism = synthetic construct
SEQUENCE: 70
gcggcagctc ggccgggcta ctactacggt atggacgtc                         39

SEQ ID NO: 71           moltype = AA  length = 13
FEATURE                 Location/Qualifiers
REGION                  1..13
                        note = Synthetic
source                  1..13
                        mol_type = protein
                        organism = synthetic construct
SEQUENCE: 71
AAARPGYYYG MDV                                                     13

SEQ ID NO: 72           moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 72
gacatccaga tgacccagtc tccatcctca ctgtctgctt ctgtaggaga cagagtcacc  60
atcacttgtc gggcgagtca gggcattagc aattatttag cctggtttca gcagaaacca  120
```

```
gggaaagccc ctaattccct gatctatgct gcatccagtt tgcaacgtgg ggtcccatca  180
aagttcagcg gcagtggatc tgggacagat ttcactctca ccatcagcag cctgcagcct  240
gaagattttg caacttatta ctgccaacag tataatagtt accctcggac gttcggccaa  300
gggaccaagg tggaaatcaa a                                            321

SEQ ID NO: 73          moltype = AA  length = 107
FEATURE                Location/Qualifiers
REGION                 1..107
                       note = Synthetic
source                 1..107
                       mol_type = protein
                       organism = synthetic construct
SEQUENCE: 73
DIQMTQSPSS LSASVGDRVT ITCRASQGIS NYLAWFQQKP GKAPNSLIYA ASSLQRGVPS  60
KFSGSGSGTD FTLTISSLQP EDFATYYCQQ YNSYPRTFGQ GTKVEIK                107

SEQ ID NO: 74          moltype = DNA  length = 18
FEATURE                Location/Qualifiers
misc_feature           1..18
                       note = Synthetic
source                 1..18
                       mol_type = other DNA
                       organism = synthetic construct
SEQUENCE: 74
cagggcatta gcaattat                                                18

SEQ ID NO: 75          moltype = AA  length = 6
FEATURE                Location/Qualifiers
REGION                 1..6
                       note = Synthetic
source                 1..6
                       mol_type = protein
                       organism = synthetic construct
SEQUENCE: 75
QGISNY                                                             6

SEQ ID NO: 76          moltype = DNA  length = 27
FEATURE                Location/Qualifiers
misc_feature           1..27
                       note = Synthetic
source                 1..27
                       mol_type = other DNA
                       organism = synthetic construct
SEQUENCE: 76
caacagtata atagttaccc tcggacg                                      27

SEQ ID NO: 77          moltype = AA  length = 9
FEATURE                Location/Qualifiers
REGION                 1..9
                       note = Synthetic
source                 1..9
                       mol_type = protein
                       organism = synthetic construct
SEQUENCE: 77
QQYNSYPRT                                                          9

SEQ ID NO: 78          moltype = DNA  length = 1353
FEATURE                Location/Qualifiers
misc_feature           1..1353
                       note = Synthetic
source                 1..1353
                       mol_type = other DNA
                       organism = synthetic construct
SEQUENCE: 78
caggtgcagc tggtggagtc tgggggaggc gtggtccagc ctgggaggtc cctgagactc  60
tcctgtgcag cgtctggatt caccttcagt tactatggca tgcactgggt ccgccaggct  120
ccaggcaagg ggctggagtg ggtggcagtt atatggtatg atggaagtaa taaattctat  180
gcagactccg tgaagggccg attcaccatc tccagagaca attccaagaa cacgctgtat  240
ctgcaaatga acagcctgag agccgaggac acggctgtgt attactgtgc ggcagctcgg  300
ccgggctact actacggtat ggacgtctgg ggccaaggga ccacggtcac cgtctcctca  360
gcctccacca agggcccatc ggtcttcccc ctggcaccct cctccaagag cacctctggg  420
ggcacagcgg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacccagacc  600
tacatctgca acgtgaatca caagcccagc aacaccaagg tggacaagaa agttgagccc  660
aaatcttgtg acaaaactca cacatgccca ccgtgcccag cacctgaact cctgggggga  720
ccgtcagtct tcctcttccc cccaaaaccc aaggacaccc tcatgatctc ccggacccct  780
gaggtcacat gcgtggtggt ggacgtgagc cacgaagacc ctgaggtcaa gttcaactgg  840
tacgtggacg gcgtggaggt gcataatgcc aagacaaagc cgcgggagga gcagtacaac  900
```

```
agcacgtacc gtgtggtcag cgtcctcacc gtcctgcacc aggactggct gaatggcaag  960
gagtacaagt gcaaggtctc caacaaagcc ctcccagccc ccatcgagaa aaccatctcc  1020
aaagccaaag ggcagccccg agaaccacag gtgtacaccc tgcccccatc ccgggatgag  1080
ctgaccaaga accaggtcag cctgacctgc ctggtcaaag gcttctatcc cagcgacatc  1140
gccgtggagt gggagagcaa tgggcagccg gagaacaact acaagaccac gcctcccgtg  1200
ctggactccg acggctcctt cttcctctac agcaagctca ccgtggacaa gagcaggtgg  1260
cagcagggga acgtcttctc atgctccgtg atgcatgagg ctctgcacaa ccactacacg  1320
cagaagtccc tctccctgtc tccgggtaaa tga                                1353

SEQ ID NO: 79          moltype = AA  length = 450
FEATURE                Location/Qualifiers
REGION                 1..450
                       note = Synthetic
source                 1..450
                       mol_type = protein
                       organism = synthetic construct
SEQUENCE: 79
QVQLVESGGG VVQPGRSLRL SCAASGFTFS YYGMHWVRQA PGKGLEWVAV IWYDGSNKFY  60
ADSVKGRFTI SRDNSKNTLY LQMNSLRAED TAVYYCAAAR PGYYYGMDVW GQGTTVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                   450

SEQ ID NO: 80          moltype = DNA  length = 645
FEATURE                Location/Qualifiers
misc_feature           1..645
                       note = Synthetic
source                 1..645
                       mol_type = other DNA
                       organism = synthetic construct
SEQUENCE: 80
gacatccaga tgacccagtc tccatcctca ctgtctgctt ctgtaggaga cagagtcacc  60
atcacttgtc gggcgagtca gggcattagc aattatttag cctggtttca gcagaaacca  120
gggaaagccc ctaattccct gatctatgct gcatccagtt tgcaacgtgg ggtcccatca  180
aagttcagcg gcagtggatc tgggacagat ttcactctca ccatcagcag cctgcagcct  240
gaagattttg caacttatta ctgccaacag tataatagtt accctcggac gttcggccaa  300
gggaccaagg tggaaatcaa acgaactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttag                  645

SEQ ID NO: 81          moltype = AA  length = 214
FEATURE                Location/Qualifiers
REGION                 1..214
                       note = Synthetic
source                 1..214
                       mol_type = protein
                       organism = synthetic construct
SEQUENCE: 81
DIQMTQSPSS LSASVGDRVT ITCRASQGIS NYLAWFQQKP GKAPNSLIYA ASSLQRGVPS  60
KFSGSGSGTD FTLTISSLQP EDFATYYCQQ YNSYPRTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                               214

SEQ ID NO: 82          moltype = DNA  length = 351
FEATURE                Location/Qualifiers
misc_feature           1..351
                       note = Synthetic
source                 1..351
                       mol_type = other DNA
                       organism = synthetic construct
SEQUENCE: 82
gaggtgcagc tggtggagtc tggaggaggc ttggtccagc ctgggggggtc cctgagactc  60
tcctgtgcag cctctgggat caccgtcagt agcaactaca tgagctgggt ccgccaggct  120
ccagggaagg ggctggagtg ggtctcagtt atttatagcg gtggtagcac attctacgca  180
gactccgtga agggccgatt caccatctcc agacacaatt ccaagaacac gctgtatctt  240
caaatgaaca gcctgagagc tgaggacacg gccgtgtatt actgtgcgag agaacgtaac  300
tttgatgctt ttgatatctg gggccaaggg acaatggtca ccgtctcttc a           351

SEQ ID NO: 83          moltype = AA  length = 117
FEATURE                Location/Qualifiers
REGION                 1..117
                       note = Synthetic
source                 1..117
```

-continued

```
                         mol_type = protein
                         organism = synthetic construct
SEQUENCE: 83
EVQLVESGGG LVQPGGSLRL SCAASGITVS SNYMSWVRQA PGKGLEWVSV IYSGGSTFYA  60
DSVKGRFTIS RHNSKNTLYL QMNSLRAEDT AVYYCARERN FDAFDIWGQG TMVTVSS     117

SEQ ID NO: 84            moltype = DNA  length = 24
FEATURE                  Location/Qualifiers
misc_feature             1..24
                         note = Synthetic
source                   1..24
                         mol_type = other DNA
                         organism = synthetic construct
SEQUENCE: 84
gggatcaccg tcagtagcaa ctac                                         24

SEQ ID NO: 85            moltype = AA  length = 8
FEATURE                  Location/Qualifiers
REGION                   1..8
                         note = Synthetic
source                   1..8
                         mol_type = protein
                         organism = synthetic construct
SEQUENCE: 85
GITVSSNY                                                           8

SEQ ID NO: 86            moltype = DNA  length = 33
FEATURE                  Location/Qualifiers
misc_feature             1..33
                         note = Synthetic
source                   1..33
                         mol_type = other DNA
                         organism = synthetic construct
SEQUENCE: 86
gcgagagaac gtaactttga tgcttttgat atc                               33

SEQ ID NO: 87            moltype = AA  length = 11
FEATURE                  Location/Qualifiers
REGION                   1..11
                         note = Synthetic
source                   1..11
                         mol_type = protein
                         organism = synthetic construct
SEQUENCE: 87
ARERNFDAFD I                                                       11

SEQ ID NO: 88            moltype = DNA  length = 324
FEATURE                  Location/Qualifiers
misc_feature             1..324
                         note = Synthetic
source                   1..324
                         mol_type = other DNA
                         organism = synthetic construct
SEQUENCE: 88
gacatccaga tgacccagtc tccatcttcc gtgtctgcat ctgtaggaga cagagtcacc  60
atcacttgtc gggcgagtca gggtattagc agctggttag cctggtatca gcagaaacca  120
gggaaagccc ctaagctcct gatctatgct gcatccagtt tgcaaagtgg ggtcccatca  180
aggttcagcg gcagtggatc tgggacagat ttcactctca ccatcagcag cctgcagcct  240
gaagattttg caacttacta ttgtcaacag gctaacagtt tccccctatt cactttcggc  300
cctgggacca aagtggatat caaa                                         324

SEQ ID NO: 89            moltype = AA  length = 108
FEATURE                  Location/Qualifiers
REGION                   1..108
                         note = Synthetic
source                   1..108
                         mol_type = protein
                         organism = synthetic construct
SEQUENCE: 89
DIQMTQSPSS VSASVGDRVT ITCRASQGIS SWLAWYQQKP GKAPKLLIYA ASSLQSGVPS  60
RFSGSGSGTD FTLTISSLQP EDFATYYCQQ ANSFPLFTFG PGTKVDIK               108

SEQ ID NO: 90            moltype = DNA  length = 18
FEATURE                  Location/Qualifiers
misc_feature             1..18
                         note = Synthetic
source                   1..18
                         mol_type = other DNA
                         organism = synthetic construct
```

```
SEQUENCE: 90
cagggtatta gcagctgg                                                18

SEQ ID NO: 91          moltype = AA  length = 6
FEATURE                Location/Qualifiers
REGION                 1..6
                       note = Synthetic
source                 1..6
                       mol_type = protein
                       organism = synthetic construct
SEQUENCE: 91
QGISSW                                                             6

SEQ ID NO: 92          moltype = DNA  length = 30
FEATURE                Location/Qualifiers
misc_feature           1..30
                       note = Synthetic
source                 1..30
                       mol_type = other DNA
                       organism = synthetic construct
SEQUENCE: 92
caacaggcta acagtttccc cctattcact                                   30

SEQ ID NO: 93          moltype = AA  length = 10
FEATURE                Location/Qualifiers
REGION                 1..10
                       note = Synthetic
source                 1..10
                       mol_type = protein
                       organism = synthetic construct
SEQUENCE: 93
QQANSFPLFT                                                         10

SEQ ID NO: 94          moltype = DNA  length = 1344
FEATURE                Location/Qualifiers
misc_feature           1..1344
                       note = Synthetic
source                 1..1344
                       mol_type = other DNA
                       organism = synthetic construct
SEQUENCE: 94
gaggtgcagc tggtggagtc tggaggaggc ttggtccagc ctggggggtc cctgagactc  60
tcctgtgcag cctctgggat caccgtcagt agcaactaca tgagctgggt ccgccaggct  120
ccagggaagg ggctggagtg ggtctcagtt atttatagcg gtggtagcac attctacgca  180
gactccgtga agggccgatt caccatctcc agacacaatt ccaagaacac gctgtatctt  240
caaatgaaca gcctgagagc tgaggacacg gccgtgtatt actgtgcgag agaacgtaac  300
tttgatgctt ttgatatctg gggccaaggg acaatggtca ccgtctcttc agcctccacc  360
aagggcccat cggtcttccc cctggcaccc tcctccaaga gcacctctgg gggcacagcg  420
gccctgggct gcctggtcaa ggactacttc cccgaaccgg tgacggtgtc gtggaactca  480
ggcgccctga ccagcggcgt gcacaccttc ccggctgtcc tacagtcctc aggactctac  540
tccctcagca gcgtggtgac cgtgccctcc agcagcttgg gcacccagac ctacatctgc  600
aacgtgaatc acaagcccag caacaccaag gtggacaaga aagttgagcc caaatcttgt  660
gacaaaactc acacatgccc accgtgccca gcacctgaac tcctgggggg accgtcagtc  720
ttcctcttcc ccccaaaacc caaggacacc ctcatgatct cccggacccc tgaggtcaca  780
tgcgtggtgg tggacgtgag ccacgaagac cctgaggtca agttcaactg gtacgtggac  840
ggcgtggagg tgcataatgc caagacaaag ccgcgggagg agcagtacaa cagcacgtac  900
cgtgtggtca gcgtcctcac cgtcctgcac caggactggc tgaatggcaa ggagtacaag  960
tgcaaggtct ccaacaaagc cctcccagcc cccatcgaga aaaccatctc caaagccaaa  1020
gggcagcccc gagaaccaca ggtgtacacc ctgcccccat cccgggatga gctgaccaag  1080
aaccaggtca gcctgacctg cctggtcaaa ggcttctatc ccagcgacat cgccgtggag  1140
tgggagagca atgggcagcc ggagaacaac tacaagacca cgcctcccgt gctggactcc  1200
gacggctcct tcttcctcta cagcaagctc accgtggaca agagcaggtg gcagcagggg  1260
aacgtcttct catgctccgt gatgcatgag gctctgcaca accactacac gcagaagtcc  1320
ctctccctgt ctccgggtaa atga                                         1344

SEQ ID NO: 95          moltype = AA  length = 447
FEATURE                Location/Qualifiers
REGION                 1..447
                       note = Synthetic
source                 1..447
                       mol_type = protein
                       organism = synthetic construct
SEQUENCE: 95
EVQLVESGGG LVQPGGSLRL SCAASGITVS SNYMSWVRQA PGKGLEWVSV IYSGGSTFYA  60
DSVKGRFTIS RHNSKNTLYL QMNSLRAEDT AVYYCARERN FDAFDIWGQG TMVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APELLGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSRDELTK  360
```

-continued

```
NQVSLTCLVK GFYPSDIAVE WESNGQPENN YKTTPPVLDS DGSFFLYSKL TVDKSRWQQG  420
NVFSCSVMHE ALHNHYTQKS LSLSPGK                                     447

SEQ ID NO: 96          moltype = DNA  length = 648
FEATURE                Location/Qualifiers
misc_feature           1..648
                       note = Synthetic
source                 1..648
                       mol_type = other DNA
                       organism = synthetic construct
SEQUENCE: 96
gacatccaga tgacccagtc tccatcttcc gtgtctgcat ctgtaggaga cagagtcacc  60
atcacttgtc gggcgagtca gggtattagc agctggttag cctggtatca gcagaaacca  120
gggaaagccc ctaagctcct gatctatgct gcatccagtt tgcaaagtgg ggtcccatca  180
aggttcagcg gcagtggatc tgggacagat ttcactctca ccatcagcag cctgcagcct  240
gaagattttg caacttacta ttgtcaacag gctaacagtt tccccctatt cactttcggc  300
cctgggacca aagtggatat caaacgaact gtggctgcac catctgtctt catcttcccg  360
ccatctgatg agcagttgaa atctggaact gcctctgttg tgtgcctgct gaataacttc  420
tatcccagag aggccaaagt acagtggaag gtggataacg ccctccaatc gggtaactcc  480
caggagagtg tcacagagca ggacagcaag gacagcacct acagcctcag cagcaccctg  540
acgctgagca aagcagacta cgagaaacac aaagtctacg cctgcgaagt cacccatcag  600
ggcctgagct cgcccgtcac aaagagcttc aacaggggag agtgttag              648

SEQ ID NO: 97          moltype = AA  length = 215
FEATURE                Location/Qualifiers
REGION                 1..215
                       note = Synthetic
source                 1..215
                       mol_type = protein
                       organism = synthetic construct
SEQUENCE: 97
DIQMTQSPSS VSASVGDRVT ITCRASQGIS SWLAWYQQKP GKAPKLLIYA ASSLQSGVPS  60
RFSGSGSGTD FTLTISSLQP EDFATYYCQQ ANSFPLFTFG PGTKVDIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 98          moltype = DNA  length = 357
FEATURE                Location/Qualifiers
misc_feature           1..357
                       note = Synthetic
source                 1..357
                       mol_type = other DNA
                       organism = synthetic construct
SEQUENCE: 98
gaggtgcagc tggtggagtc tgggggaggc ttggtacagc ctggagggtc cctgagactc  60
tcctgtgcag cctctggatt caccttcagt atttatgaaa tgaactgggt ccgccaggct  120
ccagggaagg ggctggagtg ggtttcatac attactagta gtggtactac catatactac  180
gcagactctg tgaagggccg attcaccatc tccagagaca acgccaagaa ctcactgtat  240
ctgcaaatga acagcctgag agccgaggac acggctgttt attactgtgc gagtagcagc  300
tcgtccgggt actactttga ctactggggc cagggaaccc tggtcaccgt ctcctca    357

SEQ ID NO: 99          moltype = AA  length = 119
FEATURE                Location/Qualifiers
REGION                 1..119
                       note = Synthetic
source                 1..119
                       mol_type = protein
                       organism = synthetic construct
SEQUENCE: 99
EVQLVESGGG LVQPGGSLRL SCAASGFTFS IYEMNWVRQA PGKGLEWVSY ITSSGTTIYY  60
ADSVKGRFTI SRDNAKNSLY LQMNSLRAED TAVYYCASSS SSGYYFDYWG QGTLVTVSS   119

SEQ ID NO: 100         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 100
ggattcacct tcagtattta tgaa                                        24

SEQ ID NO: 101         moltype = AA  length = 8
FEATURE                Location/Qualifiers
REGION                 1..8
                       note = Synthetic
source                 1..8
                       mol_type = protein
                       organism = synthetic construct
```

```
SEQUENCE: 101
GFTFSIYE                                                    8

SEQ ID NO: 102         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 102
attactagta gtggtactac cata                                  24

SEQ ID NO: 103         moltype = AA  length = 8
FEATURE                Location/Qualifiers
REGION                 1..8
                       note = Synthetic
source                 1..8
                       mol_type = protein
                       organism = synthetic construct
SEQUENCE: 103
ITSSGTTI                                                    8

SEQ ID NO: 104         moltype = DNA  length = 36
FEATURE                Location/Qualifiers
misc_feature           1..36
                       note = Synthetic
source                 1..36
                       mol_type = other DNA
                       organism = synthetic construct
SEQUENCE: 104
gcgagtagca gctcgtccgg gtactacttt gactac                     36

SEQ ID NO: 105         moltype = AA  length = 12
FEATURE                Location/Qualifiers
REGION                 1..12
                       note = Synthetic
source                 1..12
                       mol_type = protein
                       organism = synthetic construct
SEQUENCE: 105
ASSSSSGYYF DY                                               12

SEQ ID NO: 106         moltype = DNA  length = 339
FEATURE                Location/Qualifiers
misc_feature           1..339
                       note = Synthetic
source                 1..339
                       mol_type = other DNA
                       organism = synthetic construct
SEQUENCE: 106
gacatcgtga tgacccagtc tccagactcc ctggctgtgt ctctgggcga gagggccacc  60
atcaactgca agtccagcca gagtgtttta tacagctcca acaataagaa ctacttagct  120
tggtaccagc agaaaccagg acagcctcct aatctgctca tttactgggc atctacccgg  180
gaatccgggg tccctgaccg attcagtggc agcgggtctg ggacagattt cactctcacc  240
atcagcagcc tgcaggctga agatgtggca gtttattact gtcagcaata ttatagtact  300
cctcccactt ttggccaggg gaccaagctg gagatcaaa                  339

SEQ ID NO: 107         moltype = AA  length = 113
FEATURE                Location/Qualifiers
REGION                 1..113
                       note = Synthetic
source                 1..113
                       mol_type = protein
                       organism = synthetic construct
SEQUENCE: 107
DIVMTQSPDS LAVSLGERAT INCKSSQSVL YSSNNKNYLA WYQQKPGQPP NLLIYWASTR  60
ESGVPDRFSG SGSGTDFTLT ISSLQAEDVA VYYCQQYYST PPTFGQGTKL EIK         113

SEQ ID NO: 108         moltype = DNA  length = 36
FEATURE                Location/Qualifiers
misc_feature           1..36
                       note = Synthetic
source                 1..36
                       mol_type = other DNA
                       organism = synthetic construct
SEQUENCE: 108
cagagtgttt tatacagctc caacaataag aactac                     36
```

-continued

```
SEQ ID NO: 109         moltype = AA  length = 12
FEATURE                Location/Qualifiers
REGION                 1..12
                       note = Synthetic
source                 1..12
                       mol_type = protein
                       organism = synthetic construct
SEQUENCE: 109
QSVLYSSNNK NY                                                      12

SEQ ID NO: 110         moltype =   length =
SEQUENCE: 110
000

SEQ ID NO: 111         moltype =   length =
SEQUENCE: 111
000

SEQ ID NO: 112         moltype = DNA  length = 27
FEATURE                Location/Qualifiers
misc_feature           1..27
                       note = Synthetic
source                 1..27
                       mol_type = other DNA
                       organism = synthetic construct
SEQUENCE: 112
cagcaatatt atagtactcc tcccact                                      27

SEQ ID NO: 113         moltype = AA  length = 9
FEATURE                Location/Qualifiers
REGION                 1..9
                       note = Synthetic
source                 1..9
                       mol_type = protein
                       organism = synthetic construct
SEQUENCE: 113
QQYYSTPPT                                                          9

SEQ ID NO: 114         moltype = DNA  length = 1350
FEATURE                Location/Qualifiers
misc_feature           1..1350
                       note = Synthetic
source                 1..1350
                       mol_type = other DNA
                       organism = synthetic construct
SEQUENCE: 114
gaggtgcagc tggtggagtc tgggggaggc ttggtacagc ctggagggtc cctgagactc  60
tcctgtgcag cctctggatt caccttcagt atttatgaaa tgaactgggt ccgccaggct  120
ccagggaagg ggctggagtg ggtttcatac attactagta gtggtactac catatactac  180
gcagactctg tgaagggccg attcaccatc tccagagaca acgccaagaa ctcactgtat  240
ctgcaaatga acagcctgag agccgaggac acggctgttt attactgtgc gagtagcagc  300
tcgtccgggt actactttga ctactggggc cagggaaccc tggtcaccgt ctcctcagcc  360
tccaccaagg gcccatcggt cttccccctg gcaccctcct ccaagagcac ctctgggggc  420
acagcggccc tgggctgcct ggtcaaggac tacttccccg aaccggtgac ggtgtcgtgg  480
aactcaggcg ccctgaccag cggcgtgcac accttcccgg ctgtcctaca gtcctcagga  540
ctctactccc tcagcagcgt ggtgaccgtg ccctccagca gcttgggcac ccagacctac  600
atctgcaacg tgaatcacaa gcccagcaac accaaggtgg acaagaaagt tgagcccaaa  660
tcttgtgaca aaactcacac atgcccaccg tgcccagcac ctgaactcct ggggggaccg  720
tcagtcttcc tcttcccccc aaaacccaag gacaccctca tgatctcccg gacccctgag  780
gtcacatgcg tggtggtgga cgtgagccac gaagaccctg aggtcaagtt caactggtac  840
gtggacggcg tggaggtgca taatgccaag acaaagccgc gggaggagca gtacaacagc  900
acgtaccgtg tggtcagcgt cctcaccgtc ctgcaccagg actggctgaa tggcaaggag  960
tacaagtgca aggtctccaa caaagccctc ccagccccca tcgagaaaac catctccaaa  1020
gccaaagggc agccccgaga accacaggtg tacaccctgc ccccatcccg ggatgagctg  1080
accaagaacc aggtcagcct gacctgcctg gtcaaaggct tctatcccag cgacatcgcc  1140
gtggagtggg agagcaatgg gcagccggag aacaactaca agaccacgcc tcccgtgctg  1200
gactccgacg gctccttctt cctctacagc aagctcaccg tggacaagag caggtggcag  1260
caggggaacg tcttctcatg ctccgtgatg catgaggctc tgcacaacca ctacacgcag  1320
aagtccctct ccctgtctcc gggtaaatga                                   1350

SEQ ID NO: 115         moltype = AA  length = 449
FEATURE                Location/Qualifiers
REGION                 1..449
                       note = Synthetic
source                 1..449
                       mol_type = protein
                       organism = synthetic construct
SEQUENCE: 115
EVQLVESGGG LVQPGGSLRL SCAASGFTFS IYEMNWVRQA PGKGLEWVSY ITSSGTTIYY  60
```

```
ADSVKGRFTI SRDNAKNSLY LQMNSLRAED TAVYYCASSS SSGYYFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                   449

SEQ ID NO: 116          moltype = DNA  length = 663
FEATURE                 Location/Qualifiers
misc_feature            1..663
                        note = Synthetic
source                  1..663
                        mol_type = other DNA
                        organism = synthetic construct
SEQUENCE: 116
gacatcgtga tgacccagtc tccagactcc ctggctgtgt ctctgggcga gagggccacc  60
atcaactgca agtccagcca gagtgtttta tacagctcca acaataagaa ctacttagct  120
tggtaccagc agaaaccagg acagcctcct aatctgctca tttactgggc atctacccgg  180
gaatccgggg tccctgaccg attcagtggc agcgggtctg ggacagattt cactctcacc  240
atcagcagcc tgcaggctga agatgtggca gtttattact gtcagcaata ttatagtact  300
cctcccactt ttggccaggg gaccaagctg gagatcaaac gaactgtggc tgcaccatct  360
gtcttcatct tcccgccatc tgatgagcag ttgaaatctg gaactgcctc tgttgtgtgc  420
ctgctgaata acttctatcc cagagaggcc aaagtacagt ggaaggtgga taacgccctc  480
caatcgggta actcccagga gagtgtcaca gagcaggaca gcaaggacag cacctacagc  540
ctcagcagca ccctgacgct gagcaaagca gactacgaga aacacaaagt ctacgcctgc  600
gaagtcaccc atcagggcct gagctcgccc gtcacaaaga gcttcaacag gggagagtgt  660
tag                                                               663

SEQ ID NO: 117          moltype = AA  length = 220
FEATURE                 Location/Qualifiers
REGION                  1..220
                        note = Synthetic
source                  1..220
                        mol_type = protein
                        organism = synthetic construct
SEQUENCE: 117
DIVMTQSPDS LAVSLGERAT INCKSSQSVL YSSNNKNYLA WYQQKPGQPP NLLIYWASTR  60
ESGVPDRFSG SGSGTDFTLT ISSLQAEDVA VYYCQQYYST PPTFGQGTKL EIKRTVAAPS  120
VFIFPPSDEQ LKSGTASVVC LLNNFYPREA KVQWKVDNAL QSGNSQESVT EQDSKDSTYS  180
LSSTLTLSKA DYEKHKVYAC EVTHQGLSSP VTKSFNRGEC                        220

SEQ ID NO: 118          moltype = DNA  length = 363
FEATURE                 Location/Qualifiers
misc_feature            1..363
                        note = Synthetic
source                  1..363
                        mol_type = other DNA
                        organism = synthetic construct
SEQUENCE: 118
caggtgcagc tggtgcagtc tggggctgag gtgaagaagc ctggggcctc agtgaaggtc  60
tcctgcaagg cttctggata caccttcatt aactactata tacactgggt gcgacaggcc  120
cctggacaag ggcttgagtg gatgggatgg atcaacccta acagtggtgg cacaaactat  180
gcacagaagt ttcagggcag ggtcaccatg accagggaca cgtccatcag cacagcctac  240
atggagctga gcaggctgag atctgacgac acggccgtgt attactgtgc gattattacg  300
atttttggag tggttacctg gttcgacccc tggggccagg gaaccctggt caccgtctcc  360
tca                                                               363

SEQ ID NO: 119          moltype = AA  length = 121
FEATURE                 Location/Qualifiers
REGION                  1..121
                        note = Synthetic
source                  1..121
                        mol_type = protein
                        organism = synthetic construct
SEQUENCE: 119
QVQLVQSGAE VKKPGASVKV SCKASGYTFI NYYIHWVRQA PGQGLEWMGW INPNSGGTNY  60
AQKFQGRVTM TRDTSISTAY MELSRLRSDD TAVYYCAIIT IFGVVTWFDP WGQGTLVTVS  120
S                                                                 121

SEQ ID NO: 120          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 120
ggatacacct tcattaacta ctat                                        24
```

```
SEQ ID NO: 121          moltype = AA  length = 8
FEATURE                 Location/Qualifiers
REGION                  1..8
                        note = Synthetic
source                  1..8
                        mol_type = protein
                        organism = synthetic construct
SEQUENCE: 121
GYTFINYY                                                            8

SEQ ID NO: 122          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 122
atcaacccta acagtggtgg caca                                          24

SEQ ID NO: 123          moltype = AA  length = 8
FEATURE                 Location/Qualifiers
REGION                  1..8
                        note = Synthetic
source                  1..8
                        mol_type = protein
                        organism = synthetic construct
SEQUENCE: 123
INPNSGGT                                                            8

SEQ ID NO: 124          moltype = DNA  length = 42
FEATURE                 Location/Qualifiers
misc_feature            1..42
                        note = Synthetic
source                  1..42
                        mol_type = other DNA
                        organism = synthetic construct
SEQUENCE: 124
gcgattatta cgatttttgg agtggttacc tggttcgacc cc                      42

SEQ ID NO: 125          moltype = AA  length = 14
FEATURE                 Location/Qualifiers
REGION                  1..14
                        note = Synthetic
source                  1..14
                        mol_type = protein
                        organism = synthetic construct
SEQUENCE: 125
AIITIFGVVT WFDP                                                     14

SEQ ID NO: 126          moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 126
gacatccaga tgacccagtc tccatcctcc ctgtctgcat ctgtaggaga cagagtcacc  60
atcacttgcc gggcaagtca gagcattagc agctatttaa attggtatca gcagaaacca  120
gggaaagccc ctaagctcct gatctatgct gcatccagtt tgcaaagtgg ggtcccatca  180
aggttcagtg gcagtggatc tgggacagat ttcactctca ccatcagcag tctgcaacct  240
gaagattttg caacttacta ctgtcaacag agttacagta ccccgctcac tttcggcgga  300
gggaccaagg tggagatcaa a                                             321

SEQ ID NO: 127          moltype = AA  length = 107
FEATURE                 Location/Qualifiers
REGION                  1..107
                        note = Synthetic
source                  1..107
                        mol_type = protein
                        organism = synthetic construct
SEQUENCE: 127
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SYSTPLTFGG GTKVEIK                 107

SEQ ID NO: 128          moltype = DNA  length = 18
FEATURE                 Location/Qualifiers
```

```
misc_feature           1..18
                       note = Synthetic
source                 1..18
                       mol_type = other DNA
                       organism = synthetic construct
SEQUENCE: 128
cagagcatta gcagctat                                            18

SEQ ID NO: 129         moltype = AA  length = 6
FEATURE                Location/Qualifiers
REGION                 1..6
                       note = Synthetic
source                 1..6
                       mol_type = protein
                       organism = synthetic construct
SEQUENCE: 129
QSISSY                                                         6

SEQ ID NO: 130         moltype = DNA  length = 27
FEATURE                Location/Qualifiers
misc_feature           1..27
                       note = Synthetic
source                 1..27
                       mol_type = other DNA
                       organism = synthetic construct
SEQUENCE: 130
caacagagtt acagtacccc gctcact                                  27

SEQ ID NO: 131         moltype = AA  length = 9
FEATURE                Location/Qualifiers
REGION                 1..9
                       note = Synthetic
source                 1..9
                       mol_type = protein
                       organism = synthetic construct
SEQUENCE: 131
QQSYSTPLT                                                      9

SEQ ID NO: 132         moltype = DNA  length = 1356
FEATURE                Location/Qualifiers
misc_feature           1..1356
                       note = Synthetic
source                 1..1356
                       mol_type = other DNA
                       organism = synthetic construct
SEQUENCE: 132
caggtgcagc tggtgcagtc tggggctgag gtgaagaagc ctggggcctc agtgaaggtc  60
tcctgcaagg cttctggata caccttcatt aactactata tacactgggt gcgacaggcc  120
cctggacaag ggcttgagtg gatgggatgg atcaacccta acagtggtgg cacaaactat  180
gcacagaagt ttcagggcag ggtcaccatg accagggaca cgtccatcag cacagcctac  240
atggagctga gcaggctgag atctgacgac acggccgtgt attactgtgc gattattacg  300
atttttggag tggttacctg gttcgacccc tggggccagg gaaccctggt caccgtctcc  360
tcagcctcca ccaagggccc atcggtcttc cccctggcac cctcctccaa gagcacctct  420
gggggcacag cggccctggg ctgcctggtc aaggactact tccccgaacc ggtgacggtg  480
tcgtggaact caggcgccct gaccagcggc gtgcacacct tcccggctgt cctacagtcc  540
tcaggactct actccctcag cagcgtggtg accgtgccct ccagcagctt gggcacccag  600
acctacatct gcaacgtgaa tcacaagccc agcaacacca aggtggacaa gaaagttgag  660
cccaaatctt gtgacaaaac tcacacatgc ccaccgtgcc cagcacctga actcctgggg  720
ggaccgtcag tcttcctctt ccccccaaaa cccaaggaca ccctcatgat ctcccggacc  780
cctgaggtca catgcgtggt ggtggacgtg agccacgaag accctgaggt caagttcaac  840
tggtacgtgg acggcgtgga ggtgcataat gccaagacaa agccgcggga ggagcagtac  900
aacagcacgt accgtgtggt cagcgtcctc accgtcctgc accaggactg gctgaatggc  960
aaggagtaca agtgcaaggt ctccaacaaa gccctcccag cccccatcga gaaaaccatc  1020
tccaaagcca aagggcagcc ccgagaacca caggtgtaca ccctgccccc atcccgggat  1080
gagctgacca agaaccaggt cagcctgacc tgcctggtca aaggcttcta tcccagcgac  1140
atcgccgtgg agtgggagag caatgggcag ccggagaaca actacaagac cacgcctccc  1200
gtgctggact ccgacggctc cttcttcctc tacagcaagc tcaccgtgga caagagcagg  1260
tggcagcagg ggaacgtctt ctcatgctcc gtgatgcatg aggctctgca caaccactac  1320
acgcagaagt ccctctccct gtctccgggt aaatga                        1356

SEQ ID NO: 133         moltype = AA  length = 451
FEATURE                Location/Qualifiers
REGION                 1..451
                       note = Synthetic
source                 1..451
                       mol_type = protein
                       organism = synthetic construct
SEQUENCE: 133
QVQLVQSGAE VKKPGASVKV SCKASGYTFI NYYIHWVRQA PGQGLEWMGW INPNSGGTNY  60
```

-continued

```
AQKFQGRVTM TRDTSISTAY MELSRLRSDD TAVYYCAIIT IFGVVTWFDP WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451

SEQ ID NO: 134          moltype = DNA  length = 645
FEATURE                 Location/Qualifiers
misc_feature            1..645
                        note = Synthetic
source                  1..645
                        mol_type = other DNA
                        organism = synthetic construct
SEQUENCE: 134
gacatccaga tgacccagtc tccatcctcc ctgtctgcat ctgtaggaga cagagtcacc  60
atcacttgcc gggcaagtca gagcattagc agctatttaa attggtatca gcagaaacca  120
gggaaagccc ctaagctcct gatctatgct gcatccagtt tgcaaagtgg ggtcccatca  180
aggttcagtg gcagtggatc tgggacagat ttcactctca ccatcagcag tctgcaacct  240
gaagattttg caacttacta ctgtcaacag agttacagta ccccgctcac tttcggcgga  300
gggaccaagg tggagatcaa acgaactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttag                  645

SEQ ID NO: 135          moltype = AA  length = 214
FEATURE                 Location/Qualifiers
REGION                  1..214
                        note = Synthetic
source                  1..214
                        mol_type = protein
                        organism = synthetic construct
SEQUENCE: 135
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SYSTPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 136          moltype = DNA  length = 345
FEATURE                 Location/Qualifiers
misc_feature            1..345
                        note = Synthetic
source                  1..345
                        mol_type = other DNA
                        organism = synthetic construct
SEQUENCE: 136
caggtgcagc tgcaggagtc gggcccagga ctggtgaagc cttcggagac cctgtccctc  60
acctgcactg tctctggtgg ctccatcagt agttactact ggagttggat ccggcagccc  120
ccagggaagg gactggagtg gattgggtat atctattaca gtgggagcac caactacaac  180
ccctccctca agagtcgagt caccatatca gtagacacgt ccaagaacca gttctccctg  240
aaactgagct ctgtgaccgc tgcggacacg gccgtgtatt actgtgcgag agacccgctc  300
ctcattgact actggggcca gggaaccctg gtcaccgtct cctca                  345

SEQ ID NO: 137          moltype = AA  length = 115
FEATURE                 Location/Qualifiers
REGION                  1..115
                        note = Synthetic
source                  1..115
                        mol_type = protein
                        organism = synthetic construct
SEQUENCE: 137
QVQLQESGPG LVKPSETLSL TCTVSGGSIS SYYWSWIRQP PGKGLEWIGY IYYSGSTNYN  60
PSLKSRVTIS VDTSKNQFSL KLSSVTAADT AVYYCARDPL LIDYWGQGTL VTVSS       115

SEQ ID NO: 138          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 138
ggtggctcca tcagtagtta ctac                                         24

SEQ ID NO: 139          moltype = AA  length = 8
FEATURE                 Location/Qualifiers
```

```
REGION                  1..8
                        note = Synthetic
source                  1..8
                        mol_type = protein
                        organism = synthetic construct
SEQUENCE: 139
GGSISSYY                                                          8

SEQ ID NO: 140          moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 140
atctattaca gtgggagcac c                                           21

SEQ ID NO: 141          moltype = AA  length = 7
FEATURE                 Location/Qualifiers
REGION                  1..7
                        note = Synthetic
source                  1..7
                        mol_type = protein
                        organism = synthetic construct
SEQUENCE: 141
IYYSGST                                                           7

SEQ ID NO: 142          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 142
gcgagagacc cgctcctcat tgactac                                     27

SEQ ID NO: 143          moltype = AA  length = 9
FEATURE                 Location/Qualifiers
REGION                  1..9
                        note = Synthetic
source                  1..9
                        mol_type = protein
                        organism = synthetic construct
SEQUENCE: 143
ARDPLLIDY                                                         9

SEQ ID NO: 144          moltype = DNA  length = 324
FEATURE                 Location/Qualifiers
misc_feature            1..324
                        note = Synthetic
source                  1..324
                        mol_type = other DNA
                        organism = synthetic construct
SEQUENCE: 144
gaaattgtgt tgacgcagtc tccaggtacc ctgtctttgt ctccagggga aagagccacc  60
ctctcctgca gggccagtca gagtgttagt agaagctact tagcctggta ccagcagaaa  120
cctggccagg ctcccaggct cctcatctat ggtgtatcca gcagggccac tggcatccca  180
gacaggttca gcggcagtgg gtctgggaca gacttcactc tcaccatcag cagactggag  240
cctgaagatt ttgcagtgta ttattgtcag cagtatggta gctcacctca gacttttggc  300
caggggacca agctggagat caaa                                        324

SEQ ID NO: 145          moltype = AA  length = 108
FEATURE                 Location/Qualifiers
REGION                  1..108
                        note = Synthetic
source                  1..108
                        mol_type = protein
                        organism = synthetic construct
SEQUENCE: 145
EIVLTQSPGT LSLSPGERAT LSCRASQSVS RSYLAWYQQK PGQAPRLLIY GVSSRATGIP  60
DRFSGSGSGT DFTLTISRLE PEDFAVYYCQ QYGSSPQTFG QGTKLEIK               108

SEQ ID NO: 146          moltype = DNA  length = 21
FEATURE                 Location/Qualifiers
misc_feature            1..21
                        note = Synthetic
source                  1..21
```

```
                         mol_type = other DNA
                         organism = synthetic construct
SEQUENCE: 146
cagagtgtta gtagaagcta c                                          21

SEQ ID NO: 147           moltype = AA  length = 7
FEATURE                  Location/Qualifiers
REGION                   1..7
                         note = Synthetic
source                   1..7
                         mol_type = protein
                         organism = synthetic construct
SEQUENCE: 147
QSVSRSY                                                          7

SEQ ID NO: 148           moltype =   length =
SEQUENCE: 148
000

SEQ ID NO: 149           moltype =   length =
SEQUENCE: 149
000

SEQ ID NO: 150           moltype = DNA  length = 27
FEATURE                  Location/Qualifiers
misc_feature             1..27
                         note = Synthetic
source                   1..27
                         mol_type = other DNA
                         organism = synthetic construct
SEQUENCE: 150
cagcagtatg gtagctcacc tcagact                                    27

SEQ ID NO: 151           moltype = AA  length = 9
FEATURE                  Location/Qualifiers
REGION                   1..9
                         note = Synthetic
source                   1..9
                         mol_type = protein
                         organism = synthetic construct
SEQUENCE: 151
QQYGSSPQT                                                        9

SEQ ID NO: 152           moltype = DNA  length = 1338
FEATURE                  Location/Qualifiers
misc_feature             1..1338
                         note = Synthetic
source                   1..1338
                         mol_type = other DNA
                         organism = synthetic construct
SEQUENCE: 152
caggtgcagc tgcaggagtc gggcccagga ctggtgaagc cttcggagac cctgtccctc  60
acctgcactg tctctggtgg ctccatcagt agttactact ggagttggat ccggcagccc  120
ccagggaagg gactggagtg gattgggtat atctattaca gtgggagcac caactacaac  180
ccctccctca agagtcgagt caccatatca gtagacacgt ccaagaacca gttctccctg  240
aaactgagct ctgtgaccgc tgcggacacg gccgtgtatt actgtgcgag agacccgctc  300
ctcattgact actggggcca gggaaccctg gtcaccgtct cctcagcctc caccaagggc  360
ccatcggtct tccccctggc accctcctcc aagagcacct ctgggggcac agcggccctg  420
ggctgcctgg tcaaggacta cttccccgaa ccggtgacgg tgtcgtggaa ctcaggcgcc  480
ctgaccagcg gcgtgcacac cttcccggct gtcctacagt cctcaggact ctactccctc  540
agcagcgtgg tgaccgtgcc ctccagcagc ttgggcaccc agacctacat ctgcaacgtg  600
aatcacaagc ccagcaacac caaggtggac aagaaagttg agcccaaatc ttgtgacaaa  660
actcacacat gcccaccgtg cccagcacct gaactcctgg ggggaccgtc agtcttcctc  720
ttccccccaa aacccaagga caccctcatg atctcccgga cccctgaggt cacatgcgtg  780
gtggtggacg tgagccacga agaccctgag gtcaagttca actggtacgt ggacggcgtg  840
gaggtgcata atgccaagac aaagccgcgg gaggagcagt acaacagcac gtaccgtgtg  900
gtcagcgtcc tcaccgtcct gcaccaggac tggctgaatg gcaaggagta caagtgcaag  960
gtctccaaca aagccctccc agcccccatc gagaaaacca tctccaaagc caaagggcag  1020
ccccgagaac cacaggtgta caccctgccc ccatcccggg atgagctgac caagaaccag  1080
gtcagcctga cctgcctggt caaaggcttc tatcccagcg acatcgccgt ggagtgggag  1140
agcaatgggc agccggagaa caactacaag accacgcctc ccgtgctgga ctccgacggc  1200
tccttcttcc tctacagcaa gctcaccgtg gacaagagca ggtggcagca ggggaacgtc  1260
ttctcatgct ccgtgatgca tgaggctctg cacaaccact acacgcagaa gtccctctcc  1320
ctgtctccgg gtaaatga                                              1338

SEQ ID NO: 153           moltype = AA  length = 445
FEATURE                  Location/Qualifiers
REGION                   1..445
                         note = Synthetic
```

```
source                1..445
                      mol_type = protein
                      organism = synthetic construct
SEQUENCE: 153
QVQLQESGPG LVKPSETLSL TCTVSGGSIS SYYWSWIRQP PGKGLEWIGY IYYSGSTNYN  60
PSLKSRVTIS VDTSKNQFSL KLSSVTAADT AVYYCARDPL LIDYWGQGTL VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KKVEPKSCDK THTCPPCPAP ELLGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPGK                                      445

SEQ ID NO: 154        moltype = DNA  length = 648
FEATURE               Location/Qualifiers
misc_feature          1..648
                      note = Synthetic
source                1..648
                      mol_type = other DNA
                      organism = synthetic construct
SEQUENCE: 154
gaaattgtgt tgacgcagtc tccaggtacc ctgtctttgt ctccagggga aagagccacc  60
ctctcctgca gggccagtca gagtgttagt agaagctact tagcctggta ccagcagaaa  120
cctggccagg ctcccaggct cctcatctat ggtgtatcca gcagggccac tggcatccca  180
gacaggttca gcggcagtgg gtctgggaca gacttcactc tcaccatcag cagactggag  240
cctgaagatt ttgcagtgta ttattgtcag cagtatggta gctcacctca gacttttggc  300
caggggacca agctggagat caaacgaact gtggctgcac catctgtctt catcttcccg  360
ccatctgatg agcagttgaa atctggaact gcctctgttg tgtgcctgct gaataacttc  420
tatcccagag aggccaaagt acagtggaag gtggataacg ccctccaatc gggtaactcc  480
caggagagtg tcacagagca ggacagcaag gacagcacct acagcctcag cagcaccctg  540
acgctgagca aagcagacta cgagaaacac aaagtctacg cctgcgaagt cacccatcag  600
ggcctgagct cgcccgtcac aaagagcttc aacaggggag agtgttag              648

SEQ ID NO: 155        moltype = AA  length = 215
FEATURE               Location/Qualifiers
REGION                1..215
                      note = Synthetic
source                1..215
                      mol_type = protein
                      organism = synthetic construct
SEQUENCE: 155
EIVLTQSPGT LSLSPGERAT LSCRASQSVS RSYLAWYQQK PGQAPRLLIY GVSSRATGIP  60
DRFSGSGSGT DFTLTISRLE PEDFAVYYCQ QYGSSPQTFG QGTKLEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                            215

SEQ ID NO: 156        moltype = DNA  length = 1341
FEATURE               Location/Qualifiers
misc_feature          1..1341
                      note = Synthetic
source                1..1341
                      mol_type = other DNA
                      organism = synthetic construct
SEQUENCE: 156
caggtgcagc tggtggagtc tgggggaggc gtggtccagc ctgggaggtc cctgagactc  60
tcctgtgcag cgtctggatt caccttcagt tactatggca tgcactgggt ccgccaggct  120
ccaggcaagg ggctggagtg ggtggcagtt atatggtatg atggaagtaa taaattctat  180
gcagactccg tgaagggccg attcaccatc tccagagaca attccaagaa cacgctgtat  240
ctgcaaatga acagcctgag agccgaggac acggctgtgt attactgtgc ggcagctcgg  300
ccgggctact actacggtat ggacgtctgg ggccaaggga ccacggtcac cgtctcctca  360
gcctccacca agggcccatc ggtcttcccc ctggcgccct gctccaggag cacctccgag  420
agcacagccg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacgaagacc  600
tacacctgca acgtagatca caagcccagc aacaccaagg tggacaagag agttgagtcc  660
aaatatggtc ccccatgccc accgtgccca gcaccaggcg gtggcggacc atcagtcttc  720
ctgttccccc caaaacccaa ggacactctc atgatctccc ggacccctga ggtcacgtgc  780
gtggtggtgg acgtgagcca ggaagacccc gaggtccagt tcaactggta cgtggatggc  840
gtggaggtgc ataatgccaa gacaaagccg cgggaggagc agttcaacag cacgtaccgt  900
gtggtcagcg tcctcaccgt cctgcaccag gactggctga acggcaagga gtacaagtgc  960
aaggtctcca acaaaggcct cccgtcctcc atcgagaaaa ccatctccaa agccaaaggg  1020
cagccccgag agccacaggt gtacaccctg cccccatccc aggaggagat gaccaagaac  1080
caggtcagcc tgacctgcct ggtcaaaggc ttctacccca gcgacatcgc cgtggagtgg  1140
gagagcaatg ggcagccgga gaacaactac aagaccacgc ctcccgtgct ggactccgac  1200
ggctccttct tcctctacag caggctcacc gtggacaaga gcaggtggca ggaggggaat  1260
gtcttctcat gctccgtgat gcatgaggct ctgcacaacc actacacaca gaagtccctc  1320
tccctgtctc tgggtaaatg a                                          1341

SEQ ID NO: 157        moltype = AA  length = 446
```

```
FEATURE              Location/Qualifiers
REGION               1..446
                     note = Synthetic
source               1..446
                     mol_type = protein
                     organism = synthetic construct
SEQUENCE: 157
QVQLVESGGG VVQPGRSLRL SCAASGFTFS YYGMHWVRQA PGKGLEWVAV IWYDGSNKFY  60
ADSVKGRFTI SRDNSKNTLY LQMNSLRAED TAVYYCAAAR PGYYYGMDVW GQGTTVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APGGGGPSVF  240
LFPPKPKDTL MISRTPEVTC VVVDVSQEDP EVQFNWYVDG VEVHNAKTKP REEQFNSTYR  300
VVSVLTVLHQ DWLNGKEYKC KVSNKGLPSS IEKTISKAKG QPREPQVYTL PPSQEEMTKN  360
QVSLTCLVKG FYPSDIAVEW ESNGQPENNY KTTPPVLDSD GSFFLYSRLT VDKSRWQEGN  420
VFSCSVMHEA LHNHYTQKSL SLSLGK                                     446

SEQ ID NO: 158       moltype = DNA  length = 1332
FEATURE              Location/Qualifiers
misc_feature         1..1332
                     note = Synthetic
source               1..1332
                     mol_type = other DNA
                     organism = synthetic construct
SEQUENCE: 158
gaggtgcagc tggtggagtc tggaggaggc ttggtccagc ctgggggggtc cctgagactc  60
tcctgtgcag cctctgggat caccgtcagt agcaactaca tgagctgggt ccgccaggct  120
ccagggaagg ggctggagtg ggtctcagtt atttatagcg gtggtagcac attctacgca  180
gactccgtga agggccgatt caccatctcc agacacaatt ccaagaacac gctgtatctt  240
caaatgaaca gcctgagagc tgaggacacg gccgtgtatt actgtgcgag agaacgtaac  300
tttgatgctt ttgatatctg gggccaaggg acaatggtca ccgtctcttc agcctccacc  360
aagggcccat cggtcttccc cctggcgccc tgctccagga gcacctccga gagcacagcc  420
gccctgggct gcctggtcaa ggactacttc cccgaaccgg tgacggtgtc gtggaactca  480
ggcgccctga ccagcggcgt gcacaccttc ccggctgtcc tacagtcctc aggactctac  540
tccctcagca gcgtggtgac cgtgccctcc agcagcttgg gcacgaagac ctacacctgc  600
aacgtagatc acaagcccag caacaccaag gtggacaaga gagttgagtc caaatatggt  660
cccccatgcc caccgtgccc agcaccaggc ggtggcggac catcagtctt cctgttcccc  720
ccaaaaccca aggacactct catgatctcc cggacccctg aggtcacgtg cgtggtggtg  780
gacgtgagcc aggaagaccc cgaggtccag ttcaactggt acgtggatgg cgtggaggtg  840
cataatgcca agacaaagcc gcgggaggag cagttcaaca gcacgtaccg tgtggtcagc  900
gtcctcaccg tcctgcacca ggactggctg aacggcaagg agtacaagtg caaggtctcc  960
aacaaaggcc tcccgtcctc catcgagaaa accatctcca aagccaaagg gcagccccga  1020
gagccacagg tgtacaccct gcccccatcc caggaggaga tgaccaagaa ccaggtcagc  1080
ctgacctgcc tggtcaaagg cttctacccc agcgacatcg ccgtggagtg ggagagcaat  1140
gggcagccgg agaacaacta caagaccacg cctcccgtgc tggactccga cggctccttc  1200
ttcctctaca gcaggctcac cgtggacaag agcaggtggc aggaggggaa tgtcttctca  1260
tgctccgtga tgcatgaggc tctgcacaac cactacacac agaagtccct ctccctgtct  1320
ctgggtaaat ga                                                    1332

SEQ ID NO: 159       moltype = AA  length = 443
FEATURE              Location/Qualifiers
REGION               1..443
                     note = Synthetic
source               1..443
                     mol_type = protein
                     organism = synthetic construct
SEQUENCE: 159
EVQLVESGGG LVQPGGSLRL SCAASGITVS SNYMSWVRQA PGKGLEWVSV IYSGGSTFYA  60
DSVKGRFTIS RHNSKNTLYL QMNSLRAEDT AVYYCARERN FDAFDIWGQG TMVTVSSAST  120
KGPSVFPLAP CSRSTSESTA ALGCLVKDYF PEPVTVSWNS GALTSGVHTF PAVLQSSGLY  180
SLSSVVTVPS SSLGTKTYTC NVDHKPSNTK VDKRVESKYG PPCPPCPAPG GGGPSVFLFP  240
PKPKDTLMIS RTPEVTCVVV DVSQEDPEVQ FNWYVDGVEV HNAKTKPREE QFNSTYRVVS  300
VLTVLHQDWL NGKEYKCKVS NKGLPSSIEK TISKAKGQPR EPQVYTLPPS QEEMTKNQVS  360
LTCLVKGFYP SDIAVEWESN GQPENNYKTT PPVLDSDGSF FLYSRLTVDK SRWQEGNVFS  420
CSVMHEALHN HYTQKSLSLS LGK                                        443

SEQ ID NO: 160       moltype = DNA  length = 1338
FEATURE              Location/Qualifiers
misc_feature         1..1338
                     note = Synthetic
source               1..1338
                     mol_type = other DNA
                     organism = synthetic construct
SEQUENCE: 160
gaggtgcagc tggtggagtc tgggggaggc ttggtacagc ctggagggtc cctgagactc  60
tcctgtgcag cctctggatt caccttcagt atttatgaaa tgaactgggt ccgccaggct  120
ccagggaagg ggctggagtg ggtttcatac attactagta gtggtactac catatactac  180
gcagactctg tgaagggccg attcaccatc tccagagaca acgccaagaa ctcactgtat  240
ctgcaaatga acagcctgag agccgaggac acggctgttt attactgtgc gagtagcagc  300
tcgtccgggt actactttga ctactggggc cagggaaccc tggtcaccgt ctcctcagcc  360
```

```
tccaccaagg gcccatcggt cttccccctg gcgccctgct ccaggagcac ctccgagagc  420
acagccgccc tgggctgcct ggtcaaggac tacttccccg aaccggtgac ggtgtcgtgg  480
aactcaggcg ccctgaccag cggcgtgcac accttcccgg ctgtcctaca gtcctcagga  540
ctctactccc tcagcagcgt ggtgaccgtg ccctccagca gcttgggcac gaagacctac  600
acctgcaacg tagatcacaa gcccagcaac accaaggtgg acaagagagt tgagtccaaa  660
tatggtcccc catgcccacc gtgcccagca ccaggcggtg gcggaccatc agtcttcctg  720
ttccccccaa aacccaagga cactctcatg atctcccgga cccctgaggt cacgtgcgtg  780
gtggtggacg tgagccagga agaccccgag gtccagttca actggtacgt ggatggcgtg  840
gaggtgcata atgccaagac aaagccgcgg gaggagcagt tcaacagcac gtaccgtgtg  900
gtcagcgtcc tcaccgtcct gcaccaggac tggctgaacg gcaaggagta caagtgcaag  960
gtctccaaca aaggcctccc gtcctccatc gagaaaacca tctccaaagc caaagggcag  1020
ccccgagagc cacaggtgta caccctgccc ccatcccagg aggagatgac caagaaccag  1080
gtcagcctga cctgcctggt caaaggcttc taccccagcg acatcgccgt ggagtgggag  1140
agcaatgggc agccggagaa caactacaag accacgcctc ccgtgctgga ctccgacggc  1200
tccttcttcc tctacagcag gctcaccgtg gacaagagca ggtggcagga ggggaatgtc  1260
ttctcatgct ccgtgatgca tgaggctctg cacaaccact acacacagaa gtccctctcc  1320
ctgtctctgg gtaaatga                                                1338

SEQ ID NO: 161         moltype = AA  length = 445
FEATURE                Location/Qualifiers
REGION                 1..445
                       note = Synthetic
source                 1..445
                       mol_type = protein
                       organism = synthetic construct
SEQUENCE: 161
EVQLVESGGG LVQPGGSLRL SCAASGFTFS IYEMNWVRQA PGKGLEWVSY ITSSGTTIYY  60
ADSVKGRFTI SRDNAKNSLY LQMNSLRAED TAVYYCASSS SSGYYFDYWG QGTLVTVSSA  120
STKGPSVFPL APCSRSTSES TAALGCLVKD YFPEPVTVSW NSGALTSGVH TFPAVLQSSG  180
LYSLSSVVTV PSSSLGTKTY TCNVDHKPSN TKVDKRVESK YGPPCPPCPA PGGGGPSVFL  240
FPPKPKDTLM ISRTPEVTCV VVDVSQEDPE VQFNWYVDGV EVHNAKTKPR EEQFNSTYRV  300
VSVLTVLHQD WLNGKEYKCK VSNKGLPSSI EKTISKAKGQ PREPQVYTLP PSQEEMTKNQ  360
VSLTCLVKGF YPSDIAVEWE SNGQPENNYK TTPPVLDSDG SFFLYSRLTV DKSRWQEGNV  420
FSCSVMHEAL HNHYTQKSLS LSLGK                                        445

SEQ ID NO: 162         moltype = DNA  length = 1344
FEATURE                Location/Qualifiers
misc_feature           1..1344
                       note = Synthetic
source                 1..1344
                       mol_type = other DNA
                       organism = synthetic construct
SEQUENCE: 162
caggtgcagc tggtgcagtc tggggctgag gtgaagaagc ctggggcctc agtgaaggtc  60
tcctgcaagg cttctggata caccttcatt aactactata tacactgggt gcgacaggcc  120
cctggacaag ggcttgagtg gatgggatgg atcaacccta acagtggtgg cacaaactat  180
gcacagaagt ttcagggcag ggtcaccatg accagggaca cgtccatcag cacagcctac  240
atggagctga gcaggctgag atctgacgac acggccgtgt attactgtgc gattattacg  300
atttttggag tggttacctg gttcgacccc tggggccagg gaaccctggt caccgtctcc  360
tcagcctcca ccaagggccc atcggtcttc cccctggcgc cctgctccag gagcacctcc  420
gagagcacag ccgccctggg ctgcctggtc aaggactact tccccgaacc ggtgacggtg  480
tcgtggaact caggcgccct gaccagcggc gtgcacacct tcccggctgt cctacagtcc  540
tcaggactct actccctcag cagcgtggtg accgtgccct ccagcagctt gggcacgaag  600
acctacacct gcaacgtaga tcacaagccc agcaacacca aggtggacaa gagagttgag  660
tccaaatatg gtcccccatg cccaccgtgc ccagcaccag gcggtggcgg accatcagtc  720
ttcctgttcc ccccaaaacc caaggacact ctcatgatct cccggacccc tgaggtcacg  780
tgcgtggtgg tggacgtgag ccaggaagac cccgaggtcc agttcaactg gtacgtggat  840
ggcgtggagg tgcataatgc caagacaaag ccgcgggagg agcagttcaa cagcacgtac  900
cgtgtggtca gcgtcctcac cgtcctgcac caggactggc tgaacggcaa ggagtacaag  960
tgcaaggtct ccaacaaagg cctcccgtcc tccatcgaga aaaccatctc caaagccaaa  1020
gggcagcccc gagagccaca ggtgtacacc ctgcccccat cccaggagga gatgaccaag  1080
aaccaggtca gcctgacctg cctggtcaaa ggcttctacc ccagcgacat cgccgtggag  1140
tgggagagca atgggcagcc ggagaacaac tacaagacca cgcctcccgt gctggactcc  1200
gacggctcct tcttcctcta cagcaggctc accgtggaca agagcaggtg gcaggagggg  1260
aatgtcttct catgctccgt gatgcatgag gctctgcaca accactacac acagaagtcc  1320
ctctccctgt ctctgggtaa atga                                         1344

SEQ ID NO: 163         moltype = AA  length = 447
FEATURE                Location/Qualifiers
REGION                 1..447
                       note = Synthetic
source                 1..447
                       mol_type = protein
                       organism = synthetic construct
SEQUENCE: 163
QVQLVQSGAE VKKPGASVKV SCKASGYTFI NYYIHWVRQA PGQGLEWMGW INPNSGGTNY  60
AQKFQGRVTM TRDTSISTAY MELSRLRSDD TAVYYCAIIT IFGVVTWFDP WGQGTLVTVS  120
SASTKGPSVF PLAPCSRSTS ESTAALGCLV KDYFPEPVTV SWNSGALTSG VHTFPAVLQS  180
SGLYSLSSVV TVPSSSLGTK TYTCNVDHKP SNTKVDKRVE SKYGPPCPPC PAPGGGGPSV  240
```

-continued

```
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGK                                      447

SEQ ID NO: 164         moltype = DNA  length = 1326
FEATURE                Location/Qualifiers
misc_feature           1..1326
                       note = Synthetic
source                 1..1326
                       mol_type = other DNA
                       organism = synthetic construct
SEQUENCE: 164
caggtgcagc tgcaggagtc gggcccagga ctggtgaagc cttcggagac cctgtccctc  60
acctgcactg tctctggtgg ctccatcagt agttactact ggagttggat ccggcagccc  120
ccagggaagg gactggagtg gattgggtat atctattaca gtgggagcac caactacaac  180
ccctccctca agagtcgagt caccatatca gtagacacgt ccaagaacca gttctccctg  240
aaactgagct ctgtgaccgc tgcggacacg gccgtgtatt actgtgcgag agacccgctc  300
ctcattgact actggggcca gggaaccctg gtcaccgtct cctcagcctc caccaagggc  360
ccatcggtct tccccctggc gccctgctcc aggagcacct ccgagagcac agccgccctg  420
ggctgcctgg tcaaggacta cttccccgaa ccggtgacgg tgtcgtggaa ctcaggcgcc  480
ctgaccagcg gcgtgcacac cttcccggct gtcctacagt cctcaggact ctactccctc  540
agcagcgtgg tgaccgtgcc ctccagcagc ttgggcacga agacctacac ctgcaacgta  600
gatcacaagc ccagcaacac caaggtggac aagagagttg agtccaaata tggtccccca  660
tgcccaccgt gcccagcacc aggcggtggc ggaccatcag tcttcctgtt ccccccaaaa  720
cccaaggaca ctctcatgat ctcccggacc cctgaggtca cgtgcgtggt ggtggacgtg  780
agccaggaag accccgaggt ccagttcaac tggtacgtgg atggcgtgga ggtgcataat  840
gccaagacaa agccgcggga ggagcagttc aacagcacgt accgtgtggt cagcgtcctc  900
accgtcctgc accaggactg gctgaacggc aaggagtaca agtgcaaggt ctccaacaaa  960
ggcctcccgt cctccatcga gaaaaccatc tccaaagcca aagggcagcc ccgagagcca  1020
caggtgtaca ccctgccccc atcccaggag gagatgacca agaaccaggt cagcctgacc  1080
tgcctggtca aaggcttcta ccccagcgac atcgccgtgg agtgggagag caatgggcag  1140
ccggagaaca actacaagac cacgcctccc gtgctggact ccgacggctc cttcttcctc  1200
tacagcaggc tcaccgtgga caagagcagg tggcaggagg ggaatgtctt ctcatgctcc  1260
gtgatgcatg aggctctgca caaccactac acacagaagt ccctctccct gtctctgggt  1320
aaatga                                                             1326

SEQ ID NO: 165         moltype = AA  length = 441
FEATURE                Location/Qualifiers
REGION                 1..441
                       note = Synthetic
source                 1..441
                       mol_type = protein
                       organism = synthetic construct
SEQUENCE: 165
QVQLQESGPG LVKPSETLSL TCTVSGGSIS SYYWSWIRQP PGKGLEWIGY IYYSGSTNYN  60
PSLKSRVTIS VDTSKNQFSL KLSSVTAADT AVYYCARDPL LIDYWGQGTL VTVSSASTKG  120
PSVFPLAPCS RSTSESTAAL GCLVKDYFPE PVTVSWNSGA LTSGVHTFPA VLQSSGLYSL  180
SSVVTVPSSS LGTKTYTCNV DHKPSNTKVD KRVESKYGPP CPPCPAPGGG GPSVFLFPPK  240
PKDTLMISRT PEVTCVVVDV SQEDPEVQFN WYVDGVEVHN AKTKPREEQF NSTYRVVSVL  300
TVLHQDWLNG KEYKCKVSNK GLPSSIEKTI SKAKGQPREP QVYTLPPSQE EMTKNQVSLT  360
CLVKGFYPSD IAVEWESNGQ PENNYKTTPP VLDSDGSFFL YSRLTVDKSR WQEGNVFSCS  420
VMHEALHNHY TQKSLSLSLG K                                            441

SEQ ID NO: 166         moltype = DNA  length = 375
FEATURE                Location/Qualifiers
misc_feature           1..375
                       note = Synthetic
source                 1..375
                       mol_type = other DNA
                       organism = synthetic construct
SEQUENCE: 166
gaagtgcagc tggtggagtc tgggggaggc ttggtacagc ctggcaggtc cctgagactc  60
tcctgtgcag cctctggatt cacctttgat gattatgcca tgtactgggt ccggcaagct  120
ccagggaagg gcctggagtg ggtctcaggt attagttgga atagtggtag cataggctat  180
gcggactctg tgaagggccg attcaccatc tccagagaca acgccaagaa ctccctgtat  240
ctgcaaatga acagtctgag agctgcggac acggccttgt attactgtgc aaaagataaa  300
gactggaact cgagaggtta ctactactac ggtatggacg tctggggcca agggaccacg  360
gtcaccgtct cctca                                                   375

SEQ ID NO: 167         moltype = AA  length = 125
FEATURE                Location/Qualifiers
REGION                 1..125
                       note = Synthetic
source                 1..125
                       mol_type = protein
                       organism = synthetic construct
SEQUENCE: 167
EVQLVESGGG LVQPGRSLRL SCAASGFTFD DYAMYWVRQA PGKGLEWVSG ISWNSGSIGY  60
```

-continued

```
ADSVKGRFTI SRDNAKNSLY LQMNSLRAAD TALYYCAKDK DWNSRGYYYY GMDVWGQGTT  120
VTVSS                                                              125

SEQ ID NO: 168         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 168
ggattcacct ttgatgatta tgcc                                         24

SEQ ID NO: 169         moltype = AA  length = 8
FEATURE                Location/Qualifiers
REGION                 1..8
                       note = Synthetic
source                 1..8
                       mol_type = protein
                       organism = synthetic construct
SEQUENCE: 169
GFTFDDYA                                                           8

SEQ ID NO: 170         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 170
attagttgga atagtggtag cata                                         24

SEQ ID NO: 171         moltype = AA  length = 8
FEATURE                Location/Qualifiers
REGION                 1..8
                       note = Synthetic
source                 1..8
                       mol_type = protein
                       organism = synthetic construct
SEQUENCE: 171
ISWNSGSI                                                           8

SEQ ID NO: 172         moltype = DNA  length = 54
FEATURE                Location/Qualifiers
misc_feature           1..54
                       note = Synthetic
source                 1..54
                       mol_type = other DNA
                       organism = synthetic construct
SEQUENCE: 172
gcaaaagata aagactggaa ctcgagaggt tactactact acggtatgga cgtc        54

SEQ ID NO: 173         moltype = AA  length = 18
FEATURE                Location/Qualifiers
REGION                 1..18
                       note = Synthetic
source                 1..18
                       mol_type = protein
                       organism = synthetic construct
SEQUENCE: 173
AKDKDWNSRG YYYYGMDV                                                18

SEQ ID NO: 174         moltype = DNA  length = 321
FEATURE                Location/Qualifiers
misc_feature           1..321
                       note = Synthetic
source                 1..321
                       mol_type = other DNA
                       organism = synthetic construct
SEQUENCE: 174
gatgttgtga tgacccagtc tccatcctcc ctgtctgcat ctgtaggaga cagagtcacc  60
atcacttgcc gggcaagtca gagcattagc agctatttaa attggtatca gcagaaacca  120
gggaaagccc ctaagctcct gatctatgct gcatccagtt tgcaaagtgg ggtcccatca  180
aggttcagtg gcagtggatc tgggacagat ttcactctca ccatcagcag tctgcaacct  240
gaagattttg caacttacta ctgtcaacag agttacatta ctccgtacac ttttggccag  300
gggaccaagg tggagatcaa a                                            321

SEQ ID NO: 175         moltype = AA  length = 107
```

-continued

```
FEATURE                 Location/Qualifiers
REGION                  1..107
                        note = Synthetic
source                  1..107
                        mol_type = protein
                        organism = synthetic construct
SEQUENCE: 175
DVVMTQSPSS LSASVGDRVT ITCRASQSIS SYLNWYQQKP GKAPKLLIYA ASSLQSGVPS  60
RFSGSGSGTD FTLTISSLQP EDFATYYCQQ SYITPYTFGQ GTKVEIK                107

SEQ ID NO: 176          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 176
caacagagtt acattactcc gtacact                                      27

SEQ ID NO: 177          moltype = AA  length = 9
FEATURE                 Location/Qualifiers
REGION                  1..9
                        note = Synthetic
source                  1..9
                        mol_type = protein
                        organism = synthetic construct
SEQUENCE: 177
QQSYITPYT                                                          9

SEQ ID NO: 178          moltype = DNA  length = 1368
FEATURE                 Location/Qualifiers
misc_feature            1..1368
                        note = Synthetic
source                  1..1368
                        mol_type = other DNA
                        organism = synthetic construct
SEQUENCE: 178
gaagtgcagc tggtggagtc tgggggaggc ttggtacagc ctggcaggtc cctgagactc  60
tcctgtgcag cctctggatt cacctttgat gattatgcca tgtactgggt ccggcaagct  120
ccagggaagg gcctggagtg ggtctcaggt attagttgga atagtggtag cataggctat  180
gcggactctg tgaagggccg attcaccatc tccagagaca acgccaagaa ctccctgtat  240
ctgcaaatga acagtctgag agctgcggac acggccttgt attactgtgc aaaagataaa  300
gactggaact cgagaggtta ctactactac ggtatggacg tctggggcca agggaccacg  360
gtcaccgtct cctcagcctc caccaagggc ccatcggtct tccccctggc accctcctcc  420
aagagcacct ctgggggcac agcggccctg ggctgcctgg tcaaggacta cttccccgaa  480
ccggtgacgg tgtcgtggaa ctcaggcgcc ctgaccagcg gcgtgcacac cttcccggct  540
gtcctacagt cctcaggact ctactccctc agcagcgtgg tgaccgtgcc ctccagcagc  600
ttgggcaccc agacctacat ctgcaacgtg aatcacaagc ccagcaacac caaggtggac  660
aagaaagttg agcccaaatc ttgtgacaaa actcacacat gcccaccgtg cccagcacct  720
gaactcctgg ggggaccgtc agtcttcctc ttccccccaa aacccaagga caccctcatg  780
atctcccgga cccctgaggt cacatgcgtg gtggtggacg tgagccacga agaccctgag  840
gtcaagttca actggtacgt ggacggcgtg gaggtgcata atgccaagac aaagccgcgg  900
gaggagcagt acaacagcac gtaccgtgtg gtcagcgtcc tcaccgtcct gcaccaggac  960
tggctgaatg gcaaggagta caagtgcaag gtctccaaca aagccctccc agcccccatc  1020
gagaaaacca tctccaaagc caaagggcag ccccgagaac cacaggtgta caccctgccc  1080
ccatcccggg atgagctgac caagaaccag gtcagcctga cctgcctggt caaaggcttc  1140
tatcccagcg acatcgccgt ggagtgggag agcaatgggc agccggagaa caactacaag  1200
accacgcctc ccgtgctgga ctccgacggc tccttcttcc tctacagcaa gctcaccgtg  1260
gacaagagca ggtggcagca ggggaacgtc ttctcatgct ccgtgatgca tgaggctctg  1320
cacaaccact acacgcagaa gtccctctcc ctgtctccgg gtaaatga                1368

SEQ ID NO: 179          moltype = AA  length = 455
FEATURE                 Location/Qualifiers
REGION                  1..455
                        note = Synthetic
source                  1..455
                        mol_type = protein
                        organism = synthetic construct
SEQUENCE: 179
EVQLVESGGG LVQPGRSLRL SCAASGFTFD DYAMYWVRQA PGKGLEWVSG ISWNSGSIGY  60
ADSVKGRFTI SRDNAKNSLY LQMNSLRAAD TALYYCAKDK DWNSRGYYYY GMDVWGQGTT  120
VTVSSASTKG PSVFPLAPSS KSTSGGTAAL GCLVKDYFPE PVTVSWNSGA LTSGVHTFPA  180
VLQSSGLYSL SSVVTVPSSS LGTQTYICNV NHKPSNTKVD KKVEPKSCDK THTCPPCPAP  240
ELLGGPSVFL FPPKPKDTLM ISRTPEVTCV VVDVSHEDPE VKFNWYVDGV EVHNAKTKPR  300
EEQYNSTYRV VSVLTVLHQD WLNGKEYKCK VSNKALPAPI EKTISKAKGQ PREPQVYTLP  360
PSRDELTKNQ VSLTCLVKGF YPSDIAVEWE SNGQPENNYK TTPPVLDSDG SFFLYSKLTV  420
DKSRWQQGNV FSCSVMHEAL HNHYTQKSLS LSPGK                             455
```

-continued

```
SEQ ID NO: 180          moltype = DNA  length = 645
FEATURE                 Location/Qualifiers
misc_feature            1..645
                        note = Synthetic
source                  1..645
                        mol_type = other DNA
                        organism = synthetic construct
SEQUENCE: 180
gatgttgtga tgacccagtc tccatcctcc ctgtctgcat ctgtaggaga cagagtcacc  60
atcacttgcc gggcaagtca gagcattagc agctatttaa attggtatca gcagaaacca  120
gggaaagccc ctaagctcct gatctatgct gcatccagtt tgcaaagtgg ggtcccatca  180
aggttcagtg gcagtggatc tgggacagat ttcactctca ccatcagcag tctgcaacct  240
gaagattttg caacttacta ctgtcaacag agttacatta ctccgtacac ttttggccag  300
gggaccaagg tggagatcaa acgaactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttag                  645

SEQ ID NO: 181          moltype = AA  length = 214
FEATURE                 Location/Qualifiers
REGION                  1..214
                        note = Synthetic
source                  1..214
                        mol_type = protein
                        organism = synthetic construct
SEQUENCE: 181
DVVMTQSPSS LSASVGDRVT ITCRASQSIS SYLNWYQQKP GKAPKLLIYA ASSLQSGVPS  60
RFSGSGSGTD FTLTISSLQP EDFATYYCQQ SYITPYTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 182          moltype = DNA  length = 1356
FEATURE                 Location/Qualifiers
misc_feature            1..1356
                        note = Synthetic
source                  1..1356
                        mol_type = other DNA
                        organism = synthetic construct
SEQUENCE: 182
gaagtgcagc tggtggagtc tgggggaggc ttggtacagc ctggcaggtc cctgagactc  60
tcctgtgcag cctctggatt cacctttgat gattatgcca tgtactgggt ccggcaagct  120
ccagggaagg gcctggagtg ggtctcaggt attagttgga atagtggtag cataggctat  180
gcggactctg tgaagggccg attcaccatc tccagagaca acgccaagaa ctccctgtat  240
ctgcaaatga acagtctgag agctgcggac acggccttgt attactgtgc aaaagataaa  300
gactggaact cgagaggtta ctactactac ggtatggacg tctggggcca agggaccacg  360
gtcaccgtct cctcagcctc caccaagggc ccatcggtct tccccctggc gccctgctcc  420
aggagcacct ccgagagcac agccgccctg ggctgcctgg tcaaggacta cttccccgaa  480
ccggtgacgg tgtcgtggaa ctcaggcgcc ctgaccagcg gcgtgcacac cttcccggct  540
gtcctacagt cctcaggact ctactccctc agcagcgtgg tgaccgtgcc ctccagcagc  600
ttgggcacga agacctacac ctgcaacgta gatcacaagc ccagcaacac caaggtggac  660
aagagagttg agtccaaata tggtccccca tgcccaccgt gcccagcacc aggcggtggc  720
ggaccatcag tcttcctgtt ccccccaaaa cccaaggaca ctctcatgat ctcccggacc  780
cctgaggtca cgtgcgtggt ggtggacgtg agccaggaag accccgaggt ccagttcaac  840
tggtacgtgg atggcgtgga ggtgcataat gccaagacaa agccgcggga ggagcagttc  900
aacagcacgt accgtgtggt cagcgtcctc accgtcctgc accaggactg gctgaacggc  960
aaggagtaca agtgcaaggt ctccaacaaa ggcctcccgt cctccatcga gaaaaccatc  1020
tccaaagcca aagggcagcc ccgagagcca caggtgtaca ccctgccccc atcccaggag  1080
gagatgacca agaaccaggt cagcctgacc tgcctggtca aaggcttcta ccccagcgac  1140
atcgccgtgg agtgggagag caatgggcag ccggagaaca actacaagac cacgcctccc  1200
gtgctggact ccgacggctc cttcttcctc tacagcaggc tcaccgtgga caagagcagg  1260
tggcaggagg ggaatgtctt ctcatgctcc gtgatgcatg aggctctgca caaccactac  1320
acacagaagt ccctctccct gtctctgggt aaatga                            1356

SEQ ID NO: 183          moltype = AA  length = 451
FEATURE                 Location/Qualifiers
REGION                  1..451
                        note = Synthetic
source                  1..451
                        mol_type = protein
                        organism = synthetic construct
SEQUENCE: 183
EVQLVESGGG LVQPGRSLRL SCAASGFTFD DYAMYWVRQA PGKGLEWVSG ISWNSGSIGY  60
ADSVKGRFTI SRDNAKNSLY LQMNSLRAAD TALYYCAKDK DWNSRGYYYY GMDVWGQGTT  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPGGG  240
GPSVFLFPPK PKDTLMISRT PEVTCVVVDV SQEDPEVQFN WYVDGVEVHN AKTKPREEQF  300
NSTYRVVSVL TVLHQDWLNG KEYKCKVSNK GLPSSIEKTI SKAKGQPREP QVYTLPPSQE  360
```

-continued

```
EMTKNQVSLT CLVKGFYPSD IAVEWESNGQ PENNYKTTPP VLDSDGSFFL YSRLTVDKSR  420
WQEGNVFSCS VMHEALHNHY TQKSLSLSLG K                                451

SEQ ID NO: 184         moltype = DNA  length = 348
FEATURE                Location/Qualifiers
misc_feature           1..348
                       note = Synthetic
source                 1..348
                       mol_type = other DNA
                       organism = synthetic construct
SEQUENCE: 184
gaggtgcagc tggtggagtc tggaggaggc ttggtccagt ctggggggtc cctgagactc  60
tcctgtgcag cctctgggct caccgtcagt agcaactaca tgagctgggt ccgccaggct  120
ccagggaagg gactggagtg ggtctcagtt atttatagcg gtggtagcac attctactca  180
gactccgtga agggccgatt caccatctcc agacacaatt ccaagaacac gctgtatctt  240
caaatgaaca gcctgagagc tgaggacacg gccgtgtatt actgtgcgag agcgagggga  300
gacgcttttg atatctgggg ccaagggaca atggtcaccg tctcttca              348

SEQ ID NO: 185         moltype = AA  length = 116
FEATURE                Location/Qualifiers
REGION                 1..116
                       note = Synthetic
source                 1..116
                       mol_type = protein
                       organism = synthetic construct
SEQUENCE: 185
EVQLVESGGG LVQSGGSLRL SCAASGLTVS SNYMSWVRQA PGKGLEWVSV IYSGGSTFYS  60
DSVKGRFTIS RHNSKNTLYL QMNSLRAEDT AVYYCARARG DAFDIWGQGT MVTVSS      116

SEQ ID NO: 186         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 186
gggctcaccg tcagtagcaa ctac                                        24

SEQ ID NO: 187         moltype = AA  length = 8
FEATURE                Location/Qualifiers
REGION                 1..8
                       note = Synthetic
source                 1..8
                       mol_type = protein
                       organism = synthetic construct
SEQUENCE: 187
GLTVSSNY                                                          8

SEQ ID NO: 188         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 188
gcgagagcga ggggagacgc ttttgatatc                                  30

SEQ ID NO: 189         moltype = AA  length = 10
FEATURE                Location/Qualifiers
REGION                 1..10
                       note = Synthetic
source                 1..10
                       mol_type = protein
                       organism = synthetic construct
SEQUENCE: 189
ARARGDAFDI                                                        10

SEQ ID NO: 190         moltype = DNA  length = 324
FEATURE                Location/Qualifiers
misc_feature           1..324
                       note = Synthetic
source                 1..324
                       mol_type = other DNA
                       organism = synthetic construct
SEQUENCE: 190
gacatccaga tgacccagtc tccatcctcc ctgtctgcat ctgtgggaga cagagtcacc  60
atcacttgcc aggcgagtca gggcattagc aactatttaa attggtatca gcagaaacca  120
```

```
gggaaagccc ctaaactcct gatctccgat gcatccaatt tggaaacagg ggtcccatca  180
aggttcagtg gaagtggatc tgggacagat tttactttca ccatcagcag cctgcagcct  240
gaggatattg caacatatta ctgtcaacag tatgataatc tccgcttttt cactttcggc  300
cctgggacca aagtggatat caaa                                          324

SEQ ID NO: 191          moltype = AA  length = 108
FEATURE                 Location/Qualifiers
REGION                  1..108
                        note = Synthetic
source                  1..108
                        mol_type = protein
                        organism = synthetic construct
SEQUENCE: 191
DIQMTQSPSS LSASVGDRVT ITCQASQGIS NYLNWYQQKP GKAPKLLISD ASNLETGVPS  60
RFSGSGSGTD FTFTISSLQP EDIATYYCQQ YDNLRFFTFG PGTKVDIK                108

SEQ ID NO: 192          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 192
cagggcatta gcaactat                                                 18

SEQ ID NO: 193          moltype =   length =
SEQUENCE: 193
000

SEQ ID NO: 194          moltype =   length =
SEQUENCE: 194
000

SEQ ID NO: 195          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 195
caacagtatg ataatctccg ctttttcact                                    30

SEQ ID NO: 196          moltype = AA  length = 10
FEATURE                 Location/Qualifiers
REGION                  1..10
                        note = Synthetic
source                  1..10
                        mol_type = protein
                        organism = synthetic construct
SEQUENCE: 196
QQYDNLRFFT                                                          10

SEQ ID NO: 197          moltype = DNA  length = 1341
FEATURE                 Location/Qualifiers
misc_feature            1..1341
                        note = Synthetic
source                  1..1341
                        mol_type = other DNA
                        organism = synthetic construct
SEQUENCE: 197
gaggtgcagc tggtggagtc tggaggaggc ttggtccagt ctgggggggtc cctgagactc  60
tcctgtgcag cctctgggct caccgtcagt agcaactaca tgagctgggt ccgccaggct  120
ccagggaagg gactggagtg ggtctcagtt atttatagcg gtggtagcac attctactca  180
gactccgtga agggccgatt caccatctcc agacacaatt ccaagaacac gctgtatctt  240
caaatgaaca gcctgagagc tgaggacacg gccgtgtatt actgtgcgag agcgagggga  300
gacgcttttg atatctgggg ccaagggaca atggtcaccg tctcttcagc ctccaccaag  360
ggcccatcgg tcttccccct ggcaccctcc tccaagagca cctctggggg cacagcggcc  420
ctgggctgcc tggtcaagga ctacttcccc gaaccggtga cggtgtcgtg gaactcaggc  480
gccctgacca gcggcgtgca caccttcccg gctgtcctac agtcctcagg actctactcc  540
ctcagcagcg tggtgaccgt gccctccagc agcttgggca cccagaccta catctgcaac  600
gtgaatcaca agcccagcaa caccaaggtg gacaagaaag ttgagcccaa atcttgtgac  660
aaaactcaca catgcccacc gtgcccagca cctgaactcc tggggggacc gtcagtcttc  720
ctcttccccc caaaacccaa ggacaccctc atgatctccc ggacccctga ggtcacatgc  780
gtggtggtgg acgtgagcca cgaagaccct gaggtcaagt tcaactggta cgtggacggc  840
gtggaggtgc ataatgccaa gacaaagccg cgggaggagc agtacaacag cacgtaccgt  900
gtggtcagcg tcctcaccgt cctgcaccag gactggctga atggcaagga gtacaagtgc  960
aaggtctcca acaaagccct cccagccccc atcgagaaaa ccatctccaa agccaaaggg  1020
```

```
cagccccgag aaccacaggt gtacaccctg cccccatccc gggatgagct gaccaagaac  1080
caggtcagcc tgacctgcct ggtcaaaggc ttctatccca gcgacatcgc cgtggagtgg  1140
gagagcaatg ggcagccgga gaacaactac aagaccacgc ctcccgtgct ggactccgac  1200
ggctccttct tcctctacag caagctcacc gtggacaaga gcaggtggca gcaggggaac  1260
gtcttctcat gctccgtgat gcatgaggct ctgcacaacc actacacgca gaagtccctc  1320
tccctgtctc cgggtaaatg a                                            1341

SEQ ID NO: 198         moltype = AA  length = 446
FEATURE                Location/Qualifiers
REGION                 1..446
                       note = Synthetic
source                 1..446
                       mol_type = protein
                       organism = synthetic construct
SEQUENCE: 198
EVQLVESGGG LVQSGGSLRL SCAASGLTVS SNYMSWVRQA PGKGLEWVSV IYSGGSTFYS  60
DSVKGRFTIS RHNSKNTLYL QMNSLRAEDT AVYYCARARG DAFDIWGQGT MVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSRDELTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGK                                       446

SEQ ID NO: 199         moltype = DNA  length = 648
FEATURE                Location/Qualifiers
misc_feature           1..648
                       note = Synthetic
source                 1..648
                       mol_type = other DNA
                       organism = synthetic construct
SEQUENCE: 199
gacatccaga tgacccagtc tccatcctcc ctgtctgcat ctgtgggaga cagagtcacc  60
atcacttgcc aggcgagtca gggcattagc aactatttaa attggtatca gcagaaacca  120
gggaaagccc ctaaactcct gatctccgat gcatccaatt tggaaacagg ggtcccatca  180
aggttcagtg gaagtggatc tgggacagat tttactttca ccatcagcag cctgcagcct  240
gaggatattg caacatatta ctgtcaacag tatgataatc tccgcttttt cactttcggc  300
cctgggacca aagtggatat caaacgaact gtggctgcac catctgtctt catcttcccg  360
ccatctgatg agcagttgaa atctggaact gcctctgttg tgtgcctgct gaataacttc  420
tatcccagag aggccaaagt acagtggaag gtggataacg ccctccaatc gggtaactcc  480
caggagagtg tcacagagca ggacagcaag gacagcacct acagcctcag cagcaccctg  540
acgctgagca aagcagacta cgagaaacac aaagtctacg cctgcgaagt cacccatcag  600
ggcctgagct cgcccgtcac aaagagcttc aacaggggag agtgttag                648

SEQ ID NO: 200         moltype = AA  length = 215
FEATURE                Location/Qualifiers
REGION                 1..215
                       note = Synthetic
source                 1..215
                       mol_type = protein
                       organism = synthetic construct
SEQUENCE: 200
DIQMTQSPSS LSASVGDRVT ITCQASQGIS NYLNWYQQKP GKAPKLLISD ASNLETGVPS  60
RFSGSGSGTD FTFTISSLQP EDIATYYCQQ YDNLRFFTFG PGTKVDIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                              215

SEQ ID NO: 201         moltype = DNA  length = 360
FEATURE                Location/Qualifiers
misc_feature           1..360
                       note = Synthetic
source                 1..360
                       mol_type = other DNA
                       organism = synthetic construct
SEQUENCE: 201
caggtgcagc tggtggagtc tgggggaggc ttggtcaagc ctggagggtc cctgagactc  60
tcctgtgcag cctctggatt caccttcagt gactactaca tgagctggat ccgccaggct  120
ccagggaagg ggctggagtg ggtttcatac attacttata gtggtagtac catatactac  180
gcagactctg tgaagggccg attcaccatc tccagggaca acgccaagag ctcactgtat  240
ctgcaaatga acagcctgag agccgaggac acggccgtgt attactgtgc gagagatcgc  300
ggtacaacta tggtcccctt tgactactgg ggccagggaa ccctggtcac cgtctcctca  360

SEQ ID NO: 202         moltype = AA  length = 120
FEATURE                Location/Qualifiers
REGION                 1..120
                       note = Synthetic
source                 1..120
                       mol_type = protein
                       organism = synthetic construct
```

```
SEQUENCE: 202
QVQLVESGGG LVKPGGSLRL SCAASGFTFS DYYMSWIRQA PGKGLEWVSY ITYSGSTIYY  60
ADSVKGRFTI SRDNAKSSLY LQMNSLRAED TAVYYCARDR GTTMVPFDYW GQGTLVTVSS  120

SEQ ID NO: 203         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 203
ggattcacct tcagtgacta ctac                                        24

SEQ ID NO: 204         moltype = AA  length = 8
FEATURE                Location/Qualifiers
REGION                 1..8
                       note = Synthetic
source                 1..8
                       mol_type = protein
                       organism = synthetic construct
SEQUENCE: 204
GFTFSDYY                                                          8

SEQ ID NO: 205         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 205
attacttata gtggtagtac cata                                        24

SEQ ID NO: 206         moltype = AA  length = 8
FEATURE                Location/Qualifiers
REGION                 1..8
                       note = Synthetic
source                 1..8
                       mol_type = protein
                       organism = synthetic construct
SEQUENCE: 206
ITYSGSTI                                                          8

SEQ ID NO: 207         moltype = DNA  length = 39
FEATURE                Location/Qualifiers
misc_feature           1..39
                       note = Synthetic
source                 1..39
                       mol_type = other DNA
                       organism = synthetic construct
SEQUENCE: 207
gcgagagatc gcggtacaac tatggtcccc tttgactac                        39

SEQ ID NO: 208         moltype = AA  length = 13
FEATURE                Location/Qualifiers
REGION                 1..13
                       note = Synthetic
source                 1..13
                       mol_type = protein
                       organism = synthetic construct
SEQUENCE: 208
ARDRGTTMVP FDY                                                    13

SEQ ID NO: 209         moltype = DNA  length = 321
FEATURE                Location/Qualifiers
misc_feature           1..321
                       note = Synthetic
source                 1..321
                       mol_type = other DNA
                       organism = synthetic construct
SEQUENCE: 209
gacatccaga tgacccagtc tccatcctcc ctgtctgcat ctgtaggaga cagagtcacc  60
atcacttgcc aggcgagtca ggacattacc aactatttaa attggtatca gcagaaacca  120
gggaaagccc ctaagctcct gatctacgct gcatccaatt tggaaacagg ggtcccatca  180
aggttcagtg gaagtggatc tgggacagat tttactttca ccatcagcgg cctgcagcct  240
gaagatattg caacatatta ctgtcaacag tatgataatc tccctctcac tttcggcgga  300
gggaccaagg tggagatcaa a                                           321
```

-continued

```
SEQ ID NO: 210         moltype = AA  length = 107
FEATURE                Location/Qualifiers
REGION                 1..107
                       note = Synthetic
source                 1..107
                       mol_type = protein
                       organism = synthetic construct
SEQUENCE: 210
DIQMTQSPSS LSASVGDRVT ITCQASQDIT NYLNWYQQKP GKAPKLLIYA ASNLETGVPS  60
RFSGSGSGTD FTFTISGLQP EDIATYYCQQ YDNLPLTFGG GTKVEIK               107

SEQ ID NO: 211         moltype = DNA  length = 18
FEATURE                Location/Qualifiers
misc_feature           1..18
                       note = Synthetic
source                 1..18
                       mol_type = other DNA
                       organism = synthetic construct
SEQUENCE: 211
caggacatta ccaactat                                               18

SEQ ID NO: 212         moltype = AA  length = 6
FEATURE                Location/Qualifiers
REGION                 1..6
                       note = Synthetic
source                 1..6
                       mol_type = protein
                       organism = synthetic construct
SEQUENCE: 212
QDITNY                                                            6

SEQ ID NO: 213         moltype = DNA  length = 27
FEATURE                Location/Qualifiers
misc_feature           1..27
                       note = Synthetic
source                 1..27
                       mol_type = other DNA
                       organism = synthetic construct
SEQUENCE: 213
caacagtatg ataatctccc tctcact                                     27

SEQ ID NO: 214         moltype = AA  length = 9
FEATURE                Location/Qualifiers
REGION                 1..9
                       note = Synthetic
source                 1..9
                       mol_type = protein
                       organism = synthetic construct
SEQUENCE: 214
QQYDNLPLT                                                         9

SEQ ID NO: 215         moltype = DNA  length = 1353
FEATURE                Location/Qualifiers
misc_feature           1..1353
                       note = Synthetic
source                 1..1353
                       mol_type = other DNA
                       organism = synthetic construct
SEQUENCE: 215
caggtgcagc tggtggagtc tgggggaggc ttggtcaagc ctggagggtc cctgagactc  60
tcctgtgcag cctctggatt caccttcagt gactactaca tgagctggat ccgccaggct  120
ccagggaagg ggctggagtg ggtttcatac attacttata gtggtagtac catatactac  180
gcagactctg tgaagggccg attcaccatc tccagggaca acgccaagag ctcactgtat  240
ctgcaaatga acagcctgag agccgaggac acggccgtgt attactgtgc gagagatcgc  300
ggtacaacta tggtcccctt tgactactgg ggccagggaa ccctggtcac cgtctcctca  360
gcctccacca agggcccatc ggtcttcccc ctggcaccct cctccaagag cacctctggg  420
ggcacagcgg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacccagacc  600
tacatctgca acgtgaatca caagcccagc aacaccaagg tggacaagaa agttgagccc  660
aaatcttgtg acaaaactca cacatgccca ccgtgcccag cacctgaact cctgggggga  720
ccgtcagtct tcctcttccc cccaaaaccc aaggacaccc tcatgatctc ccggacccct  780
gaggtcacat gcgtggtggt ggacgtgagc cacgaagacc ctgaggtcaa gttcaactgg  840
tacgtggacg gcgtggaggt gcataatgcc aagacaaagc cgcgggagga gcagtacaac  900
agcacgtacc gtgtggtcag cgtcctcacc gtcctgcacc aggactggct gaatggcaag  960
gagtacaagt gcaaggtctc caacaaagcc ctcccagccc ccatcgagaa aaccatctcc  1020
aaagccaaag ggcagccccg agaaccacag gtgtacaccc tgcccccatc ccgggatgag  1080
ctgaccaaga accaggtcag cctgacctgc ctggtcaaag gcttctatcc cagcgacatc  1140
gccgtggagt gggagagcaa tgggcagccg gagaacaact acaagaccac gcctcccgtg  1200
```

-continued

```
ctggactccg acggctcctt cttcctctac agcaagctca ccgtggacaa gagcaggtgg  1260
cagcagggga acgtcttctc atgctccgtg atgcatgagg ctctgcacaa ccactacacg  1320
cagaagtccc tctccctgtc tccgggtaaa tga                               1353

SEQ ID NO: 216         moltype = AA  length = 450
FEATURE                Location/Qualifiers
REGION                 1..450
                       note = Synthetic
source                 1..450
                       mol_type = protein
                       organism = synthetic construct
SEQUENCE: 216
QVQLVESGGG LVKPGGSLRL SCAASGFTFS DYYMSWIRQA PGKGLEWVSY ITYSGSTIYY  60
ADSVKGRFTI SRDNAKSSLY LQMNSLRAED TAVYYCARDR GTTMVPFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                   450

SEQ ID NO: 217         moltype = DNA  length = 645
FEATURE                Location/Qualifiers
misc_feature           1..645
                       note = Synthetic
source                 1..645
                       mol_type = other DNA
                       organism = synthetic construct
SEQUENCE: 217
gacatccaga tgacccagtc tccatcctcc ctgtctgcat ctgtaggaga cagagtcacc  60
atcacttgcc aggcgagtca ggacattacc aactatttaa attggtatca gcagaaacca  120
gggaaagccc ctaagctcct gatctacgct gcatccaatt tggaaacagg ggtcccatca  180
aggttcagtg gaagtggatc tgggacagat tttactttca ccatcagcgg cctgcagcct  240
gaagatattg caacatatta ctgtcaacag tatgataatc tccctctcac tttcggcgga  300
gggaccaagg tggagatcaa acgaactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttag                  645

SEQ ID NO: 218         moltype = AA  length = 214
FEATURE                Location/Qualifiers
REGION                 1..214
                       note = Synthetic
source                 1..214
                       mol_type = protein
                       organism = synthetic construct
SEQUENCE: 218
DIQMTQSPSS LSASVGDRVT ITCQASQDIT NYLNWYQQKP GKAPKLLIYA ASNLETGVPS  60
RFSGSGSGTD FTFTISGLQP EDIATYYCQQ YDNLPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                               214

SEQ ID NO: 219         moltype = DNA  length = 360
FEATURE                Location/Qualifiers
misc_feature           1..360
                       note = Synthetic
source                 1..360
                       mol_type = other DNA
                       organism = synthetic construct
SEQUENCE: 219
gaggtgcagc tggtggagtc tgggggaggc ttggtaaagc ctggggggtc ccttagactc  60
tcctgtgcag cctctggaat cactttcagt aacgcctgga tgagttgggt ccgccaggct  120
ccagggaagg ggctggagtg ggttggccgt attaaaagca aaactgatgg tgggacaaca  180
gactacgccg cacccgtgaa aggcagattc accatctcaa gagatgattc aaaaaacacg  240
ctgtatctac aaatgaacag cctgaaaacc gaggacacag ccgtgtatta ctgtaccaca  300
gcgaggtggg actggtactt cgatctctgg ggccgtggca ccctggtcac tgtctcctca  360

SEQ ID NO: 220         moltype = AA  length = 120
FEATURE                Location/Qualifiers
REGION                 1..120
                       note = Synthetic
source                 1..120
                       mol_type = protein
                       organism = synthetic construct
SEQUENCE: 220
EVQLVESGGG LVKPGGSLRL SCAASGITFS NAWMSWVRQA PGKGLEWVGR IKSKTDGGTT  60
DYAAPVKGRF TISRDDSKNT LYLQMNSLKT EDTAVYYCTT ARWDWYFDLW GRGTLVTVSS  120
```

```
SEQ ID NO: 221          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 221
ggaatcactt tcagtaacgc ctgg                                         24

SEQ ID NO: 222          moltype = AA  length = 8
FEATURE                 Location/Qualifiers
REGION                  1..8
                        note = Synthetic
source                  1..8
                        mol_type = protein
                        organism = synthetic construct
SEQUENCE: 222
GITFSNAW                                                           8

SEQ ID NO: 223          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 223
attaaaagca aaactgatgg tgggacaaca                                   30

SEQ ID NO: 224          moltype = AA  length = 10
FEATURE                 Location/Qualifiers
REGION                  1..10
                        note = Synthetic
source                  1..10
                        mol_type = protein
                        organism = synthetic construct
SEQUENCE: 224
IKSKTDGGTT                                                         10

SEQ ID NO: 225          moltype = DNA  length = 33
FEATURE                 Location/Qualifiers
misc_feature            1..33
                        note = Synthetic
source                  1..33
                        mol_type = other DNA
                        organism = synthetic construct
SEQUENCE: 225
accacagcga ggtgggactg gtacttcgat ctc                               33

SEQ ID NO: 226          moltype = AA  length = 11
FEATURE                 Location/Qualifiers
REGION                  1..11
                        note = Synthetic
source                  1..11
                        mol_type = protein
                        organism = synthetic construct
SEQUENCE: 226
TTARWDWYFD L                                                       11

SEQ ID NO: 227          moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 227
gacatccaga tgacccagtc tccatcctcc ctgtctgcat ctgtaggaga cagagtcacc  60
atcacttgcc aggcgagtca ggacatttgg aattatataa attggtatca gcagaaacca  120
gggaaggccc ctaagctcct gatctacgat gcatccaatt tgaaaacagg ggtcccatca  180
aggttcagtg gaagtggatc tgggacagat tttactttca ccatcagcag cctgcagcct  240
gaagatattg caacatatta ctgtcaacag catgatgatc tccctccgac cttcggccaa  300
gggaccaagg tggaaatcaa a                                            321

SEQ ID NO: 228          moltype = AA  length = 107
FEATURE                 Location/Qualifiers
REGION                  1..107
```

```
                          note = Synthetic
source                    1..107
                          mol_type = protein
                          organism = synthetic construct
SEQUENCE: 228
DIQMTQSPSS LSASVGDRVT ITCQASQDIW NYINWYQQKP GKAPKLLIYD ASNLKTGVPS  60
RFSGSGSGTD FTFTISSLQP EDIATYYCQQ HDDLPPTFGQ GTKVEIK                107

SEQ ID NO: 229            moltype = DNA  length = 18
FEATURE                   Location/Qualifiers
misc_feature              1..18
                          note = Synthetic
source                    1..18
                          mol_type = other DNA
                          organism = synthetic construct
SEQUENCE: 229
caggacattt ggaattat                                                18

SEQ ID NO: 230            moltype = AA  length = 6
FEATURE                   Location/Qualifiers
REGION                    1..6
                          note = Synthetic
source                    1..6
                          mol_type = protein
                          organism = synthetic construct
SEQUENCE: 230
QDIWNY                                                             6

SEQ ID NO: 231            moltype = DNA  length = 27
FEATURE                   Location/Qualifiers
misc_feature              1..27
                          note = Synthetic
source                    1..27
                          mol_type = other DNA
                          organism = synthetic construct
SEQUENCE: 231
caacagcatg atgatctccc tccgacc                                      27

SEQ ID NO: 232            moltype = AA  length = 9
FEATURE                   Location/Qualifiers
REGION                    1..9
                          note = Synthetic
source                    1..9
                          mol_type = protein
                          organism = synthetic construct
SEQUENCE: 232
QQHDDLPPT                                                          9

SEQ ID NO: 233            moltype = DNA  length = 1353
FEATURE                   Location/Qualifiers
misc_feature              1..1353
                          note = Synthetic
source                    1..1353
                          mol_type = other DNA
                          organism = synthetic construct
SEQUENCE: 233
gaggtgcagc tggtggagtc tgggggaggc ttggtaaagc ctgggggggtc ccttagactc  60
tcctgtgcag cctctggaat cactttcagt aacgcctgga tgagttgggt ccgccaggct  120
ccagggaagg ggctggagtg ggttggccgt attaaaagca aaactgatgg tgggacaaca  180
gactacgccg cacccgtgaa aggcagattc accatctcaa gagatgattc aaaaaacacg  240
ctgtatctac aaatgaacag cctgaaaacc gaggacacag ccgtgtatta ctgtaccaca  300
gcgaggtggg actggtactt cgatctctgg ggccgtggca ccctggtcac tgtctcctca  360
gcctccacca agggcccatc ggtcttcccc ctggcaccct cctccaagag cacctctggg  420
ggcacagcgg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacccagacc  600
tacatctgca acgtgaatca caagcccagc aacaccaagg tggacaagaa agttgagccc  660
aaatcttgtg acaaaactca cacatgccca ccgtgcccag cacctgaact cctgggggga  720
ccgtcagtct tcctcttccc cccaaaaccc aaggacaccc tcatgatctc ccggacccct  780
gaggtcacat gcgtggtggt ggacgtgagc cacgaagacc ctgaggtcaa gttcaactgg  840
tacgtggacg gcgtggaggt gcataatgcc aagacaaagc cgcgggagga gcagtacaac  900
agcacgtacc gtgtggtcag cgtcctcacc gtcctgcacc aggactggct gaatggcaag  960
gagtacaagt gcaaggtctc caacaaagcc ctcccagccc ccatcgagaa aaccatctcc  1020
aaagccaaag ggcagccccg agaaccacag gtgtacaccc tgcccccatc ccgggatgag  1080
ctgaccaaga accaggtcag cctgacctgc ctggtcaaag gcttctatcc cagcgacatc  1140
gccgtggagt gggagagcaa tgggcagccg gagaacaact acaagaccac gcctcccgtg  1200
ctggactccg acggctcctt cttcctctac agcaagctca ccgtggacaa gagcaggtgg  1260
cagcagggga acgtcttctc atgctccgtg atgcatgagg ctctgcacaa ccactacacg  1320
cagaagtccc tctccctgtc tccgggtaaa tga                               1353
```

```
SEQ ID NO: 234          moltype = AA  length = 450
FEATURE                 Location/Qualifiers
REGION                  1..450
                        note = Synthetic
source                  1..450
                        mol_type = protein
                        organism = synthetic construct
SEQUENCE: 234
EVQLVESGGG LVKPGGSLRL SCAASGITFS NAWMSWVRQA PGKGLEWVGR IKSKTDGGTT  60
DYAAPVKGRF TISRDDSKNT LYLQMNSLKT EDTAVYYCTT ARWDWYFDLW GRGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 235          moltype = DNA  length = 645
FEATURE                 Location/Qualifiers
misc_feature            1..645
                        note = Synthetic
source                  1..645
                        mol_type = other DNA
                        organism = synthetic construct
SEQUENCE: 235
gacatccaga tgacccagtc tccatcctcc ctgtctgcat ctgtaggaga cagagtcacc  60
atcacttgcc aggcgagtca ggacatttgg aattatataa attggtatca gcagaaacca  120
gggaaggccc ctaagctcct gatctacgat gcatccaatt tgaaaacagg ggtcccatca  180
aggttcagtg gaagtggatc tgggacagat tttactttca ccatcagcag cctgcagcct  240
gaagatattg caacatatta ctgtcaacag catgatgatc tccctccgac cttcggccaa  300
gggaccaagg tggaaatcaa acgaactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttag                645

SEQ ID NO: 236          moltype = AA  length = 214
FEATURE                 Location/Qualifiers
REGION                  1..214
                        note = Synthetic
source                  1..214
                        mol_type = protein
                        organism = synthetic construct
SEQUENCE: 236
DIQMTQSPSS LSASVGDRVT ITCQASQDIW NYINWYQQKP GKAPKLLIYD ASNLKTGVPS  60
RFSGSGSGTD FTFTISSLQP EDIATYYCQQ HDDLPPTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 237          moltype = DNA  length = 360
FEATURE                 Location/Qualifiers
misc_feature            1..360
                        note = Synthetic
source                  1..360
                        mol_type = other DNA
                        organism = synthetic construct
SEQUENCE: 237
gaggtgcagc tggtggagtc tggaggaggc ttggtccagc ctgggggtc cctgagactc  60
tcctgtgcag cctctgggtt caccgtcagt agcaactaca tgagctgggt ccgccaggct  120
ccagggaagg ggctggagtg ggtctcactt atttatagcg gtggtagcac atactatgca  180
gactccgtga agggccgatt caccatctcc agacacaatt ccaagaacac gctgtatctt  240
caaatgaaca gcctgagatc tgaggacacg gccgtgtatt actgtgcgag agtccccctg  300
ggggattact actacggtat ggacgtctgg ggccaaggga ccacggtcac cgtctcctca  360

SEQ ID NO: 238          moltype = AA  length = 120
FEATURE                 Location/Qualifiers
REGION                  1..120
                        note = Synthetic
source                  1..120
                        mol_type = protein
                        organism = synthetic construct
SEQUENCE: 238
EVQLVESGGG LVQPGGSLRL SCAASGFTVS SNYMSWVRQA PGKGLEWVSL IYSGGSTYYA  60
DSVKGRFTIS RHNSKNTLYL QMNSLRSEDT AVYYCARVPL GDYYYGMDVW GQGTTVTVSS  120

SEQ ID NO: 239          moltype = DNA  length = 42
FEATURE                 Location/Qualifiers
```

```
misc_feature            1..42
                        note = Synthetic
source                  1..42
                        mol_type = other DNA
                        organism = synthetic construct
SEQUENCE: 239
gcgagagtcc ccctggggga ttactactac ggtatggacg tc                          42

SEQ ID NO: 240          moltype = AA   length = 14
FEATURE                 Location/Qualifiers
REGION                  1..14
                        note = Synthetic
source                  1..14
                        mol_type = protein
                        organism = synthetic construct
SEQUENCE: 240
ARVPLGDYYY GMDV                                                         14

SEQ ID NO: 241          moltype = DNA   length = 321
FEATURE                 Location/Qualifiers
misc_feature            1..321
                        note = Synthetic
source                  1..321
                        mol_type = other DNA
                        organism = synthetic construct
SEQUENCE: 241
gacatccaga tgacccagtc tccatcctcc ctgtctgcat ctgtaggaga cagagtcacc        60
atcacttgcc aggcgagtca ggacattaac aagtatttaa attggtatca gcagaaacca      120
gggaaagccc ctaagctcct gatctacgat gcatccaatt tggaaacagg ggtcccatca      180
aggttcagtg gaagtggatc tgggacagat tttactttca ccatcagcag cctgcagcct      240
gaagatattg caacatatta ctgtcaacag tctgataatc tccctctcac tttcggcgga      300
gggaccaagg tggagatcaa a                                                321

SEQ ID NO: 242          moltype = AA   length = 107
FEATURE                 Location/Qualifiers
REGION                  1..107
                        note = Synthetic
source                  1..107
                        mol_type = protein
                        organism = synthetic construct
SEQUENCE: 242
DIQMTQSPSS LSASVGDRVT ITCQASQDIN KYLNWYQQKP GKAPKLLIYD ASNLETGVPS        60
RFSGSGSGTD FTFTISSLQP EDIATYYCQQ SDNLPLTFGG GTKVEIK                    107

SEQ ID NO: 243          moltype = DNA   length = 18
FEATURE                 Location/Qualifiers
misc_feature            1..18
                        note = Synthetic
source                  1..18
                        mol_type = other DNA
                        organism = synthetic construct
SEQUENCE: 243
caggacatta acaagtat                                                     18

SEQ ID NO: 244          moltype = AA   length = 6
FEATURE                 Location/Qualifiers
REGION                  1..6
                        note = Synthetic
source                  1..6
                        mol_type = protein
                        organism = synthetic construct
SEQUENCE: 244
QDINKY                                                                   6

SEQ ID NO: 245          moltype = DNA   length = 27
FEATURE                 Location/Qualifiers
misc_feature            1..27
                        note = Synthetic
source                  1..27
                        mol_type = other DNA
                        organism = synthetic construct
SEQUENCE: 245
caacagtctg ataatctccc tctcact                                           27

SEQ ID NO: 246          moltype = AA   length = 9
FEATURE                 Location/Qualifiers
REGION                  1..9
                        note = Synthetic
source                  1..9
```

```
                         mol_type = protein
                         organism = synthetic construct
SEQUENCE: 246
QQSDNLPLT                                                         9

SEQ ID NO: 247           moltype = DNA  length = 1353
FEATURE                  Location/Qualifiers
misc_feature             1..1353
                         note = Synthetic
source                   1..1353
                         mol_type = other DNA
                         organism = synthetic construct
SEQUENCE: 247
gaggtgcagc tggtggagtc tggaggaggc ttggtccagc ctggggggtc cctgagactc  60
tcctgtgcag cctctgggtt caccgtcagt agcaactaca tgagctgggt ccgccaggct  120
ccagggaagg ggctggagtg ggtctcactt atttatagcg gtggtagcac atactatgca  180
gactccgtga agggccgatt caccatctcc agacacaatt ccaagaacac gctgtatctt  240
caaatgaaca gcctgagatc tgaggacacg gccgtgtatt actgtgcgag agtccccctg  300
ggggattact actacggtat ggacgtctgg ggccaaggga ccacggtcac cgtctcctca  360
gcctccacca agggcccatc ggtcttcccc ctggcaccct cctccaagag cacctctggg  420
ggcacagcgg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacccagacc  600
tacatctgca acgtgaatca caagcccagc aacaccaagg tggacaagaa agttgagccc  660
aaatcttgtg acaaaactca cacatgccca ccgtgcccag cacctgaact cctgggggga  720
ccgtcagtct tcctcttccc cccaaaaccc aaggacaccc tcatgatctc ccggacccct  780
gaggtcacat gcgtggtggt ggacgtgagc cacgaagacc ctgaggtcaa gttcaactgg  840
tacgtggacg gcgtggaggt gcataatgcc aagacaaagc cgcgggagga gcagtacaac  900
agcacgtacc gtgtggtcag cgtcctcacc gtcctgcacc aggactggct gaatggcaag  960
gagtacaagt gcaaggtctc caacaaagcc ctcccagccc ccatcgagaa aaccatctcc  1020
aaagccaaag ggcagccccg agaaccacag gtgtacaccc tgcccccatc ccgggatgag  1080
ctgaccaaga accaggtcag cctgacctgc ctggtcaaag gcttctatcc cagcgacatc  1140
gccgtggagt gggagagcaa tgggcagccg gagaacaact acaagaccac gcctcccgtg  1200
ctggactccg acggctcctt cttcctctac agcaagctca ccgtggacaa gagcaggtgg  1260
cagcagggga acgtcttctc atgctccgtg atgcatgagg ctctgcacaa ccactacacg  1320
cagaagtccc tctccctgtc tccgggtaaa tga                              1353

SEQ ID NO: 248           moltype = AA  length = 450
FEATURE                  Location/Qualifiers
REGION                   1..450
                         note = Synthetic
source                   1..450
                         mol_type = protein
                         organism = synthetic construct
SEQUENCE: 248
EVQLVESGGG LVQPGGSLRL SCAASGFTVS SNYMSWVRQA PGKGLEWVSL IYSGGSTYYA  60
DSVKGRFTIS RHNSKNTLYL QMNSLRSEDT AVYYCARVPL GDYYYGMDVW GQGTTVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 249           moltype = DNA  length = 645
FEATURE                  Location/Qualifiers
misc_feature             1..645
                         note = Synthetic
source                   1..645
                         mol_type = other DNA
                         organism = synthetic construct
SEQUENCE: 249
gacatccaga tgacccagtc tccatcctcc ctgtctgcat ctgtaggaga cagagtcacc  60
atcacttgcc aggcgagtca ggacattaac aagtatttaa attggtatca gcagaaacca  120
gggaaagccc ctaagctcct gatctacgat gcatccaatt tggaaacagg ggtcccatca  180
aggttcagtg gaagtggatc tgggacagat tttactttca ccatcagcag cctgcagcct  240
gaagatattg caacatatta ctgtcaacag tctgataatc tccctctcac tttcggcgga  300
gggaccaagg tggagatcaa acgaactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttag                 645

SEQ ID NO: 250           moltype = AA  length = 214
FEATURE                  Location/Qualifiers
REGION                   1..214
                         note = Synthetic
source                   1..214
```

```
                         mol_type = protein
                         organism = synthetic construct
SEQUENCE: 250
DIQMTQSPSS LSASVGDRVT ITCQASQDIN KYLNWYQQKP GKAPKLLIYD ASNLETGVPS  60
RFSGSGSGTD FTFTISSLQP EDIATYYCQQ SDNLPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 251           moltype = DNA  length = 372
FEATURE                  Location/Qualifiers
misc_feature             1..372
                         note = Synthetic
source                   1..372
                         mol_type = other DNA
                         organism = synthetic construct
SEQUENCE: 251
caggtgcagc tggtggagtc tgggggaggc gtggtccagc ctgggaggtc cctgagactc  60
tcctgtgcag cgtctggatt caccttcaga aactatggca tgcactgggt ccgccaggct  120
ccaggcaagg ggctggagtg ggtgtcagtt atatggtatg atggaagtaa tagatactat  180
gcagactccg tgaagggccg attcaccatc tccagagaca cttccaagaa cacgctgtat  240
ctgcaaatga acagcctgag agccgaagac acggctgtgt attactgtgc gagagatcct  300
cctataactg gaacgacggg gggcgatgct tttgatatct ggggccaagg gacaatggtc  360
accgtctctt ca                                                     372

SEQ ID NO: 252           moltype = AA  length = 124
FEATURE                  Location/Qualifiers
REGION                   1..124
                         note = Synthetic
source                   1..124
                         mol_type = protein
                         organism = synthetic construct
SEQUENCE: 252
QVQLVESGGG VVQPGRSLRL SCAASGFTFR NYGMHWVRQA PGKGLEWVSV IWYDGSNRYY  60
ADSVKGRFTI SRDTSKNTLY LQMNSLRAED TAVYYCARDP PITGTTGGDA FDIWGQGTMV  120
TVSS                                                              124

SEQ ID NO: 253           moltype = DNA  length = 24
FEATURE                  Location/Qualifiers
misc_feature             1..24
                         note = Synthetic
source                   1..24
                         mol_type = other DNA
                         organism = synthetic construct
SEQUENCE: 253
ggattcacct tcagaaacta tggc                                        24

SEQ ID NO: 254           moltype = AA  length = 8
FEATURE                  Location/Qualifiers
REGION                   1..8
                         note = Synthetic
source                   1..8
                         mol_type = protein
                         organism = synthetic construct
SEQUENCE: 254
GFTFRNYG                                                          8

SEQ ID NO: 255           moltype = DNA  length = 24
FEATURE                  Location/Qualifiers
misc_feature             1..24
                         note = Synthetic
source                   1..24
                         mol_type = other DNA
                         organism = synthetic construct
SEQUENCE: 255
atatggtatg atggaagtaa taga                                        24

SEQ ID NO: 256           moltype = AA  length = 8
FEATURE                  Location/Qualifiers
REGION                   1..8
                         note = Synthetic
source                   1..8
                         mol_type = protein
                         organism = synthetic construct
SEQUENCE: 256
IWYDGSNR                                                          8

SEQ ID NO: 257           moltype = DNA  length = 51
FEATURE                  Location/Qualifiers
misc_feature             1..51
```

```
                        note = Synthetic
source                  1..51
                        mol_type = other DNA
                        organism = synthetic construct
SEQUENCE: 257
gcgagagatc ctcctataac tggaacgacg gggggcgatg cttttgatat c           51

SEQ ID NO: 258          moltype = AA  length = 17
FEATURE                 Location/Qualifiers
REGION                  1..17
                        note = Synthetic
source                  1..17
                        mol_type = protein
                        organism = synthetic construct
SEQUENCE: 258
ARDPPITGTT GGDAFDI                                                 17

SEQ ID NO: 259          moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 259
gacatccaga tgacccagtc tccatcctcc ctgtctgcat ctgtaggaga cagagtcacc  60
atcacttgcc gggcaagtca gagcattagc agctatttaa attggtatca gcagaaacca  120
gggaaagccc ctcacctcct gatctatgct gcatccagtt tgcaaagtgg ggtcccatca  180
aggttcagtg gcagtggatc tgggacagat ttcactctca ccatcagcag tctgcaacct  240
gaagattttg caacttacta ctgtcaacag agttacagta ctccttacac ttttggccag  300
gggaccaagc tggagatcaa a                                            321

SEQ ID NO: 260          moltype = AA  length = 107
FEATURE                 Location/Qualifiers
REGION                  1..107
                        note = Synthetic
source                  1..107
                        mol_type = protein
                        organism = synthetic construct
SEQUENCE: 260
DIQMTQSPSS LSASVGDRVT ITCRASQSIS SYLNWYQQKP GKAPHLLIYA ASSLQSGVPS  60
RFSGSGSGTD FTLTISSLQP EDFATYYCQQ SYSTPYTFGQ GTKLEIK                107

SEQ ID NO: 261          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 261
caacagagtt acagtactcc ttacact                                      27

SEQ ID NO: 262          moltype = AA  length = 9
FEATURE                 Location/Qualifiers
REGION                  1..9
                        note = Synthetic
source                  1..9
                        mol_type = protein
                        organism = synthetic construct
SEQUENCE: 262
QQSYSTPYT                                                          9

SEQ ID NO: 263          moltype = DNA  length = 1365
FEATURE                 Location/Qualifiers
misc_feature            1..1365
                        note = Synthetic
source                  1..1365
                        mol_type = other DNA
                        organism = synthetic construct
SEQUENCE: 263
caggtgcagc tggtggagtc tgggggaggc gtggtccagc ctgggaggtc cctgagactc  60
tcctgtgcag cgtctggatt caccttcaga aactatggca tgcactgggt ccgccaggct  120
ccaggcaagg ggctggagtg ggtgtcagtt atatggtatg atggaagtaa tagatactat  180
gcagactccg tgaagggccg attcaccatc tccagagaca cttccaagaa cacgctgtat  240
ctgcaaatga acagcctgag agccgaagac acggctgtgt attactgtgc gagagatcct  300
cctataactg gaacgacggg gggcgatgct tttgatatct ggggccaagg gacaatggtc  360
accgtctctt cagcctccac caagggccca tcggtcttcc ccctggcacc ctcctccaag  420
agcacctctg gggcacagc ggccctgggc tgcctggtca aggactactt ccccgaaccg  480
```

-continued

```
gtgacggtgt cgtggaactc aggcgccctg accagcggcg tgcacacctt cccggctgtc  540
ctacagtcct caggactcta ctccctcagc agcgtggtga ccgtgccctc cagcagcttg  600
ggcacccaga cctacatctg caacgtgaat cacaagccca gcaacaccaa ggtggacaag  660
aaagttgagc ccaaatcttg tgacaaaact cacacatgcc caccgtgccc agcacctgaa  720
ctcctggggg gaccgtcagt cttcctcttc cccccaaaac ccaaggacac cctcatgatc  780
tcccggaccc ctgaggtcac atgcgtggtg gtggacgtga gccacgaaga ccctgaggtc  840
aagttcaact ggtacgtgga cggcgtggag gtgcataatg ccaagacaaa gccgcgggag  900
gagcagtaca acagcacgta ccgtgtggtc agcgtcctca ccgtcctgca ccaggactgg  960
ctgaatggca aggagtacaa gtgcaaggtc tccaacaaag ccctcccagc ccccatcgag  1020
aaaaccatct ccaaagccaa agggcagccc cgagaaccac aggtgtacac cctgccccca  1080
tcccgggatg agctgaccaa gaaccaggtc agcctgacct gcctggtcaa aggcttctat  1140
cccagcgaca tcgccgtgga gtgggagagc aatgggcagc cggagaacaa ctacaagacc  1200
acgcctcccg tgctggactc cgacggctcc ttcttcctct acagcaagct caccgtggac  1260
aagagcaggt ggcagcaggg gaacgtcttc tcatgctccg tgatgcatga ggctctgcac  1320
aaccactaca cgcagaagtc cctctccctg tctccgggta aatga                  1365

SEQ ID NO: 264         moltype = AA  length = 454
FEATURE                Location/Qualifiers
REGION                 1..454
                       note = Synthetic
source                 1..454
                       mol_type = protein
                       organism = synthetic construct
SEQUENCE: 264
QVQLVESGGG VVQPGRSLRL SCAASGFTFR NYGMHWVRQA PGKGLEWVSV IWYDGSNRYY  60
ADSVKGRFTI SRDTSKNTLY LQMNSLRAED TAVYYCARDP PITGTTGGDA FDIWGQGTMV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
LLGGPSVFLF PPKPKDTLMI SRTPEVTCVV VDVSHEDPEV KFNWYVDGVE VHNAKTKPRE  300
EQYNSTYRVV SVLTVLHQDW LNGKEYKCKV SNKALPAPIE KTISKAKGQP REPQVYTLPP  360
SRDELTKNQV SLTCLVKGFY PSDIAVEWES NGQPENNYKT TPPVLDSDGS FFLYSKLTVD  420
KSRWQQGNVF SCSVMHEALH NHYTQKSLSL SPGK                              454

SEQ ID NO: 265         moltype = DNA  length = 645
FEATURE                Location/Qualifiers
misc_feature           1..645
                       note = Synthetic
source                 1..645
                       mol_type = other DNA
                       organism = synthetic construct
SEQUENCE: 265
gacatccaga tgacccagtc tccatcctcc ctgtctgcat ctgtaggaga cagagtcacc  60
atcacttgcc gggcaagtca gagcattagc agctatttaa attggtatca gcagaaacca  120
gggaaagccc ctcacctcct gatctatgct gcatccagtt tgcaaagtgg ggtcccatca  180
aggttcagtg gcagtggatc tgggacagat ttcactctca ccatcagcag tctgcaacct  240
gaagattttg caacttacta ctgtcaacag agttacagta ctccttacac ttttggccag  300
gggaccaagc tggagatcaa acgaactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttag                  645

SEQ ID NO: 266         moltype = AA  length = 214
FEATURE                Location/Qualifiers
REGION                 1..214
                       note = Synthetic
source                 1..214
                       mol_type = protein
                       organism = synthetic construct
SEQUENCE: 266
DIQMTQSPSS LSASVGDRVT ITCRASQSIS SYLNWYQQKP GKAPHLLIYA ASSLQSGVPS  60
RFSGSGSGTD FTLTISSLQP EDFATYYCQQ SYSTPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 267         moltype = DNA  length = 357
FEATURE                Location/Qualifiers
misc_feature           1..357
                       note = Synthetic
source                 1..357
                       mol_type = other DNA
                       organism = synthetic construct
SEQUENCE: 267
cagatcacct tgaaggagtc tggtcctacg ctggtgaaac ccacacagac cctcacgctg  60
acctgcacct tctctgggtt ctcactcagc actaatgtag tgggtgtggg ctggatccgt  120
cagcccccag gaaaggccct ggagtggctt gcactcattt attggaatga tgataagcgc  180
tacagcccat ctctgaagag caggctcacc atcaccaagg acacctccaa aaaccaggtg  240
gtccttacaa tgaccaacat ggaccctgtg gacacagcca catattactg tgcacacggc  300
```

```
ccaactgggg actactttga ctactggggc cagggaaccc tggtcaccgt ctcctca     357

SEQ ID NO: 268         moltype = AA  length = 119
FEATURE                Location/Qualifiers
REGION                 1..119
                       note = Synthetic
source                 1..119
                       mol_type = protein
                       organism = synthetic construct
SEQUENCE: 268
QITLKESGPT LVKPTQTLTL TCTFSGFSLS TNVVGVGWIR QPPGKALEWL ALIYWNDDKR  60
YSPSLKSRLT ITKDTSKNQV VLTMTNMDPV DTATYYCAHG PTGDYFDYWG QGTLVTVSS   119

SEQ ID NO: 269         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 269
gggttctcac tcagcactaa tgtagtgggt                                    30

SEQ ID NO: 270         moltype = AA  length = 10
FEATURE                Location/Qualifiers
REGION                 1..10
                       note = Synthetic
source                 1..10
                       mol_type = protein
                       organism = synthetic construct
SEQUENCE: 270
GFSLSTNVVG                                                          10

SEQ ID NO: 271         moltype = DNA  length = 21
FEATURE                Location/Qualifiers
misc_feature           1..21
                       note = Synthetic
source                 1..21
                       mol_type = other DNA
                       organism = synthetic construct
SEQUENCE: 271
atttattgga atgatgataa g                                             21

SEQ ID NO: 272         moltype = AA  length = 7
FEATURE                Location/Qualifiers
REGION                 1..7
                       note = Synthetic
source                 1..7
                       mol_type = protein
                       organism = synthetic construct
SEQUENCE: 272
IYWNDDK                                                             7

SEQ ID NO: 273         moltype = DNA  length = 33
FEATURE                Location/Qualifiers
misc_feature           1..33
                       note = Synthetic
source                 1..33
                       mol_type = other DNA
                       organism = synthetic construct
SEQUENCE: 273
gcacacggcc caactgggga ctactttgac tac                                33

SEQ ID NO: 274         moltype = AA  length = 11
FEATURE                Location/Qualifiers
REGION                 1..11
                       note = Synthetic
source                 1..11
                       mol_type = protein
                       organism = synthetic construct
SEQUENCE: 274
AHGPTGDYFD Y                                                        11

SEQ ID NO: 275         moltype = DNA  length = 324
FEATURE                Location/Qualifiers
misc_feature           1..324
                       note = Synthetic
source                 1..324
                       mol_type = other DNA
```

```
                         organism = synthetic construct
SEQUENCE: 275
gacatccaga tgacccagtc tccatcctcc ctgtctgcat ctgtaggaga cagagtcacc  60
atcacttgcc gggcaagtca gagcattagc agctatttaa attggtatca gcagaaacca  120
gggaaagccc ctaagctcct gatctatgct gcatccagtt tacaaagtgg ggtcccatca  180
aggttcagtg gcagtggatc tgggacagat ttcactctca ccatcagcag tctgcaacct  240
gaagattttg caacttacta ctgtcaacag acttacagta ccctcatgta cacttttggc  300
caggggacca agctggagat caaa                                        324

SEQ ID NO: 276           moltype = AA  length = 108
FEATURE                  Location/Qualifiers
REGION                   1..108
                         note = Synthetic
source                   1..108
                         mol_type = protein
                         organism = synthetic construct
SEQUENCE: 276
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ TYSTLMYTFG QGTKLEIK               108

SEQ ID NO: 277           moltype = DNA  length = 30
FEATURE                  Location/Qualifiers
misc_feature             1..30
                         note = Synthetic
source                   1..30
                         mol_type = other DNA
                         organism = synthetic construct
SEQUENCE: 277
caacagactt acagtaccct catgtacact                                  30

SEQ ID NO: 278           moltype = AA  length = 10
FEATURE                  Location/Qualifiers
REGION                   1..10
                         note = Synthetic
source                   1..10
                         mol_type = protein
                         organism = synthetic construct
SEQUENCE: 278
QQTYSTLMYT                                                        10

SEQ ID NO: 279           moltype = DNA  length = 1350
FEATURE                  Location/Qualifiers
misc_feature             1..1350
                         note = Synthetic
source                   1..1350
                         mol_type = other DNA
                         organism = synthetic construct
SEQUENCE: 279
cagatcacct tgaaggagtc tggtcctacg ctggtgaaac ccacacagac cctcacgctg  60
acctgcacct tctctgggtt ctcactcagc actaatgtag tgggtgtggg ctggatccgt  120
cagcccccag gaaaggccct ggagtggctt gcactcattt attggaatga tgataagcgc  180
tacagcccat ctctgaagag caggctcacc atcaccaagg acacctccaa aaaccaggtg  240
gtccttacaa tgaccaacat ggaccctgtg gacacagcca catattactg tgcacacggc  300
ccaactgggg actactttga ctactggggc cagggaaccc tggtcaccgt ctcctcagcc  360
tccaccaagg gcccatcggt cttccccctg gcaccctcct ccaagagcac ctctgggggc  420
acagcggccc tgggctgcct ggtcaaggac tacttccccg aaccggtgac ggtgtcgtgg  480
aactcaggcg ccctgaccag cggcgtgcac accttcccgg ctgtcctaca gtcctcagga  540
ctctactccc tcagcagcgt ggtgaccgtg ccctccagca gcttgggcac ccagacctac  600
atctgcaacg tgaatcacaa gcccagcaac accaaggtgg acaagaaagt tgagcccaaa  660
tcttgtgaca aaactcacac atgcccaccg tgcccagcac ctgaactcct ggggggaccg  720
tcagtcttcc tcttcccccc aaaacccaag gacaccctca tgatctcccg gacccctgag  780
gtcacatgcg tggtggtgga cgtgagccac gaagaccctg aggtcaagtt caactggtac  840
gtggacggcg tggaggtgca taatgccaag acaaagccgc gggaggagca gtacaacagc  900
acgtaccgtg tggtcagcgt cctcaccgtc ctgcaccagg actggctgaa tggcaaggag  960
tacaagtgca aggtctccaa caaagccctc ccagccccca tcgagaaaac catctccaaa  1020
gccaaagggc agccccgaga accacaggtg tacaccctgc ccccatcccg ggatgagctg  1080
accaagaacc aggtcagcct gacctgcctg gtcaaaggct tctatcccag cgacatcgcc  1140
gtggagtggg agagcaatgg gcagccggag aacaactaca agaccacgcc tcccgtgctg  1200
gactccgacg gctccttctt cctctacagc aagctcaccg tggacaagag caggtggcag  1260
caggggaacg tcttctcatg ctccgtgatg catgaggctc tgcacaacca ctacacgcag  1320
aagtccctct ccctgtctcc gggtaaatga                                  1350

SEQ ID NO: 280           moltype = AA  length = 449
FEATURE                  Location/Qualifiers
REGION                   1..449
                         note = Synthetic
source                   1..449
                         mol_type = protein
                         organism = synthetic construct
```

-continued

```
SEQUENCE: 280
QITLKESGPT LVKPTQTLTL TCTFSGFSLS TNVVGVGWIR QPPGKALEWL ALIYWNDDKR  60
YSPSLKSRLT ITKDTSKNQV VLTMTNMDPV DTATYYCAHG PTGDYFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                   449

SEQ ID NO: 281         moltype = DNA  length = 648
FEATURE                Location/Qualifiers
misc_feature           1..648
                       note = Synthetic
source                 1..648
                       mol_type = other DNA
                       organism = synthetic construct
SEQUENCE: 281
gacatccaga tgacccagtc tccatcctcc ctgtctgcat ctgtaggaga cagagtcacc  60
atcacttgcc gggcaagtca gagcattagc agctatttaa attggtatca gcagaaacca  120
gggaaagccc ctaagctcct gatctatgct gcatccagtt tacaaagtgg ggtcccatca  180
aggttcagtg gcagtggatc tgggacagat ttcactctca ccatcagcag tctgcaacct  240
gaagattttg caacttacta ctgtcaacag acttacagta ccctcatgta cacttttggc  300
caggggacca agctggagat caaacgaact gtggctgcac catctgtctt catcttcccg  360
ccatctgatg agcagttgaa atctggaact gcctctgttg tgtgcctgct gaataacttc  420
tatcccagag aggccaaagt acagtggaag gtggataacg ccctccaatc gggtaactcc  480
caggagagtg tcacagagca ggacagcaag gacagcacct acagcctcag cagcaccctg  540
acgctgagca aagcagacta cgagaaacac aaagtctacg cctgcgaagt cacccatcag  600
ggcctgagct cgcccgtcac aaagagcttc aacaggggag agtgttag              648

SEQ ID NO: 282         moltype = AA  length = 215
FEATURE                Location/Qualifiers
REGION                 1..215
                       note = Synthetic
source                 1..215
                       mol_type = protein
                       organism = synthetic construct
SEQUENCE: 282
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ TYSTLMYTFG QGTKLEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 283         moltype = DNA  length = 366
FEATURE                Location/Qualifiers
misc_feature           1..366
                       note = Synthetic
source                 1..366
                       mol_type = other DNA
                       organism = synthetic construct
SEQUENCE: 283
gaagtgcagc tggtggagtc tgggggaggc ttggttcagc ctggcaggtc cctgagactc  60
tcctgtgcag cctctggatt cacctttgat gattatgcca tgcactgggt ccggcaagct  120
ccagggaagg gcctggagtg ggtctcaggt gttagttgga atagtggtac catagactat  180
gcggactctg tgaagggccg attcaccatt attagagaca acgctaagaa ctccctgtat  240
ctgcaaatga acagtctgag agctgaagac acggccttgt attactgttc aaaagatatg  300
gggaggctag actactactc cggtttggac gtctggggcc aagggaccac ggtcaccgtc  360
tcctca                                                            366

SEQ ID NO: 284         moltype = AA  length = 122
FEATURE                Location/Qualifiers
REGION                 1..122
                       note = Synthetic
source                 1..122
                       mol_type = protein
                       organism = synthetic construct
SEQUENCE: 284
EVQLVESGGG LVQPGRSLRL SCAASGFTFD DYAMHWVRQA PGKGLEWVSG VSWNSGTIDY  60
ADSVKGRFTI IRDNAKNSLY LQMNSLRAED TALYYCSKDM GRLDYYSGLD VWGQGTTVTV  120
SS                                                                122

SEQ ID NO: 285         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 285
```

```
gttagttgga atagtggtac cata                                        24

SEQ ID NO: 286         moltype = AA  length = 8
FEATURE                Location/Qualifiers
REGION                 1..8
                       note = Synthetic
source                 1..8
                       mol_type = protein
                       organism = synthetic construct
SEQUENCE: 286
VSWNSGTI                                                          8

SEQ ID NO: 287         moltype = DNA  length = 45
FEATURE                Location/Qualifiers
misc_feature           1..45
                       note = Synthetic
source                 1..45
                       mol_type = other DNA
                       organism = synthetic construct
SEQUENCE: 287
tcaaaagata tggggaggct agactactac tccggtttgg acgtc                 45

SEQ ID NO: 288         moltype = AA  length = 15
FEATURE                Location/Qualifiers
REGION                 1..15
                       note = Synthetic
source                 1..15
                       mol_type = protein
                       organism = synthetic construct
SEQUENCE: 288
SKDMGRLDYY SGLDV                                                  15

SEQ ID NO: 289         moltype = DNA  length = 324
FEATURE                Location/Qualifiers
misc_feature           1..324
                       note = Synthetic
source                 1..324
                       mol_type = other DNA
                       organism = synthetic construct
SEQUENCE: 289
gaaatagtgt tgacgcagtc tccaggcacc ctgtctttgt ctccagggga aagagccacc  60
ctctcctgca gggccagtca gagtgttagc agcagcgact ttgcctggta ccagcagaaa  120
cctggccagg ctcccaggct cctcatctat ggtgcatcca gcagggccac tggtatccca  180
gacaggttca gtggcagtgg gtctgggaca gatttcactc tcaccatcag cagactggag  240
cctgaagatt ttgcagtgta ttactgtcag cagtatggta gctcaccttg gacgttcggc  300
caagggacca aggtggaaat caaa                                        324

SEQ ID NO: 290         moltype = AA  length = 108
FEATURE                Location/Qualifiers
REGION                 1..108
                       note = Synthetic
source                 1..108
                       mol_type = protein
                       organism = synthetic construct
SEQUENCE: 290
EIVLTQSPGT LSLSPGERAT LSCRASQSVS SSDFAWYQQK PGQAPRLLIY GASSRATGIP  60
DRFSGSGSGT DFTLTISRLE PEDFAVYYCQ QYGSSPWTFG QGTKVEIK              108

SEQ ID NO: 291         moltype = DNA  length = 21
FEATURE                Location/Qualifiers
misc_feature           1..21
                       note = Synthetic
source                 1..21
                       mol_type = other DNA
                       organism = synthetic construct
SEQUENCE: 291
cagagtgtta gcagcagcga c                                           21

SEQ ID NO: 292         moltype = AA  length = 7
FEATURE                Location/Qualifiers
REGION                 1..7
                       note = Synthetic
source                 1..7
                       mol_type = protein
                       organism = synthetic construct
SEQUENCE: 292
QSVSSSD                                                           7

SEQ ID NO: 293         moltype =   length =
```

```
SEQUENCE: 293
000

SEQ ID NO: 294         moltype =   length =
SEQUENCE: 294
000

SEQ ID NO: 295         moltype = DNA  length = 27
FEATURE                Location/Qualifiers
misc_feature           1..27
                       note = Synthetic
source                 1..27
                       mol_type = other DNA
                       organism = synthetic construct
SEQUENCE: 295
cagcagtatg gtagctcacc ttggacg                                     27

SEQ ID NO: 296         moltype = AA  length = 9
FEATURE                Location/Qualifiers
REGION                 1..9
                       note = Synthetic
source                 1..9
                       mol_type = protein
                       organism = synthetic construct
SEQUENCE: 296
QQYGSSPWT                                                         9

SEQ ID NO: 297         moltype = DNA  length = 1359
FEATURE                Location/Qualifiers
misc_feature           1..1359
                       note = Synthetic
source                 1..1359
                       mol_type = other DNA
                       organism = synthetic construct
SEQUENCE: 297
gaagtgcagc tggtggagtc tgggggaggc ttggttcagc ctggcaggtc cctgagactc  60
tcctgtgcag cctctggatt cacctttgat gattatgcca tgcactgggt ccggcaagct  120
ccagggaagg gcctggagtg ggtctcaggt gttagttgga atagtggtac catagactat  180
gcggactctg tgaagggccg attcaccatt attagagaca acgctaagaa ctccctgtat  240
ctgcaaatga acagtctgag agctgaagac acggccttgt attactgttc aaaagatatg  300
gggaggctag actactactc cggtttggac gtctggggcc aagggaccac ggtcaccgtc  360
tcctcagcct ccaccaaggg cccatcggtc ttccccctgg caccctcctc caagagcacc  420
tctgggggca cagcggccct gggctgcctg gtcaaggact acttccccga accggtgacg  480
gtgtcgtgga actcaggcgc cctgaccagc ggcgtgcaca ccttcccggc tgtcctacag  540
tcctcaggac tctactccct cagcagcgtg gtgaccgtgc cctccagcag cttgggcacc  600
cagacctaca tctgcaacgt gaatcacaag cccagcaaca ccaaggtgga caagaaagtt  660
gagcccaaat cttgtgacaa aactcacaca tgcccaccgt gcccagcacc tgaactcctg  720
gggggaccgt cagtcttcct cttcccccca aaacccaagg acaccctcat gatctcccgg  780
acccctgagg tcacatgcgt ggtggtggac gtgagccacg aagaccctga ggtcaagttc  840
aactggtacg tggacggcgt ggaggtgcat aatgccaaga caaagccgcg ggaggagcag  900
tacaacagca cgtaccgtgt ggtcagcgtc ctcaccgtcc tgcaccagga ctggctgaat  960
ggcaaggagt acaagtgcaa ggtctccaac aaagccctcc cagcccccat cgagaaaacc  1020
atctccaaag ccaaagggca gccccgagaa ccacaggtgt acaccctgcc cccatcccgg  1080
gatgagctga ccaagaacca ggtcagcctg acctgcctgg tcaaaggctt ctatcccagc  1140
gacatcgccg tggagtggga gagcaatggg cagccggaga acaactacaa gaccacgcct  1200
cccgtgctgg actccgacgg ctccttcttc ctctacagca agctcaccgt ggacaagagc  1260
aggtggcagc aggggaacgt cttctcatgc tccgtgatgc atgaggctct gcacaaccac  1320
tacacgcaga agtccctctc cctgtctccg ggtaaatga                        1359

SEQ ID NO: 298         moltype = AA  length = 452
FEATURE                Location/Qualifiers
REGION                 1..452
                       note = Synthetic
source                 1..452
                       mol_type = protein
                       organism = synthetic construct
SEQUENCE: 298
EVQLVESGGG LVQPGRSLRL SCAASGFTFD DYAMHWVRQA PGKGLEWVSG VSWNSGTIDY  60
ADSVKGRFTI IRDNAKNSLY LQMNSLRAED TALYYCSKDM GRLDYYSGLD VWGQGTTVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
DELTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                               452

SEQ ID NO: 299         moltype = DNA  length = 648
FEATURE                Location/Qualifiers
misc_feature           1..648
```

-continued

```
                         note = Synthetic
source                   1..648
                         mol_type = other DNA
                         organism = synthetic construct
SEQUENCE: 299
gaaatagtgt tgacgcagtc tccaggcacc ctgtctttgt ctccagggga aagagccacc  60
ctctcctgca gggccagtca gagtgttagc agcagcgact ttgcctggta ccagcagaaa  120
cctggccagg ctcccaggct cctcatctat ggtgcatcca gcagggccac tggtatccca  180
gacaggttca gtggcagtgg gtctgggaca gatttcactc tcaccatcag cagactggag  240
cctgaagatt ttgcagtgta ttactgtcag cagtatggta gctcaccttg gacgttcggc  300
caagggacca aggtggaaat caaacgaact gtggctgcac catctgtctt catcttcccg  360
ccatctgatg agcagttgaa atctggaact gcctctgttg tgtgcctgct gaataacttc  420
tatcccagag aggccaaagt acagtggaag gtggataacg ccctccaatc gggtaactcc  480
caggagagtg tcacagagca ggacagcaag gacagcacct acagcctcag cagcaccctg  540
acgctgagca aagcagacta cgagaaacac aaagtctacg cctgcgaagt cacccatcag  600
ggcctgagct cgcccgtcac aaagagcttc aacaggggag agtgttag              648

SEQ ID NO: 300           moltype = AA  length = 215
FEATURE                  Location/Qualifiers
REGION                   1..215
                         note = Synthetic
source                   1..215
                         mol_type = protein
                         organism = synthetic construct
SEQUENCE: 300
EIVLTQSPGT LSLSPGERAT LSCRASQSVS SSDFAWYQQK PGQAPRLLIY GASSRATGIP  60
DRFSGSGSGT DFTLTISRLE PEDFAVYYCQ QYGSSPWTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 301           moltype = DNA  length = 354
FEATURE                  Location/Qualifiers
misc_feature             1..354
                         note = Synthetic
source                   1..354
                         mol_type = other DNA
                         organism = synthetic construct
SEQUENCE: 301
gaggtgcagc tggtggagtc tggaggaggc ttggtccagc ctgggggtc cctgagactc  60
tcctgtgcag tctctgggtt caccgtcagt agcaactaca tgagctgggt ccgccaggct  120
ccagggaagg gactggaatg ggtctcactt atttatagcg gtggtagcac attctacgca  180
gactccgtga agggccgatt caccatctcc agacacaatt ccaagaacac gctgtatctt  240
caaatgaaca gcctgagagc tgaggacacg gccgtatatt actgtgcgag agaaggtgga  300
tacagctatg attacaacta ctggggccag ggaaccctgg tcaccgtctc ctca        354

SEQ ID NO: 302           moltype = AA  length = 118
FEATURE                  Location/Qualifiers
REGION                   1..118
                         note = Synthetic
source                   1..118
                         mol_type = protein
                         organism = synthetic construct
SEQUENCE: 302
EVQLVESGGG LVQPGGSLRL SCAVSGFTVS SNYMSWVRQA PGKGLEWVSL IYSGGSTFYA  60
DSVKGRFTIS RHNSKNTLYL QMNSLRAEDT AVYYCAREGG YSYDYNYWGQ GTLVTVSS    118

SEQ ID NO: 303           moltype = DNA  length = 36
FEATURE                  Location/Qualifiers
misc_feature             1..36
                         note = Synthetic
source                   1..36
                         mol_type = other DNA
                         organism = synthetic construct
SEQUENCE: 303
gcgagagaag gtggatacag ctatgattac aactac                            36

SEQ ID NO: 304           moltype = AA  length = 12
FEATURE                  Location/Qualifiers
REGION                   1..12
                         note = Synthetic
source                   1..12
                         mol_type = protein
                         organism = synthetic construct
SEQUENCE: 304
AREGGYSYDY NY                                                      12

SEQ ID NO: 305           moltype = DNA  length = 321
FEATURE                  Location/Qualifiers
misc_feature             1..321
```

```
                        note = Synthetic
source                  1..321
                        mol_type = other DNA
                        organism = synthetic construct
SEQUENCE: 305
gacatccaga tgacccagtc tccatcctcc ctgtccgcat ctgtaggaga cagagtcacc  60
atcacgtgcc aggcgagtca ggacattaga aactatttaa attggtatca gcagaaacca  120
gggaaagccc ctaagctcct gatctacgat gcatccaatt tggaaacagg ggtcccatca  180
aggttcagtg gaattggatc tgggacagat tttactttca ccatcagcag cctgcagcct  240
gaagatattg caacatatta ctgtcaacag tatgataacc tccctatcac cttcggccaa  300
gggacacgac tggagattaa a                                            321

SEQ ID NO: 306          moltype = AA  length = 107
FEATURE                 Location/Qualifiers
REGION                  1..107
                        note = Synthetic
source                  1..107
                        mol_type = protein
                        organism = synthetic construct
SEQUENCE: 306
DIQMTQSPSS LSASVGDRVT ITCQASQDIR NYLNWYQQKP GKAPKLLIYD ASNLETGVPS  60
RFSGIGSGTD FTFTISSLQP EDIATYYCQQ YDNLPITFGQ GTRLEIK                107

SEQ ID NO: 307          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 307
caggacatta gaaactat                                                18

SEQ ID NO: 308          moltype = AA  length = 6
FEATURE                 Location/Qualifiers
REGION                  1..6
                        note = Synthetic
source                  1..6
                        mol_type = protein
                        organism = synthetic construct
SEQUENCE: 308
QDIRNY                                                             6

SEQ ID NO: 309          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 309
caacagtatg ataacctccc tatcacc                                      27

SEQ ID NO: 310          moltype = AA  length = 9
FEATURE                 Location/Qualifiers
REGION                  1..9
                        note = Synthetic
source                  1..9
                        mol_type = protein
                        organism = synthetic construct
SEQUENCE: 310
QQYDNLPIT                                                          9

SEQ ID NO: 311          moltype = DNA  length = 1347
FEATURE                 Location/Qualifiers
misc_feature            1..1347
                        note = Synthetic
source                  1..1347
                        mol_type = other DNA
                        organism = synthetic construct
SEQUENCE: 311
gaggtgcagc tggtggagtc tggaggaggc ttggtccagc ctgggggtc cctgagactc  60
tcctgtgcag tctctgggtt caccgtcagt agcaactaca tgagctgggt ccgccaggct  120
ccagggaagg gactggaatg ggtctcactt atttatagcg gtggtagcac attctacgca  180
gactccgtga agggccgatt caccatctcc agacacaatt ccaagaacac gctgtatctt  240
caaatgaaca gcctgagagc tgaggacacg gccgtatatt actgtgcgag agaaggtgga  300
tacagctatg attacaacta ctggggccag ggaaccctgg tcaccgtctc ctcagcctcc  360
accaagggcc catcggtctt ccccctggca ccctcctcca agagcacctc tgggggcaca  420
gcggccctgg gctgcctggt caaggactac ttccccgaac cggtgacggt gtcgtggaac  480
```

```
tcaggcgccc tgaccagcgg cgtgcacacc ttcccggctg tcctacagtc ctcaggactc  540
tactccctca gcagcgtggt gaccgtgccc tccagcagct tgggcaccca gacctacatc  600
tgcaacgtga atcacaagcc cagcaacacc aaggtggaca agaaagttga gcccaaatct  660
tgtgacaaaa ctcacacatg cccaccgtgc ccagcacctg aactcctggg gggaccgtca  720
gtcttcctct tccccccaaa acccaaggac accctcatga tctcccggac ccctgaggtc  780
acatgcgtgg tggtggacgt gagccacgaa gaccctgagg tcaagttcaa ctggtacgtg  840
gacggcgtgg aggtgcataa tgccaagaca aagccgcggg aggagcagta caacagcacg  900
taccgtgtgg tcagcgtcct caccgtcctg caccaggact ggctgaatgg caaggagtac  960
aagtgcaagg tctccaacaa agccctccca gcccccatcg agaaaaccat ctccaaagcc  1020
aaagggcagc cccgagaacc acaggtgtac accctgcccc catcccggga tgagctgacc  1080
aagaaccagg tcagcctgac ctgcctggtc aaaggcttct atcccagcga catcgccgtg  1140
gagtgggaga gcaatgggca gccggagaac aactacaaga ccacgcctcc cgtgctggac  1200
tccgacggct ccttcttcct ctacagcaag ctcaccgtgg acaagagcag gtggcagcag  1260
gggaacgtct tctcatgctc cgtgatgcat gaggctctgc acaaccacta cacgcagaag  1320
tccctctccc tgtctccggg taaatga                                        1347

SEQ ID NO: 312          moltype = AA  length = 448
FEATURE                 Location/Qualifiers
REGION                  1..448
                        note = Synthetic
source                  1..448
                        mol_type = protein
                        organism = synthetic construct
SEQUENCE: 312
EVQLVESGGG LVQPGGSLRL SCAVSGFTVS SNYMSWVRQA PGKGLEWVSL IYSGGSTFYA  60
DSVKGRFTIS RHNSKNTLYL QMNSLRAEDT AVYYCAREGG YSYDYNYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448

SEQ ID NO: 313          moltype = DNA  length = 645
FEATURE                 Location/Qualifiers
misc_feature            1..645
                        note = Synthetic
source                  1..645
                        mol_type = other DNA
                        organism = synthetic construct
SEQUENCE: 313
gacatccaga tgacccagtc tccatcctcc ctgtccgcat ctgtaggaga cagagtcacc  60
atcacgtgcc aggcgagtca ggacattaga aactatttaa attggtatca gcagaaacca  120
gggaaagccc ctaagctcct gatctacgat gcatccaatt tggaaacagg ggtcccatca  180
aggttcagtg gaattggatc tgggacagat tttactttca ccatcagcag cctgcagcct  240
gaagatattg caacatatta ctgtcaacag tatgataacc tccctatcac cttcggccaa  300
gggacacgac tggagattaa acgaactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttag                  645

SEQ ID NO: 314          moltype = AA  length = 214
FEATURE                 Location/Qualifiers
REGION                  1..214
                        note = Synthetic
source                  1..214
                        mol_type = protein
                        organism = synthetic construct
SEQUENCE: 314
DIQMTQSPSS LSASVGDRVT ITCQASQDIR NYLNWYQQKP GKAPKLLIYD ASNLETGVPS  60
RFSGIGSGTD FTFTISSLQP EDIATYYCQQ YDNLPITFGQ GTRLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 315          moltype = DNA  length = 351
FEATURE                 Location/Qualifiers
misc_feature            1..351
                        note = Synthetic
source                  1..351
                        mol_type = other DNA
                        organism = synthetic construct
SEQUENCE: 315
gaggtgcagc tggtggagtc tggaggaggc ttggtccagc cggggggtc cctgagactc  60
tcctgtgcag cctctgggtt aaccgtcagt agcaactaca tgaactgggt ccgccaggtt  120
ccagggaagg ggctggagtg ggtctcagtt atttatagcg gtggtagtaa attctacgta  180
gactccgtga agggccgatt caccatctcc agacacaatt ccaagaacac gctgtatctt  240
caaatgaaca gcctgagacc tgaggacacg gccgtgtatt actgtacgcg agacgcgcaa  300
```

-continued

```
tactacggta tggacgtctg gggccaaggg accacggtca ccgtctcctc a          351

SEQ ID NO: 316          moltype = AA  length = 117
FEATURE                 Location/Qualifiers
REGION                  1..117
                        note = Synthetic
source                  1..117
                        mol_type = protein
                        organism = synthetic construct
SEQUENCE: 316
EVQLVESGGG LVQPGGSLRL SCAASGLTVS SNYMNWVRQV PGKGLEWVSV IYSGGSKFYV  60
DSVKGRFTIS RHNSKNTLYL QMNSLRPEDT AVYYCTRDAQ YYGMDVWGQG TTVTVSS     117

SEQ ID NO: 317          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 317
gggttaaccg tcagtagcaa ctac                                        24

SEQ ID NO: 318          moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 318
atttatagcg gtggtagtaa a                                           21

SEQ ID NO: 319          moltype = AA  length = 7
FEATURE                 Location/Qualifiers
REGION                  1..7
                        note = Synthetic
source                  1..7
                        mol_type = protein
                        organism = synthetic construct
SEQUENCE: 319
IYSGGSK                                                           7

SEQ ID NO: 320          moltype = DNA  length = 33
FEATURE                 Location/Qualifiers
misc_feature            1..33
                        note = Synthetic
source                  1..33
                        mol_type = other DNA
                        organism = synthetic construct
SEQUENCE: 320
acgcgagacg cgcaatacta cggtatggac gtc                              33

SEQ ID NO: 321          moltype = AA  length = 11
FEATURE                 Location/Qualifiers
REGION                  1..11
                        note = Synthetic
source                  1..11
                        mol_type = protein
                        organism = synthetic construct
SEQUENCE: 321
TRDAQYYGMD V                                                      11

SEQ ID NO: 322          moltype = DNA  length = 324
FEATURE                 Location/Qualifiers
misc_feature            1..324
                        note = Synthetic
source                  1..324
                        mol_type = other DNA
                        organism = synthetic construct
SEQUENCE: 322
gacatccaga tgacccagtc tccatcctcc ctgtctgcat ctgtgggaga cagagtcacc  60
atcacttgcc gggcaagtca gagcattagc acctatttac attggtatca gcagaaacca  120
ggagaagccc ctaagctcct gatctatgct gcatccagtt tgcaaagtgg ggtcccatca  180
aggttcagtg gcagtggatc tgggacagat ttcactctca ccatcagcag tctgcaacct  240
gaagattttg caacttacta ctgtcaacag agttacagta cccctccgga gatttttggc  300
caggggacca agctggagat caaa                                        324

SEQ ID NO: 323          moltype = AA  length = 108
```

```
FEATURE                Location/Qualifiers
REGION                 1..108
                       note = Synthetic
source                 1..108
                       mol_type = protein
                       organism = synthetic construct
SEQUENCE: 323
DIQMTQSPSS LSASVGDRVT ITCRASQSIS TYLHWYQQKP GEAPKLLIYA ASSLQSGVPS  60
RFSGSGSGTD FTLTISSLQP EDFATYYCQQ SYSTPPEIFG QGTKLEIK              108

SEQ ID NO: 324         moltype = DNA  length = 18
FEATURE                Location/Qualifiers
misc_feature           1..18
                       note = Synthetic
source                 1..18
                       mol_type = other DNA
                       organism = synthetic construct
SEQUENCE: 324
cagagcatta gcacctat                                                18

SEQ ID NO: 325         moltype = AA  length = 6
FEATURE                Location/Qualifiers
REGION                 1..6
                       note = Synthetic
source                 1..6
                       mol_type = protein
                       organism = synthetic construct
SEQUENCE: 325
QSISTY                                                             6

SEQ ID NO: 326         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 326
caacagagtt acagtacccc tccggagatt                                   30

SEQ ID NO: 327         moltype = AA  length = 10
FEATURE                Location/Qualifiers
REGION                 1..10
                       note = Synthetic
source                 1..10
                       mol_type = protein
                       organism = synthetic construct
SEQUENCE: 327
QQSYSTPPEI                                                         10

SEQ ID NO: 328         moltype = DNA  length = 1344
FEATURE                Location/Qualifiers
misc_feature           1..1344
                       note = Synthetic
source                 1..1344
                       mol_type = other DNA
                       organism = synthetic construct
SEQUENCE: 328
gaggtgcagc tggtggagtc tggaggaggc ttggtccagc cggggggggtc cctgagactc  60
tcctgtgcag cctctgggtt aaccgtcagt agcaactaca tgaactgggt ccgccaggtt  120
ccagggaagg ggctggagtg ggtctcagtt atttatagcg gtggtagtaa attctacgta  180
gactccgtga agggccgatt caccatctcc agacacaatt ccaagaacac gctgtatctt  240
caaatgaaca gcctgagacc tgaggacacg gccgtgtatt actgtacgcg agacgcgcaa  300
tactacggta tggacgtctg gggccaaggg accacggtca ccgtctcctc agcctccacc  360
aagggcccat cggtcttccc cctggcaccc tcctccaaga gcacctctgg gggcacagcg  420
gccctgggct gcctggtcaa ggactacttc cccgaaccgg tgacggtgtc gtggaactca  480
ggcgccctga ccagcggcgt gcacaccttc ccggctgtcc tacagtcctc aggactctac  540
tccctcagca gcgtggtgac cgtgccctcc agcagcttgg gcacccagac ctacatctgc  600
aacgtgaatc acaagcccag caacaccaag gtggacaaga aagttgagcc caaatcttgt  660
gacaaaactc acacatgccc accgtgccca gcacctgaac tcctgggggg accgtcagtc  720
ttcctcttcc ccccaaaacc caaggacacc ctcatgatct cccggacccc tgaggtcaca  780
tgcgtggtgg tggacgtgag ccacgaagac cctgaggtca agttcaactg gtacgtggac  840
ggcgtggagg tgcataatgc caagacaaag ccgcgggagg agcagtacaa cagcacgtac  900
cgtgtggtca gcgtcctcac cgtcctgcac caggactggc tgaatggcaa ggagtacaag  960
tgcaaggtct ccaacaaagc cctcccagcc cccatcgaga aaaccatctc caaagccaaa  1020
gggcagcccc gagaaccaca ggtgtacacc ctgcccccat cccgggatga gctgaccaag  1080
aaccaggtca gcctgacctg cctggtcaaa ggcttctatc ccagcgacat cgccgtggag  1140
tgggagagca atgggcagcc ggagaacaac tacaagacca cgcctcccgt gctggactcc  1200
gacggctcct tcttcctcta cagcaagctc accgtggaca agagcaggtg gcagcagggg  1260
```

-continued

```
aacgtcttct catgctccgt gatgcatgag gctctgcaca accactacac gcagaagtcc  1320
ctctccctgt ctccgggtaa atga                                         1344

SEQ ID NO: 329         moltype = AA  length = 447
FEATURE                Location/Qualifiers
REGION                 1..447
                       note = Synthetic
source                 1..447
                       mol_type = protein
                       organism = synthetic construct
SEQUENCE: 329
EVQLVESGGG LVQPGGSLRL SCAASGLTVS SNYMNWVRQV PGKGLEWVSV IYSGGSKFYV  60
DSVKGRFTIS RHNSKNTLYL QMNSLRPEDT AVYYCTRDAQ YYGMDVWGQG TTVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APELLGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSRDELTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPGK                                      447

SEQ ID NO: 330         moltype = DNA  length = 648
FEATURE                Location/Qualifiers
misc_feature           1..648
                       note = Synthetic
source                 1..648
                       mol_type = other DNA
                       organism = synthetic construct
SEQUENCE: 330
gacatccaga tgacccagtc tccatcctcc ctgtctgcat ctgtgggaga cagagtcacc  60
atcacttgcc gggcaagtca gagcattagc acctatttac attggtatca gcagaaacca  120
ggagaagccc ctaagctcct gatctatgct gcatccagtt tgcaaagtgg ggtcccatca  180
aggttcagtg gcagtggatc tgggacagat ttcactctca ccatcagcag tctgcaacct  240
gaagattttg caacttacta ctgtcaacag agttacagta cccctccgga gatttttggc  300
caggggacca agctggagat caaacgaact gtggctgcac catctgtctt catcttcccg  360
ccatctgatg agcagttgaa atctggaact gcctctgttg tgtgcctgct gaataacttc  420
tatcccagag aggccaaagt acagtggaag gtggataacg ccctccaatc gggtaactcc  480
caggagagtg tcacagagca ggacagcaag gacagcacct acagcctcag cagcaccctg  540
acgctgagca aagcagacta cgagaaacac aaagtctacg cctgcgaagt cacccatcag  600
ggcctgagct cgcccgtcac aaagagcttc aacaggggag agtgttag              648

SEQ ID NO: 331         moltype = AA  length = 215
FEATURE                Location/Qualifiers
REGION                 1..215
                       note = Synthetic
source                 1..215
                       mol_type = protein
                       organism = synthetic construct
SEQUENCE: 331
DIQMTQSPSS LSASVGDRVT ITCRASQSIS TYLHWYQQKP GEAPKLLIYA ASSLQSGVPS  60
RFSGSGSGTD FTLTISSLQP EDFATYYCQQ SYSTPPEIFG QGTKLEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                              215

SEQ ID NO: 332         moltype = DNA  length = 354
FEATURE                Location/Qualifiers
misc_feature           1..354
                       note = Synthetic
source                 1..354
                       mol_type = other DNA
                       organism = synthetic construct
SEQUENCE: 332
gaggtgcagc tggtggagtc tggaggaggc ttggtccagc ctgggggggtc cctgagactc  60
tcctgtgcag cctctgggat caccgtcagt agcaattaca tgacctgggt ccgccaggct  120
ccagggaagg ggctggagtg ggtctcagtt atttatagcg gtggtagcac attctacgca  180
gactccgtga agggccgatt caccatctcc agacacaatt ccaagaacac gctgtatctt  240
caaatgaaca acctgagagc tgaggacacg gccgtgtatt actgtgtgag agatctagag  300
gttcggggcg gtatggacgt ctggggccaa gggaccacgg tcaccgtctc ctca        354

SEQ ID NO: 333         moltype = AA  length = 118
FEATURE                Location/Qualifiers
REGION                 1..118
                       note = Synthetic
source                 1..118
                       mol_type = protein
                       organism = synthetic construct
SEQUENCE: 333
EVQLVESGGG LVQPGGSLRL SCAASGITVS SNYMTWVRQA PGKGLEWVSV IYSGGSTFYA  60
DSVKGRFTIS RHNSKNTLYL QMNNLRAEDT AVYYCVRDLE VRGGMDVWGQ GTTVTVSS    118
```

-continued

```
SEQ ID NO: 334          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 334
gggatcaccg tcagtagcaa ttac                                        24

SEQ ID NO: 335          moltype = DNA  length = 36
FEATURE                 Location/Qualifiers
misc_feature            1..36
                        note = Synthetic
source                  1..36
                        mol_type = other DNA
                        organism = synthetic construct
SEQUENCE: 335
gtgagagatc tagaggttcg gggcggtatg gacgtc                           36

SEQ ID NO: 336          moltype = AA  length = 12
FEATURE                 Location/Qualifiers
REGION                  1..12
                        note = Synthetic
source                  1..12
                        mol_type = protein
                        organism = synthetic construct
SEQUENCE: 336
VRDLEVRGGM DV                                                     12

SEQ ID NO: 337          moltype = DNA  length = 324
FEATURE                 Location/Qualifiers
misc_feature            1..324
                        note = Synthetic
source                  1..324
                        mol_type = other DNA
                        organism = synthetic construct
SEQUENCE: 337
gaaattgtgt tgacgcagtc tccaggcacc ctgtctttgt ctccagggga aagagccacc  60
ctctcctgca gggccagtca gagttttagc agcagctact tagcctggta ccagcagaaa  120
cctggccagg ctcccaggct cctcatctat ggtgcatcca gcagggccac tggcatccca  180
gacaggttca gtggcagtgg gtctgggaca gacttcactc tcaccatcag cagactggag  240
cctgaagatt ttgcagtgta ttactgtcag cagtatggta gctcaccttg gacgttcggc  300
caagggacca aggtggaaat caaa                                        324

SEQ ID NO: 338          moltype = AA  length = 108
FEATURE                 Location/Qualifiers
REGION                  1..108
                        note = Synthetic
source                  1..108
                        mol_type = protein
                        organism = synthetic construct
SEQUENCE: 338
EIVLTQSPGT LSLSPGERAT LSCRASQSFS SSYLAWYQQK PGQAPRLLIY GASSRATGIP  60
DRFSGSGSGT DFTLTISRLE PEDFAVYYCQ QYGSSPWTFG QGTKVEIK              108

SEQ ID NO: 339          moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 339
cagagtttta gcagcagcta c                                           21

SEQ ID NO: 340          moltype = AA  length = 7
FEATURE                 Location/Qualifiers
REGION                  1..7
                        note = Synthetic
source                  1..7
                        mol_type = protein
                        organism = synthetic construct
SEQUENCE: 340
QSFSSSY                                                           7

SEQ ID NO: 341          moltype = DNA  length = 1347
FEATURE                 Location/Qualifiers
misc_feature            1..1347
```

```
                        note = Synthetic
source                  1..1347
                        mol_type = other DNA
                        organism = synthetic construct
SEQUENCE: 341
gaggtgcagc tggtggagtc tggaggaggc ttggtccagc ctggggggtc cctgagactc  60
tcctgtgcag cctctgggat caccgtcagt agcaattaca tgacctgggt ccgccaggct  120
ccagggaagg ggctggagtg ggtctcagtt atttatagcg gtggtagcac attctacgca  180
gactccgtga agggccgatt caccatctcc agacacaatt ccaagaacac gctgtatctt  240
caaatgaaca acctgagagc tgaggacacg gccgtgtatt actgtgtgag agatctagag  300
gttcggggcg gtatggacgt ctggggccaa gggaccacgg tcaccgtctc ctcagcctcc  360
accaagggcc catcggtctt ccccctggca ccctcctcca agagcacctc tgggggcaca  420
gcggccctgg gctgcctggt caaggactac ttccccgaac cggtgacggt gtcgtggaac  480
tcaggcgccc tgaccagcgg cgtgcacacc ttcccggctg tcctacagtc ctcaggactc  540
tactccctca gcagcgtggt gaccgtgccc tccagcagct tgggcaccca gacctacatc  600
tgcaacgtga atcacaagcc cagcaacacc aaggtggaca agaaagttga gcccaaatct  660
tgtgacaaaa ctcacacatg cccaccgtgc ccagcacctg aactcctggg gggaccgtca  720
gtcttcctct tccccccaaa acccaaggac accctcatga tctcccggac ccctgaggtc  780
acatgcgtgg tggtggacgt gagccacgaa gaccctgagg tcaagttcaa ctggtacgtg  840
gacggcgtgg aggtgcataa tgccaagaca aagccgcggg aggagcagta caacagcacg  900
taccgtgtgg tcagcgtcct caccgtcctg caccaggact ggctgaatgg caaggagtac  960
aagtgcaagg tctccaacaa agccctccca gcccccatcg agaaaaccat ctccaaagcc  1020
aaagggcagc cccgagaacc acaggtgtac accctgcccc catcccggga tgagctgacc  1080
aagaaccagg tcagcctgac ctgcctggtc aaaggcttct atcccagcga catcgccgtg  1140
gagtgggaga gcaatgggca gccggagaac aactacaaga ccacgcctcc cgtgctggac  1200
tccgacggct ccttcttcct ctacagcaag ctcaccgtgg acaagagcag gtggcagcag  1260
gggaacgtct tctcatgctc cgtgatgcat gaggctctgc acaaccacta cacgcagaag  1320
tccctctccc tgtctccggg taaatga                                    1347

SEQ ID NO: 342          moltype = AA  length = 448
FEATURE                 Location/Qualifiers
REGION                  1..448
                        note = Synthetic
source                  1..448
                        mol_type = protein
                        organism = synthetic construct
SEQUENCE: 342
EVQLVESGGG LVQPGGSLRL SCAASGITVS SNYMTWVRQA PGKGLEWVSV IYSGGSTFYA  60
DSVKGRFTIS RHNSKNTLYL QMNNLRAEDT AVYYCVRDLE VRGGMDVWGQ GTTVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                   448

SEQ ID NO: 343          moltype = DNA  length = 648
FEATURE                 Location/Qualifiers
misc_feature            1..648
                        note = Synthetic
source                  1..648
                        mol_type = other DNA
                        organism = synthetic construct
SEQUENCE: 343
gaaattgtgt tgacgcagtc tccaggcacc ctgtctttgt ctccagggga aagagccacc  60
ctctcctgca gggccagtca gagttttagc agcagctact tagcctggta ccagcagaaa  120
cctggccagg ctcccaggct cctcatctat ggtgcatcca gcagggccac tggcatccca  180
gacaggttca gtggcagtgg gtctgggaca gacttcactc tcaccatcag cagactggag  240
cctgaagatt ttgcagtgta ttactgtcag cagtatggta gctcaccttg gacgttcggc  300
caagggacca aggtggaaat caaacgaact gtggctgcac catctgtctt catcttcccg  360
ccatctgatg agcagttgaa atctggaact gcctctgttg tgtgcctgct gaataacttc  420
tatcccagag aggccaaagt acagtggaag gtggataacg ccctccaatc gggtaactcc  480
caggagagtg tcacagagca ggacagcaag gacagcacct acagcctcag cagcaccctg  540
acgctgagca aagcagacta cgagaaacac aaagtctacg cctgcgaagt cacccatcag  600
ggcctgagct cgcccgtcac aaagagcttc aacaggggag agtgttag              648

SEQ ID NO: 344          moltype = AA  length = 215
FEATURE                 Location/Qualifiers
REGION                  1..215
                        note = Synthetic
source                  1..215
                        mol_type = protein
                        organism = synthetic construct
SEQUENCE: 344
EIVLTQSPGT LSLSPGERAT LSCRASQSFS SSYLAWYQQK PGQAPRLLIY GASSRATGIP  60
DRFSGSGSGT DFTLTISRLE PEDFAVYYCQ QYGSSPWTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                            215
```

-continued

```
SEQ ID NO: 345          moltype = DNA  length = 1329
FEATURE                 Location/Qualifiers
misc_feature            1..1329
                        note = Synthetic
source                  1..1329
                        mol_type = other DNA
                        organism = synthetic construct
SEQUENCE: 345
gaggtgcagc tggtggagtc tggaggaggc ttggtccagt ctggggggtc cctgagactc  60
tcctgtgcag cctctgggct caccgtcagt agcaactaca tgagctgggt ccgccaggct  120
ccagggaagg gactggagtg ggtctcagtt atttatagcg gtggtagcac attctactca  180
gactccgtga agggccgatt caccatctcc agacacaatt ccaagaacac gctgtatctt  240
caaatgaaca gcctgagagc tgaggacacg gccgtgtatt actgtgcgag agcgagggga  300
gacgcttttg atatctgggg ccaagggaca atggtcaccg tctcttcagc ctccaccaag  360
ggcccatcgg tcttcccccct ggcgccctgc tccaggagca cctccgagag cacagccgcc  420
ctgggctgcc tggtcaagga ctacttcccc gaaccggtga cggtgtcgtg gaactcaggc  480
gccctgacca gcggcgtgca caccttcccg gctgtcctac agtcctcagg actctactcc  540
ctcagcagcg tggtgaccgt gccctccagc agcttgggca cgaagaccta cacctgcaac  600
gtagatcaca agcccagcaa caccaaggtg gacaagagag ttgagtccaa atatggtccc  660
ccatgcccac cgtgcccagc accaggcggt ggcggaccat cagtcttcct gttcccccca  720
aaacccaagg acactctcat gatctcccgg acccctgagg tcacgtgcgt ggtggtggac  780
gtgagccagg aagaccccga ggtccagttc aactggtacg tggatggcgt ggaggtgcat  840
aatgccaaga caaagccgcg ggaggagcag ttcaacagca cgtaccgtgt ggtcagcgtc  900
ctcaccgtcc tgcaccagga ctggctgaac ggcaaggagt acaagtgcaa ggtctccaac  960
aaaggcctcc cgtcctccat cgagaaaacc atctccaaag ccaaagggca gccccgagag  1020
ccacaggtgt acaccctgcc cccatcccag gaggagatga ccaagaacca ggtcagcctg  1080
acctgcctgg tcaaaggctt ctaccccagc gacatcgccg tggagtggga gagcaatggg  1140
cagccggaga acaactacaa gaccacgcct cccgtgctgg actccgacgg ctccttcttc  1200
ctctacagca ggctcaccgt ggacaagagc aggtggcagg aggggaatgt cttctcatgc  1260
tccgtgatgc atgaggctct gcacaaccac tacacacaga agtccctctc cctgtctctg  1320
ggtaaatga                                                          1329

SEQ ID NO: 346          moltype = AA  length = 442
FEATURE                 Location/Qualifiers
REGION                  1..442
                        note = Synthetic
source                  1..442
                        mol_type = protein
                        organism = synthetic construct
SEQUENCE: 346
EVQLVESGGG LVQSGGSLRL SCAASGLTVS SNYMSWVRQA PGKGLEWVSV IYSGGSTFYS  60
DSVKGRFTIS RHNSKNTLYL QMNSLRAEDT AVYYCARARG DAFDIWGQGT MVTVSSASTK  120
GPSVFPLAPC SRSTSESTAA LGCLVKDYFP EPVTVSWNSG ALTSGVHTFP AVLQSSGLYS  180
LSSVVTVPSS SLGTKTYTCN VDHKPSNTKV DKRVESKYGP PCPPCPAPGG GGPSVFLFPP  240
KPKDTLMISR TPEVTCVVVD VSQEDPEVQF NWYVDGVEVH NAKTKPREEQ FNSTYRVVSV  300
LTVLHQDWLN GKEYKCKVSN KGLPSSIEKT ISKAKGQPRE PQVYTLPPSQ EEMTKNQVSL  360
TCLVKGFYPS DIAVEWESNG QPENNYKTTP PVLDSDGSFF LYSRLTVDKS RWQEGNVFSC  420
SVMHEALHNH YTQKSLSLSL GK                                           442

SEQ ID NO: 347          moltype = DNA  length = 1341
FEATURE                 Location/Qualifiers
misc_feature            1..1341
                        note = Synthetic
source                  1..1341
                        mol_type = other DNA
                        organism = synthetic construct
SEQUENCE: 347
caggtgcagc tggtggagtc tgggggaggc ttggtcaagc ctggagggtc cctgagactc  60
tcctgtgcag cctctggatt caccttcagt gactactaca tgagctggat ccgccaggct  120
ccagggaagg ggctggagtg ggtttcatac attacttata gtggtagtac catatactac  180
gcagactctg tgaagggccg attcaccatc tccagggaca acgccaagag ctcactgtat  240
ctgcaaatga acagcctgag agccgaggac acggccgtgt attactgtgc gagagatcgc  300
ggtacaacta tggtcccctt tgactactgg ggccagggaa ccctggtcac cgtctcctca  360
gcctccacca agggcccatc ggtcttcccc ctggcgccct gctccaggag cacctccgag  420
agcacagccg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacgaagacc  600
tacacctgca acgtagatca caagcccagc aacaccaagg tggacaagag agttgagtcc  660
aaatatggtc ccccatgccc accgtgccca gcaccaggcg gtggcggacc atcagtcttc  720
ctgttccccc caaaacccaa ggacactctc atgatctccc ggacccctga ggtcacgtgc  780
gtggtggtgg acgtgagcca ggaagacccc gaggtccagt tcaactggta cgtggatggc  840
gtggaggtgc ataatgccaa gacaaagccg cgggaggagc agttcaacag cacgtaccgt  900
gtggtcagcg tcctcaccgt cctgcaccag gactggctga acggcaagga gtacaagtgc  960
aaggtctcca acaaaggcct cccgtcctcc atcgagaaaa ccatctccaa agccaaaggg  1020
cagccccgag agccacaggt gtacaccctg cccccatccc aggaggagat gaccaagaac  1080
caggtcagcc tgacctgcct ggtcaaaggc ttctacccca gcgacatcgc cgtggagtgg  1140
gagagcaatg ggcagccgga gaacaactac aagaccacgc ctcccgtgct ggactccgac  1200
ggctccttct tcctctacag caggctcacc gtggacaaga gcaggtggca ggaggggaat  1260
gtcttctcat gctccgtgat gcatgaggct ctgcacaacc actacacaca gaagtccctc  1320
```

-continued

```
tccctgtctc tgggtaaatg a                                         1341

SEQ ID NO: 348          moltype = AA  length = 446
FEATURE                 Location/Qualifiers
REGION                  1..446
                        note = Synthetic
source                  1..446
                        mol_type = protein
                        organism = synthetic construct
SEQUENCE: 348
QVQLVESGGG LVKPGGSLRL SCAASGFTFS DYYMSWIRQA PGKGLEWVSY ITYSGSTIYY  60
ADSVKGRFTI SRDNAKSSLY LQMNSLRAED TAVYYCARDR GTTMVPFDYW GQGTLVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APGGGGPSVF  240
LFPPKPKDTL MISRTPEVTC VVVDVSQEDP EVQFNWYVDG VEVHNAKTKP REEQFNSTYR  300
VVSVLTVLHQ DWLNGKEYKC KVSNKGLPSS IEKTISKAKG QPREPQVYTL PPSQEEMTKN  360
QVSLTCLVKG FYPSDIAVEW ESNGQPENNY KTTPPVLDSD GSFFLYSRLT VDKSRWQEGN  420
VFSCSVMHEA LHNHYTQKSL SLSLGK                                    446

SEQ ID NO: 349          moltype = DNA  length = 1341
FEATURE                 Location/Qualifiers
misc_feature            1..1341
                        note = Synthetic
source                  1..1341
                        mol_type = other DNA
                        organism = synthetic construct
SEQUENCE: 349
gaggtgcagc tggtggagtc tgggggaggc ttggtaaagc ctggggggtc ccttagactc  60
tcctgtgcag cctctggaat cactttcagt aacgcctgga tgagttgggt ccgccaggct  120
ccagggaagg ggctggagtg ggttggccgt attaaaagca aaactgatgg tgggacaaca  180
gactacgccg caccgtgaa aggcagattc accatctcaa gagatgattc aaaaaacacg  240
ctgtatctac aaatgaacag cctgaaaacc gaggacacag ccgtgtatta ctgtaccaca  300
gcgaggtggg actggtactt cgatctctgg ggccgtggca ccctggtcac tgtctcctca  360
gcctccacca agggcccatc ggtcttcccc ctggcgccct gctccaggag cacctccgag  420
agcacagccg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacgaagacc  600
tacacctgca acgtagatca caagcccagc aacaccaagg tggacaagag agttgagtcc  660
aaatatggtc ccccatgccc accgtgccca gcaccaggcg gtggcggacc atcagtcttc  720
ctgttccccc caaaacccaa ggacactctc atgatctccc ggacccctga ggtcacgtgc  780
gtggtggtgg acgtgagcca ggaagacccc gaggtccagt tcaactggta cgtggatggc  840
gtggaggtgc ataatgccaa gacaaagccg cgggaggagc agttcaacag cacgtaccgt  900
gtggtcagcg tcctcaccgt cctgcaccag gactggctga acggcaagga gtacaagtgc  960
aaggtctcca acaaaggcct cccgtcctcc atcgagaaaa ccatctccaa agccaaaggg  1020
cagccccgag agccacaggt gtacaccctg cccccatccc aggaggagat gaccaagaac  1080
caggtcagcc tgacctgcct ggtcaaaggc ttctacccca gcgacatcgc cgtggagtgg  1140
gagagcaatg ggcagccgga gaacaactac aagaccacgc ctcccgtgct ggactccgac  1200
ggctccttct tcctctacag caggctcacc gtggacaaga gcaggtggca ggaggggaat  1260
gtcttctcat gctccgtgat gcatgaggct ctgcacaacc actacacaca gaagtccctc  1320
tccctgtctc tgggtaaatg a                                         1341

SEQ ID NO: 350          moltype = AA  length = 446
FEATURE                 Location/Qualifiers
REGION                  1..446
                        note = Synthetic
source                  1..446
                        mol_type = protein
                        organism = synthetic construct
SEQUENCE: 350
EVQLVESGGG LVKPGGSLRL SCAASGITFS NAWMSWVRQA PGKGLEWVGR IKSKTDGGTT  60
DYAAPVKGRF TISRDDSKNT LYLQMNSLKT EDTAVYYCTT ARWDWYFDLW GRGTLVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APGGGGPSVF  240
LFPPKPKDTL MISRTPEVTC VVVDVSQEDP EVQFNWYVDG VEVHNAKTKP REEQFNSTYR  300
VVSVLTVLHQ DWLNGKEYKC KVSNKGLPSS IEKTISKAKG QPREPQVYTL PPSQEEMTKN  360
QVSLTCLVKG FYPSDIAVEW ESNGQPENNY KTTPPVLDSD GSFFLYSRLT VDKSRWQEGN  420
VFSCSVMHEA LHNHYTQKSL SLSLGK                                    446

SEQ ID NO: 351          moltype = DNA  length = 1341
FEATURE                 Location/Qualifiers
misc_feature            1..1341
                        note = Synthetic
source                  1..1341
                        mol_type = other DNA
                        organism = synthetic construct
SEQUENCE: 351
gaggtgcagc tggtggagtc tggaggaggc ttggtccagc ctggggggtc cctgagactc  60
tcctgtgcag cctctgggtt caccgtcagt agcaactaca tgagctgggt ccgccaggct  120
ccagggaagg ggctggagtg ggtctcactt atttatagcg gtggtagcac atactatgca  180
```

-continued

```
gactccgtga agggccgatt caccatctcc agacacaatt ccaagaacac gctgtatctt  240
caaatgaaca gcctgagatc tgaggacacg gccgtgtatt actgtgcgag agtccccctg  300
ggggattact actacggtat ggacgtctgg ggccaaggga ccacggtcac cgtctcctca  360
gcctccacca agggcccatc ggtcttcccc ctggcgccct gctccaggag cacctccgag  420
agcacagccg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacgaagacc  600
tacacctgca acgtagatca caagcccagc aacaccaagg tggacaagag agttgagtcc  660
aaatatggtc ccccatgccc accgtgccca gcaccaggcg gtggcggacc atcagtcttc  720
ctgttccccc caaaacccaa ggacactctc atgatctccc ggacccctga ggtcacgtgc  780
gtggtggtgg acgtgagcca ggaagacccc gaggtccagt tcaactggta cgtggatggc  840
gtggaggtgc ataatgccaa gacaaagccg cgggaggagc agttcaacag cacgtaccgt  900
gtggtcagcg tcctcaccgt cctgcaccag gactggctga acggcaagga gtacaagtgc  960
aaggtctcca acaaaggcct cccgtcctcc atcgagaaaa ccatctccaa agccaaaggg  1020
cagccccgag agccacaggt gtacaccctg cccccatccc aggaggagat gaccaagaac  1080
caggtcagcc tgacctgcct ggtcaaaggc ttctacccca gcgacatcgc cgtggagtgg  1140
gagagcaatg ggcagccgga gaacaactac aagaccacgc ctcccgtgct ggactccgac  1200
ggctccttct tcctctacag caggctcacc gtggacaaga gcaggtggca ggaggggaat  1260
gtcttctcat gctccgtgat gcatgaggct ctgcacaacc actacacaca gaagtccctc  1320
tccctgtctc tgggtaaatg a                                           1341

SEQ ID NO: 352         moltype = AA  length = 446
FEATURE                Location/Qualifiers
REGION                 1..446
                       note = Synthetic
source                 1..446
                       mol_type = protein
                       organism = synthetic construct
SEQUENCE: 352
EVQLVESGGG LVQPGGSLRL SCAASGFTVS SNYMSWVRQA PGKGLEWVSL IYSGGSTYYA  60
DSVKGRFTIS RHNSKNTLYL QMNSLRSEDT AVYYCARVPL GDYYYGMDVW GQGTTVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APGGGGPSVF  240
LFPPKPKDTL MISRTPEVTC VVVDVSQEDP EVQFNWYVDG VEVHNAKTKP REEQFNSTYR  300
VVSVLTVLHQ DWLNGKEYKC KVSNKGLPSS IEKTISKAKG QPREPQVYTL PPSQEEMTKN  360
QVSLTCLVKG FYPSDIAVEW ESNGQPENNY KTTPPVLDSD GSFFLYSRLT VDKSRWQEGN  420
VFSCSVMHEA LHNHYTQKSL SLSLGK                                      446

SEQ ID NO: 353         moltype = DNA  length = 1353
FEATURE                Location/Qualifiers
misc_feature           1..1353
                       note = Synthetic
source                 1..1353
                       mol_type = other DNA
                       organism = synthetic construct
SEQUENCE: 353
caggtgcagc tggtggagtc tgggggaggc gtggtccagc ctgggaggtc cctgagactc  60
tcctgtgcag cgtctggatt caccttcaga aactatggca tgcactgggt ccgccaggct  120
ccaggcaagg ggctggagtg ggtgtcagtt atatggtatg atggaagtaa tagatactat  180
gcagactccg tgaagggccg attcaccatc tccagagaca cttccaagaa cacgctgtat  240
ctgcaaatga acagcctgag agccgaagac acggctgtgt attactgtgc gagagatcct  300
cctataactg gaacgacggg gggcgatgct tttgatatct ggggccaagg gacaatggtc  360
accgtctctt cagcctccac caagggccca tcggtcttcc ccctggcgcc ctgctccagg  420
agcacctccg agagcacagc cgccctgggc tgcctggtca aggactactt ccccgaaccg  480
gtgacggtgt cgtggaactc aggcgccctg accagcggcg tgcacacctt cccggctgtc  540
ctacagtcct caggactcta ctccctcagc agcgtggtga ccgtgccctc cagcagcttg  600
ggcacgaaga cctacacctg caacgtagat cacaagccca gcaacaccaa ggtggacaag  660
agagttgagt ccaaatatgg tcccccatgc ccaccgtgcc cagcaccagg cggtggcgga  720
ccatcagtct tcctgttccc cccaaaaccc aaggacactc tcatgatctc ccggacccct  780
gaggtcacgt gcgtggtggt ggacgtgagc caggaagacc ccgaggtcca gttcaactgg  840
tacgtggatg gcgtggaggt gcataatgcc aagacaaagc cgcgggagga gcagttcaac  900
agcacgtacc gtgtggtcag cgtcctcacc gtcctgcacc aggactggct gaacggcaag  960
gagtacaagt gcaaggtctc caacaaaggc ctcccgtcct ccatcgagaa aaccatctcc  1020
aaagccaaag ggcagccccg agagccacag gtgtacaccc tgcccccatc ccaggaggag  1080
atgaccaaga accaggtcag cctgacctgc ctggtcaaag gcttctaccc cagcgacatc  1140
gccgtggagt gggagagcaa tgggcagccg gagaacaact acaagaccac gcctcccgtg  1200
ctggactccg acggctcctt cttcctctac agcaggctca ccgtggacaa gagcaggtgg  1260
caggagggga atgtcttctc atgctccgtg atgcatgagg ctctgcacaa ccactacaca  1320
cagaagtccc tctccctgtc tctgggtaaa tga                              1353

SEQ ID NO: 354         moltype = AA  length = 450
FEATURE                Location/Qualifiers
REGION                 1..450
                       note = Synthetic
source                 1..450
                       mol_type = protein
                       organism = synthetic construct
SEQUENCE: 354
QVQLVESGGG VVQPGRSLRL SCAASGFTFR NYGMHWVRQA PGKGLEWVSV IWYDGSNRYY  60
```

-continued

```
ADSVKGRFTI SRDTSKNTLY LQMNSLRAED TAVYYCARDP PITGTTGGDA FDIWGQGTMV  120
TVSSASTKGP SVFPLAPCSR STSESTAALG CLVKDYFPEP VTVSWNSGAL TSGVHTFPAV  180
LQSSGLYSLS SVVTVPSSSL GTKTYTCNVD HKPSNTKVDK RVESKYGPPC PPCPAPGGGG  240
PSVFLFPPKP KDTLMISRTP EVTCVVVDVS QEDPEVQFNW YVDGVEVHNA KTKPREEQFN  300
STYRVVSVLT VLHQDWLNGK EYKCKVSNKG LPSSIEKTIS KAKGQPREPQ VYTLPPSQEE  360
MTKNQVSLTC LVKGFYPSDI AVEWESNGQP ENNYKTTPPV LDSDGSFFLY SRLTVDKSRW  420
QEGNVFSCSV MHEALHNHYT QKSLSLSLGK                                  450

SEQ ID NO: 355          moltype = DNA  length = 1338
FEATURE                 Location/Qualifiers
misc_feature            1..1338
                        note = Synthetic
source                  1..1338
                        mol_type = other DNA
                        organism = synthetic construct
SEQUENCE: 355
cagatcacct tgaaggagtc tggtcctacg ctggtgaaac ccacacagac cctcacgctg  60
acctgcacct tctctgggtt ctcactcagc actaatgtag tgggtgtggg ctggatccgt  120
cagcccccag gaaaggccct ggagtggctt gcactcattt attggaatga tgataagcgc  180
tacagcccat ctctgaagag caggctcacc atcaccaagg acacctccaa aaaccaggtg  240
gtccttacaa tgaccaacat ggaccctgtg gacacagcca catattactg tgcacacggc  300
ccaactgggg actactttga ctactggggc cagggaaccc tggtcaccgt ctcctcagcc  360
tccaccaagg gcccatcggt cttccccctg gcgccctgct ccaggagcac ctccgagagc  420
acagccgccc tgggctgcct ggtcaaggac tacttccccg aaccggtgac ggtgtcgtgg  480
aactcaggcg ccctgaccag cggcgtgcac accttcccgg ctgtcctaca gtcctcagga  540
ctctactccc tcagcagcgt ggtgaccgtg ccctccagca gcttgggcac gaagacctac  600
acctgcaacg tagatcacaa gcccagcaac accaaggtgg acaagagagt tgagtccaaa  660
tatggtcccc catgcccacc gtgcccagca ccaggcggtg gcggaccatc agtcttcctg  720
ttccccccaa aacccaagga cactctcatg atctcccgga cccctgaggt cacgtgcgtg  780
gtggtggacg tgagccagga agaccccgag gtccagttca actggtacgt ggatggcgtg  840
gaggtgcata atgccaagac aaagccgcgg gaggagcagt tcaacagcac gtaccgtgtg  900
gtcagcgtcc tcaccgtcct gcaccaggac tggctgaacg gcaaggagta caagtgcaag  960
gtctccaaca aaggcctccc gtcctccatc gagaaaacca tctccaaagc caaagggcag  1020
ccccgagagc cacaggtgta caccctgccc ccatcccagg aggagatgac caagaaccag  1080
gtcagcctga cctgcctggt caaaggcttc taccccagcg acatcgccgt ggagtgggag  1140
agcaatgggc agccggagaa caactacaag accacgcctc ccgtgctgga ctccgacggc  1200
tccttcttcc tctacagcag gctcaccgtg gacaagagca ggtggcagga ggggaatgtc  1260
ttctcatgct ccgtgatgca tgaggctctg cacaaccact acacacagaa gtccctctcc  1320
ctgtctctgg gtaaatga                                               1338

SEQ ID NO: 356          moltype = AA  length = 445
FEATURE                 Location/Qualifiers
REGION                  1..445
                        note = Synthetic
source                  1..445
                        mol_type = protein
                        organism = synthetic construct
SEQUENCE: 356
QITLKESGPT LVKPTQTLTL TCTFSGFSLS TNVVGVGWIR QPPGKALEWL ALIYWNDDKR  60
YSPSLKSRLT ITKDTSKNQV VLTMTNMDPV DTATYYCAHG PTGDYFDYWG QGTLVTVSSA  120
STKGPSVFPL APCSRSTSES TAALGCLVKD YFPEPVTVSW NSGALTSGVH TFPAVLQSSG  180
LYSLSSVVTV PSSSLGTKTY TCNVDHKPSN TKVDKRVESK YGPPCPPCPA PGGGGPSVFL  240
FPPKPKDTLM ISRTPEVTCV VVDVSQEDPE VQFNWYVDGV EVHNAKTKPR EEQFNSTYRV  300
VSVLTVLHQD WLNGKEYKCK VSNKGLPSSI EKTISKAKGQ PREPQVYTLP PSQEEMTKNQ  360
VSLTCLVKGF YPSDIAVEWE SNGQPENNYK TTPPVLDSDG SFFLYSRLTV DKSRWQEGNV  420
FSCSVMHEAL HNHYTQKSLS LSLGK                                       445

SEQ ID NO: 357          moltype = DNA  length = 1335
FEATURE                 Location/Qualifiers
misc_feature            1..1335
                        note = Synthetic
source                  1..1335
                        mol_type = other DNA
                        organism = synthetic construct
SEQUENCE: 357
gaggtgcagc tggtggagtc tggaggaggc ttggtccagc ctgggggggtc cctgagactc  60
tcctgtgcag tctctgggtt caccgtcagt agcaactaca tgagctgggt ccgccaggct  120
ccagggaagg gactggaatg ggtctcactt atttatagcg gtggtagcac attctacgca  180
gactccgtga agggccgatt caccatctcc agacacaatt ccaagaacac gctgtatctt  240
caaatgaaca gcctgagagc tgaggacacg gccgtatatt actgtgcgag agaaggtgga  300
tacagctatg attacaacta ctggggccag ggaaccctgg tcaccgtctc ctcagcctcc  360
accaagggcc catcggtctt ccccctggcg ccctgctcca ggagcacctc cgagagcaca  420
gccgccctgg gctgcctggt caaggactac ttccccgaac cggtgacggt gtcgtggaac  480
tcaggcgccc tgaccagcgg cgtgcacacc ttcccggctg tcctacagtc ctcaggactc  540
tactccctca gcagcgtggt gaccgtgccc tccagcagct tgggcacgaa gacctacacc  600
tgcaacgtag atcacaagcc cagcaacacc aaggtggaca agagagttga gtccaaatat  660
ggtcccccat gcccaccgtg cccagcacca ggcggtggcg gaccatcagt cttcctgttc  720
cccccaaaac ccaaggacac tctcatgatc tcccggaccc ctgaggtcac gtgcgtggtg  780
gtggacgtga gccaggaaga ccccgaggtc cagttcaact ggtacgtgga tggcgtggag  840
```

-continued

```
gtgcataatg ccaagacaaa gccgcgggag gagcagttca acagcacgta ccgtgtggtc  900
agcgtcctca ccgtcctgca ccaggactgg ctgaacggca aggagtacaa gtgcaaggtc  960
tccaacaaag gcctcccgtc ctccatcgag aaaaccatct ccaaagccaa agggcagccc  1020
cgagagccac aggtgtacac cctgccccca tcccaggagg agatgaccaa gaaccaggtc  1080
agcctgacct gcctggtcaa aggcttctac cccagcgaca tcgccgtgga gtgggagagc  1140
aatgggcagc cggagaacaa ctacaagacc acgcctcccg tgctggactc cgacggctcc  1200
ttcttcctct acagcaggct caccgtggac aagagcaggt ggcaggaggg gaatgtcttc  1260
tcatgctccg tgatgcatga ggctctgcac aaccactaca cacagaagtc cctctccctg  1320
tctctgggta aatga                                                   1335

SEQ ID NO: 358         moltype = AA  length = 444
FEATURE                Location/Qualifiers
REGION                 1..444
                       note = Synthetic
source                 1..444
                       mol_type = protein
                       organism = synthetic construct
SEQUENCE: 358
EVQLVESGGG LVQPGGSLRL SCAVSGFTVS SNYMSWVRQA PGKGLEWVSL IYSGGSTFYA  60
DSVKGRFTIS RHNSKNTLYL QMNSLRAEDT AVYYCAREGG YSYDYNYWGQ GTLVTVSSAS  120
TKGPSVFPLA PCSRSTSEST AALGCLVKDY FPEPVTVSWN SGALTSGVHT FPAVLQSSGL  180
YSLSSVVTVP SSSLGTKTYT CNVDHKPSNT KVDKRVESKY GPPCPPCPAP GGGGPSVFLF  240
PPKPKDTLMI SRTPEVTCVV VDVSQEDPEV QFNWYVDGVE VHNAKTKPRE EQFNSTYRVV  300
SVLTVLHQDW LNGKEYKCKV SNKGLPSSIE KTISKAKGQP REPQVYTLPP SQEEMTKNQV  360
SLTCLVKGFY PSDIAVEWES NGQPENNYKT TPPVLDSDGS FFLYSRLTVD KSRWQEGNVF  420
SCSVMHEALH NHYTQKSLSL SLGK                                        444

SEQ ID NO: 359         moltype = DNA  length = 1332
FEATURE                Location/Qualifiers
misc_feature           1..1332
                       note = Synthetic
source                 1..1332
                       mol_type = other DNA
                       organism = synthetic construct
SEQUENCE: 359
gaggtgcagc tggtggagtc tggaggaggc ttggtccagc cggggggtc cctgagactc  60
tcctgtgcag cctctgggtt aaccgtcagt agcaactaca tgaactgggt ccgccaggtt  120
ccagggaagg ggctggagtg ggtctcagtt atttatagcg gtggtagtaa attctacgta  180
gactccgtga agggccgatt caccatctcc agacacaatt ccaagaacac gctgtatctt  240
caaatgaaca gcctgagacc tgaggacacg gccgtgtatt actgtacgcg agacgcgcaa  300
tactacggta tggacgtctg gggccaaggg accacggtca ccgtctcctc agcctccacc  360
aagggcccat cggtcttccc cctggcgccc tgctccagga gcacctccga gagcacagcc  420
gccctgggct gcctggtcaa ggactacttc cccgaaccgg tgacggtgtc gtggaactca  480
ggcgccctga ccagcggcgt gcacaccttc ccggctgtcc tacagtcctc aggactctac  540
tccctcagca gcgtggtgac cgtgccctcc agcagcttgg gcacgaagac ctacacctgc  600
aacgtagatc acaagcccag caacaccaag gtggacaaga gagttgagtc caaatatggt  660
cccccatgcc caccgtgccc agcaccaggc ggtggcggac catcagtctt cctgttcccc  720
ccaaaaccca aggacactct catgatctcc cggacccctg aggtcacgtg cgtggtggtg  780
gacgtgagcc aggaagaccc cgaggtccag ttcaactggt acgtggatgg cgtggaggtg  840
cataatgcca agacaaagcc gcgggaggag cagttcaaca gcacgtaccg tgtggtcagc  900
gtcctcaccg tcctgcacca ggactggctg aacggcaagg agtacaagtg caaggtctcc  960
aacaaaggcc tcccgtcctc catcgagaaa accatctcca aagccaaagg gcagccccga  1020
gagccacagg tgtacaccct gcccccatcc caggaggaga tgaccaagaa ccaggtcagc  1080
ctgacctgcc tggtcaaagg cttctacccc agcgacatcg ccgtggagtg ggagagcaat  1140
gggcagccgg agaacaacta caagaccacg cctcccgtgc tggactccga cggctccttc  1200
ttcctctaca gcaggctcac cgtggacaag agcaggtggc aggaggggaa tgtcttctca  1260
tgctccgtga tgcatgaggc tctgcacaac cactacacac agaagtccct ctccctgtct  1320
ctgggtaaat ga                                                      1332

SEQ ID NO: 360         moltype = AA  length = 443
FEATURE                Location/Qualifiers
REGION                 1..443
                       note = Synthetic
source                 1..443
                       mol_type = protein
                       organism = synthetic construct
SEQUENCE: 360
EVQLVESGGG LVQPGGSLRL SCAASGLTVS SNYMNWVRQV PGKGLEWVSV IYSGGSKFYV  60
DSVKGRFTIS RHNSKNTLYL QMNSLRPEDT AVYYCTRDAQ YYGMDVWGQG TTVTVSSAST  120
KGPSVFPLAP CSRSTSESTA ALGCLVKDYF PEPVTVSWNS GALTSGVHTF PAVLQSSGLY  180
SLSSVVTVPS SSLGTKTYTC NVDHKPSNTK VDKRVESKYG PPCPPCPAPG GGGPSVFLFP  240
PKPKDTLMIS RTPEVTCVVV DVSQEDPEVQ FNWYVDGVEV HNAKTKPREE QFNSTYRVVS  300
VLTVLHQDWL NGKEYKCKVS NKGLPSSIEK TISKAKGQPR EPQVYTLPPS QEEMTKNQVS  360
LTCLVKGFYP SDIAVEWESN GQPENNYKTT PPVLDSDGSF FLYSRLTVDK SRWQEGNVFS  420
CSVMHEALHN HYTQKSLSLS LGK                                         443

SEQ ID NO: 361         moltype = DNA  length = 1335
FEATURE                Location/Qualifiers
misc_feature           1..1335
```

```
                        note = Synthetic
source                  1..1335
                        mol_type = other DNA
                        organism = synthetic construct
SEQUENCE: 361
gaggtgcagc tggtggagtc tggaggaggc ttggtccagc ctggggggtc cctgagactc  60
tcctgtgcag cctctgggat caccgtcagt agcaattaca tgacctgggt ccgccaggct  120
ccagggaagg ggctggagtg ggtctcagtt atttatagcg gtggtagcac attctacgca  180
gactccgtga agggccgatt caccatctcc agacacaatt ccaagaacac gctgtatctt  240
caaatgaaca acctgagagc tgaggacacg gccgtgtatt actgtgtgag agatctagag  300
gttcggggcg gtatggacgt ctggggccaa gggaccacgg tcaccgtctc ctcagcctcc  360
accaagggcc catcggtctt ccccctggcg ccctgctcca ggagcacctc cgagagcaca  420
gccgccctgg gctgcctggt caaggactac ttccccgaac cggtgacggt gtcgtggaac  480
tcaggcgccc tgaccagcgg cgtgcacacc ttcccggctg tcctacagtc ctcaggactc  540
tactccctca gcagcgtggt gaccgtgccc tccagcagct tgggcacgaa gacctacacc  600
tgcaacgtag atcacaagcc cagcaacacc aaggtggaca agagagttga gtccaaatat  660
ggtcccccat gcccaccgtg cccagcacca ggcggtggcg gaccatcagt cttcctgttc  720
cccccaaaac ccaaggacac tctcatgatc tcccggaccc ctgaggtcac gtgcgtggtg  780
gtggacgtga gccaggaaga ccccgaggtc cagttcaact ggtacgtgga tggcgtggag  840
gtgcataatg ccaagacaaa gccgcgggag gagcagttca acagcacgta ccgtgtggtc  900
agcgtcctca ccgtcctgca ccaggactgg ctgaacggca aggagtacaa gtgcaaggtc  960
tccaacaaag gcctcccgtc ctccatcgag aaaaccatct ccaaagccaa agggcagccc  1020
cgagagccac aggtgtacac cctgccccca tcccaggagg agatgaccaa gaaccaggtc  1080
agcctgacct gcctggtcaa aggcttctac cccagcgaca tcgccgtgga gtgggagagc  1140
aatgggcagc cggagaacaa ctacaagacc acgcctcccg tgctggactc cgacggctcc  1200
ttcttcctct acagcaggct caccgtggac aagagcaggt ggcaggaggg gaatgtcttc  1260
tcatgctccg tgatgcatga ggctctgcac aaccactaca cacagaagtc cctctccctg  1320
tctctgggta aatga                                                   1335

SEQ ID NO: 362          moltype = AA  length = 444
FEATURE                 Location/Qualifiers
REGION                  1..444
                        note = Synthetic
source                  1..444
                        mol_type = protein
                        organism = synthetic construct
SEQUENCE: 362
EVQLVESGGG LVQPGGSLRL SCAASGITVS SNYMTWVRQA PGKGLEWVSV IYSGGSTFYA  60
DSVKGRFTIS RHNSKNTLYL QMNNLRAEDT AVYYCVRDLE VRGGMDVWGQ GTTVTVSSAS  120
TKGPSVFPLA PCSRSTSEST AALGCLVKDY FPEPVTVSWN SGALTSGVHT FPAVLQSSGL  180
YSLSSVVTVP SSSLGTKTYT CNVDHKPSNT KVDKRVESKY GPPCPPCPAP GGGGPSVFLF  240
PPKPKDTLMI SRTPEVTCVV VDVSQEDPEV QFNWYVDGVE VHNAKTKPRE EQFNSTYRVV  300
SVLTVLHQDW LNGKEYKCKV SNKGLPSSIE KTISKAKGQP REPQVYTLPP SQEEMTKNQV  360
SLTCLVKGFY PSDIAVEWES NGQPENNYKT TPPVLDSDGS FFLYSRLTVD KSRWQEGNVF  420
SCSVMHEALH NHYTQKSLSL SLGK                                          444

SEQ ID NO: 363          moltype = DNA  length = 1347
FEATURE                 Location/Qualifiers
misc_feature            1..1347
                        note = Synthetic
source                  1..1347
                        mol_type = other DNA
                        organism = synthetic construct
SEQUENCE: 363
gaagtgcagc tggtggagtc tgggggaggc ttggttcagc ctggcaggtc cctgagactc  60
tcctgtgcag cctctggatt cacctttgat gattatgcca tgcactgggt ccggcaagct  120
ccagggaagg gcctggagtg ggtctcaggt gttagttgga atagtggtac catagactat  180
gcggactctg tgaagggccg attcaccatt attagagaca acgctaagaa ctccctgtat  240
ctgcaaatga acagtctgag agctgaagac acggccttgt attactgttc aaaagatatg  300
gggaggctag actactactc cggtttggac gtctggggcc aagggaccac ggtcaccgtc  360
tcctcagcct ccaccaaggg cccatcggtc ttccccctgg cgccctgctc caggagcacc  420
tccgagagca cagccgccct gggctgcctg gtcaaggact acttccccga accggtgacg  480
gtgtcgtgga actcaggcgc cctgaccagc ggcgtgcaca ccttcccggc tgtcctacag  540
tcctcaggac tctactccct cagcagcgtg gtgaccgtgc cctccagcag cttgggcacg  600
aagacctaca cctgcaacgt agatcacaag cccagcaaca ccaaggtgga caagagagtt  660
gagtccaaat atggtccccc atgcccaccg tgcccagcac caggcggtgg cggaccatca  720
gtcttcctgt tccccccaaa acccaaggac actctcatga tctcccggac ccctgaggtc  780
acgtgcgtgg tggtggacgt gagccaggaa gaccccgagg tccagttcaa ctggtacgtg  840
gatggcgtgg aggtgcataa tgccaagaca aagccgcggg aggagcagtt caacagcacg  900
taccgtgtgg tcagcgtcct caccgtcctg caccaggact ggctgaacgg caaggagtac  960
aagtgcaagg tctccaacaa aggcctcccg tcctccatcg agaaaaccat ctccaaagcc  1020
aaagggcagc cccgagagcc acaggtgtac accctgcccc catcccagga ggagatgacc  1080
aagaaccagg tcagcctgac ctgcctggtc aaaggcttct accccagcga catcgccgtg  1140
gagtgggaga gcaatgggca gccggagaac aactacaaga ccacgcctcc cgtgctggac  1200
tccgacggct ccttcttcct ctacagcagg ctcaccgtgg acaagagcag gtggcaggag  1260
gggaatgtct tctcatgctc cgtgatgcat gaggctctgc acaaccacta cacacagaag  1320
tccctctccc tgtctctggg taaatga                                       1347

SEQ ID NO: 364          moltype = AA  length = 448
```

```
FEATURE                Location/Qualifiers
REGION                 1..448
                       note = Synthetic
source                 1..448
                       mol_type = protein
                       organism = synthetic construct
SEQUENCE: 364
EVQLVESGGG LVQPGRSLRL SCAASGFTFD DYAMHWVRQA PGKGLEWVSG VSWNSGTIDY  60
ADSVKGRFTI IRDNAKNSLY LQMNSLRAED TALYYCSKDM GRLDYYSGLD VWGQGTTVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPGGGGPS  240
VFLFPPKPKD TLMISRTPEV TCVVVDVSQE DPEVQFNWYV DGVEVHNAKT KPREEQFNST  300
YRVVSVLTVL HQDWLNGKEY KCKVSNKGLP SSIEKTISKA KGQPREPQVY TLPPSQEEMT  360
KNQVSLTCLV KGFYPSDIAV EWESNGQPEN NYKTTPPVLD SDGSFFLYSR LTVDKSRWQE  420
GNVFSCSVMH EALHNHYTQK SLSLSLGK                                     448

SEQ ID NO: 365         moltype = DNA  length = 357
FEATURE                Location/Qualifiers
misc_feature           1..357
                       note = Synthetic
source                 1..357
                       mol_type = other DNA
                       organism = synthetic construct
SEQUENCE: 365
gaggtgcagc tggtggagtc tgggggaggc ttggtccagc ctggggggtc actgagactc  60
tcctgtgcag cctctggaat caccgtcagt agcaactaca tgagctgggt ccgccaggct  120
ccagggaagg ggctggagtg ggtctcactt atttatagtg gtggtagcac atactacgca  180
gactccgtga agggcagatt caccatctcc agagacaatt ccaagaacac gctgtatctt  240
caaatgaaca gcctgagagt cgaggacacg gctgtgtatt actgtgcgag agatcacggt  300
atggcagcag cggggtataa ttactggggc cagggaaccc tggtcaccgt ctcctca     357

SEQ ID NO: 366         moltype = AA  length = 119
FEATURE                Location/Qualifiers
REGION                 1..119
                       note = Synthetic
source                 1..119
                       mol_type = protein
                       organism = synthetic construct
SEQUENCE: 366
EVQLVESGGG LVQPGGSLRL SCAASGITVS SNYMSWVRQA PGKGLEWVSL IYSGGSTYYA  60
DSVKGRFTIS RDNSKNTLYL QMNSLRVEDT AVYYCARDHG MAAAGYNYWG QGTLVTVSS   119

SEQ ID NO: 367         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 367
ggaatcaccg tcagtagcaa ctac                                         24

SEQ ID NO: 368         moltype = DNA  length = 21
FEATURE                Location/Qualifiers
misc_feature           1..21
                       note = Synthetic
source                 1..21
                       mol_type = other DNA
                       organism = synthetic construct
SEQUENCE: 368
atttatagtg gtggtagcac a                                            21

SEQ ID NO: 369         moltype = DNA  length = 39
FEATURE                Location/Qualifiers
misc_feature           1..39
                       note = Synthetic
source                 1..39
                       mol_type = other DNA
                       organism = synthetic construct
SEQUENCE: 369
gcgagagatc acggtatggc agcagcgggg tataattac                         39

SEQ ID NO: 370         moltype = AA  length = 13
FEATURE                Location/Qualifiers
REGION                 1..13
                       note = Synthetic
source                 1..13
                       mol_type = protein
                       organism = synthetic construct
```

```
SEQUENCE: 370
ARDHGMAAAG YNY                                                  13

SEQ ID NO: 371          moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 371
gacatccaga tgacccagtc tccatcctcc ctgtctgcgt ctgtaggaga cagagtcacc  60
atcacttgcc aggcgagtca ggacattaac aaatatttaa attggtatca gcagaaacca  120
gggaaagccc ctaagctcct gatctacgat gcatccaatt tggaaacagg ggtcccatca  180
aggttcagtg gaagtggatc tgggacagat tttactttca ccatcaacag cctgcagcct  240
gaagattttg caacatattt ctgtcaacag tatgataatc tccctccagc gttcggccaa  300
gggaccaagg tggaaatcaa a                                         321

SEQ ID NO: 372          moltype = AA  length = 107
FEATURE                 Location/Qualifiers
REGION                  1..107
                        note = Synthetic
source                  1..107
                        mol_type = protein
                        organism = synthetic construct
SEQUENCE: 372
DIQMTQSPSS LSASVGDRVT ITCQASQDIN KYLNWYQQKP GKAPKLLIYD ASNLETGVPS  60
RFSGSGSGTD FTFTINSLQP EDFATYFCQQ YDNLPPAFGQ GTKVEIK             107

SEQ ID NO: 373          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 373
caggacatta acaaatat                                             18

SEQ ID NO: 374          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 374
caacagtatg ataatctccc tccagcg                                   27

SEQ ID NO: 375          moltype = AA  length = 9
FEATURE                 Location/Qualifiers
REGION                  1..9
                        note = Synthetic
source                  1..9
                        mol_type = protein
                        organism = synthetic construct
SEQUENCE: 375
QQYDNLPPA                                                       9

SEQ ID NO: 376          moltype = DNA  length = 1350
FEATURE                 Location/Qualifiers
misc_feature            1..1350
                        note = Synthetic
source                  1..1350
                        mol_type = other DNA
                        organism = synthetic construct
SEQUENCE: 376
gaggtgcagc tggtggagtc tgggggaggc ttggtccagc ctggggggtc actgagactc  60
tcctgtgcag cctctggaat caccgtcagt agcaactaca tgagctgggt ccgccaggct  120
ccagggaagg ggctggagtg ggtctcactt atttatagtg gtggtagcac atactacgca  180
gactccgtga agggcagatt caccatctcc agagacaatt ccaagaacac gctgtatctt  240
caaatgaaca gcctgagagt cgaggacacg gctgtgtatt actgtgcgag agatcacggt  300
atggcagcag cggggtataa ttactggggc cagggaaccc tggtcaccgt ctcctcagcc  360
tccaccaagg gcccatcggt cttccccctg gcaccctcct ccaagagcac ctctgggggc  420
acagcggccc tgggctgcct ggtcaaggac tacttccccg aaccggtgac ggtgtcgtgg  480
aactcaggcg ccctgaccag cggcgtgcac accttcccgg ctgtcctaca gtcctcagga  540
ctctactccc tcagcagcgt ggtgaccgtg ccctccagca gcttgggcac ccagacctac  600
atctgcaacg tgaatcacaa gcccagcaac accaaggtgg acaagaaagt tgagcccaaa  660
tcttgtgaca aaactcacac atgcccaccg tgcccagcac ctgaactcct ggggggaccg  720
```

```
tcagtcttcc tcttcccccc aaaacccaag gacaccctca tgatctcccg gacccctgag  780
gtcacatgcg tggtggtgga cgtgagccac gaagaccctg aggtcaagtt caactggtac  840
gtggacggcg tggaggtgca taatgccaag acaaagccgc gggaggagca gtacaacagc  900
acgtaccgtg tggtcagcgt cctcaccgtc ctgcaccagg actggctgaa tggcaaggag  960
tacaagtgca aggtctccaa caaagccctc ccagccccca tcgagaaaac catctccaaa  1020
gccaaagggc agccccgaga accacaggtg tacaccctgc ccccatcccg ggatgagctg  1080
accaagaacc aggtcagcct gacctgcctg gtcaaaggct tctatcccag cgacatcgcc  1140
gtggagtggg agagcaatgg gcagccggag aacaactaca agaccacgcc tcccgtgctg  1200
gactccgacg gctccttctt cctctacagc aagctcaccg tggacaagag caggtggcag  1260
caggggaacg tcttctcatg ctccgtgatg catgaggctc tgcacaacca ctacacgcag  1320
aagtccctct ccctgtctcc gggtaaatga                                  1350

SEQ ID NO: 377         moltype = AA  length = 449
FEATURE                Location/Qualifiers
REGION                 1..449
                       note = Synthetic
source                 1..449
                       mol_type = protein
                       organism = synthetic construct
SEQUENCE: 377
EVQLVESGGG LVQPGGSLRL SCAASGITVS SNYMSWVRQA PGKGLEWVSL IYSGGSTYYA  60
DSVKGRFTIS RDNSKNTLYL QMNSLRVEDT AVYYCARDHG MAAAGYNYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                   449

SEQ ID NO: 378         moltype = DNA  length = 645
FEATURE                Location/Qualifiers
misc_feature           1..645
                       note = Synthetic
source                 1..645
                       mol_type = other DNA
                       organism = synthetic construct
SEQUENCE: 378
gacatccaga tgacccagtc tccatcctcc ctgtctgcgt ctgtaggaga cagagtcacc  60
atcacttgcc aggcgagtca ggacattaac aaatatttaa attggtatca gcagaaacca  120
gggaaagccc ctaagctcct gatctacgat gcatccaatt tggaaacagg ggtcccatca  180
aggttcagtg gaagtggatc tgggacagat tttactttca ccatcaacag cctgcagcct  240
gaagattttg caacatattt ctgtcaacag tatgataatc tccctccagc gttcggccaa  300
gggaccaagg tggaaatcaa acgaactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttag                 645

SEQ ID NO: 379         moltype = AA  length = 214
FEATURE                Location/Qualifiers
REGION                 1..214
                       note = Synthetic
source                 1..214
                       mol_type = protein
                       organism = synthetic construct
SEQUENCE: 379
DIQMTQSPSS LSASVGDRVT ITCQASQDIN KYLNWYQQKP GKAPKLLIYD ASNLETGVPS  60
RFSGSGSGTD FTFTINSLQP EDFATYFCQQ YDNLPPAFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 380         moltype = DNA  length = 345
FEATURE                Location/Qualifiers
misc_feature           1..345
                       note = Synthetic
source                 1..345
                       mol_type = other DNA
                       organism = synthetic construct
SEQUENCE: 380
gaggtgcagc tggtggagtc tgggggaggc ttggtccagc ctggggggtc cctgagagtc  60
tcctgtgcag cctctggatt caccgtcagt aggaactaca tgagttgggt ccgccaggct  120
ccagggaagg ggctggagtg ggtctcagtt atttatagcg gtggtagcac attctacgca  180
gactccgtga agggcagatt caccatctcc agagacaatt ccaagaacac gctgtatctt  240
caaatgaaca gcctgagagc cgaggacacg gctatatatt actgtgcgag atacattcct  300
aggttcgacc cctggggcca gggaaccctg gtcaccgtct cctca                 345

SEQ ID NO: 381         moltype = AA  length = 115
FEATURE                Location/Qualifiers
```

```
REGION                  1..115
                        note = Synthetic
source                  1..115
                        mol_type = protein
                        organism = synthetic construct
SEQUENCE: 381
EVQLVESGGG LVQPGGSLRV SCAASGFTVS RNYMSWVRQA PGKGLEWVSV IYSGGSTFYA  60
DSVKGRFTIS RDNSKNTLYL QMNSLRAEDT AIYYCARYIP RFDPWGQGTL VTVSS       115

SEQ ID NO: 382          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 382
ggattcaccg tcagtaggaa ctac                                         24

SEQ ID NO: 383          moltype = AA  length = 8
FEATURE                 Location/Qualifiers
REGION                  1..8
                        note = Synthetic
source                  1..8
                        mol_type = protein
                        organism = synthetic construct
SEQUENCE: 383
GFTVSRNY                                                           8

SEQ ID NO: 384          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 384
gcgagataca ttcctaggtt cgacccc                                      27

SEQ ID NO: 385          moltype = AA  length = 9
FEATURE                 Location/Qualifiers
REGION                  1..9
                        note = Synthetic
source                  1..9
                        mol_type = protein
                        organism = synthetic construct
SEQUENCE: 385
ARYIPRFDP                                                          9

SEQ ID NO: 386          moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 386
gacatccaga tgacccagtc tccatcctcc ctgtctgcat ctgtaggaga cagagtcacc  60
atcacttgcc aggcgagtca ggacattagc aactatttaa attggtttca gcagaaacca  120
gggagagccc ctaagctcct catctacgat gcatccaatt tggaaacagg ggtcccatca  180
aggttcagtg gaagtggatc tgggacagat tttactttca ccatcagcag cctgcagcct  240
gaagatattg caacatatta ctgtcaacag tatgataatc tcccgatcac cttcggccaa  300
gggacacgac tggagattaa a                                            321

SEQ ID NO: 387          moltype = AA  length = 107
FEATURE                 Location/Qualifiers
REGION                  1..107
                        note = Synthetic
source                  1..107
                        mol_type = protein
                        organism = synthetic construct
SEQUENCE: 387
DIQMTQSPSS LSASVGDRVT ITCQASQDIS NYLNWFQQKP GRAPKLLIYD ASNLETGVPS  60
RFSGSGSGTD FTFTISSLQP EDIATYYCQQ YDNLPITFGQ GTRLEIK                107

SEQ ID NO: 388          moltype = DNA  length = 18
FEATURE                 Location/Qualifiers
misc_feature            1..18
                        note = Synthetic
```

```
source                  1..18
                        mol_type = other DNA
                        organism = synthetic construct
SEQUENCE: 388
caggacatta gcaactat                                                18

SEQ ID NO: 389          moltype = AA  length = 6
FEATURE                 Location/Qualifiers
REGION                  1..6
                        note = Synthetic
source                  1..6
                        mol_type = protein
                        organism = synthetic construct
SEQUENCE: 389
QDISNY                                                             6

SEQ ID NO: 390          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 390
caacagtatg ataatctccc gatcacc                                      27

SEQ ID NO: 391          moltype = DNA  length = 1338
FEATURE                 Location/Qualifiers
misc_feature            1..1338
                        note = Synthetic
source                  1..1338
                        mol_type = other DNA
                        organism = synthetic construct
SEQUENCE: 391
gaggtgcagc tggtggagtc tgggggaggc ttggtccagc ctggggggtc cctgagagtc  60
tcctgtgcag cctctggatt caccgtcagt aggaactaca tgagttgggt ccgccaggct  120
ccagggaagg ggctggagtg ggtctcagtt atttatagcg gtggtagcac attctacgca  180
gactccgtga agggcagatt caccatctcc agagacaatt ccaagaacac gctgtatctt  240
caaatgaaca gcctgagagc cgaggacacg gctatatatt actgtgcgag atacattcct  300
aggttcgacc cctggggcca gggaaccctg gtcaccgtct cctcagcctc caccaagggc  360
ccatcggtct tccccctggc accctcctcc aagagcacct ctgggggcac agcggccctg  420
ggctgcctgg tcaaggacta cttccccgaa ccggtgacgg tgtcgtggaa ctcaggcgcc  480
ctgaccagcg gcgtgcacac cttcccggct gtcctacagt cctcaggact ctactccctc  540
agcagcgtgg tgaccgtgcc ctccagcagc ttgggcaccc agacctacat ctgcaacgtg  600
aatcacaagc ccagcaacac caaggtggac aagaaagttg agcccaaatc ttgtgacaaa  660
actcacacat gcccaccgtg cccagcacct gaactcctgg ggggaccgtc agtcttcctc  720
ttccccccaa aacccaagga caccctcatg atctcccgga cccctgaggt cacatgcgtg  780
gtggtggacg tgagccacga agaccctgag gtcaagttca actggtacgt ggacggcgtg  840
gaggtgcata atgccaagac aaagccgcgg gaggagcagt acaacagcac gtaccgtgtg  900
gtcagcgtcc tcaccgtcct gcaccaggac tggctgaatg gcaaggagta caagtgcaag  960
gtctccaaca aagccctccc agcccccatc gagaaaacca tctccaaagc caaagggcag  1020
ccccgagaac cacaggtgta caccctgccc ccatcccggg atgagctgac caagaaccag  1080
gtcagcctga cctgcctggt caaaggcttc tatcccagcg acatcgccgt ggagtgggag  1140
agcaatgggc agccggagaa caactacaag accacgcctc ccgtgctgga ctccgacggc  1200
tccttcttcc tctacagcaa gctcaccgtg gacaagagca ggtggcagca ggggaacgtc  1260
ttctcatgct ccgtgatgca tgaggctctg cacaaccact acacgcagaa gtccctctcc  1320
ctgtctccgg gtaaatga                                                1338

SEQ ID NO: 392          moltype = AA  length = 445
FEATURE                 Location/Qualifiers
REGION                  1..445
                        note = Synthetic
source                  1..445
                        mol_type = protein
                        organism = synthetic construct
SEQUENCE: 392
EVQLVESGGG LVQPGGSLRV SCAASGFTVS RNYMSWVRQA PGKGLEWVSV IYSGGSTFYA  60
DSVKGRFTIS RDNSKNTLYL QMNSLRAEDT AIYYCARYIP RFDPWGQGTL VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KKVEPKSCDK THTCPPCPAP ELLGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPGK                                        445

SEQ ID NO: 393          moltype = DNA  length = 645
FEATURE                 Location/Qualifiers
misc_feature            1..645
                        note = Synthetic
```

-continued

```
source                  1..645
                        mol_type = other DNA
                        organism = synthetic construct
SEQUENCE: 393
gacatccaga tgacccagtc tccatcctcc ctgtctgcat ctgtaggaga cagagtcacc  60
atcacttgcc aggcgagtca ggacattagc aactatttaa attggtttca gcagaaacca  120
gggagagccc ctaagctcct catctacgat gcatccaatt tggaaacagg ggtcccatca  180
aggttcagtg gaagtggatc tgggacagat tttactttca ccatcagcag cctgcagcct  240
gaagatattg caacatatta ctgtcaacag tatgataatc tcccgatcac cttcggccaa  300
gggacacgac tggagattaa acgaactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttag                  645

SEQ ID NO: 394          moltype = AA  length = 214
FEATURE                 Location/Qualifiers
REGION                  1..214
                        note = Synthetic
source                  1..214
                        mol_type = protein
                        organism = synthetic construct
SEQUENCE: 394
DIQMTQSPSS LSASVGDRVT ITCQASQDIS NYLNWFQQKP GRAPKLLIYD ASNLETGVPS  60
RFSGSGSGTD FTFTISSLQP EDIATYYCQQ YDNLPITFGQ GTRLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 395          moltype = DNA  length = 351
FEATURE                 Location/Qualifiers
misc_feature            1..351
                        note = Synthetic
source                  1..351
                        mol_type = other DNA
                        organism = synthetic construct
SEQUENCE: 395
gaggtgcagc tggtggagtc tgggggaggc ttggtccagc ctggggggtc cctgagactc  60
tcctgtgcag cctccggact caccgtcagt agcaactaca tgagctgggt ccgccaggct  120
ccagggaagg ggctggagtg ggtctcagtt atttatagcg gtggtagcac attctacgca  180
gactccgtga agggccgatt caccatctcc agagacaatt ccaagaacac gctgtatctt  240
caaatgaaca gcctgagagc tgaggacacg gctgtgtatt actgtgcgag agatcttatc  300
aaatacggta tggacgtctg gggccaaggg accacggtca ccgtctcctc a           351

SEQ ID NO: 396          moltype = AA  length = 117
FEATURE                 Location/Qualifiers
REGION                  1..117
                        note = Synthetic
source                  1..117
                        mol_type = protein
                        organism = synthetic construct
SEQUENCE: 396
EVQLVESGGG LVQPGGSLRL SCAASGLTVS SNYMSWVRQA PGKGLEWVSV IYSGGSTFYA  60
DSVKGRFTIS RDNSKNTLYL QMNSLRAEDT AVYYCARDLI KYGMDVWGQG TTVTVSS     117

SEQ ID NO: 397          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 397
ggactcaccg tcagtagcaa ctac                                         24

SEQ ID NO: 398          moltype = DNA  length = 33
FEATURE                 Location/Qualifiers
misc_feature            1..33
                        note = Synthetic
source                  1..33
                        mol_type = other DNA
                        organism = synthetic construct
SEQUENCE: 398
gcgagagatc ttatcaaata cggtatggac gtc                               33

SEQ ID NO: 399          moltype = AA  length = 11
FEATURE                 Location/Qualifiers
REGION                  1..11
                        note = Synthetic
```

```
source                  1..11
                        mol_type = protein
                        organism = synthetic construct
SEQUENCE: 399
ARDLIKYGMD V                                                    11

SEQ ID NO: 400          moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 400
gacatccaga tgacccagtc tccatcctcc ctgtctgcat ctgtaggaga cagagtcacc  60
atcacttgcc aggcgagtca ggacattagc aactatttaa attggtatca gcagaaacca  120
gggaaagccc ctaagctcct gatctacgat gcatccaatt tggaaacagg ggtcccatca  180
aggttcagtg gaagtggatc tgggacagat tttactttca ccatcagcag cctgcagcct  240
gaagatattg caacatatta ctgtcaacag tatgataatc tccctcccca tttcggccct  300
gggaccaaag tggatatcaa a                                         321

SEQ ID NO: 401          moltype = AA  length = 107
FEATURE                 Location/Qualifiers
REGION                  1..107
                        note = Synthetic
source                  1..107
                        mol_type = protein
                        organism = synthetic construct
SEQUENCE: 401
DIQMTQSPSS LSASVGDRVT ITCQASQDIS NYLNWYQQKP GKAPKLLIYD ASNLETGVPS  60
RFSGSGSGTD FTFTISSLQP EDIATYYCQQ YDNLPPHFGP GTKVDIK             107

SEQ ID NO: 402          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 402
caacagtatg ataatctccc tccccat                                   27

SEQ ID NO: 403          moltype = AA  length = 9
FEATURE                 Location/Qualifiers
REGION                  1..9
                        note = Synthetic
source                  1..9
                        mol_type = protein
                        organism = synthetic construct
SEQUENCE: 403
QQYDNLPPH                                                       9

SEQ ID NO: 404          moltype = DNA  length = 1344
FEATURE                 Location/Qualifiers
misc_feature            1..1344
                        note = Synthetic
source                  1..1344
                        mol_type = other DNA
                        organism = synthetic construct
SEQUENCE: 404
gaggtgcagc tggtggagtc tgggggaggc ttggtccagc ctggggggtc cctgagactc  60
tcctgtgcag cctccggact caccgtcagt agcaactaca tgagctgggt ccgccaggct  120
ccagggaagg ggctggagtg ggtctcagtt atttatagcg gtggtagcac attctacgca  180
gactccgtga agggccgatt caccatctcc agagacaatt ccaagaacac gctgtatctt  240
caaatgaaca gcctgagagc tgaggacacg gctgtgtatt actgtgcgag agatcttatc  300
aaatacggta tggacgtctg gggccaaggg accacggtca ccgtctcctc agcctccacc  360
aagggcccat cggtcttccc cctggcaccc tcctccaaga gcacctctgg gggcacagcg  420
gccctgggct gcctggtcaa ggactacttc cccgaaccgg tgacggtgtc gtggaactca  480
ggcgccctga ccagcggcgt gcacaccttc ccggctgtcc tacagtcctc aggactctac  540
tccctcagca gcgtggtgac cgtgccctcc agcagcttgg gcacccagac ctacatctgc  600
aacgtgaatc acaagcccag caacaccaag gtggacaaga aagttgagcc caaatcttgt  660
gacaaaactc acacatgccc accgtgccca gcacctgaac tcctgggggg accgtcagtc  720
ttcctcttcc ccccaaaacc caaggacacc ctcatgatct cccggacccc tgaggtcaca  780
tgcgtggtgg tggacgtgag ccacgaagac cctgaggtca agttcaactg gtacgtggac  840
ggcgtggagg tgcataatgc caagacaaag ccgcgggagg agcagtacaa cagcacgtac  900
cgtgtggtca gcgtcctcac cgtcctgcac caggactggc tgaatggcaa ggagtacaag  960
tgcaaggtct ccaacaaagc cctcccagcc cccatcgaga aaaccatctc caaagccaaa  1020
gggcagcccc gagaaccaca ggtgtacacc ctgcccccat cccgggatga gctgaccaag  1080
aaccaggtca gcctgacctg cctggtcaaa ggcttctatc ccagcgacat cgccgtggag  1140
```

-continued

```
tgggagagca atgggcagcc ggagaacaac tacaagacca cgcctcccgt gctggactcc  1200
gacggctcct tcttcctcta cagcaagctc accgtggaca agagcaggtg gcagcagggg  1260
aacgtcttct catgctccgt gatgcatgag gctctgcaca accactacac gcagaagtcc  1320
ctctccctgt ctccgggtaa atga                                         1344

SEQ ID NO: 405         moltype = AA  length = 447
FEATURE                Location/Qualifiers
REGION                 1..447
                       note = Synthetic
source                 1..447
                       mol_type = protein
                       organism = synthetic construct
SEQUENCE: 405
EVQLVESGGG LVQPGGSLRL SCAASGLTVS SNYMSWVRQA PGKGLEWVSV IYSGGSTFYA  60
DSVKGRFTIS RDNSKNTLYL QMNSLRAEDT AVYYCARDLI KYGMDVWGQG TTVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APELLGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSRDELTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPGK                                      447

SEQ ID NO: 406         moltype = DNA  length = 645
FEATURE                Location/Qualifiers
misc_feature           1..645
                       note = Synthetic
source                 1..645
                       mol_type = other DNA
                       organism = synthetic construct
SEQUENCE: 406
gacatccaga tgacccagtc tccatcctcc ctgtctgcat ctgtaggaga cagagtcacc  60
atcacttgcc aggcgagtca ggacattagc aactatttaa attggtatca gcagaaacca  120
gggaaagccc ctaagctcct gatctacgat gcatccaatt tggaaacagg ggtcccatca  180
aggttcagtg gaagtggatc tgggacagat tttactttca ccatcagcag cctgcagcct  240
gaagatattg caacatatta ctgtcaacag tatgataatc tccctcccca tttcggccct  300
gggaccaaag tggatatcaa acgaactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttag                  645

SEQ ID NO: 407         moltype = AA  length = 214
FEATURE                Location/Qualifiers
REGION                 1..214
                       note = Synthetic
source                 1..214
                       mol_type = protein
                       organism = synthetic construct
SEQUENCE: 407
DIQMTQSPSS LSASVGDRVT ITCQASQDIS NYLNWYQQKP GKAPKLLIYD ASNLETGVPS  60
RFSGSGSGTD FTFTISSLQP EDIATYYCQQ YDNLPPHFGP GTKVDIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 408         moltype = DNA  length = 351
FEATURE                Location/Qualifiers
misc_feature           1..351
                       note = Synthetic
source                 1..351
                       mol_type = other DNA
                       organism = synthetic construct
SEQUENCE: 408
gaggtgcagc tggtggagtc tggaggaggc ttggtccagc ctgggggtc cctgagactc  60
tcctgtgcag cctctggggt caccgtcagt agcaactata tgagctgggt ccgccaggct  120
ccagggaagg ggctggagtg ggtctcagtt atttatagcg gtggtagtac attctacgca  180
gactccgtga agggccgatt taccatctcc agagacaact ccaagaacac gctgtttctt  240
caaatgaaca gcctgagaat tgaggacacg gccgtgtatt attgtgcgag agatttaggt  300
ccttacggta tggacgtctg gggccaaggg accacggtca ccgtctcctc a           351

SEQ ID NO: 409         moltype = AA  length = 117
FEATURE                Location/Qualifiers
REGION                 1..117
                       note = Synthetic
source                 1..117
                       mol_type = protein
                       organism = synthetic construct
SEQUENCE: 409
EVQLVESGGG LVQPGGSLRL SCAASGVTVS SNYMSWVRQA PGKGLEWVSV IYSGGSTFYA  60
```

-continued

```
DSVKGRFTIS RDNSKNTLFL QMNSLRIEDT AVYYCARDLG PYGMDVWGQG TTVTVSS     117

SEQ ID NO: 410         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 410
ggggtcaccg tcagtagcaa ctat                                        24

SEQ ID NO: 411         moltype = AA  length = 8
FEATURE                Location/Qualifiers
REGION                 1..8
                       note = Synthetic
source                 1..8
                       mol_type = protein
                       organism = synthetic construct
SEQUENCE: 411
GVTVSSNY                                                          8

SEQ ID NO: 412         moltype = DNA  length = 21
FEATURE                Location/Qualifiers
misc_feature           1..21
                       note = Synthetic
source                 1..21
                       mol_type = other DNA
                       organism = synthetic construct
SEQUENCE: 412
atttatagcg gtggtagtac a                                           21

SEQ ID NO: 413         moltype = DNA  length = 33
FEATURE                Location/Qualifiers
misc_feature           1..33
                       note = Synthetic
source                 1..33
                       mol_type = other DNA
                       organism = synthetic construct
SEQUENCE: 413
gcgagagatt taggtcctta cggtatggac gtc                              33

SEQ ID NO: 414         moltype = AA  length = 11
FEATURE                Location/Qualifiers
REGION                 1..11
                       note = Synthetic
source                 1..11
                       mol_type = protein
                       organism = synthetic construct
SEQUENCE: 414
ARDLGPYGMD V                                                      11

SEQ ID NO: 415         moltype = DNA  length = 324
FEATURE                Location/Qualifiers
misc_feature           1..324
                       note = Synthetic
source                 1..324
                       mol_type = other DNA
                       organism = synthetic construct
SEQUENCE: 415
gacatccagt tgacccagtc tccatccttc ctgtctgcat ctgtaggaga cagagtcacc  60
atcacttgcc gggccagtca gggcattagc agttatttag cctggtatca gcaaaaacca  120
gggaaagccc ctaagctcct gatctatgct gcatccactt tgcaaagtgg ggtcccatca  180
aggttcagcg gcagtggatc tgggacacaa ttcattctca caatcagcag cctgcagcct  240
gaagattttg caacttatta ctgtcaacag cttaatagtt accccggatt cactttcggc  300
cctgggacca aagtggatat caaa                                        324

SEQ ID NO: 416         moltype = AA  length = 108
FEATURE                Location/Qualifiers
REGION                 1..108
                       note = Synthetic
source                 1..108
                       mol_type = protein
                       organism = synthetic construct
SEQUENCE: 416
DIQLTQSPSF LSASVGDRVT ITCRASQGIS SYLAWYQQKP GKAPKLLIYA ASTLQSGVPS  60
RFSGSGSGTQ FILTISSLQP EDFATYYCQQ LNSYPGFTFG PGTKVDIK              108

SEQ ID NO: 417         moltype = DNA  length = 30
```

-continued

```
FEATURE                Location/Qualifiers
misc_feature           1..30
                       note = Synthetic
source                 1..30
                       mol_type = other DNA
                       organism = synthetic construct
SEQUENCE: 417
caacagctta atagttaccc cggattcact                                30

SEQ ID NO: 418         moltype = AA  length = 10
FEATURE                Location/Qualifiers
REGION                 1..10
                       note = Synthetic
source                 1..10
                       mol_type = protein
                       organism = synthetic construct
SEQUENCE: 418
QQLNSYPGFT                                                      10

SEQ ID NO: 419         moltype = DNA  length = 1344
FEATURE                Location/Qualifiers
misc_feature           1..1344
                       note = Synthetic
source                 1..1344
                       mol_type = other DNA
                       organism = synthetic construct
SEQUENCE: 419
gaggtgcagc tggtggagtc tggaggaggc ttggtccagc ctggggggtc cctgagactc  60
tcctgtgcag cctctggggt caccgtcagt agcaactata tgagctgggt ccgccaggct  120
ccagggaagg ggctggagtg ggtctcagtt atttatagcg gtggtagtac attctacgca  180
gactccgtga agggccgatt taccatctcc agagacaact ccaagaacac gctgtttctt  240
caaatgaaca gcctgagaat tgaggacacg gccgtgtatt attgtgcgag agatttaggt  300
ccttacggta tggacgtctg gggccaaggg accacggtca ccgtctcctc agcctccacc  360
aagggcccat cggtcttccc cctggcaccc tcctccaaga gcacctctgg gggcacagcg  420
gccctgggct gcctggtcaa ggactacttc cccgaaccgg tgacggtgtc gtggaactca  480
ggcgccctga ccagcggcgt gcacaccttc ccggctgtcc tacagtcctc aggactctac  540
tccctcagca gcgtggtgac cgtgccctcc agcagcttgg gcacccagac ctacatctgc  600
aacgtgaatc acaagcccag caacaccaag gtggacaaga aagttgagcc caaatcttgt  660
gacaaaactc acacatgccc accgtgccca gcacctgaac tcctgggggg accgtcagtc  720
ttcctcttcc ccccaaaacc caaggacacc ctcatgatct cccggacccc tgaggtcaca  780
tgcgtggtgg tggacgtgag ccacgaagac cctgaggtca agttcaactg gtacgtggac  840
ggcgtggagg tgcataatgc caagacaaag ccgcgggagg agcagtacaa cagcacgtac  900
cgtgtggtca gcgtcctcac cgtcctgcac caggactggc tgaatggcaa ggagtacaag  960
tgcaaggtct ccaacaaagc cctcccagcc cccatcgaga aaaccatctc caaagccaaa  1020
gggcagcccc gagaaccaca ggtgtacacc ctgcccccat cccgggatga gctgaccaag  1080
aaccaggtca gcctgacctg cctggtcaaa ggcttctatc ccagcgacat cgccgtggag  1140
tgggagagca atgggcagcc ggagaacaac tacaagacca cgcctcccgt gctggactcc  1200
gacggctcct tcttcctcta cagcaagctc accgtggaca agagcaggtg gcagcagggg  1260
aacgtcttct catgctccgt gatgcatgag gctctgcaca accactacac gcagaagtcc  1320
ctctccctgt ctccgggtaa atga                                      1344

SEQ ID NO: 420         moltype = AA  length = 447
FEATURE                Location/Qualifiers
REGION                 1..447
                       note = Synthetic
source                 1..447
                       mol_type = protein
                       organism = synthetic construct
SEQUENCE: 420
EVQLVESGGG LVQPGGSLRL SCAASGVTVS SNYMSWVRQA PGKGLEWVSV IYSGGSTFYA  60
DSVKGRFTIS RDNSKNTLFL QMNSLRIEDT AVYYCARDLG PYGMDVWGQG TTVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APELLGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSRDELTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPGK                                   447

SEQ ID NO: 421         moltype = DNA  length = 648
FEATURE                Location/Qualifiers
misc_feature           1..648
                       note = Synthetic
source                 1..648
                       mol_type = other DNA
                       organism = synthetic construct
SEQUENCE: 421
gacatccagt tgacccagtc tccatccttc ctgtctgcat ctgtaggaga cagagtcacc  60
atcacttgcc gggccagtca gggcattagc agttatttag cctggtatca gcaaaaacca  120
gggaaagccc ctaagctcct gatctatgct gcatccactt tgcaaagtgg ggtcccatca  180
```

```
aggttcagcg gcagtggatc tgggacacaa ttcattctca caatcagcag cctgcagcct  240
gaagattttg caacttatta ctgtcaacag cttaatagtt accccggatt cactttcggc  300
cctgggacca aagtggatat caaacgaact gtggctgcac catctgtctt catcttcccg  360
ccatctgatg agcagttgaa atctggaact gcctctgttg tgtgcctgct gaataacttc  420
tatcccagag aggccaaagt acagtggaag gtggataacg ccctccaatc gggtaactcc  480
caggagagtg tcacagagca ggacagcaag gacagcacct acagcctcag cagcaccctg  540
acgctgagca aagcagacta cgagaaacac aaagtctacg cctgcgaagt cacccatcag  600
ggcctgagct cgcccgtcac aaagagcttc aacaggggag agtgttag               648

SEQ ID NO: 422          moltype = AA  length = 215
FEATURE                 Location/Qualifiers
REGION                  1..215
                        note = Synthetic
source                  1..215
                        mol_type = protein
                        organism = synthetic construct
SEQUENCE: 422
DIQLTQSPSF LSASVGDRVT ITCRASQGIS SYLAWYQQKP GKAPKLLIYA ASTLQSGVPS  60
RFSGSGSGTQ FILTISSLQP EDFATYYCQQ LNSYPGFTFG PGTKVDIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 423          moltype = DNA  length = 1338
FEATURE                 Location/Qualifiers
misc_feature            1..1338
                        note = Synthetic
source                  1..1338
                        mol_type = other DNA
                        organism = synthetic construct
SEQUENCE: 423
gaggtgcagc tggtggagtc tgggggaggc ttggtccagc ctgggggggtc actgagactc  60
tcctgtgcag cctctggaat caccgtcagt agcaactaca tgagctgggt ccgccaggct  120
ccagggaagg ggctggagtg ggtctcactt atttatagtg gtggtagcac atactacgca  180
gactccgtga agggcagatt caccatctcc agagacaatt ccaagaacac gctgtatctt  240
caaatgaaca gcctgagagt cgaggacacg gctgtgtatt actgtgcgag agatcacggt  300
atggcagcag cggggtataa ttactggggc cagggaaccc tggtcaccgt ctcctcagcc  360
tccaccaagg gcccatcggt cttccccctg gcgccctgct ccaggagcac ctccgagagc  420
acagccgccc tgggctgcct ggtcaaggac tacttccccg aaccggtgac ggtgtcgtgg  480
aactcaggcg ccctgaccag cggcgtgcac accttcccgg ctgtcctaca gtcctcagga  540
ctctactccc tcagcagcgt ggtgaccgtg ccctccagca gcttgggcac gaagacctac  600
acctgcaacg tagatcacaa gcccagcaac accaaggtgg acaagagagt tgagtccaaa  660
tatggtcccc catgcccacc gtgcccagca ccaggcggtg gcggaccatc agtcttcctg  720
ttccccccaa aacccaagga cactctcatg atctcccgga cccctgaggt cacgtgcgtg  780
gtggtggacg tgagccagga agaccccgag gtccagttca actggtacgt ggatggcgtg  840
gaggtgcata atgccaagac aaagccgcgg gaggagcagt tcaacagcac gtaccgtgtg  900
gtcagcgtcc tcaccgtcct gcaccaggac tggctgaacg gcaaggagta caagtgcaag  960
gtctccaaca aaggcctccc gtcctccatc gagaaaacca tctccaaagc caaagggcag  1020
ccccgagagc cacaggtgta caccctgccc ccatcccagg aggagatgac caagaaccag  1080
gtcagcctga cctgcctggt caaaggcttc taccccagcg acatcgccgt ggagtgggag  1140
agcaatgggc agccggagaa caactacaag accacgcctc ccgtgctgga ctccgacggc  1200
tccttcttcc tctacagcag gctcaccgtg gacaagagca ggtggcagga ggggaatgtc  1260
ttctcatgct ccgtgatgca tgaggctctg cacaaccact acacacagaa gtccctctcc  1320
ctgtctctgg gtaaatga                                                1338

SEQ ID NO: 424          moltype = AA  length = 445
FEATURE                 Location/Qualifiers
REGION                  1..445
                        note = Synthetic
source                  1..445
                        mol_type = protein
                        organism = synthetic construct
SEQUENCE: 424
EVQLVESGGG LVQPGGSLRL SCAASGITVS SNYMSWVRQA PGKGLEWVSL IYSGGSTYYA  60
DSVKGRFTIS RDNSKNTLYL QMNSLRVEDT AVYYCARDHG MAAAGYNYWG QGTLVTVSSA  120
STKGPSVFPL APCSRSTSES TAALGCLVKD YFPEPVTVSW NSGALTSGVH TFPAVLQSSG  180
LYSLSSVVTV PSSSLGTKTY TCNVDHKPSN TKVDKRVESK YGPPCPPCPA PGGGGPSVFL  240
FPPKPKDTLM ISRTPEVTCV VVDVSQEDPE VQFNWYVDGV EVHNAKTKPR EEQFNSTYRV  300
VSVLTVLHQD WLNGKEYKCK VSNKGLPSSI EKTISKAKGQ PREPQVYTLP PSQEEMTKNQ  360
VSLTCLVKGF YPSDIAVEWE SNGQPENNYK TTPPVLDSDG SFFLYSRLTV DKSRWQEGNV  420
FSCSVMHEAL HNHYTQKSLS LSLGK                                        445

SEQ ID NO: 425          moltype = DNA  length = 1326
FEATURE                 Location/Qualifiers
misc_feature            1..1326
                        note = Synthetic
source                  1..1326
                        mol_type = other DNA
                        organism = synthetic construct
SEQUENCE: 425
```

```
gaggtgcagc tggtggagtc tggggggaggc ttggtccagc ctggggggtc cctgagagtc  60
tcctgtgcag cctctggatt caccgtcagt aggaactaca tgagttgggt ccgccaggct  120
ccagggaagg ggctggagtg ggtctcagtt atttatagcg gtggtagcac attctacgca  180
gactccgtga agggcagatt caccatctcc agagacaatt ccaagaacac gctgtatctt  240
caaatgaaca gcctgagagc cgaggacacg gctatatatt actgtgcgag atacattcct  300
aggttcgacc cctggggcca gggaaccctg gtcaccgtct cctcagcctc caccaagggc  360
ccatcggtct tccccctggc gccctgctcc aggagcacct ccgagagcac agccgccctg  420
ggctgcctgg tcaaggacta cttccccgaa ccggtgacgg tgtcgtggaa ctcaggcgcc  480
ctgaccagcg gcgtgcacac cttcccggct gtcctacagt cctcaggact ctactccctc  540
agcagcgtgg tgaccgtgcc ctccagcagc ttgggcacga agacctacac ctgcaacgta  600
gatcacaagc ccagcaacac caaggtggac aagagagttg agtccaaata tggtccccca  660
tgcccaccgt gcccagcacc aggcggtggc ggaccatcag tcttcctgtt ccccccaaaa  720
cccaaggaca ctctcatgat ctcccggacc cctgaggtca cgtgcgtggt ggtggacgtg  780
agccaggaag accccgaggt ccagttcaac tggtacgtgg atggcgtgga ggtgcataat  840
gccaagacaa agccgcggga ggagcagttc aacagcacgt accgtgtggt cagcgtcctc  900
accgtcctgc accaggactg gctgaacggc aaggagtaca agtgcaaggt ctccaacaaa  960
ggcctcccgt cctccatcga gaaaaccatc tccaaagcca aagggcagcc ccgagagcca  1020
caggtgtaca ccctgccccc atcccaggag gagatgacca agaaccaggt cagcctgacc  1080
tgcctggtca aaggcttcta ccccagcgac atcgccgtgg agtgggagag caatgggcag  1140
ccggagaaca actacaagac cacgcctccc gtgctggact ccgacggctc cttcttcctc  1200
tacagcaggc tcaccgtgga caagagcagg tggcaggagg ggaatgtctt ctcatgctcc  1260
gtgatgcatg aggctctgca caaccactac acacagaagt ccctctccct gtctctgggt  1320
aaatga                                                             1326

SEQ ID NO: 426         moltype = AA  length = 441
FEATURE                Location/Qualifiers
REGION                 1..441
                       note = Synthetic
source                 1..441
                       mol_type = protein
                       organism = synthetic construct
SEQUENCE: 426
EVQLVESGGG LVQPGGSLRV SCAASGFTVS RNYMSWVRQA PGKGLEWVSV IYSGGSTFYA  60
DSVKGRFTIS RDNSKNTLYL QMNSLRAEDT AIYYCARYIP RFDPWGQGTL VTVSSASTKG  120
PSVFPLAPCS RSTSESTAAL GCLVKDYFPE PVTVSWNSGA LTSGVHTFPA VLQSSGLYSL  180
SSVVTVPSSS LGTKTYTCNV DHKPSNTKVD KRVESKYGPP CPPCPAPGGG GPSVFLFPPK  240
PKDTLMISRT PEVTCVVVDV SQEDPEVQFN WYVDGVEVHN AKTKPREEQF NSTYRVVSVL  300
TVLHQDWLNG KEYKCKVSNK GLPSSIEKTI SKAKGQPREP QVYTLPPSQE EMTKNQVSLT  360
CLVKGFYPSD IAVEWESNGQ PENNYKTTPP VLDSDGSFFL YSRLTVDKSR WQEGNVFSCS  420
VMHEALHNHY TQKSLSLSLG K                                            441

SEQ ID NO: 427         moltype = DNA  length = 1332
FEATURE                Location/Qualifiers
misc_feature           1..1332
                       note = Synthetic
source                 1..1332
                       mol_type = other DNA
                       organism = synthetic construct
SEQUENCE: 427
gaggtgcagc tggtggagtc tggggggaggc ttggtccagc ctggggggtc cctgagactc  60
tcctgtgcag cctccggact caccgtcagt agcaactaca tgagctgggt ccgccaggct  120
ccagggaagg ggctggagtg ggtctcagtt atttatagcg gtggtagcac attctacgca  180
gactccgtga agggccgatt caccatctcc agagacaatt ccaagaacac gctgtatctt  240
caaatgaaca gcctgagagc tgaggacacg gctgtgtatt actgtgcgag agatcttatc  300
aaatacggta tggacgtctg gggccaaggg accacggtca ccgtctcctc agcctccacc  360
aagggcccat cggtcttccc cctggcgccc tgctccagga gcacctccga gagcacagcc  420
gccctgggct gcctggtcaa ggactacttc cccgaaccgg tgacggtgtc gtggaactca  480
ggcgccctga ccagcggcgt gcacaccttc ccggctgtcc tacagtcctc aggactctac  540
tccctcagca gcgtggtgac cgtgccctcc agcagcttgg gcacgaagac ctacacctgc  600
aacgtagatc acaagcccag caacaccaag gtggacaaga gagttgagtc caaatatggt  660
cccccatgcc caccgtgccc agcaccaggc ggtggcggac catcagtctt cctgttcccc  720
ccaaaaccca aggacactct catgatctcc cggacccctg aggtcacgtg cgtggtggtg  780
gacgtgagcc aggaagaccc cgaggtccag ttcaactggt acgtggatgg cgtggaggtg  840
cataatgcca agacaaagcc gcgggaggag cagttcaaca gcacgtaccg tgtggtcagc  900
gtcctcaccg tcctgcacca ggactggctg aacggcaagg agtacaagtg caaggtctcc  960
aacaaaggcc tcccgtcctc catcgagaaa accatctcca aagccaaagg gcagccccga  1020
gagccacagg tgtacaccct gcccccatcc caggaggaga tgaccaagaa ccaggtcagc  1080
ctgacctgcc tggtcaaagg cttctacccc agcgacatcg ccgtggagtg ggagagcaat  1140
gggcagccgg agaacaacta caagaccacg cctcccgtgc tggactccga cggctccttc  1200
ttcctctaca gcaggctcac cgtggacaag agcaggtggc aggaggggaa tgtcttctca  1260
tgctccgtga tgcatgaggc tctgcacaac cactacacac agaagtccct ctccctgtct  1320
ctgggtaaat ga                                                      1332

SEQ ID NO: 428         moltype = AA  length = 443
FEATURE                Location/Qualifiers
REGION                 1..443
                       note = Synthetic
source                 1..443
                       mol_type = protein
```

```
                         organism = synthetic construct
SEQUENCE: 428
EVQLVESGGG LVQPGGSLRL SCAASGLTVS SNYMSWVRQA PGKGLEWVSV IYSGGSTFYA  60
DSVKGRFTIS RDNSKNTLYL QMNSLRAEDT AVYYCARDLI KYGMDVWGQG TTVTVSSAST  120
KGPSVFPLAP CSRSTSESTA ALGCLVKDYF PEPVTVSWNS GALTSGVHTF PAVLQSSGLY  180
SLSSVVTVPS SSLGTKTYTC NVDHKPSNTK VDKRVESKYG PPCPPCPAPG GGGPSVFLFP  240
PKPKDTLMIS RTPEVTCVVV DVSQEDPEVQ FNWYVDGVEV HNAKTKPREE QFNSTYRVVS  300
VLTVLHQDWL NGKEYKCKVS NKGLPSSIEK TISKAKGQPR EPQVYTLPPS QEEMTKNQVS  360
LTCLVKGFYP SDIAVEWESN GQPENNYKTT PPVLDSDGSF FLYSRLTVDK SRWQEGNVFS  420
CSVMHEALHN HYTQKSLSLS LGK                                          443

SEQ ID NO: 429           moltype = DNA  length = 1332
FEATURE                  Location/Qualifiers
misc_feature             1..1332
                         note = Synthetic
source                   1..1332
                         mol_type = other DNA
                         organism = synthetic construct
SEQUENCE: 429
gaggtgcagc tggtggagtc tggaggaggc ttggtccagc ctggggggtc cctgagactc  60
tcctgtgcag cctctggggt caccgtcagt agcaactata tgagctgggt ccgccaggct  120
ccagggaagg ggctggagtg ggtctcagtt atttatagcg gtggtagtac attctacgca  180
gactccgtga agggccgatt taccatctcc agagacaact ccaagaacac gctgtttctt  240
caaatgaaca gcctgagaat tgaggacacg gccgtgtatt attgtgcgag agatttaggt  300
ccttacggta tggacgtctg gggccaaggg accacggtca ccgtctcctc agcctccacc  360
aagggcccat cggtcttccc cctggcgccc tgctccagga gcacctccga gagcacagcc  420
gccctgggct gcctggtcaa ggactacttc cccgaaccgg tgacggtgtc gtggaactca  480
ggcgccctga ccagcggcgt gcacaccttc ccggctgtcc tacagtcctc aggactctac  540
tccctcagca gcgtggtgac cgtgccctcc agcagcttgg gcacgaagac ctacacctgc  600
aacgtagatc acaagcccag caacaccaag gtggacaaga gagttgagtc caaatatggt  660
cccccatgcc caccgtgccc agcaccaggc ggtggcggac catcagtctt cctgttcccc  720
ccaaaaccca aggacactct catgatctcc cggacccctg aggtcacgtg cgtggtggtg  780
gacgtgagcc aggaagaccc cgaggtccag ttcaactggt acgtggatgg cgtggaggtg  840
cataatgcca agacaaagcc gcgggaggag cagttcaaca gcacgtaccg tgtggtcagc  900
gtcctcaccg tcctgcacca ggactggctg aacggcaagg agtacaagtg caaggtctcc  960
aacaaaggcc tcccgtcctc catcgagaaa accatctcca aagccaaagg gcagccccga  1020
gagccacagg tgtacaccct gcccccatcc caggaggaga tgaccaagaa ccaggtcagc  1080
ctgacctgcc tggtcaaagg cttctacccc agcgacatcg ccgtggagtg ggagagcaat  1140
gggcagccgg agaacaacta caagaccacg cctcccgtgc tggactccga cggctccttc  1200
ttcctctaca gcaggctcac cgtggacaag agcaggtggc aggaggggaa tgtcttctca  1260
tgctccgtga tgcatgaggc tctgcacaac cactacacac agaagtccct ctccctgtct  1320
ctgggtaaat ga                                                      1332

SEQ ID NO: 430           moltype = AA  length = 443
FEATURE                  Location/Qualifiers
REGION                   1..443
                         note = Synthetic
source                   1..443
                         mol_type = protein
                         organism = synthetic construct
SEQUENCE: 430
EVQLVESGGG LVQPGGSLRL SCAASGVTVS SNYMSWVRQA PGKGLEWVSV IYSGGSTFYA  60
DSVKGRFTIS RDNSKNTLFL QMNSLRIEDT AVYYCARDLG PYGMDVWGQG TTVTVSSAST  120
KGPSVFPLAP CSRSTSESTA ALGCLVKDYF PEPVTVSWNS GALTSGVHTF PAVLQSSGLY  180
SLSSVVTVPS SSLGTKTYTC NVDHKPSNTK VDKRVESKYG PPCPPCPAPG GGGPSVFLFP  240
PKPKDTLMIS RTPEVTCVVV DVSQEDPEVQ FNWYVDGVEV HNAKTKPREE QFNSTYRVVS  300
VLTVLHQDWL NGKEYKCKVS NKGLPSSIEK TISKAKGQPR EPQVYTLPPS QEEMTKNQVS  360
LTCLVKGFYP SDIAVEWESN GQPENNYKTT PPVLDSDGSF FLYSRLTVDK SRWQEGNVFS  420
CSVMHEALHN HYTQKSLSLS LGK                                          443

SEQ ID NO: 431           moltype = DNA  length = 354
FEATURE                  Location/Qualifiers
misc_feature             1..354
                         note = Synthetic
source                   1..354
                         mol_type = other DNA
                         organism = synthetic construct
SEQUENCE: 431
caggtgcagc tgcaggagtc gggcccagga ctggtgaagc cttcggagac cctgtccctc  60
acctgcactg tctctggtgg ctccatcaat aattactact ggatctggat ccggcagccc  120
ccagggaagg gactggagtg gattgggtat atctatcaca gtgggagcac caactacaac  180
ccctccctca agagtcgagt caccatatca gtagacacgt ccaagaacca attctccctg  240
aaggtgagct ctgtgaccgc tgcggacacg gccgtgtatt actgtgcgaa tatggttcgg  300
ggagtttatg aagatgacta ctggggccag ggaaccctgg tcaccgtctc ctca        354

SEQ ID NO: 432           moltype = AA  length = 118
FEATURE                  Location/Qualifiers
REGION                   1..118
                         note = Synthetic
```

```
source                  1..118
                        mol_type = protein
                        organism = synthetic construct
SEQUENCE: 432
QVQLQESGPG LVKPSETLSL TCTVSGGSIN NYYWIWIRQP PGKGLEWIGY IYHSGSTNYN  60
PSLKSRVTIS VDTSKNQFSL KVSSVTAADT AVYYCANMVR GVYEDDYWGQ GTLVTVSS    118

SEQ ID NO: 433          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 433
ggtggctcca tcaataatta ctac                                        24

SEQ ID NO: 434          moltype = AA  length = 8
FEATURE                 Location/Qualifiers
REGION                  1..8
                        note = Synthetic
source                  1..8
                        mol_type = protein
                        organism = synthetic construct
SEQUENCE: 434
GGSINNYY                                                          8

SEQ ID NO: 435          moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 435
atctatcaca gtgggagcac c                                           21

SEQ ID NO: 436          moltype = AA  length = 7
FEATURE                 Location/Qualifiers
REGION                  1..7
                        note = Synthetic
source                  1..7
                        mol_type = protein
                        organism = synthetic construct
SEQUENCE: 436
IYHSGST                                                           7

SEQ ID NO: 437          moltype = DNA  length = 36
FEATURE                 Location/Qualifiers
misc_feature            1..36
                        note = Synthetic
source                  1..36
                        mol_type = other DNA
                        organism = synthetic construct
SEQUENCE: 437
gcgaatatgg ttcggggagt ttatgaagat gactac                           36

SEQ ID NO: 438          moltype = AA  length = 12
FEATURE                 Location/Qualifiers
REGION                  1..12
                        note = Synthetic
source                  1..12
                        mol_type = protein
                        organism = synthetic construct
SEQUENCE: 438
ANMVRGVYED DY                                                     12

SEQ ID NO: 439          moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 439
gacatccaga tgacccagtc tccatcctcc ctgtctgcat ctgtaggaga cagagtcacc  60
atcacttgcc gggcaagtca gagcattagc aactatttaa attggtatca gcagaaacca  120
gggaaagccc ctaagctcct gatctttgct gcctccagtt tgcgaagtgg ggtcccatca  180
aggttcagtg gcagtggatc tgggacagat ttcactctca ccatcagcag tctgcaccct  240
```

```
gaagattttg caacttacta ctgtcaacag aattacaata ccccctcac tttcggccct  300
gggaccaaag tggatatcaa a                                            321

SEQ ID NO: 440         moltype = AA  length = 107
FEATURE                Location/Qualifiers
REGION                 1..107
                       note = Synthetic
source                 1..107
                       mol_type = protein
                       organism = synthetic construct
SEQUENCE: 440
DIQMTQSPSS LSASVGDRVT ITCRASQSIS NYLNWYQQKP GKAPKLLIFA ASSLRSGVPS  60
RFSGSGSGTD FTLTISSLHP EDFATYYCQQ NYNTPLTFGP GTKVDIK                107

SEQ ID NO: 441         moltype = DNA  length = 18
FEATURE                Location/Qualifiers
misc_feature           1..18
                       note = Synthetic
source                 1..18
                       mol_type = other DNA
                       organism = synthetic construct
SEQUENCE: 441
cagagcatta gcaactat                                                18

SEQ ID NO: 442         moltype = AA  length = 6
FEATURE                Location/Qualifiers
REGION                 1..6
                       note = Synthetic
source                 1..6
                       mol_type = protein
                       organism = synthetic construct
SEQUENCE: 442
QSISNY                                                             6

SEQ ID NO: 443         moltype =   length =
SEQUENCE: 443
000

SEQ ID NO: 444         moltype = DNA  length = 27
FEATURE                Location/Qualifiers
misc_feature           1..27
                       note = Synthetic
source                 1..27
                       mol_type = other DNA
                       organism = synthetic construct
SEQUENCE: 444
caacagaatt acaataccc cctcact                                       27

SEQ ID NO: 445         moltype = AA  length = 9
FEATURE                Location/Qualifiers
REGION                 1..9
                       note = Synthetic
source                 1..9
                       mol_type = protein
                       organism = synthetic construct
SEQUENCE: 445
QQNYNTPLT                                                          9

SEQ ID NO: 446         moltype = DNA  length = 1347
FEATURE                Location/Qualifiers
misc_feature           1..1347
                       note = Synthetic
source                 1..1347
                       mol_type = other DNA
                       organism = synthetic construct
SEQUENCE: 446
caggtgcagc tgcaggagtc gggcccagga ctggtgaagc cttcggagac cctgtccctc  60
acctgcactg tctctggtgg ctccatcaat aattactact ggatctggat ccggcagccc  120
ccagggaagg gactggagtg gattgggtat atctatcaca gtgggagcac caactacaac  180
ccctccctca agagtcgagt caccatatca gtagacacgt ccaagaacca attctccctg  240
aaggtgagct ctgtgaccgc tgcggacacg gccgtgtatt actgtgcgaa tatggttcgg  300
ggagtttatg aagatgacta ctggggccag ggaaccctgg tcaccgtctc ctcagcctcc  360
accaagggcc catcggtctt ccccctggca ccctcctcca agagcacctc tgggggcaca  420
gcggccctgg gctgcctggt caaggactac ttccccgaac cggtgacggt gtcgtggaac  480
tcaggcgccc tgaccagcgg cgtgcacacc ttcccggctg tcctacagtc ctcaggactc  540
tactccctca gcagcgtggt gaccgtgccc tccagcagct tgggcaccca gacctacatc  600
tgcaacgtga atcacaagcc cagcaacacc aaggtggaca agaaagttga gcccaaatct  660
tgtgacaaaa ctcacacatg cccaccgtgc ccagcacctg aactcctggg gggaccgtca  720
gtcttcctct tccccccaaa acccaaggac accctcatga tctcccggac ccctgaggtc  780
```

-continued

```
acatgcgtgg tggtggacgt gagccacgaa gaccctgagg tcaagttcaa ctggtacgtg  840
gacggcgtgg aggtgcataa tgccaagaca aagccgcggg aggagcagta caacagcacg  900
taccgtgtgg tcagcgtcct caccgtcctg caccaggact ggctgaatgg caaggagtac  960
aagtgcaagg tctccaacaa agccctccca gcccccatcg agaaaaccat ctccaaagcc  1020
aaagggcagc cccgagaacc acaggtgtac accctgcccc catcccggga tgagctgacc  1080
aagaaccagg tcagcctgac ctgcctggtc aaaggcttct atcccagcga catcgccgtg  1140
gagtgggaga gcaatgggca gccggagaac aactacaaga ccacgcctcc cgtgctggac  1200
tccgacggct ccttcttcct ctacagcaag ctcaccgtgg acaagagcag gtggcagcag  1260
gggaacgtct tctcatgctc cgtgatgcat gaggctctgc acaaccacta cacgcagaag  1320
tccctctccc tgtctccggg taaatga                                     1347

SEQ ID NO: 447          moltype = AA  length = 448
FEATURE                 Location/Qualifiers
REGION                  1..448
                        note = Synthetic
source                  1..448
                        mol_type = protein
                        organism = synthetic construct
SEQUENCE: 447
QVQLQESGPG LVKPSETLSL TCTVSGGSIN NYYWIWIRQP PGKGLEWIGY IYHSGSTNYN  60
PSLKSRVTIS VDTSKNQFSL KVSSVTAADT AVYYCANMVR GVYEDDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448

SEQ ID NO: 448          moltype = DNA  length = 645
FEATURE                 Location/Qualifiers
misc_feature            1..645
                        note = Synthetic
source                  1..645
                        mol_type = other DNA
                        organism = synthetic construct
SEQUENCE: 448
gacatccaga tgacccagtc tccatcctcc ctgtctgcat ctgtaggaga cagagtcacc  60
atcacttgcc gggcaagtca gagcattagc aactatttaa attggtatca gcagaaacca  120
gggaaagccc ctaagctcct gatctttgct gcctccagtt tgcgaagtgg ggtcccatca  180
aggttcagtg gcagtggatc tgggacagat ttcactctca ccatcagcag tctgcaccct  240
gaagattttg caacttacta ctgtcaacag aattacaata ccccccctcac tttcggccct  300
gggaccaaag tggatatcaa acgaactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttag                 645

SEQ ID NO: 449          moltype = AA  length = 214
FEATURE                 Location/Qualifiers
REGION                  1..214
                        note = Synthetic
source                  1..214
                        mol_type = protein
                        organism = synthetic construct
SEQUENCE: 449
DIQMTQSPSS LSASVGDRVT ITCRASQSIS NYLNWYQQKP GKAPKLLIFA ASSLRSGVPS  60
RFSGSGSGTD FTLTISSLHP EDFATYYCQQ NYNTPLTFGP GTKVDIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 450          moltype = DNA  length = 366
FEATURE                 Location/Qualifiers
misc_feature            1..366
                        note = Synthetic
source                  1..366
                        mol_type = other DNA
                        organism = synthetic construct
SEQUENCE: 450
gaggtgcagc tggtggagtc tggaggaggc ttgatccagc ctgggggggtc cctgagactc  60
tcctgtgcag cctctgtgtt caccgtcagt tacaactaca tgagctgggt ccgccaggct  120
ccagggaagg ggctggagtg ggtctcagtt atttatagcg gtggtagcac atactacgca  180
gactccgtga agggccgatt caccatctcc agagacaatt ccaagaacac gctgtatctt  240
caaatgaaca gcctgagagc cgaggacacg gccgtgtatt actgtgcgag agccctcccc  300
gggtggggtg ggagcttcga gtactttgac tactggggcc agggaaccct ggtcaccgtc  360
tcctca                                                            366

SEQ ID NO: 451          moltype = AA  length = 122
FEATURE                 Location/Qualifiers
```

```
REGION                      1..122
                            note = Synthetic
source                      1..122
                            mol_type = protein
                            organism = synthetic construct
SEQUENCE: 451
EVQLVESGGG LIQPGGSLRL SCAASVFTVS YNYMSWVRQA PGKGLEWVSV IYSGGSTYYA    60
DSVKGRFTIS RDNSKNTLYL QMNSLRAEDT AVYYCARALP GWGGSFEYFD YWGQGTLVTV   120
SS                                                                 122

SEQ ID NO: 452              moltype = DNA  length = 24
FEATURE                     Location/Qualifiers
misc_feature                1..24
                            note = Synthetic
source                      1..24
                            mol_type = other DNA
                            organism = synthetic construct
SEQUENCE: 452
gtgttcaccg tcagttacaa ctac                                          24

SEQ ID NO: 453              moltype = AA   length = 8
FEATURE                     Location/Qualifiers
REGION                      1..8
                            note = Synthetic
source                      1..8
                            mol_type = protein
                            organism = synthetic construct
SEQUENCE: 453
VFTVSYNY                                                             8

SEQ ID NO: 454              moltype = DNA  length = 48
FEATURE                     Location/Qualifiers
misc_feature                1..48
                            note = Synthetic
source                      1..48
                            mol_type = other DNA
                            organism = synthetic construct
SEQUENCE: 454
gcgagagccc tccccgggtg gggtgggagc ttcgagtact ttgactac                 48

SEQ ID NO: 455              moltype = AA   length = 16
FEATURE                     Location/Qualifiers
REGION                      1..16
                            note = Synthetic
source                      1..16
                            mol_type = protein
                            organism = synthetic construct
SEQUENCE: 455
ARALPGWGGS FEYFDY                                                   16

SEQ ID NO: 456              moltype = DNA  length = 321
FEATURE                     Location/Qualifiers
misc_feature                1..321
                            note = Synthetic
source                      1..321
                            mol_type = other DNA
                            organism = synthetic construct
SEQUENCE: 456
gacatccaga tgacccagtc tccttccacc ctgtctgcat ctgtaggaga cagagtcacc    60
atcacttgcc gggccagtca gagtattagt agttggttgg cctggtatca gcagaaacca   120
gggaaagccc ctaagctcct gatctataag gcatctagtt tagaaagtgg ggtctcatca   180
aggttcagcg gcagtggatc tgggacagaa ttcactctca ccatcagcag cctgcagcct   240
gatgattttg caacttatta ctgccaacag tataatagtt attctgtgac gttcggccaa   300
gggaccaagg tggaaatcaa a                                             321

SEQ ID NO: 457              moltype = AA   length = 107
FEATURE                     Location/Qualifiers
REGION                      1..107
                            note = Synthetic
source                      1..107
                            mol_type = protein
                            organism = synthetic construct
SEQUENCE: 457
DIQMTQSPST LSASVGDRVT ITCRASQSIS SWLAWYQQKP GKAPKLLIYK ASSLESGVSS    60
RFSGSGSGTE FTLTISSLQP DDFATYYCQQ YNSYSVTFGQ GTKVEIK                 107

SEQ ID NO: 458              moltype = DNA  length = 18
FEATURE                     Location/Qualifiers
misc_feature                1..18
```

```
                        note = Synthetic
source                  1..18
                        mol_type = other DNA
                        organism = synthetic construct
SEQUENCE: 458
cagagtatta gtagttgg                                              18

SEQ ID NO: 459          moltype = AA  length = 6
FEATURE                 Location/Qualifiers
REGION                  1..6
                        note = Synthetic
source                  1..6
                        mol_type = protein
                        organism = synthetic construct
SEQUENCE: 459
QSISSW                                                           6

SEQ ID NO: 460          moltype =   length =
SEQUENCE: 460
000

SEQ ID NO: 461          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 461
caacagtata atagttattc tgtgacg                                    27

SEQ ID NO: 462          moltype = AA  length = 9
FEATURE                 Location/Qualifiers
REGION                  1..9
                        note = Synthetic
source                  1..9
                        mol_type = protein
                        organism = synthetic construct
SEQUENCE: 462
QQYNSYSVT                                                        9

SEQ ID NO: 463          moltype = DNA  length = 1359
FEATURE                 Location/Qualifiers
misc_feature            1..1359
                        note = Synthetic
source                  1..1359
                        mol_type = other DNA
                        organism = synthetic construct
SEQUENCE: 463
gaggtgcagc tggtggagtc tggaggaggc ttgatccagc ctgggggtc cctgagactc  60
tcctgtgcag cctctgtgtt caccgtcagt tacaactaca tgagctgggt ccgccaggct  120
ccagggaagg ggctggagtg ggtctcagtt atttatagcg gtggtagcac atactacgca  180
gactccgtga agggccgatt caccatctcc agagacaatt ccaagaacac gctgtatctt  240
caaatgaaca gcctgagagc cgaggacacg gccgtgtatt actgtgcgag agccctcccc  300
gggtggggtg ggagcttcga gtactttgac tactggggcc agggaaccct ggtcaccgtc  360
tcctcagcct ccaccaaggg cccatcggtc ttccccctgg caccctcctc caagagcacc  420
tctgggggca cagcggccct gggctgcctg gtcaaggact acttccccga accggtgacg  480
gtgtcgtgga actcaggcgc cctgaccagc ggcgtgcaca ccttcccggc tgtcctacag  540
tcctcaggac tctactccct cagcagcgtg gtgaccgtgc cctccagcag cttgggcacc  600
cagacctaca tctgcaacgt gaatcacaag cccagcaaca ccaaggtgga caagaaagtt  660
gagcccaaat cttgtgacaa aactcacaca tgcccaccgt gcccagcacc tgaactcctg  720
gggggaccgt cagtcttcct cttcccccca aaacccaagg acaccctcat gatctcccgg  780
acccctgagg tcacatgcgt ggtggtggac gtgagccacg aagaccctga ggtcaagttc  840
aactggtacg tggacggcgt ggaggtgcat aatgccaaga caaagccgcg ggaggagcag  900
tacaacagca cgtaccgtgt ggtcagcgtc ctcaccgtcc tgcaccagga ctggctgaat  960
ggcaaggagt acaagtgcaa ggtctccaac aaagccctcc cagcccccat cgagaaaacc  1020
atctccaaag ccaaagggca gccccgagaa ccacaggtgt acaccctgcc cccatcccgg  1080
gatgagctga ccaagaacca ggtcagcctg acctgcctgg tcaaaggctt ctatcccagc  1140
gacatcgccg tggagtggga gagcaatggg cagccggaga acaactacaa gaccacgcct  1200
cccgtgctgg actccgacgg ctccttcttc ctctacagca agctcaccgt ggacaagagc  1260
aggtggcagc aggggaacgt cttctcatgc tccgtgatgc atgaggctct gcacaaccac  1320
tacacgcaga agtccctctc cctgtctccg ggtaaatga                        1359

SEQ ID NO: 464          moltype = AA  length = 452
FEATURE                 Location/Qualifiers
REGION                  1..452
                        note = Synthetic
source                  1..452
                        mol_type = protein
```

```
                        organism = synthetic construct
SEQUENCE: 464
EVQLVESGGG LIQPGGSLRL SCAASVFTVS YNYMSWVRQA PGKGLEWVSV IYSGGSTYYA  60
DSVKGRFTIS RDNSKNTLYL QMNSLRAEDT AVYYCARALP GWGGSFEYFD YWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
DELTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452

SEQ ID NO: 465          moltype = DNA  length = 645
FEATURE                 Location/Qualifiers
misc_feature            1..645
                        note = Synthetic
source                  1..645
                        mol_type = other DNA
                        organism = synthetic construct
SEQUENCE: 465
gacatccaga tgacccagtc tccttccacc ctgtctgcat ctgtaggaga cagagtcacc  60
atcacttgcc gggccagtca gagtattagt agttggttgg cctggtatca gcagaaacca  120
gggaaagccc ctaagctcct gatctataag gcatctagtt tagaaagtgg ggtctcatca  180
aggttcagcg gcagtggatc tgggacagaa ttcactctca ccatcagcag cctgcagcct  240
gatgattttg caacttatta ctgccaacag tataatagtt attctgtgac gttcggccaa  300
gggaccaagg tggaaatcaa acgaactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttag                  645

SEQ ID NO: 466          moltype = AA  length = 214
FEATURE                 Location/Qualifiers
REGION                  1..214
                        note = Synthetic
source                  1..214
                        mol_type = protein
                        organism = synthetic construct
SEQUENCE: 466
DIQMTQSPST LSASVGDRVT ITCRASQSIS SWLAWYQQKP GKAPKLLIYK ASSLESGVSS  60
RFSGSGSGTE FTLTISSLQP DDFATYYCQQ YNSYSVTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 467          moltype = DNA  length = 363
FEATURE                 Location/Qualifiers
misc_feature            1..363
                        note = Synthetic
source                  1..363
                        mol_type = other DNA
                        organism = synthetic construct
SEQUENCE: 467
gaggtgcagc tggtggagtc tgggggaggc ttggtccagc ctggggggtc cctgagactc  60
tcctgtgcag cctctggact caccgtcagt agcaactaca tgagctgggt ccgccaggct  120
ccagggaagg ggctggagtg ggtctcagtt atttatagcg gtggtagtac attctacgca  180
gactccgtga agggccgatt caccatctcc agagacaatt ccaagaacac gttgtatctt  240
cagatgaaca gcctgagacc tgaggacacg gctgtgtatt actgtgcgag agagggccgt  300
atagcagcaa ctggctacgg tatggacgtc tggggccaag ggaccacggt caccgtctcc  360
tca                                                                363

SEQ ID NO: 468          moltype = AA  length = 121
FEATURE                 Location/Qualifiers
REGION                  1..121
                        note = Synthetic
source                  1..121
                        mol_type = protein
                        organism = synthetic construct
SEQUENCE: 468
EVQLVESGGG LVQPGGSLRL SCAASGLTVS SNYMSWVRQA PGKGLEWVSV IYSGGSTFYA  60
DSVKGRFTIS RDNSKNTLYL QMNSLRPEDT AVYYCAREGR IAATGYGMDV WGQGTTVTVS  120
S                                                                  121

SEQ ID NO: 469          moltype = DNA  length = 45
FEATURE                 Location/Qualifiers
misc_feature            1..45
                        note = Synthetic
source                  1..45
                        mol_type = other DNA
                        organism = synthetic construct
```

```
SEQUENCE: 469
gcgagagagg gccgtatagc agcaactggc tacggtatgg acgtc                 45

SEQ ID NO: 470          moltype = AA  length = 15
FEATURE                 Location/Qualifiers
REGION                  1..15
                        note = Synthetic
source                  1..15
                        mol_type = protein
                        organism = synthetic construct
SEQUENCE: 470
AREGRIAATG YGMDV                                                  15

SEQ ID NO: 471          moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 471
gacatccaga tgacccagtc tccatcctcc ctgtctgcat ctgtaggaga cagagtcacc  60
atcacttgcc aggcgagtca ggacattagc aactatttaa attggtatca gcagaaacca  120
gggaaagccc ctaagctcct gatctacgat gcatccaatt tgggaacagg ggtcccatca  180
aggttcagtg gaagtagatc tgggacagat tttactttca ccatcagcag cctgcagcct  240
gaagatattg cgacatatta ctgtcatcag tatgataatc tccctcaaac tttcggccct  300
gggaccaaag tggatatcaa a                                           321

SEQ ID NO: 472          moltype = AA  length = 107
FEATURE                 Location/Qualifiers
REGION                  1..107
                        note = Synthetic
source                  1..107
                        mol_type = protein
                        organism = synthetic construct
SEQUENCE: 472
DIQMTQSPSS LSASVGDRVT ITCQASQDIS NYLNWYQQKP GKAPKLLIYD ASNLGTGVPS  60
RFSGSRSGTD FTFTISSLQP EDIATYYCHQ YDNLPQTFGP GTKVDIK               107

SEQ ID NO: 473          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 473
catcagtatg ataatctccc tcaaact                                     27

SEQ ID NO: 474          moltype = AA  length = 9
FEATURE                 Location/Qualifiers
REGION                  1..9
                        note = Synthetic
source                  1..9
                        mol_type = protein
                        organism = synthetic construct
SEQUENCE: 474
HQYDNLPQT                                                         9

SEQ ID NO: 475          moltype = DNA  length = 1356
FEATURE                 Location/Qualifiers
misc_feature            1..1356
                        note = Synthetic
source                  1..1356
                        mol_type = other DNA
                        organism = synthetic construct
SEQUENCE: 475
gaggtgcagc tggtggagtc tgggggaggc ttggtccagc ctggggggtc cctgagactc  60
tcctgtgcag cctctggact caccgtcagt agcaactaca tgagctgggt ccgccaggct  120
ccagggaagg ggctggagtg ggtctcagtt atttatagcg gtggtagtac attctacgca  180
gactccgtga agggccgatt caccatctcc agagacaatt ccaagaacac gttgtatctt  240
cagatgaaca gcctgagacc tgaggacacg gctgtgtatt actgtgcgag agagggccgt  300
atagcagcaa ctggctacgg tatggacgtc tggggccaag ggaccacggt caccgtctcc  360
tcagcctcca ccaagggccc atcggtcttc cccctggcac cctcctccaa gagcacctct  420
gggggcacag cggccctggg ctgcctggtc aaggactact tccccgaacc ggtgacggtg  480
tcgtggaact caggcgccct gaccagcggc gtgcacacct tcccggctgt cctacagtcc  540
tcaggactct actccctcag cagcgtggtg accgtgccct ccagcagctt gggcacccag  600
acctacatct gcaacgtgaa tcacaagccc agcaacacca aggtggacaa gaaagttgag  660
cccaaatctt gtgacaaaac tcacacatgc ccaccgtgcc cagcacctga actcctgggg  720
```

```
ggaccgtcag tcttcctctt ccccccaaaa cccaaggaca ccctcatgat ctcccggacc  780
cctgaggtca catgcgtggt ggtggacgtg agccacgaag accctgaggt caagttcaac  840
tggtacgtgg acggcgtgga ggtgcataat gccaagacaa agccgcggga ggagcagtac  900
aacagcacgt accgtgtggt cagcgtcctc accgtcctgc accaggactg gctgaatggc  960
aaggagtaca agtgcaaggt ctccaacaaa gccctcccag cccccatcga gaaaaccatc  1020
tccaaagcca aagggcagcc ccgagaacca caggtgtaca ccctgccccc atcccgggat  1080
gagctgacca agaaccaggt cagcctgacc tgcctggtca aaggcttcta tcccagcgac  1140
atcgccgtgg agtgggagag caatgggcag ccggagaaca actacaagac cacgcctccc  1200
gtgctggact ccgacggctc cttcttcctc tacagcaagc tcaccgtgga caagagcagg  1260
tggcagcagg ggaacgtctt ctcatgctcc gtgatgcatg aggctctgca caaccactac  1320
acgcagaagt ccctctccct gtctccgggt aaatga                            1356

SEQ ID NO: 476         moltype = AA  length = 451
FEATURE                Location/Qualifiers
REGION                 1..451
                       note = Synthetic
source                 1..451
                       mol_type = protein
                       organism = synthetic construct
SEQUENCE: 476
EVQLVESGGG LVQPGGSLRL SCAASGLTVS SNYMSWVRQA PGKGLEWVSV IYSGGSTFYA  60
DSVKGRFTIS RDNSKNTLYL QMNSLRPEDT AVYYCAREGR IAATGYGMDV WGQGTTVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451

SEQ ID NO: 477         moltype = DNA  length = 645
FEATURE                Location/Qualifiers
misc_feature           1..645
                       note = Synthetic
source                 1..645
                       mol_type = other DNA
                       organism = synthetic construct
SEQUENCE: 477
gacatccaga tgacccagtc tccatcctcc ctgtctgcat ctgtaggaga cagagtcacc  60
atcacttgcc aggcgagtca ggacattagc aactatttaa attggtatca gcagaaacca  120
gggaaagccc ctaagctcct gatctacgat gcatccaatt tgggaacagg ggtcccatca  180
aggttcagtg gaagtagatc tgggacagat tttactttca ccatcagcag cctgcagcct  240
gaagatattg cgacatatta ctgtcatcag tatgataatc tccctcaaac tttcggccct  300
gggaccaaag tggatatcaa acgaactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttag                  645

SEQ ID NO: 478         moltype = AA  length = 214
FEATURE                Location/Qualifiers
REGION                 1..214
                       note = Synthetic
source                 1..214
                       mol_type = protein
                       organism = synthetic construct
SEQUENCE: 478
DIQMTQSPSS LSASVGDRVT ITCQASQDIS NYLNWYQQKP GKAPKLLIYD ASNLGTGVPS  60
RFSGSRSGTD FTFTISSLQP EDIATYYCHQ YDNLPQTFGP GTKVDIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 479         moltype = DNA  length = 342
FEATURE                Location/Qualifiers
misc_feature           1..342
                       note = Synthetic
source                 1..342
                       mol_type = other DNA
                       organism = synthetic construct
SEQUENCE: 479
gaggtgcagc tggtggagtc tgggggaggc ttggtccagc ctggggggtc cctgagactc  60
tcctgtgcag cctctggatt caccgtcagt agcaactaca tgagctgggt ccgccaggct  120
ccagggaagg ggctggagtg ggtctcagtt atttatcccg gtggtagtac attctacgca  180
gactccgtga agggcagatt caccatctcc agagacaatt ccaagaacac gctgtatctt  240
caaatgaaca gcctgagagc cgaggacacg gctgtgtatt actgtgcgag agatcaacgc  300
gattttgcct ggggccaggg aaccctggtc accgtctcct ca                     342

SEQ ID NO: 480         moltype = AA  length = 114
FEATURE                Location/Qualifiers
```

```
REGION                  1..114
                        note = Synthetic
source                  1..114
                        mol_type = protein
                        organism = synthetic construct
SEQUENCE: 480
EVQLVESGGG LVQPGGSLRL SCAASGFTVS SNYMSWVRQA PGKGLEWVSV IYPGGSTFYA  60
DSVKGRFTIS RDNSKNTLYL QMNSLRAEDT AVYYCARDQR DFAWGQGTLV TVSS        114

SEQ ID NO: 481          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 481
ggattcaccg tcagtagcaa ctac                                         24

SEQ ID NO: 482          moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 482
atttatcccg gtggtagtac a                                            21

SEQ ID NO: 483          moltype = AA  length = 7
FEATURE                 Location/Qualifiers
REGION                  1..7
                        note = Synthetic
source                  1..7
                        mol_type = protein
                        organism = synthetic construct
SEQUENCE: 483
IYPGGST                                                            7

SEQ ID NO: 484          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 484
gcgagagatc aacgcgattt tgcc                                         24

SEQ ID NO: 485          moltype = AA  length = 8
FEATURE                 Location/Qualifiers
REGION                  1..8
                        note = Synthetic
source                  1..8
                        mol_type = protein
                        organism = synthetic construct
SEQUENCE: 485
ARDQRDFA                                                           8

SEQ ID NO: 486          moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 486
gacatccaga tgacccagtc tccatcctcc ctgtctgcat ctgtaggaga cagagtcacc  60
atcacttgcc aggcgagtca ggacattagc aactatttaa attggtatca gcagaaacca  120
gggaaagccc ctaagctcct gatctacgat gcatccaatt tggaaacagg ggtcccatca  180
aggttcagtg gaagtggatc tgggacagat tttactttca ccatcagcgg cctgcagcct  240
gaagatattg caacatatta ctgtcaacag tatgataatc tccctccgac cttcggccaa  300
gggacacgac tggagattaa a                                            321

SEQ ID NO: 487          moltype = AA  length = 107
FEATURE                 Location/Qualifiers
REGION                  1..107
                        note = Synthetic
source                  1..107
```

```
                         mol_type = protein
                         organism = synthetic construct
SEQUENCE: 487
DIQMTQSPSS LSASVGDRVT ITCQASQDIS NYLNWYQQKP GKAPKLLIYD ASNLETGVPS  60
RFSGSGSGTD FTFTISGLQP EDIATYYCQQ YDNLPPTFGQ GTRLEIK               107

SEQ ID NO: 488           moltype = DNA  length = 27
FEATURE                  Location/Qualifiers
misc_feature             1..27
                         note = Synthetic
source                   1..27
                         mol_type = other DNA
                         organism = synthetic construct
SEQUENCE: 488
caacagtatg ataatctccc tccgacc                                     27

SEQ ID NO: 489           moltype = AA  length = 9
FEATURE                  Location/Qualifiers
REGION                   1..9
                         note = Synthetic
source                   1..9
                         mol_type = protein
                         organism = synthetic construct
SEQUENCE: 489
QQYDNLPPT                                                         9

SEQ ID NO: 490           moltype = DNA  length = 1335
FEATURE                  Location/Qualifiers
misc_feature             1..1335
                         note = Synthetic
source                   1..1335
                         mol_type = other DNA
                         organism = synthetic construct
SEQUENCE: 490
gaggtgcagc tggtggagtc tgggggaggc ttggtccagc ctggggggtc cctgagactc  60
tcctgtgcag cctctggatt caccgtcagt agcaactaca tgagctgggt ccgccaggct  120
ccagggaagg ggctggagtg ggtctcagtt atttatcccg gtggtagtac attctacgca  180
gactccgtga agggcagatt caccatctcc agagacaatt ccaagaacac gctgtatctt  240
caaatgaaca gcctgagagc cgaggacacg gctgtgtatt actgtgcgag agatcaacgc  300
gattttgcct ggggccaggg aaccctggtc accgtctcct cagcctccac caagggccca  360
tcggtcttcc ccctggcacc ctcctccaag agcacctctg ggggcacagc ggccctgggc  420
tgcctggtca aggactactt ccccgaaccg gtgacggtgt cgtggaactc aggcgccctg  480
accagcggcg tgcacacctt cccggctgtc ctacagtcct caggactcta ctccctcagc  540
agcgtggtga ccgtgccctc cagcagcttg ggcacccaga cctacatctg caacgtgaat  600
cacaagccca gcaacaccaa ggtggacaag aaagttgagc ccaaatcttg tgacaaaact  660
cacacatgcc caccgtgccc agcacctgaa ctcctggggg gaccgtcagt cttcctcttc  720
cccccaaaac ccaaggacac cctcatgatc tcccggaccc ctgaggtcac atgcgtggtg  780
gtggacgtga gccacgaaga ccctgaggtc aagttcaact ggtacgtgga cggcgtggag  840
gtgcataatg ccaagacaaa gccgcgggag gagcagtaca acagcacgta ccgtgtggtc  900
agcgtcctca ccgtcctgca ccaggactgg ctgaatggca aggagtacaa gtgcaaggtc  960
tccaacaaag ccctcccagc ccccatcgag aaaaccatct ccaaagccaa agggcagccc  1020
cgagaaccac aggtgtacac cctgccccca tcccgggatg agctgaccaa gaaccaggtc  1080
agcctgacct gcctggtcaa aggcttctat cccagcgaca tcgccgtgga gtgggagagc  1140
aatgggcagc cggagaacaa ctacaagacc acgcctcccg tgctggactc cgacggctcc  1200
ttcttcctct acagcaagct caccgtggac aagagcaggt ggcagcaggg gaacgtcttc  1260
tcatgctccg tgatgcatga ggctctgcac aaccactaca cgcagaagtc cctctccctg  1320
tctccgggta aatga                                                  1335

SEQ ID NO: 491           moltype = AA  length = 444
FEATURE                  Location/Qualifiers
REGION                   1..444
                         note = Synthetic
source                   1..444
                         mol_type = protein
                         organism = synthetic construct
SEQUENCE: 491
EVQLVESGGG LVQPGGSLRL SCAASGFTVS SNYMSWVRQA PGKGLEWVSV IYPGGSTFYA  60
DSVKGRFTIS RDNSKNTLYL QMNSLRAEDT AVYYCARDQR DFAWGQGTLV TVSSASTKGP  120
SVFPLAPSSK STSGGTAALG CLVKDYFPEP VTVSWNSGAL TSGVHTFPAV LQSSGLYSLS  180
SVVTVPSSSL GTQTYICNVN HKPSNTKVDK KVEPKSCDKT HTCPPCPAPE LLGGPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SNKALPAPIE KTISKAKGQP REPQVYTLPP SRDELTKNQV  360
SLTCLVKGFY PSDIAVEWES NGQPENNYKT TPPVLDSDGS FFLYSKLTVD KSRWQQGNVF  420
SCSVMHEALH NHYTQKSLSL SPGK                                        444

SEQ ID NO: 492           moltype = DNA  length = 645
FEATURE                  Location/Qualifiers
misc_feature             1..645
                         note = Synthetic
```

-continued

```
source                1..645
                      mol_type = other DNA
                      organism = synthetic construct
SEQUENCE: 492
gacatccaga tgacccagtc tccatcctcc ctgtctgcat ctgtaggaga cagagtcacc  60
atcacttgcc aggcgagtca ggacattagc aactatttaa attggtatca gcagaaacca  120
gggaaagccc ctaagctcct gatctacgat gcatccaatt tggaaacagg ggtcccatca  180
aggttcagtg gaagtggatc tgggacagat tttactttca ccatcagcgg cctgcagcct  240
gaagatattg caacatatta ctgtcaacag tatgataatc tccctccgac cttcggccaa  300
gggacacgac tggagattaa acgaactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttag                  645

SEQ ID NO: 493        moltype = AA  length = 214
FEATURE               Location/Qualifiers
REGION                1..214
                      note = Synthetic
source                1..214
                      mol_type = protein
                      organism = synthetic construct
SEQUENCE: 493
DIQMTQSPSS LSASVGDRVT ITCQASQDIS NYLNWYQQKP GKAPKLLIYD ASNLETGVPS  60
RFSGSGSGTD FTFTISGLQP EDIATYYCQQ YDNLPPTFGQ GTRLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                                214

SEQ ID NO: 494        moltype = DNA  length = 381
FEATURE               Location/Qualifiers
misc_feature          1..381
                      note = Synthetic
source                1..381
                      mol_type = other DNA
                      organism = synthetic construct
SEQUENCE: 494
caggtgcagc tggtggagtc tgggggaggc gtggtccagc ctgggaggtc cctgagactc  60
tcctgtgcag cctctggatt caccttcagt agctatgcta tgcactgggt ccgccaggct  120
ccaggcaagg ggctggagtg ggtggcagtt atatcatatg atggaagtaa taaatactac  180
gcagactccg tgaagggccg attcaccatc tccagagaca attccaagaa cacgctgtat  240
ctgcaaatga acagcctgag agctgaggac acggctgtgt attactgtgc gagagacggc  300
cggactatta ctatggttcg gggagttatt gatgatgctt ttgatatctg gggccaaggg  360
acaatggtca ccgtctcttc a                                              381

SEQ ID NO: 495        moltype = AA  length = 127
FEATURE               Location/Qualifiers
REGION                1..127
                      note = Synthetic
source                1..127
                      mol_type = protein
                      organism = synthetic construct
SEQUENCE: 495
QVQLVESGGG VVQPGRSLRL SCAASGFTFS SYAMHWVRQA PGKGLEWVAV ISYDGSNKYY  60
ADSVKGRFTI SRDNSKNTLY LQMNSLRAED TAVYYCARDG RTITMVRGVI DDAFDIWGQG  120
TMVTVSS                                                              127

SEQ ID NO: 496        moltype = DNA  length = 24
FEATURE               Location/Qualifiers
misc_feature          1..24
                      note = Synthetic
source                1..24
                      mol_type = other DNA
                      organism = synthetic construct
SEQUENCE: 496
ggattcacct tcagtagcta tgct                                           24

SEQ ID NO: 497        moltype = AA  length = 8
FEATURE               Location/Qualifiers
REGION                1..8
                      note = Synthetic
source                1..8
                      mol_type = protein
                      organism = synthetic construct
SEQUENCE: 497
GFTFSSYA                                                             8

SEQ ID NO: 498        moltype = DNA  length = 24
FEATURE               Location/Qualifiers
```

```
misc_feature           1..24
                       note = Synthetic
source                 1..24
                       mol_type = other DNA
                       organism = synthetic construct
SEQUENCE: 498
atatcatatg atggaagtaa taaa                                        24

SEQ ID NO: 499         moltype = AA  length = 8
FEATURE                Location/Qualifiers
REGION                 1..8
                       note = Synthetic
source                 1..8
                       mol_type = protein
                       organism = synthetic construct
SEQUENCE: 499
ISYDGSNK                                                          8

SEQ ID NO: 500         moltype = DNA  length = 60
FEATURE                Location/Qualifiers
misc_feature           1..60
                       note = Synthetic
source                 1..60
                       mol_type = other DNA
                       organism = synthetic construct
SEQUENCE: 500
gcgagagacg gccggactat tactatggtt cggggagtta ttgatgatgc ttttgatatc  60

SEQ ID NO: 501         moltype = AA  length = 20
FEATURE                Location/Qualifiers
REGION                 1..20
                       note = Synthetic
source                 1..20
                       mol_type = protein
                       organism = synthetic construct
SEQUENCE: 501
ARDGRTITMV RGVIDDAFDI                                             20

SEQ ID NO: 502         moltype = DNA  length = 321
FEATURE                Location/Qualifiers
misc_feature           1..321
                       note = Synthetic
source                 1..321
                       mol_type = other DNA
                       organism = synthetic construct
SEQUENCE: 502
gacatccaga tgacccagtc tccatcctcc ctgtctgcat ctgtaggaga cagagtcacc  60
atcacttgcc aggcgagtca ggacattagc aactatttaa attggtatca gcagaaacca  120
gggaaagccc ctaagctcct gatctacgat gcatccaatt tggaaacagg ggtcccatca  180
aggttcagtg gaagtggatc tgggacagat tttactttca ccatcagcag cctgcagcct  240
gaagatattg caacatatta ctgtcaacag tatgataatc tccccctcac cttcggccaa  300
gggacacgac tggagattaa a                                           321

SEQ ID NO: 503         moltype = AA  length = 107
FEATURE                Location/Qualifiers
REGION                 1..107
                       note = Synthetic
source                 1..107
                       mol_type = protein
                       organism = synthetic construct
SEQUENCE: 503
DIQMTQSPSS LSASVGDRVT ITCQASQDIS NYLNWYQQKP GKAPKLLIYD ASNLETGVPS  60
RFSGSGSGTD FTFTISSLQP EDIATYYCQQ YDNLPLTFGQ GTRLEIK               107

SEQ ID NO: 504         moltype = DNA  length = 27
FEATURE                Location/Qualifiers
misc_feature           1..27
                       note = Synthetic
source                 1..27
                       mol_type = other DNA
                       organism = synthetic construct
SEQUENCE: 504
caacagtatg ataatctccc cctcacc                                     27

SEQ ID NO: 505         moltype = DNA  length = 1374
FEATURE                Location/Qualifiers
misc_feature           1..1374
                       note = Synthetic
source                 1..1374
```

```
                         mol_type = other DNA
                         organism = synthetic construct
SEQUENCE: 505
caggtgcagc tggtggagtc tgggggaggc gtggtccagc ctgggaggtc cctgagactc  60
tcctgtgcag cctctggatt caccttcagt agctatgcta tgcactgggt ccgccaggct  120
ccaggcaagg ggctggagtg ggtggcagtt atatcatatg atggaagtaa taaatactac  180
gcagactccg tgaagggccg attcaccatc tccagagaca attccaagaa cacgctgtat  240
ctgcaaatga acagcctgag agctgaggac acggctgtgt attactgtgc gagagacggc  300
cggactatta ctatggttcg gggagttatt gatgatgctt ttgatatctg gggccaaggg  360
acaatggtca ccgtctcttc agcctccacc aagggcccat cggtcttccc cctggcaccc  420
tcctccaaga gcacctctgg gggcacagcg gccctgggct gcctggtcaa ggactacttc  480
cccgaaccgg tgacggtgtc gtggaactca ggcgccctga ccagcggcgt gcacaccttc  540
ccggctgtcc tacagtcctc aggactctac tccctcagca gcgtggtgac cgtgccctcc  600
agcagcttgg gcacccagac ctacatctgc aacgtgaatc acaagcccag caacaccaag  660
gtggacaaga aagttgagcc caaatcttgt gacaaaactc acacatgccc accgtgccca  720
gcacctgaac tcctgggggg accgtcagtc ttcctcttcc ccccaaaacc caaggacacc  780
ctcatgatct cccggacccc tgaggtcaca tgcgtggtgg tggacgtgag ccacgaagac  840
cctgaggtca agttcaactg gtacgtggac ggcgtggagg tgcataatgc caagacaaag  900
ccgcgggagg agcagtacaa cagcacgtac cgtgtggtca gcgtcctcac cgtcctgcac  960
caggactggc tgaatggcaa ggagtacaag tgcaaggtct ccaacaaagc cctcccagcc  1020
cccatcgaga aaaccatctc caaagccaaa gggcagcccc gagaaccaca ggtgtacacc  1080
ctgcccccat cccgggatga gctgaccaag aaccaggtca gcctgacctg cctggtcaaa  1140
ggcttctatc ccagcgacat cgccgtggag tgggagagca atgggcagcc ggagaacaac  1200
tacaagacca cgcctcccgt gctggactcc gacggctcct tcttcctcta cagcaagctc  1260
accgtggaca agagcaggtg gcagcagggg aacgtcttct catgctccgt gatgcatgag  1320
gctctgcaca accactacac gcagaagtcc ctctccctgt ctccgggtaa atga        1374

SEQ ID NO: 506           moltype = AA  length = 457
FEATURE                  Location/Qualifiers
REGION                   1..457
                         note = Synthetic
source                   1..457
                         mol_type = protein
                         organism = synthetic construct
SEQUENCE: 506
QVQLVESGGG VVQPGRSLRL SCAASGFTFS SYAMHWVRQA PGKGLEWVAV ISYDGSNKYY  60
ADSVKGRFTI SRDNSKNTLY LQMNSLRAED TAVYYCARDG RTITMVRGVI DDAFDIWGQG  120
TMVTVSSAST KGPSVFPLAP SSKSTSGGTA ALGCLVKDYF PEPVTVSWNS GALTSGVHTF  180
PAVLQSSGLY SLSSVVTVPS SSLGTQTYIC NVNHKPSNTK VDKKVEPKSC DKTHTCPPCP  240
APELLGGPSV FLFPPKPKDT LMISRTPEVT CVVVDVSHED PEVKFNWYVD GVEVHNAKTK  300
PREEQYNSTY RVVSVLTVLH QDWLNGKEYK CKVSNKALPA PIEKTISKAK GQPREPQVYT  360
LPPSRDELTK NQVSLTCLVK GFYPSDIAVE WESNGQPENN YKTTPPVLDS DGSFFLYSKL  420
TVDKSRWQQG NVFSCSVMHE ALHNHYTQKS LSLSPGK                           457

SEQ ID NO: 507           moltype = DNA  length = 645
FEATURE                  Location/Qualifiers
misc_feature             1..645
                         note = Synthetic
source                   1..645
                         mol_type = other DNA
                         organism = synthetic construct
SEQUENCE: 507
gacatccaga tgacccagtc tccatcctcc ctgtctgcat ctgtaggaga cagagtcacc  60
atcacttgcc aggcgagtca ggacattagc aactatttaa attggtatca gcagaaacca  120
gggaaagccc ctaagctcct gatctacgat gcatccaatt tggaaacagg ggtcccatca  180
aggttcagtg gaagtggatc tgggacagat tttactttca ccatcagcag cctgcagcct  240
gaagatattg caacatatta ctgtcaacag tatgataatc tcccccctcac cttcggccaa  300
gggacacgac tggagattaa acgaactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttag                  645

SEQ ID NO: 508           moltype = AA  length = 214
FEATURE                  Location/Qualifiers
REGION                   1..214
                         note = Synthetic
source                   1..214
                         mol_type = protein
                         organism = synthetic construct
SEQUENCE: 508
DIQMTQSPSS LSASVGDRVT ITCQASQDIS NYLNWYQQKP GKAPKLLIYD ASNLETGVPS  60
RFSGSGSGTD FTFTISSLQP EDIATYYCQQ YDNLPLTFGQ GTRLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 509           moltype = DNA  length = 360
FEATURE                  Location/Qualifiers
```

```
misc_feature          1..360
                      note = Synthetic
source                1..360
                      mol_type = other DNA
                      organism = synthetic construct
SEQUENCE: 509
gaggtgcagc tggtggagtc tgggggaggc ttggtccagc ctgggggtc cctgagactc  60
tcctgtgcag cctctggatt caccgtcagt agcaactaca tgagctgggt ccgccaggct  120
ccagggaagg ggctggagtg ggtctcagtt atttatagcg gtggtagtac atactacgca  180
gactccgtga agggccgatt caccatctcc agagacaatt ccaagaacac gctgtatctt  240
caaatgaaca gactgagagc tgacgacacg gctgtctatt actgtgtgag agatccggtg  300
gggcgctact actacggtat ggacgtctgg ggccaaggga ccacggtcac cgtctcctca  360

SEQ ID NO: 510        moltype = AA  length = 120
FEATURE               Location/Qualifiers
REGION                1..120
                      note = Synthetic
source                1..120
                      mol_type = protein
                      organism = synthetic construct
SEQUENCE: 510
EVQLVESGGG LVQPGGSLRL SCAASGFTVS SNYMSWVRQA PGKGLEWVSV IYSGGSTYYA  60
DSVKGRFTIS RDNSKNTLYL QMNRLRADDT AVYYCVRDPV GRYYYGMDVW GQGTTVTVSS  120

SEQ ID NO: 511        moltype = DNA  length = 42
FEATURE               Location/Qualifiers
misc_feature          1..42
                      note = Synthetic
source                1..42
                      mol_type = other DNA
                      organism = synthetic construct
SEQUENCE: 511
gtgagagatc cggtggggcg ctactactac ggtatggacg tc                    42

SEQ ID NO: 512        moltype = AA  length = 14
FEATURE               Location/Qualifiers
REGION                1..14
                      note = Synthetic
source                1..14
                      mol_type = protein
                      organism = synthetic construct
SEQUENCE: 512
VRDPVGRYYY GMDV                                                   14

SEQ ID NO: 513        moltype = DNA  length = 321
FEATURE               Location/Qualifiers
misc_feature          1..321
                      note = Synthetic
source                1..321
                      mol_type = other DNA
                      organism = synthetic construct
SEQUENCE: 513
gacatccaga tgacccagtc tccatcctcc ctgtctgcat ctgtaggaga cagagtcacc  60
atcacttgcc aggcgagtca ggacattaac aactatttaa attggtatca gcagaaacca  120
gggaaagccc ctaagctcct gatctacgat gcatccaatt tggaaacagg ggtcccatca  180
aggttcagtg gaagtggatc tgggacagat tttactttca ccatcagcag cctgcagcct  240
gaagatattg caacatatta ttgtcaacag tatgataatc tccctcgcac tttcggcgga  300
gggaccaagg tggagatcaa a                                           321

SEQ ID NO: 514        moltype = AA  length = 107
FEATURE               Location/Qualifiers
REGION                1..107
                      note = Synthetic
source                1..107
                      mol_type = protein
                      organism = synthetic construct
SEQUENCE: 514
DIQMTQSPSS LSASVGDRVT ITCQASQDIN NYLNWYQQKP GKAPKLLIYD ASNLETGVPS  60
RFSGSGSGTD FTFTISSLQP EDIATYYCQQ YDNLPRTFGG GTKVEIK               107

SEQ ID NO: 515        moltype = DNA  length = 18
FEATURE               Location/Qualifiers
misc_feature          1..18
                      note = Synthetic
source                1..18
                      mol_type = other DNA
                      organism = synthetic construct
SEQUENCE: 515
caggacatta acaactat                                               18
```

```
SEQ ID NO: 516         moltype = AA  length = 6
FEATURE                Location/Qualifiers
REGION                 1..6
                       note = Synthetic
source                 1..6
                       mol_type = protein
                       organism = synthetic construct
SEQUENCE: 516
QDINNY                                                            6

SEQ ID NO: 517         moltype = DNA  length = 27
FEATURE                Location/Qualifiers
misc_feature           1..27
                       note = Synthetic
source                 1..27
                       mol_type = other DNA
                       organism = synthetic construct
SEQUENCE: 517
caacagtatg ataatctccc tcgcact                                     27

SEQ ID NO: 518         moltype = AA  length = 9
FEATURE                Location/Qualifiers
REGION                 1..9
                       note = Synthetic
source                 1..9
                       mol_type = protein
                       organism = synthetic construct
SEQUENCE: 518
QQYDNLPRT                                                         9

SEQ ID NO: 519         moltype = DNA  length = 1353
FEATURE                Location/Qualifiers
misc_feature           1..1353
                       note = Synthetic
source                 1..1353
                       mol_type = other DNA
                       organism = synthetic construct
SEQUENCE: 519
gaggtgcagc tggtggagtc tgggggaggc ttggtccagc ctggggggtc cctgagactc  60
tcctgtgcag cctctggatt caccgtcagt agcaactaca tgagctgggt ccgccaggct  120
ccagggaagg ggctggagtg ggtctcagtt atttatagcg gtggtagtac atactacgca  180
gactccgtga agggccgatt caccatctcc agagacaatt ccaagaacac gctgtatctt  240
caaatgaaca gactgagagc tgacgacacg gctgtctatt actgtgtgag agatccggtg  300
gggcgctact actacggtat ggacgtctgg ggccaaggga ccacggtcac cgtctcctca  360
gcctccacca agggcccatc ggtcttcccc ctggcaccct cctccaagag cacctctggg  420
ggcacagcgg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacccagacc  600
tacatctgca acgtgaatca caagcccagc aacaccaagg tggacaagaa agttgagccc  660
aaatcttgtg acaaaactca cacatgccca ccgtgcccag cacctgaact cctgggggga  720
ccgtcagtct tcctcttccc cccaaaaccc aaggacaccc tcatgatctc ccggacccct  780
gaggtcacat gcgtggtggt ggacgtgagc cacgaagacc ctgaggtcaa gttcaactgg  840
tacgtggacg gcgtggaggt gcataatgcc aagacaaagc cgcgggagga gcagtacaac  900
agcacgtacc gtgtggtcag cgtcctcacc gtcctgcacc aggactggct gaatggcaag  960
gagtacaagt gcaaggtctc caacaaagcc ctcccagccc ccatcgagaa aaccatctcc  1020
aaagccaaag ggcagccccg agaaccacag gtgtacaccc tgcccccatc ccgggatgag  1080
ctgaccaaga accaggtcag cctgacctgc ctggtcaaag gcttctatcc cagcgacatc  1140
gccgtggagt gggagagcaa tgggcagccg gagaacaact acaagaccac gcctcccgtg  1200
ctggactccg acggctcctt cttcctctac agcaagctca ccgtggacaa gagcaggtgg  1260
cagcagggga acgtcttctc atgctccgtg atgcatgagg ctctgcacaa ccactacacg  1320
cagaagtccc tctccctgtc tccgggtaaa tga                              1353

SEQ ID NO: 520         moltype = AA  length = 450
FEATURE                Location/Qualifiers
REGION                 1..450
                       note = Synthetic
source                 1..450
                       mol_type = protein
                       organism = synthetic construct
SEQUENCE: 520
EVQLVESGGG LVQPGGSLRL SCAASGFTVS SNYMSWVRQA PGKGLEWVSV IYSGGSTYYA  60
DSVKGRFTIS RDNSKNTLYL QMNRLRADDT AVYYCVRDPV GRYYYGMDVW GQGTTVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450
```

```
SEQ ID NO: 521         moltype = DNA  length = 645
FEATURE                Location/Qualifiers
misc_feature           1..645
                       note = Synthetic
source                 1..645
                       mol_type = other DNA
                       organism = synthetic construct
SEQUENCE: 521
gacatccaga tgacccagtc tccatcctcc ctgtctgcat ctgtaggaga cagagtcacc  60
atcacttgcc aggcgagtca ggacattaac aactatttaa attggtatca gcagaaacca  120
gggaaagccc ctaagctcct gatctacgat gcatccaatt tggaaacagg ggtcccatca  180
aggttcagtg gaagtggatc tgggacagat tttactttca ccatcagcag cctgcagcct  240
gaagatattg caacatatta ttgtcaacag tatgataatc tccctcgcac tttcggcgga  300
gggaccaagg tggagatcaa acgaactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttag                  645

SEQ ID NO: 522         moltype = AA  length = 214
FEATURE                Location/Qualifiers
REGION                 1..214
                       note = Synthetic
source                 1..214
                       mol_type = protein
                       organism = synthetic construct
SEQUENCE: 522
DIQMTQSPSS LSASVGDRVT ITCQASQDIN NYLNWYQQKP GKAPKLLIYD ASNLETGVPS  60
RFSGSGSGTD FTFTISSLQP EDIATYYCQQ YDNLPRTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 523         moltype = DNA  length = 351
FEATURE                Location/Qualifiers
misc_feature           1..351
                       note = Synthetic
source                 1..351
                       mol_type = other DNA
                       organism = synthetic construct
SEQUENCE: 523
gaggtgcagc tggtggagtc tggaggaggc ttgatccagc ctggggggtc cctgagactc  60
tcctgtgcag cctctggggt caccgtcagt agcaactaca tgagctgggt ccgccaggct  120
ccagggaagg ggctggagtg ggtctcagtc atttatagcg gcggtagcac attctactca  180
gactccgtga agggccgatt cagcatctcc agagacaatt ccaagaacac actgtatctt  240
caaatgaaca gcctgagagc cgaggacacg gccgtgtatt actgtgcgag agacctctac  300
tactacggta tggacgtctg gggccaaggg accacggtca ccgtctcctc a           351

SEQ ID NO: 524         moltype = AA  length = 117
FEATURE                Location/Qualifiers
REGION                 1..117
                       note = Synthetic
source                 1..117
                       mol_type = protein
                       organism = synthetic construct
SEQUENCE: 524
EVQLVESGGG LIQPGGSLRL SCAASGVTVS SNYMSWVRQA PGKGLEWVSV IYSGGSTFYS  60
DSVKGRFSIS RDNSKNTLYL QMNSLRAEDT AVYYCARDLY YYGMDVWGQG TTVTVSS     117

SEQ ID NO: 525         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 525
ggggtcaccg tcagtagcaa ctac                                         24

SEQ ID NO: 526         moltype = DNA  length = 21
FEATURE                Location/Qualifiers
misc_feature           1..21
                       note = Synthetic
source                 1..21
                       mol_type = other DNA
                       organism = synthetic construct
SEQUENCE: 526
atttatagcg gcggtagcac a                                            21
```

```
SEQ ID NO: 527          moltype = DNA  length = 33
FEATURE                 Location/Qualifiers
misc_feature            1..33
                        note = Synthetic
source                  1..33
                        mol_type = other DNA
                        organism = synthetic construct
SEQUENCE: 527
gcgagagacc tctactacta cggtatggac gtc                              33

SEQ ID NO: 528          moltype = AA  length = 11
FEATURE                 Location/Qualifiers
REGION                  1..11
                        note = Synthetic
source                  1..11
                        mol_type = protein
                        organism = synthetic construct
SEQUENCE: 528
ARDLYYYGMD V                                                      11

SEQ ID NO: 529          moltype = DNA  length = 324
FEATURE                 Location/Qualifiers
misc_feature            1..324
                        note = Synthetic
source                  1..324
                        mol_type = other DNA
                        organism = synthetic construct
SEQUENCE: 529
gacatccagt tgacccagtc tccatccttc ctgtctgcat ctgtaggaga cagagtcacc  60
atcacttgcc gggccagtca gggcattagc acttatttag cctggtatca gcaaaaacca  120
gggaaagccc ctaagctcct gatctatgct gcatccactt tgcaaagtgg ggtcccatca  180
aggttcagcg gcagtggatc tgggacagaa ttcactctca caatcagcag cctgcagcct  240
gaagattttg caacttatta ctgtcaacag cttgatagtt accctgggct cactttcggc  300
ggagggacca aggtggagat caaa                                         324

SEQ ID NO: 530          moltype = AA  length = 108
FEATURE                 Location/Qualifiers
REGION                  1..108
                        note = Synthetic
source                  1..108
                        mol_type = protein
                        organism = synthetic construct
SEQUENCE: 530
DIQLTQSPSF LSASVGDRVT ITCRASQGIS TYLAWYQQKP GKAPKLLIYA ASTLQSGVPS  60
RFSGSGSGTE FTLTISSLQP EDFATYYCQQ LDSYPGLTFG GGTKVEIK              108

SEQ ID NO: 531          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 531
cagggcatta gcacttat                                               18

SEQ ID NO: 532          moltype = AA  length = 6
FEATURE                 Location/Qualifiers
REGION                  1..6
                        note = Synthetic
source                  1..6
                        mol_type = protein
                        organism = synthetic construct
SEQUENCE: 532
QGISTY                                                            6

SEQ ID NO: 533          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 533
caacagcttg atagttaccc tgggctcact                                  30

SEQ ID NO: 534          moltype = AA  length = 10
FEATURE                 Location/Qualifiers
```

-continued

```
REGION                  1..10
                        note = Synthetic
source                  1..10
                        mol_type = protein
                        organism = synthetic construct
SEQUENCE: 534
QQLDSYPGLT                                                          10

SEQ ID NO: 535          moltype = DNA  length = 1344
FEATURE                 Location/Qualifiers
misc_feature            1..1344
                        note = Synthetic
source                  1..1344
                        mol_type = other DNA
                        organism = synthetic construct
SEQUENCE: 535
gaggtgcagc tggtggagtc tggaggaggc ttgatccagc ctgggggtc cctgagactc  60
tcctgtgcag cctctggggt caccgtcagt agcaactaca tgagctgggt ccgccaggct  120
ccagggaagg ggctggagtg ggtctcagtc atttatagcg gcggtagcac attctactca  180
gactccgtga agggccgatt cagcatctcc agagacaatt ccaagaacac actgtatctt  240
caaatgaaca gcctgagagc cgaggacacg gccgtgtatt actgtgcgag agacctctac  300
tactacggta tggacgtctg gggccaaggg accacggtca ccgtctcctc agcctccacc  360
aagggcccat cggtcttccc cctggcaccc tcctccaaga gcacctctgg gggcacagcg  420
gccctgggct gcctggtcaa ggactacttc cccgaaccgg tgacggtgtc gtggaactca  480
ggcgccctga ccagcggcgt gcacaccttc ccggctgtcc tacagtcctc aggactctac  540
tccctcagca gcgtggtgac cgtgccctcc agcagcttgg gcacccagac ctacatctgc  600
aacgtgaatc acaagcccag caacaccaag gtggacaaga aagttgagcc caaatcttgt  660
gacaaaactc acacatgccc accgtgccca gcacctgaac tcctgggggg accgtcagtc  720
ttcctcttcc ccccaaaacc caaggacacc ctcatgatct cccggacccc tgaggtcaca  780
tgcgtggtgg tggacgtgag ccacgaagac cctgaggtca agttcaactg gtacgtggac  840
ggcgtggagg tgcataatgc caagacaaag ccgcgggagg agcagtacaa cagcacgtac  900
cgtgtggtca gcgtcctcac cgtcctgcac caggactggc tgaatggcaa ggagtacaag  960
tgcaaggtct ccaacaaagc cctcccagcc cccatcgaga aaaccatctc caaagccaaa  1020
gggcagcccc gagaaccaca ggtgtacacc ctgcccccat cccgggatga gctgaccaag  1080
aaccaggtca gcctgacctg cctggtcaaa ggcttctatc ccagcgacat cgccgtggag  1140
tgggagagca atgggcagcc ggagaacaac tacaagacca cgcctcccgt gctggactcc  1200
gacggctcct tcttcctcta cagcaagctc accgtggaca agagcaggtg gcagcagggg  1260
aacgtcttct catgctccgt gatgcatgag gctctgcaca accactacac gcagaagtcc  1320
ctctccctgt ctccgggtaa atga                                          1344

SEQ ID NO: 536          moltype = AA  length = 447
FEATURE                 Location/Qualifiers
REGION                  1..447
                        note = Synthetic
source                  1..447
                        mol_type = protein
                        organism = synthetic construct
SEQUENCE: 536
EVQLVESGGG LIQPGGSLRL SCAASGVTVS SNYMSWVRQA PGKGLEWVSV IYSGGSTFYS  60
DSVKGRFSIS RDNSKNTLYL QMNSLRAEDT AVYYCARDLY YYGMDVWGQG TTVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APELLGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSRDELTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPGK                                       447

SEQ ID NO: 537          moltype = DNA  length = 648
FEATURE                 Location/Qualifiers
misc_feature            1..648
                        note = Synthetic
source                  1..648
                        mol_type = other DNA
                        organism = synthetic construct
SEQUENCE: 537
gacatccagt tgacccagtc tccatccttc ctgtctgcat ctgtaggaga cagagtcacc  60
atcacttgcc gggccagtca gggcattagc acttatttag cctggtatca gcaaaaacca  120
gggaaagccc ctaagctcct gatctatgct gcatccactt tgcaaagtgg ggtcccatca  180
aggttcagcg gcagtggatc tgggacagaa ttcactctca caatcagcag cctgcagcct  240
gaagattttg caacttatta ctgtcaacag cttgatagtt accctgggct cactttcggc  300
ggagggacca aggtggagat caaacgaact gtggctgcac catctgtctt catcttcccg  360
ccatctgatg agcagttgaa atctggaact gcctctgttg tgtgcctgct gaataacttc  420
tatcccagag aggccaaagt acagtggaag gtggataacg ccctccaatc gggtaactcc  480
caggagagtg tcacagagca ggacagcaag gacagcacct acagcctcag cagcaccctg  540
acgctgagca aagcagacta cgagaaacac aaagtctacg cctgcgaagt cacccatcag  600
ggcctgagct cgcccgtcac aaagagcttc aacaggggag agtgttag               648

SEQ ID NO: 538          moltype = AA  length = 215
FEATURE                 Location/Qualifiers
```

-continued

```
REGION                 1..215
                       note = Synthetic
source                 1..215
                       mol_type = protein
                       organism = synthetic construct
SEQUENCE: 538
DIQLTQSPSF LSASVGDRVT ITCRASQGIS TYLAWYQQKP GKAPKLLIYA ASTLQSGVPS  60
RFSGSGSGTE FTLTISSLQP EDFATYYCQQ LDSYPGLTFG GGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                            215

SEQ ID NO: 539         moltype = DNA  length = 1335
FEATURE                Location/Qualifiers
misc_feature           1..1335
                       note = Synthetic
source                 1..1335
                       mol_type = other DNA
                       organism = synthetic construct
SEQUENCE: 539
caggtgcagc tgcaggagtc gggcccagga ctggtgaagc cttcggagac cctgtccctc  60
acctgcactg tctctggtgg ctccatcaat aattactact ggatctggat ccggcagccc  120
ccagggaagg gactggagtg gattgggtat atctatcaca gtgggagcac caactacaac  180
ccctccctca agagtcgagt caccatatca gtagacacgt ccaagaacca attctccctg  240
aaggtgagct ctgtgaccgc tgcggacacg gccgtgtatt actgtgcgaa tatggttcgg  300
ggagtttatg aagatgacta ctggggccag ggaaccctgg tcaccgtctc ctcagcctcc  360
accaagggcc catcggtctt ccccctggcg ccctgctcca ggagcacctc cgagagcaca  420
gccgccctgg gctgcctggt caaggactac ttccccgaac cggtgacggt gtcgtggaac  480
tcaggcgccc tgaccagcgg cgtgcacacc ttcccggctg tcctacagtc ctcaggactc  540
tactccctca gcagcgtggt gaccgtgccc tccagcagct tgggcacgaa gacctacacc  600
tgcaacgtag atcacaagcc cagcaacacc aaggtggaca agagagttga gtccaaatat  660
ggtcccccat gcccaccgtg cccagcacca ggcggtggcg gaccatcagt cttcctgttc  720
cccccaaaac ccaaggacac tctcatgatc tcccggaccc ctgaggtcac gtgcgtggtg  780
gtggacgtga gccaggaaga ccccgaggtc cagttcaact ggtacgtgga tggcgtggag  840
gtgcataatg ccaagacaaa gccgcgggag gagcagttca acagcacgta ccgtgtggtc  900
agcgtcctca ccgtcctgca ccaggactgg ctgaacggca aggagtacaa gtgcaaggtc  960
tccaacaaag gcctcccgtc ctccatcgag aaaaccatct ccaaagccaa agggcagccc  1020
cgagagccac aggtgtacac cctgcccccca tcccaggagg agatgaccaa gaaccaggtc  1080
agcctgacct gcctggtcaa aggcttctac cccagcgaca tcgccgtgga gtgggagagc  1140
aatgggcagc cggagaacaa ctacaagacc acgcctcccg tgctggactc cgacggctcc  1200
ttcttcctct acagcaggct caccgtggac aagagcaggt ggcaggaggg gaatgtcttc  1260
tcatgctccg tgatgcatga ggctctgcac aaccactaca cacagaagtc cctctccctg  1320
tctctgggta aatga                                                  1335

SEQ ID NO: 540         moltype = AA  length = 444
FEATURE                Location/Qualifiers
REGION                 1..444
                       note = Synthetic
source                 1..444
                       mol_type = protein
                       organism = synthetic construct
SEQUENCE: 540
QVQLQESGPG LVKPSETLSL TCTVSGGSIN NYYWIWIRQP PGKGLEWIGY IYHSGSTNYN  60
PSLKSRVTIS VDTSKNQFSL KVSSVTAADT AVYYCANMVR GVYEDDYWGQ GTLVTVSSAS  120
TKGPSVFPLA PCSRSTSEST AALGCLVKDY FPEPVTVSWN SGALTSGVHT FPAVLQSSGL  180
YSLSSVVTVP SSSLGTKTYT CNVDHKPSNT KVDKRVESKY GPPCPPCPAP GGGGPSVFLF  240
PPKPKDTLMI SRTPEVTCVV VDVSQEDPEV QFNWYVDGVE VHNAKTKPRE EQFNSTYRVV  300
SVLTVLHQDW LNGKEYKCKV SNKGLPSSIE KTISKAKGQP REPQVYTLPP SQEEMTKNQV  360
SLTCLVKGFY PSDIAVEWES NGQPENNYKT TPPVLDSDGS FFLYSRLTVD KSRWQEGNVF  420
SCSVMHEALH NHYTQKSLSL SLGK                                        444

SEQ ID NO: 541         moltype = DNA  length = 1347
FEATURE                Location/Qualifiers
misc_feature           1..1347
                       note = Synthetic
source                 1..1347
                       mol_type = other DNA
                       organism = synthetic construct
SEQUENCE: 541
gaggtgcagc tggtggagtc tggaggaggc ttgatccagc ctgggggggtc cctgagactc  60
tcctgtgcag cctctgtgtt caccgtcagt tacaactaca tgagctgggt ccgccaggct  120
ccagggaagg ggctggagtg ggtctcagtt atttatagcg gtggtagcac atactacgca  180
gactccgtga agggccgatt caccatctcc agagacaatt ccaagaacac gctgtatctt  240
caaatgaaca gcctgagagc cgaggacacg gccgtgtatt actgtgcgag agccctcccc  300
gggtggggtg ggagcttcga gtactttgac tactggggcc agggaaccct ggtcaccgtc  360
tcctcagcct ccaccaaggg cccatcggtc ttccccctgg cgccctgctc caggagcacc  420
tccgagagca cagccgccct gggctgcctg gtcaaggact acttccccga accggtgacg  480
gtgtcgtgga actcaggcgc cctgaccagc ggcgtgcaca ccttcccggc tgtcctacag  540
tcctcaggac tctactccct cagcagcgtg gtgaccgtgc cctccagcag cttgggcacg  600
aagacctaca cctgcaacgt agatcacaag cccagcaaca ccaaggtgga caagagagtt  660
```

-continued

```
gagtccaaat atggtccccc atgcccaccg tgcccagcac caggcggtgg cggaccatca  720
gtcttcctgt tccccccaaa acccaaggac actctcatga tctcccggac ccctgaggtc  780
acgtgcgtgg tggtggacgt gagccaggaa gaccccgagg tccagttcaa ctggtacgtg  840
gatggcgtgg aggtgcataa tgccaagaca aagccgcggg aggagcagtt caacagcacg  900
taccgtgtgg tcagcgtcct caccgtcctg caccaggact ggctgaacgg caaggagtac  960
aagtgcaagg tctccaacaa aggcctcccg tcctccatcg agaaaaccat ctccaaagcc  1020
aaagggcagc cccgagagcc acaggtgtac accctgcccc catcccagga ggagatgacc  1080
aagaaccagg tcagcctgac ctgcctggtc aaaggcttct accccagcga catcgccgtg  1140
gagtgggaga gcaatgggca gccggagaac aactacaaga ccacgcctcc cgtgctggac  1200
tccgacggct ccttcttcct ctacagcagg ctcaccgtgg acaagagcag gtggcaggag  1260
gggaatgtct tctcatgctc cgtgatgcat gaggctctgc acaaccacta cacacagaag  1320
tccctctccc tgtctctggg taaatga                                     1347

SEQ ID NO: 542         moltype = AA  length = 448
FEATURE                Location/Qualifiers
REGION                 1..448
                       note = Synthetic
source                 1..448
                       mol_type = protein
                       organism = synthetic construct
SEQUENCE: 542
EVQLVESGGG LIQPGGSLRL SCAASVFTVS YNYMSWVRQA PGKGLEWVSV IYSGGSTYYA  60
DSVKGRFTIS RDNSKNTLYL QMNSLRAEDT AVYYCARALP GWGGSFEYFD YWGQGTLVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPGGGGPS  240
VFLFPPKPKD TLMISRTPEV TCVVVDVSQE DPEVQFNWYV DGVEVHNAKT KPREEQFNST  300
YRVVSVLTVL HQDWLNGKEY KCKVSNKGLP SSIEKTISKA KGQPREPQVY TLPPSQEEMT  360
KNQVSLTCLV KGFYPSDIAV EWESNGQPEN NYKTTPPVLD SDGSFFLYSR LTVDKSRWQE  420
GNVFSCSVMH EALHNHYTQK SLSLSLGK                                    448

SEQ ID NO: 543         moltype = DNA  length = 1344
FEATURE                Location/Qualifiers
misc_feature           1..1344
                       note = Synthetic
source                 1..1344
                       mol_type = other DNA
                       organism = synthetic construct
SEQUENCE: 543
gaggtgcagc tggtggagtc tgggggaggc ttggtccagc ctggggggtc cctgagactc  60
tcctgtgcag cctctggact caccgtcagt agcaactaca tgagctgggt ccgccaggct  120
ccagggaagg ggctggagtg ggtctcagtt atttatagcg gtggtagtac attctacgca  180
gactccgtga agggccgatt caccatctcc agagacaatt ccaagaacac gttgtatctt  240
cagatgaaca gcctgagacc tgaggacacg gctgtgtatt actgtgcgag agagggccgt  300
atagcagcaa ctggctacgg tatggacgtc tggggccaag ggaccacggt caccgtctcc  360
tcagcctcca ccaagggccc atcggtcttc cccctggcgc cctgctccag gagcacctcc  420
gagagcacag ccgccctggg ctgcctggtc aaggactact tccccgaacc ggtgacggtg  480
tcgtggaact caggcgccct gaccagcggc gtgcacacct tcccggctgt cctacagtcc  540
tcaggactct actccctcag cagcgtggtg accgtgccct ccagcagctt gggcacgaag  600
acctacacct gcaacgtaga tcacaagccc agcaacacca aggtggacaa gagagttgag  660
tccaaatatg gtcccccatg cccaccgtgc ccagcaccag gcggtggcgg accatcagtc  720
ttcctgttcc ccccaaaacc caaggacact ctcatgatct cccggacccc tgaggtcacg  780
tgcgtggtgg tggacgtgag ccaggaagac cccgaggtcc agttcaactg gtacgtggat  840
ggcgtggagg tgcataatgc caagacaaag ccgcgggagg agcagttcaa cagcacgtac  900
cgtgtggtca gcgtcctcac cgtcctgcac caggactggc tgaacggcaa ggagtacaag  960
tgcaaggtct ccaacaaagg cctcccgtcc tccatcgaga aaaccatctc caaagccaaa  1020
gggcagcccc gagagccaca ggtgtacacc ctgcccccat cccaggagga gatgaccaag  1080
aaccaggtca gcctgacctg cctggtcaaa ggcttctacc ccagcgacat cgccgtggag  1140
tgggagagca atgggcagcc ggagaacaac tacaagacca cgcctcccgt gctggactcc  1200
gacggctcct tcttcctcta cagcaggctc accgtggaca agagcaggtg gcaggagggg  1260
aatgtcttct catgctccgt gatgcatgag gctctgcaca accactacac acagaagtcc  1320
ctctccctgt ctctgggtaa atga                                        1344

SEQ ID NO: 544         moltype = AA  length = 447
FEATURE                Location/Qualifiers
REGION                 1..447
                       note = Synthetic
source                 1..447
                       mol_type = protein
                       organism = synthetic construct
SEQUENCE: 544
EVQLVESGGG LVQPGGSLRL SCAASGLTVS SNYMSWVRQA PGKGLEWVSV IYSGGSTFYA  60
DSVKGRFTIS RDNSKNTLYL QMNSLRPEDT AVYYCAREGR IAATGYGMDV WGQGTTVTVS  120
SASTKGPSVF PLAPCSRSTS ESTAALGCLV KDYFPEPVTV SWNSGALTSG VHTFPAVLQS  180
SGLYSLSSVV TVPSSSLGTK TYTCNVDHKP SNTKVDKRVE SKYGPPCPPC PAPGGGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGK                                     447
```

```
SEQ ID NO: 545         moltype = DNA  length = 1323
FEATURE                Location/Qualifiers
misc_feature           1..1323
                       note = Synthetic
source                 1..1323
                       mol_type = other DNA
                       organism = synthetic construct
SEQUENCE: 545
gaggtgcagc tggtggagtc tggggggaggc ttggtccagc ctggggggtc cctgagactc  60
tcctgtgcag cctctggatt caccgtcagt agcaactaca tgagctgggt ccgccaggct  120
ccagggaagg ggctggagtg ggtctcagtt atttatcccg gtggtagtac attctacgca  180
gactccgtga agggcagatt caccatctcc agagacaatt ccaagaacac gctgtatctt  240
caaatgaaca gcctgagagc cgaggacacg gctgtgtatt actgtgcgag agatcaacgc  300
gattttgcct ggggccaggg aaccctggtc accgtctcct cagcctccac caagggccca  360
tcggtcttcc ccctggcgcc ctgctccagg agcacctccg agagcacagc cgccctgggc  420
tgcctggtca aggactactt ccccgaaccg gtgacggtgt cgtggaactc aggcgccctg  480
accagcggcg tgcacacctt cccggctgtc ctacagtcct caggactcta ctccctcagc  540
agcgtggtga ccgtgccctc cagcagcttg ggcacgaaga cctacacctg caacgtagat  600
cacaagccca gcaacaccaa ggtggacaag agagttgagt ccaaatatgg tcccccatgc  660
ccaccgtgcc cagcaccagg cggtggcgga ccatcagtct tcctgttccc cccaaaaccc  720
aaggacactc tcatgatctc ccggaccccct gaggtcacgt gcgtggtggt ggacgtgagc  780
caggaagacc ccgaggtcca gttcaactgg tacgtggatg gcgtggaggt gcataatgcc  840
aagacaaagc cgcgggagga gcagttcaac agcacgtacc gtgtggtcag cgtcctcacc  900
gtcctgcacc aggactggct gaacggcaag gagtacaagt gcaaggtctc caacaaaggc  960
ctcccgtcct ccatcgagaa aaccatctcc aaagccaaag ggcagccccg agagccacag  1020
gtgtacaccc tgcccccatc ccaggaggag atgaccaaga accaggtcag cctgacctgc  1080
ctggtcaaag gcttctaccc cagcgacatc gccgtggagt gggagagcaa tgggcagccg  1140
gagaacaact acaagaccac gcctcccgtg ctggactccg acggctcctt cttcctctac  1200
agcaggctca ccgtggacaa gagcaggtgg caggaggggga atgtcttctc atgctccgtg  1260
atgcatgagg ctctgcacaa ccactacaca cagaagtccc tctccctgtc tctgggtaaa  1320
tga                                                                 1323

SEQ ID NO: 546         moltype = AA  length = 440
FEATURE                Location/Qualifiers
REGION                 1..440
                       note = Synthetic
source                 1..440
                       mol_type = protein
                       organism = synthetic construct
SEQUENCE: 546
EVQLVESGGG LVQPGGSLRL SCAASGFTVS SNYMSWVRQA PGKGLEWVSV IYPGGSTFYA  60
DSVKGRFTIS RDNSKNTLYL QMNSLRAEDT AVYYCARDQR DFAWGQGTLV TVSSASTKGP  120
SVFPLAPCSR STSESTAALG CLVKDYFPEP VTVSWNSGAL TSGVHTFPAV LQSSGLYSLS  180
SVVTVPSSSL GTKTYTCNVD HKPSNTKVDK RVESKYGPPC PPCPAPGGGG PSVFLFPPKP  240
KDTLMISRTP EVTCVVVDVS QEDPEVQFNW YVDGVEVHNA KTKPREEQFN STYRVVSVLT  300
VLHQDWLNGK EYKCKVSNKG LPSSIEKTIS KAKGQPREPQ VYTLPPSQEE MTKNQVSLTC  360
LVKGFYPSDI AVEWESNGQP ENNYKTTPPV LDSDGSFFLY SRLTVDKSRW QEGNVFSCSV  420
MHEALHNHYT QKSLSLSLGK                                                440

SEQ ID NO: 547         moltype = DNA  length = 369
FEATURE                Location/Qualifiers
misc_feature           1..369
                       note = Synthetic
source                 1..369
                       mol_type = other DNA
                       organism = synthetic construct
SEQUENCE: 547
caggtgcagc tggtgcagtc tggggctgag gtgaagaagc ctgggtcctc ggtgaaggtc  60
tcctgcaagg cttctggagg caccttcagc agctatgcta tcacctgggt gcgacaggcc  120
cctggacaag ggcttgagtg gatgggaagg atcatcccta tgtttggtat agcaaactac  180
gcacagaagt tccagggcag agtcacgatt accgcggaca aatccacgag cacagcctac  240
atggaggtga gcagcctgag atctgaggac acggccgtgt attactgtgc gagaacaccg  300
ttttactatg atagtagtgg ttattacctt gactactggg gccagggaac cctggtcacc  360
gtctcctca                                                           369

SEQ ID NO: 548         moltype = AA  length = 123
FEATURE                Location/Qualifiers
REGION                 1..123
                       note = Synthetic
source                 1..123
                       mol_type = protein
                       organism = synthetic construct
SEQUENCE: 548
QVQLVQSGAE VKKPGSSVKV SCKASGGTFS SYAITWVRQA PGQGLEWMGR IIPMFGIANY  60
AQKFQGRVTI TADKSTSTAY MEVSSLRSED TAVYYCARTP FYYDSSGYYL DYWGQGTLVT  120
VSS                                                                  123

SEQ ID NO: 549         moltype = DNA  length = 24
FEATURE                Location/Qualifiers
```

```
misc_feature          1..24
                      note = Synthetic
source                1..24
                      mol_type = other DNA
                      organism = synthetic construct
SEQUENCE: 549
ggaggcacct tcagcagcta tgct                                          24

SEQ ID NO: 550        moltype = AA  length = 8
FEATURE               Location/Qualifiers
REGION                1..8
                      note = Synthetic
source                1..8
                      mol_type = protein
                      organism = synthetic construct
SEQUENCE: 550
GGTFSSYA                                                            8

SEQ ID NO: 551        moltype = DNA  length = 24
FEATURE               Location/Qualifiers
misc_feature          1..24
                      note = Synthetic
source                1..24
                      mol_type = other DNA
                      organism = synthetic construct
SEQUENCE: 551
atcatcccta tgtttggtat agca                                          24

SEQ ID NO: 552        moltype = AA  length = 8
FEATURE               Location/Qualifiers
REGION                1..8
                      note = Synthetic
source                1..8
                      mol_type = protein
                      organism = synthetic construct
SEQUENCE: 552
IIPMFGIA                                                            8

SEQ ID NO: 553        moltype = DNA  length = 48
FEATURE               Location/Qualifiers
misc_feature          1..48
                      note = Synthetic
source                1..48
                      mol_type = other DNA
                      organism = synthetic construct
SEQUENCE: 553
gcgagaacac cgttttacta tgatagtagt ggttattacc ttgactac                48

SEQ ID NO: 554        moltype = AA  length = 16
FEATURE               Location/Qualifiers
REGION                1..16
                      note = Synthetic
source                1..16
                      mol_type = protein
                      organism = synthetic construct
SEQUENCE: 554
ARTPFYYDSS GYYLDY                                                   16

SEQ ID NO: 555        moltype = DNA  length = 324
FEATURE               Location/Qualifiers
misc_feature          1..324
                      note = Synthetic
source                1..324
                      mol_type = other DNA
                      organism = synthetic construct
SEQUENCE: 555
gaaattgtgt tgacgcagtc tccaggcacc ctgtctttgt ctccagggga aagagccacc  60
ctctcttgca gggccagtca gagtgttagc agcaactact tagcctggta ccagcagagt  120
cctggccagg ctcccaggct cctcatctat ggtgcatcca gcagggccac tggcatccca  180
gacaggttca gtggcagtgg gtctgggaca gacttcactc tcaccatcag cagactggag  240
cctgaagatt ttgcagttta ttactgtcag cagtatgtta ggtcaccccg gacgttcggc  300
caagggacca aggtggaaat caaa                                          324

SEQ ID NO: 556        moltype = AA  length = 108
FEATURE               Location/Qualifiers
REGION                1..108
                      note = Synthetic
source                1..108
                      mol_type = protein
```

```
                        organism = synthetic construct
SEQUENCE: 556
EIVLTQSPGT LSLSPGERAT LSCRASQSVS SNYLAWYQQS PGQAPRLLIY GASSRATGIP  60
DRFSGSGSGT DFTLTISRLE PEDFAVYYCQ QYVRSPRTFG QGTKVEIK              108

SEQ ID NO: 557          moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 557
cagagtgtta gcagcaacta c                                           21

SEQ ID NO: 558          moltype = AA  length = 7
FEATURE                 Location/Qualifiers
REGION                  1..7
                        note = Synthetic
source                  1..7
                        mol_type = protein
                        organism = synthetic construct
SEQUENCE: 558
QSVSSNY                                                           7

SEQ ID NO: 559          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 559
cagcagtatg ttaggtcacc ccggacg                                     27

SEQ ID NO: 560          moltype = AA  length = 9
FEATURE                 Location/Qualifiers
REGION                  1..9
                        note = Synthetic
source                  1..9
                        mol_type = protein
                        organism = synthetic construct
SEQUENCE: 560
QQYVRSPRT                                                         9

SEQ ID NO: 561          moltype = DNA  length = 1362
FEATURE                 Location/Qualifiers
misc_feature            1..1362
                        note = Synthetic
source                  1..1362
                        mol_type = other DNA
                        organism = synthetic construct
SEQUENCE: 561
caggtgcagc tggtgcagtc tggggctgag gtgaagaagc ctgggtcctc ggtgaaggtc  60
tcctgcaagg cttctggagg caccttcagc agctatgcta tcacctgggt gcgacaggcc  120
cctggacaag ggcttgagtg gatgggaagg atcatcccta tgtttggtat agcaaactac  180
gcacagaagt tccagggcag agtcacgatt accgcggaca aatccacgag cacagcctac  240
atggaggtga gcagcctgag atctgaggac acggccgtgt attactgtgc gagaacaccg  300
ttttactatg atagtagtgg ttattacctt gactactggg gccagggaac cctggtcacc  360
gtctcctcag cctccaccaa gggcccatcg gtcttccccc tggcaccctc ctccaagagc  420
acctctgggg gcacagcggc cctgggctgc ctggtcaagg actacttccc cgaaccggtg  480
acggtgtcgt ggaactcagg cgccctgacc agcggcgtgc acaccttccc ggctgtccta  540
cagtcctcag gactctactc cctcagcagc gtggtgaccg tgccctccag cagcttgggc  600
acccagacct acatctgcaa cgtgaatcac aagcccagca acaccaaggt ggacaagaaa  660
gttgagccca aatcttgtga caaaactcac acatgcccac cgtgcccagc acctgaactc  720
ctggggggac cgtcagtctt cctcttcccc ccaaaaccca aggacaccct catgatctcc  780
cggacccctg aggtcacatg cgtggtggtg gacgtgagcc acgaagaccc tgaggtcaag  840
ttcaactggt acgtggacgg cgtggaggtg cataatgcca agacaaagcc gcgggaggag  900
cagtacaaca gcacgtaccg tgtggtcagc gtcctcaccg tcctgcacca ggactggctg  960
aatggcaagg agtacaagtg caaggtctcc aacaaagccc tcccagcccc catcgagaaa  1020
accatctcca aagccaaagg gcagccccga gaaccacagg tgtacaccct gcccccatcc  1080
cgggatgagc tgaccaagaa ccaggtcagc ctgacctgcc tggtcaaagg cttctatccc  1140
agcgacatcg ccgtggagtg ggagagcaat gggcagccgg agaacaacta caagaccacg  1200
cctcccgtgc tggactccga cggctccttc ttcctctaca gcaagctcac cgtggacaag  1260
agcaggtggc agcaggggaa cgtcttctca tgctccgtga tgcatgaggc tctgcacaac  1320
cactacacgc agaagtccct ctccctgtct ccgggtaaat ga                    1362

SEQ ID NO: 562          moltype = AA  length = 453
FEATURE                 Location/Qualifiers
```

```
REGION                  1..453
                        note = Synthetic
source                  1..453
                        mol_type = protein
                        organism = synthetic construct
SEQUENCE: 562
QVQLVQSGAE VKKPGSSVKV SCKASGGTFS SYAITWVRQA PGQGLEWMGR IIPMFGIANY  60
AQKFQGRVTI TADKSTSTAY MEVSSLRSED TAVYYCARTP FYYDSSGYYL DYWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
LGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                              453

SEQ ID NO: 563          moltype = DNA  length = 648
FEATURE                 Location/Qualifiers
misc_feature            1..648
                        note = Synthetic
source                  1..648
                        mol_type = other DNA
                        organism = synthetic construct
SEQUENCE: 563
gaaattgtgt tgacgcagtc tccaggcacc ctgtctttgt ctccagggga aagagccacc  60
ctctcttgca gggccagtca gagtgttagc agcaactact tagcctggta ccagcagagt  120
cctggccagg ctcccaggct cctcatctat ggtgcatcca gcagggccac tggcatccca  180
gacaggttca gtggcagtgg gtctgggaca gacttcactc tcaccatcag cagactggag  240
cctgaagatt ttgcagttta ttactgtcag cagtatgtta ggtcaccccg gacgttcggc  300
caagggacca aggtggaaat caaacgaact gtggctgcac catctgtctt catcttcccg  360
ccatctgatg agcagttgaa atctggaact gcctctgttg tgtgcctgct gaataacttc  420
tatcccagag aggccaaagt acagtggaag gtggataacg ccctccaatc gggtaactcc  480
caggagagtg tcacagagca ggacagcaag gacagcacct acagcctcag cagcaccctg  540
acgctgagca aagcagacta cgagaaacac aaagtctacg cctgcgaagt cacccatcag  600
ggcctgagct cgcccgtcac aaagagcttc aacaggggag agtgttag              648

SEQ ID NO: 564          moltype = AA  length = 215
FEATURE                 Location/Qualifiers
REGION                  1..215
                        note = Synthetic
source                  1..215
                        mol_type = protein
                        organism = synthetic construct
SEQUENCE: 564
EIVLTQSPGT LSLSPGERAT LSCRASQSVS SNYLAWYQQS PGQAPRLLIY GASSRATGIP  60
DRFSGSGSGT DFTLTISRLE PEDFAVYYCQ QYVRSPRTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                            215

SEQ ID NO: 565          moltype = DNA  length = 1362
FEATURE                 Location/Qualifiers
misc_feature            1..1362
                        note = Synthetic
source                  1..1362
                        mol_type = other DNA
                        organism = synthetic construct
SEQUENCE: 565
caggtgcagc tggtggagtc tgggggaggc gtggtccagc ctgggaggtc cctgagactc  60
tcctgtgcag cctctggatt caccttcagt agctatgcta tgcactgggt ccgccaggct  120
ccaggcaagg ggctggagtg ggtggcagtt atatcatatg atggaagtaa taaatactac  180
gcagactccg tgaagggccg attcaccatc tccagagaca attccaagaa cacgctgtat  240
ctgcaaatga acagcctgag agctgaggac acggctgtgt attactgtgc gagagacggc  300
cggactatta ctatggttcg gggagttatt gatgatgctt ttgatatctg gggccaaggg  360
acaatggtca ccgtctcttc agcctccacc aagggcccat cggtcttccc cctggcgccc  420
tgctccagga gcacctccga gagcacagcc gccctgggct gcctggtcaa ggactacttc  480
cccgaaccgg tgacggtgtc gtggaactca ggcgccctga ccagcggcgt gcacaccttc  540
ccggctgtcc tacagtcctc aggactctac tccctcagca gcgtggtgac cgtgccctcc  600
agcagcttgg gcacgaagac ctacacctgc aacgtagatc acaagcccag caacaccaag  660
gtggacaaga gagttgagtc caaatatggt cccccatgcc caccgtgccc agcaccaggc  720
ggtggcggac catcagtctt cctgttcccc ccaaaaccca aggacactct catgatctcc  780
cggacccctg aggtcacgtg cgtggtggtg gacgtgagcc aggaagaccc cgaggtccag  840
ttcaactggt acgtggatgg cgtggaggtg cataatgcca agacaaagcc gcgggaggag  900
cagttcaaca gcacgtaccg tgtggtcagc gtcctcaccg tcctgcacca ggactggctg  960
aacggcaagg agtacaagtg caaggtctcc aacaaaggcc tcccgtcctc catcgagaaa  1020
accatctcca aagccaaagg gcagccccga gagccacagg tgtacaccct gcccccatcc  1080
caggaggaga tgaccaagaa ccaggtcagc ctgacctgcc tggtcaaagg cttctacccc  1140
agcgacatcg ccgtggagtg ggagagcaat gggcagccgg agaacaacta caagaccacg  1200
cctcccgtgc tggactccga cggctccttc ttcctctaca gcaggctcac cgtggacaag  1260
agcaggtggc aggaggggaa tgtcttctca tgctccgtga tgcatgaggc tctgcacaac  1320
cactacacac agaagtccct ctccctgtct ctgggtaaat ga                    1362
```

```
SEQ ID NO: 566         moltype = AA  length = 453
FEATURE                Location/Qualifiers
REGION                 1..453
                       note = Synthetic
source                 1..453
                       mol_type = protein
                       organism = synthetic construct
SEQUENCE: 566
QVQLVESGGG VVQPGRSLRL SCAASGFTFS SYAMHWVRQA PGKGLEWVAV ISYDGSNKYY  60
ADSVKGRFTI SRDNSKNTLY LQMNSLRAED TAVYYCARDG RTITMVRGVI DDAFDIWGQG  120
TMVTVSSAST KGPSVFPLAP CSRSTSESTA ALGCLVKDYF PEPVTVSWNS GALTSGVHTF  180
PAVLQSSGLY SLSSVVTVPS SSLGTKTYTC NVDHKPSNTK VDKRVESKYG PPCPPCPAPG  240
GGGPSVFLFP PKPKDTLMIS RTPEVTCVVV DVSQEDPEVQ FNWYVDGVEV HNAKTKPREE  300
QFNSTYRVVS VLTVLHQDWL NGKEYKCKVS NKGLPSSIEK TISKAKGQPR EPQVYTLPPS  360
QEEMTKNQVS LTCLVKGFYP SDIAVEWESN GQPENNYKTT PPVLDSDGSF FLYSRLTVDK  420
SRWQEGNVFS CSVMHEALHN HYTQKSLSLS LGK                                453

SEQ ID NO: 567         moltype = DNA  length = 1341
FEATURE                Location/Qualifiers
misc_feature           1..1341
                       note = Synthetic
source                 1..1341
                       mol_type = other DNA
                       organism = synthetic construct
SEQUENCE: 567
gaggtgcagc tggtggagtc tgggggaggc ttggtccagc ctggggggtc cctgagactc  60
tcctgtgcag cctctggatt caccgtcagt agcaactaca tgagctgggt ccgccaggct  120
ccagggaagg ggctggagtg ggtctcagtt atttatagcg gtggtagtac atactacgca  180
gactccgtga agggccgatt caccatctcc agagacaatt ccaagaacac gctgtatctt  240
caaatgaaca gactgagagc tgacgacacg gctgtctatt actgtgtgag agatccggtg  300
gggcgctact actacggtat ggacgtctgg ggccaaggga ccacggtcac cgtctcctca  360
gcctccacca agggcccatc ggtcttcccc ctggcgccct gctccaggag cacctccgag  420
agcacagccg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacgaagacc  600
tacacctgca acgtagatca caagcccagc aacaccaagg tggacaagag agttgagtcc  660
aaatatggtc ccccatgccc accgtgccca gcaccaggcg gtggcggacc atcagtcttc  720
ctgttccccc caaaacccaa ggacactctc atgatctccc ggacccctga ggtcacgtgc  780
gtggtggtgg acgtgagcca ggaagacccc gaggtccagt tcaactggta cgtggatggc  840
gtggaggtgc ataatgccaa gacaaagccg cgggaggagc agttcaacag cacgtaccgt  900
gtggtcagcg tcctcaccgt cctgcaccag gactggctga acggcaagga gtacaagtgc  960
aaggtctcca acaaaggcct cccgtcctcc atcgagaaaa ccatctccaa agccaaaggg  1020
cagccccgag agccacaggt gtacaccctg cccccatccc aggaggagat gaccaagaac  1080
caggtcagcc tgacctgcct ggtcaaaggc ttctacccca gcgacatcgc cgtggagtgg  1140
gagagcaatg ggcagccgga gaacaactac aagaccacgc ctcccgtgct ggactccgac  1200
ggctccttct tcctctacag caggctcacc gtggacaaga gcaggtggca ggaggggaat  1260
gtcttctcat gctccgtgat gcatgaggct ctgcacaacc actacacaca gaagtccctc  1320
tccctgtctc tgggtaaatg a                                             1341

SEQ ID NO: 568         moltype = AA  length = 446
FEATURE                Location/Qualifiers
REGION                 1..446
                       note = Synthetic
source                 1..446
                       mol_type = protein
                       organism = synthetic construct
SEQUENCE: 568
EVQLVESGGG LVQPGGSLRL SCAASGFTVS SNYMSWVRQA PGKGLEWVSV IYSGGSTYYA  60
DSVKGRFTIS RDNSKNTLYL QMNRLRADDT AVYYCVRDPV GRYYYGMDVW GQGTTVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APGGGGPSVF  240
LFPPKPKDTL MISRTPEVTC VVVDVSQEDP EVQFNWYVDG VEVHNAKTKP REEQFNSTYR  300
VVSVLTVLHQ DWLNGKEYKC KVSNKGLPSS IEKTISKAKG QPREPQVYTL PPSQEEMTKN  360
QVSLTCLVKG FYPSDIAVEW ESNGQPENNY KTTPPVLDSD GSFFLYSRLT VDKSRWQEGN  420
VFSCSVMHEA LHNHYTQKSL SLSLGK                                        446

SEQ ID NO: 569         moltype = DNA  length = 1332
FEATURE                Location/Qualifiers
misc_feature           1..1332
                       note = Synthetic
source                 1..1332
                       mol_type = other DNA
                       organism = synthetic construct
SEQUENCE: 569
gaggtgcagc tggtggagtc tggaggaggc ttgatccagc ctggggggtc cctgagactc  60
tcctgtgcag cctctggggt caccgtcagt agcaactaca tgagctgggt ccgccaggct  120
ccagggaagg ggctggagtg ggtctcagtc atttatagcg gcggtagcac attctactca  180
gactccgtga agggccgatt cagcatctcc agagacaatt ccaagaacac actgtatctt  240
```

```
caaatgaaca gcctgagagc cgaggacacg gccgtgtatt actgtgcgag agacctctac  300
tactacggta tggacgtctg gggccaaggg accacggtca ccgtctcctc agcctccacc  360
aagggcccat cggtcttccc cctggcgccc tgctccagga gcacctccga gagcacagcc  420
gccctgggct gcctggtcaa ggactacttc cccgaaccgg tgacggtgtc gtggaactca  480
ggcgccctga ccagcggcgt gcacaccttc ccggctgtcc tacagtcctc aggactctac  540
tccctcagca gcgtggtgac cgtgccctcc agcagcttgg gcacgaagac ctacacctgc  600
aacgtagatc acaagcccag caacaccaag gtggacaaga gagttgagtc caaatatggt  660
cccccatgcc caccgtgccc agcaccaggc ggtggcggac catcagtctt cctgttcccc  720
ccaaaaccca aggacactct catgatctcc cggacccctg aggtcacgtg cgtggtggtg  780
gacgtgagcc aggaagaccc cgaggtccag ttcaactggt acgtggatgg cgtggaggtg  840
cataatgcca agacaaagcc gcgggaggag cagttcaaca gcacgtaccg tgtggtcagc  900
gtcctcaccg tcctgcacca ggactggctg aacggcaagg agtacaagtg caaggtctcc  960
aacaaaggcc tcccgtcctc catcgagaaa accatctcca aagccaaagg gcagccccga  1020
gagccacagg tgtacaccct gcccccatcc caggaggaga tgaccaagaa ccaggtcagc  1080
ctgacctgcc tggtcaaagg cttctacccc agcgacatcg ccgtggagtg ggagagcaat  1140
gggcagccgg agaacaacta caagaccacg cctcccgtgc tggactccga cggctccttc  1200
ttcctctaca gcaggctcac cgtggacaag agcaggtggc aggaggggaa tgtcttctca  1260
tgctccgtga tgcatgaggc tctgcacaac cactacacac agaagtccct ctccctgtct  1320
ctgggtaaat ga                                                        1332

SEQ ID NO: 570          moltype = AA  length = 443
FEATURE                 Location/Qualifiers
REGION                  1..443
                        note = Synthetic
source                  1..443
                        mol_type = protein
                        organism = synthetic construct
SEQUENCE: 570
EVQLVESGGG LIQPGGSLRL SCAASGVTVS SNYMSWVRQA PGKGLEWVSV IYSGGSTFYS  60
DSVKGRFSIS RDNSKNTLYL QMNSLRAEDT AVYYCARDLY YYGMDVWGQG TTVTVSSAST  120
KGPSVFPLAP CSRSTSESTA ALGCLVKDYF PEPVTVSWNS GALTSGVHTF PAVLQSSGLY  180
SLSSVVTVPS SSLGTKTYTC NVDHKPSNTK VDKRVESKYG PPCPPCPAPG GGGPSVFLFP  240
PKPKDTLMIS RTPEVTCVVV DVSQEDPEVQ FNWYVDGVEV HNAKTKPREE QFNSTYRVVS  300
VLTVLHQDWL NGKEYKCKVS NKGLPSSIEK TISKAKGQPR EPQVYTLPPS QEEMTKNQVS  360
LTCLVKGFYP SDIAVEWESN GQPENNYKTT PPVLDSDGSF FLYSRLTVDK SRWQEGNVFS  420
CSVMHEALHN HYTQKSLSLS LGK                                            443

SEQ ID NO: 571          moltype = DNA  length = 1350
FEATURE                 Location/Qualifiers
misc_feature            1..1350
                        note = Synthetic
source                  1..1350
                        mol_type = other DNA
                        organism = synthetic construct
SEQUENCE: 571
caggtgcagc tggtgcagtc tggggctgag gtgaagaagc ctgggtcctc ggtgaaggtc  60
tcctgcaagg cttctggagg caccttcagc agctatgcta tcacctgggt gcgacaggcc  120
cctggacaag ggcttgagtg gatgggaagg atcatcccta tgtttggtat agcaaactac  180
gcacagaagt tccagggcag agtcacgatt accgcggaca aatccacgag cacagcctac  240
atggaggtga gcagcctgag atctgaggac acggccgtgt attactgtgc gagaacaccg  300
ttttactatg atagtagtgg ttattacctt gactactggg gccagggaac cctggtcacc  360
gtctcctcag cctccaccaa gggcccatcg gtcttccccc tggcgccctg ctccaggagc  420
acctccgaga gcacagccgc cctgggctgc ctggtcaagg actacttccc cgaaccggtg  480
acggtgtcgt ggaactcagg cgccctgacc agcggcgtgc acaccttccc ggctgtccta  540
cagtcctcag gactctactc cctcagcagc gtggtgaccg tgccctccag cagcttgggc  600
acgaagacct acacctgcaa cgtagatcac aagcccagca acaccaaggt ggacaagaga  660
gttgagtcca aatatggtcc cccatgccca ccgtgcccag caccaggcgg tggcggacca  720
tcagtcttcc tgttcccccc aaaacccaag gacactctca tgatctcccg gacccctgag  780
gtcacgtgcg tggtggtgga cgtgagccag gaagaccccg aggtccagtt caactggtac  840
gtggatggcg tggaggtgca taatgccaag acaaagccgc gggaggagca gttcaacagc  900
acgtaccgtg tggtcagcgt cctcaccgtc ctgcaccagg actggctgaa cggcaaggag  960
tacaagtgca aggtctccaa caaaggcctc ccgtcctcca tcgagaaaac catctccaaa  1020
gccaaagggc agccccgaga gccacaggtg tacaccctgc ccccatccca ggaggagatg  1080
accaagaacc aggtcagcct gacctgcctg gtcaaaggct tctaccccag cgacatcgcc  1140
gtggagtggg agagcaatgg gcagccggag aacaactaca agaccacgcc tcccgtgctg  1200
gactccgacg gctccttctt cctctacagc aggctcaccg tggacaagag caggtggcag  1260
gaggggaatg tcttctcatg ctccgtgatg catgaggctc tgcacaacca ctacacacag  1320
aagtccctct ccctgtctct gggtaaatga                                    1350

SEQ ID NO: 572          moltype = AA  length = 449
FEATURE                 Location/Qualifiers
REGION                  1..449
                        note = Synthetic
source                  1..449
                        mol_type = protein
                        organism = synthetic construct
SEQUENCE: 572
QVQLVQSGAE VKKPGSSVKV SCKASGGTFS SYAITWVRQA PGQGLEWMGR IIPMFGIANY  60
AQKFQGRVTI TADKSTSTAY MEVSSLRSED TAVYYCARTP FYYDSSGYYL DYWGQGTLVT  120
```

```
VSSASTKGPS VFPLAPCSRS TSESTAALGC LVKDYFPEPV TVSWNSGALT SGVHTFPAVL  180
QSSGLYSLSS VVTVPSSSLG TKTYTCNVDH KPSNTKVDKR VESKYGPPCP PCPAPGGGGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
TKNQVSLTCL VKGFYPSDIA VEWESNGQPE NNYKTTPPVL DSDGSFFLYS RLTVDKSRWQ  420
EGNVFSCSVM HEALHNHYTQ KSLSLSLGK                                    449

SEQ ID NO: 573         moltype = DNA  length = 357
FEATURE                Location/Qualifiers
misc_feature           1..357
                       note = Synthetic
source                 1..357
                       mol_type = other DNA
                       organism = synthetic construct
SEQUENCE: 573
gaggtgcagc tggtggagtc tggaggaggc ttggtccagc ctgggggggtc cctgagactc  60
tcctgtgcag cctctgggct caccgtcagt agcaactaca tgagctgggt ccgccaggct  120
ccagggaagg gactggagtg ggtctcagtt atttatagcg gaggtaccac atactacgca  180
gactccgtga agggccgatt caccatctcc agacacaatt ccaagaacac gctgtctctt  240
caaatgaaca gcctgagagc tgaggacacg gccgtgtatt actgtgcgcg aggggagggg  300
gccaactact acggtatgga cgtctggggc caagggacca cggtcaccgt ctcctca     357

SEQ ID NO: 574         moltype = AA  length = 119
FEATURE                Location/Qualifiers
REGION                 1..119
                       note = Synthetic
source                 1..119
                       mol_type = protein
                       organism = synthetic construct
SEQUENCE: 574
EVQLVESGGG LVQPGGSLRL SCAASGLTVS SNYMSWVRQA PGKGLEWVSV IYSGGTTYYA  60
DSVKGRFTIS RHNSKNTLSL QMNSLRAEDT AVYYCARGEG ANYYGMDVWG QGTTVTVSS   119

SEQ ID NO: 575         moltype = DNA  length = 21
FEATURE                Location/Qualifiers
misc_feature           1..21
                       note = Synthetic
source                 1..21
                       mol_type = other DNA
                       organism = synthetic construct
SEQUENCE: 575
atttatagcg gaggtaccac a                                            21

SEQ ID NO: 576         moltype = AA  length = 7
FEATURE                Location/Qualifiers
REGION                 1..7
                       note = Synthetic
source                 1..7
                       mol_type = protein
                       organism = synthetic construct
SEQUENCE: 576
IYSGGTT                                                            7

SEQ ID NO: 577         moltype = DNA  length = 39
FEATURE                Location/Qualifiers
misc_feature           1..39
                       note = Synthetic
source                 1..39
                       mol_type = other DNA
                       organism = synthetic construct
SEQUENCE: 577
gcgcgagggg agggggccaa ctactacggt atggacgtc                         39

SEQ ID NO: 578         moltype = AA  length = 13
FEATURE                Location/Qualifiers
REGION                 1..13
                       note = Synthetic
source                 1..13
                       mol_type = protein
                       organism = synthetic construct
SEQUENCE: 578
ARGEGANYYG MDV                                                     13

SEQ ID NO: 579         moltype = DNA  length = 336
FEATURE                Location/Qualifiers
misc_feature           1..336
                       note = Synthetic
source                 1..336
                       mol_type = other DNA
```

```
                         organism = synthetic construct
SEQUENCE: 579
cagtctgtgc tgacgcagcc gccctcagtg tctggggccc cagggcagag ggtcaccatc  60
tcctgcactg ggagcagctc caacatcggg acaggttatg atgtacactg gtaccagcag  120
cttccaggaa cagcccccaa actcctcatc tatggtaaca gcaatcggcc ctcaggggtc  180
cctgaccgat tctctggctc caagtctggc acctcagcct ccctggccat cactgggctc  240
caggctgagg atgaggctga ttattactgc cagtcctatg acagcagcct gagtggttat  300
gtggtattcg gcggagggac caagctgacc gtccta                            336

SEQ ID NO: 580         moltype = AA  length = 112
FEATURE                Location/Qualifiers
REGION                 1..112
                       note = Synthetic
source                 1..112
                       mol_type = protein
                       organism = synthetic construct
SEQUENCE: 580
QSVLTQPPSV SGAPGQRVTI SCTGSSSNIG TGYDVHWYQQ LPGTAPKLLI YGNSNRPSGV  60
PDRFSGSKSG TSASLAITGL QAEDEADYYC QSYDSSLSGY VVFGGGTKLT VL          112

SEQ ID NO: 581         moltype = DNA  length = 27
FEATURE                Location/Qualifiers
misc_feature           1..27
                       note = Synthetic
source                 1..27
                       mol_type = other DNA
                       organism = synthetic construct
SEQUENCE: 581
agctccaaca tcgggacagg ttatgat                                      27

SEQ ID NO: 582         moltype = AA  length = 9
FEATURE                Location/Qualifiers
REGION                 1..9
                       note = Synthetic
source                 1..9
                       mol_type = protein
                       organism = synthetic construct
SEQUENCE: 582
SSNIGTGYD                                                          9

SEQ ID NO: 583         moltype =   length =
SEQUENCE: 583
000

SEQ ID NO: 584         moltype =   length =
SEQUENCE: 584
000

SEQ ID NO: 585         moltype = DNA  length = 36
FEATURE                Location/Qualifiers
misc_feature           1..36
                       note = Synthetic
source                 1..36
                       mol_type = other DNA
                       organism = synthetic construct
SEQUENCE: 585
cagtcctatg acagcagcct gagtggttat gtggta                            36

SEQ ID NO: 586         moltype = AA  length = 12
FEATURE                Location/Qualifiers
REGION                 1..12
                       note = Synthetic
source                 1..12
                       mol_type = protein
                       organism = synthetic construct
SEQUENCE: 586
QSYDSSLSGY VV                                                      12

SEQ ID NO: 587         moltype = DNA  length = 1350
FEATURE                Location/Qualifiers
misc_feature           1..1350
                       note = Synthetic
source                 1..1350
                       mol_type = other DNA
                       organism = synthetic construct
SEQUENCE: 587
gaggtgcagc tggtggagtc tggaggaggc ttggtccagc ctgggggggtc cctgagactc  60
tcctgtgcag cctctgggct caccgtcagt agcaactaca tgagctgggt ccgccaggct  120
ccagggaagg gactggagtg ggtctcagtt atttatagcg gaggtaccac atactacgca  180
```

-continued

```
gactccgtga agggccgatt caccatctcc agacacaatt ccaagaacac gctgtctctt  240
caaatgaaca gcctgagagc tgaggacacg gccgtgtatt actgtgcgcg aggggagggg  300
gccaactact acggtatgga cgtctggggc caagggacca cggtcaccgt ctcctcagcc  360
tccaccaagg gcccatcggt cttccccctg gcaccctcct ccaagagcac ctctgggggc  420
acagcggccc tgggctgcct ggtcaaggac tacttccccg aaccggtgac ggtgtcgtgg  480
aactcaggcg ccctgaccag cggcgtgcac accttcccgg ctgtcctaca gtcctcagga  540
ctctactccc tcagcagcgt ggtgaccgtg ccctccagca gcttgggcac ccagacctac  600
atctgcaacg tgaatcacaa gcccagcaac accaaggtgg acaagaaagt tgagcccaaa  660
tcttgtgaca aaactcacac atgcccaccg tgcccagcac ctgaactcct ggggggaccg  720
tcagtcttcc tcttcccccc aaaacccaag gacaccctca tgatctcccg gacccctgag  780
gtcacatgcg tggtggtgga cgtgagccac gaagaccctg aggtcaagtt caactggtac  840
gtggacggcg tggaggtgca taatgccaag acaaagccgc gggaggagca gtacaacagc  900
acgtaccgtg tggtcagcgt cctcaccgtc ctgcaccagg actggctgaa tggcaaggag  960
tacaagtgca aggtctccaa caaagccctc ccagccccca tcgagaaaac catctccaaa  1020
gccaaagggc agccccgaga accacaggtg tacaccctgc ccccatcccg ggatgagctg  1080
accaagaacc aggtcagcct gacctgcctg gtcaaaggct tctatcccag cgacatcgcc  1140
gtggagtggg agagcaatgg gcagccggag aacaactaca agaccacgcc tcccgtgctg  1200
gactccgacg gctccttctt cctctacagc aagctcaccg tggacaagag caggtggcag  1260
caggggaacg tcttctcatg ctccgtgatg catgaggctc tgcacaacca ctacacgcag  1320
aagtccctct ccctgtctcc gggtaaatga                                  1350

SEQ ID NO: 588          moltype = AA  length = 449
FEATURE                 Location/Qualifiers
REGION                  1..449
                        note = Synthetic
source                  1..449
                        mol_type = protein
                        organism = synthetic construct
SEQUENCE: 588
EVQLVESGGG LVQPGGSLRL SCAASGLTVS SNYMSWVRQA PGKGLEWVSV IYSGGTTYYA  60
DSVKGRFTIS RHNSKNTLSL QMNSLRAEDT AVYYCARGEG ANYYGMDVWG QGTTVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                   449

SEQ ID NO: 589          moltype = DNA  length = 657
FEATURE                 Location/Qualifiers
misc_feature            1..657
                        note = Synthetic
source                  1..657
                        mol_type = other DNA
                        organism = synthetic construct
SEQUENCE: 589
cagtctgtgc tgacgcagcc gccctcagtg tctggggccc cagggcagag ggtcaccatc  60
tcctgcactg ggagcagctc caacatcggg acaggttatg atgtacactg gtaccagcag  120
cttccaggaa cagcccccaa actcctcatc tatggtaaca gcaatcggcc ctcaggggtc  180
cctgaccgat tctctggctc caagtctggc acctcagcct ccctggccat cactgggctc  240
caggctgagg atgaggctga ttattactgc cagtcctatg acagcagcct gagtggttat  300
gtggtattcg gcggagggac caagctgacc gtcctaggcc agcccaaggc cgcccccctcc  360
gtgaccctgt tccccccctc ctccgaggag ctgcaggcca acaaggccac cctggtgtgc  420
ctgatctccg acttctaccc cggcgccgtg accgtggcct ggaaggccga ctcctccccc  480
gtgaaggccg gcgtggagac caccaccccc tccaagcagt ccaacaacaa gtacgccgcc  540
tcctcctacc tgtccctgac ccccgagcag tggaagtccc accggtccta ctcctgccag  600
gtgacccacg agggctccac cgtggagaag accgtggccc ccaccgagtg ctcctga     657

SEQ ID NO: 590          moltype = AA  length = 218
FEATURE                 Location/Qualifiers
REGION                  1..218
                        note = Synthetic
source                  1..218
                        mol_type = protein
                        organism = synthetic construct
SEQUENCE: 590
QSVLTQPPSV SGAPGQRVTI SCTGSSSNIG TGYDVHWYQQ LPGTAPKLLI YGNSNRPSGV  60
PDRFSGSKSG TSASLAITGL QAEDEADYYC QSYDSSLSGY VVFGGGTKLT VLGQPKAAPS  120
VTLFPPSSEE LQANKATLVC LISDFYPGAV TVAWKADSSP VKAGVETTTP SKQSNNKYAA  180
SSYLSLTPEQ WKSHRSYSCQ VTHEGSTVEK TVAPTECS                         218

SEQ ID NO: 591          moltype = DNA  length = 1338
FEATURE                 Location/Qualifiers
misc_feature            1..1338
                        note = Synthetic
source                  1..1338
                        mol_type = other DNA
                        organism = synthetic construct
SEQUENCE: 591
```

```
gaggtgcagc tggtggagtc tggaggaggc ttggtccagc ctgggggggtc cctgagactc  60
tcctgtgcag cctctgggct caccgtcagt agcaactaca tgagctgggt ccgccaggct  120
ccagggaagg gactggagtg ggtctcagtt atttatagcg gaggtaccac atactacgca  180
gactccgtga agggccgatt caccatctcc agacacaatt ccaagaacac gctgtctctt  240
caaatgaaca gcctgagagc tgaggacacg gccgtgtatt actgtgcgcg aggggagggg  300
gccaactact acggtatgga cgtctggggc caagggacca cggtcaccgt ctcctcagcc  360
tccaccaagg gcccatcggt cttccccctg gcgccctgct ccaggagcac ctccgagagc  420
acagccgccc tgggctgcct ggtcaaggac tacttccccg aaccggtgac ggtgtcgtgg  480
aactcaggcg ccctgaccag cggcgtgcac accttcccgg ctgtcctaca gtcctcagga  540
ctctactccc tcagcagcgt ggtgaccgtg ccctccagca gcttgggcac gaagacctac  600
acctgcaacg tagatcacaa gcccagcaac accaaggtgg acaagagagt tgagtccaaa  660
tatggtcccc catgcccacc gtgcccagca ccaggcggtg gcggaccatc agtcttcctg  720
ttccccccaa aacccaagga cactctcatg atctcccgga cccctgaggt cacgtgcgtg  780
gtggtggacg tgagccagga agaccccgag gtccagttca actggtacgt ggatggcgtg  840
gaggtgcata atgccaagac aaagccgcgg gaggagcagt tcaacagcac gtaccgtgtg  900
gtcagcgtcc tcaccgtcct gcaccaggac tggctgaacg gcaaggagta caagtgcaag  960
gtctccaaca aaggcctccc gtcctccatc gagaaaacca tctccaaagc caaagggcag  1020
ccccgagagc cacaggtgta caccctgccc ccatcccagg aggagatgac caagaaccag  1080
gtcagcctga cctgcctggt caaaggcttc taccccagcg acatcgccgt ggagtgggag  1140
agcaatgggc agccggagaa caactacaag accacgcctc ccgtgctgga ctccgacggc  1200
tccttcttcc tctacagcag gctcaccgtg gacaagagca ggtggcagga ggggaatgtc  1260
ttctcatgct ccgtgatgca tgaggctctg cacaaccact acacacagaa gtccctctcc  1320
ctgtctctgg gtaaatga                                                 1338
```

```
SEQ ID NO: 592          moltype = AA  length = 445
FEATURE                 Location/Qualifiers
REGION                  1..445
                        note = Synthetic
source                  1..445
                        mol_type = protein
                        organism = synthetic construct
SEQUENCE: 592
EVQLVESGGG LVQPGGSLRL SCAASGLTVS SNYMSWVRQA PGKGLEWVSV IYSGGTTYYA  60
DSVKGRFTIS RHNSKNTLSL QMNSLRAEDT AVYYCARGEG ANYYGMDVWG QGTTVTVSSA  120
STKGPSVFPL APCSRSTSES TAALGCLVKD YFPEPVTVSW NSGALTSGVH TFPAVLQSSG  180
LYSLSSVVTV PSSSLGTKTY TCNVDHKPSN TKVDKRVESK YGPPCPPCPA PGGGGPSVFL  240
FPPKPKDTLM ISRTPEVTCV VVDVSQEDPE VQFNWYVDGV EVHNAKTKPR EEQFNSTYRV  300
VSVLTVLHQD WLNGKEYKCK VSNKGLPSSI EKTISKAKGQ PREPQVYTLP PSQEEMTKNQ  360
VSLTCLVKGF YPSDIAVEWE SNGQPENNYK TTPPVLDSDG SFFLYSRLTV DKSRWQEGNV  420
FSCSVMHEAL HNHYTQKSLS LSLGK                                         445
```

```
SEQ ID NO: 593          moltype = DNA  length = 357
FEATURE                 Location/Qualifiers
misc_feature            1..357
                        note = Synthetic
source                  1..357
                        mol_type = other DNA
                        organism = synthetic construct
SEQUENCE: 593
gaggtgcagc tggtggagtc tgggggaggc ttggtccagc ctgggggggtc cctgagactc  60
tcctgtgcag cctctggact caccgtcaat cgcaactaca tgagctgggt ccgccaggct  120
ccagggaagg ggctggagtg ggtctcactt atttatagcg gtggtagcac atactacgca  180
gactccgtta agggccgatt caccatctcc agagacaatt ccaagaacac gctgtatctt  240
caaatgaaca gcctgagact tgaggacacg gctgtgtatt actgtgcgag aggtgaactg  300
gggatcccct acggtatgga cgtctggggc caagggacca cggtcaccgt ctcctca     357
```

```
SEQ ID NO: 594          moltype = AA  length = 119
FEATURE                 Location/Qualifiers
REGION                  1..119
                        note = Synthetic
source                  1..119
                        mol_type = protein
                        organism = synthetic construct
SEQUENCE: 594
EVQLVESGGG LVQPGGSLRL SCAASGLTVN RNYMSWVRQA PGKGLEWVSL IYSGGSTYYA  60
DSVKGRFTIS RDNSKNTLYL QMNSLRLEDT AVYYCARGEL GIPYGMDVWG QGTTVTVSS   119
```

```
SEQ ID NO: 595          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 595
ggactcaccg tcaatcgcaa ctac                                          24
```

```
SEQ ID NO: 596          moltype = AA  length = 8
FEATURE                 Location/Qualifiers
```

```
REGION                  1..8
                        note = Synthetic
source                  1..8
                        mol_type = protein
                        organism = synthetic construct
SEQUENCE: 596
GLTVNRNY                                                    8

SEQ ID NO: 597          moltype = DNA  length = 39
FEATURE                 Location/Qualifiers
misc_feature            1..39
                        note = Synthetic
source                  1..39
                        mol_type = other DNA
                        organism = synthetic construct
SEQUENCE: 597
gcgagaggtg aactggggat cccctacggt atggacgtc                  39

SEQ ID NO: 598          moltype = AA  length = 13
FEATURE                 Location/Qualifiers
REGION                  1..13
                        note = Synthetic
source                  1..13
                        mol_type = protein
                        organism = synthetic construct
SEQUENCE: 598
ARGELGIPYG MDV                                              13

SEQ ID NO: 599          moltype = DNA  length = 330
FEATURE                 Location/Qualifiers
misc_feature            1..330
                        note = Synthetic
source                  1..330
                        mol_type = other DNA
                        organism = synthetic construct
SEQUENCE: 599
cagtctgtgt tgacgcagcc gccctcagtg tctgcggccc caggacagaa ggtcaccatc  60
tcctgctctg gaagcagctc caacattggg aataattatg tatcctggta ccagcagctc  120
ccaggaacag cccccaaact cctcatttat gacaataata agcgaccctc agggattcct  180
gaccgcttct ctggctccaa gtctggcacg tcagccaccc tgggcatcac cggactccag  240
actggggacg aggccgatta ttactgcgga acatgggata gcagcctgag tgctggggtg  300
ttcggcggag ggaccaagct gaccgtccta                            330

SEQ ID NO: 600          moltype = AA  length = 110
FEATURE                 Location/Qualifiers
REGION                  1..110
                        note = Synthetic
source                  1..110
                        mol_type = protein
                        organism = synthetic construct
SEQUENCE: 600
QSVLTQPPSV SAAPGQKVTI SCSGSSSNIG NNYVSWYQQL PGTAPKLLIY DNNKRPSGIP  60
DRFSGSKSGT SATLGITGLQ TGDEADYYCG TWDSSLSAGV FGGGTKLTVL            110

SEQ ID NO: 601          moltype = DNA  length = 33
FEATURE                 Location/Qualifiers
misc_feature            1..33
                        note = Synthetic
source                  1..33
                        mol_type = other DNA
                        organism = synthetic construct
SEQUENCE: 601
ggaacatggg atagcagcct gagtgctggg gtg                        33

SEQ ID NO: 602          moltype = AA  length = 11
FEATURE                 Location/Qualifiers
REGION                  1..11
                        note = Synthetic
source                  1..11
                        mol_type = protein
                        organism = synthetic construct
SEQUENCE: 602
GTWDSSLSAG V                                                11

SEQ ID NO: 603          moltype = DNA  length = 1350
FEATURE                 Location/Qualifiers
misc_feature            1..1350
                        note = Synthetic
source                  1..1350
```

```
                        mol_type = other DNA
                        organism = synthetic construct
SEQUENCE: 603
gaggtgcagc tggtggagtc tgggggaggc ttggtccagc ctggggggtc cctgagactc  60
tcctgtgcag cctctggact caccgtcaat cgcaactaca tgagctgggt ccgccaggct  120
ccagggaagg ggctggagtg ggtctcactt atttatagcg gtggtagcac atactacgca  180
gactccgtta agggccgatt caccatctcc agagacaatt ccaagaacac gctgtatctt  240
caaatgaaca gcctgagact tgaggacacg gctgtgtatt actgtgcgag aggtgaactg  300
gggatcccct acggtatgga cgtctggggc caagggacca cggtcaccgt ctcctcagcc  360
tccaccaagg gcccatcggt cttccccctg gcaccctcct ccaagagcac ctctgggggc  420
acagcggccc tgggctgcct ggtcaaggac tacttccccg aaccggtgac ggtgtcgtgg  480
aactcaggcg ccctgaccag cggcgtgcac accttcccgg ctgtcctaca gtcctcagga  540
ctctactccc tcagcagcgt ggtgaccgtg ccctccagca gcttgggcac ccagacctac  600
atctgcaacg tgaatcacaa gcccagcaac accaaggtgg acaagaaagt tgagcccaaa  660
tcttgtgaca aaactcacac atgcccaccg tgcccagcac ctgaactcct ggggggaccg  720
tcagtcttcc tcttcccccc aaaacccaag gacaccctca tgatctcccg gacccctgag  780
gtcacatgcg tggtggtgga cgtgagccac gaagaccctg aggtcaagtt caactggtac  840
gtggacggcg tggaggtgca taatgccaag acaaagccgc gggaggagca gtacaacagc  900
acgtaccgtg tggtcagcgt cctcaccgtc ctgcaccagg actggctgaa tggcaaggag  960
tacaagtgca aggtctccaa caaagccctc ccagccccca tcgagaaaac catctccaaa  1020
gccaaagggc agccccgaga accacaggtg tacaccctgc ccccatcccg ggatgagctg  1080
accaagaacc aggtcagcct gacctgcctg gtcaaaggct tctatcccag cgacatcgcc  1140
gtggagtggg agagcaatgg gcagccggag aacaactaca agaccacgcc tcccgtgctg  1200
gactccgacg gctccttctt cctctacagc aagctcaccg tggacaagag caggtggcag  1260
caggggaacg tcttctcatg ctccgtgatg catgaggctc tgcacaacca ctacacgcag  1320
aagtccctct ccctgtctcc gggtaaatga                                   1350

SEQ ID NO: 604          moltype = AA  length = 449
FEATURE                 Location/Qualifiers
REGION                  1..449
                        note = Synthetic
source                  1..449
                        mol_type = protein
                        organism = synthetic construct
SEQUENCE: 604
EVQLVESGGG LVQPGGSLRL SCAASGLTVN RNYMSWVRQA PGKGLEWVSL IYSGGSTYYA  60
DSVKGRFTIS RDNSKNTLYL QMNSLRLEDT AVYYCARGEL GIPYGMDVWG QGTTVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                   449

SEQ ID NO: 605          moltype = DNA  length = 651
FEATURE                 Location/Qualifiers
misc_feature            1..651
                        note = Synthetic
source                  1..651
                        mol_type = other DNA
                        organism = synthetic construct
SEQUENCE: 605
cagtctgtgt tgacgcagcc gccctcagtg tctgcggccc caggacagaa ggtcaccatc  60
tcctgctctg gaagcagctc caacattggg aataattatg tatcctggta ccagcagctc  120
ccaggaacag cccccaaact cctcatttat gacaataata agcgaccctc agggattcct  180
gaccgcttct ctggctccaa gtctggcacg tcagccaccc tgggcatcac cggactccag  240
actggggacg aggccgatta ttactgcgga acatgggata gcagcctgag tgctggggtg  300
ttcggcggag ggaccaagct gaccgtccta ggccagccca aggccgcccc ctccgtgacc  360
ctgttccccc cctcctccga ggagctgcag gccaacaagg ccaccctggt gtgcctgatc  420
tccgacttct accccggcgc cgtgaccgtg gcctggaagg ccgactcctc ccccgtgaag  480
gccggcgtgg agaccaccac cccctccaag cagtccaaca acaagtacgc cgcctcctcc  540
tacctgtccc tgacccccga gcagtggaag tcccaccggt cctactcctg ccaggtgacc  600
cacgagggct ccaccgtgga gaagaccgtg gcccccaccg agtgctcctg a           651

SEQ ID NO: 606          moltype = AA  length = 216
FEATURE                 Location/Qualifiers
REGION                  1..216
                        note = Synthetic
source                  1..216
                        mol_type = protein
                        organism = synthetic construct
SEQUENCE: 606
QSVLTQPPSV SAAPGQKVTI SCSGSSSNIG NNYVSWYQQL PGTAPKLLIY DNNKRPSGIP  60
DRFSGSKSGT SATLGITGLQ TGDEADYYCG TWDSSLSAGV FGGGTKLTVL GQPKAAPSVT  120
LFPPSSEELQ ANKATLVCLI SDFYPGAVTV AWKADSSPVK AGVETTTPSK QSNNKYAASS  180
YLSLTPEQWK SHRSYSCQVT HEGSTVEKTV APTECS                            216

SEQ ID NO: 607          moltype = DNA  length = 384
FEATURE                 Location/Qualifiers
```

```
misc_feature           1..384
                       note = Synthetic
source                 1..384
                       mol_type = other DNA
                       organism = synthetic construct
SEQUENCE: 607
gaagtgcagc tggtggagtc tgggggaggc ttggtacagc ctggcaggtc cctgagactc  60
tcctgtgcag cctctggatt cacctttgat gattatgcca tgcactgggt ccggcaagct  120
ccagggaagg gcctggagtg ggtctcaggt attagttgga ataggggtag cataggctat  180
gcggactctg tgaagggccg attcaccatc tccagagaca acgccaagaa ctccctgtat  240
ctgcaaatga gcagtctgag agctgaggac acggccttgt attactgcgc aaaagatggc  300
gagagatggg atagtgtagt agtaccatct gctaggaacg gtatggacgt ctggggccaa  360
gggaccacgg tcaccgtctc ctca                                        384

SEQ ID NO: 608         moltype = AA  length = 128
FEATURE                Location/Qualifiers
REGION                 1..128
                       note = Synthetic
source                 1..128
                       mol_type = protein
                       organism = synthetic construct
SEQUENCE: 608
EVQLVESGGG LVQPGRSLRL SCAASGFTFD DYAMHWVRQA PGKGLEWVSG ISWNRGSIGY  60
ADSVKGRFTI SRDNAKNSLY LQMSSLRAED TALYYCAKDG ERWDSVVVPS ARNGMDVWGQ  120
GTTVTVSS                                                          128

SEQ ID NO: 609         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 609
attagttgga ataggggtag cata                                        24

SEQ ID NO: 610         moltype = AA  length = 8
FEATURE                Location/Qualifiers
REGION                 1..8
                       note = Synthetic
source                 1..8
                       mol_type = protein
                       organism = synthetic construct
SEQUENCE: 610
ISWNRGSI                                                          8

SEQ ID NO: 611         moltype = DNA  length = 63
FEATURE                Location/Qualifiers
misc_feature           1..63
                       note = Synthetic
source                 1..63
                       mol_type = other DNA
                       organism = synthetic construct
SEQUENCE: 611
gcaaaagatg gcgagagatg ggatagtgta gtagtaccat ctgctaggaa cggtatggac  60
gtc                                                               63

SEQ ID NO: 612         moltype = AA  length = 21
FEATURE                Location/Qualifiers
REGION                 1..21
                       note = Synthetic
source                 1..21
                       mol_type = protein
                       organism = synthetic construct
SEQUENCE: 612
AKDGERWDSV VVPSARNGMD V                                           21

SEQ ID NO: 613         moltype = DNA  length = 336
FEATURE                Location/Qualifiers
misc_feature           1..336
                       note = Synthetic
source                 1..336
                       mol_type = other DNA
                       organism = synthetic construct
SEQUENCE: 613
cagtctgtgc tgacgcagcc gccctcagtg tctggggccc cagggcagag ggtcaccatc  60
tcctgcactg ggagcagctc caacatcggg gcaggttatg atgtacattg gtaccagcag  120
cttccaggaa cagcccccaa actcctcatc tatggtaaca gcaatcggcc ctcaggggtc  180
cctgaccgat tctctggctc caagtctggc acctcagcct ccctggccat cactgggctc  240
```

-continued

```
caggctgagg atgaggctga ttattactgc cagtcctatg acagcagcct gagtggctct  300
tatgtcttcg gaactgggac caaggtcacc gtccta                            336

SEQ ID NO: 614          moltype = AA  length = 112
FEATURE                 Location/Qualifiers
REGION                  1..112
                        note = Synthetic
source                  1..112
                        mol_type = protein
                        organism = synthetic construct
SEQUENCE: 614
QSVLTQPPSV SGAPGQRVTI SCTGSSSNIG AGYDVHWYQQ LPGTAPKLLI YGNSNRPSGV  60
PDRFSGSKSG TSASLAITGL QAEDEADYYC QSYDSSLSGS YVFGTGTKVT VL          112

SEQ ID NO: 615          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 615
agctccaaca tcggggcagg ttatgat                                      27

SEQ ID NO: 616          moltype = AA  length = 9
FEATURE                 Location/Qualifiers
REGION                  1..9
                        note = Synthetic
source                  1..9
                        mol_type = protein
                        organism = synthetic construct
SEQUENCE: 616
SSNIGAGYD                                                          9

SEQ ID NO: 617          moltype = DNA  length = 36
FEATURE                 Location/Qualifiers
misc_feature            1..36
                        note = Synthetic
source                  1..36
                        mol_type = other DNA
                        organism = synthetic construct
SEQUENCE: 617
cagtcctatg acagcagcct gagtggctct tatgtc                            36

SEQ ID NO: 618          moltype = AA  length = 12
FEATURE                 Location/Qualifiers
REGION                  1..12
                        note = Synthetic
source                  1..12
                        mol_type = protein
                        organism = synthetic construct
SEQUENCE: 618
QSYDSSLSGS YV                                                      12

SEQ ID NO: 619          moltype = DNA  length = 1377
FEATURE                 Location/Qualifiers
misc_feature            1..1377
                        note = Synthetic
source                  1..1377
                        mol_type = other DNA
                        organism = synthetic construct
SEQUENCE: 619
gaagtgcagc tggtggagtc tgggggaggc ttggtacagc ctggcaggtc cctgagactc  60
tcctgtgcag cctctggatt cacctttgat gattatgcca tgcactgggt ccggcaagct  120
ccagggaagg gcctggagtg ggtctcaggt attagttgga atagggggtag cataggctat  180
gcggactctg tgaagggccg attcaccatc tccagagaca acgccaagaa ctccctgtat  240
ctgcaaatga gcagtctgag agctgaggac acggccttgt attactgcgc aaaagatggc  300
gagagatggg atagtgtagt agtaccatct gctaggaacg gtatggacgt ctggggccaa  360
gggaccacgg tcaccgtctc ctcagcctcc accaagggcc catcggtctt ccccctggca  420
ccctcctcca agagcacctc tgggggcaca gcggccctgg gctgcctggt caaggactac  480
ttccccgaac cggtgacggt gtcgtggaac tcaggcgccc tgaccagcgg cgtgcacacc  540
ttcccggctg tcctacagtc ctcaggactc tactccctca gcagcgtggt gaccgtgccc  600
tccagcagct tgggcaccca gacctacatc tgcaacgtga atcacaagcc cagcaacacc  660
aaggtggaca agaaagttga gcccaaatct tgtgacaaaa ctcacacatg cccaccgtgc  720
ccagcacctg aactcctggg gggaccgtca gtcttcctct tcccccccaaa acccaaggac  780
accctcatga tctcccggac ccctgaggtc acatgcgtgg tggtggacgt gagccacgaa  840
gaccctgagg tcaagttcaa ctggtacgtg gacggcgtgg aggtgcataa tgccaagaca  900
aagccgcggg aggagcagta caacagcacg taccgtgtgg tcagcgtcct caccgtcctg  960
caccaggact ggctgaatgg caaggagtac aagtgcaagg tctccaacaa agccctccca  1020
```

```
gcccccatcg agaaaaccat ctccaaagcc aaagggcagc cccgagaacc acaggtgtac  1080
accctgcccc catcccggga tgagctgacc aagaaccagg tcagcctgac ctgcctggtc  1140
aaaggcttct atcccagcga catcgccgtg gagtgggaga gcaatgggca gccggagaac  1200
aactacaaga ccacgcctcc cgtgctggac tccgacggct ccttcttcct ctacagcaag  1260
ctcaccgtgg acaagagcag gtggcagcag gggaacgtct tctcatgctc cgtgatgcat  1320
gaggctctgc acaaccacta cacgcagaag tccctctccc tgtctccggg taaatga     1377

SEQ ID NO: 620         moltype = AA  length = 458
FEATURE                Location/Qualifiers
REGION                 1..458
                       note = Synthetic
source                 1..458
                       mol_type = protein
                       organism = synthetic construct
SEQUENCE: 620
EVQLVESGGG LVQPGRSLRL SCAASGFTFD DYAMHWVRQA PGKGLEWVSG ISWNRGSIGY  60
ADSVKGRFTI SRDNAKNSLY LQMSSLRAED TALYYCAKDG ERWDSVVVPS ARNGMDVWGQ  120
GTTVTVSSAS TKGPSVFPLA PSSKSTSGGT AALGCLVKDY FPEPVTVSWN SGALTSGVHT  180
FPAVLQSSGL YSLSSVVTVP SSSLGTQTYI CNVNHKPSNT KVDKKVEPKS CDKTHTCPPC  240
PAPELLGGPS VFLFPPKPKD TLMISRTPEV TCVVVDVSHE DPEVKFNWYV DGVEVHNAKT  300
KPREEQYNST YRVVSVLTVL HQDWLNGKEY KCKVSNKALP APIEKTISKA KGQPREPQVY  360
TLPPSRDELT KNQVSLTCLV KGFYPSDIAV EWESNGQPEN NYKTTPPVLD SDGSFFLYSK  420
LTVDKSRWQQ GNVFSCSVMH EALHNHYTQK SLSLSPGK                          458

SEQ ID NO: 621         moltype = DNA  length = 657
FEATURE                Location/Qualifiers
misc_feature           1..657
                       note = Synthetic
source                 1..657
                       mol_type = other DNA
                       organism = synthetic construct
SEQUENCE: 621
cagtctgtgc tgacgcagcc gccctcagtg tctggggccc cagggcagag ggtcaccatc  60
tcctgcactg ggagcagctc caacatcggg gcaggttatg atgtacattg gtaccagcag  120
cttccaggaa cagcccccaa actcctcatc tatggtaaca gcaatcggcc ctcaggggtc  180
cctgaccgat tctctggctc caagtctggc acctcagcct ccctggccat cactgggctc  240
caggctgagg atgaggctga ttattactgc cagtcctatg acagcagcct gagtggctct  300
tatgtcttcg gaactgggac caaggtcacc gtcctaggcc agcccaaggc cgccccctcc  360
gtgaccctgt tccccccctc ctccgaggag ctgcaggcca acaaggccac cctggtgtgc  420
ctgatctccg acttctaccc cggcgccgtg accgtggcct ggaaggccga ctcctccccc  480
gtgaaggccg gcgtggagac caccaccccc tccaagcagt ccaacaacaa gtacgccgcc  540
tcctcctacc tgtccctgac ccccgagcag tggaagtccc accggtccta ctcctgccag  600
gtgacccacg agggctccac cgtggagaag accgtggccc ccaccgagtg ctcctga     657

SEQ ID NO: 622         moltype = AA  length = 218
FEATURE                Location/Qualifiers
REGION                 1..218
                       note = Synthetic
source                 1..218
                       mol_type = protein
                       organism = synthetic construct
SEQUENCE: 622
QSVLTQPPSV SGAPGQRVTI SCTGSSSNIG AGYDVHWYQQ LPGTAPKLLI YGNSNRPSGV  60
PDRFSGSKSG TSASLAITGL QAEDEADYYC QSYDSSLSGS YVFGTGTKVT VLGQPKAAPS  120
VTLFPPSSEE LQANKATLVC LISDFYPGAV TVAWKADSSP VKAGVETTTP SKQSNNKYAA  180
SSYLSLTPEQ WKSHRSYSCQ VTHEGSTVEK TVAPTECS                          218

SEQ ID NO: 623         moltype = DNA  length = 357
FEATURE                Location/Qualifiers
misc_feature           1..357
                       note = Synthetic
source                 1..357
                       mol_type = other DNA
                       organism = synthetic construct
SEQUENCE: 623
gaggtgcagc tggtggagtc tgggggaggc ttggtccagc ctgggggtc cctgagactc  60
tcctgtgcag cctctgaatt caccgtcagt agcaactaca tgagctgggt ccgccaggct  120
ccagggaagg ggctagagtg ggtctcagtt atttatagcg gtggtagcac attttacgca  180
gactccgtga agggcagatt caccatctcc agagacaatt ccaagaacac gttgtatctt  240
caaatgaaca gtctgagagc cgaggacacg gctgtatatt actgtgcgag agctcttccc  300
tacggtgact tgcattttga ctactggggc cagggaaccc tggtcaccgt ctcctca     357

SEQ ID NO: 624         moltype = AA  length = 119
FEATURE                Location/Qualifiers
REGION                 1..119
                       note = Synthetic
source                 1..119
                       mol_type = protein
                       organism = synthetic construct
```

```
SEQUENCE: 624
EVQLVESGGG LVQPGGSLRL SCAASEFTVS SNYMSWVRQA PGKGLEWVSV IYSGGSTFYA  60
DSVKGRFTIS RDNSKNTLYL QMNSLRAEDT AVYYCARALP YGDLHFDYWG QGTLVTVSS   119

SEQ ID NO: 625         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 625
gaattcaccg tcagtagcaa ctac                                        24

SEQ ID NO: 626         moltype = AA  length = 8
FEATURE                Location/Qualifiers
REGION                 1..8
                       note = Synthetic
source                 1..8
                       mol_type = protein
                       organism = synthetic construct
SEQUENCE: 626
EFTVSSNY                                                          8

SEQ ID NO: 627         moltype = DNA  length = 39
FEATURE                Location/Qualifiers
misc_feature           1..39
                       note = Synthetic
source                 1..39
                       mol_type = other DNA
                       organism = synthetic construct
SEQUENCE: 627
gcgagagctc ttccctacgg tgacttgcat tttgactac                        39

SEQ ID NO: 628         moltype = AA  length = 13
FEATURE                Location/Qualifiers
REGION                 1..13
                       note = Synthetic
source                 1..13
                       mol_type = protein
                       organism = synthetic construct
SEQUENCE: 628
ARALPYGDLH FDY                                                    13

SEQ ID NO: 629         moltype = DNA  length = 336
FEATURE                Location/Qualifiers
misc_feature           1..336
                       note = Synthetic
source                 1..336
                       mol_type = other DNA
                       organism = synthetic construct
SEQUENCE: 629
cagtctgtgc tgacgcagcc gccctcagtg tctggggccc cagggcagag ggtcaccatc  60
tcctgcactg ggagcagctc caacatcggg acaggttatg atgtacactg gtaccagcag  120
cttccaggaa cagcccccaa actcctcatc tatggtaaca ccaatcggcc ctcaggggtc  180
cctgaccgat tctctggctc caagtctggc acctcagcct ccctggccat cactgggctc  240
caggctgagg atgaggctga ttattactgc cagtcctatg acagcagcct gagtgactct  300
tatgtcttcg gaactgggac caaggtcacc gtccta                           336

SEQ ID NO: 630         moltype = AA  length = 112
FEATURE                Location/Qualifiers
REGION                 1..112
                       note = Synthetic
source                 1..112
                       mol_type = protein
                       organism = synthetic construct
SEQUENCE: 630
QSVLTQPPSV SGAPGQRVTI SCTGSSSNIG TGYDVHWYQQ LPGTAPKLLI YGNTNRPSGV  60
PDRFSGSKSG TSASLAITGL QAEDEADYYC QSYDSSLSDS YVFGTGTKVT VL         112

SEQ ID NO: 631         moltype =   length =
SEQUENCE: 631
000

SEQ ID NO: 632         moltype =   length =
SEQUENCE: 632
000

SEQ ID NO: 633         moltype = DNA  length = 36
```

```
FEATURE                Location/Qualifiers
misc_feature           1..36
                       note = Synthetic
source                 1..36
                       mol_type = other DNA
                       organism = synthetic construct
SEQUENCE: 633
cagtcctatg acagcagcct gagtgactct tatgtc                            36

SEQ ID NO: 634         moltype = AA  length = 12
FEATURE                Location/Qualifiers
REGION                 1..12
                       note = Synthetic
source                 1..12
                       mol_type = protein
                       organism = synthetic construct
SEQUENCE: 634
QSYDSSLSDS YV                                                      12

SEQ ID NO: 635         moltype = DNA  length = 1350
FEATURE                Location/Qualifiers
misc_feature           1..1350
                       note = Synthetic
source                 1..1350
                       mol_type = other DNA
                       organism = synthetic construct
SEQUENCE: 635
gaggtgcagc tggtggagtc tgggggaggc ttggtccagc ctggggggtc cctgagactc  60
tcctgtgcag cctctgaatt caccgtcagt agcaactaca tgagctgggt ccgccaggct  120
ccagggaagg ggctagagtg ggtctcagtt atttatagcg gtggtagcac attttacgca  180
gactccgtga agggcagatt caccatctcc agagacaatt ccaagaacac gttgtatctt  240
caaatgaaca gtctgagagc cgaggacacg gctgtatatt actgtgcgag agctcttccc  300
tacggtgact tgcattttga ctactggggc cagggaaccc tggtcaccgt ctcctcagcc  360
tccaccaagg gcccatcggt cttccccctg gcaccctcct ccaagagcac ctctgggggc  420
acagcggccc tgggctgcct ggtcaaggac tacttccccg aaccggtgac ggtgtcgtgg  480
aactcaggcg ccctgaccag cggcgtgcac accttcccgg ctgtcctaca gtcctcagga  540
ctctactccc tcagcagcgt ggtgaccgtg ccctccagca gcttgggcac ccagacctac  600
atctgcaacg tgaatcacaa gcccagcaac accaaggtgg acaagaaagt tgagcccaaa  660
tcttgtgaca aaactcacac atgcccaccg tgcccagcac ctgaactcct ggggggaccg  720
tcagtcttcc tcttcccccc aaaacccaag gacaccctca tgatctcccg gacccctgag  780
gtcacatgcg tggtggtgga cgtgagccac gaagaccctg aggtcaagtt caactggtac  840
gtggacggcg tggaggtgca taatgccaag acaaagccgc gggaggagca gtacaacagc  900
acgtaccgtg tggtcagcgt cctcaccgtc ctgcaccagg actggctgaa tggcaaggag  960
tacaagtgca aggtctccaa caaagccctc ccagccccca tcgagaaaac catctccaaa  1020
gccaaagggc agccccgaga accacaggtg tacaccctgc ccccatcccg ggatgagctg  1080
accaagaacc aggtcagcct gacctgcctg gtcaaaggct tctatcccag cgacatcgcc  1140
gtggagtggg agagcaatgg gcagccggag aacaactaca agaccacgcc tcccgtgctg  1200
gactccgacg gctccttctt cctctacagc aagctcaccg tggacaagag caggtggcag  1260
caggggaacg tcttctcatg ctccgtgatg catgaggctc tgcacaacca ctacacgcag  1320
aagtccctct ccctgtctcc gggtaaatga                                   1350

SEQ ID NO: 636         moltype = AA  length = 449
FEATURE                Location/Qualifiers
REGION                 1..449
                       note = Synthetic
source                 1..449
                       mol_type = protein
                       organism = synthetic construct
SEQUENCE: 636
EVQLVESGGG LVQPGGSLRL SCAASEFTVS SNYMSWVRQA PGKGLEWVSV IYSGGSTFYA  60
DSVKGRFTIS RDNSKNTLYL QMNSLRAEDT AVYYCARALP YGDLHFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                    449

SEQ ID NO: 637         moltype = DNA  length = 657
FEATURE                Location/Qualifiers
misc_feature           1..657
                       note = Synthetic
source                 1..657
                       mol_type = other DNA
                       organism = synthetic construct
SEQUENCE: 637
cagtctgtgc tgacgcagcc gccctcagtg tctggggccc cagggcagag ggtcaccatc  60
tcctgcactg ggagcagctc caacatcggg acaggttatg atgtacactg gtaccagcag  120
cttccaggaa cagcccccaa actcctcatc tatggtaaca ccaatcggcc ctcaggggtc  180
```

-continued

```
cctgaccgat tctctggctc caagtctggc acctcagcct ccctggccat cactgggctc  240
caggctgagg atgaggctga ttattactgc cagtcctatg acagcagcct gagtgactct  300
tatgtcttcg gaactgggac caaggtcacc gtcctaggcc agcccaaggc cgccccctcc  360
gtgaccctgt tccccccctc ctccgaggag ctgcaggcca acaaggccac cctggtgtgc  420
ctgatctccg acttctaccc cggcgccgtg accgtggcct ggaaggccga ctcctccccc  480
gtgaaggccg gcgtggagac caccaccccc tccaagcagt ccaacaacaa gtacgccgcc  540
tcctcctacc tgtccctgac ccccgagcag tggaagtccc accggtccta ctcctgccag  600
gtgacccacg agggctccac cgtggagaag accgtggccc ccaccgagtg ctcctga     657

SEQ ID NO: 638          moltype = AA  length = 218
FEATURE                 Location/Qualifiers
REGION                  1..218
                        note = Synthetic
source                  1..218
                        mol_type = protein
                        organism = synthetic construct
SEQUENCE: 638
QSVLTQPPSV SGAPGQRVTI SCTGSSSNIG TGYDVHWYQQ LPGTAPKLLI YGNTNRPSGV  60
PDRFSGSKSG TSASLAITGL QAEDEADYYC QSYDSSLSDS YVFGTGTKVT VLGQPKAAPS  120
VTLFPPSSEE LQANKATLVC LISDFYPGAV TVAWKADSSP VKAGVETTTP SKQSNNKYAA  180
SSYLSLTPEQ WKSHRSYSCQ VTHEGSTVEK TVAPTECS                         218

SEQ ID NO: 639          moltype = DNA  length = 360
FEATURE                 Location/Qualifiers
misc_feature            1..360
                        note = Synthetic
source                  1..360
                        mol_type = other DNA
                        organism = synthetic construct
SEQUENCE: 639
caggtgcagc tggtggagtc tgggggaggc gtggtccagc ctgggaggtc cctgagactc  60
tcctgtgcag cctctggatt caccttcagt aactatgcta tgtactgggt ccgccaggct  120
ccaggcaagg ggctggagtg ggtggcagtt atatcatatg atggaagtaa taaatactat  180
gcagactccg tgaagggccg attcaccatc tccagagaca attccaagaa cacgctgtat  240
ctgcaaatga acagcctgag aactgaggac acggctgtgt attactgtgc gagtggctcc  300
gactacggtg actacttatt ggtttactgg ggccagggaa ccctggtcac cgtctcctca  360

SEQ ID NO: 640          moltype = AA  length = 120
FEATURE                 Location/Qualifiers
REGION                  1..120
                        note = Synthetic
source                  1..120
                        mol_type = protein
                        organism = synthetic construct
SEQUENCE: 640
QVQLVESGGG VVQPGRSLRL SCAASGFTFS NYAMYWVRQA PGKGLEWVAV ISYDGSNKYY  60
ADSVKGRFTI SRDNSKNTLY LQMNSLRTED TAVYYCASGS DYGDYLLVYW GQGTLVTVSS  120

SEQ ID NO: 641          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 641
ggattcacct tcagtaacta tgct                                        24

SEQ ID NO: 642          moltype = AA  length = 8
FEATURE                 Location/Qualifiers
REGION                  1..8
                        note = Synthetic
source                  1..8
                        mol_type = protein
                        organism = synthetic construct
SEQUENCE: 642
GFTFSNYA                                                          8

SEQ ID NO: 643          moltype = DNA  length = 39
FEATURE                 Location/Qualifiers
misc_feature            1..39
                        note = Synthetic
source                  1..39
                        mol_type = other DNA
                        organism = synthetic construct
SEQUENCE: 643
gcgagtggct ccgactacgg tgactactta ttggtttac                        39

SEQ ID NO: 644          moltype = AA  length = 13
```

```
FEATURE               Location/Qualifiers
REGION                1..13
                      note = Synthetic
source                1..13
                      mol_type = protein
                      organism = synthetic construct
SEQUENCE: 644
ASGSDYGDYL LVY                                                     13

SEQ ID NO: 645        moltype = DNA  length = 330
FEATURE               Location/Qualifiers
misc_feature          1..330
                      note = Synthetic
source                1..330
                      mol_type = other DNA
                      organism = synthetic construct
SEQUENCE: 645
cagtctgccc tgactcagcc tgcctccgtg tctgggtctc ctggacagtc gatcaccatc  60
tcctgcactg gaaccagcag tgacgttggt ggttataact atgtctcctg gtaccaacaa  120
cacccaggca aagcccccaa actcatgatt tatgatgtca gtaagcggcc ctcaggggtt  180
tctaatcgct tctctggctc caagtctggc aacacggcct ccctgaccat ctctgggctc  240
cagtctgagg acgaggctga ttattactgc aactctttga caagcatcag cacttgggtg  300
ttcggcggag ggaccaagct gaccgtccta                                   330

SEQ ID NO: 646        moltype = AA  length = 110
FEATURE               Location/Qualifiers
REGION                1..110
                      note = Synthetic
source                1..110
                      mol_type = protein
                      organism = synthetic construct
SEQUENCE: 646
QSALTQPASV SGSPGQSITI SCTGTSSDVG GYNYVSWYQQ HPGKAPKLMI YDVSKRPSGV  60
SNRFSGSKSG NTASLTISGL QSEDEADYYC NSLTSISTWV FGGGTKLTVL              110

SEQ ID NO: 647        moltype = DNA  length = 27
FEATURE               Location/Qualifiers
misc_feature          1..27
                      note = Synthetic
source                1..27
                      mol_type = other DNA
                      organism = synthetic construct
SEQUENCE: 647
agcagtgacg ttggtggtta taactat                                      27

SEQ ID NO: 648        moltype = AA  length = 9
FEATURE               Location/Qualifiers
REGION                1..9
                      note = Synthetic
source                1..9
                      mol_type = protein
                      organism = synthetic construct
SEQUENCE: 648
SSDVGGYNY                                                          9

SEQ ID NO: 649        moltype =   length =
SEQUENCE: 649
000

SEQ ID NO: 650        moltype =   length =
SEQUENCE: 650
000

SEQ ID NO: 651        moltype = DNA  length = 30
FEATURE               Location/Qualifiers
misc_feature          1..30
                      note = Synthetic
source                1..30
                      mol_type = other DNA
                      organism = synthetic construct
SEQUENCE: 651
aactctttga caagcatcag cacttgggtg                                   30

SEQ ID NO: 652        moltype = AA  length = 10
FEATURE               Location/Qualifiers
REGION                1..10
                      note = Synthetic
source                1..10
                      mol_type = protein
```

```
                         organism = synthetic construct
SEQUENCE: 652
NSLTSISTWV                                                        10

SEQ ID NO: 653           moltype = DNA  length = 1353
FEATURE                  Location/Qualifiers
misc_feature             1..1353
                         note = Synthetic
source                   1..1353
                         mol_type = other DNA
                         organism = synthetic construct
SEQUENCE: 653
caggtgcagc tggtggagtc tgggggaggc gtggtccagc ctgggaggtc cctgagactc  60
tcctgtgcag cctctggatt caccttcagt aactatgcta tgtactgggt ccgccaggct  120
ccaggcaagg ggctggagtg ggtggcagtt atatcatatg atggaagtaa taaatactat  180
gcagactccg tgaagggccg attcaccatc tccagagaca attccaagaa cacgctgtat  240
ctgcaaatga acagcctgag aactgaggac acggctgtgt attactgtgc gagtggctcc  300
gactacggtg actacttatt ggtttactgg ggccagggaa ccctggtcac cgtctcctca  360
gcctccacca agggcccatc ggtcttcccc ctggcaccct cctccaagag cacctctggg  420
ggcacagcgg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacccagacc  600
tacatctgca acgtgaatca caagcccagc aacaccaagg tggacaagaa agttgagccc  660
aaatcttgtg acaaaactca cacatgccca ccgtgcccag cacctgaact cctgggggga  720
ccgtcagtct tcctcttccc cccaaaaccc aaggacaccc tcatgatctc ccggacccct  780
gaggtcacat gcgtggtggt ggacgtgagc cacgaagacc ctgaggtcaa gttcaactgg  840
tacgtggacg gcgtggaggt gcataatgcc aagacaaagc cgcgggagga gcagtacaac  900
agcacgtacc gtgtggtcag cgtcctcacc gtcctgcacc aggactggct gaatggcaag  960
gagtacaagt gcaaggtctc caacaaagcc ctcccagccc ccatcgagaa aaccatctcc  1020
aaagccaaag ggcagccccg agaaccacag gtgtacaccc tgcccccatc ccgggatgag  1080
ctgaccaaga accaggtcag cctgacctgc ctggtcaaag gcttctatcc cagcgacatc  1140
gccgtggagt gggagagcaa tgggcagccg gagaacaact acaagaccac gcctcccgtg  1200
ctggactccg acggctcctt cttcctctac agcaagctca ccgtggacaa gagcaggtgg  1260
cagcagggga acgtcttctc atgctccgtg atgcatgagg ctctgcacaa ccactacacg  1320
cagaagtccc tctccctgtc tccgggtaaa tga                              1353

SEQ ID NO: 654           moltype = AA  length = 450
FEATURE                  Location/Qualifiers
REGION                   1..450
                         note = Synthetic
source                   1..450
                         mol_type = protein
                         organism = synthetic construct
SEQUENCE: 654
QVQLVESGGG VVQPGRSLRL SCAASGFTFS NYAMYWVRQA PGKGLEWVAV ISYDGSNKYY  60
ADSVKGRFTI SRDNSKNTLY LQMNSLRTED TAVYYCASGS DYGDYLLVYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 655           moltype = DNA  length = 651
FEATURE                  Location/Qualifiers
misc_feature             1..651
                         note = Synthetic
source                   1..651
                         mol_type = other DNA
                         organism = synthetic construct
SEQUENCE: 655
cagtctgccc tgactcagcc tgcctccgtg tctgggtctc ctggacagtc gatcaccatc  60
tcctgcactg gaaccagcag tgacgttggt ggttataact atgtctcctg gtaccaacaa  120
cacccaggca aagcccccaa actcatgatt tatgatgtca gtaagcggcc ctcaggggtt  180
tctaatcgct tctctggctc caagtctggc aacacggcct ccctgaccat ctctgggctc  240
cagtctgagg acgaggctga ttattactgc aactctttga caagcatcag cacttgggtg  300
ttcggcggag ggaccaagct gaccgtccta ggccagccca aggccgcccc ctccgtgacc  360
ctgttccccc cctcctccga ggagctgcag gccaacaagg ccaccctggt gtgcctgatc  420
tccgacttct accccggcgc cgtgaccgtg gcctggaagg ccgactcctc ccccgtgaag  480
gccggcgtgg agaccaccac cccctccaag cagtccaaca acaagtacgc cgcctcctcc  540
tacctgtccc tgacccccga gcagtggaag tcccaccggt cctactcctg ccaggtgacc  600
cacgagggct ccaccgtgga gaagaccgtg gcccccaccg agtgctcctg a          651

SEQ ID NO: 656           moltype = AA  length = 216
FEATURE                  Location/Qualifiers
REGION                   1..216
                         note = Synthetic
source                   1..216
                         mol_type = protein
```

```
                        organism = synthetic construct
SEQUENCE: 656
QSALTQPASV SGSPGQSITI SCTGTSSDVG GYNYVSWYQQ HPGKAPKLMI YDVSKRPSGV  60
SNRFSGSKSG NTASLTISGL QSEDEADYYC NSLTSISTWV FGGGTKLTVL GQPKAAPSVT  120
LFPPSSEELQ ANKATLVCLI SDFYPGAVTV AWKADSSPVK AGVETTTPSK QSNNKYAASS  180
YLSLTPEQWK SHRSYSCQVT HEGSTVEKTV APTECS                            216

SEQ ID NO: 657          moltype = DNA  length = 381
FEATURE                 Location/Qualifiers
misc_feature            1..381
                        note = Synthetic
source                  1..381
                        mol_type = other DNA
                        organism = synthetic construct
SEQUENCE: 657
gaggtgcagc tggtggagtc tgggggaggc ttggtacagc ctggagggtc cctgagactc  60
tcctgtacag cctctggatt caccttcagt aattatgaaa tgaactgggt ccgccaggct  120
ccagggaagg ggctggagtg ggtttcatac attagtagta ggagtggtag taccctacac  180
tacgcagact ctgtgaaggg ccgattcacc atctccagag acaacgccaa gaactcactg  240
tatctgcaaa tgaacagcct gagagccgag gacacggctg tttattactg tgcgagaagg  300
ggcgatggta ccagctccct aatccaccac tactactaca tggacgtctg gggcaaaggg  360
accacggtca ccgtctcctc a                                            381

SEQ ID NO: 658          moltype = AA  length = 127
FEATURE                 Location/Qualifiers
REGION                  1..127
                        note = Synthetic
source                  1..127
                        mol_type = protein
                        organism = synthetic construct
SEQUENCE: 658
EVQLVESGGG LVQPGGSLRL SCTASGFTFS NYEMNWVRQA PGKGLEWVSY ISSRSGSTLH  60
YADSVKGRFT ISRDNAKNSL YLQMNSLRAE DTAVYYCARR GDGTSSLIHH YYYMDVWGKG  120
TTVTVSS                                                            127

SEQ ID NO: 659          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 659
ggattcacct tcagtaatta tgaa                                         24

SEQ ID NO: 660          moltype = AA  length = 8
FEATURE                 Location/Qualifiers
REGION                  1..8
                        note = Synthetic
source                  1..8
                        mol_type = protein
                        organism = synthetic construct
SEQUENCE: 660
GFTFSNYE                                                           8

SEQ ID NO: 661          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 661
attagtagta ggagtggtag tacccta                                      27

SEQ ID NO: 662          moltype = AA  length = 9
FEATURE                 Location/Qualifiers
REGION                  1..9
                        note = Synthetic
source                  1..9
                        mol_type = protein
                        organism = synthetic construct
SEQUENCE: 662
ISSRSGSTL                                                          9

SEQ ID NO: 663          moltype = DNA  length = 57
FEATURE                 Location/Qualifiers
misc_feature            1..57
                        note = Synthetic
```

```
source                  1..57
                        mol_type = other DNA
                        organism = synthetic construct
SEQUENCE: 663
gcgagaaggg gcgatggtac cagctcccta atccaccact actactacat ggacgtc     57

SEQ ID NO: 664          moltype = AA  length = 19
FEATURE                 Location/Qualifiers
REGION                  1..19
                        note = Synthetic
source                  1..19
                        mol_type = protein
                        organism = synthetic construct
SEQUENCE: 664
ARRGDGTSSL IHHYYYMDV                                               19

SEQ ID NO: 665          moltype = DNA  length = 330
FEATURE                 Location/Qualifiers
misc_feature            1..330
                        note = Synthetic
source                  1..330
                        mol_type = other DNA
                        organism = synthetic construct
SEQUENCE: 665
cagtctgtgc tgactcagcc accctcagcg tctgggaccc ccgggcagag ggtcaccatc  60
tcttgttctg gaagcagctc caacatcgga agtaatactg taaactggta ccaacagctc  120
ccaggaacgg cccccaaact cctcatctat agtaataatc agcggccctc aggggtccct  180
gaccgattct ctggctccaa gtctggcacc tcagcctccc tggccatcag tgggctccag  240
tctgaggatg aggctgatta ttactgtgca gcatgggatg acagcctgaa tggtccggta  300
ttcggcggag ggaccaagct gaccgtccta                                   330

SEQ ID NO: 666          moltype = AA  length = 110
FEATURE                 Location/Qualifiers
REGION                  1..110
                        note = Synthetic
source                  1..110
                        mol_type = protein
                        organism = synthetic construct
SEQUENCE: 666
QSVLTQPPSA SGTPGQRVTI SCSGSSSNIG SNTVNWYQQL PGTAPKLLIY SNNQRPSGVP  60
DRFSGSKSGT SASLAISGLQ SEDEADYYCA AWDDSLNGPV FGGGTKLTVL             110

SEQ ID NO: 667          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 667
agctccaaca tcggaagtaa tact                                         24

SEQ ID NO: 668          moltype = AA  length = 8
FEATURE                 Location/Qualifiers
REGION                  1..8
                        note = Synthetic
source                  1..8
                        mol_type = protein
                        organism = synthetic construct
SEQUENCE: 668
SSNIGSNT                                                           8

SEQ ID NO: 669          moltype =   length =
SEQUENCE: 669
000

SEQ ID NO: 670          moltype =   length =
SEQUENCE: 670
000

SEQ ID NO: 671          moltype = DNA  length = 33
FEATURE                 Location/Qualifiers
misc_feature            1..33
                        note = Synthetic
source                  1..33
                        mol_type = other DNA
                        organism = synthetic construct
SEQUENCE: 671
gcagcatggg atgacagcct gaatggtccg gta                               33
```

```
SEQ ID NO: 672          moltype = AA  length = 11
FEATURE                 Location/Qualifiers
REGION                  1..11
                        note = Synthetic
source                  1..11
                        mol_type = protein
                        organism = synthetic construct
SEQUENCE: 672
AAWDDSLNGP V                                                       11

SEQ ID NO: 673          moltype = DNA  length = 1374
FEATURE                 Location/Qualifiers
misc_feature            1..1374
                        note = Synthetic
source                  1..1374
                        mol_type = other DNA
                        organism = synthetic construct
SEQUENCE: 673
gaggtgcagc tggtggagtc tgggggaggc ttggtacagc ctggagggtc cctgagactc  60
tcctgtacag cctctggatt caccttcagt aattatgaaa tgaactgggt ccgccaggct  120
ccagggaagg ggctggagtg ggtttcatac attagtagta ggagtggtag taccctacac  180
tacgcagact ctgtgaaggg ccgattcacc atctccagag acaacgccaa gaactcactg  240
tatctgcaaa tgaacagcct gagagccgag gacacggctg tttattactg tgcgagaagg  300
ggcgatggta ccagctccct aatccaccac tactactaca tggacgtctg gggcaaaggg  360
accacggtca ccgtctcctc agcctccacc aagggcccat cggtcttccc cctggcaccc  420
tcctccaaga gcacctctgg gggcacagcg gccctgggct gcctggtcaa ggactacttc  480
cccgaaccgg tgacggtgtc gtggaactca ggcgccctga ccagcggcgt gcacaccttc  540
ccggctgtcc tacagtcctc aggactctac tccctcagca gcgtggtgac cgtgccctcc  600
agcagcttgg gcacccagac ctacatctgc aacgtgaatc acaagcccag caacaccaag  660
gtggacaaga aagttgagcc caaatcttgt gacaaaactc acacatgccc accgtgccca  720
gcacctgaac tcctgggggg accgtcagtc ttcctcttcc ccccaaaacc caaggacacc  780
ctcatgatct cccggacccc tgaggtcaca tgcgtggtgg tggacgtgag ccacgaagac  840
cctgaggtca agttcaactg gtacgtggac ggcgtggagg tgcataatgc caagacaaag  900
ccgcgggagg agcagtacaa cagcacgtac cgtgtggtca gcgtcctcac cgtcctgcac  960
caggactggc tgaatggcaa ggagtacaag tgcaaggtct ccaacaaagc cctcccagcc  1020
cccatcgaga aaaccatctc caaagccaaa gggcagcccc gagaaccaca ggtgtacacc  1080
ctgcccccat cccgggatga gctgaccaag aaccaggtca gcctgacctg cctggtcaaa  1140
ggcttctatc ccagcgacat cgccgtggag tgggagagca atgggcagcc ggagaacaac  1200
tacaagacca cgcctcccgt gctggactcc gacggctcct tcttcctcta cagcaagctc  1260
accgtggaca agagcaggtg gcagcagggg aacgtcttct catgctccgt gatgcatgag  1320
gctctgcaca accactacac gcagaagtcc ctctccctgt ctccgggtaa atga        1374

SEQ ID NO: 674          moltype = AA  length = 457
FEATURE                 Location/Qualifiers
REGION                  1..457
                        note = Synthetic
source                  1..457
                        mol_type = protein
                        organism = synthetic construct
SEQUENCE: 674
EVQLVESGGG LVQPGGSLRL SCTASGFTFS NYEMNWVRQA PGKGLEWVSY ISSRSGSTLH  60
YADSVKGRFT ISRDNAKNSL YLQMNSLRAE DTAVYYCARR GDGTSSLIHH YYYMDVWGKG  120
TTVTVSSAST KGPSVFPLAP SSKSTSGGTA ALGCLVKDYF PEPVTVSWNS GALTSGVHTF  180
PAVLQSSGLY SLSSVVTVPS SSLGTQTYIC NVNHKPSNTK VDKKVEPKSC DKTHTCPPCP  240
APELLGGPSV FLFPPKPKDT LMISRTPEVT CVVVDVSHED PEVKFNWYVD GVEVHNAKTK  300
PREEQYNSTY RVVSVLTVLH QDWLNGKEYK CKVSNKALPA PIEKTISKAK GQPREPQVYT  360
LPPSRDELTK NQVSLTCLVK GFYPSDIAVE WESNGQPENN YKTTPPVLDS DGSFFLYSKL  420
TVDKSRWQQG NVFSCSVMHE ALHNHYTQKS LSLSPGK                           457

SEQ ID NO: 675          moltype = DNA  length = 651
FEATURE                 Location/Qualifiers
misc_feature            1..651
                        note = Synthetic
source                  1..651
                        mol_type = other DNA
                        organism = synthetic construct
SEQUENCE: 675
cagtctgtgc tgactcagcc accctcagcg tctgggaccc ccgggcagag ggtcaccatc  60
tcttgttctg gaagcagctc caacatcgga agtaatactg taaactggta ccaacagctc  120
ccaggaacgg cccccaaact cctcatctat agtaataatc agcggccctc aggggtccct  180
gaccgattct ctggctccaa gtctggcacc tcagcctccc tggccatcag tgggctccag  240
tctgaggatg aggctgatta ttactgtgca gcatgggatg acagcctgaa tggtccggta  300
ttcggcggag ggaccaagct gaccgtccta ggccagccca aggccgcccc ctccgtgacc  360
ctgttccccc cctcctccga ggagctgcag gccaacaagg ccaccctggt gtgcctgatc  420
tccgacttct accccggcgc cgtgaccgtg gcctggaagg ccgactcctc ccccgtgaag  480
gccggcgtgg agaccaccac cccctccaag cagtccaaca acaagtacgc cgcctcctcc  540
tacctgtccc tgacccccga gcagtggaag tcccaccggt cctactcctg ccaggtgacc  600
cacgagggct ccaccgtgga gaagaccgtg gcccccaccg agtgctcctg a           651
```

```
SEQ ID NO: 676          moltype = AA  length = 216
FEATURE                 Location/Qualifiers
REGION                  1..216
                        note = Synthetic
source                  1..216
                        mol_type = protein
                        organism = synthetic construct
SEQUENCE: 676
QSVLTQPPSA SGTPGQRVTI SCSGSSSNIG SNTVNWYQQL PGTAPKLLIY SNNQRPSGVP  60
DRFSGSKSGT SASLAISGLQ SEDEADYYCA AWDDSLNGPV FGGGTKLTVL GQPKAAPSVT  120
LFPPSSEELQ ANKATLVCLI SDFYPGAVTV AWKADSSPVK AGVETTTPSK QSNNKYAASS  180
YLSLTPEQWK SHRSYSCQVT HEGSTVEKTV APTECS                            216

SEQ ID NO: 677          moltype = DNA  length = 369
FEATURE                 Location/Qualifiers
misc_feature            1..369
                        note = Synthetic
source                  1..369
                        mol_type = other DNA
                        organism = synthetic construct
SEQUENCE: 677
caggtgcagc tggtgcagtc tggggctgag gtgaagaagc ctggggcctc agtgaaggtc  60
tcctgcaagg cttctggata catcttcacc ggctactata tgcactgggt gcgacaggcc  120
cctggacagg ggcttgagtg gatgggatgg atcaacccta acagtggtgg cgcaaactat  180
gcacagaagt ttcagggcag ggtcaccctg accagggaca cgtccatcac cacagtctac  240
atggaactga gcaggctgag atttgacgac acggccgtgt attactgtgc gagaggatcc  300
cggtatgact ggaaccagaa caactggttc gacccctggg gccagggaac cctggtcacc  360
gtctcctca                                                          369

SEQ ID NO: 678          moltype = AA  length = 123
FEATURE                 Location/Qualifiers
REGION                  1..123
                        note = Synthetic
source                  1..123
                        mol_type = protein
                        organism = synthetic construct
SEQUENCE: 678
QVQLVQSGAE VKKPGASVKV SCKASGYIFT GYYMHWVRQA PGQGLEWMGW INPNSGGANY  60
AQKFQGRVTL TRDTSITTVY MELSRLRFDD TAVYYCARGS RYDWNQNNWF DPWGQGTLVT  120
VSS                                                                123

SEQ ID NO: 679          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 679
ggatacatct tcaccggcta ctat                                         24

SEQ ID NO: 680          moltype = AA  length = 8
FEATURE                 Location/Qualifiers
REGION                  1..8
                        note = Synthetic
source                  1..8
                        mol_type = protein
                        organism = synthetic construct
SEQUENCE: 680
GYIFTGYY                                                           8

SEQ ID NO: 681          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 681
atcaacccta acagtggtgg cgca                                         24

SEQ ID NO: 682          moltype = AA  length = 8
FEATURE                 Location/Qualifiers
REGION                  1..8
                        note = Synthetic
source                  1..8
                        mol_type = protein
                        organism = synthetic construct
```

```
SEQUENCE: 682
INPNSGGA                                                          8

SEQ ID NO: 683          moltype = DNA  length = 48
FEATURE                 Location/Qualifiers
misc_feature            1..48
                        note = Synthetic
source                  1..48
                        mol_type = other DNA
                        organism = synthetic construct
SEQUENCE: 683
gcgagaggat cccggtatga ctggaaccag aacaactggt tcgacccc              48

SEQ ID NO: 684          moltype = AA  length = 16
FEATURE                 Location/Qualifiers
REGION                  1..16
                        note = Synthetic
source                  1..16
                        mol_type = protein
                        organism = synthetic construct
SEQUENCE: 684
ARGSRYDWNQ NNWFDP                                                 16

SEQ ID NO: 685          moltype = DNA  length = 330
FEATURE                 Location/Qualifiers
misc_feature            1..330
                        note = Synthetic
source                  1..330
                        mol_type = other DNA
                        organism = synthetic construct
SEQUENCE: 685
cagtctgccc tgactcagcc tgcctccgtg tctgggtctc ctggacagtc gatcaccatc  60
tcctgcactg gaaccagcag tgacgttggt acttataact atgtctcctg gtaccaacaa  120
cacccaggca aagcccccaa actcatgatt tttgatgtca gtaatcggcc ctcaggggtt  180
tctgatcgct tctctggctc caagtctggc aacacggcct ccctgaccat ctctgggctc  240
caggctgagg acgaggctga ttattactgc agctcattta caaccagcag cactgtggtt  300
ttcggcggag ggaccaagct gaccgtccta                                  330

SEQ ID NO: 686          moltype = AA  length = 110
FEATURE                 Location/Qualifiers
REGION                  1..110
                        note = Synthetic
source                  1..110
                        mol_type = protein
                        organism = synthetic construct
SEQUENCE: 686
QSALTQPASV SGSPGQSITI SCTGTSSDVG TYNYVSWYQQ HPGKAPKLMI FDVSNRPSGV  60
SDRFSGSKSG NTASLTISGL QAEDEADYYC SSFTTSSTVV FGGGTKLTVL            110

SEQ ID NO: 687          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 687
agcagtgacg ttggtactta taactat                                     27

SEQ ID NO: 688          moltype = AA  length = 9
FEATURE                 Location/Qualifiers
REGION                  1..9
                        note = Synthetic
source                  1..9
                        mol_type = protein
                        organism = synthetic construct
SEQUENCE: 688
SSDVGTYNY                                                         9

SEQ ID NO: 689          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 689
agctcattta caaccagcag cactgtggtt                                  30
```

```
SEQ ID NO: 690          moltype = AA  length = 10
FEATURE                 Location/Qualifiers
REGION                  1..10
                        note = Synthetic
source                  1..10
                        mol_type = protein
                        organism = synthetic construct
SEQUENCE: 690
SSFTTSSTVV                                                        10

SEQ ID NO: 691          moltype = DNA  length = 1362
FEATURE                 Location/Qualifiers
misc_feature            1..1362
                        note = Synthetic
source                  1..1362
                        mol_type = other DNA
                        organism = synthetic construct
SEQUENCE: 691
caggtgcagc tggtgcagtc tggggctgag gtgaagaagc ctggggcctc agtgaaggtc  60
tcctgcaagg cttctggata catcttcacc ggctactata tgcactgggt gcgacaggcc  120
cctggacagg ggcttgagtg gatgggatgg atcaacccta acagtggtgg cgcaaactat  180
gcacagaagt ttcagggcag ggtcaccctg accagggaca cgtccatcac cacagtctac  240
atggaactga gcaggctgag atttgacgac acggccgtgt attactgtgc gagaggatcc  300
cggtatgact ggaaccagaa caactggttc gacccctggg gccagggaac cctggtcacc  360
gtctcctcag cctccaccaa gggcccatcg gtcttccccc tggcaccctc ctccaagagc  420
acctctgggg gcacagcggc cctgggctgc ctggtcaagg actacttccc cgaaccggtg  480
acggtgtcgt ggaactcagg cgccctgacc agcggcgtgc acaccttccc ggctgtccta  540
cagtcctcag gactctactc cctcagcagc gtggtgaccg tgccctccag cagcttgggc  600
acccagacct acatctgcaa cgtgaatcac aagcccagca acaccaaggt ggacaagaaa  660
gttgagccca aatcttgtga caaaactcac acatgcccac cgtgcccagc acctgaactc  720
ctggggggac cgtcagtctt cctcttcccc ccaaaaccca aggacaccct catgatctcc  780
cggacccctg aggtcacatg cgtggtggtg gacgtgagcc acgaagaccc tgaggtcaag  840
ttcaactggt acgtggacgg cgtggaggtg cataatgcca agacaaagcc gcgggaggag  900
cagtacaaca gcacgtaccg tgtggtcagc gtcctcaccg tcctgcacca ggactggctg  960
aatggcaagg agtacaagtg caaggtctcc aacaaagccc tcccagcccc catcgagaaa  1020
accatctcca aagccaaagg gcagccccga gaaccacagg tgtacaccct gcccccatcc  1080
cgggatgagc tgaccaagaa ccaggtcagc ctgacctgcc tggtcaaagg cttctatccc  1140
agcgacatcg ccgtggagtg ggagagcaat gggcagccgg agaacaacta caagaccacg  1200
cctcccgtgc tggactccga cggctccttc ttcctctaca gcaagctcac cgtggacaag  1260
agcaggtggc agcaggggaa cgtcttctca tgctccgtga tgcatgaggc tctgcacaac  1320
cactacacgc agaagtccct ctccctgtct ccgggtaaat ga                    1362

SEQ ID NO: 692          moltype = AA  length = 453
FEATURE                 Location/Qualifiers
REGION                  1..453
                        note = Synthetic
source                  1..453
                        mol_type = protein
                        organism = synthetic construct
SEQUENCE: 692
QVQLVQSGAE VKKPGASVKV SCKASGYIFT GYYMHWVRQA PGQGLEWMGW INPNSGGANY  60
AQKFQGRVTL TRDTSITTVY MELSRLRFDD TAVYYCARGS RYDWNQNNWF DPWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
LGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                               453

SEQ ID NO: 693          moltype = DNA  length = 651
FEATURE                 Location/Qualifiers
misc_feature            1..651
                        note = Synthetic
source                  1..651
                        mol_type = other DNA
                        organism = synthetic construct
SEQUENCE: 693
cagtctgccc tgactcagcc tgcctccgtg tctgggtctc ctggacagtc gatcaccatc  60
tcctgcactg gaaccagcag tgacgttggt acttataact atgtctcctg gtaccaacaa  120
cacccaggca aagcccccaa actcatgatt tttgatgtca gtaatcggcc ctcaggggtt  180
tctgatcgct tctctggctc caagtctggc aacacggcct ccctgaccat ctctgggctc  240
caggctgagg acgaggctga ttattactgc agctcattta caaccagcag cactgtggtt  300
ttcggcggag ggaccaagct gaccgtccta ggccagccca aggccgcccc ctccgtgacc  360
ctgttccccc cctcctccga ggagctgcag gccaacaagg ccaccctggt gtgcctgatc  420
tccgacttct accccggcgc cgtgaccgtg gcctggaagg ccgactcctc ccccgtgaag  480
gccggcgtgg agaccaccac cccctccaag cagtccaaca acaagtacgc cgcctcctcc  540
tacctgtccc tgacccccga gcagtggaag tcccaccggt cctactcctg ccaggtgacc  600
cacgagggct ccaccgtgga gaagaccgtg gcccccaccg agtgctcctg a           651
```

-continued

```
SEQ ID NO: 694          moltype = AA  length = 216
FEATURE                 Location/Qualifiers
REGION                  1..216
                        note = Synthetic
source                  1..216
                        mol_type = protein
                        organism = synthetic construct
SEQUENCE: 694
QSALTQPASV SGSPGQSITI SCTGTSSDVG TYNYVSWYQQ HPGKAPKLMI FDVSNRPSGV  60
SDRFSGSKSG NTASLTISGL QAEDEADYYC SSFTTSSTVV FGGGTKLTVL GQPKAAPSVT  120
LFPPSSEELQ ANKATLVCLI SDFYPGAVTV AWKADSSPVK AGVETTTPSK QSNNKYAASS  180
YLSLTPEQWK SHRSYSCQVT HEGSTVEKTV APTECS                            216

SEQ ID NO: 695          moltype = DNA  length = 1338
FEATURE                 Location/Qualifiers
misc_feature            1..1338
                        note = Synthetic
source                  1..1338
                        mol_type = other DNA
                        organism = synthetic construct
SEQUENCE: 695
gaggtgcagc tggtggagtc tgggggaggc ttggtccagc ctggggggtc cctgagactc  60
tcctgtgcag cctctggact caccgtcaat cgcaactaca tgagctgggt ccgccaggct  120
ccagggaagg ggctggagtg ggtctcactt atttatagcg gtggtagcac atactacgca  180
gactccgtta agggccgatt caccatctcc agagacaatt ccaagaacac gctgtatctt  240
caaatgaaca gcctgagact tgaggacacg gctgtgtatt actgtgcgag aggtgaactg  300
gggatcccct acggtatgga cgtctggggc caagggacca cggtcaccgt ctcctcagcc  360
tccaccaagg gcccatcggt cttccccctg gcgccctgct ccaggagcac ctccgagagc  420
acagccgccc tgggctgcct ggtcaaggac tacttccccg aaccggtgac ggtgtcgtgg  480
aactcaggcg ccctgaccag cggcgtgcac accttcccgg ctgtcctaca gtcctcagga  540
ctctactccc tcagcagcgt ggtgaccgtg ccctccagca gcttgggcac gaagacctac  600
acctgcaacg tagatcacaa gcccagcaac accaaggtgg acaagagagt tgagtccaaa  660
tatggtcccc catgcccacc gtgcccagca ccaggcggtg gcggaccatc agtcttcctg  720
ttccccccaa aacccaagga cactctcatg atctcccgga cccctgaggt cacgtgcgtg  780
gtggtggacg tgagccagga agaccccgag gtccagttca actggtacgt ggatggcgtg  840
gaggtgcata atgccaagac aaagccgcgg gaggagcagt tcaacagcac gtaccgtgtg  900
gtcagcgtcc tcaccgtcct gcaccaggac tggctgaacg gcaaggagta caagtgcaag  960
gtctccaaca aaggcctccc gtcctccatc gagaaaacca tctccaaagc caaagggcag  1020
ccccgagagc cacaggtgta caccctgccc ccatcccagg aggagatgac caagaaccag  1080
gtcagcctga cctgcctggt caaaggcttc taccccagcg acatcgccgt ggagtgggag  1140
agcaatgggc agccggagaa caactacaag accacgcctc ccgtgctgga ctccgacggc  1200
tccttcttcc tctacagcag gctcaccgtg gacaagagca ggtggcagga ggggaatgtc  1260
ttctcatgct ccgtgatgca tgaggctctg cacaaccact acacacagaa gtccctctcc  1320
ctgtctctgg gtaaatga                                                1338

SEQ ID NO: 696          moltype = AA  length = 445
FEATURE                 Location/Qualifiers
REGION                  1..445
                        note = Synthetic
source                  1..445
                        mol_type = protein
                        organism = synthetic construct
SEQUENCE: 696
EVQLVESGGG LVQPGGSLRL SCAASGLTVN RNYMSWVRQA PGKGLEWVSL IYSGGSTYYA  60
DSVKGRFTIS RDNSKNTLYL QMNSLRLEDT AVYYCARGEL GIPYGMDVWG QGTTVTVSSA  120
STKGPSVFPL APCSRSTSES TAALGCLVKD YFPEPVTVSW NSGALTSGVH TFPAVLQSSG  180
LYSLSSVVTV PSSSLGTKTY TCNVDHKPSN TKVDKRVESK YGPPCPPCPA PGGGGPSVFL  240
FPPKPKDTLM ISRTPEVTCV VVDVSQEDPE VQFNWYVDGV EVHNAKTKPR EEQFNSTYRV  300
VSVLTVLHQD WLNGKEYKCK VSNKGLPSSI EKTISKAKGQ PREPQVYTLP PSQEEMTKNQ  360
VSLTCLVKGF YPSDIAVEWE SNGQPENNYK TTPPVLDSDG SFFLYSRLTV DKSRWQEGNV  420
FSCSVMHEAL HNHYTQKSLS LSLGK                                        445

SEQ ID NO: 697          moltype = DNA  length = 1365
FEATURE                 Location/Qualifiers
misc_feature            1..1365
                        note = Synthetic
source                  1..1365
                        mol_type = other DNA
                        organism = synthetic construct
SEQUENCE: 697
gaagtgcagc tggtggagtc tgggggaggc ttggtacagc ctggcaggtc cctgagactc  60
tcctgtgcag cctctggatt cacctttgat gattatgcca tgcactgggt ccggcaagct  120
ccagggaagg gcctggagtg ggtctcaggt attagttgga ataggggtag cataggctat  180
gcggactctg tgaagggccg attcaccatc tccagagaca acgccaagaa ctccctgtat  240
ctgcaaatga gcagtctgag agctgaggac acggccttgt attactgcgc aaaagatggc  300
gagagatggg atagtgtagt agtaccatct gctaggaacg gtatggacgt ctggggccaa  360
gggaccacgg tcaccgtctc ctcagcctcc accaagggcc catcggtctt ccccctggcg  420
ccctgctcca ggagcacctc cgagagcaca gccgccctgg gctgcctggt caaggactac  480
ttccccgaac cggtgacggt gtcgtggaac tcaggcgccc tgaccagcgg cgtgcacacc  540
```

-continued

```
ttcccggctg tcctacagtc ctcaggactc tactccctca gcagcgtggt gaccgtgccc  600
tccagcagct tgggcacgaa gacctacacc tgcaacgtag atcacaagcc cagcaacacc  660
aaggtggaca agagagttga gtccaaatat ggtcccccat gcccaccgtg cccagcacca  720
ggcggtggcg gaccatcagt cttcctgttc cccccaaaac ccaaggacac tctcatgatc  780
tcccggaccc ctgaggtcac gtgcgtggtg gtggacgtga gccaggaaga ccccgaggtc  840
cagttcaact ggtacgtgga tggcgtggag gtgcataatg ccaagacaaa gccgcgggag  900
gagcagttca acagcacgta ccgtgtggtc agcgtcctca ccgtcctgca ccaggactgg  960
ctgaacggca aggagtacaa gtgcaaggtc tccaacaaag gcctcccgtc ctccatcgag  1020
aaaaccatct ccaaagccaa agggcagccc cgagagccac aggtgtacac cctgccccca  1080
tcccaggagg agatgaccaa gaaccaggtc agcctgacct gcctggtcaa aggcttctac  1140
cccagcgaca tcgccgtgga gtgggagagc aatgggcagc cggagaacaa ctacaagacc  1200
acgcctcccg tgctggactc cgacggctcc ttcttcctct acagcaggct caccgtggac  1260
aagagcaggt ggcaggaggg gaatgtcttc tcatgctccg tgatgcatga ggctctgcac  1320
aaccactaca cacagaagtc cctctccctg tctctgggta aatga                 1365

SEQ ID NO: 698          moltype = AA  length = 454
FEATURE                 Location/Qualifiers
REGION                  1..454
                        note = Synthetic
source                  1..454
                        mol_type = protein
                        organism = synthetic construct
SEQUENCE: 698
EVQLVESGGG LVQPGRSLRL SCAASGFTFD DYAMHWVRQA PGKGLEWVSG ISWNRGSIGY  60
ADSVKGRFTI SRDNAKNSLY LQMSSLRAED TALYYCAKDG ERWDSVVVPS ARNGMDVWGQ  120
GTTVTVSSAS TKGPSVFPLA PCSRSTSEST AALGCLVKDY FPEPVTVSWN SGALTSGVHT  180
FPAVLQSSGL YSLSSVVTVP SSSLGTKTYT CNVDHKPSNT KVDKRVESKY GPPCPPCPAP  240
GGGGPSVFLF PPKPKDTLMI SRTPEVTCVV VDVSQEDPEV QFNWYVDGVE VHNAKTKPRE  300
EQFNSTYRVV SVLTVLHQDW LNGKEYKCKV SNKGLPSSIE KTISKAKGQP REPQVYTLPP  360
SQEEMTKNQV SLTCLVKGFY PSDIAVEWES NGQPENNYKT TPPVLDSDGS FFLYSRLTVD  420
KSRWQEGNVF SCSVMHEALH NHYTQKSLSL SLGK                            454

SEQ ID NO: 699          moltype = DNA  length = 1338
FEATURE                 Location/Qualifiers
misc_feature            1..1338
                        note = Synthetic
source                  1..1338
                        mol_type = other DNA
                        organism = synthetic construct
SEQUENCE: 699
gaggtgcagc tggtggagtc tgggggaggc ttggtccagc ctgggggtc cctgagactc  60
tcctgtgcag cctctgaatt caccgtcagt agcaactaca tgagctgggt ccgccaggct  120
ccagggaagg ggctagagtg ggtctcagtt atttatagcg gtggtagcac attttacgca  180
gactccgtga agggcagatt caccatctcc agagacaatt ccaagaacac gttgtatctt  240
caaatgaaca gtctgagagc cgaggacacg gctgtatatt actgtgcgag agctcttccc  300
tacggtgact tgcattttga ctactggggc cagggaaccc tggtcaccgt ctcctcagcc  360
tccaccaagg gcccatcggt cttccccctg gcgccctgct ccaggagcac ctccgagagc  420
acagccgccc tgggctgcct ggtcaaggac tacttccccg aaccggtgac ggtgtcgtgg  480
aactcaggcg ccctgaccag cggcgtgcac accttcccgg ctgtcctaca gtcctcagga  540
ctctactccc tcagcagcgt ggtgaccgtg ccctccagca gcttgggcac gaagacctac  600
acctgcaacg tagatcacaa gcccagcaac accaaggtgg acaagagagt tgagtccaaa  660
tatggtcccc catgcccacc gtgcccagca ccaggcggtg gcggaccatc agtcttcctg  720
ttccccccaa aacccaagga cactctcatg atctcccgga cccctgaggt cacgtgcgtg  780
gtggtggacg tgagccagga agaccccgag gtccagttca actggtacgt ggatggcgtg  840
gaggtgcata atgccaagac aaagccgcgg gaggagcagt tcaacagcac gtaccgtgtg  900
gtcagcgtcc tcaccgtcct gcaccaggac tggctgaacg gcaaggagta caagtgcaag  960
gtctccaaca aaggcctccc gtcctccatc gagaaaacca tctccaaagc caaagggcag  1020
ccccgagagc cacaggtgta caccctgccc ccatcccagg aggagatgac caagaaccag  1080
gtcagcctga cctgcctggt caaaggcttc taccccagcg acatcgccgt ggagtgggag  1140
agcaatgggc agccggagaa caactacaag accacgcctc ccgtgctgga ctccgacggc  1200
tccttcttcc tctacagcag gctcaccgtg gacaagagca ggtggcagga ggggaatgtc  1260
ttctcatgct ccgtgatgca tgaggctctg cacaaccact acacacagaa gtccctctcc  1320
ctgtctctgg gtaaatga                                                1338

SEQ ID NO: 700          moltype = AA  length = 445
FEATURE                 Location/Qualifiers
REGION                  1..445
                        note = Synthetic
source                  1..445
                        mol_type = protein
                        organism = synthetic construct
SEQUENCE: 700
EVQLVESGGG LVQPGGSLRL SCAASEFTVS SNYMSWVRQA PGKGLEWVSV IYSGGSTFYA  60
DSVKGRFTIS RDNSKNTLYL QMNSLRAEDT AVYYCARALP YGDLHFDYWG QGTLVTVSSA  120
STKGPSVFPL APCSRSTSES TAALGCLVKD YFPEPVTVSW NSGALTSGVH TFPAVLQSSG  180
LYSLSSVVTV PSSSLGTKTY TCNVDHKPSN TKVDKRVESK YGPPCPPCPA PGGGGPSVFL  240
FPPKPKDTLM ISRTPEVTCV VVDVSQEDPE VQFNWYVDGV EVHNAKTKPR EEQFNSTYRV  300
VSVLTVLHQD WLNGKEYKCK VSNKGLPSSI EKTISKAKGQ PREPQVYTLP PSQEEMTKNQ  360
VSLTCLVKGF YPSDIAVEWE SNGQPENNYK TTPPVLDSDG SFFLYSRLTV DKSRWQEGNV  420
```

```
FSCSVMHEAL HNHYTQKSLS LSLGK                                      445

SEQ ID NO: 701         moltype = DNA  length = 1341
FEATURE                Location/Qualifiers
misc_feature           1..1341
                       note = Synthetic
source                 1..1341
                       mol_type = other DNA
                       organism = synthetic construct
SEQUENCE: 701
caggtgcagc tggtggagtc tgggggaggc gtggtccagc ctgggaggtc cctgagactc  60
tcctgtgcag cctctggatt caccttcagt aactatgcta tgtactgggt ccgccaggct  120
ccaggcaagg ggctggagtg ggtggcagtt atatcatatg atggaagtaa taaatactat  180
gcagactccg tgaagggccg attcaccatc tccagagaca attccaagaa cacgctgtat  240
ctgcaaatga acagcctgag aactgaggac acggctgtgt attactgtgc gagtggctcc  300
gactacggtg actacttatt ggtttactgg ggccagggaa ccctggtcac cgtctcctca  360
gcctccacca agggcccatc ggtcttcccc ctggcgccct gctccaggag cacctccgag  420
agcacagccg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacgaagacc  600
tacacctgca acgtagatca caagcccagc aacaccaagg tggacaagag agttgagtcc  660
aaatatggtc ccccatgccc accgtgccca gcaccaggcg gtggcggacc atcagtcttc  720
ctgttccccc caaaacccaa ggacactctc atgatctccc ggacccctga ggtcacgtgc  780
gtggtggtgg acgtgagcca ggaagacccc gaggtccagt tcaactggta cgtggatggc  840
gtggaggtgc ataatgccaa gacaaagccg cgggaggagc agttcaacag cacgtaccgt  900
gtggtcagcg tcctcaccgt cctgcaccag gactggctga acggcaagga gtacaagtgc  960
aaggtctcca acaaaggcct cccgtcctcc atcgagaaaa ccatctccaa agccaaaggg  1020
cagccccgag agccacaggt gtacaccctg cccccatccc aggaggagat gaccaagaac  1080
caggtcagcc tgacctgcct ggtcaaaggc ttctacccca gcgacatcgc cgtggagtgg  1140
gagagcaatg ggcagccgga gaacaactac aagaccacgc ctcccgtgct ggactccgac  1200
ggctccttct tcctctacag caggctcacc gtggacaaga gcaggtggca ggaggggaat  1260
gtcttctcat gctccgtgat gcatgaggct ctgcacaacc actacacaca gaagtccctc  1320
tccctgtctc tgggtaaatg a                                          1341

SEQ ID NO: 702         moltype = AA  length = 446
FEATURE                Location/Qualifiers
REGION                 1..446
                       note = Synthetic
source                 1..446
                       mol_type = protein
                       organism = synthetic construct
SEQUENCE: 702
QVQLVESGGG VVQPGRSLRL SCAASGFTFS NYAMYWVRQA PGKGLEWVAV ISYDGSNKYY  60
ADSVKGRFTI SRDNSKNTLY LQMNSLRTED TAVYYCASGS DYGDYLLVYW GQGTLVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APGGGGPSVF  240
LFPPKPKDTL MISRTPEVTC VVVDVSQEDP EVQFNWYVDG VEVHNAKTKP REEQFNSTYR  300
VVSVLTVLHQ DWLNGKEYKC KVSNKGLPSS IEKTISKAKG QPREPQVYTL PPSQEEMTKN  360
QVSLTCLVKG FYPSDIAVEW ESNGQPENNY KTTPPVLDSD GSFFLYSRLT VDKSRWQEGN  420
VFSCSVMHEA LHNHYTQKSL SLSLGK                                     446

SEQ ID NO: 703         moltype = DNA  length = 1362
FEATURE                Location/Qualifiers
misc_feature           1..1362
                       note = Synthetic
source                 1..1362
                       mol_type = other DNA
                       organism = synthetic construct
SEQUENCE: 703
gaggtgcagc tggtggagtc tgggggaggc ttggtacagc ctggagggtc cctgagactc  60
tcctgtacag cctctggatt caccttcagt aattatgaaa tgaactgggt ccgccaggct  120
ccagggaagg ggctggagtg ggtttcatac attagtagta ggagtggtag taccctacac  180
tacgcagact ctgtgaaggg ccgattcacc atctccagag acaacgccaa gaactcactg  240
tatctgcaaa tgaacagcct gagagccgag gacacggctg tttattactg tgcgagaagg  300
ggcgatggta ccagctccct aatccaccac tactactaca tggacgtctg gggcaaaggg  360
accacggtca ccgtctcctc agcctccacc aagggcccat cggtcttccc cctggcgccc  420
tgctccagga gcacctccga gagcacagcc gccctgggct gcctggtcaa ggactacttc  480
cccgaaccgg tgacggtgtc gtggaactca ggcgccctga ccagcggcgt gcacaccttc  540
ccggctgtcc tacagtcctc aggactctac tccctcagca gcgtggtgac cgtgccctcc  600
agcagcttgg gcacgaagac ctacacctgc aacgtagatc acaagcccag caacaccaag  660
gtggacaaga gagttgagtc caaatatggt cccccatgcc caccgtgccc agcaccaggc  720
ggtggcggac catcagtctt cctgttcccc ccaaaaccca aggacactct catgatctcc  780
cggacccctg aggtcacgtg cgtggtggtg gacgtgagcc aggaagaccc cgaggtccag  840
ttcaactggt acgtggatgg cgtggaggtg cataatgcca agacaaagcc gcgggaggag  900
cagttcaaca gcacgtaccg tgtggtcagc gtcctcaccg tcctgcacca ggactggctg  960
aacggcaagg agtacaagtg caaggtctcc aacaaaggcc tcccgtcctc catcgagaaa  1020
accatctcca aagccaaagg gcagccccga gagccacagg tgtacaccct gcccccatcc  1080
caggaggaga tgaccaagaa ccaggtcagc ctgacctgcc tggtcaaagg cttctacccc  1140
agcgacatcg ccgtggagtg ggagagcaat gggcagccgg agaacaacta caagaccacg  1200
```

```
cctcccgtgc tggactccga cggctccttc ttcctctaca gcaggctcac cgtggacaag  1260
agcaggtggc aggaggggaa tgtcttctca tgctccgtga tgcatgaggc tctgcacaac  1320
cactacacac agaagtccct ctccctgtct ctgggtaaat ga                     1362

SEQ ID NO: 704         moltype = AA  length = 453
FEATURE                Location/Qualifiers
REGION                 1..453
                       note = Synthetic
source                 1..453
                       mol_type = protein
                       organism = synthetic construct
SEQUENCE: 704
EVQLVESGGG LVQPGGSLRL SCTASGFTFS NYEMNWVRQA PGKGLEWVSY ISSRSGSTLH  60
YADSVKGRFT ISRDNAKNSL YLQMNSLRAE DTAVYYCARR GDGTSSLIHH YYYMDVWGKG  120
TTVTVSSAST KGPSVFPLAP CSRSTSESTA ALGCLVKDYF PEPVTVSWNS GALTSGVHTF  180
PAVLQSSGLY SLSSVVTVPS SSLGTKTYTC NVDHKPSNTK VDKRVESKYG PPCPPCPAPG  240
GGGPSVFLFP PKPKDTLMIS RTPEVTCVVV DVSQEDPEVQ FNWYVDGVEV HNAKTKPREE  300
QFNSTYRVVS VLTVLHQDWL NGKEYKCKVS NKGLPSSIEK TISKAKGQPR EPQVYTLPPS  360
QEEMTKNQVS LTCLVKGFYP SDIAVEWESN GQPENNYKTT PPVLDSDGSF FLYSRLTVDK  420
SRWQEGNVFS CSVMHEALHN HYTQKSLSLS LGK                               453

SEQ ID NO: 705         moltype = DNA  length = 1350
FEATURE                Location/Qualifiers
misc_feature           1..1350
                       note = Synthetic
source                 1..1350
                       mol_type = other DNA
                       organism = synthetic construct
SEQUENCE: 705
caggtgcagc tggtgcagtc tggggctgag gtgaagaagc ctggggcctc agtgaaggtc  60
tcctgcaagg cttctggata catcttcacc ggctactata tgcactgggt gcgacaggcc  120
cctggacagg ggcttgagtg gatgggatgg atcaacccta acagtggtgg cgcaaactat  180
gcacagaagt ttcagggcag ggtcaccctg accagggaca cgtccatcac cacagtctac  240
atggaactga gcaggctgag atttgacgac acggccgtgt attactgtgc gagaggatcc  300
cggtatgact ggaaccagaa caactggttc gacccctggg gccagggaac cctggtcacc  360
gtctcctcag cctccaccaa gggcccatcg gtcttccccc tggcgccctg ctccaggagc  420
acctccgaga gcacagccgc cctgggctgc ctggtcaagg actacttccc cgaaccggtg  480
acggtgtcgt ggaactcagg cgccctgacc agcggcgtgc acaccttccc ggctgtccta  540
cagtcctcag gactctactc cctcagcagc gtggtgaccg tgccctccag cagcttgggc  600
acgaagacct acacctgcaa cgtagatcac aagcccagca acaccaaggt ggacaagaga  660
gttgagtcca aatatggtcc cccatgccca ccgtgcccag caccaggcgg tggcggacca  720
tcagtcttcc tgttcccccc aaaacccaag gacactctca tgatctcccg gacccctgag  780
gtcacgtgcg tggtggtgga cgtgagccag gaagaccccg aggtccagtt caactggtac  840
gtggatggcg tggaggtgca taatgccaag acaaagccgc gggaggagca gttcaacagc  900
acgtaccgtg tggtcagcgt cctcaccgtc ctgcaccagg actggctgaa cggcaaggag  960
tacaagtgca aggtctccaa caaaggcctc ccgtcctcca tcgagaaaac catctccaaa  1020
gccaaagggc agccccgaga gccacaggtg tacaccctgc ccccatccca ggaggagatg  1080
accaagaacc aggtcagcct gacctgcctg gtcaaaggct tctaccccag cgacatcgcc  1140
gtggagtggg agagcaatgg gcagccggag aacaactaca agaccacgcc tcccgtgctg  1200
gactccgacg gctccttctt cctctacagc aggctcaccg tggacaagag caggtggcag  1260
gaggggaatg tcttctcatg ctccgtgatg catgaggctc tgcacaacca ctacacacag  1320
aagtccctct ccctgtctct gggtaaatga                                   1350

SEQ ID NO: 706         moltype = AA  length = 449
FEATURE                Location/Qualifiers
REGION                 1..449
                       note = Synthetic
source                 1..449
                       mol_type = protein
                       organism = synthetic construct
SEQUENCE: 706
QVQLVQSGAE VKKPGASVKV SCKASGYIFT GYYMHWVRQA PGQGLEWMGW INPNSGGANY  60
AQKFQGRVTL TRDTSITTVY MELSRLRFDD TAVYYCARGS RYDWNQNNWF DPWGQGTLVT  120
VSSASTKGPS VFPLAPCSRS TSESTAALGC LVKDYFPEPV TVSWNSGALT SGVHTFPAVL  180
QSSGLYSLSS VVTVPSSSLG TKTYTCNVDH KPSNTKVDKR VESKYGPPCP PCPAPGGGGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
TKNQVSLTCL VKGFYPSDIA VEWESNGQPE NNYKTTPPVL DSDGSFFLYS RLTVDKSRWQ  420
EGNVFSCSVM HEALHNHYTQ KSLSLSLGK                                    449

SEQ ID NO: 707         moltype = DNA  length = 351
FEATURE                Location/Qualifiers
misc_feature           1..351
                       note = Synthetic
source                 1..351
                       mol_type = other DNA
                       organism = synthetic construct
SEQUENCE: 707
gaggtgcaga tggtggagtc tggaggaggc ttggtccagc ctgggggtc cctgagactc  60
```

```
tcctgtgcag cctctgggtt caccgtcagt agtaactaca tgacctgggt ccgccaggct  120
ccagggaagg ggctggagtg ggtctcagtt atttatagcg gtggtagcac atactacgca  180
gactccgtga agggccgatt caccatctcc agacacaatt ccaagaacac gctgtatctt  240
caaatgaaca gcctgagagc tgaggacacg gccgtgtatt actgtgcgag agatggggta  300
tcctacggta tggacgtctg gggccaaggg accacggtca ccgtctcctc a           351

SEQ ID NO: 708         moltype = AA  length = 117
FEATURE                Location/Qualifiers
REGION                 1..117
                       note = Synthetic
source                 1..117
                       mol_type = protein
                       organism = synthetic construct
SEQUENCE: 708
EVQMVESGGG LVQPGGSLRL SCAASGFTVS SNYMTWVRQA PGKGLEWVSV IYSGGSTYYA  60
DSVKGRFTIS RHNSKNTLYL QMNSLRAEDT AVYYCARDGV SYGMDVWGQG TTVTVSS     117

SEQ ID NO: 709         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 709
gggttcaccg tcagtagtaa ctac                                         24

SEQ ID NO: 710         moltype = DNA  length = 33
FEATURE                Location/Qualifiers
misc_feature           1..33
                       note = Synthetic
source                 1..33
                       mol_type = other DNA
                       organism = synthetic construct
SEQUENCE: 710
gcgagagatg gggtatccta cggtatggac gtc                               33

SEQ ID NO: 711         moltype = AA  length = 11
FEATURE                Location/Qualifiers
REGION                 1..11
                       note = Synthetic
source                 1..11
                       mol_type = protein
                       organism = synthetic construct
SEQUENCE: 711
ARDGVSYGMD V                                                       11

SEQ ID NO: 712         moltype = DNA  length = 324
FEATURE                Location/Qualifiers
misc_feature           1..324
                       note = Synthetic
source                 1..324
                       mol_type = other DNA
                       organism = synthetic construct
SEQUENCE: 712
gacatccaga tgacccagtc tccatcctcc ctgtctgcat ctgtaggaga cagagtcacc  60
atcacttgcc gggcaagtca gagcattagc agctatttaa attggtatca gcagaaacca  120
gggaaagccc ctaagctcct gatctatgct gcatccagtt tgcaaagtgg ggtcccgtca  180
aggttcagtg gcagtggatc tgggacagat ttcactctca ccatcagcag tctgcaacct  240
gaagattttg caacttacta ctgtcaacag agttacagta cccctccgat caccttcggc  300
caagggacac gactggagat taaa                                         324

SEQ ID NO: 713         moltype = AA  length = 108
FEATURE                Location/Qualifiers
REGION                 1..108
                       note = Synthetic
source                 1..108
                       mol_type = protein
                       organism = synthetic construct
SEQUENCE: 713
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SYSTPPITFG QGTRLEIK               108

SEQ ID NO: 714         moltype = DNA  length = 30
FEATURE                Location/Qualifiers
misc_feature           1..30
                       note = Synthetic
source                 1..30
                       mol_type = other DNA
```

```
                         organism = synthetic construct
SEQUENCE: 714
caacagagtt acagtacccc tccgatcacc                                   30

SEQ ID NO: 715           moltype = AA  length = 10
FEATURE                  Location/Qualifiers
REGION                   1..10
                         note = Synthetic
source                   1..10
                         mol_type = protein
                         organism = synthetic construct
SEQUENCE: 715
QQSYSTPPIT                                                         10

SEQ ID NO: 716           moltype = DNA  length = 1344
FEATURE                  Location/Qualifiers
misc_feature             1..1344
                         note = Synthetic
source                   1..1344
                         mol_type = other DNA
                         organism = synthetic construct
SEQUENCE: 716
gaggtgcaga tggtggagtc tggaggaggc ttggtccagc ctgggggggtc cctgagactc  60
tcctgtgcag cctctgggtt caccgtcagt agtaactaca tgacctgggt ccgccaggct  120
ccagggaagg ggctggagtg ggtctcagtt atttatagcg gtggtagcac atactacgca  180
gactccgtga agggccgatt caccatctcc agacacaatt ccaagaacac gctgtatctt  240
caaatgaaca gcctgagagc tgaggacacg gccgtgtatt actgtgcgag agatggggta  300
tcctacggta tggacgtctg gggccaaggg accacggtca ccgtctcctc agcctccacc  360
aagggcccat cggtcttccc cctggcaccc tcctccaaga gcacctctgg gggcacagcg  420
gccctgggct gcctggtcaa ggactacttc cccgaaccgg tgacggtgtc gtggaactca  480
ggcgccctga ccagcggcgt gcacaccttc ccggctgtcc tacagtcctc aggactctac  540
tccctcagca gcgtggtgac cgtgccctcc agcagcttgg gcacccagac ctacatctgc  600
aacgtgaatc acaagcccag caacaccaag gtggacaaga aagttgagcc caaatcttgt  660
gacaaaactc acacatgccc accgtgccca gcacctgaac tcctgggggg accgtcagtc  720
ttcctcttcc ccccaaaacc caaggacacc ctcatgatct cccggacccc tgaggtcaca  780
tgcgtggtgg tggacgtgag ccacgaagac cctgaggtca agttcaactg gtacgtggac  840
ggcgtggagg tgcataatgc caagacaaag ccgcgggagg agcagtacaa cagcacgtac  900
cgtgtggtca gcgtcctcac cgtcctgcac caggactggc tgaatggcaa ggagtacaag  960
tgcaaggtct ccaacaaagc cctcccagcc cccatcgaga aaaccatctc caaagccaaa  1020
gggcagcccc gagaaccaca ggtgtacacc ctgcccccat cccgggatga gctgaccaag  1080
aaccaggtca gcctgacctg cctggtcaaa ggcttctatc ccagcgacat cgccgtggag  1140
tgggagagca atgggcagcc ggagaacaac tacaagacca cgcctcccgt gctggactcc  1200
gacggctcct tcttcctcta cagcaagctc accgtggaca agagcaggtg gcagcagggg  1260
aacgtcttct catgctccgt gatgcatgag gctctgcaca accactacac gcagaagtcc  1320
ctctccctgt ctccgggtaa atga                                         1344

SEQ ID NO: 717           moltype = AA  length = 447
FEATURE                  Location/Qualifiers
REGION                   1..447
                         note = Synthetic
source                   1..447
                         mol_type = protein
                         organism = synthetic construct
SEQUENCE: 717
EVQMVESGGG LVQPGGSLRL SCAASGFTVS SNYMTWVRQA PGKGLEWVSV IYSGGSTYYA  60
DSVKGRFTIS RHNSKNTLYL QMNSLRAEDT AVYYCARDGV SYGMDVWGQG TTVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APELLGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSRDELTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPGK                                      447

SEQ ID NO: 718           moltype = DNA  length = 648
FEATURE                  Location/Qualifiers
misc_feature             1..648
                         note = Synthetic
source                   1..648
                         mol_type = other DNA
                         organism = synthetic construct
SEQUENCE: 718
gacatccaga tgacccagtc tccatcctcc ctgtctgcat ctgtaggaga cagagtcacc  60
atcacttgcc gggcaagtca gagcattagc agctatttaa attggtatca gcagaaacca  120
gggaaagccc ctaagctcct gatctatgct gcatccagtt tgcaaagtgg ggtcccgtca  180
aggttcagtg gcagtggatc tgggacagat ttcactctca ccatcagcag tctgcaacct  240
gaagattttg caacttacta ctgtcaacag agttacagta cccctccgat caccttcggc  300
caagggacac gactggagat taaacgaact gtggctgcac catctgtctt catcttcccg  360
ccatctgatg agcagttgaa atctggaact gcctctgttg tgtgcctgct gaataacttc  420
tatcccagag aggccaaagt acagtggaag gtggataacg ccctccaatc gggtaactcc  480
```

-continued

```
caggagagtg tcacagagca ggacagcaag gacagcacct acagcctcag cagcaccctg  540
acgctgagca aagcagacta cgagaaacac aaagtctacg cctgcgaagt cacccatcag  600
ggcctgagct cgcccgtcac aaagagcttc aacaggggag agtgttag               648

SEQ ID NO: 719          moltype = AA  length = 215
FEATURE                 Location/Qualifiers
REGION                  1..215
                        note = Synthetic
source                  1..215
                        mol_type = protein
                        organism = synthetic construct
SEQUENCE: 719
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SYSTPPITFG QGTRLEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 720          moltype = DNA  length = 1332
FEATURE                 Location/Qualifiers
misc_feature            1..1332
                        note = Synthetic
source                  1..1332
                        mol_type = other DNA
                        organism = synthetic construct
SEQUENCE: 720
gaggtgcaga tggtggagtc tggaggaggc ttggtccagc ctgggggggtc cctgagactc  60
tcctgtgcag cctctgggtt caccgtcagt agtaactaca tgacctgggt ccgccaggct  120
ccagggaagg ggctggagtg ggtctcagtt atttatagcg gtggtagcac atactacgca  180
gactccgtga agggccgatt caccatctcc agacacaatt ccaagaacac gctgtatctt  240
caaatgaaca gcctgagagc tgaggacacg gccgtgtatt actgtgcgag agatggggta  300
tcctacggta tggacgtctg gggccaaggg accacggtca ccgtctcctc agcctccacc  360
aagggcccat cggtcttccc cctggcgccc tgctccagga gcacctccga gagcacagcc  420
gccctgggct gcctggtcaa ggactacttc cccgaaccgg tgacggtgtc gtggaactca  480
ggcgccctga ccagcggcgt gcacaccttc ccggctgtcc tacagtcctc aggactctac  540
tccctcagca gcgtggtgac cgtgccctcc agcagcttgg gcacgaagac ctacacctgc  600
aacgtagatc acaagcccag caacaccaag gtggacaaga gagttgagtc caaatatggt  660
cccccatgcc caccgtgccc agcaccaggc ggtggcggac catcagtctt cctgttcccc  720
ccaaaaccca aggacactct catgatctcc cggacccctg aggtcacgtg cgtggtggtg  780
gacgtgagcc aggaagaccc cgaggtccag ttcaactggt acgtggatgg cgtggaggtg  840
cataatgcca agacaaagcc gcgggaggag cagttcaaca gcacgtaccg tgtggtcagc  900
gtcctcaccg tcctgcacca ggactggctg aacggcaagg agtacaagtg caaggtctcc  960
aacaaaggcc tcccgtcctc catcgagaaa accatctcca aagccaaagg gcagccccga  1020
gagccacagg tgtacaccct gcccccatcc caggaggaga tgaccaagaa ccaggtcagc  1080
ctgacctgcc tggtcaaagg cttctacccc agcgacatcg ccgtggagtg ggagagcaat  1140
gggcagccgg agaacaacta caagaccacg cctcccgtgc tggactccga cggctccttc  1200
ttcctctaca gcaggctcac cgtggacaag agcaggtggc aggaggggaa tgtcttctca  1260
tgctccgtga tgcatgaggc tctgcacaac cactacacac agaagtccct ctccctgtct  1320
ctgggtaaat ga                                                      1332

SEQ ID NO: 721          moltype = AA  length = 443
FEATURE                 Location/Qualifiers
REGION                  1..443
                        note = Synthetic
source                  1..443
                        mol_type = protein
                        organism = synthetic construct
SEQUENCE: 721
EVQMVESGGG LVQPGGSLRL SCAASGFTVS SNYMTWVRQA PGKGLEWVSV IYSGGSTYYA  60
DSVKGRFTIS RHNSKNTLYL QMNSLRAEDT AVYYCARDGV SYGMDVWGQG TTVTVSSAST  120
KGPSVFPLAP CSRSTSESTA ALGCLVKDYF PEPVTVSWNS GALTSGVHTF PAVLQSSGLY  180
SLSSVVTVPS SSLGTKTYTC NVDHKPSNTK VDKRVESKYG PPCPPCPAPG GGGPSVFLFP  240
PKPKDTLMIS RTPEVTCVVV DVSQEDPEVQ FNWYVDGVEV HNAKTKPREE QFNSTYRVVS  300
VLTVLHQDWL NGKEYKCKVS NKGLPSSIEK TISKAKGQPR EPQVYTLPPS QEEMTKNQVS  360
LTCLVKGFYP SDIAVEWESN GQPENNYKTT PPVLDSDGSF FLYSRLTVDK SRWQEGNVFS  420
CSVMHEALHN HYTQKSLSLS LGK                                          443

SEQ ID NO: 722          moltype = DNA  length = 357
FEATURE                 Location/Qualifiers
misc_feature            1..357
                        note = Synthetic
source                  1..357
                        mol_type = other DNA
                        organism = synthetic construct
SEQUENCE: 722
gaggtgcagc tggtggagtc tggaggaggc ttggtccacc ctgggggggtc cctgagactc  60
tcctgtgcag cctctgggct caccgtcagt agcaactaca tgagctgggt ccgccaggct  120
ccagggaagg ggctggagtg ggtctcagtt atttatagcg gtggtagcac atactacgca  180
gactccgtga agggccgatt caccatctcc agacacaatt ccaagaacac gctgtttctt  240
caaatgaaca gcctgagagc tgaggacacg gccgtgtatt actgtgcgag agatcggcca  300
```

-continued

```
ataactggaa ccactttgga cgtctggggc caagggacca cggtcaccgt ctcctca     357

SEQ ID NO: 723         moltype = AA  length = 119
FEATURE                Location/Qualifiers
REGION                 1..119
                       note = Synthetic
source                 1..119
                       mol_type = protein
                       organism = synthetic construct
SEQUENCE: 723
EVQLVESGGG LVHPGGSLRL SCAASGLTVS SNYMSWVRQA PGKGLEWVSV IYSGGSTYYA  60
DSVKGRFTIS RHNSKNTLFL QMNSLRAEDT AVYYCARDRP ITGTTLDVWG QGTTVTVSS   119

SEQ ID NO: 724         moltype = DNA  length = 39
FEATURE                Location/Qualifiers
misc_feature           1..39
                       note = Synthetic
source                 1..39
                       mol_type = other DNA
                       organism = synthetic construct
SEQUENCE: 724
gcgagagatc ggccaataac tggaaccact ttggacgtc                         39

SEQ ID NO: 725         moltype = AA  length = 13
FEATURE                Location/Qualifiers
REGION                 1..13
                       note = Synthetic
source                 1..13
                       mol_type = protein
                       organism = synthetic construct
SEQUENCE: 725
ARDRPITGTT LDV                                                     13

SEQ ID NO: 726         moltype = DNA  length = 324
FEATURE                Location/Qualifiers
misc_feature           1..324
                       note = Synthetic
source                 1..324
                       mol_type = other DNA
                       organism = synthetic construct
SEQUENCE: 726
gacatccaga tgacccagtc tccatcctcc ctgtttgcat ctgtagggga cagagtcacc  60
atcacttgcc gggcaagtca gagcattagc agctatttaa attggtatca gcagaaacca  120
gggaaagccc ctaagctcct gatctatgct gcatccagtt tgcaaagtgg ggtcccatca  180
aggttcagtg gcagtggatc tgggacagat ttcactctca ccatcagcag tctgcaacct  240
gaagattttg cattttacta ctgtcaacag acttacagta cccctccgat caccttcggc  300
caagggacac gactggagat taaa                                         324

SEQ ID NO: 727         moltype = AA  length = 108
FEATURE                Location/Qualifiers
REGION                 1..108
                       note = Synthetic
source                 1..108
                       mol_type = protein
                       organism = synthetic construct
SEQUENCE: 727
DIQMTQSPSS LFASVGDRVT ITCRASQSIS SYLNWYQQKP GKAPKLLIYA ASSLQSGVPS  60
RFSGSGSGTD FTLTISSLQP EDFAFYYCQQ TYSTPPITFG QGTRLEIK               108

SEQ ID NO: 728         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 728
caacagactt acagtacccc tccgatcacc                                   30

SEQ ID NO: 729         moltype = AA  length = 10
FEATURE                Location/Qualifiers
REGION                 1..10
                       note = Synthetic
source                 1..10
                       mol_type = protein
                       organism = synthetic construct
SEQUENCE: 729
QQTYSTPPIT                                                         10
```

```
SEQ ID NO: 730          moltype = DNA  length = 1350
FEATURE                 Location/Qualifiers
misc_feature            1..1350
                        note = Synthetic
source                  1..1350
                        mol_type = other DNA
                        organism = synthetic construct
SEQUENCE: 730
gaggtgcagc tggtggagtc tggaggaggc ttggtccacc ctgggggggtc cctgagactc  60
tcctgtgcag cctctgggct caccgtcagt agcaactaca tgagctgggt ccgccaggct  120
ccagggaagg ggctggagtg ggtctcagtt atttatagcg gtggtagcac atactacgca  180
gactccgtga agggccgatt caccatctcc agacacaatt ccaagaacac gctgtttctt  240
caaatgaaca gcctgagagc tgaggacacg gccgtgtatt actgtgcgag agatcggcca  300
ataactggaa ccactttgga cgtctggggc caagggacca cggtcaccgt ctcctcagcc  360
tccaccaagg gcccatcggt cttccccctg gcaccctcct ccaagagcac ctctgggggc  420
acagcggccc tgggctgcct ggtcaaggac tacttccccg aaccggtgac ggtgtcgtgg  480
aactcaggcg ccctgaccag cggcgtgcac accttcccgg ctgtcctaca gtcctcagga  540
ctctactccc tcagcagcgt ggtgaccgtg ccctccagca gcttgggcac ccagacctac  600
atctgcaacg tgaatcacaa gcccagcaac accaaggtgg acaagaaagt tgagcccaaa  660
tcttgtgaca aaactcacac atgcccaccg tgcccagcac ctgaactcct ggggggaccg  720
tcagtcttcc tcttcccccc aaaacccaag gacaccctca tgatctcccg gacccctgag  780
gtcacatgcg tggtggtgga cgtgagccac gaagaccctg aggtcaagtt caactggtac  840
gtggacggcg tggaggtgca taatgccaag acaaagccgc gggaggagca gtacaacagc  900
acgtaccgtg tggtcagcgt cctcaccgtc ctgcaccagg actggctgaa tggcaaggag  960
tacaagtgca aggtctccaa caaagccctc ccagccccca tcgagaaaac catctccaaa  1020
gccaaagggc agccccgaga accacaggtg tacaccctgc ccccatcccg ggatgagctg  1080
accaagaacc aggtcagcct gacctgcctg gtcaaaggct tctatcccag cgacatcgcc  1140
gtggagtggg agagcaatgg gcagccggag aacaactaca agaccacgcc tcccgtgctg  1200
gactccgacg gctccttctt cctctacagc aagctcaccg tggacaagag caggtggcag  1260
caggggaacg tcttctcatg ctccgtgatg catgaggctc tgcacaacca ctacacgcag  1320
aagtccctct ccctgtctcc gggtaaatga                                  1350

SEQ ID NO: 731          moltype = AA  length = 449
FEATURE                 Location/Qualifiers
REGION                  1..449
                        note = Synthetic
source                  1..449
                        mol_type = protein
                        organism = synthetic construct
SEQUENCE: 731
EVQLVESGGG LVHPGGSLRL SCAASGLTVS SNYMSWVRQA PGKGLEWVSV IYSGGSTYYA  60
DSVKGRFTIS RHNSKNTLFL QMNSLRAEDT AVYYCARDRP ITGTTLDVWG QGTTVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                  449

SEQ ID NO: 732          moltype = DNA  length = 648
FEATURE                 Location/Qualifiers
misc_feature            1..648
                        note = Synthetic
source                  1..648
                        mol_type = other DNA
                        organism = synthetic construct
SEQUENCE: 732
gacatccaga tgacccagtc tccatcctcc ctgtttgcat ctgtagggga cagagtcacc  60
atcacttgcc gggcaagtca gagcattagc agctatttaa attggtatca gcagaaacca  120
gggaaagccc ctaagctcct gatctatgct gcatccagtt tgcaaagtgg ggtcccatca  180
aggttcagtg gcagtggatc tgggacagat ttcactctca ccatcagcag tctgcaacct  240
gaagattttg cattttacta ctgtcaacag acttacagta cccctccgat caccttcggc  300
caagggacac gactggagat taaacgaact gtggctgcac catctgtctt catcttcccg  360
ccatctgatg agcagttgaa atctggaact gcctctgttg tgtgcctgct gaataacttc  420
tatcccagag aggccaaagt acagtggaag gtggataacg ccctccaatc gggtaactcc  480
caggagagtg tcacagagca ggacagcaag gacagcacct acagcctcag cagcaccctg  540
acgctgagca aagcagacta cgagaaacac aaagtctacg cctgcgaagt cacccatcag  600
ggcctgagct cgcccgtcac aaagagcttc aacaggggag agtgttag              648

SEQ ID NO: 733          moltype = AA  length = 215
FEATURE                 Location/Qualifiers
REGION                  1..215
                        note = Synthetic
source                  1..215
                        mol_type = protein
                        organism = synthetic construct
SEQUENCE: 733
DIQMTQSPSS LFASVGDRVT ITCRASQSIS SYLNWYQQKP GKAPKLLIYA ASSLQSGVPS  60
RFSGSGSGTD FTLTISSLQP EDFAFYYCQQ TYSTPPITFG QGTRLEIKRT VAAPSVFIFP  120
```

```
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 734          moltype = DNA  length = 1338
FEATURE                 Location/Qualifiers
misc_feature            1..1338
                        note = Synthetic
source                  1..1338
                        mol_type = other DNA
                        organism = synthetic construct
SEQUENCE: 734
gaggtgcagc tggtggagtc tggaggaggc ttggtccacc ctggggggtc cctgagactc  60
tcctgtgcag cctctgggct caccgtcagt agcaactaca tgagctgggt ccgccaggct  120
ccagggaagg ggctggagtg ggtctcagtt atttatagcg gtggtagcac atactacgca  180
gactccgtga agggccgatt caccatctcc agacacaatt ccaagaacac gctgtttctt  240
caaatgaaca gcctgagagc tgaggacacg gccgtgtatt actgtgcgag agatcggcca  300
ataactggaa ccactttgga cgtctggggc caagggacca cggtcaccgt ctcctcagcc  360
tccaccaagg gcccatcggt cttccccctg gcgccctgct ccaggagcac ctccgagagc  420
acagccgccc tgggctgcct ggtcaaggac tacttccccg aaccggtgac ggtgtcgtgg  480
aactcaggcg ccctgaccag cggcgtgcac accttcccgg ctgtcctaca gtcctcagga  540
ctctactccc tcagcagcgt ggtgaccgtg ccctccagca gcttgggcac gaagacctac  600
acctgcaacg tagatcacaa gcccagcaac accaaggtgg acaagagagt tgagtccaaa  660
tatggtcccc catgcccacc gtgcccagca ccaggcggtg gcggaccatc agtcttcctg  720
ttccccccaa aacccaagga cactctcatg atctcccgga cccctgaggt cacgtgcgtg  780
gtggtggacg tgagccagga agaccccgag gtccagttca actggtacgt ggatggcgtg  840
gaggtgcata atgccaagac aaagccgcgg gaggagcagt tcaacagcac gtaccgtgtg  900
gtcagcgtcc tcaccgtcct gcaccaggac tggctgaacg gcaaggagta caagtgcaag  960
gtctccaaca aaggcctccc gtcctccatc gagaaaacca tctccaaagc caaagggcag  1020
ccccgagagc cacaggtgta caccctgccc ccatcccagg aggagatgac caagaaccag  1080
gtcagcctga cctgcctggt caaaggcttc taccccagcg acatcgccgt ggagtgggag  1140
agcaatgggc agccggagaa caactacaag accacgcctc ccgtgctgga ctccgacggc  1200
tccttcttcc tctacagcag gctcaccgtg gacaagagca ggtggcagga ggggaatgtc  1260
ttctcatgct ccgtgatgca tgaggctctg cacaaccact acacacagaa gtccctctcc  1320
ctgtctctgg gtaaatga                                                1338

SEQ ID NO: 735          moltype = AA  length = 445
FEATURE                 Location/Qualifiers
REGION                  1..445
                        note = Synthetic
source                  1..445
                        mol_type = protein
                        organism = synthetic construct
SEQUENCE: 735
EVQLVESGGG LVHPGGSLRL SCAASGLTVS SNYMSWVRQA PGKGLEWVSV IYSGGSTYYA  60
DSVKGRFTIS RHNSKNTLFL QMNSLRAEDT AVYYCARDRP ITGTTLDVWG QGTTVTVSSA  120
STKGPSVFPL APCSRSTSES TAALGCLVKD YFPEPVTVSW NSGALTSGVH TFPAVLQSSG  180
LYSLSSVVTV PSSSLGTKTY TCNVDHKPSN TKVDKRVESK YGPPCPPCPA PGGGGPSVFL  240
FPPKPKDTLM ISRTPEVTCV VVDVSQEDPE VQFNWYVDGV EVHNAKTKPR EEQFNSTYRV  300
VSVLTVLHQD WLNGKEYKCK VSNKGLPSSI EKTISKAKGQ PREPQVYTLP PSQEEMTKNQ  360
VSLTCLVKGF YPSDIAVEWE SNGQPENNYK TTPPVLDSDG SFFLYSRLTV DKSRWQEGNV  420
FSCSVMHEAL HNHYTQKSLS LSLGK                                        445

SEQ ID NO: 736          moltype = DNA  length = 351
FEATURE                 Location/Qualifiers
misc_feature            1..351
                        note = Synthetic
source                  1..351
                        mol_type = other DNA
                        organism = synthetic construct
SEQUENCE: 736
gaggtgcagc tggtggagtc tggaggaggc ttggtccagc ctggggggtc cctgagactc  60
tcctgtgcag cctctgggtt caccgtcagt agcaactaca tgaactgggt ccgccaggct  120
ccagggaagg ggctggagtg ggtctcagtt atttatagcg gtggtagcac attctacgca  180
gactccgtga ggggccgatt caccatctcc agacacaatt ccaagaacac gctgtatctt  240
caaatgaaca gcctgagagc tgaggacacg gccgtgtatt actgtgcgag agatgggagc  300
gcctacggta tggacgtctg gggccaaggg accacggtca ccgtctcctc a           351

SEQ ID NO: 737          moltype = AA  length = 117
FEATURE                 Location/Qualifiers
REGION                  1..117
                        note = Synthetic
source                  1..117
                        mol_type = protein
                        organism = synthetic construct
SEQUENCE: 737
EVQLVESGGG LVQPGGSLRL SCAASGFTVS SNYMNWVRQA PGKGLEWVSV IYSGGSTFYA  60
DSVRGRFTIS RHNSKNTLYL QMNSLRAEDT AVYYCARDGS AYGMDVWGQG TTVTVSS     117

SEQ ID NO: 738          moltype = DNA  length = 33
```

```
FEATURE                 Location/Qualifiers
misc_feature            1..33
                        note = Synthetic
source                  1..33
                        mol_type = other DNA
                        organism = synthetic construct
SEQUENCE: 738
gcgagagatg ggagcgccta cggtatggac gtc                               33

SEQ ID NO: 739          moltype = AA  length = 11
FEATURE                 Location/Qualifiers
REGION                  1..11
                        note = Synthetic
source                  1..11
                        mol_type = protein
                        organism = synthetic construct
SEQUENCE: 739
ARDGSAYGMD V                                                       11

SEQ ID NO: 740          moltype = DNA  length = 324
FEATURE                 Location/Qualifiers
misc_feature            1..324
                        note = Synthetic
source                  1..324
                        mol_type = other DNA
                        organism = synthetic construct
SEQUENCE: 740
gacatccaga tgacccagtc tccatcctcc ctgtctgcat ctgtaggaga cagagtcacc  60
atcacttgcc gggcaagtca gagcattagt agttttttaa attggtatca gcagaaacca  120
gggaaagccc ctaagctcct gatctatgct gcatccagtt tgcaaagtgg ggtcccatca  180
aggttcagtg gcagtggatc tgggacagat ttcactctca ccatcagcag tctgcaacct  240
gaagattttg caacttacta ctgtcaacag agttacagta gtcctccgat caccttcggc  300
caagggacac gactggagat taaa                                         324

SEQ ID NO: 741          moltype = AA  length = 108
FEATURE                 Location/Qualifiers
REGION                  1..108
                        note = Synthetic
source                  1..108
                        mol_type = protein
                        organism = synthetic construct
SEQUENCE: 741
DIQMTQSPSS LSASVGDRVT ITCRASQSIS SFLNWYQQKP GKAPKLLIYA ASSLQSGVPS  60
RFSGSGSGTD FTLTISSLQP EDFATYYCQQ SYSSPPITFG QGTRLEIK                108

SEQ ID NO: 742          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 742
cagagcatta gtagtttt                                                18

SEQ ID NO: 743          moltype = AA  length = 6
FEATURE                 Location/Qualifiers
REGION                  1..6
                        note = Synthetic
source                  1..6
                        mol_type = protein
                        organism = synthetic construct
SEQUENCE: 743
QSISSF                                                             6

SEQ ID NO: 744          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 744
caacagagtt acagtagtcc tccgatcacc                                   30

SEQ ID NO: 745          moltype = AA  length = 10
FEATURE                 Location/Qualifiers
REGION                  1..10
                        note = Synthetic
```

```
source                  1..10
                        mol_type = protein
                        organism = synthetic construct
SEQUENCE: 745
QQSYSSPPIT                                                10

SEQ ID NO: 746          moltype = DNA  length = 1344
FEATURE                 Location/Qualifiers
misc_feature            1..1344
                        note = Synthetic
source                  1..1344
                        mol_type = other DNA
                        organism = synthetic construct
SEQUENCE: 746
gaggtgcagc tggtggagtc tggaggaggc ttggtccagc ctggggggtc cctgagactc  60
tcctgtgcag cctctgggtt caccgtcagt agcaactaca tgaactgggt ccgccaggct  120
ccagggaagg ggctggagtg ggtctcagtt atttatagcg gtggtagcac attctacgca  180
gactccgtga ggggccgatt caccatctcc agacacaatt ccaagaacac gctgtatctt  240
caaatgaaca gcctgagagc tgaggacacg gccgtgtatt actgtgcgag agatgggagc  300
gcctacggta tggacgtctg gggccaaggg accacggtca ccgtctcctc agcctccacc  360
aagggcccat cggtcttccc cctggcaccc tcctccaaga gcacctctgg gggcacagcg  420
gccctgggct gcctggtcaa ggactacttc cccgaaccgg tgacggtgtc gtggaactca  480
ggcgccctga ccagcggcgt gcacaccttc ccggctgtcc tacagtcctc aggactctac  540
tccctcagca gcgtggtgac cgtgccctcc agcagcttgg gcacccagac ctacatctgc  600
aacgtgaatc acaagcccag caacaccaag gtggacaaga aagttgagcc caaatcttgt  660
gacaaaactc acacatgccc accgtgccca gcacctgaac tcctgggggg accgtcagtc  720
ttcctcttcc ccccaaaacc caaggacacc ctcatgatct cccggacccc tgaggtcaca  780
tgcgtggtgg tggacgtgag ccacgaagac cctgaggtca agttcaactg gtacgtggac  840
ggcgtggagg tgcataatgc caagacaaag ccgcgggagg agcagtacaa cagcacgtac  900
cgtgtggtca gcgtcctcac cgtcctgcac caggactggc tgaatggcaa ggagtacaag  960
tgcaaggtct ccaacaaagc cctcccagcc cccatcgaga aaaccatctc caaagccaaa  1020
gggcagcccc gagaaccaca ggtgtacacc ctgcccccat cccgggatga gctgaccaag  1080
aaccaggtca gcctgacctg cctggtcaaa ggcttctatc ccagcgacat cgccgtggag  1140
tgggagagca atgggcagcc ggagaacaac tacaagacca cgcctcccgt gctggactcc  1200
gacggctcct tcttcctcta cagcaagctc accgtggaca agagcaggtg gcagcagggg  1260
aacgtcttct catgctccgt gatgcatgag gctctgcaca accactacac gcagaagtcc  1320
ctctccctgt ctccgggtaa atga                                1344

SEQ ID NO: 747          moltype = AA  length = 447
FEATURE                 Location/Qualifiers
REGION                  1..447
                        note = Synthetic
source                  1..447
                        mol_type = protein
                        organism = synthetic construct
SEQUENCE: 747
EVQLVESGGG LVQPGGSLRL SCAASGFTVS SNYMNWVRQA PGKGLEWVSV IYSGGSTFYA  60
DSVRGRFTIS RHNSKNTLYL QMNSLRAEDT AVYYCARDGS AYGMDVWGQG TTVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APELLGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSRDELTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPGK                             447

SEQ ID NO: 748          moltype = DNA  length = 648
FEATURE                 Location/Qualifiers
misc_feature            1..648
                        note = Synthetic
source                  1..648
                        mol_type = other DNA
                        organism = synthetic construct
SEQUENCE: 748
gacatccaga tgacccagtc tccatcctcc ctgtctgcat ctgtaggaga cagagtcacc  60
atcacttgcc gggcaagtca gagcattagt agtttttttaa attggtatca gcagaaacca  120
gggaaagccc ctaagctcct gatctatgct gcatccagtt tgcaaagtgg ggtcccatca  180
aggttcagtg gcagtggatc tgggacagat ttcactctca ccatcagcag tctgcaacct  240
gaagattttg caacttacta ctgtcaacag agttacagta gtcctccgat caccttcggc  300
caagggacac gactggagat taaacgaact gtggctgcac catctgtctt catcttcccg  360
ccatctgatg agcagttgaa atctggaact gcctctgttg tgtgcctgct gaataacttc  420
tatcccagag aggccaaagt acagtggaag gtggataacg ccctccaatc gggtaactcc  480
caggagagtg tcacagagca ggacagcaag gacagcacct acagcctcag cagcaccctg  540
acgctgagca aagcagacta cgagaaacac aaagtctacg cctgcgaagt cacccatcag  600
ggcctgagct cgcccgtcac aaagagcttc aacaggggag agtgttag          648

SEQ ID NO: 749          moltype = AA  length = 215
FEATURE                 Location/Qualifiers
REGION                  1..215
                        note = Synthetic
```

```
source                  1..215
                        mol_type = protein
                        organism = synthetic construct
SEQUENCE: 749
DIQMTQSPSS LSASVGDRVT ITCRASQSIS SFLNWYQQKP GKAPKLLIYA ASSLQSGVPS  60
RFSGSGSGTD FTLTISSLQP EDFATYYCQQ SYSSPPITFG QGTRLEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 750          moltype = DNA  length = 1332
FEATURE                 Location/Qualifiers
misc_feature            1..1332
                        note = Synthetic
source                  1..1332
                        mol_type = other DNA
                        organism = synthetic construct
SEQUENCE: 750
gaggtgcagc tggtggagtc tggaggaggc ttggtccagc ctggggggtc cctgagactc  60
tcctgtgcag cctctgggtt caccgtcagt agcaactaca tgaactgggt ccgccaggct  120
ccagggaagg ggctggagtg ggtctcagtt atttatagcg gtggtagcac attctacgca  180
gactccgtga ggggccgatt caccatctcc agacacaatt ccaagaacac gctgtatctt  240
caaatgaaca gcctgagagc tgaggacacg gccgtgtatt actgtgcgag agatgggagc  300
gcctacggta tggacgtctg gggccaaggg accacggtca ccgtctcctc agcctccacc  360
aagggcccat cggtcttccc cctggcgccc tgctccagga gcacctccga gagcacagcc  420
gccctgggct gcctggtcaa ggactacttc cccgaaccgg tgacggtgtc gtggaactca  480
ggcgccctga ccagcggcgt gcacaccttc ccggctgtcc tacagtcctc aggactctac  540
tccctcagca gcgtggtgac cgtgccctcc agcagcttgg gcacgaagac ctacacctgc  600
aacgtagatc acaagcccag caacaccaag gtggacaaga gagttgagtc caaatatggt  660
cccccatgcc caccgtgccc agcaccaggc ggtggcggac catcagtctt cctgttcccc  720
ccaaaaccca aggacactct catgatctcc cggacccctg aggtcacgtg cgtggtggtg  780
gacgtgagcc aggaagaccc cgaggtccag ttcaactggt acgtggatgg cgtggaggtg  840
cataatgcca agacaaagcc gcgggaggag cagttcaaca gcacgtaccg tgtggtcagc  900
gtcctcaccg tcctgcacca ggactggctg aacggcaagg agtacaagtg caaggtctcc  960
aacaaaggcc tcccgtcctc catcgagaaa accatctcca aagccaaagg gcagccccga  1020
gagccacagg tgtacaccct gcccccatcc caggaggaga tgaccaagaa ccaggtcagc  1080
ctgacctgcc tggtcaaagg cttctacccc agcgacatcg ccgtggagtg ggagagcaat  1140
gggcagccgg agaacaacta caagaccacg cctcccgtgc tggactccga cggctccttc  1200
ttcctctaca gcaggctcac cgtggacaag agcaggtggc aggaggggaa tgtcttctca  1260
tgctccgtga tgcatgaggc tctgcacaac cactacacac agaagtccct ctccctgtct  1320
ctgggtaaat ga                                                      1332

SEQ ID NO: 751          moltype = AA  length = 443
FEATURE                 Location/Qualifiers
REGION                  1..443
                        note = Synthetic
source                  1..443
                        mol_type = protein
                        organism = synthetic construct
SEQUENCE: 751
EVQLVESGGG LVQPGGSLRL SCAASGFTVS SNYMNWVRQA PGKGLEWVSV IYSGGSTFYA  60
DSVRGRFTIS RHNSKNTLYL QMNSLRAEDT AVYYCARDGS AYGMDVWGQG TTVTVSSAST  120
KGPSVFPLAP CSRSTSESTA ALGCLVKDYF PEPVTVSWNS GALTSGVHTF PAVLQSSGLY  180
SLSSVVTVPS SSLGTKTYTC NVDHKPSNTK VDKRVESKYG PPCPPCPAPG GGGPSVFLFP  240
PKPKDTLMIS RTPEVTCVVV DVSQEDPEVQ FNWYVDGVEV HNAKTKPREE QFNSTYRVVS  300
VLTVLHQDWL NGKEYKCKVS NKGLPSSIEK TISKAKGQPR EPQVYTLPPS QEEMTKNQVS  360
LTCLVKGFYP SDIAVEWESN GQPENNYKTT PPVLDSDGSF FLYSRLTVDK SRWQEGNVFS  420
CSVMHEALHN HYTQKSLSLS LGK                                          443

SEQ ID NO: 752          moltype = DNA  length = 345
FEATURE                 Location/Qualifiers
misc_feature            1..345
                        note = Synthetic
source                  1..345
                        mol_type = other DNA
                        organism = synthetic construct
SEQUENCE: 752
gaggtgcagc tggtggagtc tggaggaggc ttggtccagc ctggggggtc cctgagactc  60
tcctgtgcag cctctgggtt caccgtcagt agcaactaca tgagctgggt ccgccaggct  120
ccagggaagg ggctggagtg ggtctcagtt atttatagcg gtggtagcac attctacgca  180
gactccgtga agggccgatt caccatctcc agacacaatt ccaagaacac gctgtatctt  240
caaatgaaca gcctgagagc tgaggacacg gccgtgtatt actgtgcgag agagggctac  300
ggtatggacg tctggggcca agggaccacg gtcaccgtct cctca                  345

SEQ ID NO: 753          moltype = AA  length = 115
FEATURE                 Location/Qualifiers
REGION                  1..115
                        note = Synthetic
source                  1..115
                        mol_type = protein
```

```
                        organism = synthetic construct
SEQUENCE: 753
EVQLVESGGG LVQPGGSLRL SCAASGFTVS SNYMSWVRQA PGKGLEWVSV IYSGGSTFYA  60
DSVKGRFTIS RHNSKNTLYL QMNSLRAEDT AVYYCAREGY GMDVWGQGTT VTVSS       115

SEQ ID NO: 754          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 754
gcgagagagg gctacggtat ggacgtc                                      27

SEQ ID NO: 755          moltype = AA  length = 9
FEATURE                 Location/Qualifiers
REGION                  1..9
                        note = Synthetic
source                  1..9
                        mol_type = protein
                        organism = synthetic construct
SEQUENCE: 755
AREGYGMDV                                                          9

SEQ ID NO: 756          moltype = DNA  length = 1338
FEATURE                 Location/Qualifiers
misc_feature            1..1338
                        note = Synthetic
source                  1..1338
                        mol_type = other DNA
                        organism = synthetic construct
SEQUENCE: 756
gaggtgcagc tggtggagtc tggaggaggc ttggtccagc ctgggggtc cctgagactc  60
tcctgtgcag cctctgggtt caccgtcagt agcaactaca tgagctgggt ccgccaggct  120
ccagggaagg ggctggagtg ggtctcagtt atttatagcg gtggtagcac attctacgca  180
gactccgtga agggccgatt caccatctcc agacacaatt ccaagaacac gctgtatctt  240
caaatgaaca gcctgagagc tgaggacacg gccgtgtatt actgtgcgag agagggctac  300
ggtatggacg tctggggcca agggaccacg gtcaccgtct cctcagcctc caccaagggc  360
ccatcggtct tccccctggc accctcctcc aagagcacct ctgggggcac agcggccctg  420
ggctgcctgg tcaaggacta cttccccgaa ccggtgacgg tgtcgtggaa ctcaggcgcc  480
ctgaccagcg gcgtgcacac cttcccggct gtcctacagt cctcaggact ctactccctc  540
agcagcgtgg tgaccgtgcc ctccagcagc ttgggcaccc agacctacat ctgcaacgtg  600
aatcacaagc ccagcaacac caaggtggac aagaaagttg agcccaaatc ttgtgacaaa  660
actcacacat gcccaccgtg cccagcacct gaactcctgg ggggaccgtc agtcttcctc  720
ttccccccaa aacccaagga caccctcatg atctcccgga cccctgaggt cacatgcgtg  780
gtggtggacg tgagccacga agaccctgag gtcaagttca actggtacgt ggacggcgtg  840
gaggtgcata atgccaagac aaagccgcgg gaggagcagt acaacagcac gtaccgtgtg  900
gtcagcgtcc tcaccgtcct gcaccaggac tggctgaatg gcaaggagta caagtgcaag  960
gtctccaaca aagccctccc agcccccatc gagaaaacca tctccaaagc caaagggcag  1020
ccccgagaac cacaggtgta caccctgccc ccatcccggg atgagctgac caagaaccag  1080
gtcagcctga cctgcctggt caaaggcttc tatcccagcg acatcgccgt ggagtgggag  1140
agcaatgggc agccggagaa caactacaag accacgcctc ccgtgctgga ctccgacggc  1200
tccttcttcc tctacagcaa gctcaccgtg gacaagagca ggtggcagca ggggaacgtc  1260
ttctcatgct ccgtgatgca tgaggctctg cacaaccact acacgcagaa gtccctctcc  1320
ctgtctccgg gtaaatga                                                1338

SEQ ID NO: 757          moltype = AA  length = 445
FEATURE                 Location/Qualifiers
REGION                  1..445
                        note = Synthetic
source                  1..445
                        mol_type = protein
                        organism = synthetic construct
SEQUENCE: 757
EVQLVESGGG LVQPGGSLRL SCAASGFTVS SNYMSWVRQA PGKGLEWVSV IYSGGSTFYA  60
DSVKGRFTIS RHNSKNTLYL QMNSLRAEDT AVYYCAREGY GMDVWGQGTT VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KKVEPKSCDK THTCPPCPAP ELLGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPGK                                        445

SEQ ID NO: 758          moltype = DNA  length = 1326
FEATURE                 Location/Qualifiers
misc_feature            1..1326
                        note = Synthetic
source                  1..1326
```

```
                        mol_type = other DNA
                        organism = synthetic construct
SEQUENCE: 758
gaggtgcagc tggtggagtc tggaggaggc ttggtccagc ctggggggtc cctgagactc  60
tcctgtgcag cctctgggtt caccgtcagt agcaactaca tgagctgggt ccgccaggct  120
ccagggaagg ggctggagtg ggtctcagtt atttatagcg gtggtagcac attctacgca  180
gactccgtga agggccgatt caccatctcc agacacaatt ccaagaacac gctgtatctt  240
caaatgaaca gcctgagagc tgaggacacg gccgtgtatt actgtgcgag agagggctac  300
ggtatggacg tctggggcca agggaccacg gtcaccgtct cctcagcctc caccaagggc  360
ccatcggtct tccccctggc gccctgctcc aggagcacct ccgagagcac agccgccctg  420
ggctgcctgg tcaaggacta cttccccgaa ccggtgacgg tgtcgtggaa ctcaggcgcc  480
ctgaccagcg gcgtgcacac cttcccggct gtcctacagt cctcaggact ctactccctc  540
agcagcgtgg tgaccgtgcc ctccagcagc ttgggcacga agacctacac ctgcaacgta  600
gatcacaagc ccagcaacac caaggtggac aagagagttg agtccaaata tggtccccca  660
tgcccaccgt gcccagcacc aggcggtggc ggaccatcag tcttcctgtt ccccccaaaa  720
cccaaggaca ctctcatgat ctcccggacc cctgaggtca cgtgcgtggt ggtggacgtg  780
agccaggaag accccgaggt ccagttcaac tggtacgtgg atggcgtgga ggtgcataat  840
gccaagacaa agccgcggga ggagcagttc aacagcacgt accgtgtggt cagcgtcctc  900
accgtcctgc accaggactg gctgaacggc aaggagtaca agtgcaaggt ctccaacaaa  960
ggcctcccgt cctccatcga gaaaaccatc tccaaagcca aagggcagcc ccgagagcca  1020
caggtgtaca ccctgcccc atcccaggag gagatgacca agaaccaggt cagcctgacc  1080
tgcctggtca aaggcttcta ccccagcgac atcgccgtgg agtgggagag caatgggcag  1140
ccggagaaca actacaagac cacgcctccc gtgctggact ccgacggctc cttcttcctc  1200
tacagcaggc tcaccgtgga caagagcagg tggcaggagg ggaatgtctt ctcatgctcc  1260
gtgatgcatg aggctctgca caaccactac acacagaagt ccctctccct gtctctgggt  1320
aaatga                                                              1326

SEQ ID NO: 759          moltype = AA  length = 441
FEATURE                 Location/Qualifiers
REGION                  1..441
                        note = Synthetic
source                  1..441
                        mol_type = protein
                        organism = synthetic construct
SEQUENCE: 759
EVQLVESGGG LVQPGGSLRL SCAASGFTVS SNYMSWVRQA PGKGLEWVSV IYSGGSTFYA  60
DSVKGRFTIS RHNSKNTLYL QMNSLRAEDT AVYYCAREGY GMDVWGQGTT VTVSSASTKG  120
PSVFPLAPCS RSTSESTAAL GCLVKDYFPE PVTVSWNSGA LTSGVHTFPA VLQSSGLYSL  180
SSVVTVPSSS LGTKTYTCNV DHKPSNTKVD KRVESKYGPP CPPCPAPGGG GPSVFLFPPK  240
PKDTLMISRT PEVTCVVVDV SQEDPEVQFN WYVDGVEVHN AKTKPREEQF NSTYRVVSVL  300
TVLHQDWLNG KEYKCKVSNK GLPSSIEKTI SKAKGQPREP QVYTLPPSQE EMTKNQVSLT  360
CLVKGFYPSD IAVEWESNGQ PENNYKTTPP VLDSDGSFFL YSRLTVDKSR WQEGNVFSCS  420
VMHEALHNHY TQKSLSLSLG K                                             441

SEQ ID NO: 760          moltype = DNA  length = 351
FEATURE                 Location/Qualifiers
misc_feature            1..351
                        note = Synthetic
source                  1..351
                        mol_type = other DNA
                        organism = synthetic construct
SEQUENCE: 760
gaggtgcagc tggtggagtc tggaggaggc ttggtccagc ctggggggtc cctgagactc  60
tcctgtgcag cctctgggtt aatagtcagt cgcaactaca tgatctgggt ccgccaggct  120
ccagggaagg ggctggagtg ggtctcagtt atttatagcg gtggtagcac attctacgca  180
gactccgtga agggccgatt caccatctcc agacacaatt ccaagaacac gctgtatctt  240
caaatgaaca gcctgagggc tgaggacacg gccgtatatt actgtgcgag agatctgggt  300
acaggaggta tggacgtctg gggccaaggg accacggtca ccgtctcctc a           351

SEQ ID NO: 761          moltype = DNA  length = 1344
FEATURE                 Location/Qualifiers
misc_feature            1..1344
                        note = Synthetic
source                  1..1344
                        mol_type = other DNA
                        organism = synthetic construct
SEQUENCE: 761
gaggtgcagc tggtggagtc tggaggaggc ttggtccagc ctggggggtc cctgagactc  60
tcctgtgcag cctctgggtt aatagtcagt cgcaactaca tgatctgggt ccgccaggct  120
ccagggaagg ggctggagtg ggtctcagtt atttatagcg gtggtagcac attctacgca  180
gactccgtga agggccgatt caccatctcc agacacaatt ccaagaacac gctgtatctt  240
caaatgaaca gcctgagggc tgaggacacg gccgtatatt actgtgcgag agatctgggt  300
acaggaggta tggacgtctg gggccaaggg accacggtca ccgtctcctc agcctccacc  360
aagggcccat cggtcttccc cctggcaccc tcctccaaga gcacctctgg gggcacagcg  420
gccctgggct gcctggtcaa ggactacttc cccgaaccgg tgacggtgtc gtggaactca  480
ggcgccctga ccagcggcgt gcacaccttc ccggctgtcc tacagtcctc aggactctac  540
tccctcagca gcgtggtgac cgtgccctcc agcagcttgg gcacccagac ctacatctgc  600
aacgtgaatc acaagcccag caacaccaag gtggacaaga aagttgagcc caaatcttgt  660
gacaaaactc acacatgccc accgtgccca gcacctgaac tcctgggggg accgtcagtc  720
```

-continued

```
ttcctcttcc ccccaaaacc caaggacacc ctcatgatct cccggacccc tgaggtcaca  780
tgcgtggtgg tggacgtgag ccacgaagac cctgaggtca agttcaactg gtacgtggac  840
ggcgtggagg tgcataatgc caagacaaag ccgcgggagg agcagtacaa cagcacgtac  900
cgtgtggtca gcgtcctcac cgtcctgcac caggactggc tgaatggcaa ggagtacaag  960
tgcaaggtct ccaacaaagc cctcccagcc cccatcgaga aaaccatctc caaagccaaa  1020
gggcagcccc gagaaccaca ggtgtacacc ctgcccccat cccgggatga gctgaccaag  1080
aaccaggtca gcctgacctg cctggtcaaa ggcttctatc ccagcgacat cgccgtggag  1140
tgggagagca atgggcagcc ggagaacaac tacaagacca cgcctcccgt gctggactcc  1200
gacggctcct tcttcctcta cagcaagctc accgtggaca agagcaggtg gcagcagggg  1260
aacgtcttct catgctccgt gatgcatgag gctctgcaca accactacac gcagaagtcc  1320
ctctccctgt ctccgggtaa atga                                          1344

SEQ ID NO: 762         moltype = AA  length = 447
FEATURE                Location/Qualifiers
REGION                 1..447
                       note = Synthetic
source                 1..447
                       mol_type = protein
                       organism = synthetic construct
SEQUENCE: 762
EVQLVESGGG LVQPGGSLRL SCAASGLIVS RNYMIWVRQA PGKGLEWVSV IYSGGSTFYA  60
DSVKGRFTIS RHNSKNTLYL QMNSLRAEDT AVYYCARDLG TGGMDVWGQG TTVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APELLGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSRDELTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPGK                                       447

SEQ ID NO: 763         moltype = DNA  length = 360
FEATURE                Location/Qualifiers
misc_feature           1..360
                       note = Synthetic
source                 1..360
                       mol_type = other DNA
                       organism = synthetic construct
SEQUENCE: 763
caggtgcagc tggtggagtc tgggggaggc gtggtccagc ctgggaggtc cctgagactc  60
tcctgtgtag cctctggatt caccttcagt atttatggca tggactgggt ccgccaggct  120
ccaggcaagg ggctggagtg ggtggcagtt atatcatatg atggaagtaa taaatactat  180
gcagactccg tgaagggccg attcaccatc tccagagaca attccaagaa cacgctgtat  240
ctgcaaatga acagcctgag acctgaggac acggctgtgt attactgtgc gaaagatagg  300
gaggcagctg cggatgcttt tgatatctgg ggccaaggga caatggtcac cgtctcttca  360

SEQ ID NO: 764         moltype = AA  length = 120
FEATURE                Location/Qualifiers
REGION                 1..120
                       note = Synthetic
source                 1..120
                       mol_type = protein
                       organism = synthetic construct
SEQUENCE: 764
QVQLVESGGG VVQPGRSLRL SCVASGFTFS IYGMDWVRQA PGKGLEWVAV ISYDGSNKYY  60
ADSVKGRFTI SRDNSKNTLY LQMNSLRPED TAVYYCAKDR EAAADAFDIW GQGTMVTVSS  120

SEQ ID NO: 765         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 765
ggattcacct tcagtattta tggc                                          24

SEQ ID NO: 766         moltype = AA  length = 8
FEATURE                Location/Qualifiers
REGION                 1..8
                       note = Synthetic
source                 1..8
                       mol_type = protein
                       organism = synthetic construct
SEQUENCE: 766
GFTFSIYG                                                            8

SEQ ID NO: 767         moltype = DNA  length = 39
FEATURE                Location/Qualifiers
misc_feature           1..39
                       note = Synthetic
```

```
source                  1..39
                        mol_type = other DNA
                        organism = synthetic construct
SEQUENCE: 767
gcgaaagata gggaggcagc tgcggatgct tttgatatc                    39

SEQ ID NO: 768          moltype = AA  length = 13
FEATURE                 Location/Qualifiers
REGION                  1..13
                        note = Synthetic
source                  1..13
                        mol_type = protein
                        organism = synthetic construct
SEQUENCE: 768
AKDREAAADA FDI                                                13

SEQ ID NO: 769          moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 769
gacatccaga tgacccagtc tccatcttcc gtgtctgcat ctgtaggaga cagagtcacc  60
atcacttgtc gggcgagtca gggtattagc agctggttag cctggtatca gcagaaacca  120
gggaaagccc ctaagctcct gatctatgct gcatccagtt tgcacagtgg ggtcccatca  180
aggttcagcg gcagtggatc tgggacagat ttcactctca ccatcagcag cctgcagcct  240
gaagattttg caacttacta ttgtcaacag gctaacagtt tccgtctcac tttcggcgga  300
gggaccaagg tggagatcaa a                                       321

SEQ ID NO: 770          moltype = AA  length = 107
FEATURE                 Location/Qualifiers
REGION                  1..107
                        note = Synthetic
source                  1..107
                        mol_type = protein
                        organism = synthetic construct
SEQUENCE: 770
DIQMTQSPSS VSASVGDRVT ITCRASQGIS SWLAWYQQKP GKAPKLLIYA ASSLHSGVPS  60
RFSGSGSGTD FTLTISSLQP EDFATYYCQQ ANSFRLTFGG GTKVEIK             107

SEQ ID NO: 771          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 771
caacaggcta acagtttccg tctcact                                 27

SEQ ID NO: 772          moltype = AA  length = 9
FEATURE                 Location/Qualifiers
REGION                  1..9
                        note = Synthetic
source                  1..9
                        mol_type = protein
                        organism = synthetic construct
SEQUENCE: 772
QQANSFRLT                                                     9

SEQ ID NO: 773          moltype = DNA  length = 1353
FEATURE                 Location/Qualifiers
misc_feature            1..1353
                        note = Synthetic
source                  1..1353
                        mol_type = other DNA
                        organism = synthetic construct
SEQUENCE: 773
caggtgcagc tggtggagtc tgggggaggc gtggtccagc ctgggaggtc cctgagactc  60
tcctgtgtag cctctggatt caccttcagt atttatggca tggactgggt ccgccaggct  120
ccaggcaagg ggctggagtg ggtggcagtt atatcatatg atggaagtaa taaatactat  180
gcagactccg tgaagggccg attcaccatc tccagagaca attccaagaa cacgctgtat  240
ctgcaaatga acagcctgag acctgaggac acggctgtgt attactgtgc gaaagatagg  300
gaggcagctg cggatgcttt tgatatctgg ggccaaggga caatggtcac cgtctcttca  360
gcctccacca agggcccatc ggtcttcccc ctggcaccct cctccaagag cacctctggg  420
ggcacagcgg ccctgggctg cctggtcaag gactacttcc ccgaaccggt gacggtgtcg  480
tggaactcag gcgccctgac cagcggcgtg cacaccttcc cggctgtcct acagtcctca  540
```

-continued

```
ggactctact ccctcagcag cgtggtgacc gtgccctcca gcagcttggg cacccagacc  600
tacatctgca acgtgaatca caagcccagc aacaccaagg tggacaagaa agttgagccc  660
aaatcttgtg acaaaactca cacatgccca ccgtgcccag cacctgaact cctgggggga  720
ccgtcagtct tcctcttccc cccaaaaccc aaggacaccc tcatgatctc ccggacccct  780
gaggtcacat gcgtggtggt ggacgtgagc cacgaagacc ctgaggtcaa gttcaactgg  840
tacgtggacg gcgtggaggt gcataatgcc aagacaaagc cgcgggagga gcagtacaac  900
agcacgtacc gtgtggtcag cgtcctcacc gtcctgcacc aggactggct gaatggcaag  960
gagtacaagt gcaaggtctc caacaaagcc ctcccagccc ccatcgagaa aaccatctcc  1020
aaagccaaag ggcagccccg agaaccacag gtgtacaccc tgcccccatc ccgggatgag  1080
ctgaccaaga accaggtcag cctgacctgc ctggtcaaag gcttctatcc cagcgacatc  1140
gccgtggagt gggagagcaa tgggcagccg gagaacaact acaagaccac gcctcccgtg  1200
ctggactccg acggctcctt cttcctctac agcaagctca ccgtggacaa gagcaggtgg  1260
cagcagggga acgtcttctc atgctccgtg atgcatgagg ctctgcacaa ccactacacg  1320
cagaagtccc tctccctgtc tccgggtaaa tga                               1353

SEQ ID NO: 774         moltype = AA  length = 450
FEATURE                Location/Qualifiers
REGION                 1..450
                       note = Synthetic
source                 1..450
                       mol_type = protein
                       organism = synthetic construct
SEQUENCE: 774
QVQLVESGGG VVQPGRSLRL SCVASGFTFS IYGMDWVRQA PGKGLEWVAV ISYDGSNKYY  60
ADSVKGRFTI SRDNSKNTLY LQMNSLRPED TAVYYCAKDR EAAADAFDIW GQGTMVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 775         moltype = DNA  length = 645
FEATURE                Location/Qualifiers
misc_feature           1..645
                       note = Synthetic
source                 1..645
                       mol_type = other DNA
                       organism = synthetic construct
SEQUENCE: 775
gacatccaga tgacccagtc tccatcttcc gtgtctgcat ctgtaggaga cagagtcacc  60
atcacttgtc gggcgagtca gggtattagc agctggttag cctggtatca gcagaaacca  120
gggaaagccc ctaagctcct gatctatgct gcatccagtt tgcacagtgg ggtcccatca  180
aggttcagcg gcagtggatc tgggacagat ttcactctca ccatcagcag cctgcagcct  240
gaagattttg caacttacta ttgtcaacag gctaacagtt tccgtctcac tttcggcgga  300
gggaccaagg tggagatcaa acgaactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttag                  645

SEQ ID NO: 776         moltype = AA  length = 214
FEATURE                Location/Qualifiers
REGION                 1..214
                       note = Synthetic
source                 1..214
                       mol_type = protein
                       organism = synthetic construct
SEQUENCE: 776
DIQMTQSPSS VSASVGDRVT ITCRASQGIS SWLAWYQQKP GKAPKLLIYA ASSLHSGVPS  60
RFSGSGSGTD FTLTISSLQP EDFATYYCQQ ANSFRLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 777         moltype = DNA  length = 1341
FEATURE                Location/Qualifiers
misc_feature           1..1341
                       note = Synthetic
source                 1..1341
                       mol_type = other DNA
                       organism = synthetic construct
SEQUENCE: 777
caggtgcagc tggtggagtc tgggggaggc gtggtccagc ctgggaggtc cctgagactc  60
tcctgtgtag cctctggatt caccttcagt atttatggca tggactgggt ccgccaggct  120
ccaggcaagg ggctggagtg ggtggcagtt atatcatatg atggaagtaa taaatactat  180
gcagactccg tgaagggccg attcaccatc tccagagaca attccaagaa cacgctgtat  240
ctgcaaatga acagcctgag acctgaggac acggctgtgt attactgtgc gaaagatagg  300
gaggcagctg cggatgcttt tgatatctgg ggccaaggga caatggtcac cgtctcttca  360
```

-continued

```
gcctccacca agggcccatc ggtcttcccc ctggcgccct gctccaggag cacctccgag  420
agcacagccg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacgaagacc  600
tacacctgca acgtagatca caagcccagc aacaccaagg tggacaagag agttgagtcc  660
aaatatggtc ccccatgccc accgtgccca gcaccaggcg gtggcggacc atcagtcttc  720
ctgttccccc caaaacccaa ggacactctc atgatctccc ggacccctga ggtcacgtgc  780
gtggtggtgg acgtgagcca ggaagacccc gaggtccagt tcaactggta cgtggatggc  840
gtggaggtgc ataatgccaa gacaaagccg cgggaggagc agttcaacag cacgtaccgt  900
gtggtcagcg tcctcaccgt cctgcaccag gactggctga acggcaagga gtacaagtgc  960
aaggtctcca acaaaggcct cccgtcctcc atcgagaaaa ccatctccaa agccaaaggg  1020
cagccccgag agccacaggt gtacaccctg cccccatccc aggaggagat gaccaagaac  1080
caggtcagcc tgacctgcct ggtcaaaggc ttctacccca gcgacatcgc cgtggagtgg  1140
gagagcaatg ggcagccgga gaacaactac aagaccacgc ctcccgtgct ggactccgac  1200
ggctccttct tcctctacag caggctcacc gtggacaaga gcaggtggca ggaggggaat  1260
gtcttctcat gctccgtgat gcatgaggct ctgcacaacc actacacaca gaagtccctc  1320
tccctgtctc tgggtaaatg a                                            1341

SEQ ID NO: 778          moltype = AA  length = 446
FEATURE                 Location/Qualifiers
REGION                  1..446
                        note = Synthetic
source                  1..446
                        mol_type = protein
                        organism = synthetic construct
SEQUENCE: 778
QVQLVESGGG VVQPGRSLRL SCVASGFTFS IYGMDWVRQA PGKGLEWVAV ISYDGSNKYY  60
ADSVKGRFTI SRDNSKNTLY LQMNSLRPED TAVYYCAKDR EAAADAFDIW GQGTMVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APGGGGPSVF  240
LFPPKPKDTL MISRTPEVTC VVVDVSQEDP EVQFNWYVDG VEVHNAKTKP REEQFNSTYR  300
VVSVLTVLHQ DWLNGKEYKC KVSNKGLPSS IEKTISKAKG QPREPQVYTL PPSQEEMTKN  360
QVSLTCLVKG FYPSDIAVEW ESNGQPENNY KTTPPVLDSD GSFFLYSRLT VDKSRWQEGN  420
VFSCSVMHEA LHNHYTQKSL SLSLGK                                      446

SEQ ID NO: 779          moltype = DNA  length = 348
FEATURE                 Location/Qualifiers
misc_feature            1..348
                        note = Synthetic
source                  1..348
                        mol_type = other DNA
                        organism = synthetic construct
SEQUENCE: 779
gaggtgcagc tggtggagtc tggaggaggc ttggtccagc ctgggggggtc cctgagactc  60
tcctgtgcag cctctgggtt cattgtcagt aggaactaca tgagctgggt ccgccaggct  120
ccagggaagg gactggagtg ggtctcagtt atttatagcg gtggtagcac attctacgca  180
gactccgtga agggccgctt caccatctcc cgacacaatt ccaagaacac gctgtatctt  240
caaatgaaca gcctgaaagc tgaggacacg gccgtgtatt actgtgcgag agagctacga  300
gggtactttg actactgggg ccagggaacc ctggtcaccg tctcctca               348

SEQ ID NO: 780          moltype = AA  length = 116
FEATURE                 Location/Qualifiers
REGION                  1..116
                        note = Synthetic
source                  1..116
                        mol_type = protein
                        organism = synthetic construct
SEQUENCE: 780
EVQLVESGGG LVQPGGSLRL SCAASGFIVS RNYMSWVRQA PGKGLEWVSV IYSGGSTFYA  60
DSVKGRFTIS RHNSKNTLYL QMNSLKAEDT AVYYCARELR GYFDYWGQGT LVTVSS      116

SEQ ID NO: 781          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 781
gggttcattg tcagtaggaa ctac                                         24

SEQ ID NO: 782          moltype = AA  length = 8
FEATURE                 Location/Qualifiers
REGION                  1..8
                        note = Synthetic
source                  1..8
                        mol_type = protein
                        organism = synthetic construct
SEQUENCE: 782
```

```
GFIVSRNY                                                    8

SEQ ID NO: 783          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 783
gcgagagagc tacgagggta ctttgactac                            30

SEQ ID NO: 784          moltype = AA  length = 10
FEATURE                 Location/Qualifiers
REGION                  1..10
                        note = Synthetic
source                  1..10
                        mol_type = protein
                        organism = synthetic construct
SEQUENCE: 784
ARELRGYFDY                                                  10

SEQ ID NO: 785          moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 785
gacatccagt tgacccagtc tccatccttc ctgtctgcat ctgtaggaga cagagtcacc  60
atcacttgct gggccagtca gggcattagc agttatttag cctggtatca gcaaaaacca  120
gggaaagccc ctaagctcct gatctatgct gcatccactt tgcaaagtgg ggtcccatca  180
aggttcagcg gcagtggatc tgggacagaa ttcactctca caatcagcag cctgcagcct  240
gaagattttg caacttatta ctgtcaactg cttaatagtt acccgtacac ttttggccag  300
gggaccaagc tggagatcaa a                                     321

SEQ ID NO: 786          moltype = AA  length = 107
FEATURE                 Location/Qualifiers
REGION                  1..107
                        note = Synthetic
source                  1..107
                        mol_type = protein
                        organism = synthetic construct
SEQUENCE: 786
DIQLTQSPSF LSASVGDRVT ITCWASQGIS SYLAWYQQKP GKAPKLLIYA ASTLQSGVPS  60
RFSGSGSGTE FTLTISSLQP EDFATYYCQL LNSYPYTFGQ GTKLEIK         107

SEQ ID NO: 787          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 787
caactgctta atagttaccc gtacact                               27

SEQ ID NO: 788          moltype = AA  length = 9
FEATURE                 Location/Qualifiers
REGION                  1..9
                        note = Synthetic
source                  1..9
                        mol_type = protein
                        organism = synthetic construct
SEQUENCE: 788
QLLNSYPYT                                                   9

SEQ ID NO: 789          moltype = DNA  length = 1341
FEATURE                 Location/Qualifiers
misc_feature            1..1341
                        note = Synthetic
source                  1..1341
                        mol_type = other DNA
                        organism = synthetic construct
SEQUENCE: 789
gaggtgcagc tggtggagtc tggaggaggc ttggtccagc ctgggggggtc cctgagactc  60
tcctgtgcag cctctgggtt cattgtcagt aggaactaca tgagctgggt ccgccaggct  120
ccagggaagg gactggagtg ggtctcagtt atttatagcg gtggtagcac attctacgca  180
```

```
gactccgtga agggccgctt caccatctcc cgacacaatt ccaagaacac gctgtatctt  240
caaatgaaca gcctgaaagc tgaggacacg gccgtgtatt actgtgcgag agagctacga  300
gggtactttg actactgggg ccagggaacc ctggtcaccg tctcctcagc ctccaccaag  360
ggcccatcgg tcttccccct ggcaccctcc tccaagagca cctctggggg cacagcggcc  420
ctgggctgcc tggtcaagga ctacttcccc gaaccggtga cggtgtcgtg gaactcaggc  480
gccctgacca gcggcgtgca caccttcccg gctgtcctac agtcctcagg actctactcc  540
ctcagcagcg tggtgaccgt gccctccagc agcttgggca cccagaccta catctgcaac  600
gtgaatcaca agcccagcaa caccaaggtg gacaagaaag ttgagcccaa atcttgtgac  660
aaaactcaca catgcccacc gtgcccagca cctgaactcc tggggggacc gtcagtcttc  720
ctcttccccc caaaacccaa ggacaccctc atgatctccc ggacccctga ggtcacatgc  780
gtggtggtgg acgtgagcca cgaagaccct gaggtcaagt tcaactggta cgtggacggc  840
gtggaggtgc ataatgccaa gacaaagccg cgggaggagc agtacaacag cacgtaccgt  900
gtggtcagcg tcctcaccgt cctgcaccag gactggctga atggcaagga gtacaagtgc  960
aaggtctcca acaaagccct cccagccccc atcgagaaaa ccatctccaa agccaaaggg  1020
cagccccgag aaccacaggt gtacaccctg cccccatccc gggatgagct gaccaagaac  1080
caggtcagcc tgacctgcct ggtcaaaggc ttctatccca gcgacatcgc cgtggagtgg  1140
gagagcaatg ggcagccgga gaacaactac aagaccacgc ctcccgtgct ggactccgac  1200
ggctccttct tcctctacag caagctcacc gtggacaaga gcaggtggca gcaggggaac  1260
gtcttctcat gctccgtgat gcatgaggct ctgcacaacc actacacgca gaagtccctc  1320
tccctgtctc cgggtaaatg a                                            1341

SEQ ID NO: 790          moltype = AA  length = 446
FEATURE                 Location/Qualifiers
REGION                  1..446
                        note = Synthetic
source                  1..446
                        mol_type = protein
                        organism = synthetic construct
SEQUENCE: 790
EVQLVESGGG LVQPGGSLRL SCAASGFIVS RNYMSWVRQA PGKGLEWVSV IYSGGSTFYA  60
DSVKGRFTIS RHNSKNTLYL QMNSLKAEDT AVYYCARELR GYFDYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSRDELTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGK                                      446

SEQ ID NO: 791          moltype = DNA  length = 645
FEATURE                 Location/Qualifiers
misc_feature            1..645
                        note = Synthetic
source                  1..645
                        mol_type = other DNA
                        organism = synthetic construct
SEQUENCE: 791
gacatccagt tgacccagtc tccatccttc ctgtctgcat ctgtaggaga cagagtcacc  60
atcacttgct gggccagtca gggcattagc agttatttag cctggtatca gcaaaaacca  120
gggaaagccc ctaagctcct gatctatgct gcatccactt tgcaaagtgg ggtcccatca  180
aggttcagcg gcagtggatc tgggacagaa ttcactctca caatcagcag cctgcagcct  240
gaagattttg caacttatta ctgtcaactg cttaatagtt acccgtacac ttttggccag  300
gggaccaagc tggagatcaa acgaactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttag                  645

SEQ ID NO: 792          moltype = AA  length = 214
FEATURE                 Location/Qualifiers
REGION                  1..214
                        note = Synthetic
source                  1..214
                        mol_type = protein
                        organism = synthetic construct
SEQUENCE: 792
DIQLTQSPSF LSASVGDRVT ITCWASQGIS SYLAWYQQKP GKAPKLLIYA ASTLQSGVPS  60
RFSGSGSGTE FTLTISSLQP EDFATYYCQL LNSYPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 793          moltype = DNA  length = 1329
FEATURE                 Location/Qualifiers
misc_feature            1..1329
                        note = Synthetic
source                  1..1329
                        mol_type = other DNA
                        organism = synthetic construct
SEQUENCE: 793
```

```
gaggtgcagc tggtggagtc tggaggaggc ttggtccagc ctgggggtc cctgagactc  60
tcctgtgcag cctctgggtt cattgtcagt aggaactaca tgagctgggt ccgccaggct  120
ccagggaagg gactggagtg ggtctcagtt atttatagcg gtggtagcac attctacgca  180
gactccgtga agggccgctt caccatctcc cgacacaatt ccaagaacac gctgtatctt  240
caaatgaaca gcctgaaagc tgaggacacg gccgtgtatt actgtgcgag agagctacga  300
gggtactttg actactgggg ccagggaacc ctggtcaccg tctcctcagc ctccaccaag  360
ggcccatcgg tcttccccct ggcgccctgc tccaggagca cctccgagag cacagccgcc  420
ctgggctgcc tggtcaagga ctacttcccc gaaccggtga cggtgtcgtg gaactcaggc  480
gccctgacca gcggcgtgca caccttcccg gctgtcctac agtcctcagg actctactcc  540
ctcagcagcg tggtgaccgt gccctccagc agcttgggca cgaagaccta cacctgcaac  600
gtagatcaca agcccagcaa caccaaggtg gacaagagag ttgagtccaa atatggtccc  660
ccatgcccac cgtgcccagc accaggcggt ggcggaccat cagtcttcct gttcccccca  720
aaacccaagg acactctcat gatctcccgg acccctgagg tcacgtgcgt ggtggtggac  780
gtgagccagg aagaccccga ggtccagttc aactggtacg tggatggcgt ggaggtgcat  840
aatgccaaga caaagccgcg ggaggagcag ttcaacagca cgtaccgtgt ggtcagcgtc  900
ctcaccgtcc tgcaccagga ctggctgaac ggcaaggagt acaagtgcaa ggtctccaac  960
aaaggcctcc cgtcctccat cgagaaaacc atctccaaag ccaaagggca gccccgagag  1020
ccacaggtgt acaccctgcc cccatcccag gaggagatga ccaagaacca ggtcagcctg  1080
acctgcctgg tcaaaggctt ctaccccagc gacatcgccg tggagtggga gagcaatggg  1140
cagccggaga acaactacaa gaccacgcct cccgtgctgg actccgacgg ctccttcttc  1200
ctctacagca ggctcaccgt ggacaagagc aggtggcagg aggggaatgt cttctcatgc  1260
tccgtgatgc atgaggctct gcacaaccac tacacacaga agtccctctc cctgtctctg  1320
ggtaaatga                                                        1329

SEQ ID NO: 794          moltype = AA  length = 442
FEATURE                 Location/Qualifiers
REGION                  1..442
                        note = Synthetic
source                  1..442
                        mol_type = protein
                        organism = synthetic construct
SEQUENCE: 794
EVQLVESGGG LVQPGGSLRL SCAASGFIVS RNYMSWVRQA PGKGLEWVSV IYSGGSTFYA  60
DSVKGRFTIS RHNSKNTLYL QMNSLKAEDT AVYYCARELR GYFDYWGQGT LVTVSSASTK  120
GPSVFPLAPC SRSTSESTAA LGCLVKDYFP EPVTVSWNSG ALTSGVHTFP AVLQSSGLYS  180
LSSVVTVPSS SLGTKTYTCN VDHKPSNTKV DKRVESKYGP PCPPCPAPGG GGPSVFLFPP  240
KPKDTLMISR TPEVTCVVVD VSQEDPEVQF NWYVDGVEVH NAKTKPREEQ FNSTYRVVSV  300
LTVLHQDWLN GKEYKCKVSN KGLPSSIEKT ISKAKGQPRE PQVYTLPPSQ EEMTKNQVSL  360
TCLVKGFYPS DIAVEWESNG QPENNYKTTP PVLDSDGSFF LYSRLTVDKS RWQEGNVFSC  420
SVMHEALHNH YTQKSLSLSL GK                                         442

SEQ ID NO: 795          moltype = DNA  length = 351
FEATURE                 Location/Qualifiers
misc_feature            1..351
                        note = Synthetic
source                  1..351
                        mol_type = other DNA
                        organism = synthetic construct
SEQUENCE: 795
gaggtgcagc tggtggagtc tggaggaggc ttggtccagc ctgggggtc cctgagactc  60
tcctgtgcag cctctgggtt caccgtcagt agtaactaca tgacctgggt ccgccaggct  120
ccagggaagg ggctggagtg ggtctcagtt atttatagcg gtggtagcac attctacgca  180
gactccgtga agggccgatt caccatctcc agacacaatt ccgagaacac gctgtatctt  240
caaatgaaca gcctgagagc tgaggacacg gccgtgtatt actgtgcgag agatctagca  300
gcagctggta cagactactg gggccaggga gccctggtca ccgtctcctc a         351

SEQ ID NO: 796          moltype = AA  length = 117
FEATURE                 Location/Qualifiers
REGION                  1..117
                        note = Synthetic
source                  1..117
                        mol_type = protein
                        organism = synthetic construct
SEQUENCE: 796
EVQLVESGGG LVQPGGSLRL SCAASGFTVS SNYMTWVRQA PGKGLEWVSV IYSGGSTFYA  60
DSVKGRFTIS RHNSENTLYL QMNSLRAEDT AVYYCARDLA AAGTDYWGQG ALVTVSS     117

SEQ ID NO: 797          moltype = DNA  length = 33
FEATURE                 Location/Qualifiers
misc_feature            1..33
                        note = Synthetic
source                  1..33
                        mol_type = other DNA
                        organism = synthetic construct
SEQUENCE: 797
gcgagagatc tagcagcagc tggtacagac tac                             33

SEQ ID NO: 798          moltype = AA  length = 11
FEATURE                 Location/Qualifiers
```

```
REGION                  1..11
                        note = Synthetic
source                  1..11
                        mol_type = protein
                        organism = synthetic construct
SEQUENCE: 798
ARDLAAAGTD Y                                                         11

SEQ ID NO: 799          moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 799
gacatccagt tgacccagtc tccatccttc ctgtctgcat ctgtaggaga cagagtcacc  60
atcacttgct gggccagtca gggcattagc agttatttag cctggtatca gcaaaaacca  120
gggaaagccc ctaagctcct gatctatgct gcatccactt tgcaaagtgg ggtcccatca  180
aggttcagcg gcagtggatc tgggacagaa ttcactctca caatcagcag cctgcagcct  240
gatgattttg caacttatta ctgtcaacac cttaatagtt acctgtacac ttttggccag  300
gggaccaagc tggagatcaa a                                              321

SEQ ID NO: 800          moltype = AA  length = 107
FEATURE                 Location/Qualifiers
REGION                  1..107
                        note = Synthetic
source                  1..107
                        mol_type = protein
                        organism = synthetic construct
SEQUENCE: 800
DIQLTQSPSF LSASVGDRVT ITCWASQGIS SYLAWYQQKP GKAPKLLIYA ASTLQSGVPS  60
RFSGSGSGTE FTLTISSLQP DDFATYYCQH LNSYLYTFGQ GTKLEIK                  107

SEQ ID NO: 801          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 801
caacacctta atagttacct gtacact                                        27

SEQ ID NO: 802          moltype = AA  length = 9
FEATURE                 Location/Qualifiers
REGION                  1..9
                        note = Synthetic
source                  1..9
                        mol_type = protein
                        organism = synthetic construct
SEQUENCE: 802
QHLNSYLYT                                                            9

SEQ ID NO: 803          moltype = DNA  length = 1344
FEATURE                 Location/Qualifiers
misc_feature            1..1344
                        note = Synthetic
source                  1..1344
                        mol_type = other DNA
                        organism = synthetic construct
SEQUENCE: 803
gaggtgcagc tggtggagtc tggaggaggc ttggtccagc ctgggggtc cctgagactc  60
tcctgtgcag cctctgggtt caccgtcagt agtaactaca tgacctgggt ccgccaggct  120
ccagggaagg ggctggagtg ggtctcagtt atttatagcg gtggtagcac attctacgca  180
gactccgtga agggccgatt caccatctcc agacacaatt ccgagaacac gctgtatctt  240
caaatgaaca gcctgagagc tgaggacacg gccgtgtatt actgtgcgag agatctagca  300
gcagctggta cagactactg gggccaggga gccctggtca ccgtctcctc agcctccacc  360
aagggcccat cggtcttccc cctggcaccc tcctccaaga gcacctctgg gggcacagcg  420
gccctgggct gcctggtcaa ggactacttc cccgaaccgg tgacggtgtc gtggaactca  480
ggcgccctga ccagcggcgt gcacaccttc ccggctgtcc tacagtcctc aggactctac  540
tccctcagca gcgtggtgac cgtgccctcc agcagcttgg gcacccagac ctacatctgc  600
aacgtgaatc acaagcccag caacaccaag gtggacaaga aagttgagcc caaatcttgt  660
gacaaaactc acacatgccc accgtgccca gcacctgaac tcctgggggg accgtcagtc  720
ttcctcttcc ccccaaaacc caaggacacc ctcatgatct cccggacccc tgaggtcaca  780
tgcgtggtgg tggacgtgag ccacgaagac cctgaggtca agttcaactg gtacgtggac  840
ggcgtggagg tgcataatgc caagacaaag ccgcgggagg agcagtacaa cagcacgtac  900
cgtgtggtca gcgtcctcac cgtcctgcac caggactggc tgaatggcaa ggagtacaag  960
tgcaaggtct ccaacaaagc cctcccagcc cccatcgaga aaaccatctc caaagccaaa  1020
```

-continued

```
gggcagcccc gagaaccaca ggtgtacacc ctgcccccat cccgggatga gctgaccaag  1080
aaccaggtca gcctgacctg cctggtcaaa ggcttctatc ccagcgacat cgccgtggag  1140
tgggagagca atgggcagcc ggagaacaac tacaagacca cgcctcccgt gctggactcc  1200
gacggctcct tcttcctcta cagcaagctc accgtggaca agagcaggtg gcagcagggg  1260
aacgtcttct catgctccgt gatgcatgag gctctgcaca accactacac gcagaagtcc  1320
ctctccctgt ctccgggtaa atga                                        1344

SEQ ID NO: 804          moltype = AA  length = 447
FEATURE                 Location/Qualifiers
REGION                  1..447
                        note = Synthetic
source                  1..447
                        mol_type = protein
                        organism = synthetic construct
SEQUENCE: 804
EVQLVESGGG LVQPGGSLRL SCAASGFTVS SNYMTWVRQA PGKGLEWVSV IYSGGSTFYA  60
DSVKGRFTIS RHNSENTLYL QMNSLRAEDT AVYYCARDLA AAGTDYWGQG ALVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APELLGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSRDELTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPGK                                     447

SEQ ID NO: 805          moltype = DNA  length = 645
FEATURE                 Location/Qualifiers
misc_feature            1..645
                        note = Synthetic
source                  1..645
                        mol_type = other DNA
                        organism = synthetic construct
SEQUENCE: 805
gacatccagt tgacccagtc tccatccttc ctgtctgcat ctgtaggaga cagagtcacc  60
atcacttgct gggccagtca gggcattagc agttatttag cctggtatca gcaaaaacca  120
gggaaagccc ctaagctcct gatctatgct gcatccactt tgcaaagtgg ggtcccatca  180
aggttcagcg gcagtggatc tgggacagaa ttcactctca caatcagcag cctgcagcct  240
gatgattttg caacttatta ctgtcaacac cttaatagtt acctgtacac ttttggccag  300
gggaccaagc tggagatcaa acgaactgtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttag                  645

SEQ ID NO: 806          moltype = AA  length = 214
FEATURE                 Location/Qualifiers
REGION                  1..214
                        note = Synthetic
source                  1..214
                        mol_type = protein
                        organism = synthetic construct
SEQUENCE: 806
DIQLTQSPSF LSASVGDRVT ITCWASQGIS SYLAWYQQKP GKAPKLLIYA ASTLQSGVPS  60
RFSGSGSGTE FTLTISSLQP DDFATYYCQH LNSYLYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 807          moltype = DNA  length = 1332
FEATURE                 Location/Qualifiers
misc_feature            1..1332
                        note = Synthetic
source                  1..1332
                        mol_type = other DNA
                        organism = synthetic construct
SEQUENCE: 807
gaggtgcagc tggtggagtc tggaggaggc ttggtccagc ctgggggtc cctgagactc  60
tcctgtgcag cctctgggtt caccgtcagt agtaactaca tgacctgggt ccgccaggct  120
ccagggaagg ggctggagtg ggtctcagtt atttatagcg gtggtagcac attctacgca  180
gactccgtga agggccgatt caccatctcc agacacaatt ccgagaacac gctgtatctt  240
caaatgaaca gcctgagagc tgaggacacg gccgtgtatt actgtgcgag agatctagca  300
gcagctggta cagactactg gggccaggga gccctggtca ccgtctcctc agcctccacc  360
aagggcccat cggtcttccc cctggcgccc tgctccagga gcacctccga gagcacagcc  420
gccctgggct gcctggtcaa ggactacttc cccgaaccgg tgacggtgtc gtggaactca  480
ggcgccctga ccagcggcgt gcacaccttc ccggctgtcc tacagtcctc aggactctac  540
tccctcagca gcgtggtgac cgtgccctcc agcagcttgg gcacgaagac ctacacctgc  600
aacgtagatc acaagcccag caacaccaag gtggacaaga gagttgagtc caaatatggt  660
cccccatgcc caccgtgccc agcaccaggc ggtggcggac catcagtctt cctgttcccc  720
ccaaaaccca aggacactct catgatctcc cggacccctg aggtcacgtg cgtggtggtg  780
gacgtgagcc aggaagaccc cgaggtccag ttcaactggt acgtggatgg cgtggaggtg  840
```

```
cataatgcca agacaaagcc gcgggaggag cagttcaaca gcacgtaccg tgtggtcagc  900
gtcctcaccg tcctgcacca ggactggctg aacggcaagg agtacaagtg caaggtctcc  960
aacaaaggcc tcccgtcctc catcgagaaa accatctcca aagccaaagg gcagccccga  1020
gagccacagg tgtacaccct gcccccatcc caggaggaga tgaccaagaa ccaggtcagc  1080
ctgacctgcc tggtcaaagg cttctacccc agcgacatcg ccgtggagtg ggagagcaat  1140
gggcagccgg agaacaacta caagaccacg cctcccgtgc tggactccga cggctccttc  1200
ttcctctaca gcaggctcac cgtggacaag agcaggtggc aggaggggaa tgtcttctca  1260
tgctccgtga tgcatgaggc tctgcacaac cactacacac agaagtccct ctccctgtct  1320
ctgggtaaat ga                                                      1332

SEQ ID NO: 808         moltype = AA  length = 443
FEATURE                Location/Qualifiers
REGION                 1..443
                       note = Synthetic
source                 1..443
                       mol_type = protein
                       organism = synthetic construct
SEQUENCE: 808
EVQLVESGGG LVQPGGSLRL SCAASGFTVS SNYMTWVRQA PGKGLEWVSV IYSGGSTFYA  60
DSVKGRFTIS RHNSENTLYL QMNSLRAEDT AVYYCARDLA AAGTDYWGQG ALVTVSSAST  120
KGPSVFPLAP CSRSTSESTA ALGCLVKDYF PEPVTVSWNS GALTSGVHTF PAVLQSSGLY  180
SLSSVVTVPS SSLGTKTYTC NVDHKPSNTK VDKRVESKYG PPCPPCPAPG GGGPSVFLFP  240
PKPKDTLMIS RTPEVTCVVV DVSQEDPEVQ FNWYVDGVEV HNAKTKPREE QFNSTYRVVS  300
VLTVLHQDWL NGKEYKCKVS NKGLPSSIEK TISKAKGQPR EPQVYTLPPS QEEMTKNQVS  360
LTCLVKGFYP SDIAVEWESN GQPENNYKTT PPVLDSDGSF FLYSRLTVDK SRWQEGNVFS  420
CSVMHEALHN HYTQKSLSLS LGK                                          443

SEQ ID NO: 809         moltype = DNA  length = 360
FEATURE                Location/Qualifiers
misc_feature           1..360
                       note = Synthetic
source                 1..360
                       mol_type = other DNA
                       organism = synthetic construct
SEQUENCE: 809
caggtgcagc tggtggagtc tgggggaggc gtggtccagc ctgggaggtc cctgagactc  60
tcctgtgcag cctctggatt caccttcagt agctatggca tgcactgggt ccgccaggct  120
ccaggcaagg ggctggagtg ggtggcagtt atatcatatg atggaagtta taagtactat  180
gcagactccg tgaagggccg attcaccatc tccagagaca attccaagaa cacgctgtat  240
ctgcaaatga acagcctgag agctgaggac acggctgtgt attactgtgc gatagatggg  300
gggacagtga ctacgatttt tgactactgg ggccagggaa ccctggtcac cgtctcctca  360

SEQ ID NO: 810         moltype = AA  length = 120
FEATURE                Location/Qualifiers
REGION                 1..120
                       note = Synthetic
source                 1..120
                       mol_type = protein
                       organism = synthetic construct
SEQUENCE: 810
QVQLVESGGG VVQPGRSLRL SCAASGFTFS SYGMHWVRQA PGKGLEWVAV ISYDGSYKYY  60
ADSVKGRFTI SRDNSKNTLY LQMNSLRAED TAVYYCAIDG GTVTTIFDYW GQGTLVTVSS  120

SEQ ID NO: 811         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 811
ggattcacct tcagtagcta tggc                                         24

SEQ ID NO: 812         moltype = AA  length = 8
FEATURE                Location/Qualifiers
REGION                 1..8
                       note = Synthetic
source                 1..8
                       mol_type = protein
                       organism = synthetic construct
SEQUENCE: 812
GFTFSSYG                                                           8

SEQ ID NO: 813         moltype = DNA  length = 24
FEATURE                Location/Qualifiers
misc_feature           1..24
                       note = Synthetic
source                 1..24
                       mol_type = other DNA
```

-continued

```
                        organism = synthetic construct
SEQUENCE: 813
atatcatatg atggaagtta taag                                        24

SEQ ID NO: 814          moltype = AA  length = 8
FEATURE                 Location/Qualifiers
REGION                  1..8
                        note = Synthetic
source                  1..8
                        mol_type = protein
                        organism = synthetic construct
SEQUENCE: 814
ISYDGSYK                                                          8

SEQ ID NO: 815          moltype = DNA  length = 39
FEATURE                 Location/Qualifiers
misc_feature            1..39
                        note = Synthetic
source                  1..39
                        mol_type = other DNA
                        organism = synthetic construct
SEQUENCE: 815
gcgatagatg gggggacagt gactacgatt tttgactac                        39

SEQ ID NO: 816          moltype = AA  length = 13
FEATURE                 Location/Qualifiers
REGION                  1..13
                        note = Synthetic
source                  1..13
                        mol_type = protein
                        organism = synthetic construct
SEQUENCE: 816
AIDGGTVTTI FDY                                                    13

SEQ ID NO: 817          moltype = DNA  length = 324
FEATURE                 Location/Qualifiers
misc_feature            1..324
                        note = Synthetic
source                  1..324
                        mol_type = other DNA
                        organism = synthetic construct
SEQUENCE: 817
gacatccaga tgacccagtc tccatcctcc ctgtctgcat ctgtaggaga cagagtcacc  60
atcacttgcc gggcaagtca gagcattagc agctatttaa attggtatca gcagaaacca  120
gggaaagccc ctaagctcct gatctatact gcatccagtt tgcaaagtgg ggtcccatca  180
aggttcagtg gcagtggatc tgggacagat ttcactctca ccatcagcag tctgcaacct  240
gaagattttg caacttacta ctgtcaacag agttacagta cccctccgtg gacgttcggc  300
caagggacca aggtggaaat caaa                                        324

SEQ ID NO: 818          moltype = AA  length = 108
FEATURE                 Location/Qualifiers
REGION                  1..108
                        note = Synthetic
source                  1..108
                        mol_type = protein
                        organism = synthetic construct
SEQUENCE: 818
DIQMTQSPSS LSASVGDRVT ITCRASQSIS SYLNWYQQKP GKAPKLLIYT ASSLQSGVPS  60
RFSGSGSGTD FTLTISSLQP EDFATYYCQQ SYSTPPWTFG QGTKVEIK              108

SEQ ID NO: 819          moltype =   length =
SEQUENCE: 819
000

SEQ ID NO: 820          moltype =   length =
SEQUENCE: 820
000

SEQ ID NO: 821          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 821
caacagagtt acagtacccc tccgtggacg                                  30

SEQ ID NO: 822          moltype = AA  length = 10
```

```
FEATURE               Location/Qualifiers
REGION                1..10
                      note = Synthetic
source                1..10
                      mol_type = protein
                      organism = synthetic construct
SEQUENCE: 822
QQSYSTPPWT                                                        10

SEQ ID NO: 823        moltype = DNA  length = 1353
FEATURE               Location/Qualifiers
misc_feature          1..1353
                      note = Synthetic
source                1..1353
                      mol_type = other DNA
                      organism = synthetic construct
SEQUENCE: 823
caggtgcagc tggtggagtc tgggggaggc gtggtccagc ctgggaggtc cctgagactc  60
tcctgtgcag cctctggatt caccttcagt agctatggca tgcactgggt ccgccaggct  120
ccaggcaagg ggctggagtg ggtggcagtt atatcatatg atggaagtta taagtactat  180
gcagactccg tgaagggccg attcaccatc tccagagaca attccaagaa cacgctgtat  240
ctgcaaatga acagcctgag agctgaggac acggctgtgt attactgtgc gatagatggg  300
gggacagtga ctacgatttt tgactactgg ggccagggaa ccctggtcac cgtctcctca  360
gcctccacca agggcccatc ggtcttcccc ctggcaccct cctccaagag cacctctggg  420
ggcacagcgg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacccagacc  600
tacatctgca acgtgaatca caagcccagc aacaccaagg tggacaagaa agttgagccc  660
aaatcttgtg acaaaactca cacatgccca ccgtgcccag cacctgaact cctgggggga  720
ccgtcagtct tcctcttccc cccaaaaccc aaggacaccc tcatgatctc ccggacccct  780
gaggtcacat gcgtggtggt ggacgtgagc cacgaagacc ctgaggtcaa gttcaactgg  840
tacgtggacg gcgtggaggt gcataatgcc aagacaaagc cgcgggagga gcagtacaac  900
agcacgtacc gtgtggtcag cgtcctcacc gtcctgcacc aggactggct gaatggcaag  960
gagtacaagt gcaaggtctc caacaaagcc ctcccagccc ccatcgagaa aaccatctcc  1020
aaagccaaag ggcagccccg agaaccacag gtgtacaccc tgcccccatc ccgggatgag  1080
ctgaccaaga accaggtcag cctgacctgc ctggtcaaag gcttctatcc cagcgacatc  1140
gccgtggagt gggagagcaa tgggcagccg gagaacaact acaagaccac gcctcccgtg  1200
ctggactccg acggctcctt cttcctctac agcaagctca ccgtggacaa gagcaggtgg  1260
cagcagggga acgtcttctc atgctccgtg atgcatgagg ctctgcacaa ccactacacg  1320
cagaagtccc tctccctgtc tccgggtaaa tga                              1353

SEQ ID NO: 824        moltype = AA  length = 450
FEATURE               Location/Qualifiers
REGION                1..450
                      note = Synthetic
source                1..450
                      mol_type = protein
                      organism = synthetic construct
SEQUENCE: 824
QVQLVESGGG VVQPGRSLRL SCAASGFTFS SYGMHWVRQA PGKGLEWVAV ISYDGSYKYY  60
ADSVKGRFTI SRDNSKNTLY LQMNSLRAED TAVYYCAIDG GTVTTIFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 825        moltype = DNA  length = 648
FEATURE               Location/Qualifiers
misc_feature          1..648
                      note = Synthetic
source                1..648
                      mol_type = other DNA
                      organism = synthetic construct
SEQUENCE: 825
gacatccaga tgacccagtc tccatcctcc ctgtctgcat ctgtaggaga cagagtcacc  60
atcacttgcc gggcaagtca gagcattagc agctatttaa attggtatca gcagaaacca  120
gggaaagccc ctaagctcct gatctatact gcatccagtt tgcaaagtgg ggtcccatca  180
aggttcagtg gcagtggatc tgggacagat ttcactctca ccatcagcag tctgcaacct  240
gaagattttg caacttacta ctgtcaacag agttacagta cccctccgtg gacgttcggc  300
caagggacca aggtggaaat caaacgaact gtggctgcac catctgtctt catcttcccg  360
ccatctgatg agcagttgaa atctggaact gcctctgttg tgtgcctgct gaataacttc  420
tatcccagag aggccaaagt acagtggaag gtggataacg ccctccaatc gggtaactcc  480
caggagagtg tcacagagca ggacagcaag gacagcacct acagcctcag cagcaccctg  540
acgctgagca aagcagacta cgagaaacac aaagtctacg cctgcgaagt cacccatcag  600
ggcctgagct cgcccgtcac aaagagcttc aacaggggag agtgttag              648

SEQ ID NO: 826        moltype = AA  length = 215
```

```
FEATURE                Location/Qualifiers
REGION                 1..215
                       note = Synthetic
source                 1..215
                       mol_type = protein
                       organism = synthetic construct
SEQUENCE: 826
DIQMTQSPSS LSASVGDRVT ITCRASQSIS SYLNWYQQKP GKAPKLLIYT ASSLQSGVPS  60
RFSGSGSGTD FTLTISSLQP EDFATYYCQQ SYSTPPWTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 827         moltype = DNA  length = 1341
FEATURE                Location/Qualifiers
misc_feature           1..1341
                       note = Synthetic
source                 1..1341
                       mol_type = other DNA
                       organism = synthetic construct
SEQUENCE: 827
caggtgcagc tggtggagtc tgggggaggc gtggtccagc ctgggaggtc cctgagactc  60
tcctgtgcag cctctggatt caccttcagt agctatggca tgcactgggt ccgccaggct  120
ccaggcaagg ggctggagtg ggtggcagtt atatcatatg atggaagtta taagtactat  180
gcagactccg tgaagggccg attcaccatc tccagagaca attccaagaa cacgctgtat  240
ctgcaaatga acagcctgag agctgaggac acggctgtgt attactgtgc gatagatggg  300
gggacagtga ctacgatttt tgactactgg ggccagggaa ccctggtcac cgtctcctca  360
gcctccacca agggcccatc ggtcttcccc ctggcgccct gctccaggag cacctccgag  420
agcacagccg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacgaagacc  600
tacacctgca acgtagatca caagcccagc aacaccaagg tggacaagag agttgagtcc  660
aaatatggtc ccccatgccc accgtgccca gcaccaggcg gtggcggacc atcagtcttc  720
ctgttccccc caaaacccaa ggacactctc atgatctccc ggacccctga ggtcacgtgc  780
gtggtggtgg acgtgagcca ggaagacccc gaggtccagt tcaactggta cgtggatggc  840
gtggaggtgc ataatgccaa gacaaagccg cgggaggagc agttcaacag cacgtaccgt  900
gtggtcagcg tcctcaccgt cctgcaccag gactggctga acggcaagga gtacaagtgc  960
aaggtctcca acaaaggcct cccgtcctcc atcgagaaaa ccatctccaa agccaaaggg  1020
cagccccgag agccacaggt gtacaccctg cccccatccc aggaggagat gaccaagaac  1080
caggtcagcc tgacctgcct ggtcaaaggc ttctacccca gcgacatcgc cgtggagtgg  1140
gagagcaatg ggcagccgga gaacaactac aagaccacgc ctcccgtgct ggactccgac  1200
ggctccttct tcctctacag caggctcacc gtggacaaga gcaggtggca ggaggggaat  1260
gtcttctcat gctccgtgat gcatgaggct ctgcacaacc actacacaca gaagtccctc  1320
tccctgtctc tgggtaaatg a                                            1341

SEQ ID NO: 828         moltype = AA  length = 446
FEATURE                Location/Qualifiers
REGION                 1..446
                       note = Synthetic
source                 1..446
                       mol_type = protein
                       organism = synthetic construct
SEQUENCE: 828
QVQLVESGGG VVQPGRSLRL SCAASGFTFS SYGMHWVRQA PGKGLEWVAV ISYDGSYKYY  60
ADSVKGRFTI SRDNSKNTLY LQMNSLRAED TAVYYCAIDG GTVTTIFDYW GQGTLVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APGGGGPSVF  240
LFPPKPKDTL MISRTPEVTC VVVDVSQEDP EVQFNWYVDG VEVHNAKTKP REEQFNSTYR  300
VVSVLTVLHQ DWLNGKEYKC KVSNKGLPSS IEKTISKAKG QPREPQVYTL PPSQEEMTKN  360
QVSLTCLVKG FYPSDIAVEW ESNGQPENNY KTTPPVLDSD GSFFLYSRLT VDKSRWQEGN  420
VFSCSVMHEA LHNHYTQKSL SLSLGK                                       446

SEQ ID NO: 829         moltype = AA  length = 251
FEATURE                Location/Qualifiers
REGION                 1..251
                       note = Synthetic
source                 1..251
                       mol_type = protein
                       organism = synthetic construct
SEQUENCE: 829
RVQPTESIVR FPNITNLCPF GEVFNATRFA SVYAWNRKRI SNCVADYSVL YNSASFSTFK  60
CYGVSPTKLN DLCFTNVYAD SFVIRGDEVR QIAPGQTGKI ADYNYKLPDD FTGCVIAWNS  120
NNLDSKVGGN YNYLYRLFRK SNLKPFERDI STEIYQAGST PCNGVEGFNC YFPLQSYGFQ  180
PTNGVGYQPY RVVVLSFELL HAPATVCGPK KSTNLVKNKC VNFEQKLISE EDLGGEQKLI  240
SEEDLHHHHH H                                                       251

SEQ ID NO: 830         moltype = AA  length = 456
FEATURE                Location/Qualifiers
REGION                 1..456
                       note = Synthetic
```

```
source                  1..456
                        mol_type = protein
                        organism = synthetic construct
SEQUENCE: 830
RVQPTESIVR FPNITNLCPF GEVFNATRFA SVYAWNRKRI SNCVADYSVL YNSASFSTFK  60
CYGVSPTKLN DLCFTNVYAD SFVIRGDEVR QIAPGQTGKI ADYNYKLPDD FTGCVIAWNS  120
NNLDSKVGGN YNYLYRLFRK SNLKPFERDI STEIYQAGST PCNGVEGFNC YFPLQSYGFQ  180
PTNGVGYQPY RVVVLSFELL HAPATVCGPK KSTNLVKNKC VNFEPRGPTI KPCPPCKCPA  240
PNLLGGPSVF IFPPKIKDVL MISLSPIVTC VVVDVSEDDP DVQISWFVNN VEVHTAQTQT  300
HREDYNSTLR VVSALPIQHQ DWMSGKEFKC KVNNKDLPAP IERTISKPKG SVRAPQVYVL  360
PPPEEEMTKK QVTLTCMVTD FMPEDIYVEW TNNGKTELNY KNTEPVLDSD GSYFMYSKLR  420
VEKKNWVERN SYSCSVVHEG LHNHHTTKSF SRTPGK                            456

SEQ ID NO: 831          moltype = AA  length = 450
FEATURE                 Location/Qualifiers
REGION                  1..450
                        note = Synthetic
source                  1..450
                        mol_type = protein
                        organism = synthetic construct
SEQUENCE: 831
RVQPTESIVR FPNITNLCPF GEVFNATRFA SVYAWNRKRI SNCVADYSVL YNSASFSTFK  60
CYGVSPTKLN DLCFTNVYAD SFVIRGDEVR QIAPGQTGKI ADYNYKLPDD FTGCVIAWNS  120
NNLDSKVGGN YNYLYRLFRK SNLKPFERDI STEIYQAGST PCNGVEGFNC YFPLQSYGFQ  180
PTNGVGYQPY RVVVLSFELL HAPATVCGPK KSTNLVKNKC VNFDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 832          moltype = AA  length = 1273
FEATURE                 Location/Qualifiers
REGION                  1..1273
                        note = Synthetic
source                  1..1273
                        mol_type = protein
                        organism = synthetic construct
SEQUENCE: 832
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDKVEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPWYIWLGF IAGLIAIVMV TIMLCCMTSC CSCLKGCCSC GSCCKFDEDD  1260
SEPVLKGVKL HYT                                                    1273

SEQ ID NO: 833          moltype = AA  length = 1196
FEATURE                 Location/Qualifiers
REGION                  1..1196
                        note = Synthetic
source                  1..1196
                        mol_type = protein
                        organism = synthetic construct
SEQUENCE: 833
VNLTTRTQLP PAYTNSFTRG VYYPDKVFRS SVLHSTQDLF LPFFSNVTWF HAIHVSGTNG  60
TKRFDNPVLP FNDGVYFAST EKSNIIRGWI FGTTLDSKTQ SLLIVNNATN VVIKVCEFQF  120
CNDPFLGVYY HKNNKSWMES EFRVYSSANN CTFEYVSQPF LMDLEGKQGN FKNLREFVFK  180
NIDGYFKIYS KHTPINLVRD LPQGFSALEP LVDLPIGINI TRFQTLLALH RSYLTPGDSS  240
SGWTAGAAAY YVGYLQPRTF LLKYNENGTI TDAVDCALDP LSETKCTLKS FTVEKGIYQT  300
SNFRVQPTES IVRFPNITNL CPFGEVFNAT RFASVYAWNR KRISNCVADY SVLYNSASFS  360
TFKCYGVSPT KLNDLCFTNV YADSFVIRGD EVRQIAPGQT GKIADYNYKL PDDFTGCVIA  420
WNSNNLDSKV GGNYNYLYRL FRKSNLKPFE RDISTEIYQA GSTPCNGVEG FNCYFPLQSY  480
GFQPTNGVGY QPYRVVVLSF ELLHAPATVC GPKKSTNLVK NKCVNFNFNG LTGTGVLTES  540
NKKFLPFQQF GRDIADTTDA VRDPQTLEIL DITPCSFGGV SVITPGTNTS NQVAVLYQDV  600
```

-continued

```
NCTEVPVAIH ADQLTPTWRV YSTGSNVFQT RAGCLIGAEH VNNSYECDIP IGAGICASYQ  660
TQTNSPRRAR SVASQSIIAY TMSLGAENSV AYSNNSIAIP TNFTISVTTE ILPVSMTKTS  720
VDCTMYICGD STECSNLLLQ YGSFCTQLNR ALTGIAVEQD KNTQEVFAQV KQIYKTPPIK  780
DFGGFNFSQI LPDPSKPSKR SFIEDLLFNK VTLADAGFIK QYGDCLGDIA ARDLICAQKF  840
NGLTVLPPLL TDEMIAQYTS ALLAGTITSG WTFGAGAALQ IPFAMQMAYR FNGIGVTQNV  900
LYENQKLIAN QFNSAIGKIQ DSLSSTASAL GKLQDVVNQN AQALNTLVKQ LSSNFGAISS  960
VLNDILSRLD KVEAEVQIDR LITGRLQSLQ TYVTQQLIRA AEIRASANLA ATKMSECVLG  1020
QSKRVDFCGK GYHLMSFPQS APHGVVFLHV TYVPAQEKNF TTAPAICHDG KAHFPREGVF  1080
VSNGTHWFVT QRNFYEPQII TTDNTFVSGN CDVVIGIVNN TVYDPLQPEL DSFKEELDKY  1140
FKNHTSPDVD LGDISGINAS VVNIQKEIDR LNEVAKNLNE SLIDLQELGK YEQYIK      1196

SEQ ID NO: 834          moltype = AA  length = 5
FEATURE                 Location/Qualifiers
REGION                  1..5
                        note = Synthetic
source                  1..5
                        mol_type = protein
                        organism = synthetic construct
SEQUENCE: 834
GGGGS                                                              5

SEQ ID NO: 835          moltype = AA  length = 47
FEATURE                 Location/Qualifiers
REGION                  1..47
                        note = Synthetic
source                  1..47
                        mol_type = protein
                        organism = synthetic construct
SEQUENCE: 835
DISTEIYQAG STPCNGVEGF NCYFPLQSYG FQPTNGVGYQ PYRVVVL                47

SEQ ID NO: 836          moltype = AA  length = 21
FEATURE                 Location/Qualifiers
REGION                  1..21
                        note = Synthetic
source                  1..21
                        mol_type = protein
                        organism = synthetic construct
SEQUENCE: 836
CVIAWNSNNL DSKVGGNYNY L                                            21

SEQ ID NO: 837          moltype = AA  length = 8
FEATURE                 Location/Qualifiers
REGION                  1..8
                        note = Synthetic
source                  1..8
                        mol_type = protein
                        organism = synthetic construct
SEQUENCE: 837
DISTEIYQ                                                           8

SEQ ID NO: 838          moltype = AA  length = 34
FEATURE                 Location/Qualifiers
REGION                  1..34
                        note = Synthetic
source                  1..34
                        mol_type = protein
                        organism = synthetic construct
SEQUENCE: 838
CNGVEGFNCY FPLQSYGFQP TNGVGYQPYR VVVL                              34

SEQ ID NO: 839          moltype = AA  length = 44
FEATURE                 Location/Qualifiers
REGION                  1..44
                        note = Synthetic
source                  1..44
                        mol_type = protein
                        organism = synthetic construct
SEQUENCE: 839
DISTEIYQAG STPCNGVEGF NCYFPLQSYG FQPTNGVGYQ PYRV                   44

SEQ ID NO: 840          moltype = AA  length = 16
FEATURE                 Location/Qualifiers
REGION                  1..16
                        note = Synthetic
source                  1..16
                        mol_type = protein
                        organism = synthetic construct
SEQUENCE: 840
```

```
EIYQAGSTPC NGVEGF                                                   16

SEQ ID NO: 841          moltype = AA  length = 25
FEATURE                 Location/Qualifiers
REGION                  1..25
                        note = Synthetic
source                  1..25
                        mol_type = protein
                        organism = synthetic construct
SEQUENCE: 841
PLQSYGFQPT NGVGYQPYRV VVLSF                                         25

SEQ ID NO: 842          moltype = AA  length = 10
FEATURE                 Location/Qualifiers
REGION                  1..10
                        note = Synthetic
source                  1..10
                        mol_type = protein
                        organism = synthetic construct
SEQUENCE: 842
YAWNRKRISN                                                          10

SEQ ID NO: 843          moltype = AA  length = 20
FEATURE                 Location/Qualifiers
REGION                  1..20
                        note = Synthetic
source                  1..20
                        mol_type = protein
                        organism = synthetic construct
SEQUENCE: 843
DISTEIYQAG STPCNGVEGF                                               20

SEQ ID NO: 844          moltype = AA  length = 23
FEATURE                 Location/Qualifiers
REGION                  1..23
                        note = Synthetic
source                  1..23
                        mol_type = protein
                        organism = synthetic construct
SEQUENCE: 844
PLQSYGFQPT NGVGYQPYRV VVL                                           23

SEQ ID NO: 845          moltype = AA  length = 23
FEATURE                 Location/Qualifiers
REGION                  1..23
                        note = Synthetic
source                  1..23
                        mol_type = protein
                        organism = synthetic construct
SEQUENCE: 845
FVIRGDEVRQ IAPGQTGKIA DYN                                           23

SEQ ID NO: 846          moltype = AA  length = 34
FEATURE                 Location/Qualifiers
REGION                  1..34
                        note = Synthetic
source                  1..34
                        mol_type = protein
                        organism = synthetic construct
SEQUENCE: 846
YRLFRKSNLK PFERDISTEI YQAGSTPCNG VEGF                               34

SEQ ID NO: 847          moltype = AA  length = 26
FEATURE                 Location/Qualifiers
REGION                  1..26
                        note = Synthetic
source                  1..26
                        mol_type = protein
                        organism = synthetic construct
SEQUENCE: 847
FPLQSYGFQP TNGVGYQPYR VVVLSF                                        26

SEQ ID NO: 848          moltype = AA  length = 24
FEATURE                 Location/Qualifiers
REGION                  1..24
                        note = Synthetic
source                  1..24
                        mol_type = protein
                        organism = synthetic construct
```

-continued

```
SEQUENCE: 848
VIRGDEVRQI APGQTGKIAD YNYK                                         24

SEQ ID NO: 849         moltype = AA  length = 43
FEATURE                Location/Qualifiers
REGION                 1..43
                       note = Synthetic
source                 1..43
                       mol_type = protein
                       organism = synthetic construct
SEQUENCE: 849
EIYQAGSTPC NGVEGFNCYF PLQSYGFQPT NGVGYQPYRV VVL                    43

SEQ ID NO: 850         moltype = AA  length = 14
FEATURE                Location/Qualifiers
REGION                 1..14
                       note = Synthetic
source                 1..14
                       mol_type = protein
                       organism = synthetic construct
SEQUENCE: 850
YAWNRKRISN CVAD                                                    14
```